(12) United States Patent
Cleland et al.

(10) Patent No.: US 9,808,531 B2
(45) Date of Patent: Nov. 7, 2017

(54) COMPOUNDS AND COMPOSITIONS FOR THE TREATMENT OF OCULAR DISORDERS

(71) Applicant: Graybug Vision, Inc., Redwood City, CA (US)

(72) Inventors: Jeffrey L. Cleland, San Carlos, CA (US); Ming Yang, Lutherville-Timonium, MD (US); John G. Bauman, El Sobrante, CA (US); Nu Hoang, Annapolis, MD (US); Emmett Cunningham, Hillsborough, CA (US)

(73) Assignee: Graybug Vision, Inc., Redwood City, CA (US)

( * ) Notice: Subject to any disclaimer, the term of this patent is extended or adjusted under 35 U.S.C. 154(b) by 0 days.

(21) Appl. No.: 15/273,686

(22) Filed: Sep. 22, 2016

(65) Prior Publication Data
US 2017/0080092 A1    Mar. 23, 2017

Related U.S. Application Data

(60) Provisional application No. 62/222,095, filed on Sep. 22, 2015.

(51) Int. Cl.
| | | |
|---|---|---|
| *A61K 47/48* | (2006.01) | |
| *C07D 495/04* | (2006.01) | |
| *C07D 513/04* | (2006.01) | |
| *C07C 69/73* | (2006.01) | |
| *C07D 403/06* | (2006.01) | |

(52) U.S. Cl.
CPC .............. *A61K 47/481* (2013.01); *C07C 69/73* (2013.01); *C07D 403/06* (2013.01); *C07D 495/04* (2013.01); *C07D 513/04* (2013.01); *C07C 2101/08* (2013.01)

(58) Field of Classification Search
None
See application file for complete search history.

(56) References Cited

U.S. PATENT DOCUMENTS

| | | | |
|---|---|---|---|
| 3,853,963 | A | 12/1974 | Morozowich |
| 5,292,754 | A | 3/1994 | Kishi et al. |
| 5,446,041 | A | 8/1995 | Chan et al. |

(Continued)

FOREIGN PATENT DOCUMENTS

| | | |
|---|---|---|
| EP | 0667160 A2 | 8/1995 |
| EP | 0850926 A2 | 7/1998 |

(Continued)

OTHER PUBLICATIONS

Database Caplus Chemical Abstracts Service, Columbus, Ohio, US; Database Accession No. 1973:15582, Abstract of Doria et al., Tetrahedron Letters (1972), (42), 4307-10.*

(Continued)

*Primary Examiner* — Karl J Puttlitz
(74) *Attorney, Agent, or Firm* — Knowles Intellectual Property Strategies, LLC

(57) ABSTRACT

The disclosure describes prodrugs and derivatives of prostaglandins, carbonic anhydrase inhibitors, kinase inhibitors, beta-adrenergic receptor antagonists and other drugs, as well as controlled delivery formulations containing such prodrugs and derivatives, for the treatment of ocular disorders.

27 Claims, 15 Drawing Sheets

(56) References Cited

U.S. PATENT DOCUMENTS

| | | | |
|---|---|---|---|
| 5,767,154 | A | 6/1998 | Woodward et al. |
| 6,573,293 | B2 | 6/2003 | Tang et al. |
| 6,586,468 | B1 | 7/2003 | Maruyama et al. |
| 6,680,339 | B2 | 1/2004 | Klimko et al. |
| 6,891,062 | B2 | 5/2005 | Oida et al. |
| 7,125,905 | B2 | 10/2006 | Tang et al. |
| 7,211,600 | B2 | 5/2007 | Lipson et al. |
| 7,470,717 | B2 | 12/2008 | Ohta et al. |
| 8,058,467 | B2 | 11/2011 | Ongini et al. |
| 8,426,471 | B1 | 4/2013 | Kalayoglu et al. |
| 8,889,193 | B2 | 11/2014 | McDonnell et al. |
| 8,889,735 | B2 | 11/2014 | Ueno |
| 8,957,034 | B2 | 2/2015 | Hanes et al. |
| 8,962,577 | B2 | 2/2015 | Hanes et al. |
| 9,056,057 | B2 | 6/2015 | Popov et al. |
| 9,327,037 | B2 | 5/2016 | Suk et al. |
| 9,415,020 | B2 | 8/2016 | Ensign et al. |
| 2007/0172523 | A1 | 7/2007 | Hashitera et al. |
| 2013/0183244 | A1 | 7/2013 | Hanes et al. |
| 2013/0272994 | A1 | 10/2013 | Fu et al. |
| 2013/0281637 | A1 | 10/2013 | Ueno et al. |
| 2014/0329913 | A1 | 11/2014 | Hanes et al. |
| 2014/0350104 | A1 | 11/2014 | Kalayoglu et al. |
| 2015/0086484 | A1 | 3/2015 | Hanes et al. |
| 2015/0118279 | A1 | 4/2015 | Ghebremeskel et al. |

FOREIGN PATENT DOCUMENTS

| | | |
|---|---|---|
| EP | 0930296 A1 | 7/1999 |
| EP | 1329453 B1 | 6/2004 |
| GB | 844946 | 8/1960 |
| JP | 2000080075 A | 3/2000 |
| WO | WO 8807044 | 9/1988 |
| WO | WO 9730710 | 8/1997 |
| WO | WO 0038663 | 7/2000 |
| WO | WO 03074481 A2 | 9/2003 |
| WO | WO 2005002588 A1 | 1/2005 |
| WO | WO 2007000642 A1 | 1/2007 |
| WO | WO 2008030557 A2 | 3/2008 |
| WO | WO 2008041054 A1 | 4/2008 |
| WO | WO 2009035565 A1 | 3/2009 |
| WO | WO 2012061703 A1 | 5/2012 |
| WO | WO 2012099942 A2 | 7/2012 |
| WO | WO 2012141334 A1 | 10/2012 |
| WO | WO 2013174780 A1 | 11/2013 |
| WO | WO 2014146486 A1 | 9/2014 |
| WO | WO 2014177524 A1 | 11/2014 |
| WO | WO 2014200117 A1 | 12/2014 |
| WO | WO 2015025980 A1 | 2/2015 |
| WO | WO 2015050277 A1 | 4/2015 |
| WO | WO 2016025215 A1 | 2/2016 |
| WO | WO 2016100380 A1 | 6/2016 |
| WO | WO 2016100392 A1 | 6/2016 |
| WO | WO 2016118506 A1 | 7/2016 |

OTHER PUBLICATIONS

Vallikivi, I., et al. (2005). "The modelling and kinetic investigation of the lipase-catalyzed acetylation of stereoisomeric prostaglandins" J. Mol. Catal. 25 B: Enzym. 35(1-3): 62-69.

Parve, O., et al. (1999). "Lipase-catalyzed acylation of prostanoids" Bioorg. Med. Chem. Lett. 9(13): 1853-1858.

Carmely, S., et al. (1980). "New prostaglandin (PGF) derivatives from the soft coral Lobophyton depressum" Tetrahedron Lett.21(9): 875-878.

International Search Report and Written Opinion for International Application No. PCT/US2016/53210; International Filing Date: Sep. 22, 2016; dated Feb. 3, 2017; 12 pages.

* cited by examiner

COMPOUNDS AND COMPOSITIONS FOR THE TREATMENT OF OCULAR DISORDERS

CROSS-REFERENCE TO RELATED APPLICATIONS

This application claims the benefit of provisional U.S. Application No. 62/222,095, filed Sep. 22, 2015, and the entirety of the application is hereby incorporated by reference for all purposes.

BACKGROUND

The eye is a complex organ with unique anatomy and physiology. The structure of the eye can be divided into two parts, the anterior and posterior. The cornea, conjunctiva, aqueous humor, iris, ciliary body and lens are in the anterior portion. The posterior portion includes the sclera, choroid, retinal pigment epithelium, neural retina, optic nerve and vitreous humor. The most important diseases affecting the anterior segment include glaucoma, allergic conjunctivitis, anterior uveitis and cataracts. The most prevalent diseases affecting the posterior segment of the eye are dry and wet age-related macular degeneration (AMD) and diabetic retinopathy.

Typical routes of drug delivery to the eye are topical, systemic, subconjunctival, intravitreal, puntal, intrasceral, transscleral, anterior or posterior sub-Tenon's, suprachoroidal, choroidal, subchoroidal, and subretinal.

To address issues of ocular delivery, a large number of types of delivery systems have been devised. Such include conventional (solution, suspension, emulsion, ointment, inserts and gels); vesicular (liposomes, exosomes, niosomes, discomes and pharmacosomes), advanced materials (scleral plugs, gene delivery, siRNA and stem cells); and controlled release systems (implants, hydrogels, dendrimers, iontophoresis, collagen shields, polymeric solutions, therapeutic contact lenses, cyclodextrin carriers, microneedles and microemulsions and particulates (microparticles and nanoparticles)).

Topical drops are the most widely used non-invasive routes of drug administration to treat anterior ocular diseases. However, a number of barriers exist to effective topical delivery, including tear turnover, nasolacrimal drainage, reflex blinking, and the barrier of the mucosal membrane. It is considered that less than 5% of topically applied dosages reach the deeper ocular tissue.

The patient may be required to instill topical drops up to four times a day. Indeed, certain patients, including corneal transplant recipients, require therapeutic doses of medications to be continuously maintained in the corneal tissues and some patients are required to endure lengthy and arduous dosing regimens that often involve up to hourly application. Each repeat dosing not only requires a further investment of a patient's time, but also increases the chance of irritation and non-compliance.

Drug delivery to the posterior area of the eye usually requires a different mode of administration from topical drops, and is typically achieved via an intravitreal injection, periocular injection or systemic administration. Systemic administration is not preferred given the ratio of volume of the eye to the entire body and thus unnecessary potential systemic toxicity. Therefore, intravitreal injections are currently the most common form of drug administration for posterior disorders. However, intravitreal injections also risk problems due to the common side effect of inflammation to the eye caused by administration of foreign material to this sensitive area, endophthalmitis, hemorrhage, retinal detachment and poor patient compliance.

Transscleral delivery with periocular administration is seen as an alternative to intravitreal injections, however, ocular barriers such as the sclera, choroid, retinal pigment epithelium, lymphatic flow and general blood flow compromise efficacy.

To treat ocular diseases, and in particular disease of the posterior chamber, the drug must be delivered in an amount and for a duration to achieve efficacy. This seemingly straightforward goal is difficult to achieve in practice.

Examples of common drug classes used for ocular disorders include: prostaglandins, carbonic anhydrase inhibitors, receptor tyrosine kinase inhibitors (RTKIs), beta-blockers, alpha-adrenergic agonists, parasympathomimetics, epinephrine, and hyperosmotic agents.

Although a number of prostaglandin carboxylic acids are effective in treating eye disorders, for example, lowering intraocular pressure (IOP), their hydrophilic nature can lead to rapid clearance from the surface of the eye before effective therapy can be achieved. As a result, prostaglandins are dosed in the form of selected esters to allow entry to the eye and a "prolonged" residence. When in the eye, native esterase enzymes cleave the prostaglandin ester to release the active species. Despite this innovation, current drop administered prostaglandins, for example, latanoprost, bimatoprost, and travoprost, still require daily or several times daily dosing regimens and may cause irritation or hyperemia to the eye in some patients. In addition, nearly half of patients on prostaglandin therapy for glaucoma require a second agent for control of IOP (Physician Drug and Diagnosis Audit (PDDA) from Verispan, L.L.C. January-June, 2003) Carbonic anhydrase inhibitors (CAIs) are used as an alternative and sometimes in conjunction with prostaglandins to treat eye disorders. Unfortunately, compliancy issues can occur as these medications also require daily or dosing up to four times a day, and may also cause irritation or hyperemia to the eye in some patients.

Another potential avenue for the treatment of ocular disorders involves protecting neurons directly. Preliminary data on receptor tyrosine kinase inhibitors (RTKIs) and dual leucine zipper kinase inhibitors (DLKIs) suggests that instead of treating increasing ocular pressure, molecules such as Sunitinib and Crizotinib can prevent the nerve damage that is associated with it.

Unfortunately, Sunitinib has had observed hepatotoxicity in both clinical trials and post-marketing clinical use.

References that describe treatments of ocular disorders and the synthesis of compounds related to treating ocular disorders include the following: Ongini et al., U.S. Pat. No. 8,058,467 titled "Prostaglandin derivatives"; Qlt Plug Delivery Inc, WO2009/035565 titled "Prostaglandin analogues for implant devices and methods"; Allergan Inc, U.S. Pat. No. 5,446,041 titled "Intraocular pressure reducing 11-acyl prostaglandins"; Upjohn Co., DE2263393 titled "9-O-Acylated prostaglandins F2a"; Shionogi & Co. patent publication 948,179 titled "Treatment for hypertension or glaucoma in eyes"; Ragactive, EP1329453 titled "Method for obtaining 4-(n-alkylamine)-5, 6-dihydro-4h-thieno-(2,3-b)-thiopyran-2-sulfonamide-7, 7-dioxides and intermediate products"; and American Cyanamid Co. GB844946 titled "2-(N-Substituted)acylamino-1,3,4-thiadiazole-5-sulfonamides".

Other publications include Vallikivi, I., et al. (2005). "The modelling and kinetic investigation of the lipase-catalyzed acetylation of stereoisomeric prostaglandins." J. Mol. Catal. B: Enzym. 35(1-3): 62-69; Parve, O., et al. (1999). "Lipase-catalyzed acylation of prostanoids." Bioorg. Med. Chem.

Lett. 9(13): 1853-1858; and Carmely, S., et al. (1980). and "New prostaglandin (PGF) derivatives from the soft coral Lobophyton depressum." Tetrahedron Lett. 21(9): 875-878.

Patent applications that describe DLK inhibitors include: Zhejiang DTRM Biopharma Co., patent publication WO2014146486 titled "Three-level cyclic amine ALK kinase inhibitor for treating cancer"; Kyowa Hakko Kogyo Co., patent publication WO2005012257 titled "Indazole Derivatives"; Genetech, patent publication WO2014177524 titled "C-linked heterocycloalkyl substituted pyrimidines and their uses", and patent publication WO2013174780 titled "Substituted dipyridylamines and uses thereof".

Patent applications that describe derivatives of prostaglandins include: Allergan, 5,767,154 titled "5-tran-prostaglandins of the F series and their use as ocular hypotensives", U.S. Pat. No. 5,767,154 titled "5-trans-prostaglandins of the F series and their use as ocular hypotensives"; Alcon Laboratories, EP0667160A2 titled "Use of certain prostaglandin analogues to treat glaucoma and ocular hypertension", EP667160 titled "Use of certain prostaglandin analogues to treat glaucoma and ocular hypertension; Asahi glass company and Santen Pharmaceutical Co., EP0850926A2 titled "Difluoroprostaglandin derivatives and their use"; Asahi Glass Co., JP2000080075 titled "Preparation of 15-deoxy-15,15-difluoroprostaglandins as selective and chemically-stable drugs", JP11255740 titled "Preparation of 15-deoxy-15-monofluoroprostaglandin derivatives", JP10087607 titled "Preparation of fluorine-containing prostaglandins as agents for inducing labor and controlling animal sexual cycle", WO9812175 titled "Preparation of fluorinated prostaglandin derivatives for treatment of glaucoma"; Santen Pharmaceutical Co., JP10259179 titled "Preparation of multi-substituted aryloxy-group containing prostaglandins and their use", EP850926 titled "Preparation of difluoroprostaglandin derivatives and their use for treatment of an eye disease";

The object of this invention is to provide improved compounds, compositions and methods to treat ocular disorders.

SUMMARY

The present invention includes new compounds and compositions, including controlled release compositions, with improved properties for ocular therapy. In one embodiment, the invention is an improved method for delivering an active drug to the eye that includes presenting the drug, which achieves a controlled release of the active material, including when administered in a sustained delivery system such as a polymeric composition, a hydrophobic liquid, a hydrophobic solid, or a form of slow release reservoir or encapsulation. Often, ocular therapies are delivered to the eye in a form that is hydrophilic to be soluble in ocular fluid. In this invention, a highly hydrophobic prodrug or derivative of an active compound which can be delivered in a polymeric controlled delivery system is provided wherein the hydrophobic compound is more soluble within polymeric material than the ocular fluid, which slows release into ocular aqueous fluid.

Commercial prostaglandins are generally provided as lower alkyl chain esters (e.g., up to pivaloyl). Also see for example, WO2009/035565 titled "Prostaglandin analogues for implant devices and methods" which disclosed the presentation of a prostaglandin with a long chain alkyl ester, however, the presently disclosed prostaglandin derivatives represent improvements over these compounds with either increased masking of hydroxyl groups remaining on the molecule or alternative hydrophobic prodrug moieties that can provide enhanced performance.

In another embodiment, the compounds provided herein are designed to deliver two active compounds with different, but additive or synergistic mechanisms of action for ocular therapy to the eye. This represents a contribution to the art over simple combination therapy, including for glaucoma, wherein multiple eye drops or a mixture of multiple eye drops are delivered.

In certain embodiments of the invention, at least one of the active therapeutic agents delivered in modified form is selected from a kinase inhibitor (for example, a tyrosine kinase inhibitor or a dual leucine zipper kinase inhibitor), a prostaglandin or a carbonic anhydrase inhibitor. Non-limiting examples of active therapeutic agents include Sunitinib or a derivatized version of Sunitinib (for example, with a hydroxyl, amino, thio, carboxy, keto or other functional group instead of fluoro that can be used to covalently connect the hydrophobic moiety), Latanoprost, Dinoprost, Travoprost, Tafluprost, Unoprostone, Timolol, Brinzolamide, Dorzolamide, Acetazolamide, Methazolamide, Crizotinib, KW-2449, and Tozasertib.

One achievement of the invention is to provide for the controlled administration of active compounds to the eye, over a period of at least two, three, four, five or six months or more in a manner that maintains at least a concentration in the eye that is effective for the disorder to be treated. In one embodiment, the drug is administered in a polymeric formulation that provides a controlled release that is linear. In another embodiment, the release is not linear; however, even the lowest concentration of release over the designated time period is at or above a therapeutically effective dose. In one embodiment, this is achieved by formulating a hydrophobic prodrug of the invention in a polymeric delivery material such as a polymer or copolymer that includes at least lactic acid, glycolic acid, propylene oxide or ethylene oxide. In a particular embodiment, the polymeric delivery system includes polylactide-co-glycolide with or without polyethylene glycol. For example, the hydrophobic drug may be delivered in a mixture of PLGA and PLGA-PEG or PEG. In another embodiment, the polymer includes a polyethylene oxide (PEO) or polypropylene oxide (PPO). In certain aspects, the polymer can be a random, diblock, triblock or multiblock copolymer (for example example, a polylactide, a polylactide-co-glycolide, polyglycolide or Pluronic). For injection into the eye, the polymer is pharmaceutically acceptable and typically biodegradable so that it does not have to be removed.

The decreased rate of release of the active material to the ocular compartment may result in decreased inflammation, which has been a significant side effect of ocular therapy to date.

It is also important that the decreased rate of release of the drug while maintaining efficacy over an extended time of up to 4, 5 or 6 months be achieved using a particle that is small enough for administration through a needle without causing significant damage or discomfort to the eye and not to give the illusion to the patient of black spots floating in the eye. This typically means the controlled release particle should be less than approximately 300, 250, 200, 150, 100, 50, 45, 40, 35, or 30 m, such as less than approximately 29, 28, 27, 26, 25, 24, 23, 22 21, or 20 m. In one aspect, the particles do not agglomerate in vivo to form larger particles, but instead in general maintain their administered size and decrease in size over time.

The hydrophobicity of the conjugated drug can be measured using a partition coefficient (P; such as Log P in octanol/water), or distribution coefficient (D; such as Log D in octanol/water) according to methods well known to those of skill in the art. Log P is typically used for compounds that are substantially un-ionized in water and Log D is typically used to evaluate compounds that ionize in water. In certain embodiments, the conjugated derivatized drug has a Log P or Log D of greater than approximately 2.5, 3, 3.5, 4, 4.5, 5, 5.5 or 6. In other embodiments, the conjugated derivatized drug has a Log P or Log D which is at least approximately 1, 1.5, 2, 2.5, 3, 3.5 or 4 Log P or Log D units, respectively, higher than the parent hydrophilic drug.

This invention includes an active compound of Formula I, Formula II, Formula II', Formula III, Formula IV, Formula V, Formula VI, Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, Formula XXIII, or a pharmaceutically acceptable salt or composition thereof. In one embodiment, an active compound or its salt or composition, as described herein, is used to treat a medical disorder which is glaucoma, a disorder mediated by carbonic anhydrase, a disorder or abnormality related to an increase in intraocular pressure (IOP), a disorder mediated by nitric oxide synthase (NOS), or a disorder requiring neuroprotection such as to regenerate/repair optic nerves. In another embodiment more generally, the disorder treated is allergic conjunctivitis, anterior uveitis, cataracts, dry or wet age-related macular degeneration (AMD) or diabetic retinopathy.

Compounds of Formula I and Formula II are prodrugs or derivatives of prostaglandins.

In one embodiment compounds of Formula I and Formula II are hydrophobic prodrugs of prostaglandins.

Compounds of Formula III, Formula IV, Formula V, and Formula VI are prodrugs of the carbonic anhydrase inhibitors Brinzolamide, Dorzolamide, Acetazolamide, and Methazolamide respectively.

Compounds of Formula VII are single agent prodrug conjugates of a prostaglandin and a carbonic anhydrase inhibitor allowing release of both compounds in the eye. In one embodiment both compounds are released concurrently.

In one embodiment compounds of Formula VIII are single agent prodrug conjugates of a prostaglandin and a Sunitinib derivative allowing release of both compounds in the eye. In one embodiment both compounds are released concurrently.

In an alternative embodiment compounds of Formula VIII are single agent prodrug conjugates of a carbonic anhydrase inhibitor and a Sunitinib derivative allowing release of both compounds in the eye. In one embodiment both compounds are released concurrently.

Compounds of Formula IX, Formula X, Formula XI, and Formula XII are prodrugs of the dual leucine zipper kinase inhibitors Crizotinib, KW2449, piperidino analogs, and a Tozasertib derivative respectively.

Compounds of Formula XIV are prodrugs or derivatives of Sunitinib analgoues (Sunitinib with a heteroatom or carboxy instead of a fluoro group).

In one embodiment compounds of Formula XIV are hydrophobic prodrugs of Sunitinib derivatives.

Compounds of Formula XV are single agent prodrug conjugates of a Sunitinib derivative and a carbonic anhydrase inhibitor allowing release of both compounds in the eye. In one embodiment both compounds are released concurrently.

Compounds of Formula XVI are prodrugs or derivatives of Timolol.

In one embodiment compounds of Formula XVI are hydrophobic prodrugs of Timolol.

In one embodiment compounds of Formula XVII are single agent prodrug conjugates of Timolol and a carbonic anhydrase inhibitor allowing release of both compounds in the eye. In one embodiment both compounds are released concurrently.

In an alternative embodiment compounds of Formula XVII are single agent prodrug conjugates of Timolol and a prostaglandin allowing release of both compounds in the eye. In one embodiment both compounds are released concurrently.

These compounds can be used to treat ocular disorders in a host in need thereof, typically a human. In one embodiment, a method for the treatment of such a disorder is provided that includes the administration of an effective amount of a compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII or a pharmaceutically acceptable salt thereof, optionally in a pharmaceutically acceptable carrier, including a polymeric carrier, as described in more detail below.

Another embodiment is provided that includes the administration of an effective amount of an active compound or a pharmaceutically acceptable salt thereof, optionally in a pharmaceutically acceptable carrier, including a polymeric carrier, to a host to treat an ocular or other disorder that can benefit from topical or local delivery. The therapy can be delivery to the anterior or posterior chamber of the eye. In specific aspects, the active compound is administered to treat a disorder of the cornea, conjunctiva, aqueous humor, iris, ciliary body, lens sclera, choroid, retinal pigment epithelium, neural retina, optic nerve or vitreous humor.

Any of the compounds described herein (Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII) can be administered to the eye in a composition as described further herein in any desired form of administration, including via intravitreal, intrastromal, intracameral, sub-tenon, sub-retinal, retro-bulbar, peribulbar, suprachoroidal, choroidal, subchoroidal, conjunctival, subconjunctival, episcleral, posterior juxtascleral, circumcorneal, and tear duct injections, or through a mucus, mucin, or a mucosal barrier, in an immediate or controlled release fashion.

In certain embodiments, the conjugated active drug is delivered in a biodegradable microparticle or nanoparticle that has at least approximately 5, 7.5, 10, 12.5, 15, 20, 25 or 30% by weight conjugated active drug. In some embodiments, the biodegradable microparticle degrades over a period of time of at least approximately 3 months, 4 months, 5 months or 6 months or more. In some embodiments, the loaded microparticles are administered via subconjunctival or subchoroidal injection.

In all of the polymer moieties described in this specification, where the structures are depicted as block copolymers (for example, blocks of "x" followed by blocks of "y"), it is intended that the polymer can be a random or alternating copolymer (for example, "x" and "y" are either randomly distributed or alternate).

Non-limiting examples of Formula I and Formula II include at least hydrophobic prodrugs or derivatives of the following prostaglandins:

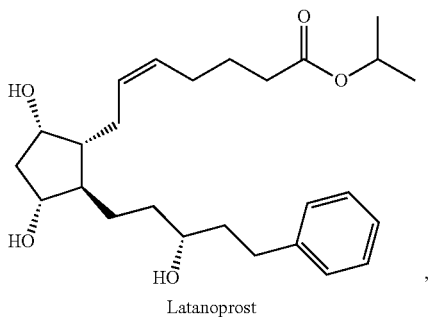
Latanoprost

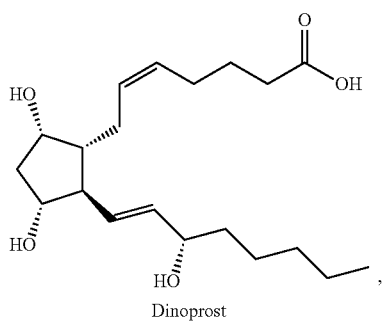
Dinoprost

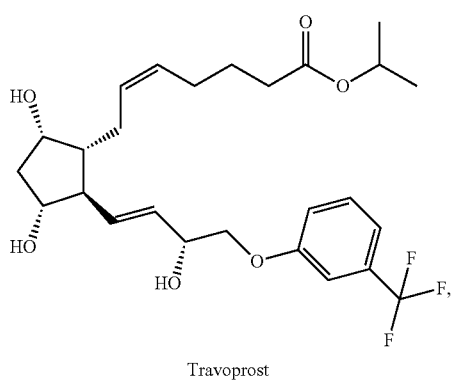
Travoprost

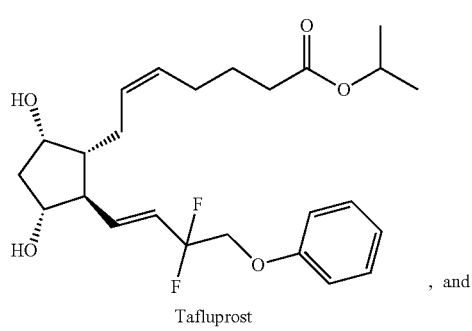
Tafluprost

, and

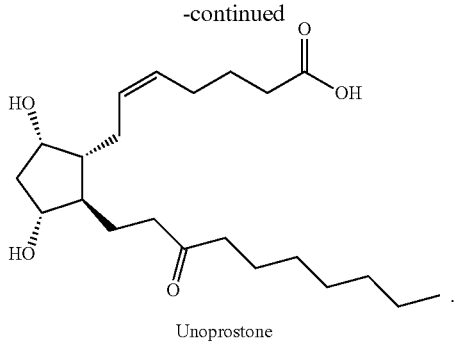
Unoprostone

Non-limiting examples of Formula III, Formula IV, Formula V, and Formula VI are prodrugs of Brinzolamide, Dorzolamide, Acetazolamide, and Methazolamide respectively.

The disclosure provides a prostaglandin prodrug of Formula I:

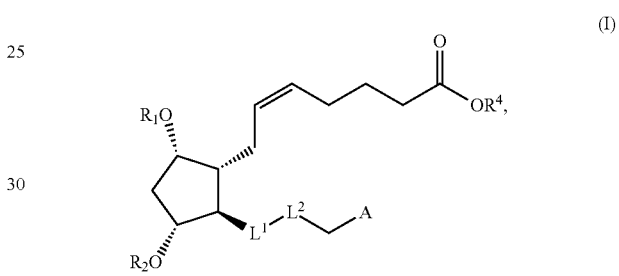

(I)

or a pharmaceutically acceptable composition, salt, or isotopic derivative thereof.

$L^1$ is selected from:

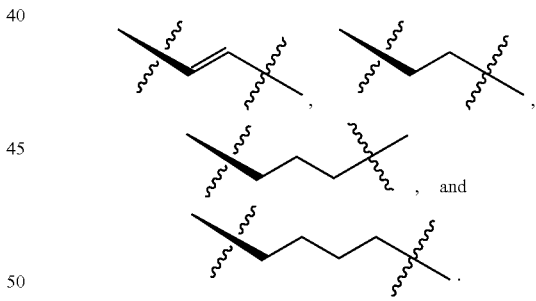

$L^2$ is selected from:

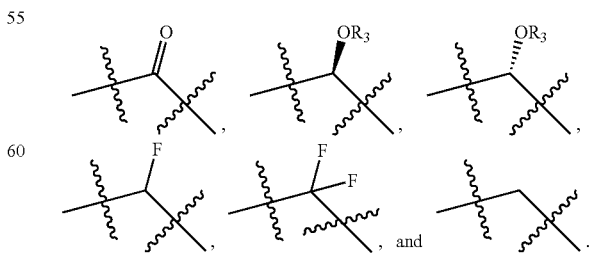

A is selected from: H, alkyl, cycloalkyl, cycloalkylalkyl, heterocycle, heterocycloalkyl, aryl, arylalkyl, heteroaryl, heteroarylalkyl, aryloxy, and alkyloxy wherein each group can be optionally substituted with another desired substituent group which is pharmaceutically acceptable and sufficiently stable under the conditions of use, for example selected from $R^5$.

Non-limiting examples of Formula I include:

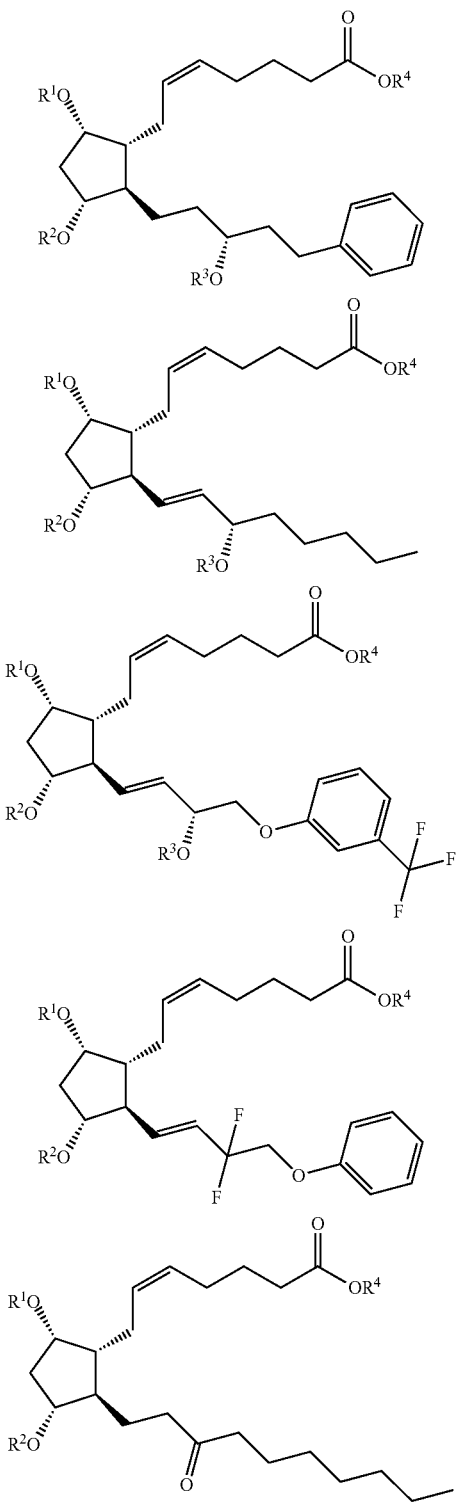

$R^1$, $R^2$, and $R^3$ are selected from: —C(O)$R^4$, C(O)A, and hydrogen wherein either $R^1$ or $R^2$ cannot be hydrogen and wherein $R^1$, $R^2$, and $R^3$ can be further optionally substituted with $R^5$.

$R^4$ is selected from:

(i) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl;

(ii) an unsaturated fatty acid residue including but not limited to the carbon chains from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alpha-linolenic acid (—$(CH_2)_8(CHCHCH_2)_3CH_3$)), stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid, and wherein, if desired, each of which can be substituted with $R^5$.

Non-limiting examples of $R^4$ include:

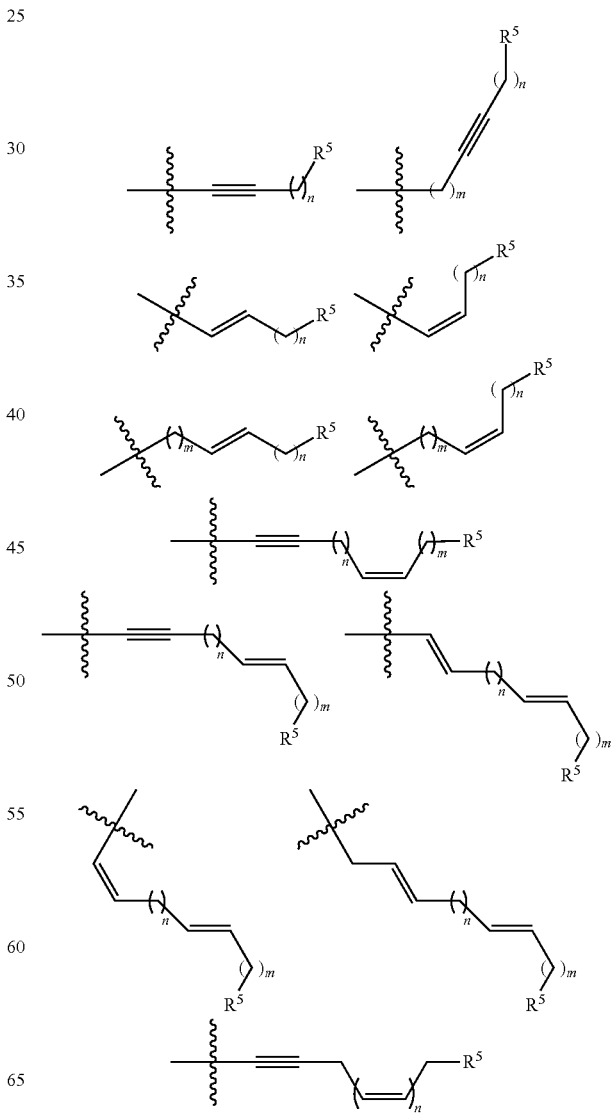

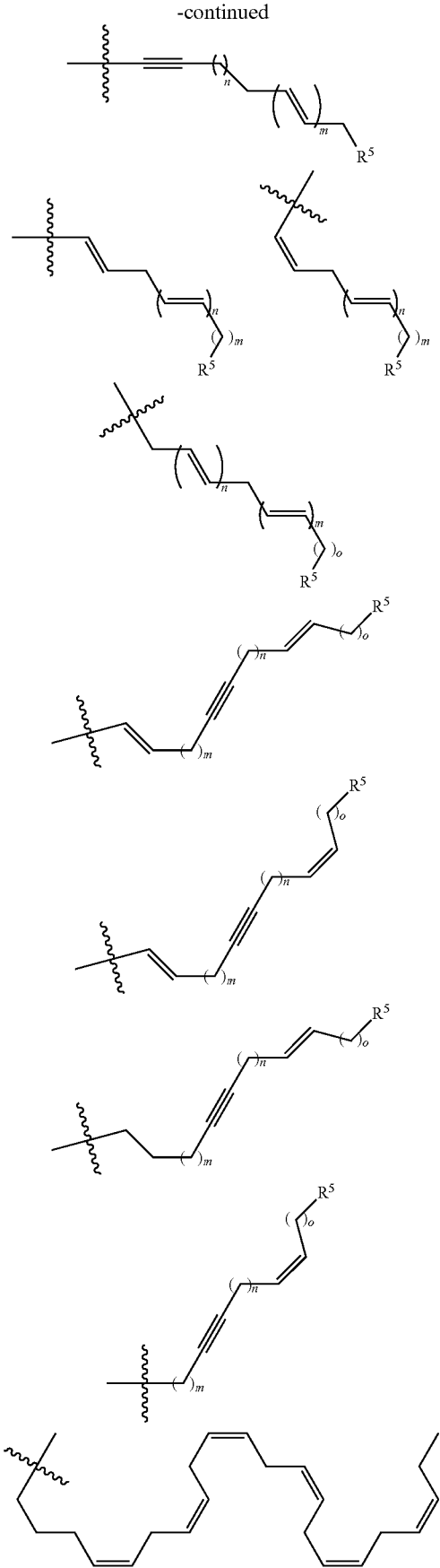

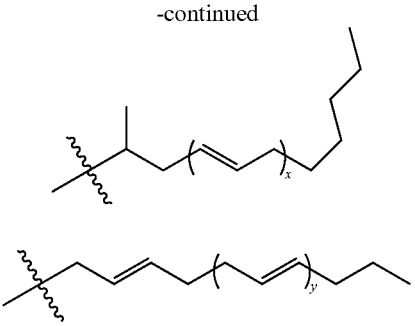

wherein n, m, and o can be any integer between 0 and 29 (1, 2, 3, 4, 5, 6, 7, 8, 9, 10, 11, 12, 13, 14, 15, 16, 17, 18, 19, 20, 21, 22, 23, 24, 25, 26, 27, 28 or 29) wherein n+m+o is 7 to 30 carbons and wherein x and y can be any integer between 1 and 30 (1, 2, 3, 4, 5, 6, 7, 8, 9, 10, 11, 12, 13, 14, 15, 16, 17, 18, 19, 20, 21, 22, 23, 24, 25, 26, 27, 28, 29 or 30). In one embodiment x and y are independently selected from the following ranges: 1 to 5, 6 to 11, 12 to 17, 18 to 23, and 24 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30).

In one embodiment, —$C_{10}$-$C_{30}$ as used in the definition of $R^4$ is —$C_{10}$-$C_{28}$, —$C_{10}$-$C_{26}$, —$C_{10}$-$C_{24}$, —$C_{10}$-$C_{22}$, —$C_{10}$-$C_{20}$, —$C_{10}$-$C_{18}$, —$C_{10}$-$C_{16}$, —$C_{10}$-$C_{14}$, or —$C_{10}$-$C_{12}$.

$R^5$ is selected from: halogen, hydroxyl, cyano, mercapto, amino, alkyl, alkoxy, alkenyl, alkynyl, cycloalkyl, cycloalkylalkyl, heterocyclyl, heterocycloalkyl, aryl, arylalkyl, heteroaryl, heteroarylalkyl, aryloxy, —S(O)$_2$alkyl, —S(O)alkyl, —P(O)(Oalkyl)$_2$, B(OH)$_2$, —Si(CH$_3$)$_3$, —COOH, —COOalkyl, and —CONH$_2$, each of which except halogen, cyano, and —Si(CH$_3$)$_3$ may be optionally substituted, for example with halogen, alkyl, aryl, heterocycle or heteroaryl if desired and if the resulting compound achieves the desired purpose, wherein the group cannot be substituted with itself, for example alkyl would not be substituted with alkyl.

While various structures are depicted as block copolymers (i.e, blocks of "x" followed by blocks of "y") in some embodiments, the polymer can be a random or alternating copolymer ("x" and "y" are either randomly distributed or alternate).

The disclosure also provides a compound of Formula II:

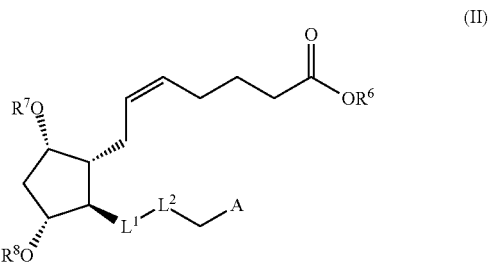

(II)

or a pharmaceutically acceptable composition, salt, or isotopic derivative thereof.

Non-limiting examples of Formula II include:

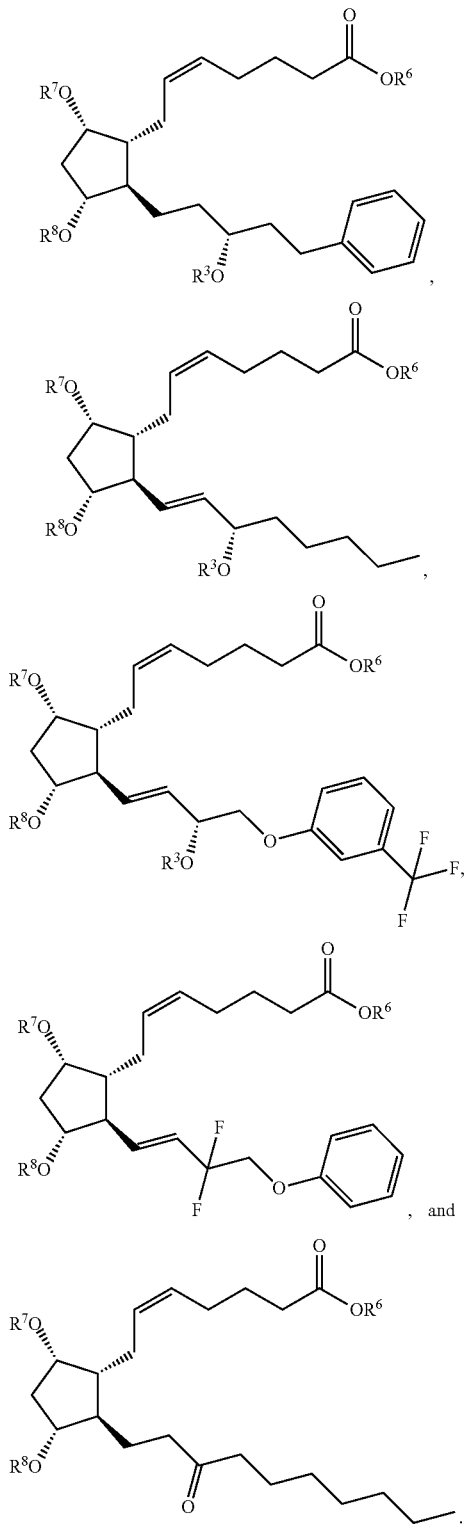

$R^6$ is selected from:

(i) polyethylene glycol, polypropylene glycol, polypropylene oxide, polylactic acid, and poly(lactic-co-glycolic acid) including:

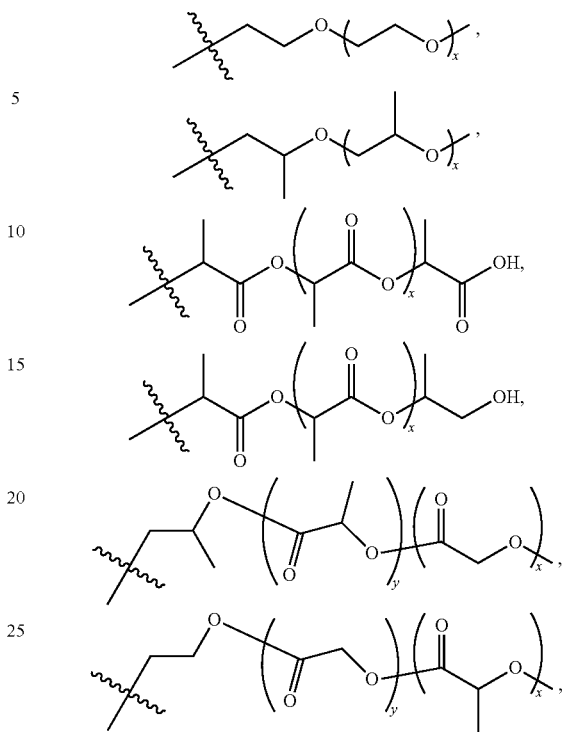

or polyglycolic acid, or a polyester, polyamide, or other biodegradable polymer, each of which can be capped to complete the terminal valence. In some embodiments, the compound can be capped with hydrogen, or can be capped to create a terminal ester or ether. For example, the moiety can be capped with a terminal hydroxyl or carboxy which can be further derivatized to an ether or ester;

(ii) —$C_{10}$-$C_{30}$alkylR, —$C_{10}$-$C_{30}$alkenylR, —$C_{10}$-$C_{30}$alkynylR, —$C_{10}$-$C_{30}$alkenylalkynylR$^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl;

(iii) an unsaturated fatty acid residue including but not limited the carbon fragment taken from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alpha-linolenic acid (—$(CH_2)_8(CHCHCH_2)_3CH_3$)) stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid or mead acid;

(iv) alkyl, cycloalkyl, cycloalkylalkyl, heterocycle, heterocycloalkyl, arylalkyl, heteroarylalkyl;

wherein $R^6$ can only be selected from (ii), (iii), and (iv) above if at least one of $R^7$ and $R^8$, is selected to be $R^{50}$.

In one embodiment, —$C_{10}$-$C_{30}$ as used in the definition of $R^6$ is —$C_{10}$-$C_{28}$, —$C_{10}$-$C_{26}$, —$C_{10}$-$C_{24}$, —$C_{10}$-$C_{22}$, —$C_{10}$-$C_{20}$, —$C_{10}$-$C_{18}$, —$C_{10}$-$C_{16}$, —$C_{10}$-$C_{14}$, or —$C_{10}$-$C_{12}$.

$R^7$ and $R^8$, are independently selected from: —C(O)$R^4$, —C(O)A, hydrogen, and $R^{50}$.

$R^{50}$ is selected from carbonyl derivatives of polyethylene glycol, polypropylene glycol, polypropylene oxide, polylactic acid, and poly(lactic-co-glycolic acid) including:

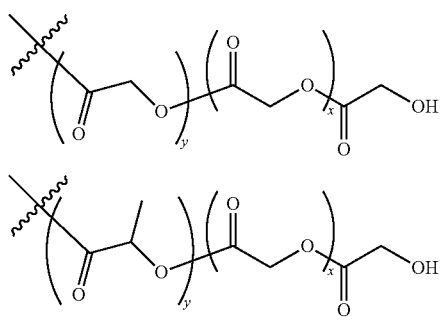

-continued

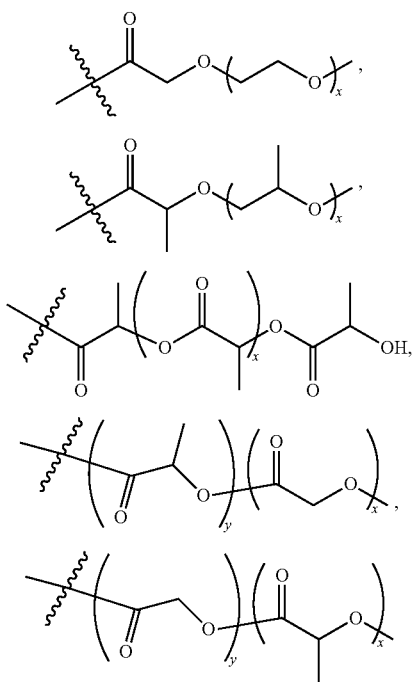


wherein x and y are as defined above.

Additional non-limiting examples of $R^{50}$ include:

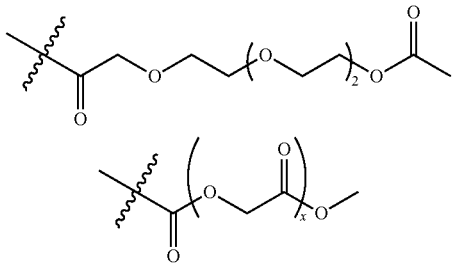

or polyglycolic acid, or a polyester, polyamide, or other biodegradable polymer, each of which can be capped to complete the terminal valence. In some embodiments, the compound can be capped with hydrogen, or can be capped to create a terminal ester or ether. For example, the moiety can be capped with a terminal hydroxyl or carboxy which can be further derivatized to an ether or ester.

Non-limiting examples of $R^{50}$ include:

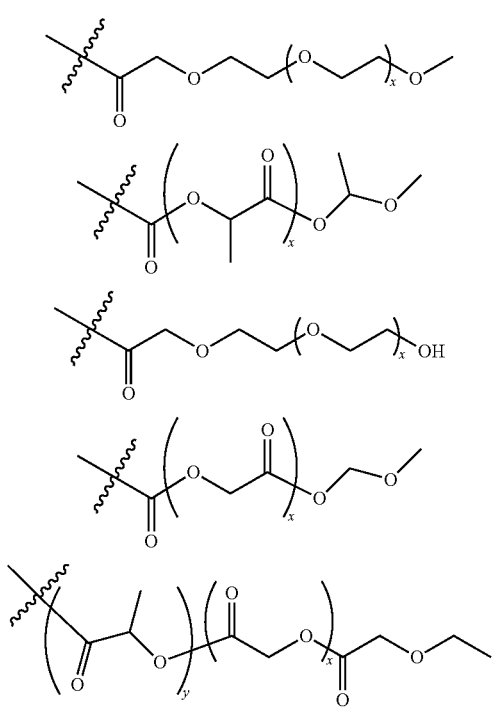


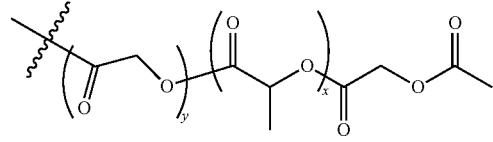

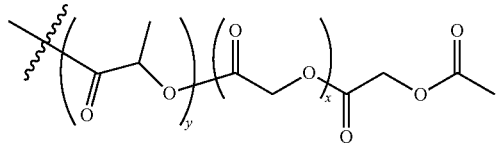

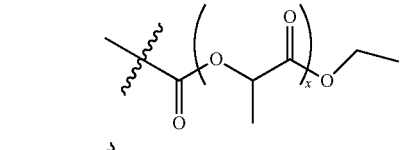

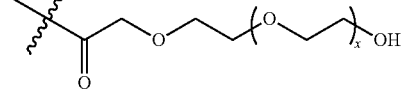

-continued

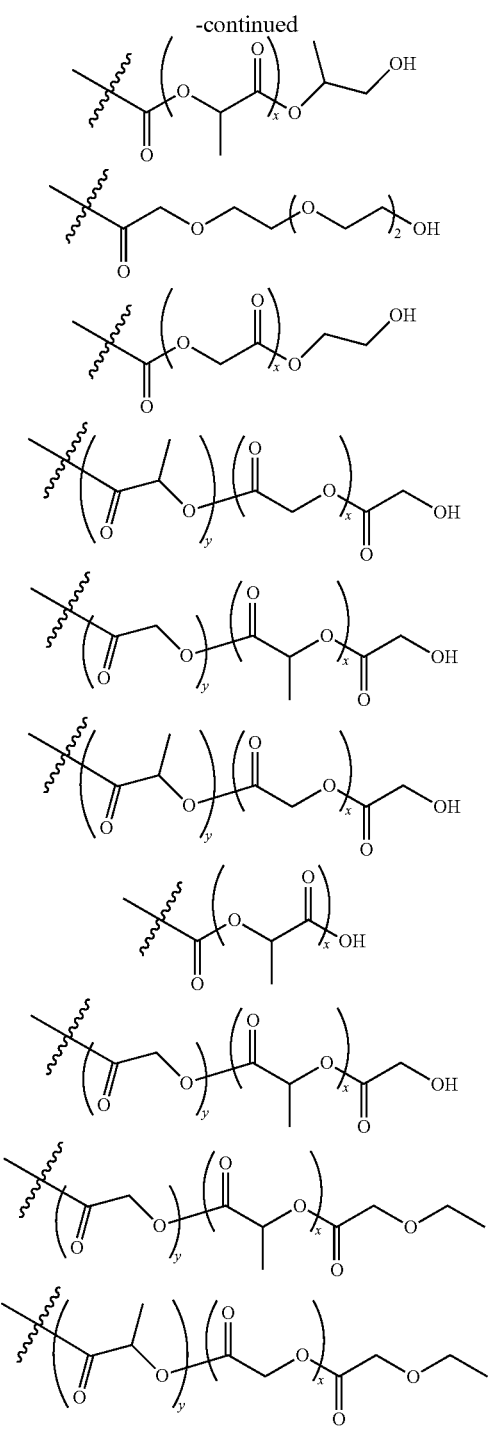

wherein x and y are as defined above.

In one embodiment $R^6$ is isopropyl.

In one embodiment a compound of Formula I or Formula II is hydrolysable by an enzyme in vivo, such as an esterase.

In another embodiment a compound of Formula I or Formula II or a composition thereof is for use in the cosmetic enhancement of eyelash hair or eyebrow hair.

In another embodiment a compound of Formula I or Formula II or a composition thereof is used for the growth of eyelash or eyebrow hair.

The disclosure also provides a compound of Formula II':

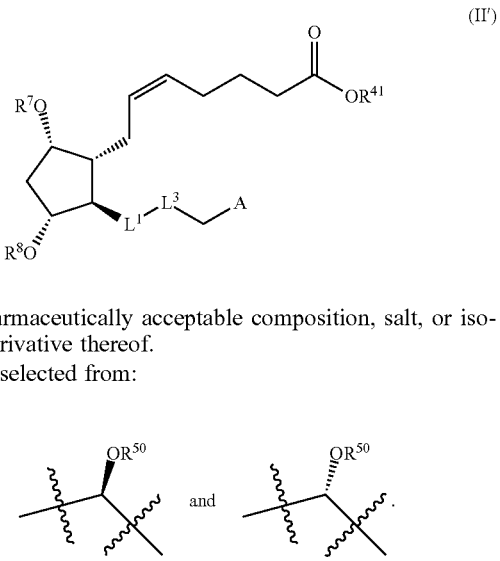

(II')

or a pharmaceutically acceptable composition, salt, or isotopic derivative thereof.

$L^3$ is selected from:

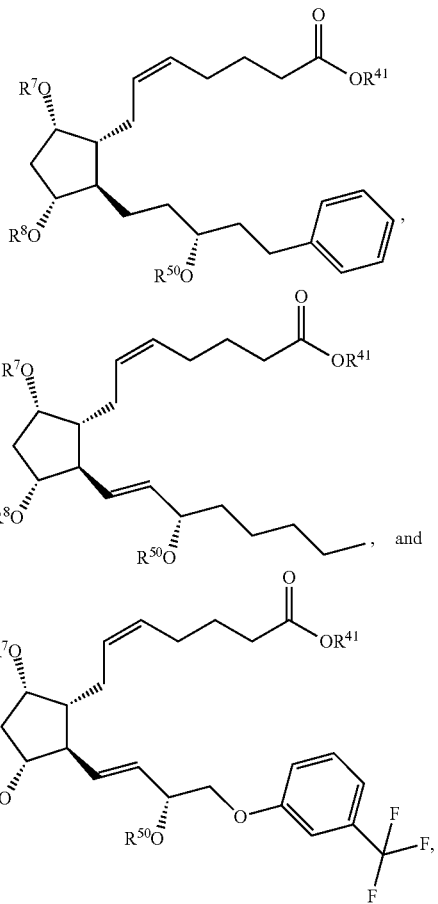

Non-limiting examples of Formula II' include:

$R^{41}$ is selected from:
(i) polyethylene glycol, polypropylene glycol, polypropylene oxide, polylactic acid, and poly(lactic-co-glycolic acid),

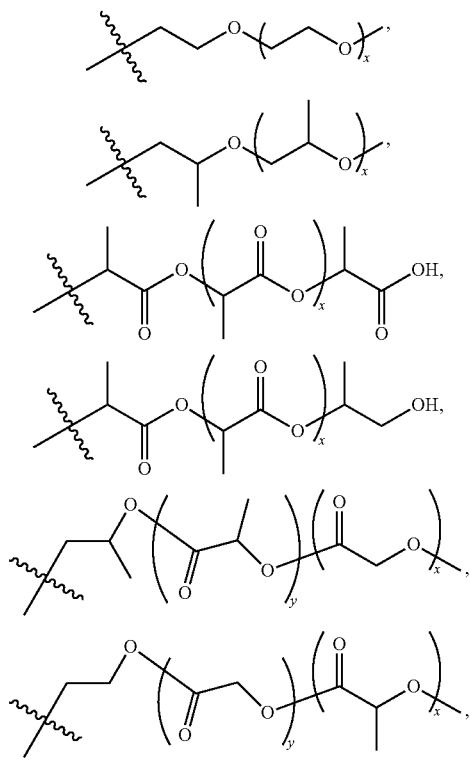

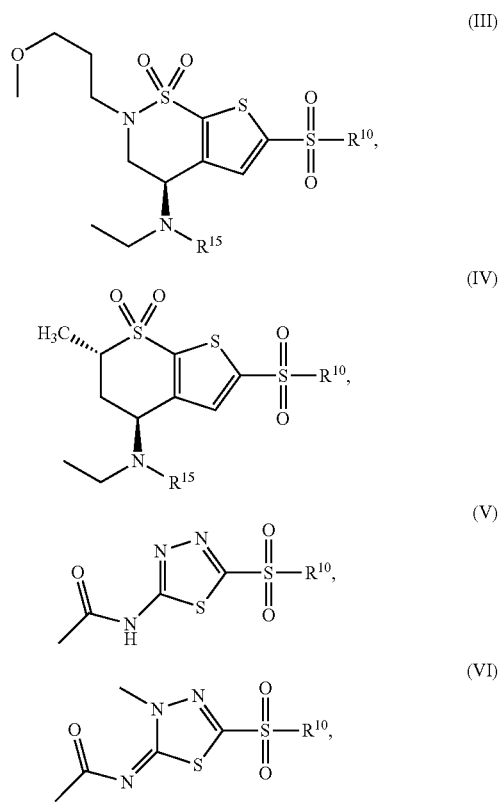

polyglycolic acid, a polyester, a polyamide, or other biodegradable polymer, wherein in some embodiments a terminal hydroxy or carboxy group can be substituted to create an ether or ester;

(ii) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl (iii) an unsaturated fatty acid residue including but not limited the carbon fragment taken from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alpha-linolenic acid (—$(CH_2)_8(CHCHCH_2)_3CH_3$)) stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid or mead acid;

(iv) alkyl, cycloalkyl, cycloalkylalkyl, heterocycle, heterocycloalkyl, arylalkyl, heteroarylalkyl;

In one embodiment, —$C_{10}$-$C_{30}$ as used in the definition of $R^{41}$ is —$C_{12}$-$C_{28}$, —$C_{12}$-$C_{26}$, —$C_{12}$-$C_{24}$, —$C_{14}$-$C_{22}$, —$C_{14}$-$C_{20}$, —$C_{14}$-$C_{18}$, —$C_{14}$-$C_{16}$, or —$C_{12}$-$C_{14}$.

In one embodiment the disclosure provides a prodrug of a carbonic anhydrase inhibitor for ocular therapy, which can be released from a therapeutic, including a polymeric, delivery system while maintaining efficacy over an extended time such as up to 4, 5 or 6 months.

The disclosure also provides prodrugs of Formula III, Formula IV, Formula V and Formula VI:

or a pharmaceutically acceptable composition, salt, or isotopic derivative thereof.

$R^{10}$ is selected from:

(i) N=$C_4$-$C_{30}$alkenyl$R^5$, —N=$C_4$-$C_{30}$alkynyl$R^5$, —N=$C_4$-$C_{30}$alkenylalkynyl$R^5$, —N=$C_1$-$C_{30}$alkyl$R^5$, —N=$C_4$-$C_{30}$alkenyl, —N=$C_4$-$C_{30}$alkynyl, —N=$C_4$-$C_{30}$alkenylalkynyl, —N=$C_1$-$C_{30}$alkyl;

(ii) an unsaturated fatty acid residue including but not limited to derivatives of linoleic acid (—N=CH$(CH_2)_7$$(CH)_2CH_2(CH)_2(CH_2)_4CH_3$), docosahexaenoic acid (—N=CH$(CH_2)_2(CHCHCH_2)_6CH_3$), eicosapentaenoic acid (—N=CH$(CH_2)_3(CHCHCH_2)_5CH_3$), alpha-linolenic acid (—N=CH$(CH_2)_7(CHCHCH_2)_3CH_3$), stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid or mead acid, each of which can be further substituted with $R^5$ (including for example a second $R^5$) if valence permits, a stable compound is formed, and the resulting compound is pharmaceutically acceptable;

(iii) polypropylene glycol, polypropylene oxide, polylactic acid, or poly(lactic-co-glycolic acid) including:

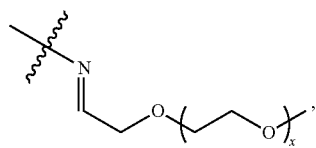

-continued

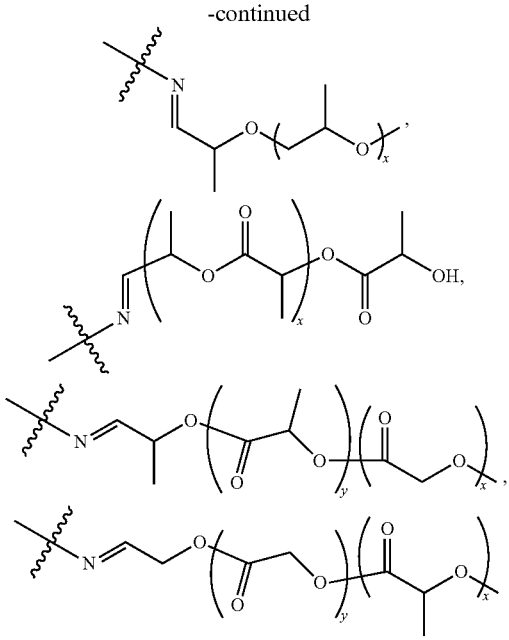

or polyglycolic acid, or a polyester, polyamide, or other biodegradable polymer, each of which can be capped to complete the terminal valence. In some embodiments, the compound can be capped with hydrogen, or can be capped to create a terminal ester or ether. For example, the moiety can be capped with a terminal hydroxyl or carboxy which can be further derivatized to an ether or ester. And wherein each of which can be further substituted with $R^5$ if valence permits, a stable compound is formed, and the resulting compound is pharmaceutically acceptable; and wherein in some embodiments a terminal hydroxy or carboxy group can be substituted to create an ether or ester;

(iv) $NH_2$ wherein $R^{15}$ is $R^{16}$;

In an alternative embodiment, $R^{10}$ is
—NHC(O)$C_{1-20}$alkyl, —NHC(O)$C_{1-20}$alkenyl, —NHC(O)$C_{1-20}$alkynyl, —NHC(O)($C_{1-20}$alkyl with at least one $R^5$ substituent on the alkyl chain), —NHC(O)($C_{1-20}$alkenyl, with at least one $R^5$ substituent on the alkenyl chain) —NHC(O)($C_{1-20}$alkynyl, with at least one $R^5$ substituent on the alkynyl chain), —NH(lactic acid)$_{2-20}$C(O)$C_{1-20}$alkyl, —NH(lactic acid)$_{2-10}$C(O)$C_{1-20}$alkyl, —NH(lactic acid)$_{4-20}$C(O)$C_{1-20}$alkyl, —NH(lactic acid)$_{2-20}$C(O)$C_{1-10}$alkyl, —NH(lactic acid)$_{2-20}$C(O)$C_{4-20}$alkyl, —NH(lactic acid)$_{2-20}$C(O)OH, —NH(lactic acid)$_{2-10}$C(O)OH, —NH(lactic acid)$_{4-20}$C(O)OH, —NH(lactic acid)$_{2-10}$C(O)OH, —NH(lactic acid)$_{4-10}$C(O)OH, —NH(lactide-co-glycolide)$_{2-10}$C(O)$_{1-20}$alkyl, —NH(lactide-co-glycolide)$_{4-10}$C(O)$C_{1-20}$alkyl, —NH(lactide-co-glycolide)$_{2-10}$C(O)$C_{1-10}$alkyl, —NH(lactide-co-glycolide)$_{2-10}$C(O)$C_{4-20}$alkyl, —NH(glycolic acid)$_{2-10}$C(O)$C_{1-10}$alkyl, —NH(glycolic acid)$_{4-10}$C(O)$C_{1-10}$alkyl, —NH(lactic acid)$_{4-10}$C(O)$C_{1-10}$alkyl, —NH(lactic acid)$_{2-10}$C(O)$C_{1-10}$alkyl, NH(lactic acid)$_{2-10}$C(O)$C_{4-10}$alkyl, —NH(lactic acid)$_{2-10}$C(O)$C_{4-10}$alkyl, or —NH(lactic acid)$_{2-10}$C(O)$C_{4-10}$alkyl.

$R^{15}$ is selected from $R^{16}$ and $R^{17}$.

$R^{16}$ is selected from:
(i) —C(O)$C_3$-$C_{30}$alkylR$^5$, —C(O)$C_3$-$C_{30}$alkenylR$^5$, —C(O)$C_3$-$C_{30}$alkynylR$^5$, —C(O)$C_3$-$C_{30}$alkenylalkynylR$^5$, —C(O)$C_3$-$C_{30}$alkyl, —C(O)$C_3$-$C_{30}$alkenyl, —C(O)$C_3$-$C_{30}$alkynyl, and —C(O)$C_3$-$C_{30}$alkenylalkynyl;

(ii) an unsaturated fatty acid residue including but not limited the carbonyl fragment taken from linoleic acid (—C(O)(CH$_2$)$_7$(CH)$_2$CH$_2$(CH)$_2$(CH$_2$)$_4$CH$_3$)), docosahexaenoic acid (—C(O)(CH$_2$)$_2$(CHCHCH$_2$)$_6$CH$_3$)), eicosapentaenoic acid (—C(O)(CH$_2$)$_3$(CHCHCH$_2$)$_5$CH$_3$)), alpha-linolenic acid (—C(O)(CH$_2$)$_7$(CHCHCH$_2$)$_3$CH$_3$)) stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid;

(iii) polyethylene glycol, polypropylene glycol, polypropylene oxide, polylactic acid, and poly(lactic-co-glycolic acid) including:

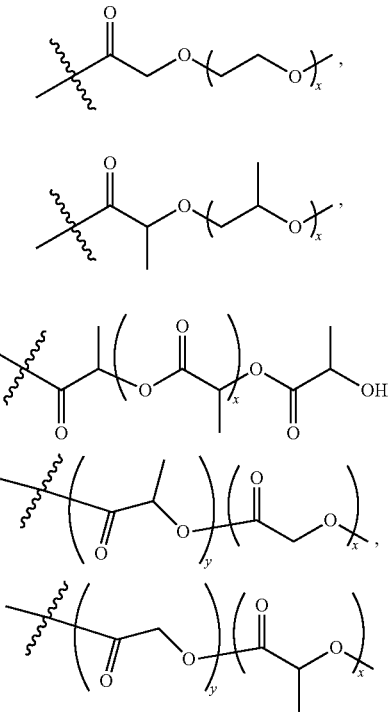

or polyglycolic acid, or a polyester, polyamide, or other biodegradable polymer, each of which can be capped to complete the terminal valence. In some embodiments, the compound can be capped with hydrogen, or can be capped to create a terminal ester or ether. For example, the moiety can be capped with a terminal hydroxyl or carboxy which can be further derivatized to an ether or ester.

$R^{17}$ is selected from: H and —C(O)A.

In one embodiment, —$C_3$-$C_{30}$ as used in the definition of $R^{10}$ is —$C_3$-$C_{28}$, —$C_3$-$C_{26}$, —$C_3$-$C_{24}$, —$C_3$-$C_{22}$, —$C_3$-$C_{20}$, —$C_3$-$C_{18}$, —$C_3$-$C_{16}$, —$C_3$-$C_{14}$, —$C_3$-$C_{12}$, —$C_5$-$C_{12}$, —$C_7$-$C_{12}$, or —$C_7$-$C_{10}$.

In one embodiment $R^{10}$ is selected from:
(i) —N=CH—$C_3$-$C_{30}$alkenylR$^5$, —N=CH—$C_3$-$C_{30}$alkynylR$^5$, —N=CH—$C_3$-$C_{30}$alkenylalkynylR$^5$, —N=$C_1$-$C_{30}$alkylR$^5$, —N=CH—$C_3$-$C_{30}$alkenyl, —N=CH—$C_3$-$C_{30}$alkynyl, —N=CH—$C_3$-$C_{30}$alkenylalkynyl, —N=$C_1$-$C_{30}$alkyl;

Non-limiting examples of $R^{10}$ include:
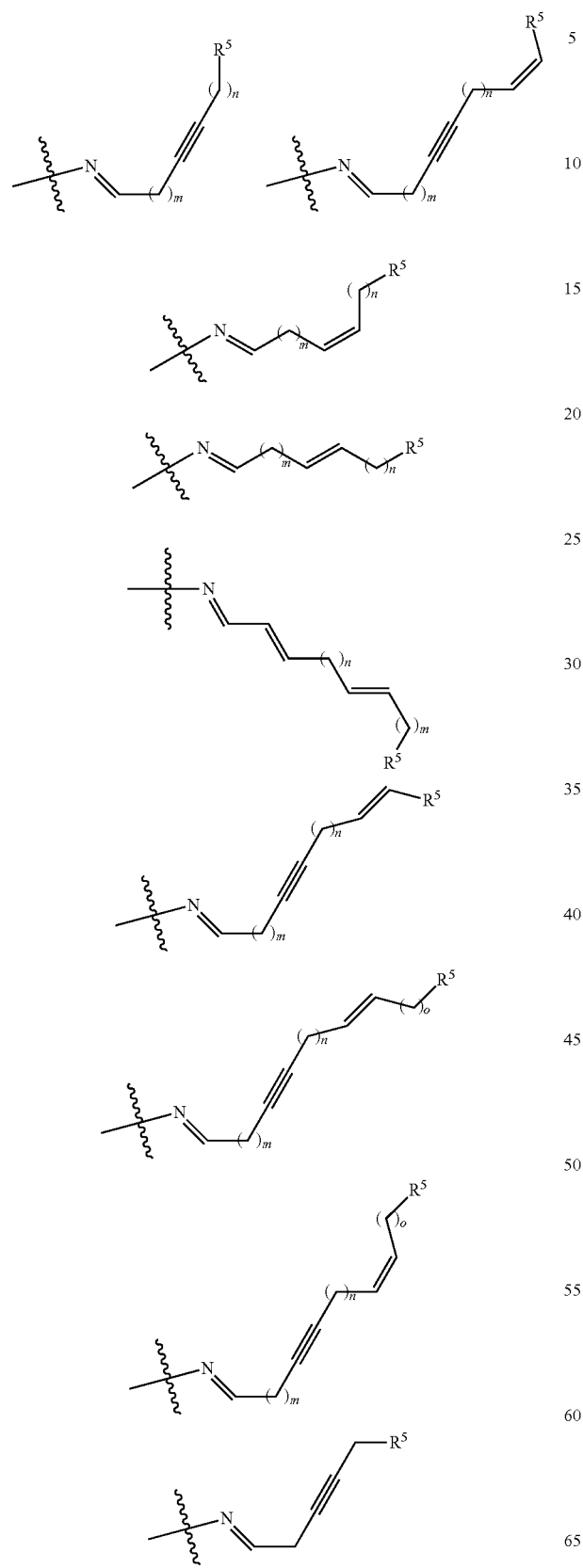
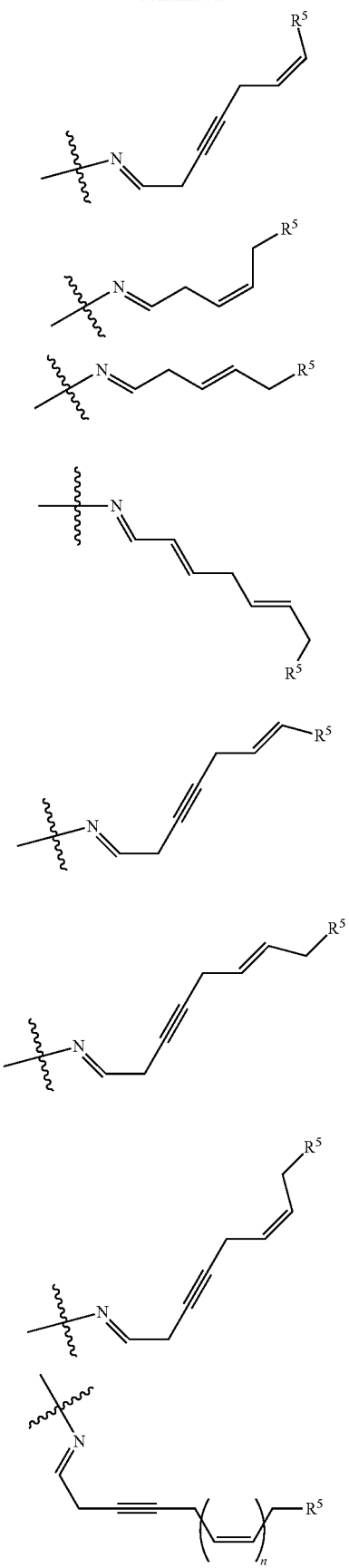

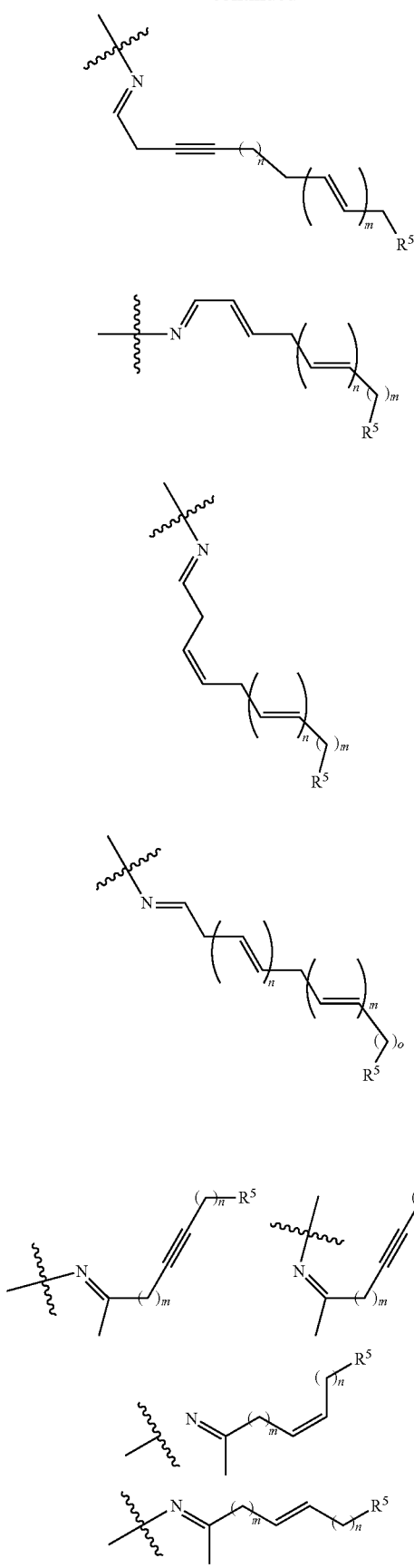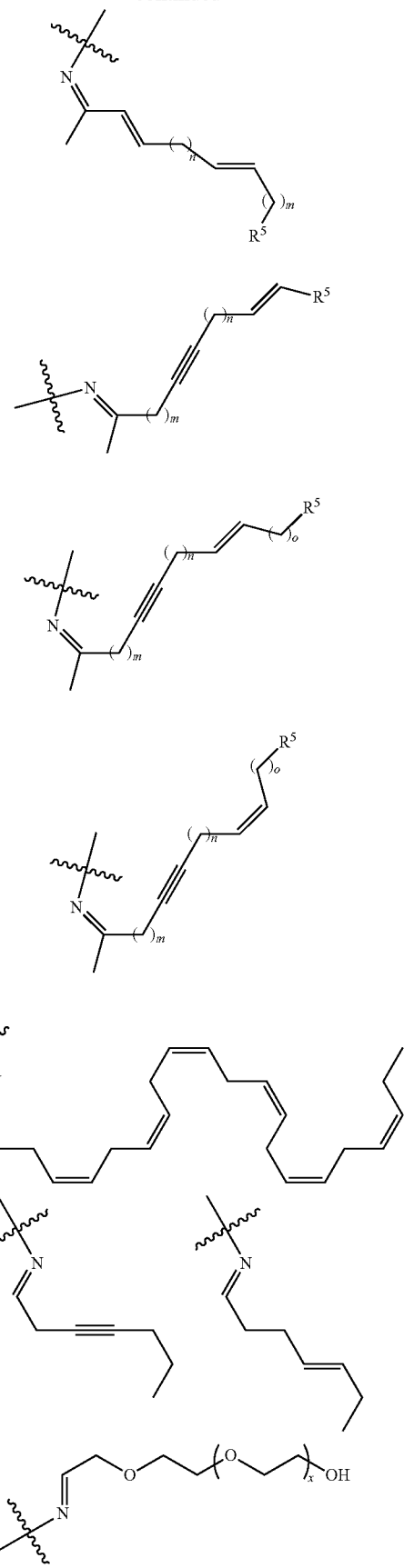

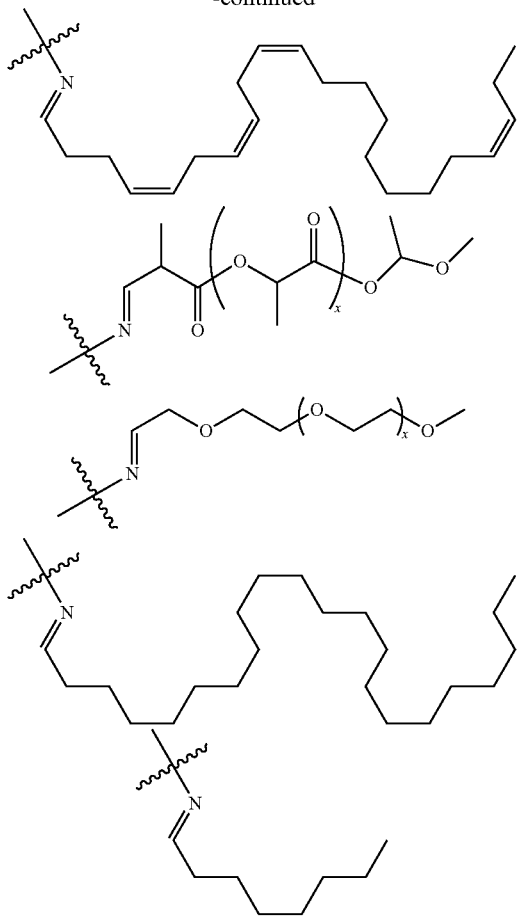

wherein n, m, o, x and y are as defined above.

The disclosure also provides prodrugs of Formula III', Formula IV', Formula V' and Formula VI':

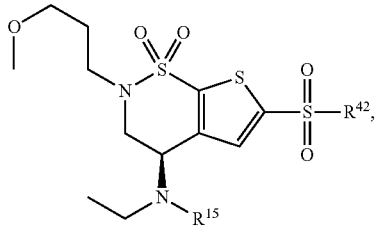
(III')

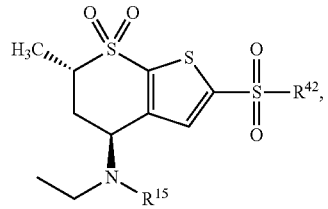
(IV')

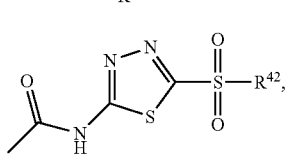
(V')

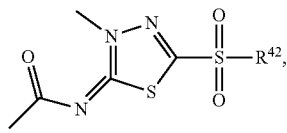
(VI')

or a pharmaceutically acceptable composition, salt, or isotopic derivative thereof.

$R^{42}$ is selected from:

(i) $-N=(CH-C_3-C_3\text{alkenyl}R$, $-N=CH-C_3-C_3\text{alkynyl}R^5$, $-N=CH-C_3-C_{30}\text{alkenylalkynyl}R^5$, $-N=C_1-C_{30}\text{alkyl}R^5$, $-N=CH-C_3-C_{30}\text{alkenyl}$, $-N=CH-C_3-C_{30}\text{alkynyl}$, $-N=CH-C_3-C_{30}\text{alkenylalkynyl}$, $-N=C_1-C_{30}\text{alkyl}$, $-NHC_3-C_{30}\text{alkenyl}R^5$, $-NH-C_3-C_{30}\text{alkynyl}R^5$, $-NH-C_5-C_{30}\text{alkenylalkynyl}R^5$, $-NHC_0-C_{30}\text{alkyl}R^5$, $-NHC_3-C_{30}\text{alkenyl}R^{16}$, $-NH-C_3-C_{30}\text{alkynyl}R^{16}$, $-NH-C_5-C_{30}\text{alkenylalkynyl}R^{16}$, $-NHC_0-C_{30}\text{alkyl}R^{16}$, (ii) An imine, amine or amide linked unsaturated fatty acid residue including but not limited to derivatives of linoleic acid ($-N=CH(CH_2)_7(CH)_2CH_2(CH)_2(CH_2)_4CH_3$—$NHCH_2(CH_2)_7(CH)_2CH_2(CH)_2(CH_2)_4CH_3$, or $NHC(O)(CH_2)_7(CH)_2CH_2(CH)_2(CH_2)_4CH_3$), docosahexaenoic acid ($-N=CH(CH_2)_2(CHCHCH_2)_6CH_3$—$NH(CH_2)_3(CHCHCH_2)_6CH_3$, $NHC(O)(CH_2)_2(CHCHCH_2)_6CH_3$), eicosapentaenoic acid ($-N=CH(CH_2)_3(CHCHCH_2)_5CH_3$, $-NH(CH_2)_4(CHCHCH_2)_5CH_3$, or $NHC(O)(CH_2)_3(CHCHCH_2)_5CH_3$), alpha-linolenic acid ($-N=CH(CH_2)_7(CHCHCH_2)_3CH_3$, $-NH(CH_2)_4(CHCHCH_2)_5CH_3$, or $NHC(O)(CH_2)_3(CHCHCH_2)_5CH_3$), stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid or mead acid, each of which can be further substituted with $R^5$ (including for example a second $R^5$) if valence permits, a stable compound is formed, and the resulting compound is pharmaceutically acceptable;

(iii) An imine, amine or amide linked polypropylene glycol, an imine, amine or amide linked polypropylene oxide, an imine, amine or amide linked polylactic acid, or an imine, amine or amide linked poly(lactic-co-glycolic acid),

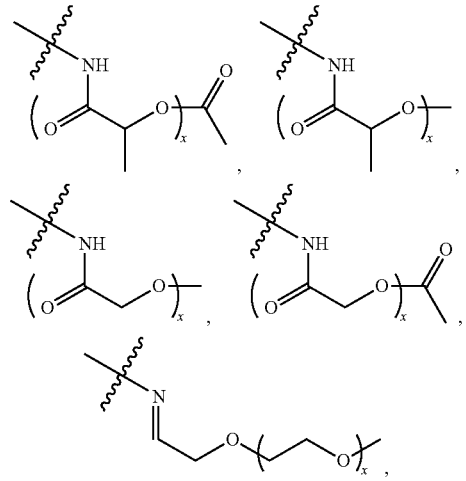

-continued

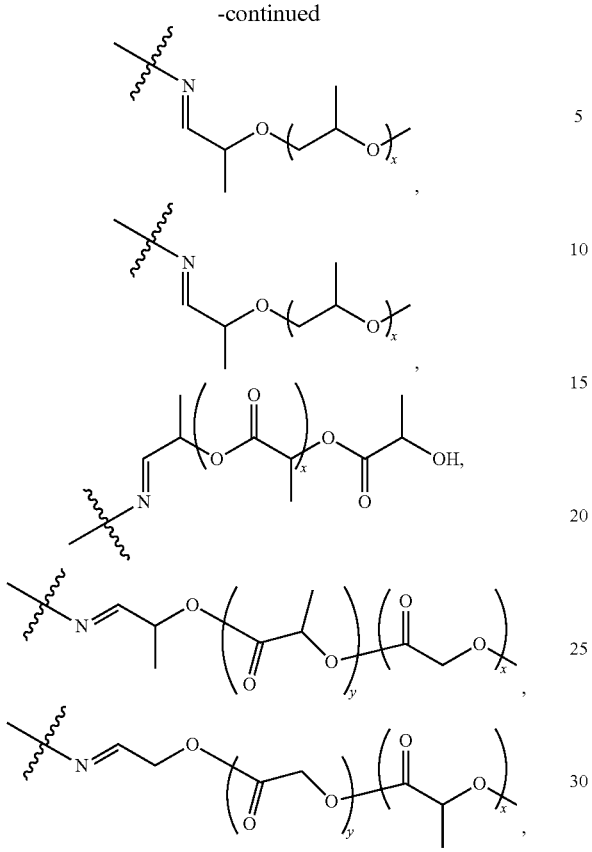

imine, amine or amide linked polyglycolic acid, a polyester, a polyamide, or other biodegradable polymer, each of which can be further substituted with $R^5$ if valence permits, a stable compound is formed, and the resulting compound is pharmaceutically acceptable; and wherein in some embodiments a terminal hydroxy or carboxy group can be substituted to create an ether or ester, respectively;

(iv) —NHC(O)$C_{1-20}$alkyl, —NHC(O)$C_{1-20}$alkenyl, —NHC(O)$C_{1-20}$alkynyl, —NHC(O)($C_{1-20}$alkyl with at least one $R^5$ substituent on the alkyl chain), —NHC(O)($C_{1-20}$alkenyl, with at least one $R^5$ substituent on the alkenyl chain) —NHC(O)($C_{1-20}$alkynyl, with at least one $R^5$ substituent on the alkynyl chain), —NH(lactic acid)$_{2-20}$C(O)$C_{1-20}$alkyl, —NH(lactic acid)$_{2-10}$C(O)$C_{1-20}$alkyl, —NH(lactic acid)$_{4-20}$C(O)$C_{1-20}$alkyl, —NH(lactic acid)$_{2-20}$C(O)$C_{1-10}$alkyl, —NH(lactic acid)$_{2-20}$C(O)$C_{4-10}$alkyl, —NH(lactic acid)$_{2-20}$C(O)OH, —NH(lactic acid)$_{2-10}$C(O)OH, —NH(lactic acid)$_{4-20}$C(O)OH, —NH(lactic acid)$_{2-10}$C(O)OH, —NH(lactic acid)$_{4-10}$C(O)OH, —NH(lactide-co-glycolide)$_{2-10}$C(O)$_{C1}$-2alkyl, —NH(lactide-co-glycolide)$_{4-10}$C(O)$_{C1-20}$alkyl, —NH(lactide-co-glycolide)$_{2-10}$C(O)$_{C1-10}$alkyl, —NH(lactide-co-glycolide)$_{2-10}$C(O)$_{C4-20}$alkyl, —NH(glycolic acid)$_{2-10}$C(O)$_{C1-10}$alkyl, —NH(glycolic acid)$_{4-10}$C(O)$_{C1-10}$alkyl, —NH(lactic acid)$_{4-10}$C(O)$_{C1-10}$alkyl, —NH(lactic acid)$_{2-10}$C(O)$_{C1-10}$alkyl, NH(lactic acid)$_{2-10}$C(O)$_{C4-10}$alkyl, —NH(lactic acid)$_{2-10}$C(O)$_{C4-10}$alkyl, or —NH(lactic acid)$_{2-10}$C(O)$_{C4-10}$alkyl wherein $R^5$, $R^{15}$, x, and y are as defined above.

In one embodiment, —$C_3$-$C_{30}$ as used in the definition of $R^{42}$ is —$C_3$-$C_{28}$, —$C_3$-$C_{26}$, —$C_3$-$C_{24}$, —$C_3$-$C_{22}$, —$C_3$-$C_{20}$, —$C_3$-$C_{18}$, —$C_3$-$C_{16}$, —$C_3$-$C_{14}$, —$C_3$-$C_{12}$, —$C_5$-$C_{12}$, —$C_7$-$C_{12}$, or —$C_7$-$C_{10}$.

Additional non-limiting examples of $R^{16}$ include:

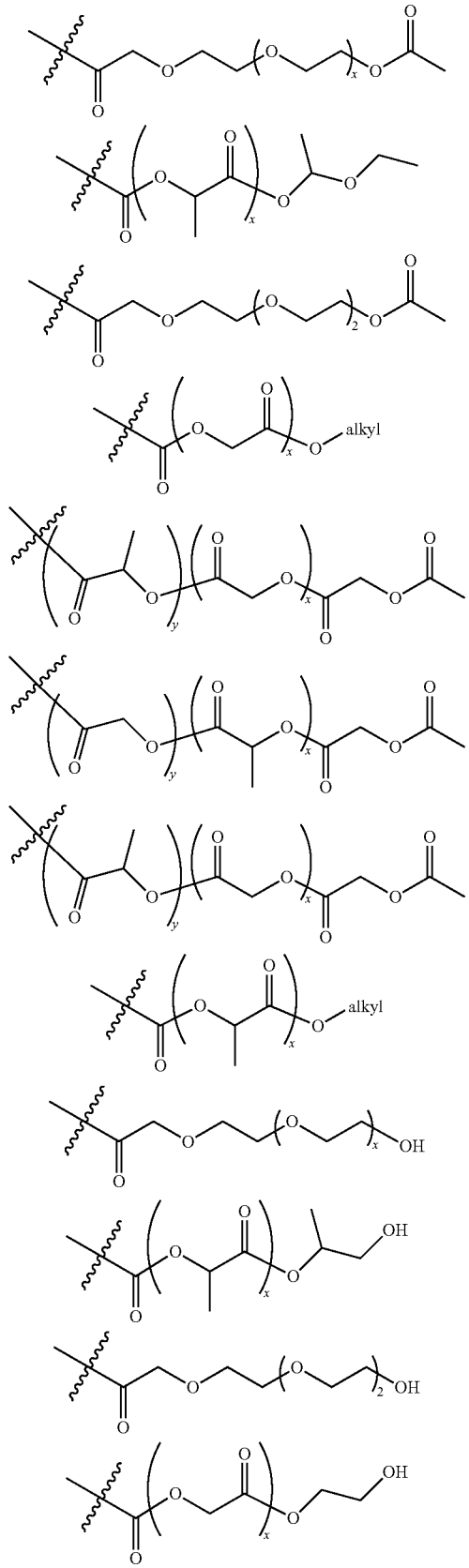

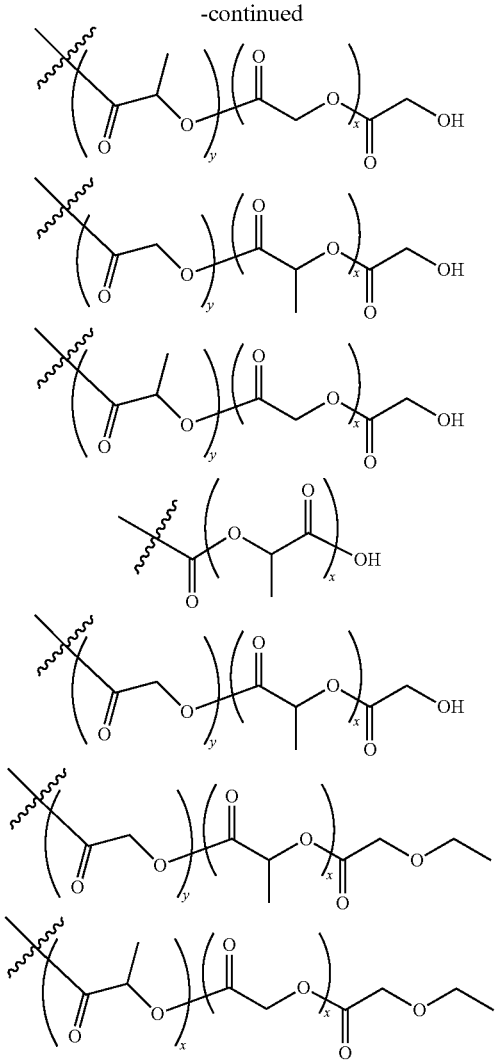

The disclosure also provides a prodrug of Formula VII:

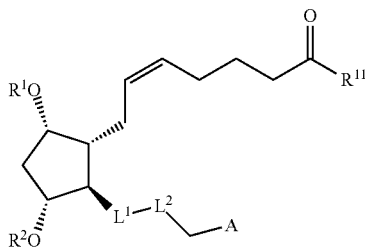
(VII)

or a pharmaceutically acceptable composition, salt, or isotopic derivative thereof.

$R^{11}$ is selected from:
(i) $R^{12}$;
(ii) —NH—$C_4$-$C_{30}$alkenyl-C(O)$R^{12}$, —NH—$C_4$-$C_{30}$alkynyl-C(O)$R^{12}$, —NH—$C_4$-$C_{30}$alkenylalkynyl-C(O)$R^{12}$, —NH—$C_2$-$C_{30}$alkyl-C(O)$R^{12}$, —O—$C_4$-$C_{30}$alkenyl-C(O)$R^{12}$, —O—$C_4$-$C_{30}$alkynyl-C(O)$R^{12}$, —O—$C_4$-$C_{30}$alkenylalkynyl-C(O)$R^{12}$, and —O—$C_2$-$C_{30}$alkyl-C(O)$R^{12}$;

(iii) —NH—$C_4$-$C_{30}$alkenyl=$R^{13}$, —NH—$C_4$-$C_{30}$alkynyl=$R^{13}$, —NH—$C_4$-$C_{30}$alkenylalkynyl=$R^{13}$, —NH—$C_2$-$C_{30}$alkyl=$R^{13}$, —O—$C_4$-$C_{30}$alkenyl=$R^{13}$, —O—$C_4$-$C_{30}$alkynyl=$R^{13}$, —O—$C_4$-$C_{30}$alkenylalkynyl=$R^{13}$, —O—$C_2$-$C_{30}$alkyl=$R^{13}$;

(iv) functionalized polyethylene glycol, polypropylene glycol, polypropylene oxide, polylactic acid, and poly(lactic-co-glycolic acid) including:

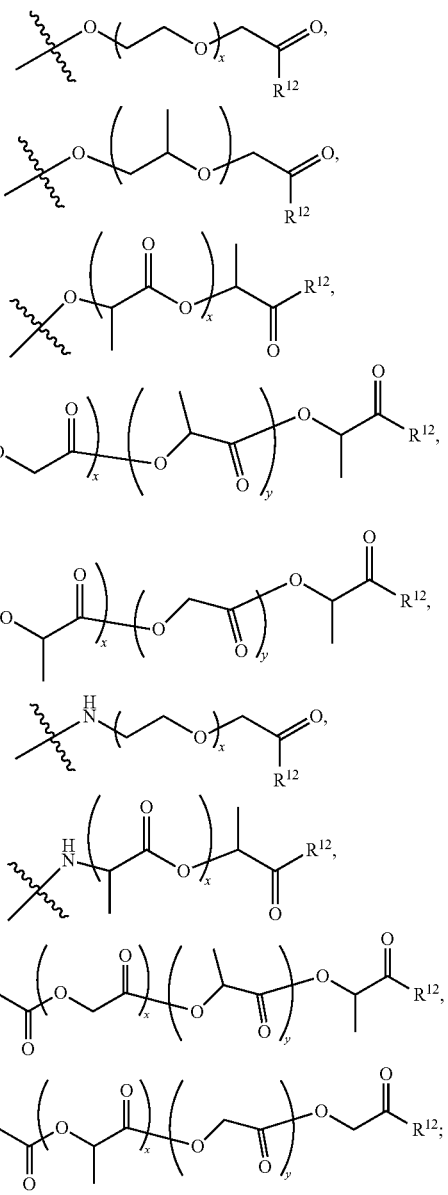

(v) functionalized polyethylene glycol, polypropylene glycol, polypropylene oxide, polylactic acid, and poly(lactic-co-glycolic acid) including:

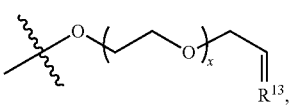

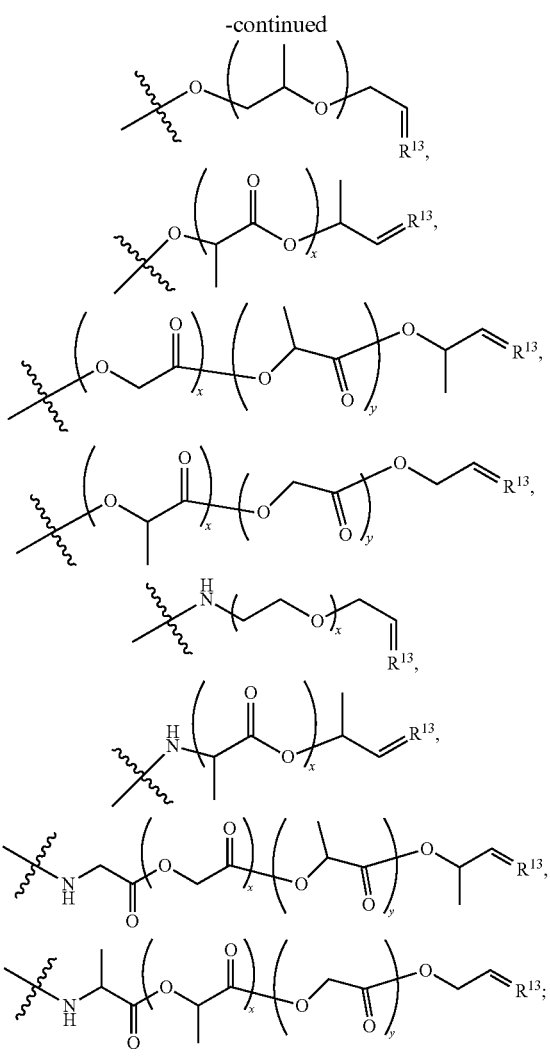

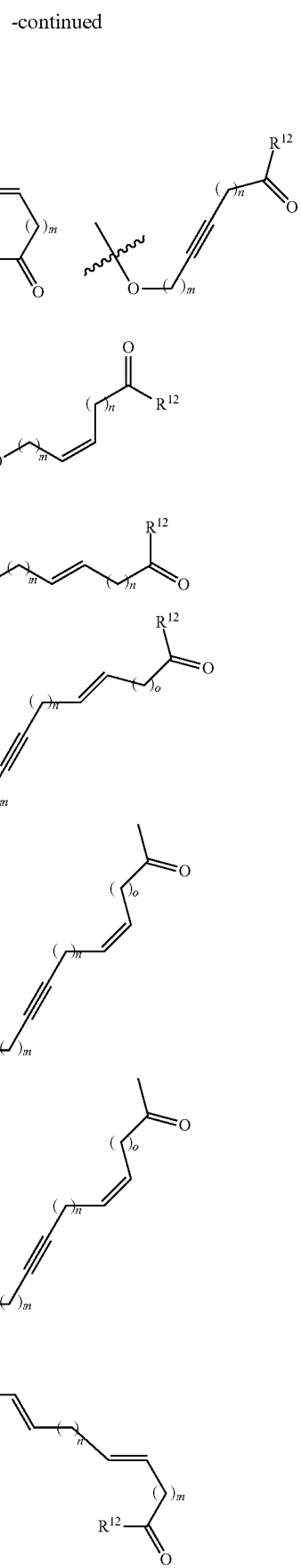

wherein R[11] can be further substituted with R[5] if valence permits, a stable compound is formed, and the resulting compound is pharmaceutically acceptable.

In one embodiment R[11] is selected from:

—NH—C$_4$-C$_{29}$alkenyl-CH=R[13], —NH—C$_4$-C$_{29}$alkynyl-CH=R[13], —NH—C$_4$-C$_{29}$alkenylalkynyl-CH=R[13], —NH—C$_2$-C$_{29}$alkyl-CH=R[13], —O—C$_4$-C$_{29}$alkenyl-CH=R[13], —O—C$_4$-C$_{29}$alkynyl-CH=R[13], —O—C$_4$-C$_{29}$alkenylalkynyl-CH=R[13], and —O—C$_2$-C$_{29}$alkyl-CH=R[13].

Non-limiting examples of R[11] include:

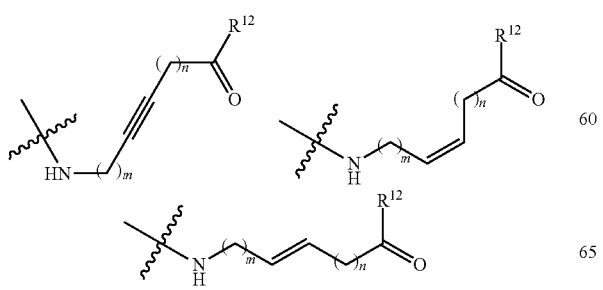

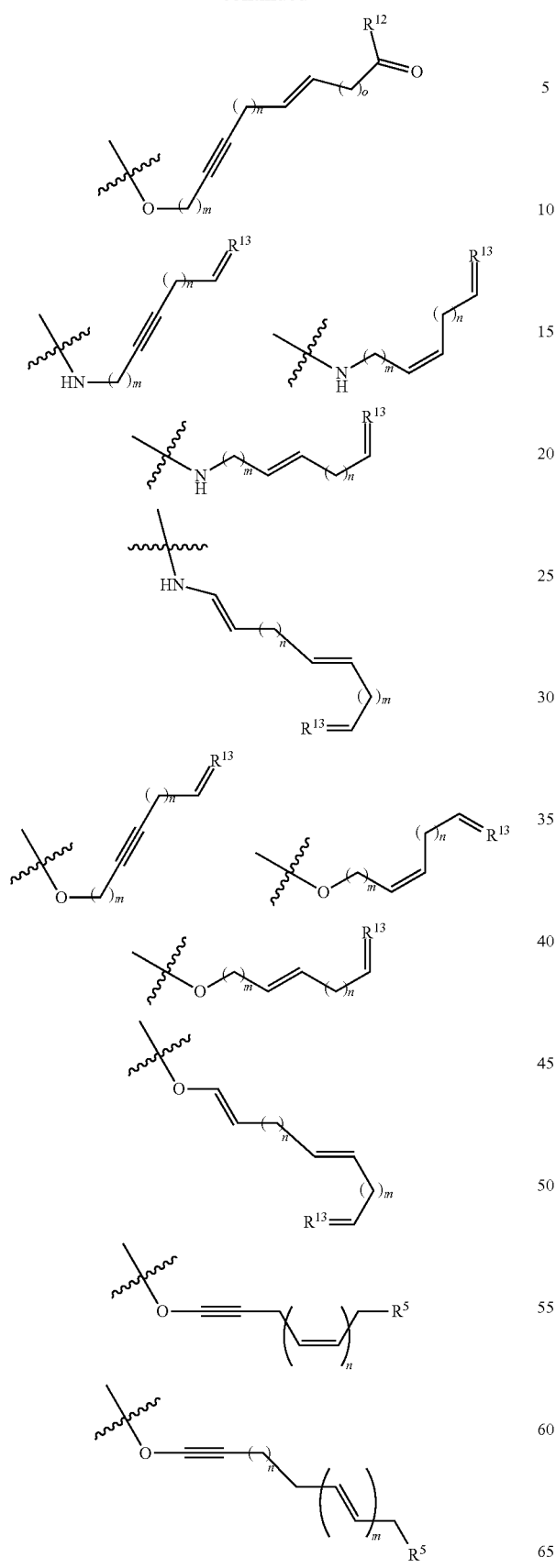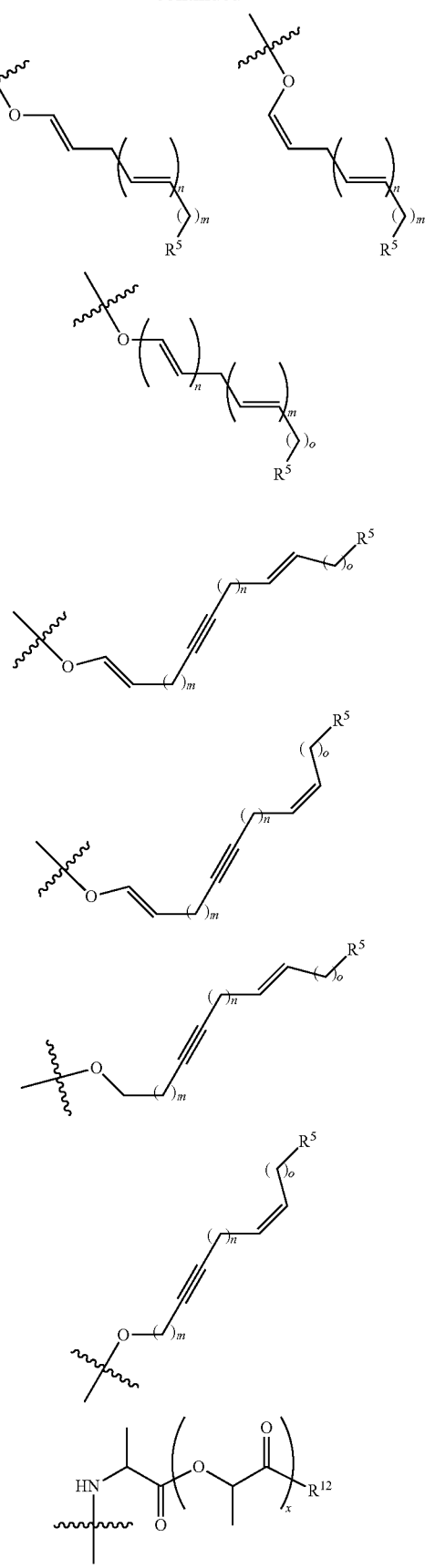

-continued
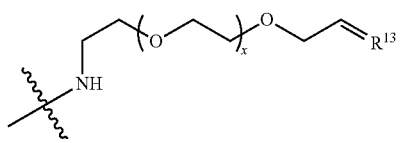
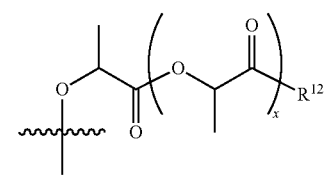
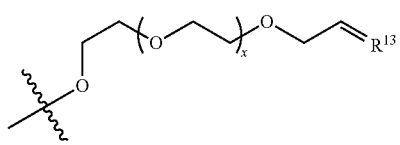
wherein n, m, o, x, and y are as defined above.
$R^{12}$ is selected from:
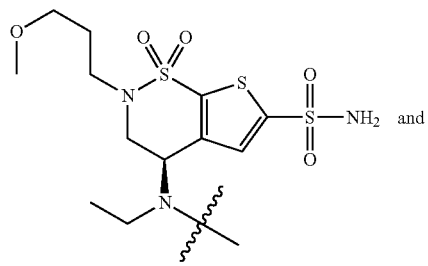
and
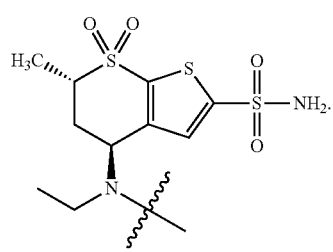
$R^{13}$ is selected from:
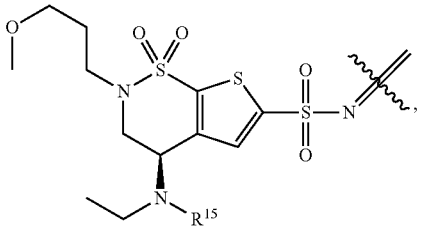
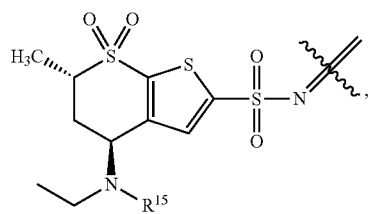
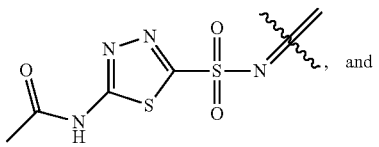
, and
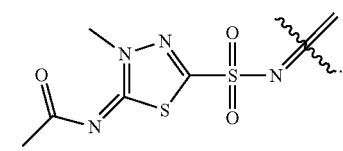
In various different embodiments, $-C_4-C_{29}$ as used in the definition of $R^{11}$ may be $-C_4-C_{28}$, $-C_4-C_{26}$, $-C_4-C_{24}$, $-C_6-C_{22}$, $-C_6-C_{20}$, $-C_8-C_{18}$, $-C_8-C_{16}$, $-C_8-C_{14}$, $-C_8-C_{12}$, $-C_8-C_{20}$, or $-C_6-C_{24}$
Non-limiting examples of Formula VII include:
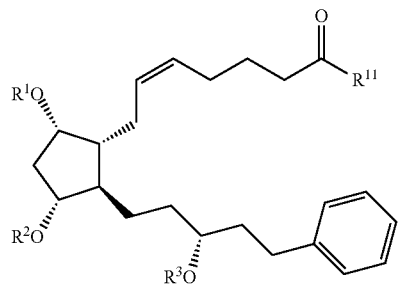
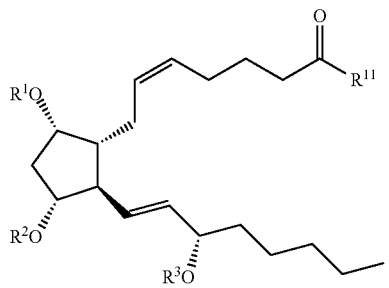

-continued
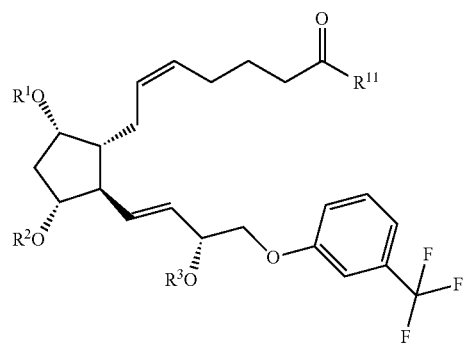
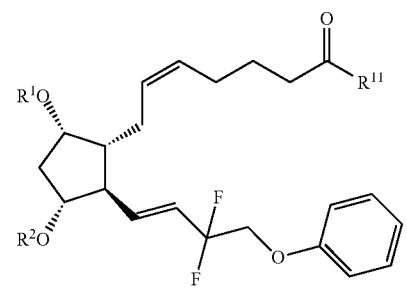
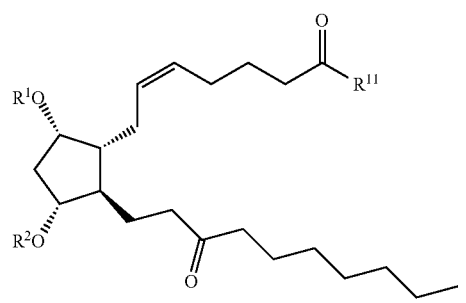
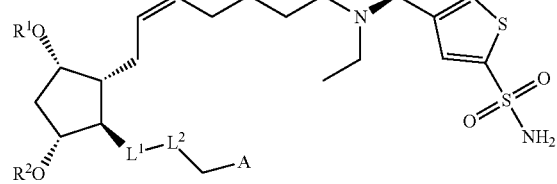
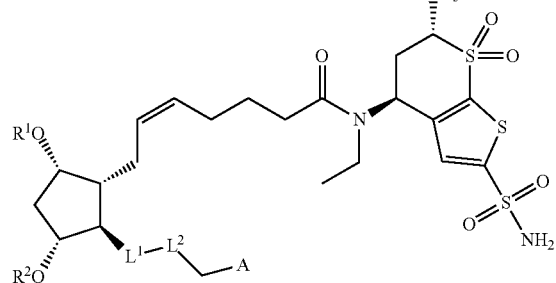
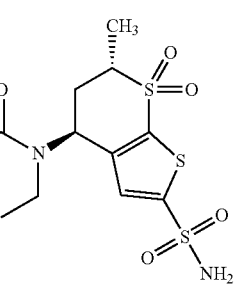
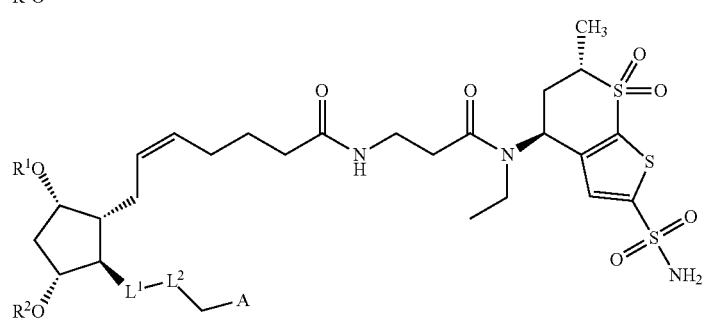
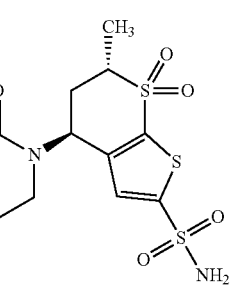

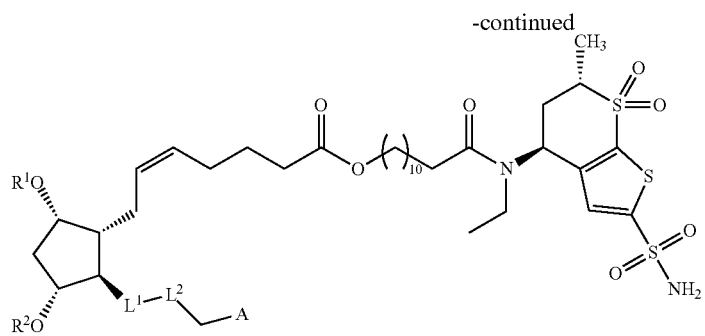
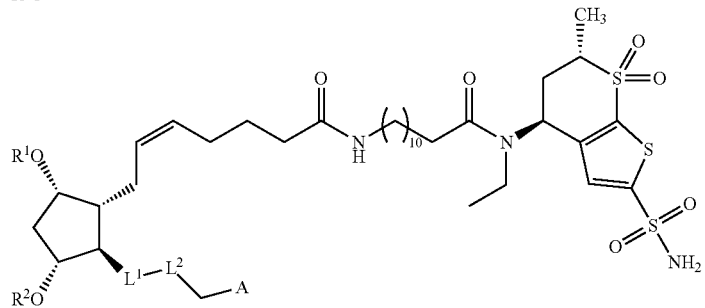
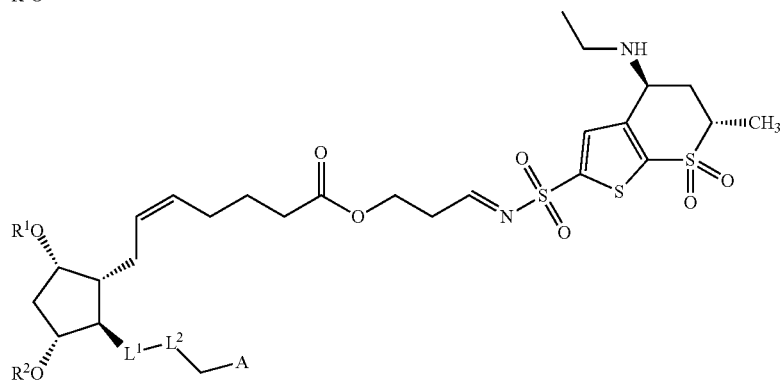
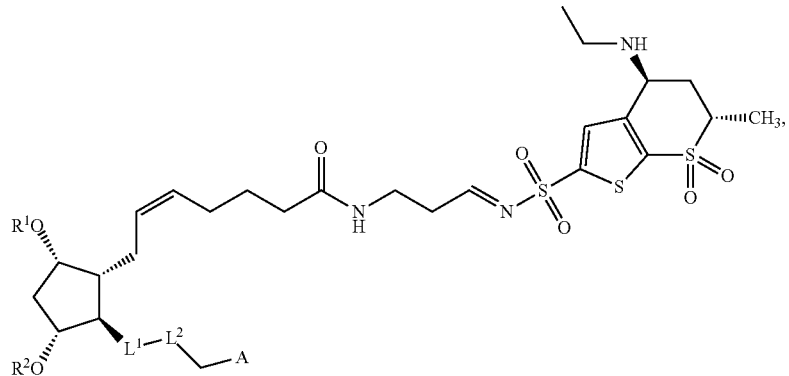
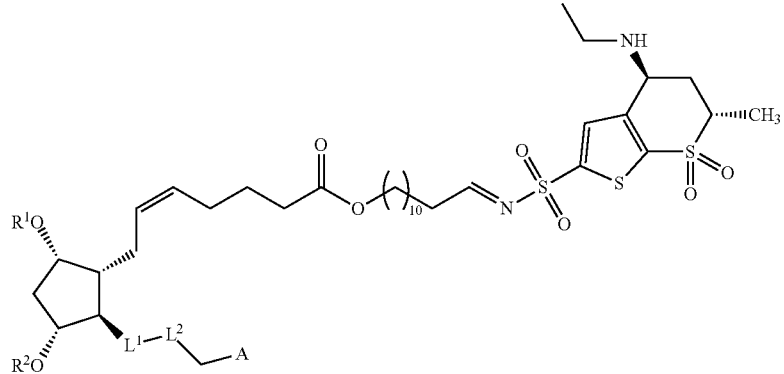

-continued

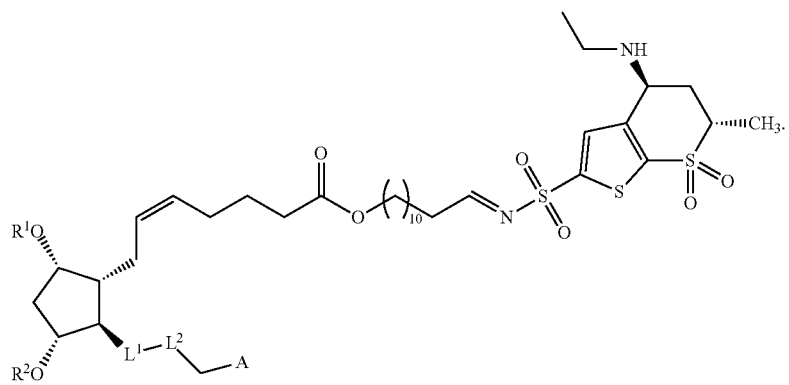

The disclosure also provides a prodrug of Formula VII':

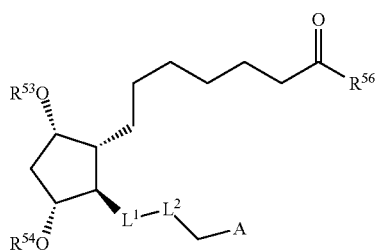

(VII')

or a pharmaceutically acceptable composition, salt, or isotopic derivative thereof.

$R^{53}$ and $R^{54}$ are independently selected from: —C(O)$R^4$, —C(O)A, and hydrogen, each of which except hydrogen can be optionally substituted with $R^5$;

$R^{56}$ is selected from:
(i) $R^{57}$;
(ii) —NH—$C_4$-$C_{30}$alkenyl-C(O)$R^{57}$, —NH—$C_4$-$C_{30}$alkynyl-C(O)$R^{57}$, —NH—$C_4$-$C_{30}$alkenylalkynyl-C(O)$R^{57}$, —NH—$C_2$-$C_{30}$alkyl-C(O)$R^{57}$, —O—$C_4$-$C_{30}$alkenyl-C(O)$R^{57}$, —O—$C_4$-$C_{30}$alkynyl-C(O)$R^{57}$, —O—$C_4$-$C_3$alkenylalkynyl-C(O)$R^{57}$, —O—$C_2$-$C_{30}$alkyl-C(O)$R^{57}$, —NH—$C_4$-$C_{30}$alkenyl$R^{57}$, —NH—$C_4$-$C_{30}$alkynyl$R^{57}$, —NH—$C_4$-$C_{30}$alkenylalkynyl$R^{57}$, —NH—$C_2$-$C_{30}$alkyl$R^{57}$, —O—$C_4$-$C_{30}$alkenyl$R^{57}$, —O—$C_4$-$C_{30}$alkynyl$R^{57}$, —O—$C_4$-$C_{30}$alkenylalkynyl$R^{57}$, and —O—$C_2$-$C_{30}$alkyl$R^{57}$;
(iii) —NH—$C_4$-$C_{29}$alkenyl-CH=$R^{58}$, —NH—$C_4$-$C_{29}$alkynyl-CH=$R^{58}$, —NH—$C_4$-$C_{29}$alkenylalkynyl-CH=$R^{58}$, —NH—$C_2$-$C_{29}$alkyl-CH=$R^{58}$, —O—$C_4$-$C_{29}$alkenyl-CH=$R^{58}$, —O—$C_4$-$C_{29}$alkynyl-CH=$R^{58}$, —O—$C_4$-$C_{29}$alkenylalkynyl-CH=$R^{58}$, and —O—$C_2$-$C_{29}$alkyl-CH=$R^{58}$;
(iv) polyethylene glycol, polypropylene glycol, polypropylene oxide, polylactic acid, and poly(lactic-co-glycolic acid), polyglycolic acid, or a polyester, polyamide, or other biodegradable polymer, each of which is substituted with at least one $L^4$-$R^{57}$;
(v) polyethylene glycol, polypropylene glycol, polypropylene oxide, polylactic acid, and poly(lactic-co-glycolic acid), polyglycolic acid, or a polyester, polyamide, or other biodegradable polymer, each of which is substituted with at least one moiety of $L^5$=$R^{58}$, wherein $R^{56}$ can be further substituted with $R^5$ if valence permits, a stable compound is formed, and the resulting compound is pharmaceutically acceptable.

$L^4$ is bond, alkyl, alkenyl, alkynyl, —C(O)—, —C(S)—, —NH—, —N(alkyl)-, —O—, or alkyl-C(O)—;

$L^5$ is double bond, alkyl, or alkenyl;

In one embodiment, —$C_4$-$C_{29}$ as used in the definition of $R^{56}$ is —$C_4$-$C_{28}$, —$C_4$-$C_{26}$, —$C_4$-$C_{24}$, —$C_6$-$C_{22}$, —$C_6$-$C_{20}$, —$C_8$-$C_{18}$, —$C_8$-$C_{16}$, —$C_8$-$C_{14}$, or —$C_8$-$C_{12}$.

$R^{57}$ is selected from:

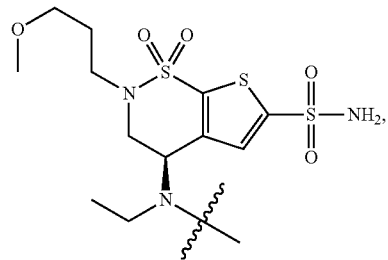

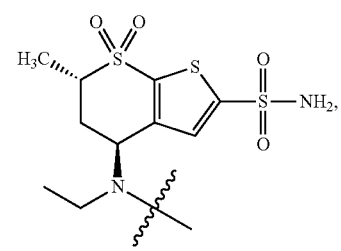

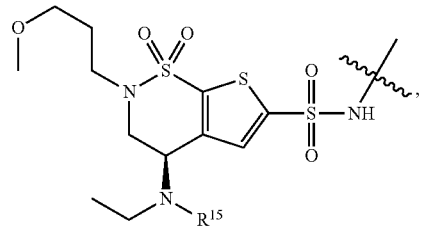

-continued
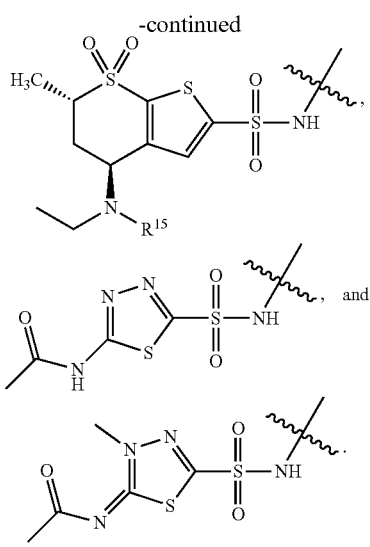
$R^{58}$ is selected from:
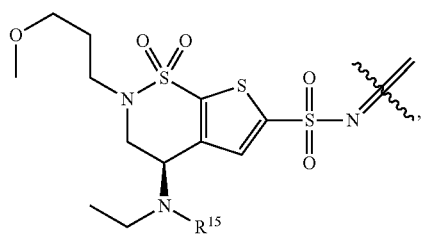
-continued
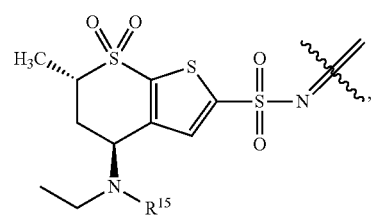
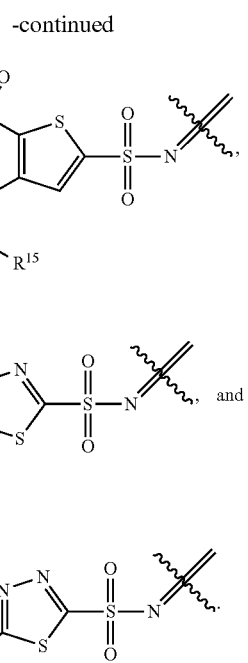
wherein A, $R^4$, $R^5$, $R^{15}$, $L^1$, and $L^2$ are defined above.
Non-limiting examples of compounds of Formula VII' include:
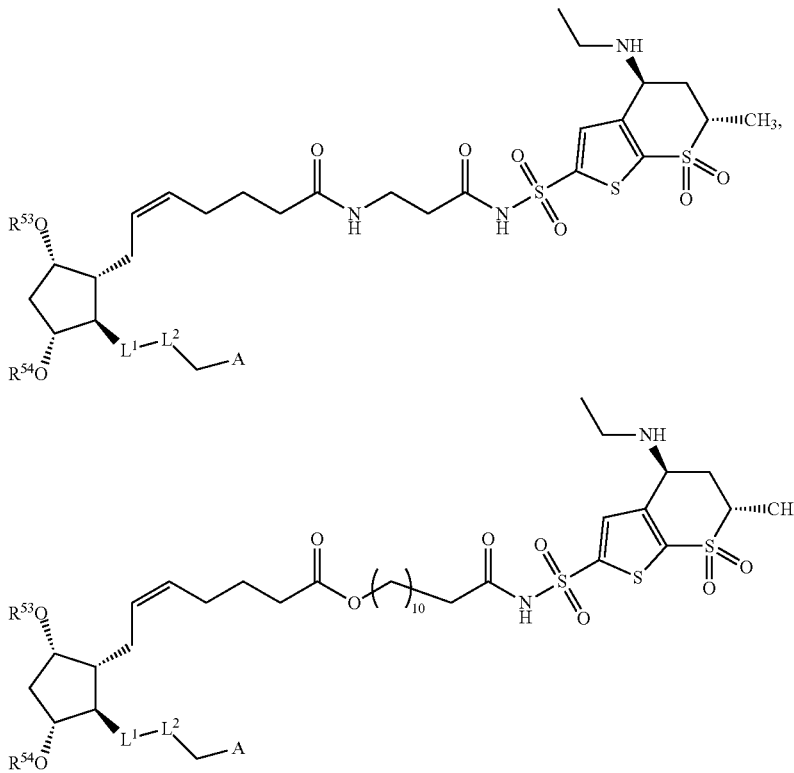

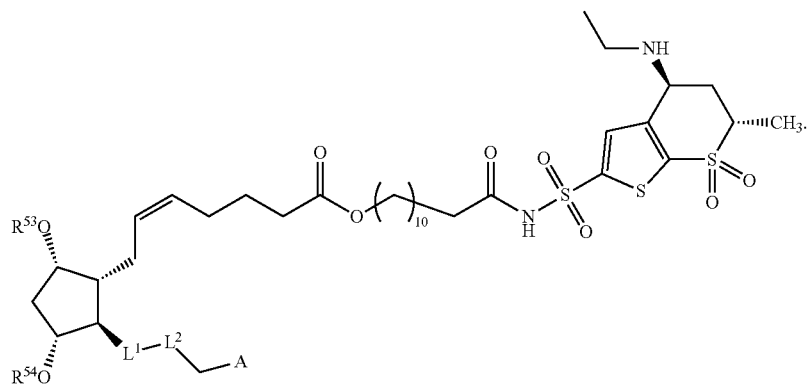

The disclosure also provides a prodrug of Formula VIII:

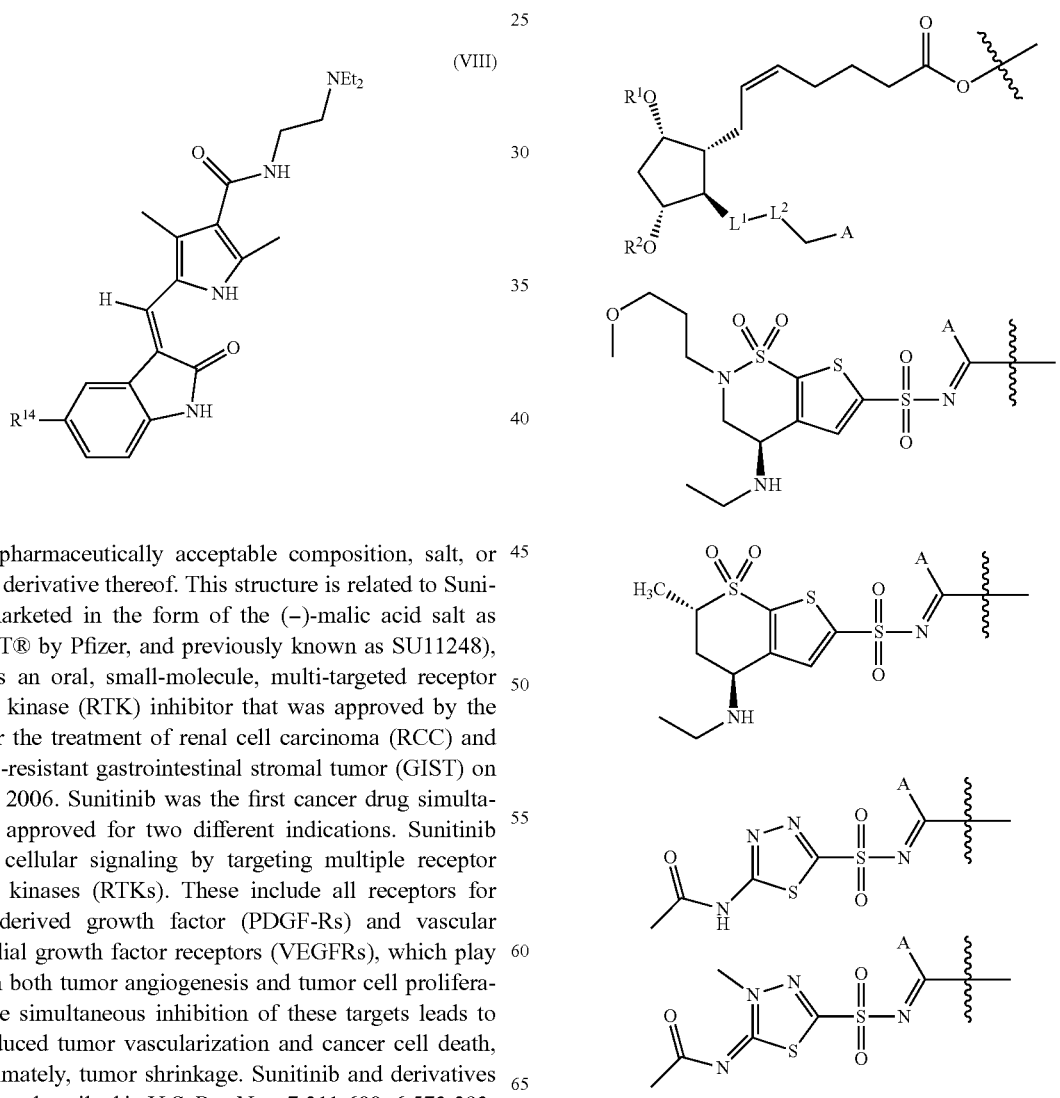

or a pharmaceutically acceptable composition, salt, or isotopic derivative thereof. This structure is related to Sunitinib (marketed in the form of the (−)-malic acid salt as SUTENT® by Pfizer, and previously known as SU11248), which is an oral, small-molecule, multi-targeted receptor tyrosine kinase (RTK) inhibitor that was approved by the FDA for the treatment of renal cell carcinoma (RCC) and imatinib-resistant gastrointestinal stromal tumor (GIST) on Jan. 26, 2006. Sunitinib was the first cancer drug simultaneously approved for two different indications. Sunitinib inhibits cellular signaling by targeting multiple receptor tyrosine kinases (RTKs). These include all receptors for platelet-derived growth factor (PDGF-Rs) and vascular endothelial growth factor receptors (VEGFRs), which play a role in both tumor angiogenesis and tumor cell proliferation. The simultaneous inhibition of these targets leads to both reduced tumor vascularization and cancer cell death, and, ultimately, tumor shrinkage. Sunitinib and derivatives thereof are described in U.S. Pat. Nos. 7,211,600; 6,573,293; and 7,125,905.

The disclosure also provides a prodrug of Formula IX:

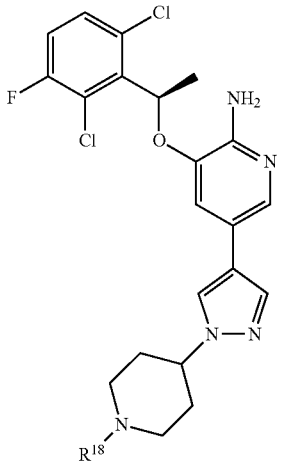

(IX)

or a pharmaceutically acceptable composition, salt, or isotopic derivative thereof.

$R^{18}$ is selected from: —C(O)CH$_2$CH$_2$C$_{19}$-C$_{30}$alkylR$^5$, —C(O)CH$_2$CH$_2$C$_{19}$-C$_{30}$alkenylR$^5$, —C(O)CH$_2$CH$_2$C$_{19}$-C$_{30}$alkynylR$^5$, —C(O)CH$_2$CH$_2$C$_{19}$-C$_{30}$alkenylalkynylR$^5$, —C(O)CH$_2$CH$_2$C$_{19}$-C$_{30}$alkyl, —C(O)CH$_2$CH$_2$C$_{19}$-C$_{30}$alkenyl, —C(O)CH$_2$CH$_2$C$_{19}$-C$_{30}$alkynyl, —C(O)CH$_2$CH$_2$C$_{19}$-C$_{30}$alkenylalkynyl, and $R^{19}$ wherein $R^{18}$ can be further optionally further substituted with $R^5$ (including for example a second $R^5$) if valence permits, a stable compound is formed, and the resulting compound is pharmaceutically acceptable; In various different embodiments, —C$_{19}$-C$_{30}$ as used in the definition of $R^{18}$ is —C$_{19}$-C$_{28}$, —C$_{19}$-C$_{26}$, —C$_{19}$-C$_{24}$, —C$_{19}$-C$_{22}$, —C$_{19}$-C$_{20}$, —C$_{20}$-C$_{28}$, —C$_{20}$-C$_{26}$, —C$_{20}$-C$_{24}$, —C$_{20}$-C$_{22}$, —C$_{22}$-C$_{28}$, —C$_{22}$-C$_{26}$, —C$_{22}$-C$_{24}$, or —C$_{26}$-C$_{28}$.

$R^{19}$ is selected from:

(i) an unsaturated fatty acid residue including but not limited to the carbonyl fragment taken from docosahexaenoic acid (—C(O)(CH$_2$)$_2$(CHCHCH$_2$)$_6$CH$_3$)), docosatetraenoic acid, euric acid, or nervonic acid;

(ii) polyethylene glycol, polypropylene glycol, polypropylene oxide, polylactic acid, or poly(lactic-co-glycolic acid) including

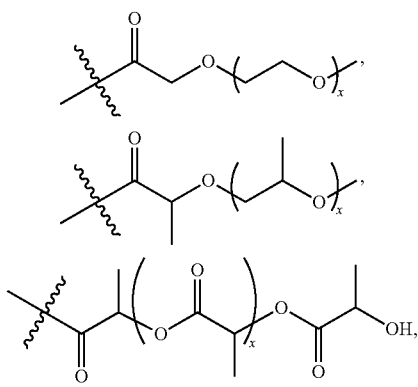

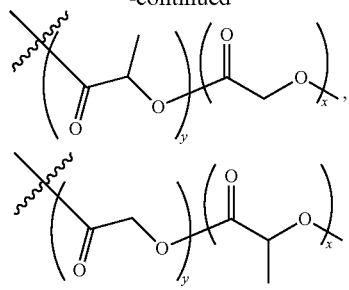

or polyglycolic acid, or a polyester, polyamide, or other biodegradable polymer, each of which can be capped to complete the terminal valence or to create a terminal ether.

The disclosure also provides a prodrug of Formula X:

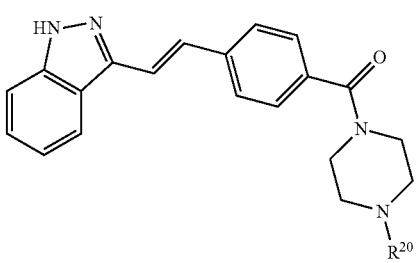

(X)

or a pharmaceutically acceptable composition, salt, or isotopic derivative thereof.

$R^{20}$ is selected from: —C(O)CH$_2$CH$_2$C$_9$-C$_{30}$alkylR$^5$, —C(O)CH$_2$CH$_2$C$_9$-C$_{30}$alkenylR$^5$, —C(O)CH$_2$CH$_2$C$_9$-C$_{30}$alkynylR$^5$, —C(O)CH$_2$CH$_2$C$_9$-C$_{30}$alkenylalkynylR$^5$, —C(O)CH$_2$CH$_2$C$_9$-C$_{30}$alkyl, —C(O)CH$_2$CH$_2$C$_9$-C$_{30}$alkenyl, —C(O)CH$_2$CH$_2$C$_9$-C$_{30}$alkynyl, —C(O)CH$_2$CH$_2$C$_9$-C$_{30}$alkenylalkynyl, and $R^{21}$.

In one embodiment, —C$_9$-C$_{30}$ as used in the definition of $R^{20}$ is —C$_{10}$-C$_{28}$, —C$_{11}$-C$_{26}$, —C$_{11}$-C$_{24}$, —C$_{12}$-C$_{22}$, —C$_{12}$-C$_{20}$, —C$_{12}$-C$_{18}$, —C$_{12}$-C$_{16}$, or —C$_{12}$-C$_{14}$ $R^{21}$ is selected from:

(i) an unsaturated fatty acid residue including but not limited the carbonyl fragment taken from linoleic acid (—C(O)(CH$_2$)$_7$(CH)$_2$CH$_2$(CH)$_2$(CH$_2$)$_4$CH$_3$), docosahexaenoic acid (—C(O)(CH$_2$)$_2$(CHCHCH$_2$)$_6$CH$_3$)), eicosapentaenoic acid (—C(O)(CH$_2$)$_3$(CHCHCH$_2$)$_5$CH$_3$)), alpha-linolenic acid (—C(O)(CH$_2$)$_7$(CHCHCH$_2$)$_3$CH$_3$)) stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid and mead acid, each of which can be further substituted with $R^5$ if valence permits, a stable compound is formed, and the resulting compound is pharmaceutically acceptable;

(ii) polyethylene glycol, polypropylene glycol, polypropylene oxide, polylactic acid, and poly(lactic-co-glycolic acid) including:

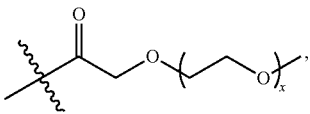

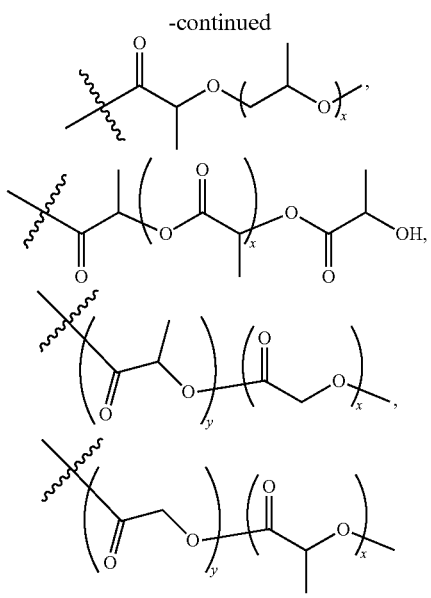

or polyglycolic acid, or a polyester, polyamide, or other biodegradable polymer, each of which can be capped to complete the terminal valence or to create a terminal ether.

The disclosure also provides a prodrug of Formula XI:

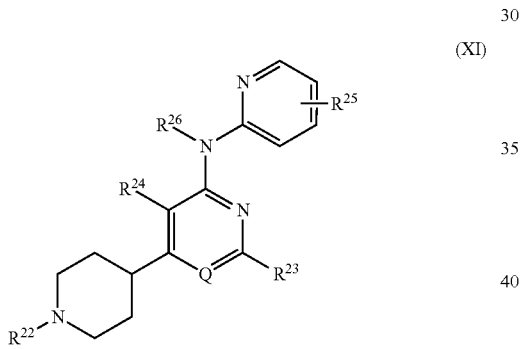

(XI)

or a pharmaceutically acceptable composition, salt, or isotopic derivative thereof.

Q is selected from: N, CH, and $CR^{23}$.

$R^{22}$ is selected from: $-C(O)CH_2CH_2C_{11}-C_{30}alkylR^5$, $-C(O)CH_2CH_2C_{11}-C_{30}alkenylR^5$, $-C(O)CH_2CH_2C_{11}-C_{30}alkynylR^5$, $-C(O)CH_2CH_2C_{11}-C_{30}alkenylalkynylR^5$, $-C(O)CH_2CH_2C_{11}-C_{30}alkyl$, $-C(O)CH_2CH_2C_{11}-C_{30}alkenyl$, $-C(O)CH_2CH_2C_{11}-C_{30}alkynyl$, $-C(O)CH_2CH_2C_{11}-C_{30}alkenylalkynyl$ and $R^{21}$ and wherein $R^{22}$ can be further substituted with $R^5$ (including for example a second $R^5$) if valence permits, a stable compound is formed, and the resulting compound is pharmaceutically acceptable.

In one embodiment, $-C_{11}-C_{30}$ as used in the definition of $R^{22}$ is $-C_{12}-C_{28}$, $-C_{13}-C_{26}$, $-C_{13}-C_{24}$, $-C_{13}-C_{22}$, $-C_{13}-C_{20}$, $-C_{13}-C_{18}$, $-C_{13}-C_{16}$, or $-C_{13}-C_{14}$.

$R^{23}$, $R^{24}$, and $R^{25}$ are independently selected from: hydrogen, halogen, hydroxyl, cyano, mercapto, nitro, amino, aryl, alkyl, alkoxy, alkenyl, alkynyl cycloalkyl, cycloalkylalkyl, heterocyclyl, heterocycloalkyl, aryl, arylalkyl, heteroaryl, heteroarylalkyl, aryloxy, $-S(O)_2alkyl$, $-S(O)alkyl$, $-P(O)(Oalkyl)_2$, $B(OH)_2$, $-Si(CH_3)_3$, $-COOH$, $-COOalkyl$, $-CONH_2$,

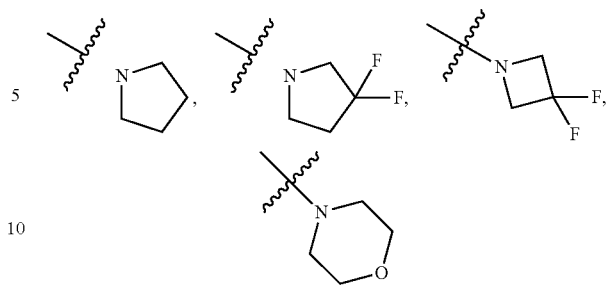

each of which except halogen, nitro, and cyano, may be optionally substituted, for example with halogen, alkyl, aryl, heterocycle or heteroaryl.

$R^{26}$ is selected from H, C(O)A, $-C_0-C_{10}alkylR^5$, $-C_2-C_{10}alkenylR^5$, $-C_2-C_{10}alkynylR^5$, $-C_2-C_{10}alkenyl$, and $-C_2-C_{10}alkynyl$.

In one embodiment, $-C_2-C_{10}$ as used in $R^{26}$ is $-C_4-C_{10}$, $-C_6-C_{10}$, or $-C_8-C_{10}$.

The disclosure also provides a prodrug of Formula XII:

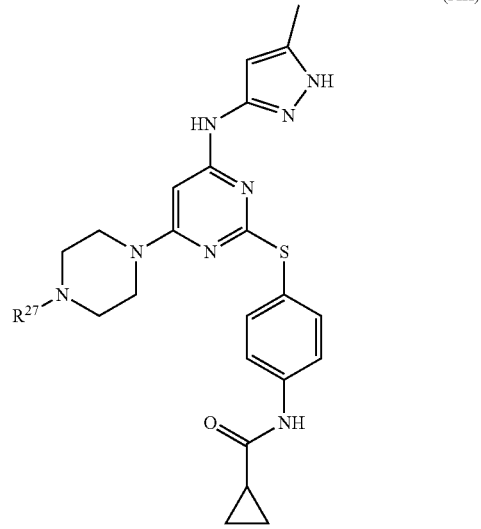

(XII)

or a pharmaceutically acceptable composition, salt, or isotopic derivative thereof.

$R^{27}$ is selected from: $-C(O)CH_2CH_2C_0-C_{30}alkylR^5$, $-C(O)CH_2CH_2C_0-C_{30}alkenylR^5$, $-C(O)CH_2CH_2C_0-C_{30}alkynylR^5$, $-C(O)CH_2CH_2C_0-C_{30}alkenylalkynylR^5$, $-C(O)CH_2CH_2C_0-C_{30}alkyl$, $-C(O)CH_2CH_2C_0-C_{30}alkenyl$, $-C(O)CH_2CH_2C_0-C_{30}alkynyl$, $-C(O)CH_2CH_2C_0-C_{30}alkenylalkynyl$, and $R^{21}$.

In various different embodiments, $-C_0-C_{30}$ as used in $R^{27}$ is $-C_0-C_{28}$, $-C_0-C_{26}$, $-C_0-C_{24}$, $-C_0-C_{22}$, $-C_0-C_{20}$, $-C_0-C_{18}$, $-C_0-C_{16}$, $-C_0-C_{14}$, $-C_0-C_{12}$, or $-C_0-C_{11}$, $-C_0-C_{10}$, $-C_0-C_8$, $-C_0-C_6$, $-C_0-C_4$, $-C_0-C_2$, $-C_2-C_{28}$, $-C_4-C_{26}$, $-C_4-C_{24}$, $-C_4-C_{22}$, $-C_4-C_{20}$, $-C_6-C_{18}$, $-C_6-C_{16}$, $-C_6-C_{14}$, $-C_6-C_{12}$, $-C_4-C_{11}$, $-C_0-C_{10}$, $-C_0-C_8$, $-C_0-C_6$, $-C_0-C_4$, or $-C_0-C_2$.

The disclosure also provides a prodrug of Formula XIV:

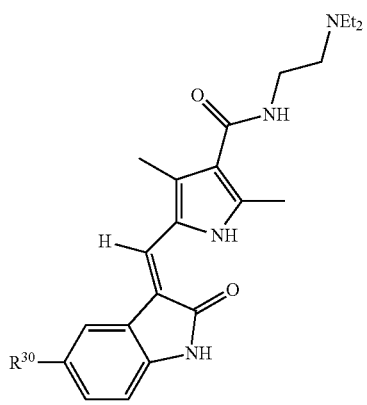

(XIV)

or a pharmaceutically acceptable composition, salt, or isotopic derivative thereof.

$R^{30}$ is selected from: polyethylene glycol, polypropylene glycol, polypropylene oxide, polylactic acid, poly(lactic-co-glycolic acid), a polyglycolic acid, a polyester, a polyamide,

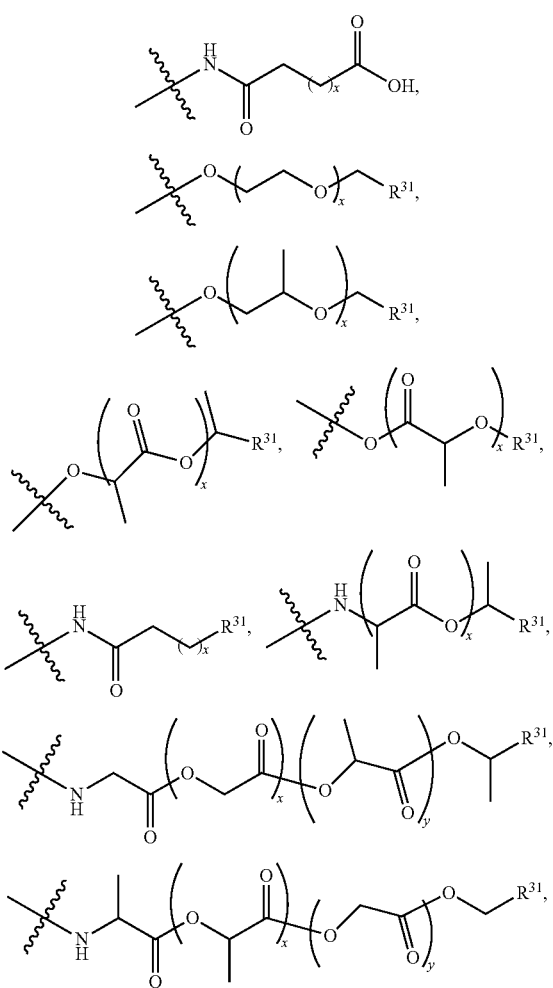

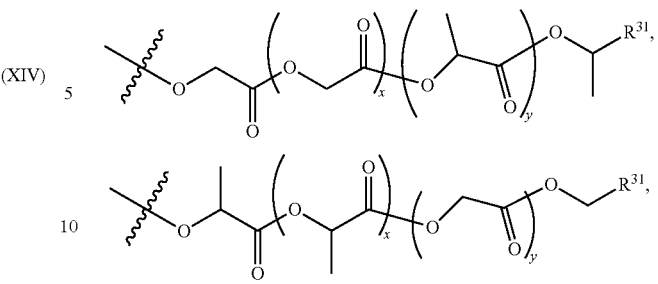

and other biodegradable polymers, wherein $R^{30}$ is optionally substituted with $R^{31}$, and wherein each $R^{30}$ with a terminal hydroxy or carboxy group can be substituted to create an ether or ester;

$R^{31}$ is hydrogen, A, —COOH, —C(O)A, aryl, alkyl, alkoxy, alkenyl, alkynyl cycloalkyl, cycloalkylalkyl, heterocyclyl, heterocycloalkyl, aryl, arylalkyl, heteroaryl, heteroarylalkyl, aryloxy, polyethylene glycol, or

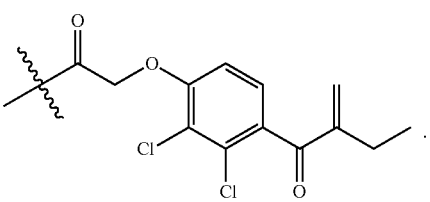

wherein x, y, and A are defined above.

The disclosure also provides a prodrug of Formula XV:

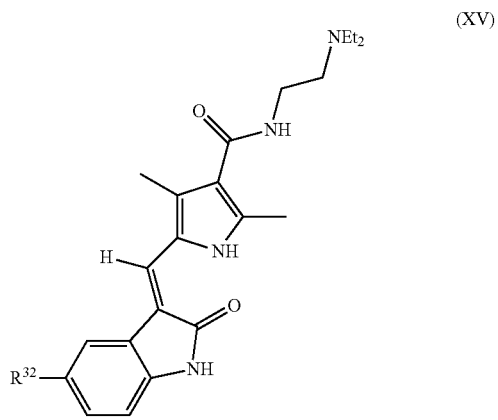

(XV)

or a pharmaceutically acceptable composition, salt, or isotopic derivative thereof.

$R^{32}$ is selected from: $R^{35}$, $R^{51}$, alkyl, alkyloxy, polyethylene glycol, polypropylene glycol, polypropylene oxide, polylactic acid, poly(lactic-co-glycolic acid), a polyglycolic acid, a polyester, polyamide, or other biodegradable polymer, wherein each $R^{32}$ other than $R^{35}$ and $R^{51}$ is substituted with at least one $L^4$-$R^{51}$;

wherein $R^{32}$ can be further substituted with $R^5$ if valence permits, a stable compound is formed, and the resulting compound is pharmaceutically acceptable.

$R^{35}$ is selected from:
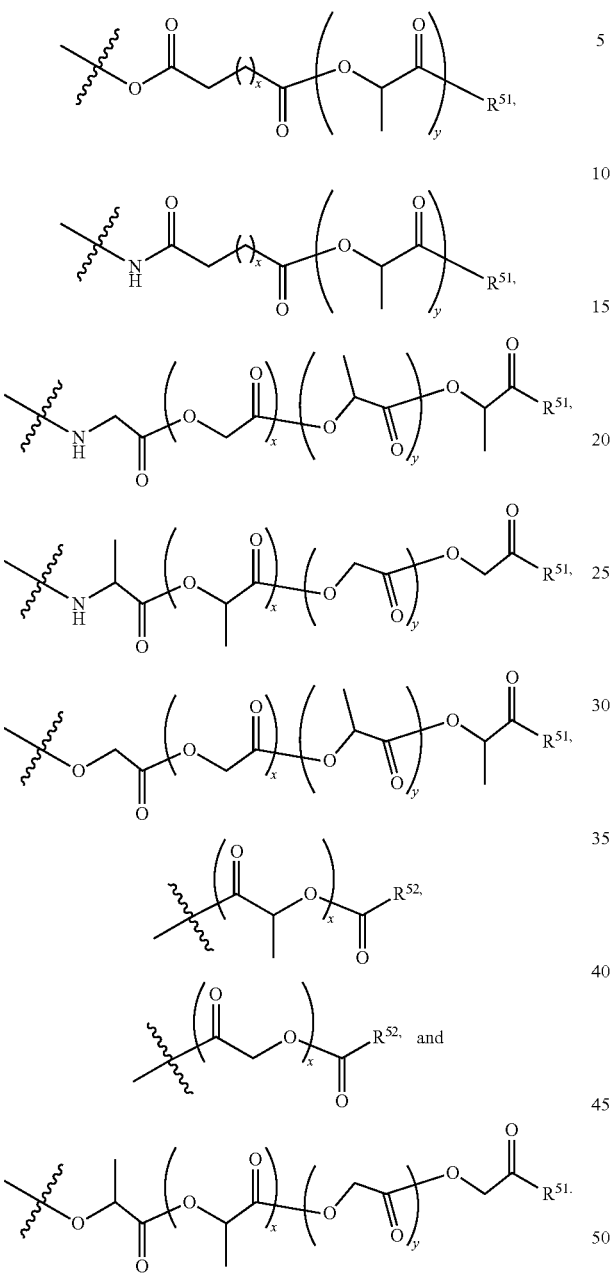
$R^{51}$ is selected from
-continued
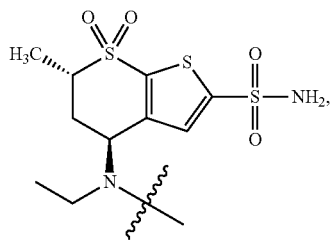
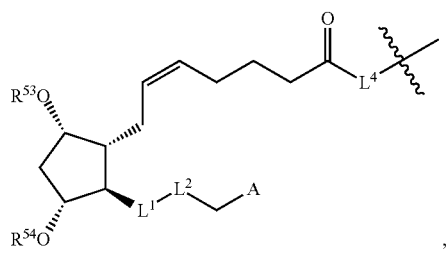
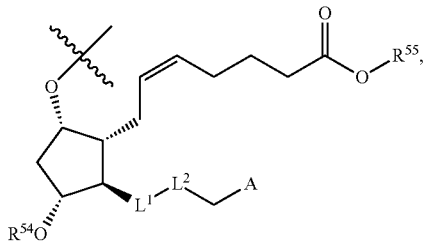
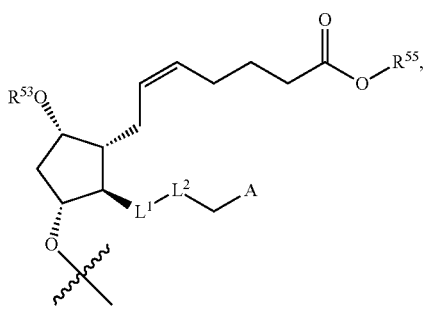
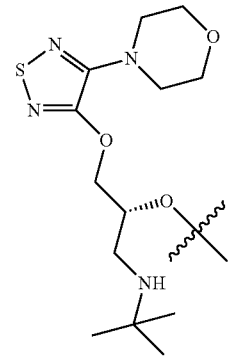
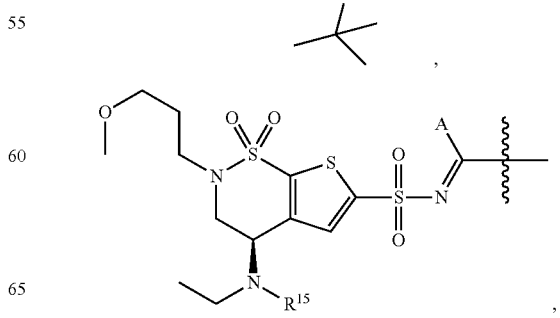

-continued

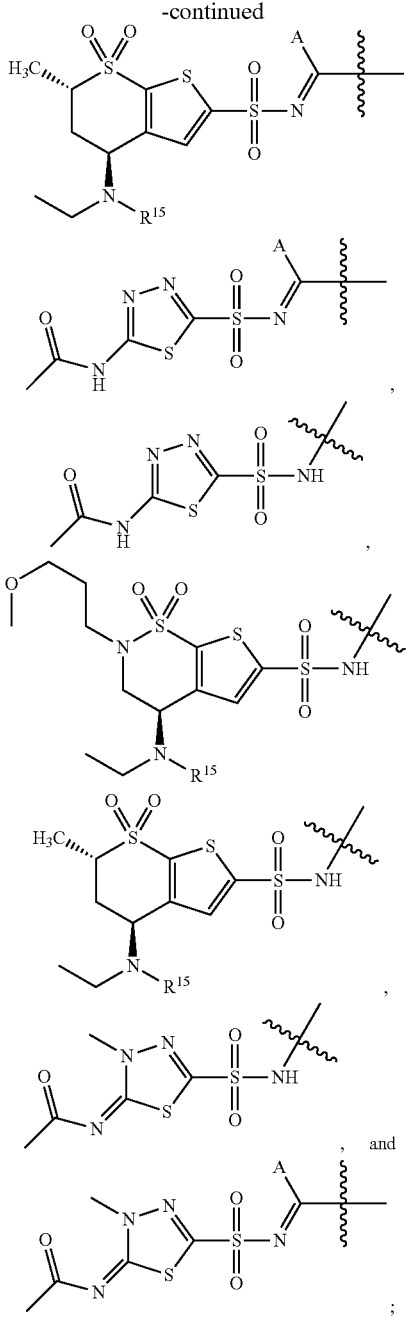

$R^{53}$ and $R^{54}$ are independently selected from: —C(O)$R^4$, C(O)A, and hydrogen, each of which except hydrogen can be optionally substituted with $R^5$;

$R^{55}$ is selected from:
(i) polyethylene glycol, polypropylene glycol, polypropylene oxide, polylactic acid, and poly(lactic-co-glycolic acid), polyglycolic acid, or a polyester, a polyamide, or other biodegradable polymer, wherein a terminal hydroxy or carboxy group can be substituted to create an ether or ester, respectively;
(ii) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl;
(iii) an unsaturated fatty acid residue including but not limited the carbon fragment taken from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alpha-linolenic acid (—$(CH_2)_8(CHCHCH_2)_3CH_3$)) stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid or mead acid;
(iv) alkyl, cycloalkyl, cycloalkylalkyl, heterocycle, heterocycloalkyl, arylalkyl, heteroarylalkyl;

wherein A, x, y, $R^5$, $L^1$, and $L^2$ are defined above.

Non-limiting examples of $R^{55}$ include:

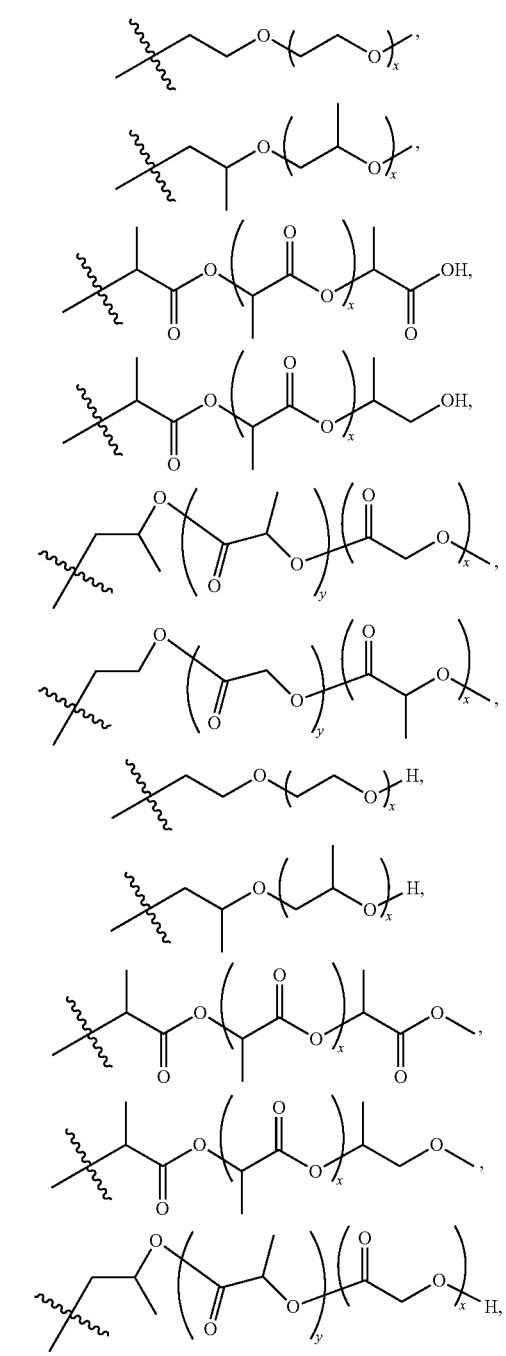

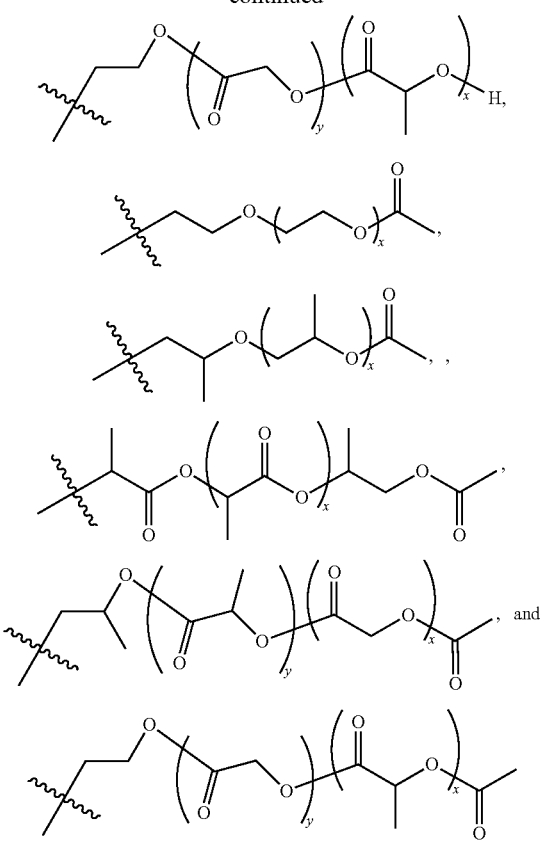

The disclosure also provides a prodrug of Formula XVI:

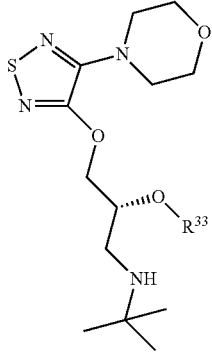

(XVI)

or a pharmaceutically acceptable composition, salt, or isotopic derivative thereof.

$R^{33}$ is selected from: carbonyl linked polyethylene glycol, carbonyl linked polypropylene glycol, carbonyl linked polypropylene oxide, polylactic acid, and poly(lactic-co-glycolic acid), a polyglycolic acid, a polyester, polyamide,

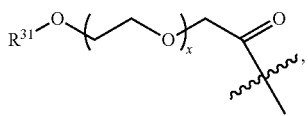

or other biodegradable polymer, wherein each $R^{33}$ is optionally substituted with $R^{31}$, and wherein each of $R^{33}$ with a terminal hydroxy or carboxy group can be substituted to create an ether or ester, respectively.

In one embodiment $R^{31}$ is —C(O)A, alkyl, or PEG.
In one embodiment $R^{31}$ is —C(O)A, wherein A is methyl.
In one embodiment $R^{33}$ is

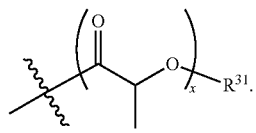

The disclosure also provides a prodrug of Formula XVII:

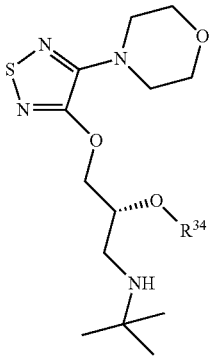

(XVII)

or a pharmaceutically acceptable composition, salt, or isotopic derivative thereof.

$R^{34}$ is selected from: $R^{36}$, carbonyl linked polyethylene glycol, carbonyl linked polypropylene glycol, carbonyl linked polypropylene oxide, polylactic acid, and poly(lactic-co-glycolic acid), a polyglycolic acid, a polyester, polyamide,
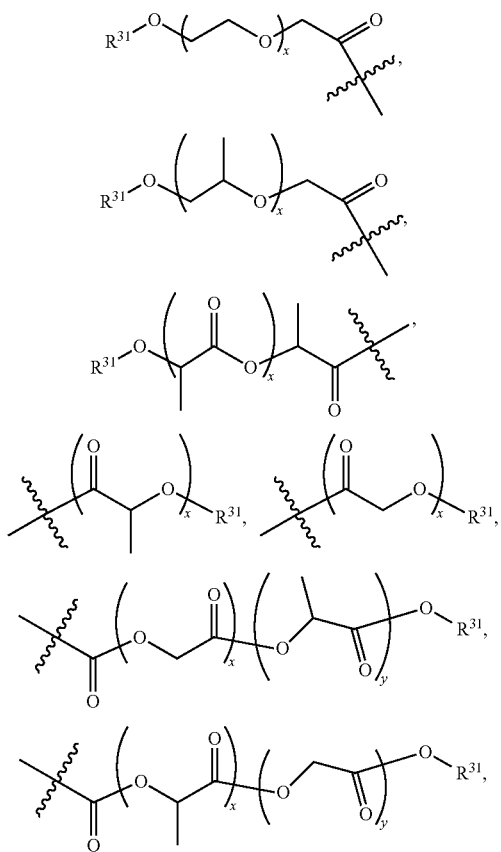
or other biodegradable polymer, wherein each $R^{34}$ other than $R^{36}$ is substituted with at least one $L^4$-$R^{52}$;
$R^{36}$ is selected from:
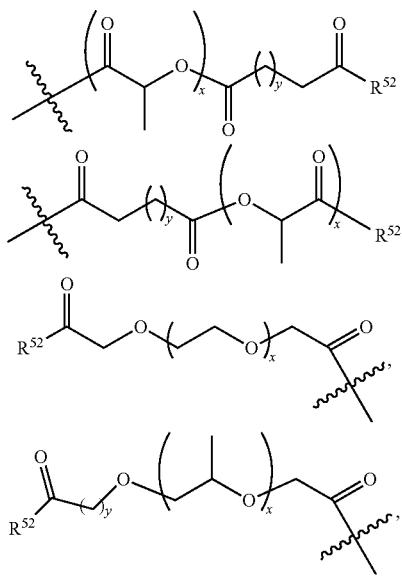
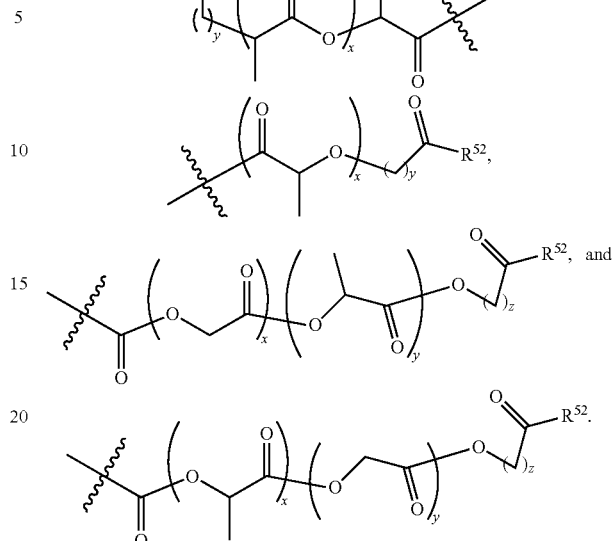
$R^{52}$ is selected from
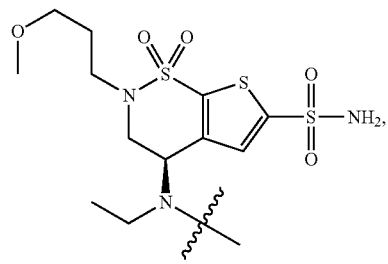
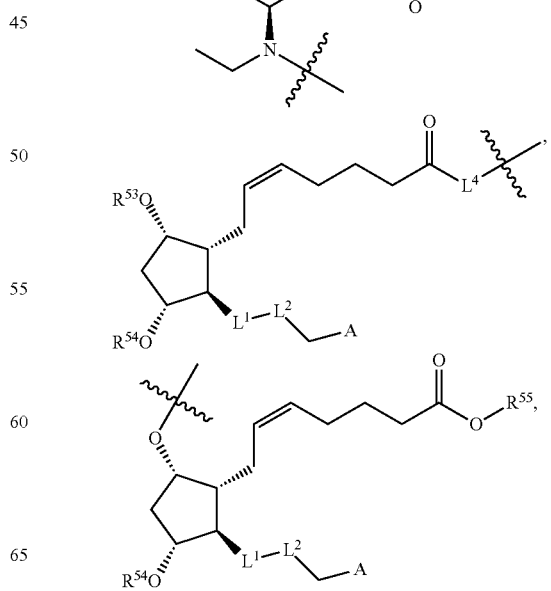

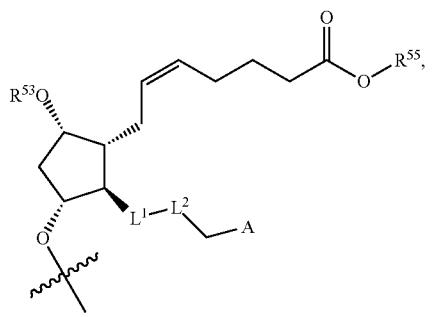

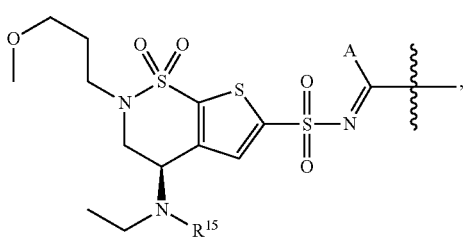

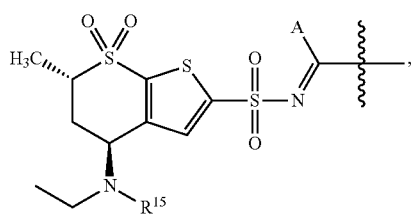

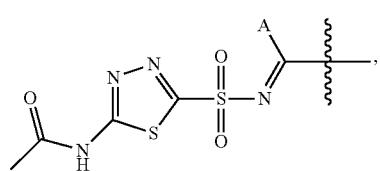

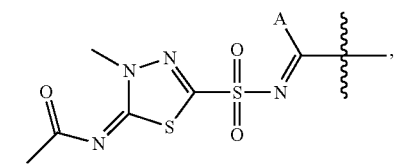

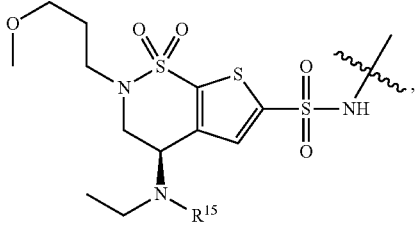

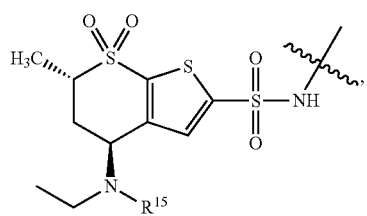

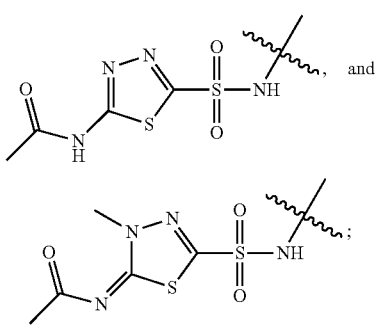

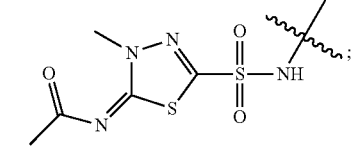

z is 0, 1, 2, 3, 4 or 5;

$R^{53}$ and $R^{54}$ are independently selected from: —C(O)$R^4$, C(O)A, and hydrogen, each of which except hydrogen can be optionally substituted with $R^5$;

$R^{55}$ is selected from:

(i) polyethylene glycol, polypropylene glycol, polypropylene oxide, polylactic acid, and poly(lactic-co-glycolic acid), polyglycolic acid, or a polyester, a polyamide, or other biodegradable polymers, wherein a terminal hydroxy or carboxy group can be substituted to create an ether or ester, respectively;

(ii) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl;

(iii) an unsaturated fatty acid residue including but not limited the carbon fragment taken from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alpha-linolenic acid (—$(CH_2)_8(CHCHCH_2)_3CH_3$)) stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid or mead acid;

(iv) alkyl, cycloalkyl, cycloalkylalkyl, heterocycle, heterocycloalkyl, arylalkyl, heteroarylalkyl;

wherein A, x, y, $R^5$, $L^1$, and $L^2$ are defined above.

The disclosure also provides a prodrug of Formula XVIII or Formula XIX:

(XVIII)

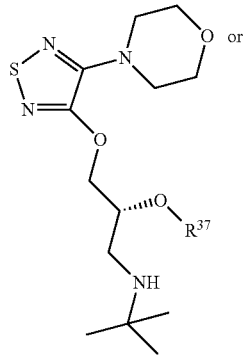

-continued

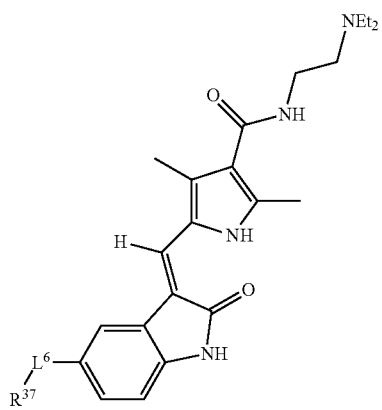

or a pharmaceutically acceptable composition, salt, or isotopic derivative thereof.

$R^{37}$ is selected from: $R^{38}$, polyethylene glycol, polypropylene glycol, polypropylene oxide, polylactic acid, poly(lactic-co-glycolic acid), a polyglycolic acid, a polyester, a polyamide, or other biodegradable polymer, wherein each $R^{37}$ other than $R^{38}$ is substituted with at least one $L^4$-$R^{59}$;

$L^6$ is selected from —O—, —NH—, —N(alkyl)$_{1-4}$-, —C(O)O—, —S—, —C(O)— and —OC(O)—;

$R^{38}$ is selected from:

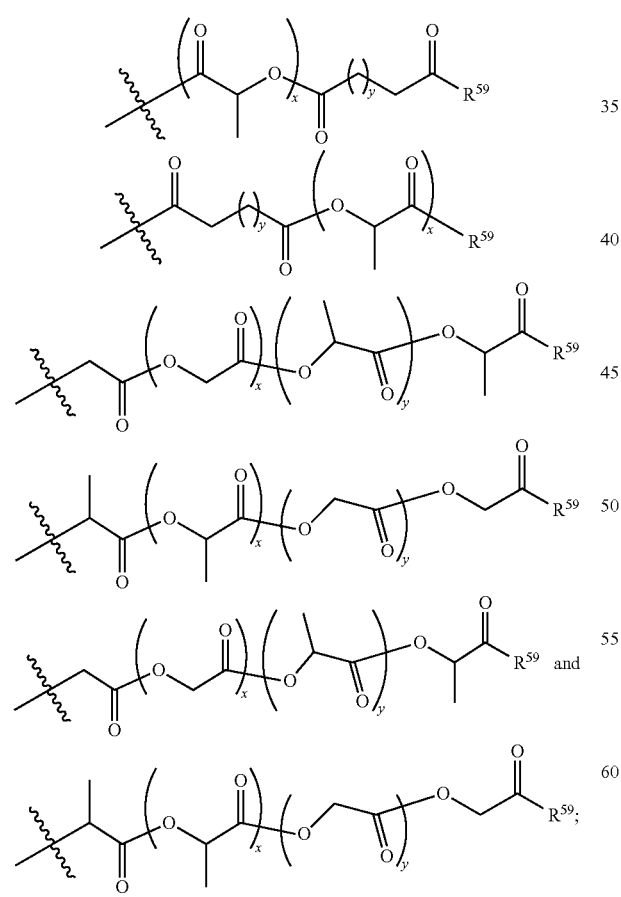

and $R^{59}$ is selected from

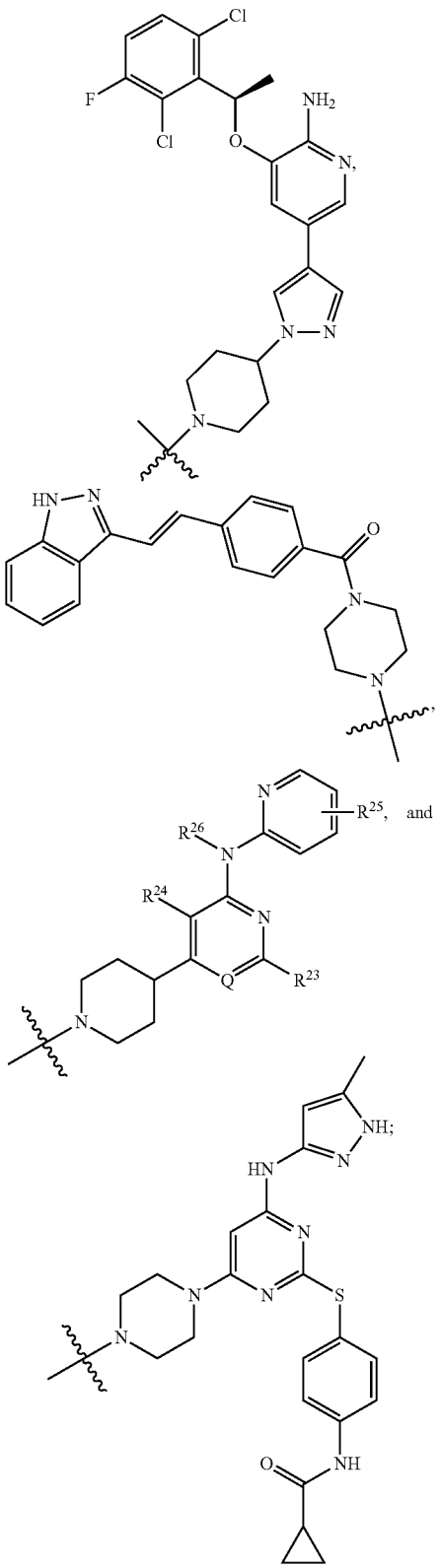

wherein x, y, $R^{24}$, $R^{25}$, $R^{26}$, and $L^4$ are as defined above.

The disclosure also provides a prodrug of Formula XX, Formula XXI, Formula XXII, Formula XXIII:

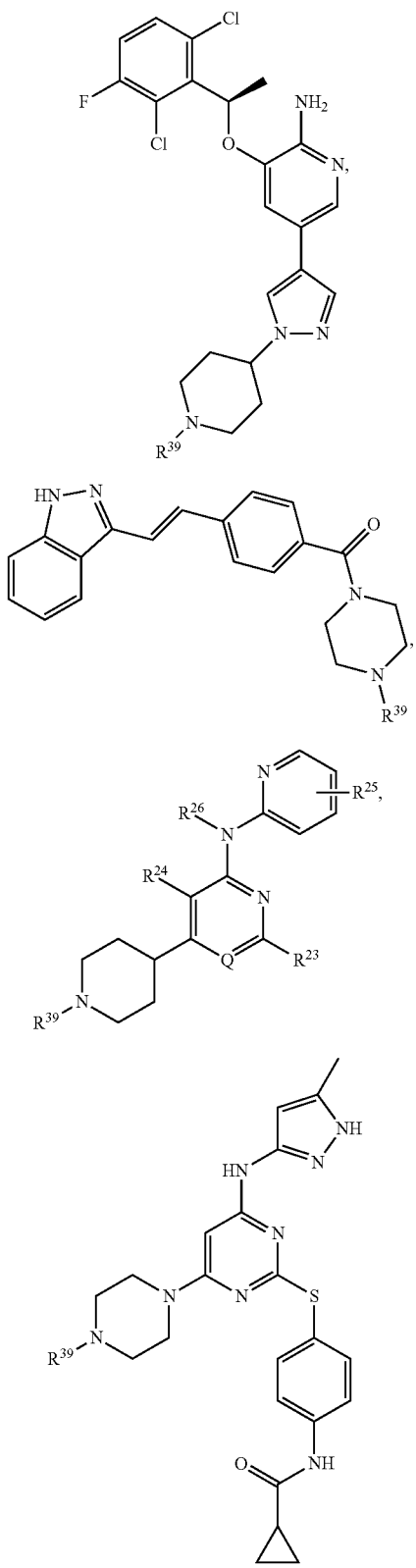

(XX)

(XXI)

(XXII)

(XXIII)

or a pharmaceutically acceptable composition, salt, or isotopic derivative thereof.

$R^{39}$ is selected from: $R^{40}$, carbonyl linked polyethylene glycol, carbonyl linked polypropylene glycol, carbonyl linked polypropylene oxide, polylactic acid, and poly(lactic-co-glycolic acid), a polyglycolic acid, a polyester, polyamide,

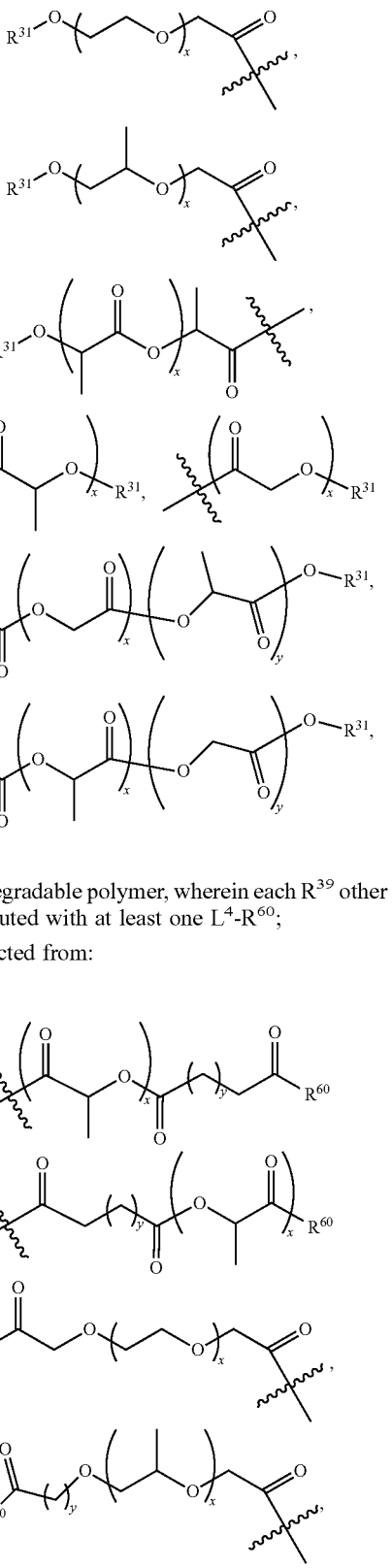

or other biodegradable polymer, wherein each $R^{39}$ other than $R^{40}$ is substituted with at least one $L^4$-$R^{60}$;

$R^{40}$ is selected from:

69
-continued
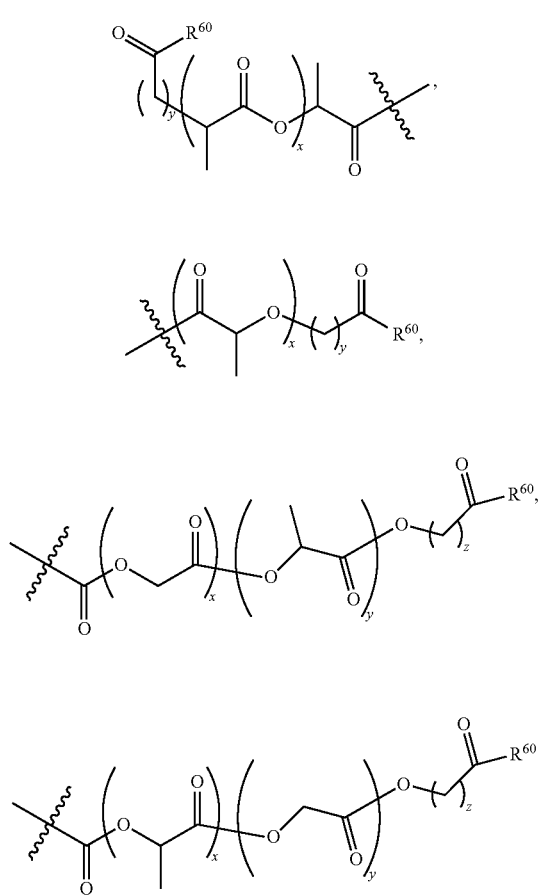
R<sup>60</sup> is selected from:
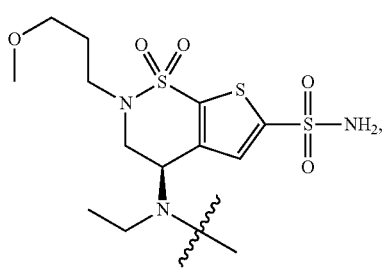
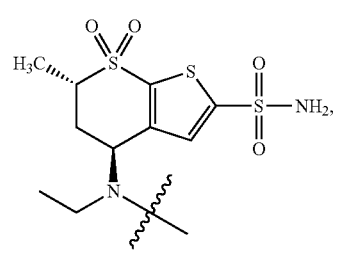
70
-continued
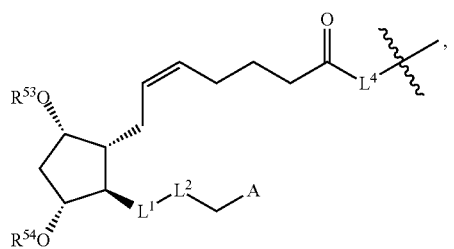
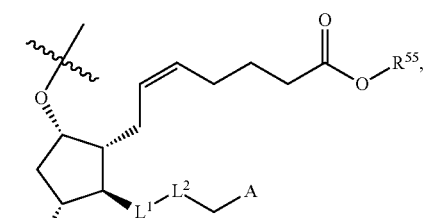
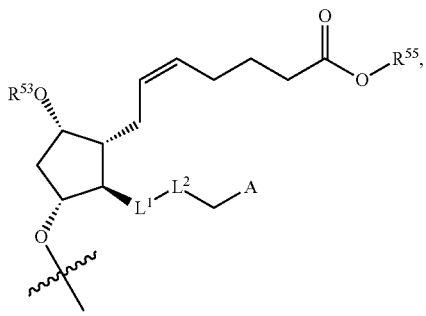
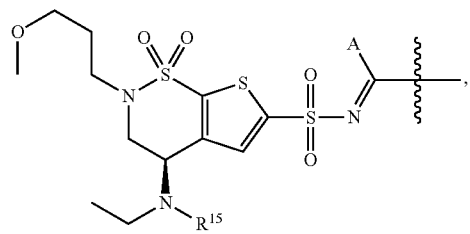
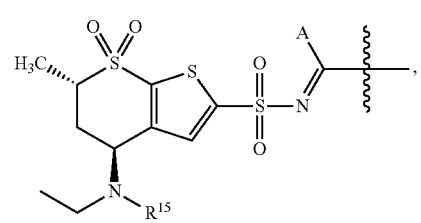
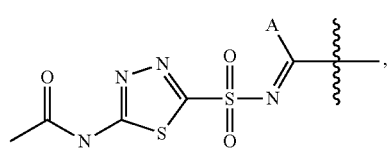
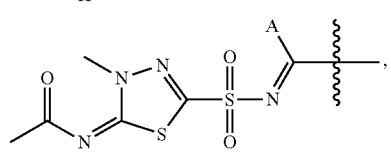

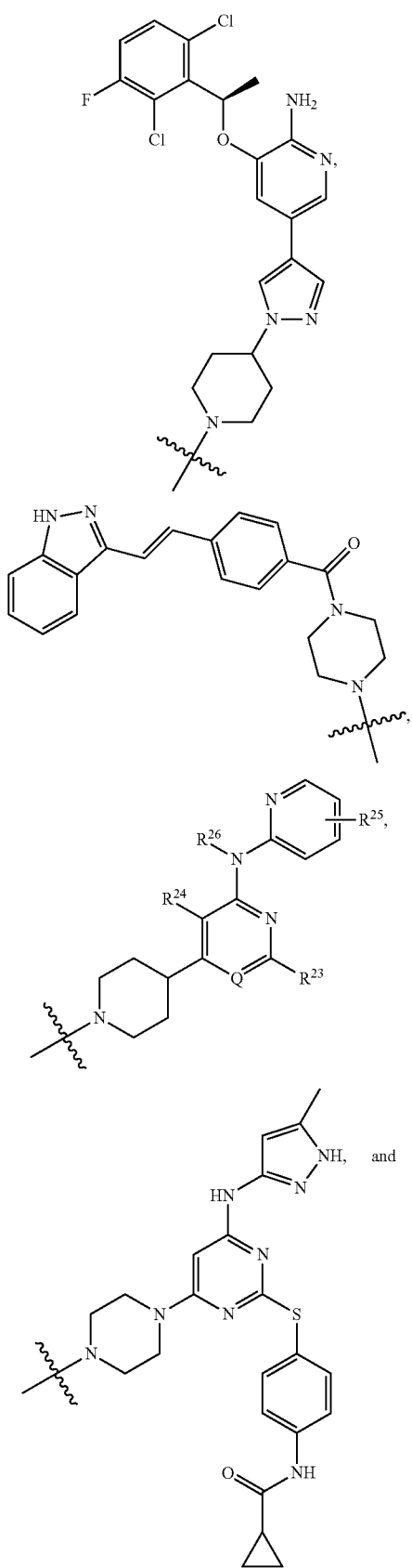
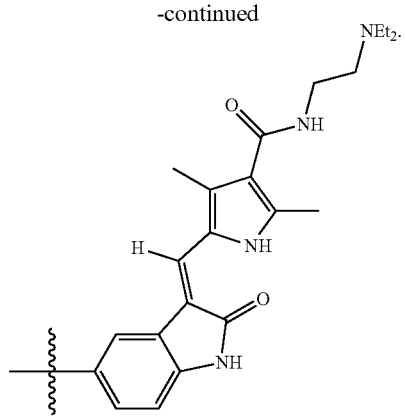
In an alternative embodiment, a
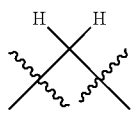
moiety in a R group that can be substituted with $R^5$ as defined herein is instead substituted with oxo to form
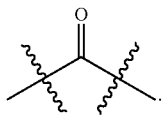 [SMILES: *C(*)=O]
In another alternative embodiment, x is 0.
In another alternative embodiment, y is 0.
In another embodiment, a compound selected from the following is provided:
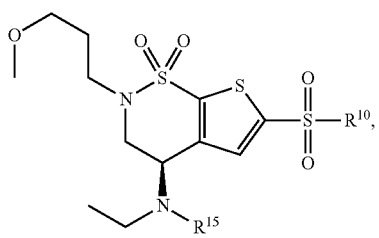
(III)
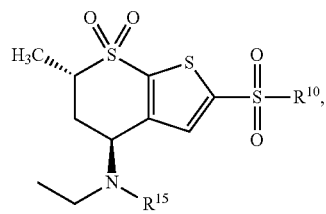
(IV)
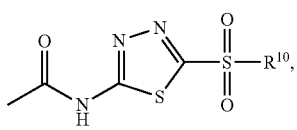
(V)

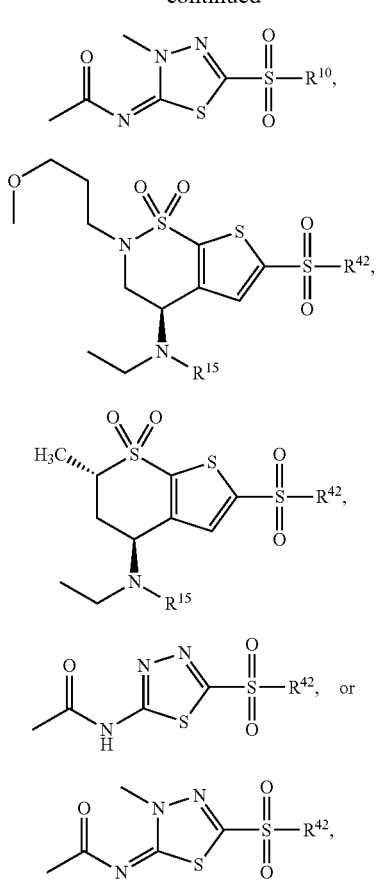

wherein $R^{15}$ is as defined above and $R^{10}$ or $R^{42}$ is selected from: —NHC(O)$C_{1-20}$alkyl, —NHC(O)$C_{1-20}$alkenyl, —NHC(O)$C_{1-20}$alkynyl, —NHC(O)($C_{1-20}$alkyl with at least one $R^5$ substituent on the alkyl chain), —NHC(O) ($C_{1-20}$alkenyl, with at least one $R^5$ substituent on the alkenyl chain) —NHC(O)($C_{1-20}$alkynyl, with at least one $R^5$ substituent on the alkynyl chain), —NH(lactic acid)$_{2-20}$C(O) $C_{1-20}$alkyl, —NH(lactic acid)$_{2-10}$C(O)$C_{1-20}$alkyl, —NH(lactic acid)$_{4-20}$C(O)$C_{1-20}$alkyl, —NH(lactic acid)$_{2-20}$C(O) $C_{1-10}$alkyl, —NH(lactic acid)$_{2-20}$C(O)$C_{4-10}$alkyl, —NH(lactic acid)$_{2-20}$C(O)OH, —NH(lactic acid)$_{2-10}$C(O)OH, —NH (lactic acid)$_{4-20}$C(O)OH, —NH(lactic acid)$_{2-10}$C(O)OH, —NH(lactic acid)$_{4-10}$C(O)OH, —NH(lactide-co-glycolide)$_{2-10}$C(O)$_{C1-20}$alkyl, —NH(lactide-co-glycolide)$_{4-10}$C(O)$_{C1-20}$alkyl, —NH(lactide-co-glycolide)$_{2-10}$C(O)$_{C1-10}$alkyl, —NH(lactide-co-glycolide)$_{2-10}$C(O)$_{C4-20}$alkyl, —NH(glycolic acid)$_{2-10}$ C(O)$_{C1-10}$alkyl, —NH(glycolic acid)$_{4-10}$C(O)$_{C1-10}$alkyl, —NH(lactic acid)$_{4-10}$C(O)$_{C1-10}$alkyl, —NH(lactic acid)$_{2-10}$C(O)$_{C1-10}$ alkyl, NH(lactic acid)$_{2-10}$C(O)$_{C4-10}$alkyl, —NH(lactic acid)$_{2-10}$C(O)$_{C4-10}$alkyl, and —NH(lactic acid)$_{2-10}$C(O)$_{C4-10}$alkyl.

Pharmaceutical compositions comprising a compound or salt of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII together with a pharmaceutically acceptable carrier are also disclosed.

Methods of treating or preventing ocular disorders, including glaucoma, a disorder mediated by carbonic anhydrase, a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD) or diabetic retinopathy are disclosed comprising administering a therapeutically effective amount of a compound or salt or Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII to a host, including a human, in need of such treatment.

In another embodiment, an effective amount of a compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII is provided to decrease intraocular pressure (IOP) caused by glaucoma. In an alternative embodiment, the compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII can be used to decrease intraocular pressure (IOP), regardless of whether it is associated with glaucoma.

In one embodiment, the disorder is associated with an increase in intraocular pressure (IOP) caused by potential or previously poor patient compliance to glaucoma treatment. In yet another embodiment, the disorder is associated with potential or poor neuroprotection through neuronal nitric oxide synthase (NOS). The active compound or its salt or prodrug provided herein may thus dampen or inhibit glaucoma in a host, by administration of an effective amount in a suitable manner to a host, typically a human, in need thereof.

Methods for the treatment of a disorder associated with glaucoma, increased intraocular pressure (IOP), and optic nerve damage caused by either high intraocular pressure (IOP) or neuronal nitric oxide synthase (NOS) are provided that includes the administration of an effective amount of a compound Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII or a pharmaceutically acceptable salt thereof, optionally in a pharmaceutically acceptable carrier are also disclosed.

Methods for the treatment of a disorder associated with age-related macular degeneration (AMD) are provided that includes the administration of an effective amount of a compound Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII or a pharmaceutically acceptable salt thereof, optionally in a pharmaceutically acceptable carrier are also disclosed.

Methods for treatment of a disorder that using a carbonic anhydrase inhibitor to treat a patient in need thereof also disclosed.

The present invention includes at least the following features:

(a) a compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII as described herein, and pharmaceutically acceptable salts and prodrugs thereof (each of which and all subgenuses and species thereof are considered individually and specifically described);

(b) Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII as described herein, and pharmaceutically acceptable salts and prodrugs thereof, for use in treating or preventing an ocular disorder as further described herein;

(c) Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII as described herein, and pharmaceutically acceptable salts and prodrugs thereof, for use in treating or preventing disorders related to an ocular disorder such as glaucoma, a disorder mediated by carbonic anhydrase, a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD) or diabetic retinopathy;

(d) use of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII and pharmaceutically acceptable salts and prodrugs thereof in the manufacture of a medicament for use in treating or preventing glaucoma and disorders involving increased intraocular pressure (IOP) or nerve damage related to either IOP or nitric oxide synthase (NOS) and other disorders described further herein;

(e) use of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII and pharmaceutically acceptable salts and prodrugs thereof in the manufacture of a medicament for use in treating or preventing age-related macular degeneration (AMD) and other disorders described further herein;

(f) a process for manufacturing a medicament intended for the therapeutic use for treating or preventing glaucoma and disorders involving nerve damage related to both (IOP) and nitric oxide synthase (NOS) and other disorders described further herein characterized in that Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII as described herein is used in the manufacture;

(g) a pharmaceutical formulation comprising an effective host-treating amount of the Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII or a pharmaceutically acceptable salt or prodrug thereof together with a pharmaceutically acceptable carrier or diluent;

(h) Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII as described herein in substantially pure form, (e.g., at least 90 or 95%);

(i) processes for the manufacture of the compounds Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII and salts, compositions, dosage forms thereof; and (j) processes for the preparation of therapeutic products including drug delivery agents that contain an effective amount of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII as described herein.

DETAILED DESCRIPTION

I. TERMINOLOGY

Figure 1:
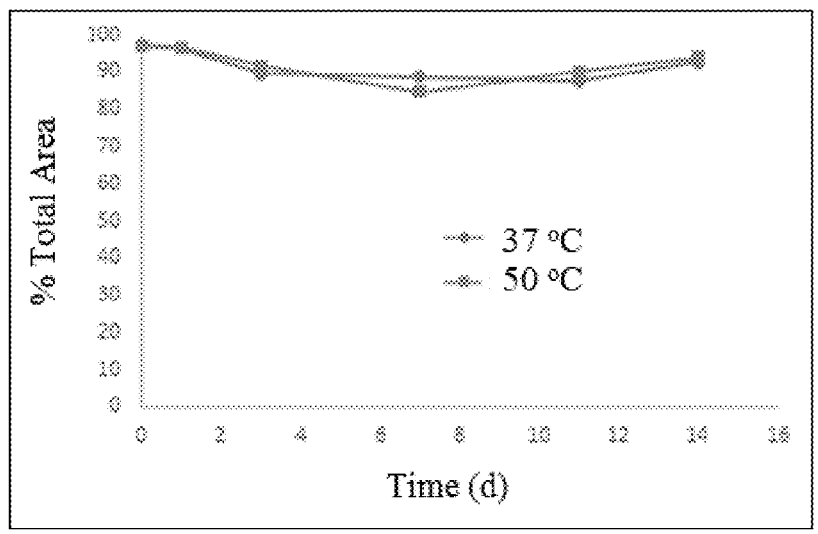
FIG. 1 illustrates the stability of brinzolamide at physiological conditions (37° C.) and at accelerated degradation conditions (50° C.) over 14 days. The x-axis represents time (days) and the y-axis represents the amount of undegraded brinzolamide as a percentage of the total brinzolamide amount as analyzed by RP-HPLC.

The presently disclosed subject matter may be embodied in many different forms and should not be construed as limited to the embodiments set forth herein. Indeed, many modifications and other embodiments of the presently disclosed subject matter will come to mind for one skilled in the art to which the presently disclosed subject matter pertains having the benefit of the teachings presented in the descriptions included herein. Therefore, it is to be understood that the presently disclosed subject matter is not to be limited to the specific embodiments disclosed and that modifications and other embodiments are intended to be included within the scope of the disclosed subject matter.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, cis/trans isomers, tautomers, racemates and other isomers, such as rotamers, as if each is specifically described.

The compounds in any of the Formulas may be prepared by chiral or asymmetric synthesis from a suitable optically pure precursor or obtained from a racemate or mixture of enantiomers or diastereomers by any conventional technique, for example, by chromatographic resolution using a chiral column, TLC or by the preparation of diastereoisomers, separation thereof and regeneration of the desired enantiomer or diastereomer. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron,* 2725 (1977); E. L. Eliel *Stereochemistry of Carbon Compounds* (McGraw-Hill, N Y, 1962); and S. H. Wilen *Tables of Resolving Agents and Optical Resolutions* 268 (E. L. Eliel ed., Univ. of Notre Dame Press, Notre Dame, Ind., 1972, *Stereochemistry of Organic Compounds,* Ernest L. Eliel, Samuel H. Wilen and Lewis N. Manda (1994 John Wiley & Sons, Inc.), and *Stereoselective Synthesis A Practical Approach,* Mihaly Nõgrãdi (1995 VCH Publishers, Inc., NY, NY).

The terms "a" and "an" do not denote a limitation of quantity, but rather denote the presence of at least one of the referenced item. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and are independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII and the use of compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorus, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes isotopically modified compounds of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII. Isotopically labeled compounds of this invention and prodrugs thereof can generally be prepared by carrying out the procedures disclosed in the schemes or in the examples and preparations described below by substituting an isotopically labeled reagent for a non-isotopically labeled reagent.

By way of general example and without limitation, isotopes of hydrogen, for example, deuterium ($^2$H) and tritium ($^3$H) may be used anywhere in described structures that achieves the desired result. Alternatively or in addition, isotopes of carbon, e.g., $^{13}$C and $^{14}$C, may be used. In one embodiment, the isotopic substitution is deuterium for hydrogen at one or more locations on the molecule to improve the performance of the drug, for example, the pharmacodynamics, pharmacokinetics, biodistribution, half-life, stability, AUC, $T_{max}$, $C_{max}$, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched at any location of interest. In one embodiment deuterium is 90, 95 or 99% enriched at a desired location.

In one embodiment, the substitution of a hydrogen atom for a deuterium atom can be provided in any of A, $L^1$, or $L^2$. In one embodiment, the substitution of a hydrogen atom for a deuterium atom occurs within an R group selected from any of R, $R^1$, $R^2$, $R^3$, $R^4$, $R^5$, $R^6$, $R^{6'}$, $R^7$, $R^8$, $R^{8'}$, $R^{11}$, $R^{12}$, $R^{13}$, $R^{14}$, $R^{15}$, $R^{16}$, $R^{17}$, $R^{18}$, $R^{19}$ $R^{20}$, $R^{21}$, $R^{22}$, $R^{23}$, $R^{24}$, $R^{25}$, $R^{26}$, $R^{27}$, $R^{31}$, $R^{32}$, $R^{33}$, $R^{34}$, $R^{35}$ $R^{36}$ $R^{37}$ $R^{38}$ $R^{39}$ $R^{40}$, $R^{50}$, $R^{51}$, $R^{52}$, $R^{53}$ $R^{54}$ $R^{54}$ $R^{56}$ $R^{57}$ $R^{58}$ $R^{59}$ $R^{60}$. For example, when any of R groups are, or contain for example through substitution, methyl, ethyl, or methoxy, the alkyl residue may be deuterated (in non-limiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, $OCDH_2$, $OCD_2H$, or $OCD_3$ etc.

The compound of the present invention may form a solvate with a solvent (including water). Therefore, in one embodiment, the invention includes a solvated form of the active compound. The term "solvate" refers to a molecular complex of a compound of the present invention (including salts thereof) with one or more solvent molecules. Examples of solvents are water, ethanol, dimethyl sulfoxide, acetone and other common organic solvents. The term "hydrate" refers to a molecular complex comprising a compound of the invention and water.

Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") is defined by context and can in addition to its literary meaning indicate a point of attachment for a substituent. For example, —(C=O)NH$_2$ is attached through carbon of the keto (C=O) group. A dash ("-") can also indicate a bond within a chemical structure. For example —C(O)—NH$_2$ is attached through carbon of the keto group which is bound to an amino group (NH$_2$).

An equal sign ("=") is defined by context and can in addition to its literary meaning indicate a point of attachment for a substituent wherein the attachment is through a double bond. For example, =CH$_2$ represents a fragment that is doubly bonded to the parent structure and consists of one carbon with two hydrogens bonded in a terminal fashion. =CHCH$_3$ on the other hand represents a fragment that is doubly bonded to the parent structure and consists of two carbons. In the above example it should be noted that the stereoisomer is not delineated and that both the cis and trans isomer are independently represented by the group.

The term "substituted", as used herein, means that any one or more hydrogens on the designated atom or group is replaced with a moiety selected from the indicated group, provided that the designated atom's normal valence is not exceeded. For example, when the substituent is oxo (i.e., =O), then in one embodiment, two hydrogens on the atom are replaced. When an oxo group replaces two hydrogens in an aromatic moiety, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates.

A stable compound or stable structure refers to a compound with a long enough residence time to either be used as a synthetic intermediate or as a therapeutic agent, as relevant in context.

"Alkyl" is a straight chain saturated aliphatic hydrocarbon group. In certain embodiments, the alkyl is $C_1$-$C_2$, $C_1$-$C_3$, $C_1$-$C_6$, or $C_1$-$C_{30}$ (i.e., the alkyl chain can be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbons in length). The specified ranges as used herein indicate an alkyl group with length of each member of the range described as an independent species. For example, the term $C_1$-$C_6$ alkyl as used herein indicates a straight alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$alkyl($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl($C_3$-$C_7$cycloalkyl). Alkyls can be further substituted with alkyl to make branched alkyls. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane and 2,3-dimethylbutane. In one embodiment, the alkyl group is optionally substituted as described above.

"Alkenyl" is a straight chain aliphatic hydrocarbon group having one or more carbon-carbon double bonds each of which is independently either cis or trans that may occur at a stable point along the chain. In one embodiment, the double bond in a long chain similar to a fatty acid has the stereochemistry as commonly found in nature. Non-limiting examples are $C_2$-$C_{30}$alkenyl, $C_{10}$-$C_{30}$alkenyl (i.e., having 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbons), and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. Alkenyls can be further substituted with alkyl to make branched alkenyls. In one embodiment, the alkenyl group is optionally substituted as described above.

"Alkynyl" is a straight chain aliphatic hydrocarbon group having one or more carbon-carbon triple bonds that may occur at any stable point along the chain, for example, $C_2$-$C_8$alkynyl or $C_{10}$-$C_{30}$alkynyl (i.e., having 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbons). The specified ranges as used herein indicate an alkynyl group having each member of the range described as an independent species, as described above for the alkyl moiety. Alkynyls can be further substituted with alkyl to make branched alkynyls. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1 to 8 carbon moiety, 1 to 6 carbon moiety, or an indicated number of carbon atoms, for example $C_1$-$C_4$alkylene, $C_1$-$C_3$alkylene, or $C_1$-$C_2$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkenylalkynyl" in one embodiment is a bivalent hydrocarbon having at least one carbon-carbon double bond and at least one carbon-carbon triple bond. It will be recognized to one skilled in the art that the bivalent hydrocarbon will not result in hypervalency, for example, hydrocarbons that include —C=C=C—C or —C≡C=C—C, and must be stable. Alkenylalkynyls, for example, can be a 4 to 8 carbon moiety, 4 to 6 carbon moiety, or an indicated number of carbon atoms, for example $C_4$-$C_6$alkenylalkynyls.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Amide" or "carboxamide" is —C(O)NR$^a$R$^b$ wherein R$^a$ and R$^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, R$^a$ and R$^b$ can form a $C_3$-$C_7$heterocyclic ring. In one embodiment, the R$^a$ and R$^b$ groups are each independently optionally substituted as described above.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms. In another embodiment, a carbocyclic ring comprises a caged carbocyclic group. In one embodiment, a carbocyclic ring comprises a bridged carbocyclic group. An example of a caged carbocyclic group is adamantane. An example of a bridged carbocyclic group includes bicyclo[2.2.1]heptane (norbornane). In one embodiment, the caged carbocyclic group is optionally substituted as described above. In one embodiment, the bridged carbocyclic group is optionally substituted as described above.

"Hydroxyalkyl" is an alkyl group as previously described, substituted with at least one hydroxyl substituent.

"Halo" or "halogen" indicates independently any of fluoro, chloro, bromo, and iodo.

"Aryl" indicates aromatic groups containing only carbon in the aromatic ring or rings. In one embodiment, the aryl groups contain 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 4 to 7-membered saturated cyclic group that optionally contains 1 or 2 heteroatoms independently chosen from N, O, B, and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above. In one embodiment, aryl groups include, for example, dihydroindole, dihydrobenzofuran, isoindoline-1-one and indolin-2-one that can be optionally substituted.

The term "heterocycle," or "heterocyclic ring" as used herein refers to a saturated or a partially unsaturated (i.e., having one or more double and/or triple bonds within the ring without aromaticity) carbocyclic radical of 3 to about 12, and more typically 3, 5, 6, 7 to 10 ring atoms in which at least one ring atom is a heteroatom selected from nitrogen, oxygen, phosphorus, silicon, boron and sulfur, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, and S) or a bicycle having 5 to 10 ring members (4 to 9 carbon atoms and 1 to 6 heteroatoms selected from N, O, P, and S), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocycle groups herein are optionally substituted independently with one or more substituents described herein.

"Heteroaryl" indicates a stable monocyclic aromatic ring which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1, 2, 3, or 4, or in some embodiments from 1 or 2, heteroatoms chosen from N, O, B, and S, with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 to 7 ring atoms.

In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Heteroaryl groups are optionally substituted independently with one or more substituents described herein.

"Heterocycloalkyl" is a saturated ring group. It may have, for example, 1, 2, 3, or 4 heteroatoms independently chosen from N, S, and O, with remaining ring atoms being carbon. In a typical embodiment, nitrogen is the heteroatom. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "esterase" refers to an enzyme that catalyzes the hydrolysis of an ester. As used herein, the esterase can catalyze the hydrolysis of prostaglandins described herein. In certain instances, the esterase includes an enzyme that can catalyze the hydrolysis of amide bonds of prostaglandins.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

A "pharmaceutical composition" is a composition comprising at least one active agent, such as a compound or salt of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII, and at least one other substance, such as a pharmaceutically acceptable carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" includes a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salt can be prepared by reacting free acid forms of these compounds with a stoichiometric amount of the appropriate base (such as Na, Ca, Mg, or K hydroxide, carbonate, bicarbonate, or the like), or by reacting a free base form of the compound with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in Remington's Pharmaceutical Sciences, 17th ed., Mack Publishing Company, Easton, Pa., p. 1418 (1985).

The term "carrier" refers to a diluent, excipient, or vehicle with which an active compound is provided.

A "patient" or "host" or "subject" is typically a human, however, may be more generally a mammal. In an alternative embodiment it can refer to for example, a cow, sheep, goat, horses, dog, cat, rabbit, rat, mice, fish, bird and the like.

A "prodrug" as used herein, means a compound which when administered to a host in vivo is converted into a parent drug. As used herein, the term "parent drug" means the active form of the compounds that renders the biological effect to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Non-limiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others. In certain aspects of the present invention, at least one hydrophobic group is covalently bound to the parent drug to slow release of the parent drug in vivo.

A "therapeutically effective amount" of a pharmaceutical composition/combination of this invention means an amount effective, when administered to a patient, to provide a therapeutic benefit such as an amelioration of symptoms of the selected disorder, typically an ocular disorder In certain aspects, the disorder is glaucoma, a disorder mediated by carbonic anhydrase, a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD) or diabetic retinopathy.

"γ-linolenic acid" is gamma-linolenic acid.

The term "polymer" as used herein includes oligomers.

II. DETAILED DESCRIPTION OF THE ACTIVE COMPOUNDS

According to the present invention, compounds of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII are provided:

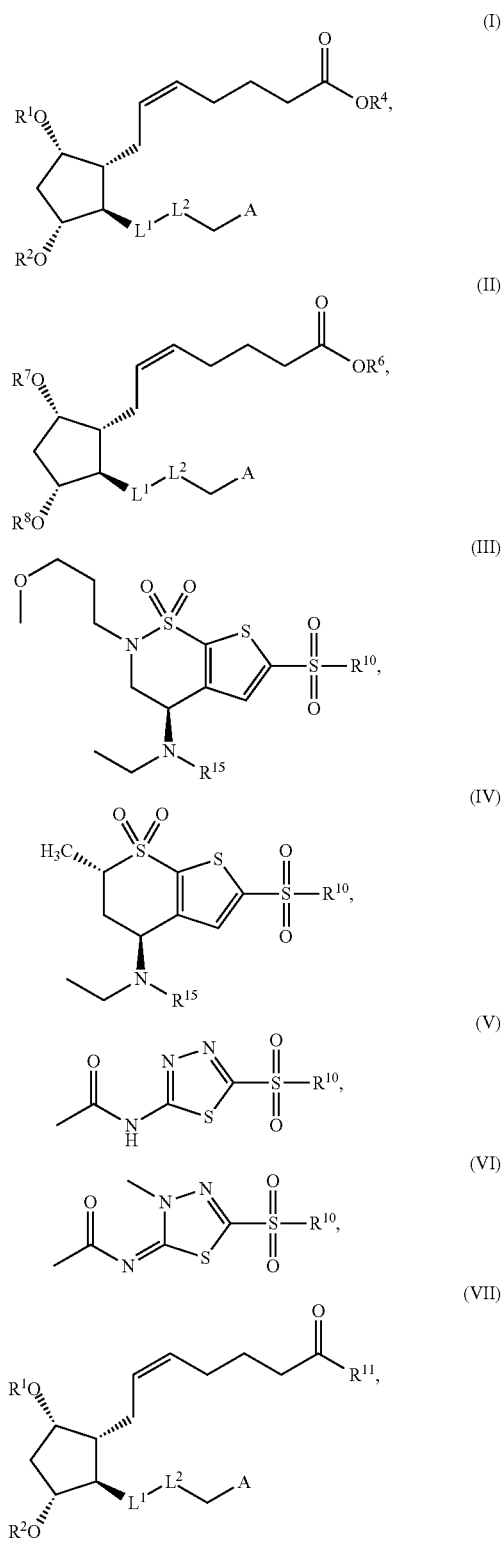

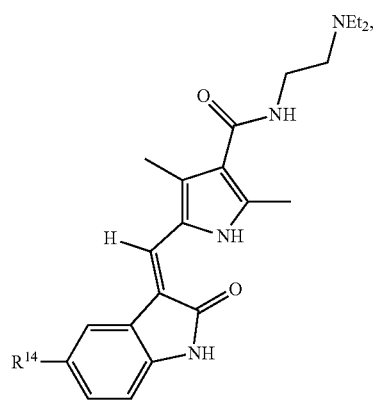
(VIII)
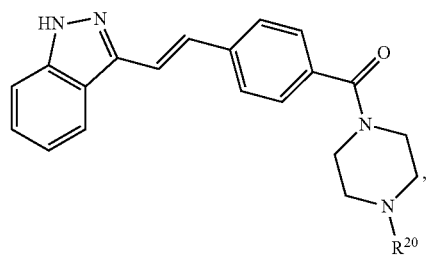
(IX)
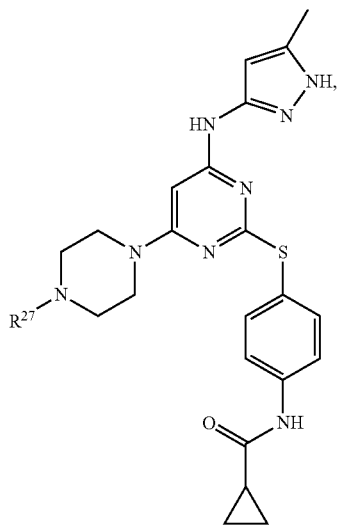
(X)
(XI)
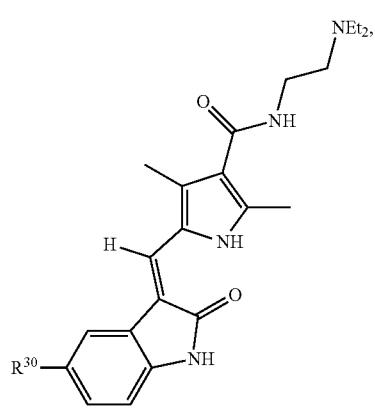
(XII)
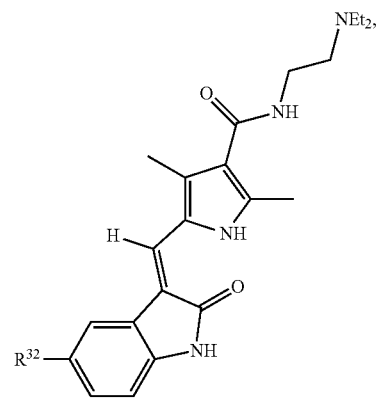
(XIV)
(XV)

(XVI)
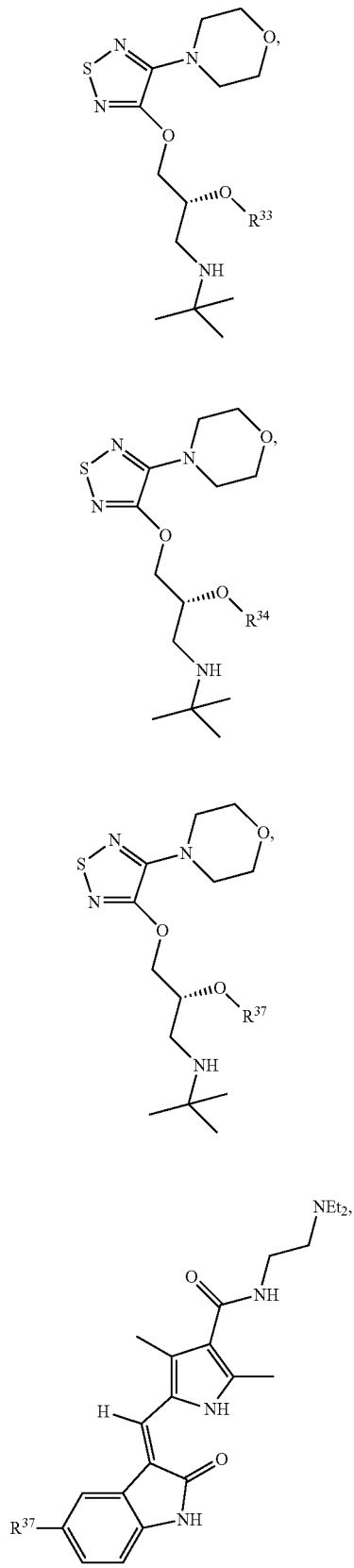
(XVII)
(XVIII)
(XIX)
(XX)
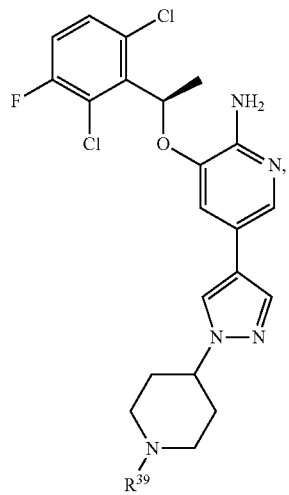
(XXI)
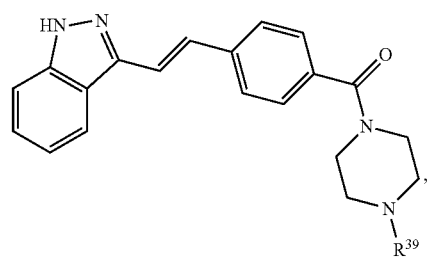
(XXII)
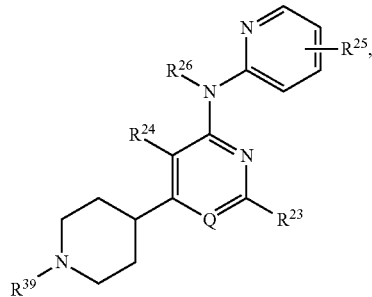
(XXIII)
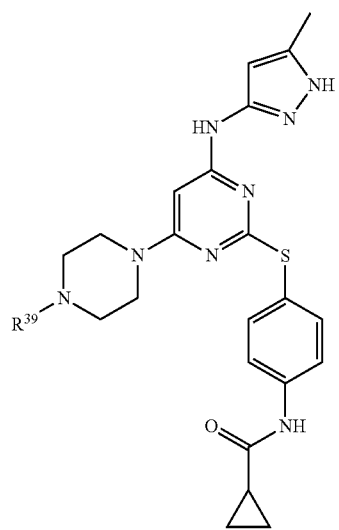
as well as the pharmaceutically acceptable salts and compositions thereof. Formula I and Formula II can be considered a prostaglandin covalently bound to a hydrophobic moiety through an ester linkage that may be metabolized in the eye to afford the parent prostaglandin. Formula III can be considered Brinzolamide covalently bound to a hydrophobic moiety through an N-sulfonyl aldimine or ketimine linkage that may be metabolized in the eye to afford Brinzolamide. Formula IV can be considered Dorzolamide covalently bound to a hydrophobic moiety through an N-sulfonyl aldimine or ketimine linkage that may be metabolized in the eye to afford Dorzolamide. Formula V can be considered Acetazolamide covalently bound to a hydrophobic moiety through an N-sulfonyl aldimine or ketimine linkage that may be metabolized in the eye to afford Acetazolamide. Formula VI can be considered Methazolamide covalently bound to a hydrophobic moiety through an N-sulfonyl aldimine or ketimine linkage that may be metabolized in the eye to afford Methazolamide. Formula VII can be considered a prostaglandin covalently bound to a carbonic anhydrase inhibitor through either a direct bond or a connecting fragment bound to both species that may be metabolized in the eye to afford the parent prostaglandin and a carbonic anhydrase inhibitor. Formula VIII can be considered a derivative of Sunitinib covalently bound to either a prostaglandin or a carbonic anhydrase inhibitor through an ester or N-sulfonyl aldimine/ketimine linkage respectively that may be metabolized in the eye to afford the parent Sunitinib derivative as well as either a prostaglandin or a carbonic anhydrase inhibitor. Formula IX can be considered Crizotinib covalently bound to a hydrophobic moiety through an amide bond that may be metabolized in the eye to release Crizotinib. Formula X can be considered KW-2449 covalently bound to a hydrophobic moiety through an amide bond that may be metabolized in the eye to release KW-2449. Formula XI can be considered an active DLK inhibitor covalently bound to a hydrophobic moiety through an amide bond that may be metabolized in the eye to release the active DLK inhibitor. Formula XII can be considered a derivative of Tozasertib covalently bound to a hydrophobic moiety through an amide bond that may be metabolized in the eye to release Tozasertib. In one embodiment, the compound is a treatment for glaucoma, and therefore can be used as an effective amount to treat a host in need of glaucoma treatment. In another embodiment, the compound acts through a mechanism other than those associated with glaucoma to treat a disorder described herein in a host, typically a human.

The compounds, as described herein, may include, for example, prodrugs, which are hydrolysable to form the active carboxylic acid compound. Thus, when a compound of Formula I or Formula II is administered to a mammalian subject, typically a human, the ester modifications may be cleaved to release the parent free acid compound of Formula XIII.

(XIII)

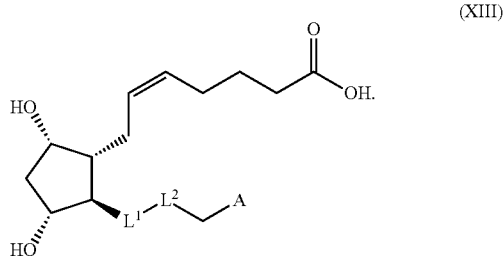

The compounds, as described herein, may include, for example, prodrugs, which are hydrolysable to form the active sulfonamide compound. Thus when a compound of Formula III Formula IV, Formula V, or Formula VI is administered to a mammalian subject, typically a human, the aldimine or ketimine modifications may be cleaved to release Brinzolamide, Dorzolamide, Acetazolamide, or Methazolamide respectively.

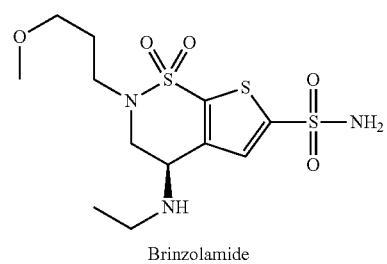

Brinzolamide

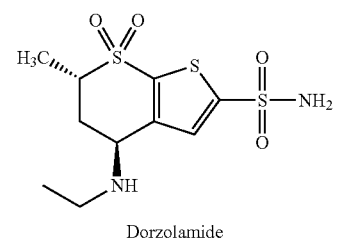

Dorzolamide

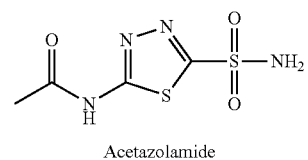

Acetazolamide

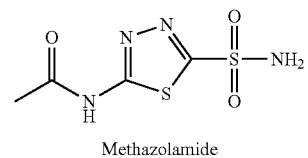

Methazolamide

The compounds, as described herein, may include, for example, prodrugs, which are hydrolysable to form the active sulfonamide and carboxylic acid compound. Thus when a compound of Formula VII is administered to a mammalian subject, typically a human, the prodrug may be cleaved to release the parent compounds of Formula XIII and Brinzolamide or Dorzolamide or Acetazolamide, or Methazolamide.

The compounds, as described herein, may include, for example, prodrugs, which are hydrolysable to form the active Sunitinib derivative and an active carboxylic acid or an active sulfonamide compound. Thus when a compound of Formula VIII is administered to a mammalian subject, typically a human, the prodrug may be cleaved to release the parent Sunitinib derivative and a compound of Formula XIII, or Brinzolamide, or Dorzolamide, or Acetazolamide, or Methazolamide. The active Sunitinib derivative is a phenol compound that has been demonstrated in the literature to be an active RTKI (Kuchar, M., et al. (2012). "Radioiodinated Sunitinib as a potential radiotracer for imaging angiogenesis-radiosynthesis and first radiopharmacological evaluation of 5-[125I]Iodo-Sunitinib." Bioorg Med Chem Lett 22(8): 2850-2855.

The compounds, as described herein, may include, for example, prodrugs, which are hydrolysable to release the active DLK inhibitor. Thus when a compound of Formula IX, Formula X, Formula XI, or Formula XII is administered to a mammalian subject, typically a human, the amide bond may be cleaved to release Crizotinib, KW-2449, a piperidino DLK inhibitor, or a Tozasertib derivative respectively.

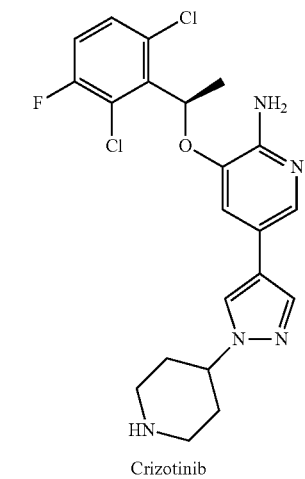
Crizotinib

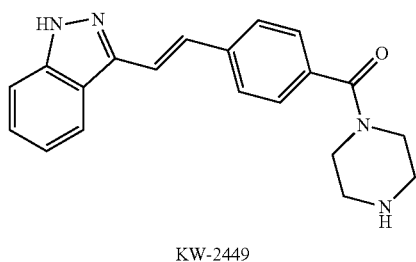
KW-2449

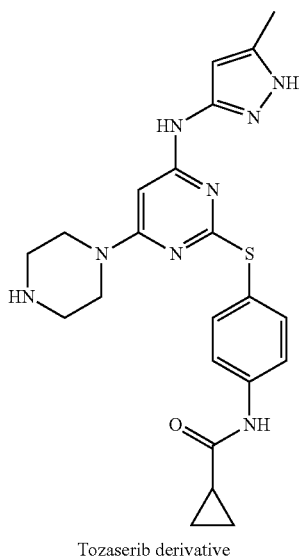
Tozaserib derivative

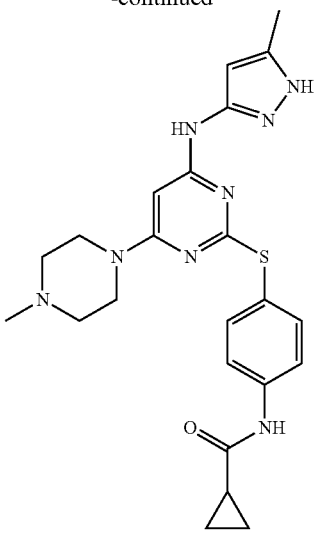
Tozaserib

The amides and esters of commercial prostaglandins are believed to act as prodrugs in the eye, in that the ester or amide form, is hydrolyzed by an endogenous ocular enzyme, releasing the parent compound as a free acid which is the active pharmacologic agent. However, this also releases a potentially toxic and potentially irritating small aliphatic alcohol, for example, isobutanol into the eye. While effective in reducing intraocular pressure, most drugs currently in use, including latanoprost, bimatoprost, travoprost, may cause a significant level of eye irritation in some patients.

In addition to the foregoing, the isopropyl esters of prostaglandins, for example, latanoprost and fluprostenol, are highly viscous, glassy oils, which can be difficult to handle and to formulate into ophthalmic solutions. In addition, these compounds can be prone to the retention of potentially toxic process solvents. The higher alkyl esters or amides of prostaglandins can be easier to handle and may not release as irritating of an alcohol or amine upon hydrolysis.

In addition to the irritation caused by the prostaglandins themselves, and particularly the naturally-occurring and synthetic prostaglandins of the type presently on the market, the preservatives typically used in ophthalmic solutions are known to potentially irritate a percentage of the population. Thus, despite the fact that the prostaglandins represent an important class of potent therapeutic agents for the treatment of glaucoma, the unwanted side effects of these drugs, particularly ocular irritation and inflammation, may limit patient use and can be related to patient withdrawal from the use of these drugs. The higher alkyl esters and amides of prostaglandins as disclosed herein, can be less irritating to patients yet therapeutically effective.

Non-limiting examples of compounds falling Formula I, Formula II, Formula III, Formula IV, Formula V, Formula VI, Formula VII, Formula VIII, Formula IX, Formula X, Formula XI, Formula XII, with variations in the variables e.g., $L^1$, $L^2$, $R^1$-$R^{27}$, and A, are illustrated below. The disclosure includes all combinations of these definitions so long as a stable compound results.

97
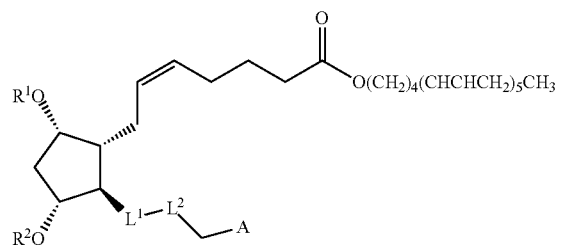
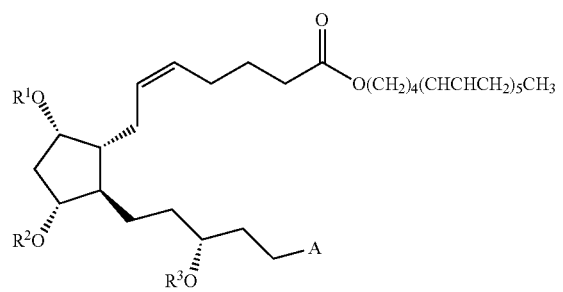
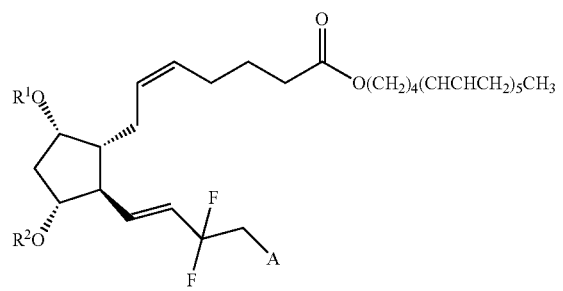
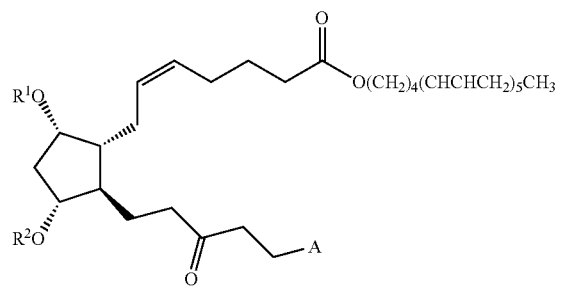
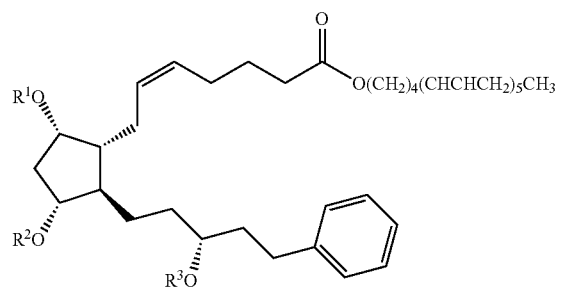
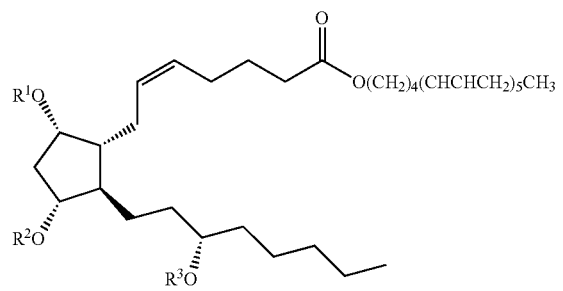
98
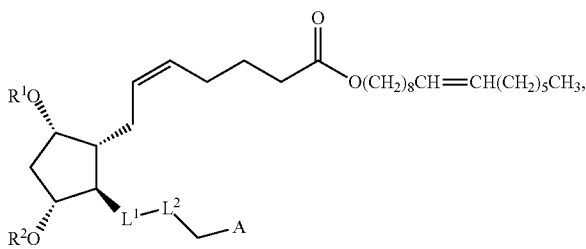
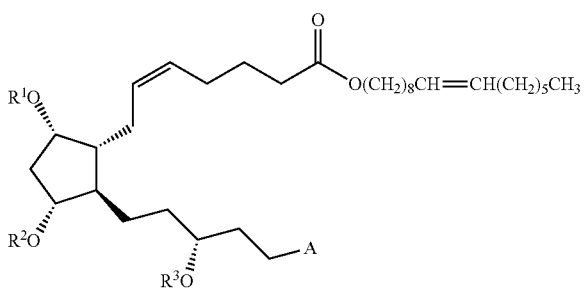
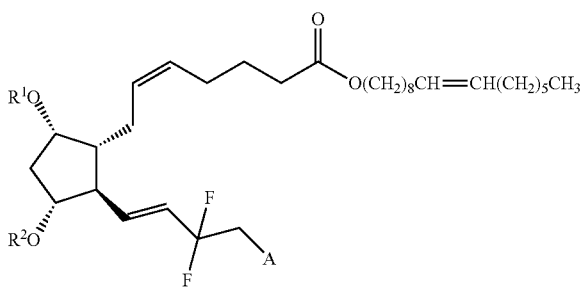
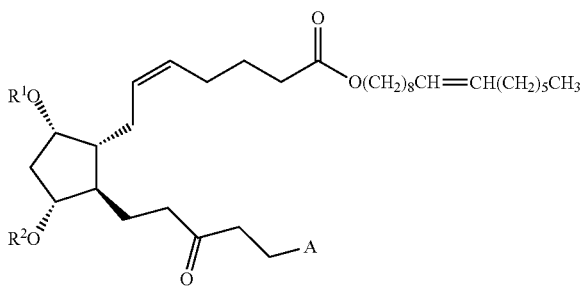
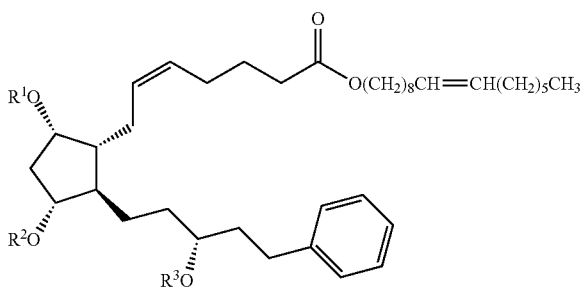
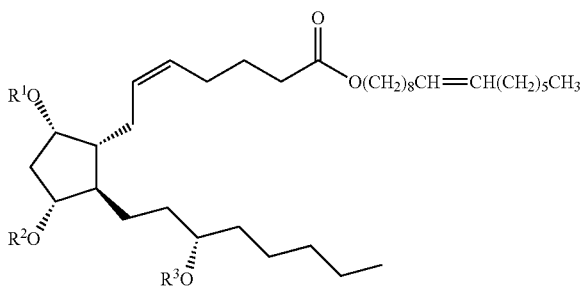

| 99 | 100 |
|---|---|
| 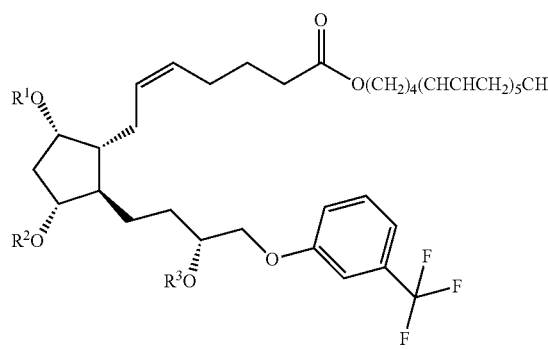 | 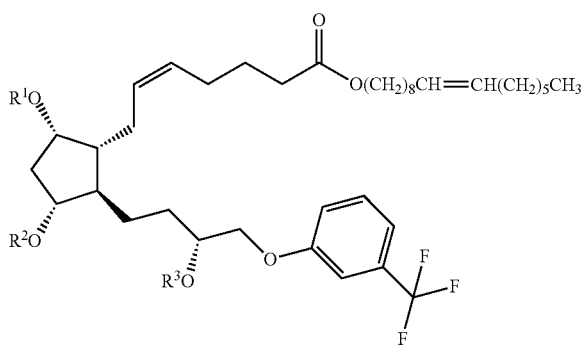 |
| 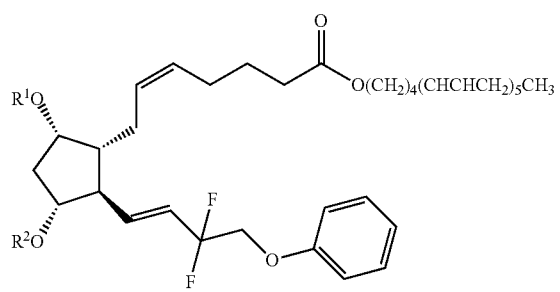 | 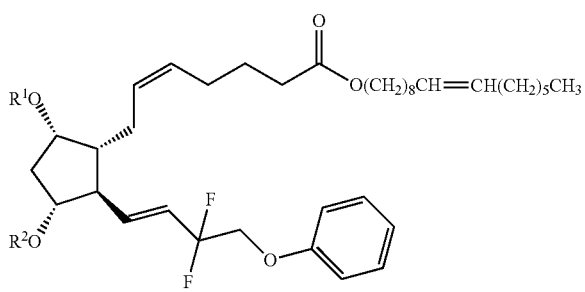 |
| 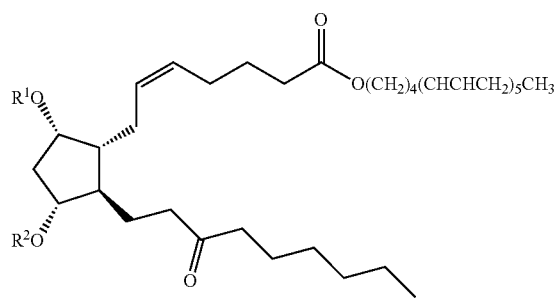 | 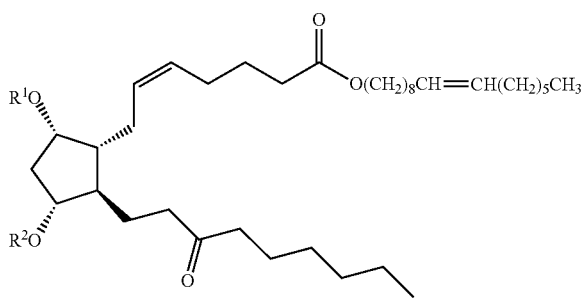 |
| 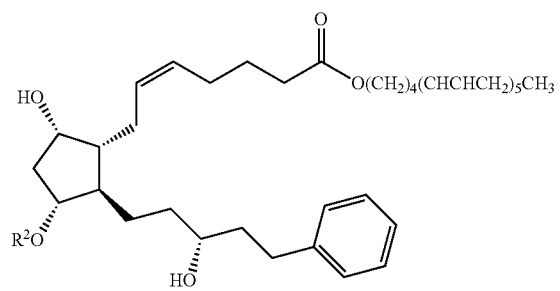 | 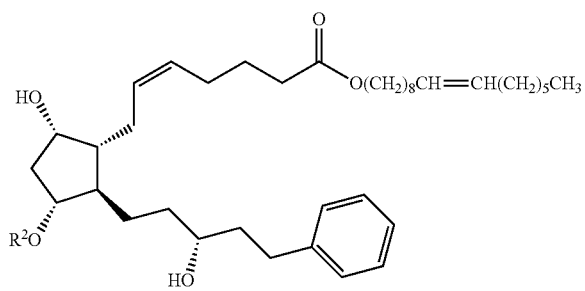 |
| 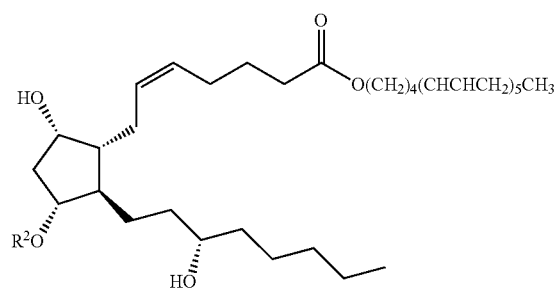 | 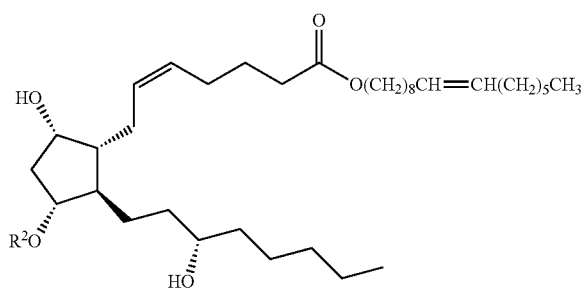 |
-continued -continued
101
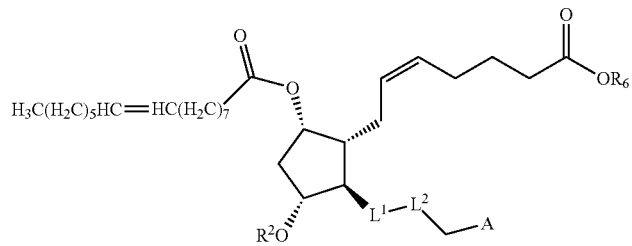
102
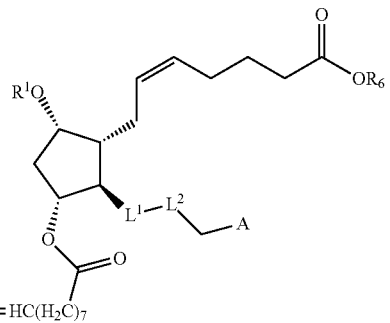
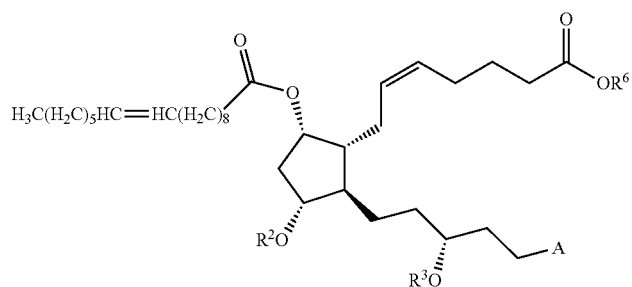
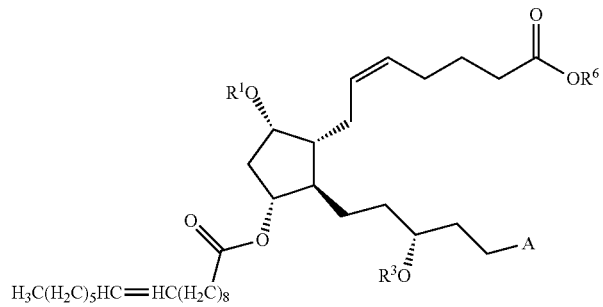
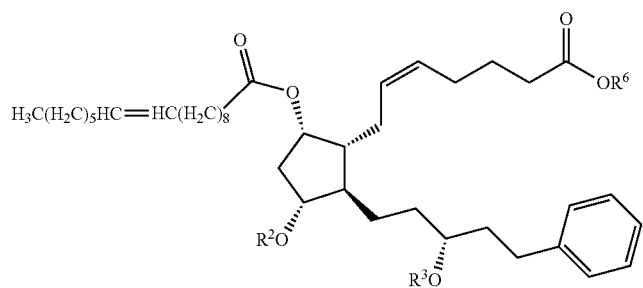
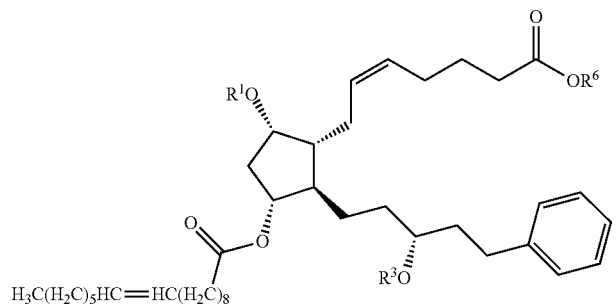

-continued
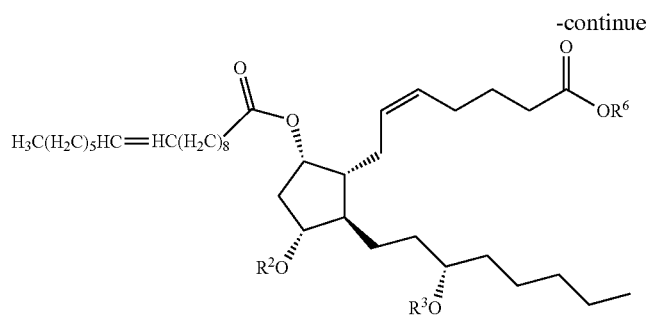
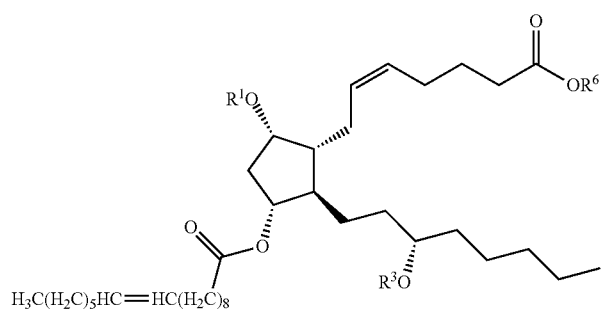
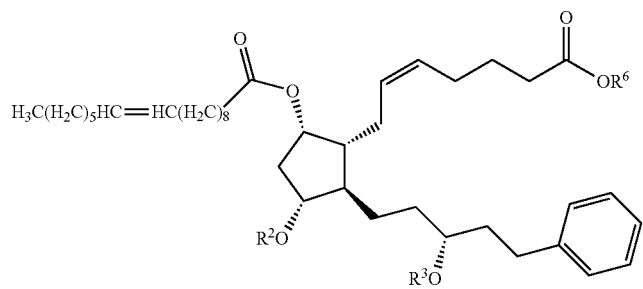
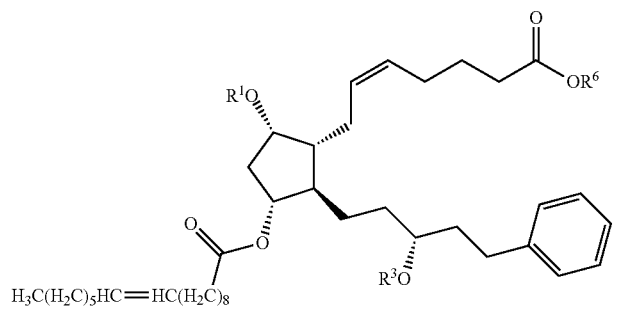
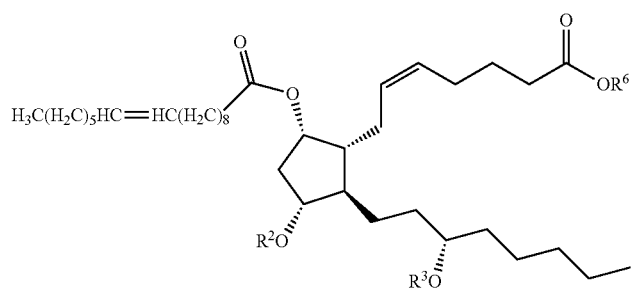

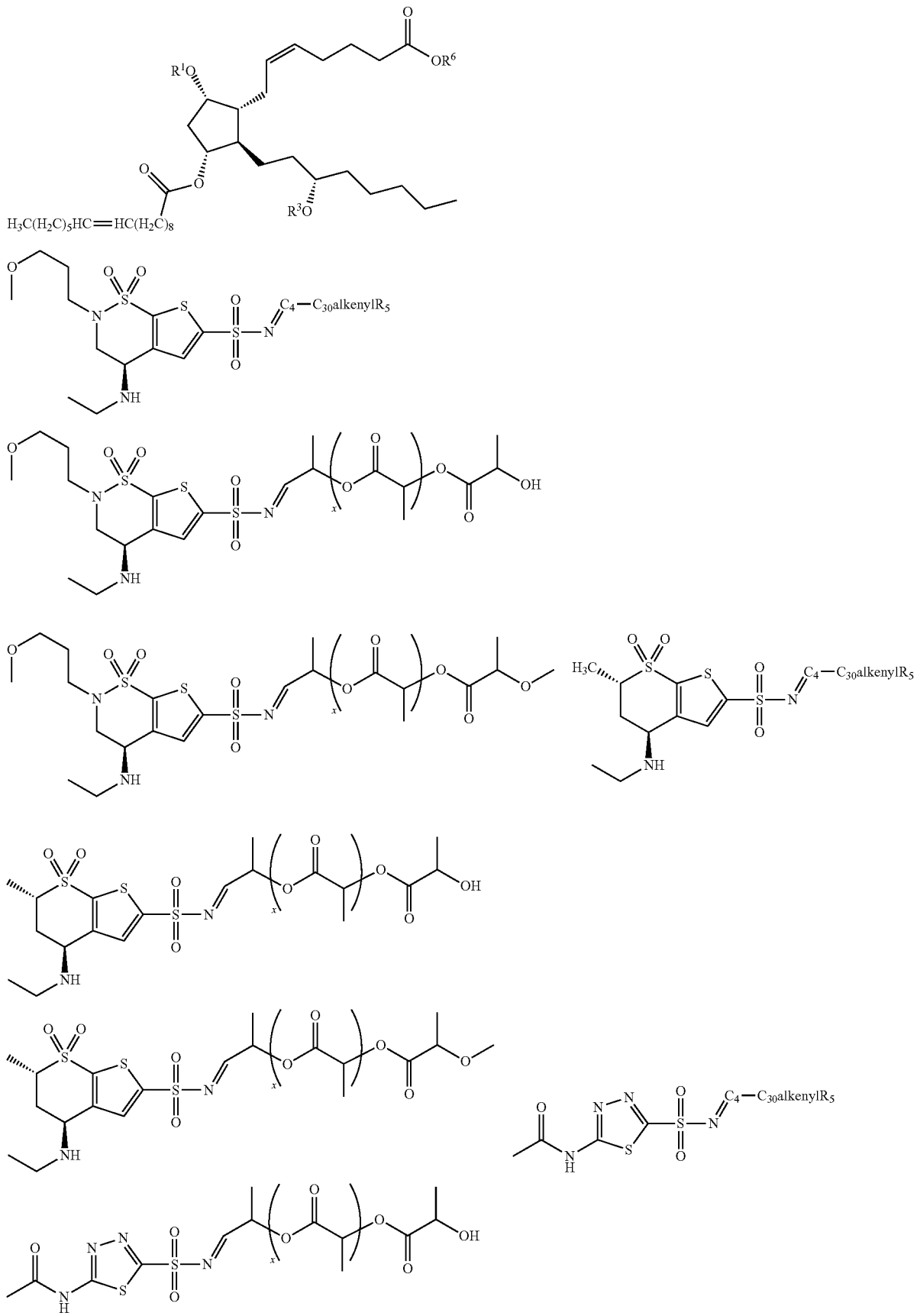

107
108
-continued
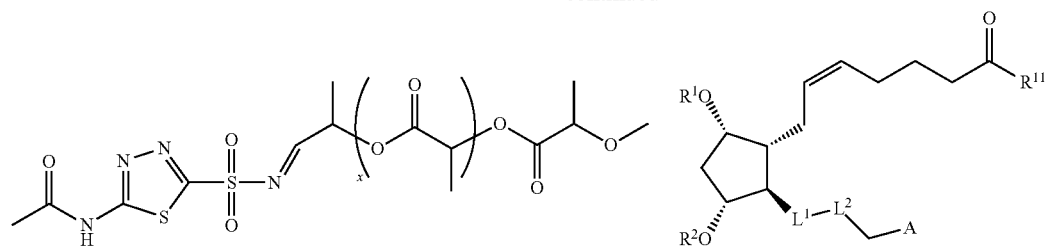
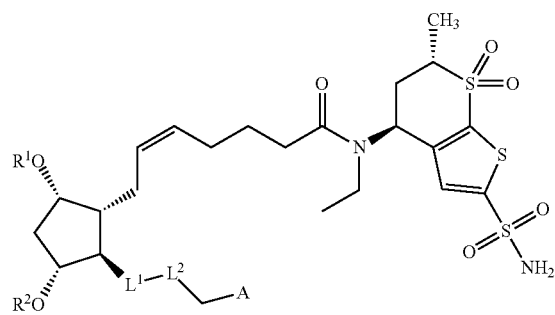
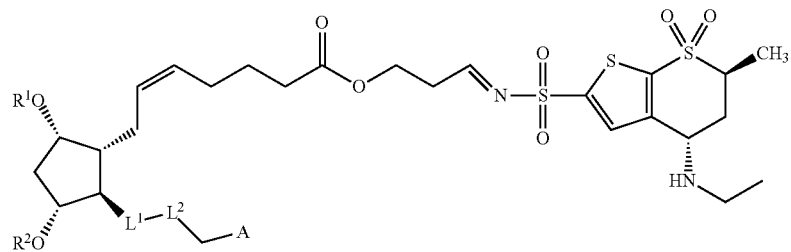
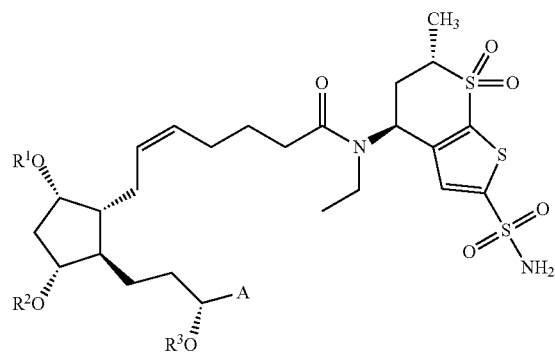
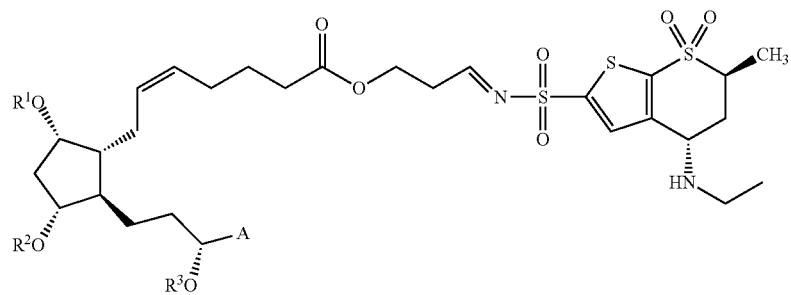

-continued
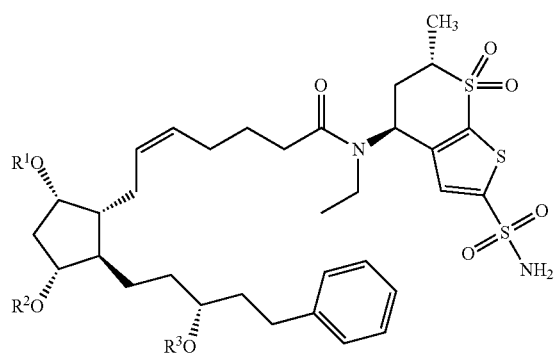
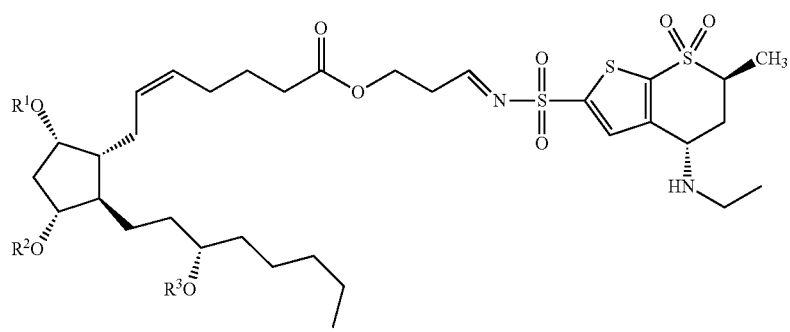
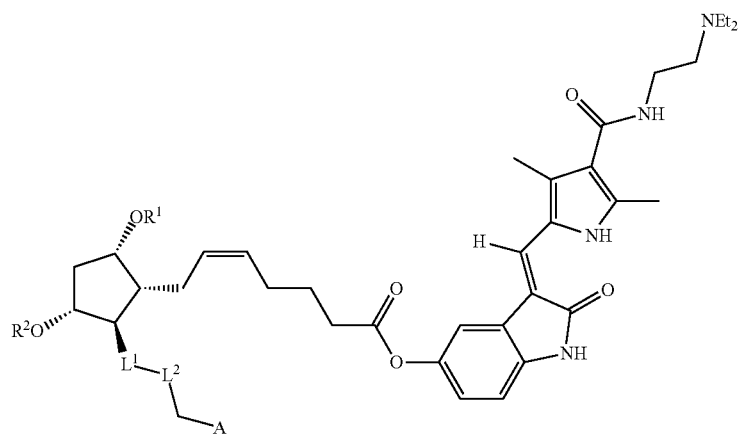
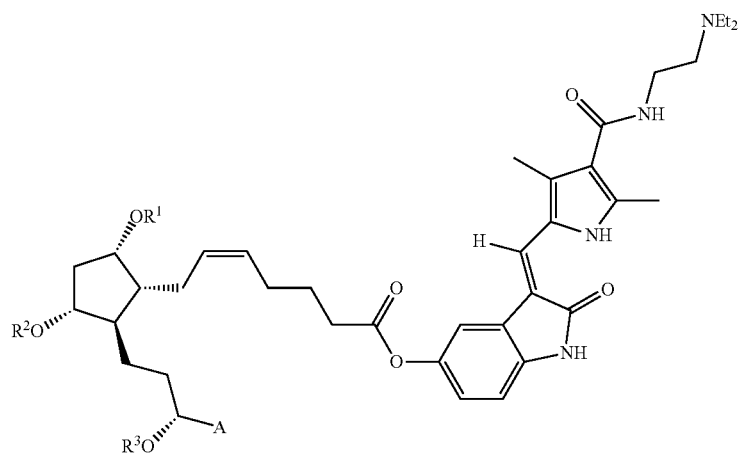

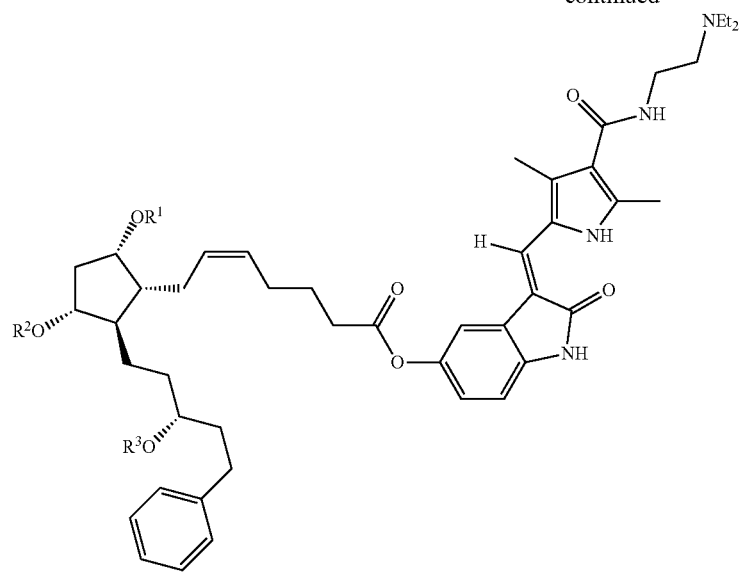
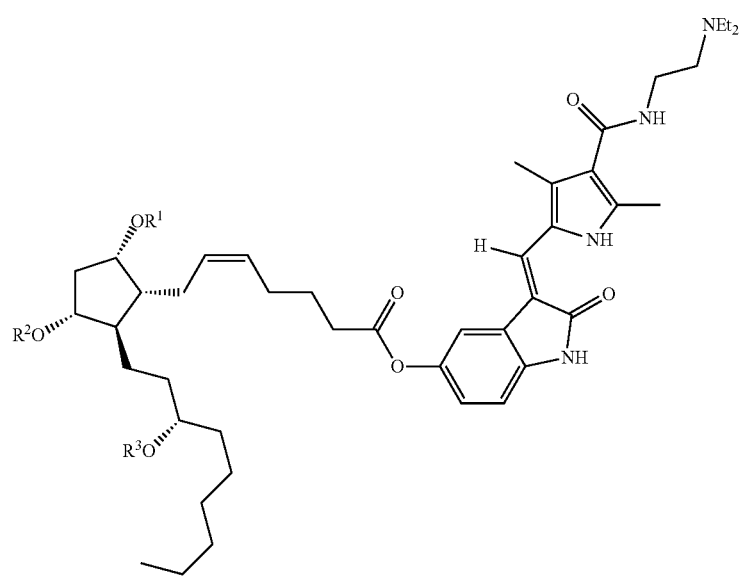
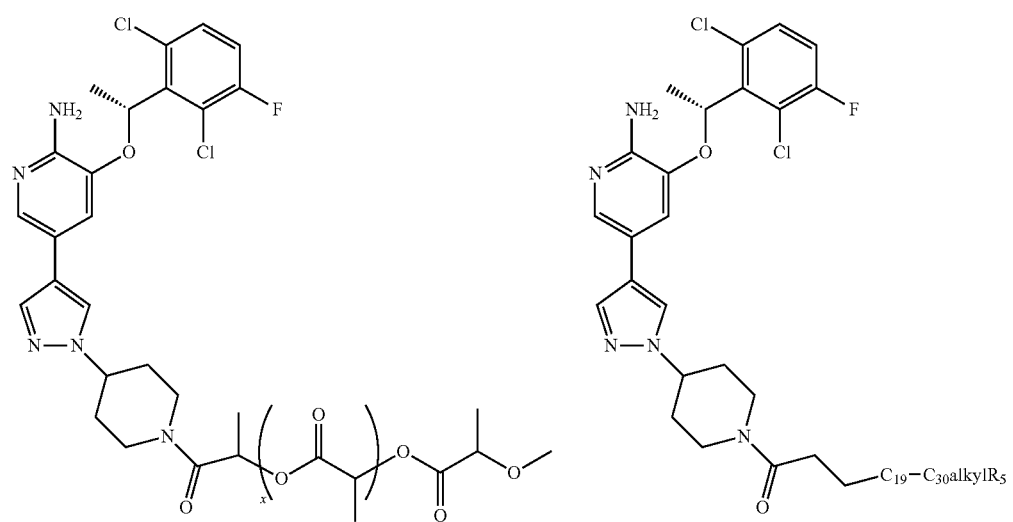

-continued
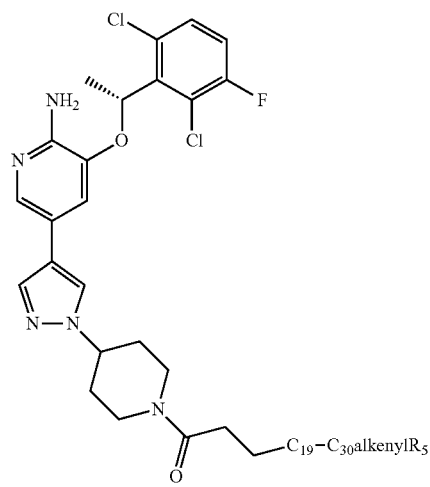
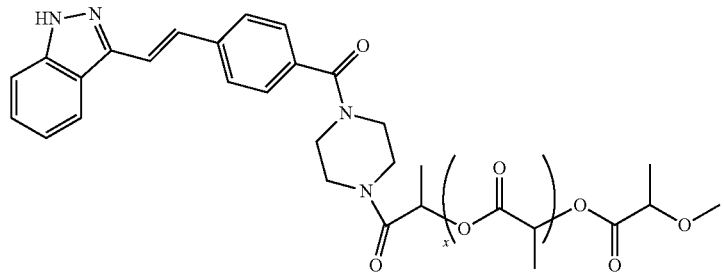
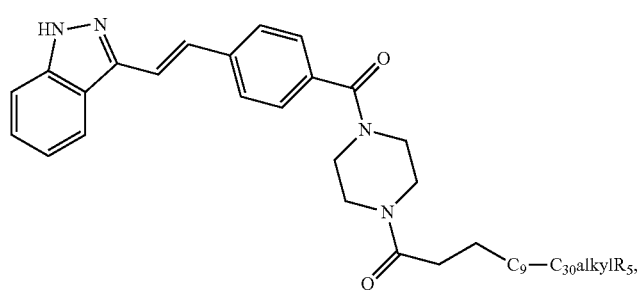
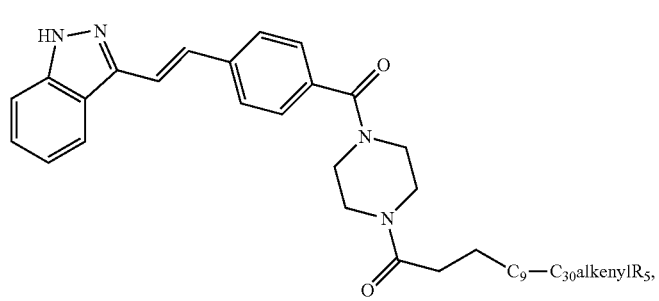
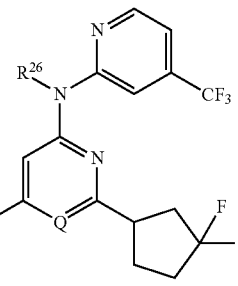
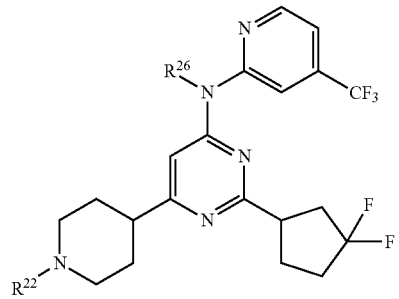
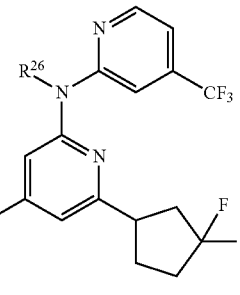
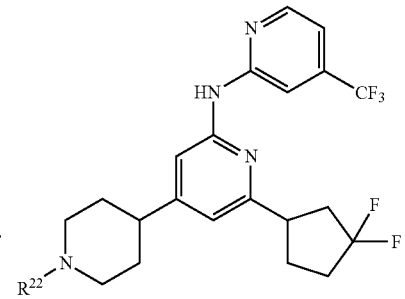
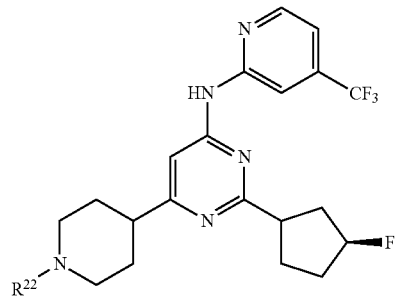
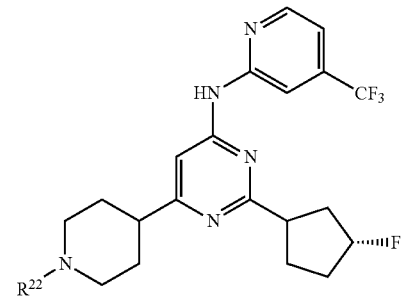
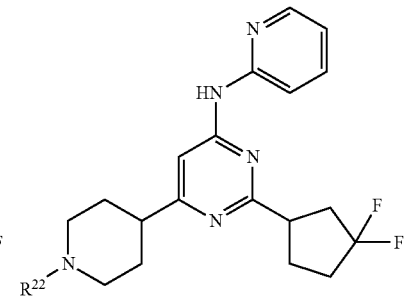

-continued

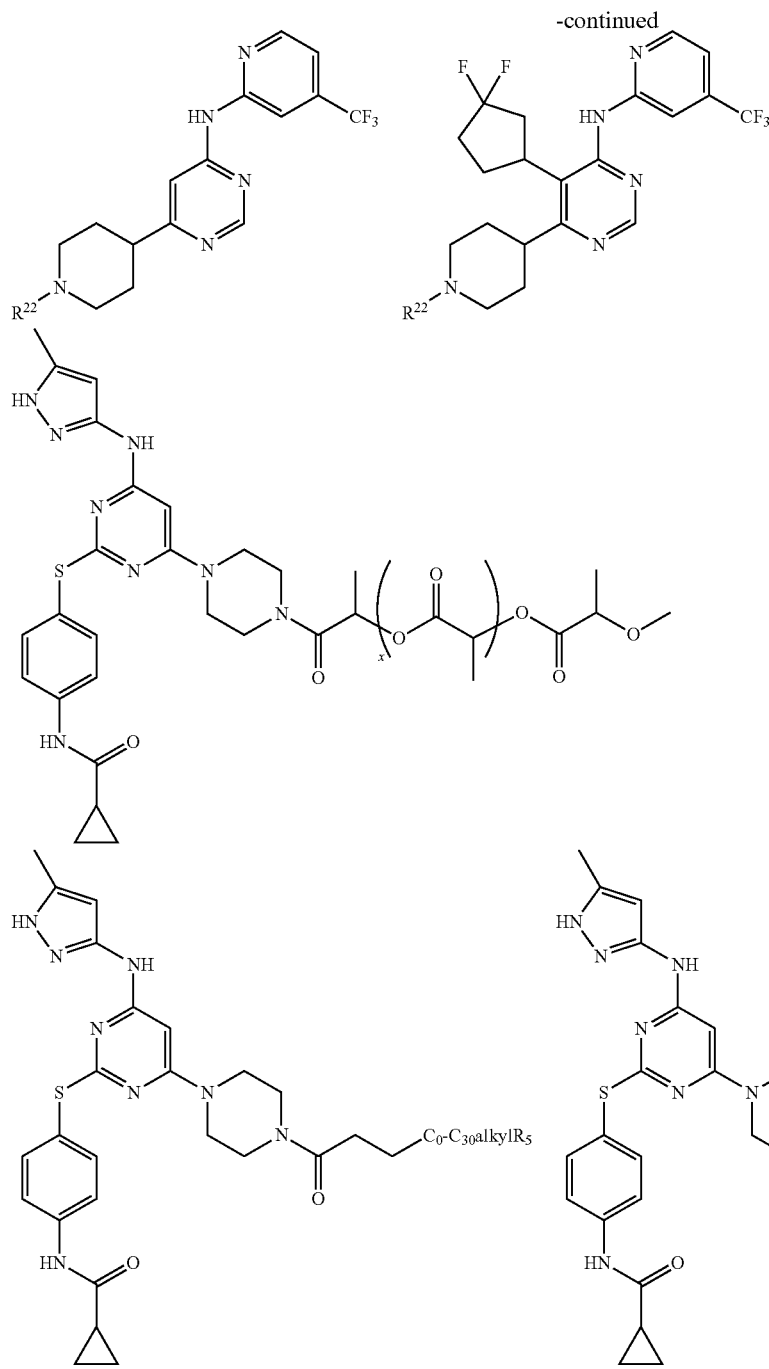

III. PHARMACEUTICAL PREPARATIONS

One embodiment provides compositions including the compounds described herein. In certain embodiments, the composition includes a compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII in combination with a pharmaceutically acceptable carrier, excipient or diluent. In one embodiment, the composition is a pharmaceutical composition for treating an eye disorder or eye disease. Non-limiting exemplary eye disorder or disease treatable with the composition includes age related macular degeneration, alkaline erosive keratoconjunctivitis, allergic conjunctivitis, allergic keratitis, anterior uveitis, Behcet's disease, blepharitis, blood-aqueous barrier disruption, chorioiditis, chronic uveitis, conjunctivitis, contact lens-induced keratoconjunctivitis, corneal abrasion, corneal trauma, corneal ulcer, crystalline retinopathy, cystoid macular edema, dacryocystitis, diabetic keratophathy, diabetic macular edema, diabetic retinopathy, dry eye disease, dry age-related macular degeneration, eosinophilic granuloma, episcleritis, exudative macular edema, Fuchs' Dystrophy, giant cell arteritis, giant papillary conjunctivitis, glaucoma, glaucoma surgery failure, graft rejection, herpes zoster, inflammation after cataract surgery, iridocorneal endothelial syndrome, iritis, keratoconjunctiva sicca, keratoconjunctival inflammatory disease, keratoconus, lattice dystrophy, map-dot-fingerprint dystrophy, necrotic keratitis, neovascular diseases involving the retina, uveal tract or cornea, for example, neovascular glaucoma, corneal neovascularization, neovascularization resulting following a combined vitrectomy and lensectomy, neovascularization of the optic nerve, and neovascularization due to penetration of the eye or contusive ocular injury, neuroparalytic keratitis, non-infectious uveitisocular herpes, ocular lymphoma, ocular rosacea, ophthalmic infections, ophthalmic pemphigoid, optic neuritis, panuveitis, papillitis, pars planitis, persistent macular edema, phacoanaphylaxis, posterior uveitis, post-operative inflammation, proliferative diabetic retinopathy, proliferative sickle cell retinopathy, proliferative vitreoretinopathy, retinal artery occlusion, retinal detachment, retinal vein occlusion, retinitis pigmentosa, retinopathy of prematurity, rubeosis iritis, scleritis, Stevens-Johnson syndrome, sympathetic ophthalmia, temporal arteritis, thyroid associated ophthalmopathy, uveitis, vernal conjunctivitis, vitamin A insufficiency-induced keratomalacia, vitreitis, and wet age-related macular degeneration.

Compounds of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII or its salt, can be delivered by any method known for ocular delivery. Methods include but are not limited to conventional (solution, suspension, emulsion, ointment, inserts and gels); vesicular (liposomes, niosomes, discomes and pharmacosomes), particulates (microparticles and nanoparticles), advanced materials (scleral plugs, gene delivery, siRNA and stem cells); and controlled release systems (implants, hydrogels, dendrimeres, iontoporesis, collagen shields, polymeric solutions, therapeutic contact lenses, cyclodextrin carriers, microneedles and microemulsions).

In certain aspects, a delivery system is used including but not limited to the following; i) a degradable polymeric composition; ii) a non-degradable polymeric composition; (iii) a hydrogel; (iv) a depot; (v) a particle containing a core; vi) a surface-coated particle; vii) a multi-layered polymeric or non-polymeric or mixed polymeric and non-polymeric particle; viii) a polymer blend and/or ix) a particle with a coating on the surface of the particle. The polymers can include, for example, hydrophobic regions. In some embodiments, at least about 30, 40 or 50% of the hydrophobic regions in the coating molecules have a molecular mass of least about 2 kDa. In some embodiments, at least about 30, 40 or 50% of the hydrophobic regions in the coating molecules have a molecular mass of least about 3 kDa. In some embodiments, at least about 30, or 50% of the hydrophobic regions in the coating molecules have a molecular mass of least about 4 kDa. In some embodiments, at least about 30, 40 or 50% of the hydrophobic regions in the coating molecules have a molecular mass of least about 5 kDa. In certain embodiments, up to 5, 10, 20, 30, 40, 50, 60, 70, 80, 90 or even 95% or more of a copolymer or polymer blend consists of a hydrophobic polymer or polymer segment. In some embodiments, the polymeric material includes up to 2, 3, 4, 5, 6, 7, 8, 9, or 10% or more hydrophilic polymer. In one embodiment, the hydrophobic polymer is a polymer or copolymer of lactic acid or glycolic acid, including PLGA. In one embodiment, the hydrophilic polymer is polyethylene glycol. In certain embodiments a triblock polymer such as a Pluronic is used. The drug delivery system can be suitable for administration into an eye compartment of a patient, for example by injection into the eye compartment. In some embodiments, the core includes a biocompatible polymer. As used herein, unless the context indicates otherwise, "drug delivery system", "carrier", and "particle composition" can all be used interchangeably. In a typical embodiment this delivery system is used for ocular delivery.

The particle in the drug delivery system can be of any desired size that achieves the desired result. The appropriate particle size can vary based on the method of administration, the eye compartment to which the drug delivery system is administered, the therapeutic agent employed and the eye disorder to be treated, as will be appreciated by a person of skill in the art in light of the teachings disclosed herein. For example, in some embodiments the particle has a diameter of at least about 1 nm, or from about 1 nm to about 50 microns. The particle can also have a diameter of, for example, from about 1 nm to about 15, 16, 17, 18, 19, 2, 21, 22, 23, 24, 25, 26, 27, 28, 29 or 30 microns; or from about 10 nm to about less than 30, 35, 40, 45 or 50 microns; or from about nm to about less than 28 microns; from about 1 nm to about 5 microns; less than about 1 nm; from about 1 nm to about 3 microns; or from about 1 nm to about 1000 nm; or from about 25 nm to about 75 nm; or from about 20 nm to less than or about 30 nm; or from about 100 nm to about 300 nm. In some embodiments, the average particle size can be about up to 1 nm, 10 nm, 25 nm, nm, 50 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, or more. In some embodiments, the particle size can be about 100 microns or less, about 50 microns or less, about microns or less, about 10 microns or less, about 6 microns or less, about 5 microns or less, about 3 microns or less, about 1000 nm or less, about 800 nm or less, about 600 nm or less, about 500 nm or less, about 400 nm or less, about 300 nm or less, about 200 nm or less, or about 100 nm or less. In some embodiments, the particle can be a nanoparticle or a microparticle. In some embodiments, the drug delivery system can contain a plurality of sizes particles. The particles can be all nanoparticles, all microparticles, or a combination of nanoparticles and microparticles.

When delivering the active material in a polymeric delivery composition, the active material can be distributed homogeneously, heterogeneously, or in one or more polymeric layers of a multi-layered composition, including in a polymer coated core or a bare uncoated core.

In some embodiments, the drug delivery system includes a particle comprising a core. In some embodiments a compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII can be present in the core in a suitable amount, e.g., at least about 1% weight (wt), at least about 5% wt, at least about 10% wt, at least about 20% wt, at least about 30% wt, at least about 40% wt, at least about 50% wt, at least about 60% wt, at least about 70% wt, at least about 80% wt, at least about 85% wt, at least about 90% wt, at least about 95% wt, or at least about 99% wt of the core. In one embodiment, the core is formed of 100% wt of the pharmaceutical agent. In some cases, the pharmaceutical agent may be present in the core at less than or equal to about 100% wt, less than or equal to about 90% wt, less than or equal to about 80% wt, less than or equal to about 70% wt, less than or equal to about 60% wt, less than or equal to about 50% wt, less than or equal to about 40% wt, less than or equal to about 30% wt, less than or equal to about 20% wt, less than or equal to about 10% wt, less than or equal to about 5% wt, less than or equal to about 2% wt, or less than or equal to about 1% wt. Combinations of the above-referenced ranges are also possible (e.g., present in an amount of at least about 80% wt and less than or equal to about 100% wt). Other ranges are also possible.

In embodiments in which the core particles comprise relatively high amounts of a pharmaceutical agent (e.g., at least about 50% wt of the core particle), the core particles generally have an increased loading of the pharmaceutical agent compared to particles that are formed by encapsulating agents into polymeric carriers. This is an advantage for drug delivery applications, since higher drug loadings mean that fewer numbers of particles may be needed to achieve a desired effect compared to the use of particles containing polymeric carriers.

In some embodiments, the core is formed of a solid material having a relatively low aqueous solubility (i.e., a solubility in water, optionally with one or more buffers), and/or a relatively low solubility in the solution in which the solid material is being coated with a surface-altering agent. For example, the solid material may have an aqueous solubility (or a solubility in a coating solution) of less than or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, less than or equal to about 0.01 mg/mL, less than or equal to about 1 µg/mL, less than or equal to about 0.1 µg/mL, less than or equal to about 0.01 µg/mL, less than or equal to about 1 ng/mL, less than or equal to about 0.1 ng/mL, or less than or equal to about 0.01 ng/mL at 25° C. In some embodiments, the solid material may have an aqueous solubility (or a solubility in a coating solution) of at least about 1 pg/mL, at least about pg/mL, at least about 0.1 ng/mL, at least about 1 ng/mL, at least about 10 ng/mL, at least about 0.1 µg/mL, at least about 1 µg/mL, at least about 5 µg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility or a solubility in a coating solution of at least about 10 pg/mL and less than or equal to about 1 mg/mL). Other ranges are also possible. The solid material may have these or other ranges of aqueous solubilities at any point throughout the pH range (e.g., from pH 1 to pH 14).

In some embodiments, the core may be formed of a material within one of the ranges of solubilities classified by the U.S. Pharmacopeia Convention: e.g., very soluble: >1,000 mg/mL; freely soluble: 100-1,000 mg/mL; soluble: 33-100 mg/mL; sparingly soluble: 10-33 mg/mL; slightly soluble: 1-10 mg/mL; very slightly soluble: 0.1-1 mg/mL; and practically insoluble: <0.1 mg/mL.

Although a core may be hydrophobic or hydrophilic, in many embodiments described herein, the core is substantially hydrophobic. "Hydrophobic" and "hydrophilic" are given their ordinary meaning in the art and, as will be understood by those skilled in the art, in many instances herein, are relative terms. Relative hydrophobicities and hydrophilicities of materials can be determined by measuring the contact angle of a water droplet on a planar surface of the substance to be measured, e.g., using an instrument such as a contact angle goniometer and a packed powder of the core material.

In some embodiments, the core particles described herein may be produced by nanomilling of a solid material (e.g., a compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII) in the presence of one or more stabilizers/surface-altering agents. Small particles of a solid material may require the presence of one or more stabilizers/surface-altering agents, particularly on the surface of the particles, in order to stabilize a suspension of particles without agglomeration or aggregation in a liquid solution. In some such embodiments, the stabilizer may act as a surface-altering agent, forming a coating on the particle.

In a wet milling process, milling can be performed in a dispersion (e.g., an aqueous dispersion) containing one or more stabilizers (e.g., a surface-altering agent), a grinding medium, a solid to be milled (e.g., a solid pharmaceutical agent), and a solvent. Any suitable amount of a stabilizer/surface-altering agent can be included in the solvent. In some embodiments, a stabilizer/surface-altering agent may be present in the solvent in an amount of at least about 0.001% (wt or % weight to volume (w:v)), at least about 0.01, at least about 0.1, at least about 0.5, at least about 1, at least about 2, at least about 3, at least about 4, at least about 5, at least about 6, at least about 7, at least about 8, at least about 10, at least about 12, at least about 15, at least about 20, at least about 40, at least about 60, or at least about 80% of the solvent. In some cases, the stabilizer may be present in the solvent in an amount of about 100% (e.g., in an instance where the stabilizer/surface-altering agent is the solvent). In other embodiments, the stabilizer may be present in the solvent in an amount of less than or equal to about 100, less than or equal to about 80, less than or equal to about 60, less than or equal to about 40, less than or equal to about 20, less than or equal to about 15, less than or equal to about 12, less than or equal to about 10, less than or equal to about 8, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 5% and at least about 1% of the solvent). Other ranges are also possible. The particular range chosen may influence factors that may affect the ability of the particles to penetrate mucus such as the stability of the coating of the stabilizer/surface-altering agent on the particle surface, the average thickness of the coating of the stabilizer/surface-altering agent on the particles, the orientation of the stabilizer/surface-altering agent on the particles, the density of the stabilizer/surface altering agent on the particles, stabilizer/drug ratio, drug concentration, the size and polydispersity of the particles formed, and the morphology of the particles formed.

The compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII (or salt thereof) may be present in the solvent in any suitable amount. In some embodiments, the pharmaceutical agent (or salt thereof) is present in an amount of at least about 0.001% (wt % or % weight to volume (w:v)), at least about 0.01%, at least about 0.1%, at least about 0.5%, at least about 1%, at least about 2%, at least about 3%, at least about 4%, at least about 5%, at least about 6%, at least about 7%, at least about 8%, at least about 10%, at least about 12%, at least about 15%, at least about 20%, at least about 40%, at least about 60%, or at least about 80% of the solvent. In some cases, the pharmaceutical agent (or salt thereof) may be present in the solvent in an amount of less than or equal to about 100%, less than or equal to about 90%, less than or equal to about 80%, less than or equal to about 60%, less than or equal to about 40%, less than or equal to about 20%, less than or equal to about 15%, less than or equal to about 12%, less than or equal to about 10%, less than or equal to about 8%, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 20% and at least about 1% of the solvent). In some embodiments, the pharmaceutical agent is present in the above ranges but in w:v.

The ratio of stabilizer/surface-altering agent to pharmaceutical agent (or salt thereof) in a solvent may also vary. In some embodiments, the ratio of stabilizer/surface-altering agent to pharmaceutical agent (or salt thereof) may be at least 0.001:1 (weight ratio, molar ratio, or w:v ratio), at least 0.01:1, at least 0.01:1, at least 1:1, at least 2:1, at least 3:1, at least 5:1, at least 10:1, at least 25:1, at least 50:1, at least 100:1, or at least 500:1. In some cases, the ratio of stabilizer/surface-altering agent to pharmaceutical agent (or salt thereof) may be less than or equal to 1000:1 (weight ratio or molar ratio), less than or equal to 500:1, less than or equal to 100:1, less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible.

Stabilizers/surface-altering agents may be, for example, polymers or surfactants. Examples of polymers are those suitable for use in coatings, as described in more detail below. Non-limiting examples of surfactants include L-α-phosphatidylcholine (PC), 1,2-dipalmitoylphosphatidycholine (DPPC), oleic acid, sorbitan trioleate, sorbitan monooleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil. Derivatives of the above-noted compounds are also possible. Combinations of the above-noted compounds and others described herein may also be used as surface-altering agents in the inventive particles. As described herein, in some embodiments a surface-altering agent may act as a stabilizer, a surfactant, and/or an emulsifier. In some embodiments, the surface altering agent may aid particle transport in mucus.

It should be appreciated that while in some embodiments the stabilizer used for milling forms a coating on a particle surface, which coating renders particle mucus penetrating, in other embodiments, the stabilizer may be exchanged with one or more other surface-altering agents after the particle has been formed. For example, in one set of methods, a first stabilizer/surface-altering agent may be used during a milling process and may coat a surface of a core particle, and then all or portions of the first stabilizer/surface-altering agent may be exchanged with a second stabilizer/surface-altering agent to coat all or portions of the core particle surface. In some cases, the second stabilizer/surface-altering agent may render the particle mucus penetrating more than the first stabilizer/surface-altering agent. In some embodiments, a core particle having a coating including multiple surface-altering agents may be formed.

In other embodiments, core particles may be formed by a precipitation technique. Precipitation techniques (e.g., microprecipitation techniques, nanoprecipitation techniques) may involve forming a first solution comprising a compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII and a solvent, wherein the material is substantially soluble in the solvent. The solution may be added to a second solution comprising another solvent in which the material is substantially insoluble, thereby forming a plurality of particles comprising the material. In some cases, one or more surface-altering agents, surfactants, materials, and/or bioactive agents may be present in the first and/or second solutions. A coating may be formed during the process of precipitating the core (e.g., the precipitating and coating steps may be performed substantially simultaneously). In other embodiments, the particles are first formed using a precipitation technique, following by coating of the particles with a surface-altering agent.

In some embodiments, a precipitation technique may be used to form particles (e.g., nanocrystals) of a salt of a compound of Formula I, Formula II, Formula II', Formula III, Formula IV, Formula V, Formula VI, Formula III', Formula IV', Formula V', Formula VI', Formula VII, Formula VII', Formula VIII, Formula IX, Formula X, Formula XI, Formula XII, Formula XIV, Formula XV, Formula XVI, Formula XVII, Formula XVIII, Formula XIX, Formula XX, Formula XXI, Formula XXII, or Formula XXIII. Generally, a precipitation technique involves dissolving the material to be used as the core in a solvent, which is then added to a miscible anti-solvent with or without excipients to form the core particle. This technique may be useful for preparing particles of pharmaceutical agents that are soluble in aqueous solutions (e.g., agents having a relatively high aqueous solubility). In some embodiments, pharmaceutical agents having one or more charged or ionizable groups can interact with a counter ion (e.g., a cation or an anion) to form a salt complex.

As described herein, in some embodiments, a method of forming a core particle involves choosing a stabilizer that is suitable for both nanomilling and for forming a coating on the particle and rendering the particle mucus penetrating.

For example, as described in more detail below, it has been demonstrated that 200-500 nm nanoparticles of a model compound pyrene produced by nanomilling of pyrene in the presence of Pluronic® F127 resulted in particles that can penetrate physiological mucus samples at the same rate as well-established polymer-based MPP. Interestingly, it was observed that only a handful of stabilizers/surface-altering agents tested fit the criteria of being suitable for both nanomilling and for forming a coating on the particle that renders the particle mucus penetrating, as described in more detail below.

IV. DESCRIPTION OF POLYMERIC DELIVERY MATERIALS

The particles of the drug delivery system can include a biocompatible polymer. As used herein, the term "biocompatible polymer" encompasses any polymer than can be administered to a patient without an unacceptable adverse effects to the patient.

Examples of biocompatible polymers include but are not limited to polystyrenes; poly(hydroxy acid); poly(lactic acid); poly(glycolic acid); poly(lactic acid-co-glycolic acid); poly(lactic-co-glycolic acid); poly(lactide); poly(glycolide); poly(lactide-co-glycolide); polyanhydrides; polyorthoesters; polyamides; polycarbonates; polyalkylenes; polyethylenes; polypropylene; polyalkylene glycols; poly(ethylene glycol); polyalkylene oxides; poly(ethylene oxides); polyalkylene terephthalates; poly(ethylene terephthalate); polyvinyl alcohols; polyvinyl ethers; polyvinyl esters; polyvinyl halides; poly(vinyl chloride); polyvinylpyrrolidone; polysiloxanes; poly(vinyl alcohols); poly(vinyl acetate); polyurethanes; copolymers of polyurethanes; derivativized celluloses; alkyl cellulose; hydroxyalkyl celluloses; cellulose ethers; cellulose esters; nitro celluloses; methyl cellulose; ethyl cellulose; hydroxypropyl cellulose; hydroxy-propyl methyl cellulose; hydroxybutyl methyl cellulose; cellulose acetate; cellulose propionate; cellulose acetate butyrate; cellulose acetate phthalate; carboxylethyl cellulose; cellulose triacetate; cellulose sulfate sodium salt; polymers of acrylic acid; methacrylic acid; copolymers of methacrylic acid; derivatives of methacrylic acid; poly(methyl methacrylate); poly(ethyl methacrylate); poly(butylmethacrylate); poly(isobutyl methacrylate); poly(hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); copolymers of poly(lactide-co-caprolactone); blends of poly(lactide-co-caprolactone); hydroxyethyl methacrylate (HEMA); copolymers of HEMA with acrylate; copolymers of HEMA with polymethylmethacrylate (PMMA); polyvinylpyrrolidone/vinyl acetate copolymer (PVP/VA); acrylate polymers/copolymers; acrylate/carboxyl polymers; acrylate hydroxyl and/or carboxyl copolymers; polycarbonate-urethane polymers; silicone-urethane polymers; epoxy polymers; cellulose nitrates; polytetramethylene ether glycol urethane; polymethylmethacrylate-2-hydroxyethylmethacrylate copolymer; polyethylmethacrylate-2-hydroxyethylmethacrylate copolymer; polypropylmethacrylate-2-hydroxyethylmethacrylate copolymer; polybutylmethacrylate-2-hydroxyethylmethacrylate copolymer; polymethylacrylate-2-hydroxyethylmethacrylate copolymer; polyethylacrylate-2-hydroxyethylmethacrylate copolymer; polypropylacrylate-2-hydroxymethacrylate copolymer; polybutylacrylate-2-hydroxyethylmethacrylate copolymer; copolymermethylvinylether maleicanhydride copolymer; poly (2-hydroxyethyl methacrylate) polymer/copolymer; acrylate carboxyl and/or hydroxy copolymer; olefin acrylic acid copolymer; ethylene acrylic acid copolymer; polyamide polymers/copolymers; polyimide polymers/copolymers; ethylene vinylacetate copolymer; polycarbonate urethane; silicone urethane; polyvinylpyridine copolymers; polyether sulfones; polygalactin, poly-(isobutyl cyanoacrylate), and poly(2-hydroxyethyl-L-glutamine); polydimethyl siloxane; poly(caprolactones); poly(ortho esters); polyamines; polyethers; polyesters; polycarbamates; polyureas; polyimides; polysulfones; polyacetylenes; polyethyeneimines; polyisocyanates; polyacrylates; polymethacrylates; polyacrylonitriles; polyarylates; and combinations, copolymers and/or mixtures of two or more of any of the foregoing. In some cases, the particle includes a hydrophobic material and at least one bioactive agent. In certain embodiments, the hydrophobic material is used instead of a polymer. In other embodiments, the hydrophobic material is used in addition to a polymer.

An active compound as described herein can be physically mixed in the polymeric material, including in an interpenetrating polymer network or can be covalently bound to the polymeric material Linear, non-linear or linear multiblock polymers or copolymers can be used to form nanoparticles, microparticles, and implants (e.g., rods, discs, wafers, etc.) useful for the delivery to the eye. The polymers can contain one or more hydrophobic polymer segments and one or more hydrophilic polymer segments covalently connected through a linear link or multivalent branch point to form a non-linear multiblock copolymer containing at least three polymeric segments. The polymer can be a conjugate further containing one or more therapeutic, prophylactic, or diagnostic agents covalently attached to the one or more polymer segments. By employing a polymer-drug conjugate, particles can be formed with more controlled drug loading and drug release profiles. In addition, the solubility of the conjugate can be controlled so as to minimize soluble drug concentration and, therefore, toxicity.

The one or more hydrophobic polymer segments, independently, can be any biocompatible hydrophobic polymer or copolymer. In some cases, the one or more hydrophobic polymer segments are also biodegradable. Examples of suitable hydrophobic polymers include polyesters such as polylactic acid, polyglycolic acid, or polycaprolactone, polyanhydrides, such as polysebacic anhydride, and copolymers thereof. In certain embodiments, the hydrophobic polymer is a polyanhydride, such as polysebacic anhydride or a copolymer thereof. The one or more hydrophilic polymer segments can be any hydrophilic, biocompatible, nontoxic polymer or copolymer. The hydrophilic polymer segment can be, for example, a poly(alkylene glycol), a polysaccharide, poly(vinyl alcohol), polypyrrolidone, a polyoxyethylene block copolymer (PLURONIC®) or a copolymers thereof. In preferred embodiments, the one or more hydrophilic polymer segments are, or are composed of, polyethylene glycol (PEG).

WO 2016/100380A1 and WO 2016/100392 A1 describe certain sunitinib delivery systems, which can also be used in the present invention to deliver sunitinib or another active agent provided by the current invention, and as described further herein. For example, WO 2016/100380A1 and WO 2016/100392 A1 describe that a polymeric sunitinib drug formulation can be prepared by: (i) dissolving or dispersing sunitinib or its salt in an organic solvent optionally with an alkaline agent; (ii) mixing the solution/dispersion of step (i) with a polymer solution that has a viscosity of at least about 300 cPs (or perhaps at least about 350, 400, 500, 600, 700 or 800 or more cPs); (iii) mixing the drug polymer solution/dispersion of step (ii) with an aqueous non-acidic or alkaline solution (for example at least approximately a pH of 7, 8, or 9 and typically not higher than about 10) optionally with a surfactant or emulsifier, to form a solvent-laden sunitinib encapsulated microparticle, (iv) isolating the microparticles. When sunitinib malate or another pharmaceutically acceptable salt of sunitinib is used, it was reported that it may be useful to include the alkaline agent in the organic solvent. However, when sunitinib free base is used, then it was reported that adding an acid to the organic solvent can improve drug loading of the microparticle. Examples were provided demonstrating that polyesters such as PLGA, PEG-PLGA(PLA) and PEG-PLGA/PLGA blend microparticles display sustained release of sunitinib or its analog or pharmaceutically acceptable salt. The PCT references describe that polymer microparticles composed of PLGA and PEG covalently conjugated to PLGA (Mw 45 kDa) (PLGA45k-PEG5k) loaded with sunitinib malate were prepared using a single emulsion solvent evaporation method. Loading improvement was achieved by increasing the alkalinity of sunitinib malate in solution, up to 16.1% with PEG-PLGA, which could be further increased by adding DMF, compared to only 1% with no alkaline added. Sunitinib malate loading was further increased by increasing the pH of the aqueous solution as well as the polymer solution. Still further significant increases in sunitinib malate loading in the microparticles was achieved by increasing polymer concentration or viscosity. It was reported in these PCT applications that the loading of sunitinib can be increased by increasing the alkalinity of the sunitinib in solution during encapsulation. This can be achieved by selection of the solvent, adding alkalizing agents to the solvent, or including alkaline drugs with the sunitinib. Examples of compounds that can be added for this purpose include solvents or solvent additives such as dimethylacetamide (DMA), DMTA, triethylamine (TEA), aniline, ammonium, and sodium hydroxide, drugs such as Vitamin B4, caffeine, alkaloids, nicotine, the analgesic morphine, the antibacterial berberine, the anticancer compound vincristine, the antihypertension agent reserpine, the cholinomimetic galantamine, the anticholinergic agent atropine, the vasodilator vincamine, the antiarrhythmia compound quinidine, the antiasthma therapeutic ephedrine, and the antimalarial drug quinine. Surfactants include anionic, cationic and non-ionic surfactants, such as, but not limited to, polyvinyl alcohol, F-127, lectin, fatty acids, phospholipids, polyoxyethylene sorbitan fatty acid derivatives, tocopherols and castor oil. The PCTs also reported that drug loading in the particle is significantly affected by the acid value. For example, raising the pH by addition of alkaline significantly increases the amount of sunitinib malate incorporated. Loading also can be increased by changing the water phase pH. For example, when water phase (such as PBS) pH is raised from 6.8 to 7.4. Drug loading can also be increased by increasing both polymer and drug concentration, polymer molecular weight. The preferred aqueous pH is higher than 6 and lower than 10, more for example between pH 6 and 8. According to WO 2016/100380A1 and WO 2016/100392 A1, polymer concentration and viscosity can affect encapsulation efficiency. For example, it was reported that for the same formulation composition (99% PLGA 75:25 4A and 1% PLGA-PEG (PEG MW 5 Kd, PLGA MW~45 Kd)) at different polymer concentrations in dichloromethane (DCM), the encapsulation efficiency increases to over 50% at 100 mg/mL polymer concentration. The dynamic viscosity of this polymer solution in DCM, prior to mixing with sunitinib malate solution in DMSO, is estimated to be around 350 cPs. The preferred minimal viscosity of polymer solution in DCM is about 350 cPs. In a preferred embodiment, the polymer concentration in DCM is 140 mg/mL, which is approximately 720 cPs by calculation. Particles made of 99% PLGA 7525 6E and 1% PLGA-PEG (PEG MW 5 Kd, PLGA MW~45 Kd) can have a polymer concentration in DCM ranging from 100-200 mg/mL. Since PLGA 7525 6E is a polymer with higher Mw than that of PLGA 7525 4A, the polymer solution in DCM is more viscous with a dynamic viscosity of about 830 cPs. Drug loading is also significantly affected by the method of making and the solvent used. For example, S/O/W single emulsion method will yield a higher loading than O/W single emulsion method even without control the acid value. In addition, W/O/W double emulsions have been shown to significantly improve drug loading of less hydrophobic salt forms over single O/W emulstions. The ratio of continuous phase to dispersed phase can also significantly alter the encapsulation efficiency and drug loading by modulation of the rate of particle solidification. The rate of polymer solidification with the evaporation of solvent affects the degree of porosity within microparticles. A large CP:DP ratio results in faster polymer precipitation, less porosity, and higher encapsulation efficiency and drug loading. However, decreasing the rate of evaporation of the solvent during particle preparation can also lead to improvements in drug loading of highly polar compounds. As the organic phase phase evaporates, highly polar compounds within the organic phase is driven to the surface of the particles resulting in poor encapsulation and drug loading. By decreasing the rate of solvent evaporation by decreasing the temperature or rate of stirring, encapsulation efficiency and % drug loading can be increased for highly polar compounds.

These technologies can be used by one of skill in the art to deliver any of the active compounds as described generally in this specification.

U.S. Pat. No. 8,889,193 and PCT/US2011/026321 disclose, for example, a method for treating an eye disorder in a patient in need thereof, comprising administering into the eye, for example, by intravitreal injection into the vitreous chamber of the eye, an effective amount of a drug delivery system which comprises: (i) a microparticle including a core which includes the biodegradable polymer polylactide-co-glycolide; (ii) a coating associated with the core which is non-covalently associated with the microparticle particle; wherein the coating molecule has a hydrophilic region and a hydrophobic region, and wherein the hydrophilic region is polyethylene glycol; and (iii) a therapeutically effective amount of a therapeutic agent, wherein the drug delivery system provides sustained release of the therapeutic agent into the vitreous chamber over a period of time of at least three months; and wherein the vitreous chamber of the eye exhibits at least 10% less inflammation or intraocular pressure than if the particle were uncoated. In certain embodiments, the microparticle can be about 50 or 30 microns or less. The delivery system described in U.S. Pat. No. 8,889,193 and PCT/US2011/026321 can be used to deliver any of the active agents described herein.

In some embodiments, the drug delivery systems contain a particle with a coating on the surface, wherein the coating molecules have hydrophilic regions and, optionally, hydrophobic regions, The drug delivery system can include a coating. The coating can be disposed on the surface of the particle, for example by bonding, adsorption or by complexation. The coating can also be intermingled or dispersed within the particle as well as disposed on the surface of the particle.

The homogeneous or heterogenous polymer or polymeric coating can be, for example, polyethylene glycol, polyvinyl alcohol (PVA), or similar substances. The coating can be, for example, vitamin E-PEG 1k or vitamin E-PEG 5k or the like. Vitamin E-PEG 5k can help present a dense coating of PEG on the surface of a particle. The coating can also include nonionic surfactants such as those composed of polyalkylene oxide, e.g., polyoxyethylene (PEO), also referred to herein as polyethylene glycol; or polyoxypropylene (PPO), also referred to herein as polypropylene glycol (PPG), and can include a copolymer of more than one alkylene oxide.

The polymer or copolymer can be, for example, a random copolymer, an alternating copolymer, a block copolymer or graft copolymer.

In some embodiments, the coating can include a polyoxyethylene-polyoxypropylene copolymer, e.g., block copolymer of ethylene oxide and propylene oxide. (i.e., poloxamers). Examples of poloxamers suitable for use in the present invention include, for example, poloxamers 188, 237, 338 and 407. These poloxamers are available under the trade name Pluronic® (available from BASF, Mount Olive, N.J.) and correspond to Pluronic® F-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,7000 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about $E_{101}P_{56}E_{101}$ to about $E_{106}P_{70}E_{106}$, or about $E_{101}P_{56}E_{101}$, or about $E_{106}P_{70}E_{106}$, with an average molecular mass of about 10,000 to about 15,000 Da, or about 12,000 to about 14,000 Da, or about 12,000 to about 13,000 Da, or about 12,600 Da. For example, the NF forms of poloxamers or Pluronic® polymers can be used.

In some embodiments, the polymer can be, for example Pluronic® P103 or Pluronic® P105. Pluronic® P103 is a block copolymer with an average molecular mass of about 3,000 Da to about 6,000 Da, or about 4,000 Da to about 6,000 Da, or about 4,950 Da. Pluronic® P105 is a block copolymer with an average molecular mass of about 5,000 Da to about 8,000 Da, or about 6,000 Da to about 7,000 Da, or about 6,500 Da.

In some embodiments, the polymer can have an average molecular weight of about 9,000 Da or greater, about 10,000 Da or greater, about 11,000 Da or greater or about 12,000 Da or greater. In exemplary embodiments, the polymer can have an average molecular weight of from about 10,000 to about 15,000 Da, or about 12,000 to about 14,000 Da, or about 12,000 to about 13,000 Da, or about 12,600 Da. In some embodiments, the polymer can be selected from Pluronic® P103, P105, F-68, F-87, F-108 and F-127, from Pluronic® P103, P105, F-87, F-108 and F-127, or from Pluronic® P103, P105, F-108 and F-127, or from Pluronic® P103, P105 and F-127. In some embodiments, the polymer can be Pluronic® F-127. In representative embodiments, the polymer is associated with the particles. For example, the polymer can be covalently attached to the particles. In representative embodiments, the polymer comprises polyethylene glycol, which is covalently attached to a selected polymer, yielding what is commonly referred to as a PEGylated particle.

In some embodiments, a coating is non-covalently associated with a core particle. This association can be held together by any force or mechanism of molecular interaction that permits two substances to remain in substantially the same positions relative to each other, including intermolecular forces, dipole-dipole interactions, van der Waals forces, hydrophobic interactions, electrostatic interactions and the like. In some embodiments, the coating is adsorbed onto the particle. According to representative embodiments, a non-covalently bound coating can be comprised of portions or segments that promote association with the particle, for example by electrostatic or van der Waals forces. In some embodiments, the interaction is between a hydrophobic portion of the coating and the particle. Embodiments include particle coating combinations which, however attached to the particle, present a hydrophilic region, e.g. a PEG rich region, to the environment around the particle coating combination. The particle coating combination can provide both a hydrophilic surface and an uncharged or substantially neutrally-charged surface, which can be biologically inert.

Suitable polymers for use according to the compositions and methods disclosed herein can be made up of molecules having hydrophobic regions as well as hydrophilic regions. Without wishing to be bound by any particular theory, when used as a coating, it is believed that the hydrophobic regions of the molecules are able to form adsorptive interactions with the surface of the particle, and thus maintain a non-covalent association with it, while the hydrophilic regions orient toward the surrounding, frequently aqueous, environment. In some embodiments the hydrophilic regions are characterized in that they avoid or minimize adhesive interactions with substances in the surrounding environment. Suitable hydrophobic regions in a coatings can include, for example, PPO, vitamin E and the like, either alone or in combination with each other or with other substances. Suitable hydrophilic regions in the coatings can include, for example, PEG, heparin, polymers that form hydrogels and the like, alone or in combination with each other or with other substances.

Representative coatings according to the compositions and methods disclosed herein can include molecules having, for example, hydrophobic segments such as PPO segments with molecular weights of at least about 1.8 kDa, or at least about 2 kDa, or at least about 2.4 kDa, or at least about 2.8 kDa, or at least about 3.2 kDa, or at least about 3.6 kDa, or at least about 4.0 kDa, or at least about 4.4 kDa, or at least about 4.8 kDa or at least about 5.2 kDa, or at least 5.6 kDa, or at least 6.0 kDa, or at least 6.4 kDa or more. In some embodiments, the coatings can have PPO segments with molecular weights of from about 1.8 kDa to about 10 kDa, or from about 2 kDa to about 5 kDa, or from about 2.5 kDa to about 4.5 kDa, or from about 2.5 kDa to about 3.5 kDa. In some embodiments, at least about 10%, or at least about 25%, or at least about 50%, or at least about 75%, or at least about 90%, or at least about 95%, or at least about 99% or more of the hydrophobic regions in these coatings have molecular weights within these ranges. In some embodiments, the coatings are biologically inert. Compounds that generate both a hydrophilic surface and an uncharged or substantially neutrally-charged surface can be biologically inert.

Representative coatings according to the compositions and methods disclosed herein can include molecules having, for example, hydrophobic segments such as PEG segments with molecular weights of at least about 1.8 kDa, or at least about 2 kDa, or at least about 2.4 kDa, or at least about 2.8 kDa, or at least about 3.2 kDa, or at least about 3.6 kDa, or at least about 4.0 kDa, or at least about 4.4 kDa, or at least about 4.8 kDa, or at least about 5.2 kDa, or at least 5.6 kDa, or at least 6.0 kDa, or at least 6.4 kDa or more. In some embodiments, the coatings can have PEG segments with molecular weights of from about 1.8 kDa to about 10 kDa, or from about 2 kDa to about 5 kDa, or from about 2.5 kDa to about 4.5 kDa, or from about 2.5 kDa to about 3.5 kDa. In some embodiments, at least about 10%, or at least about 25%, or at least about 50%, or at least about 75%, or at least about 90%, or at least about 95%, or at least about 99% or more of the hydrophobic regions in these coatings have molecular weights within these ranges. In some embodiments, the coatings are biologically inert. Compounds that generate both a hydrophilic surface and an uncharged or substantially neutrally-charged surface can be biologically inert.

Representative coatings according to the compositions and methods disclosed herein can include molecules having, for example, segments such as PLGA segments with molecular weights of at least about 4 kDa, or at least about 8 kDa, or at least about 12 kDa, or at least about 16 kDa, or at least about 20 kDa, or at least about 24 kDa, or at least about 28 kDa, or at least about 32 kDa, or at least about 36 kDa, or at least about 40 kDa, or at least about 44 kDa, of at least about 48 kDa, or at least about 52 kDa, or at least about 56 kDa, or at least about 60 kDa, or at least about 64 kDa, or at least about 68 kDa, or at least about 72 kDa, or at least about 76 kDa, or at least about 80 kDa, or at least about 84 kDa, or at least about 88 kDa or more. In some embodiments, at least about 10%, or at least about 25%, or at least about 50%, or at least about 75%, or at least about 90%, or at least about 95%, or at least about 99% or more of the regions in these coatings have molecular weights within these ranges. In some embodiments, the coatings are biologically inert. Compounds that generate both a hydrophilic surface and an uncharged or substantially neutrally-charged surface can be biologically inert.

In some embodiments, s coating can include, for example, one or more of the following: anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin), mucolytic agents, N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin J34, dornase alfa, neltenexine, erdosteine, various DNases including rhDNase, agar, agarose, alginic acid, amylopectin, amylose, beta-glucan, callose, carrageenan, cellodextrins, cellulin, cellulose, chitin, chitosan, chrysolaminarin, curdlan, cyclodextrin, dextrin, ficoll, fructan, fucoidan, galactomannan, gellan gum, glucan, glucomannan, glycocalyx, glycogen, hemicellulose, hydroxyethyl starch, kefiran, laminarin, mucilage, glycosaminoglycan, natural gum, paramylon, pectin, polysaccharide peptide, schizophyllan, sialyl lewis x, starch, starch gelatinization, sugammadex, xanthan gum, xyloglucan, L-phosphatidylcholine (PC), 1,2-dipalmitoylphosphatidylcholine (DPPC), oleic acid, sorbitan trioleate, sorbitan monooleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, polyoxyethylene (4) lauryl ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, sunflower seed oil, lecithin, oleic acid, sorbitan trioleate, and combinations of two or more of any of the foregoing.

A particle-coating combinations can be made up of any combination of particle and coating substances disclosed or suggested herein. Examples of such combinations include, for example, polystyrene-PEG, or PLGA-Pluronic® F-127.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In another aspect of the present invention, the nanoparticle or microparticle is coated with a surface agent that facilitates passage of the particle through mucus. Said nanoparticles and microparticles have a higher concentration of surface agent than has been previously achieved, leading to the unexpected property of extremely fast diffusion through mucus. The present invention further comprises a method of producing said particles. The present invention further comprises methods of using said particles to treat a patient.

A number of companies have developed microparticles for treatment of eye disorders that can be used in conjunction with the present invention. For example, Allergan has disclosed a biodegradable microsphere to deliver a therapeutic agent that is formulated in a high viscosity carrier suitable for intraocular injection or to treat a non-ocular disorder (see U.S. publication 2010/0074957 and U.S. publication 2015/0147406). In one embodiment, the '957 application describes a biocompatible, intraocular drug delivery system that includes a plurality of biodegradable microspheres, a therapeutic agent, and a viscous carrier, wherein the carrier has a viscosity of at least about 10 cps at a shear rate of 0.1/second at 25° C. Allergan has also disclosed a composite drug delivery material that can be injected into the eye of a patient that includes a plurality of microparticles dispersed in a media, wherein the microparticles contain a drug and a biodegradable or bioerodible coating and the media includes the drug dispersed in a depot-forming material, wherein the media composition may gel or solidify on injection into the eye (see WO 2013/112434 A1, claiming priority to Jan. 23, 2012). Allergan states that this invention can be used to provide a depot means to implant a solid sustained drug delivery system into the eye without an incision. In general, the depot on injection transforms to a material that has a viscosity that may be difficult or impossible to administer by injection. In addition, Allergan has disclosed biodegradable microspheres between 40 and 200 μm in diameter, with a mean diameter between 60 and 150 μm that are effectively retained in the anterior chamber of the eye without producing hyperemia, see, US 2014/0294986. The microspheres contain a drug effective for an ocular condition with greater than seven day release following administration to the anterior chamber of the eye. The administration of these large particles is intended to overcome the disadvantages of injecting 1-30 µm particles which are generally poorly tolerated.

In another embodiment any of the above delivery systems can be used to facilitate or enhance delivery through mucus.

Common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

Solvent Evaporation

In this method, the drug (or polymer matrix and one or more Drugs) is dissolved in a volatile organic solvent, such as methylene chloride. The organic solution containing the drug is then suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

Drugs which contain labile polymers, such as certain polyanhydrides, may degrade during the fabrication process due to the presence of water. For these polymers, the following two methods, which are performed in completely anhydrous organic solvents, can be used.

Solvent Removal

Solvent removal can also be used to prepare particles from drugs that are hydrolytically unstable. In this method, the drug (or polymer matrix and one or more Drugs) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment a compound of the present invention is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

Spray Drying

In this method, the drug (or polymer matrix and one or more Drugs) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Particles ranging between 0.1-10 microns can be obtained using this method.

In one embodiment a compound of the present invention is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated.

Phase Inversion

Particles can be formed from drugs using a phase inversion method. In this method, the drug (or polymer matrix and one or more Drugs) is dissolved in a "good" solvent, and the solution is poured into a strong non solvent for the drug to spontaneously produce, under favorable conditions, microparticles or nanoparticles. The method can be used to produce nanoparticles in a wide range of sizes, including, for example, about 100 nanometers to about 10 microns, typically possessing a narrow particle size distribution.

In one embodiment a compound of the present invention is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Coacervation

Techniques for particle formation using coacervation are known in the art, for example, in GB-B-929 406; GB-B-929 40 1; and U.S. Pat. Nos. 3,266,987, 4,794,000, and 4,460, 563. Coacervation involves the separation of a drug (or polymer matrix and one or more Drugs) solution into two immiscible liquid phases. One phase is a dense coacervate phase, which contains a high concentration of the drug, while the second phase contains a low concentration of the drug. Within the dense coacervate phase, the drug forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment a compound of the present invention is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Low Temperature Casting

Methods for very low temperature casting of controlled release microspheres are described in U.S. Pat. No. 5,019,400 to Gombotz et al. In this method, the drug (or polymer matrix and Sunitinib) is dissolved in a solvent. The mixture is then atomized into a vessel containing a liquid non-solvent at a temperature below the freezing point of the drug solution which freezes the drug droplets. As the droplets and non-solvent for the drug are warmed, the solvent in the droplets thaws and is extracted into the non-solvent, hardening the microspheres.

In one embodiment a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

V. CONTROLLED RELEASE OF THERAPEUTIC AGENT

The rate of release of the therapeutic agent can be related to the concentration of therapeutic agent dissolved in polymeric material. In many embodiments, the polymeric composition includes non-therapeutic agents that are selected to provide a desired solubility of the therapeutic agent. The selection of polymer can be made to provide the desired solubility of the therapeutic agent in the matrix, for example, a hydrogel may promote solubility of hydrophilic material. In some embodiments, functional groups can be added to the polymer to increase the desired solubility of the therapeutic agent in the matrix. In some embodiments, additives may be used to control the release kinetics of therapeutic agent, for example, the additives may be used to control the concentration of therapeutic agent by increasing or decreasing solubility of the therapeutic agent in the polymer so as to control the release kinetics of the therapeutic agent. The solubility may be controlled by including appropriate molecules and/or substances that increase and/or decrease the solubility of the dissolved from of the therapeutic agent to the matrix. The solubility of the therapeutic agent may be related to the hydrophobic and/or hydrophilic properties of the matrix and therapeutic agent. Oils and hydrophobic molecules and can be added to the polymer to increase the solubility of hydrophobic treatment agent in the matrix.

Instead of or in addition to controlling the rate of migration based on the concentration of therapeutic agent dissolved in the matrix, the surface area of the polymeric composition can be controlled to attain the desired rate of drug migration out of the composition. For example, a larger exposed surface area will increase the rate of migration of the active agent to the surface, and a smaller exposed surface area will decrease the rate of migration of the active agent to the surface. The exposed surface area can be increased in any number of ways, for example, by any of castellation of the exposed surface, a porous surface having exposed channels connected with the tear or tear film, indentation of the exposed surface, protrusion of the exposed surface. The exposed surface can be made porous by the addition of salts that dissolve and leave a porous cavity once the salt dissolves. In the present invention, these trends can be used to decrease the release rate of the active material from the polymeric composition by avoiding these paths to quicker release. For example, the surface area can be minimized, or channels avoided.

Further, an implant may be used that includes the ability to release two or more drugs in combination, for example, the structure disclosed in U.S. Pat. No. 4,281,654 (Shell), for example, in the case of glaucoma treatment, it may be desirable to treat a patient with multiple prostaglandins or a prostaglandin and a cholinergic agent or an adrenergic antagonist (beta blocker), for example, Alphagan (Allegan, Irvine, Calif., USA), or a prostaglandin and a carbonic anhydrase inhibitor.

In addition, drug impregnated meshes may be used, for example, those disclosed in U.S. Patent Application Publication No. 2002/0055701 or layering of biostable polymers as described in U.S. Patent Application Publication No. 2005/0129731. Certain polymer processes may be used to incorporate drug into the devices, as described herein, for example, so-called "self-delivering drugs" or Polymer Drugs (Polymerix Corporation, Piscataway, N.J., USA) are designed to degrade only into therapeutically useful compounds and physiologically inert linker molecules, further detailed in U.S. Patent Application Publication No. 2005/0048121 (East), hereby incorporated by reference in its entirety. Such delivery polymers may be employed in the devices, as described herein, to provide a release rate that is equal to the rate of polymer erosion and degradation and is constant throughout the course of therapy. Such delivery polymers may be used as device coatings or in the form of microspheres for a drug depot injectable (for example, a reservoir described herein). A further polymer delivery technology may also be adapted to the devices, as described herein, for example, that described in U.S. Patent Application Publication No. 2004/0170685 (Carpenter), and technologies available from Medivas (San Diego, Calif., USA).

VI. PROCESS OF PREPARATION OF COMPOUNDS OF FORMULA I, FORMULA II, FORMULA II', FORMULA III, FORMULA IV, FORMULA V, FORMULA VI, FORMULA III', FORMULA IV', FORMULA V', FORMULA VI', FORMULA VII, FORMULA VII', FORMULA VIII, FORMULA IX, FORMULA X, FORMULA XI, FORMULA XII, FORMULA XIV, FORMULA XV, FORMULA XVI, FORMULA XVII, FORMULA XVIII, FORMULA XIX, FORMULA XX, FORMULA XXI, FORMULA XXII, OR FORMULA XXIII

Abbreviations

CAN Acetonitrile
Ac Acetyl
$Ac_2O$ Acetic anhydride
AcOEt, EtOAc ethyl acetate
AcOH Acetic acid
$Boc_2O$ di-tert-butyl dicarbonate
Bu Butyl
CAN Ceric ammonium nitrate
CBz Carboxybenzyl
CDI Carbonyldiimidazole
$CH_3OH$, MeOH Methanol
CsF Cesium fluoride
CuI Cuprous iodide
DCM, $CH_2Cl_2$ Dichloromethane
DIEA, DIPEA N,N-diisopropylethylamine
DMA N,N-dimethylacetamide
DMAP 4-Dimethylaminopyridine
DMF N,N-dimethylformamide
DMS Dimethyl sulfide
DMSO Dimethylsulfoxide
DPPA Diphenyl phosphoryl azide
EDCI 1-Ethyl-3-(3-dimethylaminopropyl)carbodiimide
Et Ethyl
$Et_3N$, TEA Triethylamine
EtOAc Ethylacetate
EtOH Ethanol
HATU 1-[Bis(dimethylamino)methylene]-1H-1,2,3-triazolo[4,5-b]pyridinium3-oxide hexafluorophosphate
HCl Hydrochloric acid
HOBT Hydroxybenzotriazole
iBu, i-Bu, isoBu Isobutyl
iPr, i-Pr, isoPr Isopropyl
$iPr_2NEt$ N,N-diisopropylethylamine
$K_2CO_3$ Potassium carbonate
$K_2CO_3$ Potassium carbonate
LiOH Lithium hydroxide
Me Methyl
MeI Methyl iodide
Ms Mesyl
MsCl Mesylchloride
MTBE Methyl tbutylether
$Na_2SO_4$ Sodium sulfate
NaCl Sodium chloride
NaH Sodium hydride
$NaHCO_3$ Sodium bicarbonate
NBS N-bromo succinimide
NCS N-chloro succinimide
$NEt_3$ Trimethylamine
NMP N-Methyl-2-pyrrolidone
PCC Pyridinium chlorochromate
$Pd(OAc)_2$ Palladium acetate
$Pd(dppf)Cl_2$ [1,1'-Bis(diphenylphosphino) ferrocene]dichloropalladium(II)
$Pd(PPh_3)_2Cl_2$ Bis(triphenylphosphine)palladium(II) dichloride
$Pd(PPh_3)_4$ Tetrakis(triphenylphosphine)palladium(0)
Pd/C Palladium on carbon
$Pd_2(dba)_3$ Tris(dibenzylideneacetone)dipalladium(0)
PMB 4-Methoxybenzyl ether
$PPh_3$ Triphenylphosphine
Pr Propyl
Py, py Pyridine
RT Room temperature
TBAF Tetra-n-butylammonium fluoride
TBAT Tetrabutylammonium difluorotriphenylsilicate
tBu, t-Bu Tertbutyl
tBuOK Potassium tert-butoxide
TEA Trimethylamine
$Tf_2O$ Trifluoromethanesulfonic anhydride
TFA Trifluoroacetic acid
THF Tetrahydrofuran
TMS Trimethylsilane
TMSBr Bromotrimethylsilane
tR Retention time
Troc 2,2,2-Trichlorethoxycarbonyl chloride
$Zn(CN)_2$ Zinc cyanide General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

Example 1. Synthetic Examples of Ester Intermediates for the Preparation of Final Prodrugs Scheme 1: (S)-2-(tert-Butyl-diphenyl-silanyloxy)-propionic acid (S)-1-carboxy-ethyl ester (1-4):

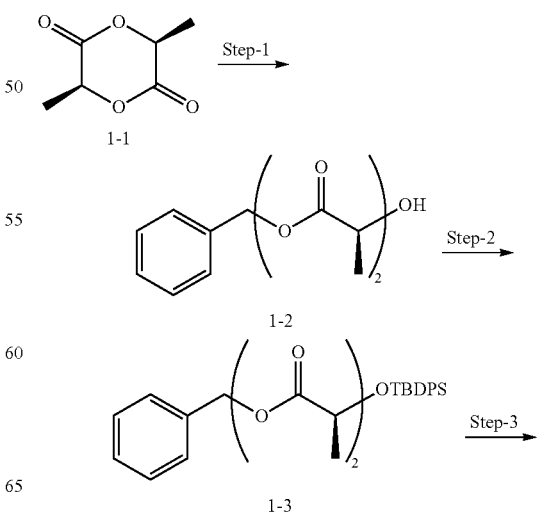

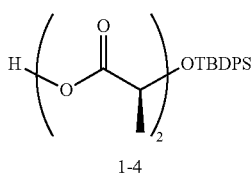

1-4

Step 1: (S)-2-Hydroxy-propionic acid (S)-1-benzyloxycarbonyl-ethyl ester (1-2)

To a solution of (3S,6S)-3,6-dimethyl-[1,4]dioxane-2,5-dione (1-1) (5.0 g, 34.72 mmol) in toluene (100 mL) was added benzyl alcohol (3.2 mL, 31.72 mmol) and camphorsulfonic acid (0.8 g, 3.47 mmol) at 25-30° C. After stirring at 80° C. for 2 hours, the resulting reaction mixture was diluted with ethyl acetate (800 mL) and washed with water (2×400 mL). Following evaporation of volatiles, the reaction mixture was purified by silica gel (230-400) column chromatography (5% methanol in dichloromethane) to afford product 1-2 as a pale yellow liquid (8.0 g, 91%). $^1$H NMR (400 MHz, DMSO-$d_6$) δ 7.41-7.32 (m, 5H), 5.48 (d, J=5.6 Hz, 1H), 5.15 (s, 2H), 5.1 (q, J=8.0 Hz, 1H), 4.20-4.18 (m, 1H), 1.42 (d, J=7.2 Hz, 3H), 1.16 (d, J=7.2 Hz, 3H). MS m/z (M+H) 253.4; MS m/z (M+NH$_4$) 270.3.

Step 2: (S)-2-(tert-Butyl-diphenyl-silanyloxy)-propionic acid (S)-1-benzyloxycarbonyl-ethyl ester (1-3)

To a solution of (S)-2-hydroxy-propionic acid (S)-1-benzyloxycarbonyl-ethyl ester (1-2) (0.1 g, 0.23 mmol) in dichloromethane (2 mL) was added triethylamine (0.23 mL, 1.61 mmol), TBDPS-C$_1$ (0.43 mL, 1.618 mmol), and a catalytic amount of 4-dimethylaminopyridine at 0° C. After stirring at room temperature for 8 hours, the resulting reaction mixture was quenched with water (20 mL) and extracted with ethyl acetate (2×50 mL). Evaporation of volatiles under reduced pressure afforded product 1-3 as a colorless liquid (200 mg, 74%).

Step 3: (S)-2-(tert-Butyl-diphenyl-silanyloxy)-propionic acid (S)-1-carboxy-ethyl ester (1-4)

A solution of (S)-2-(tert-butyl-diphenyl-silanyloxy)-propionic acid (S)-1-benzyloxycarbonyl-ethyl ester (1-3) (1.5 g) in methanol (20 mL) and 10% Pd/C (0.3 g, 50% wet) were added to a 100 mL autoclave vessel at 25-30° C. The reaction mixture was stirred at room temperature under hydrogen pressure (5 kg/cm$^2$) for 2 hours. After completion of the reaction, the reaction mixture was filtered through celite and concentrated under reduced pressure. The crude product obtained upon evaporation of volatiles was purified by silica gel (60-120) column chromatography (10% methanol in dichloromethane) to afford pure product 1-4 as a colorless liquid (700 mg, 58%). $^1$H NMR (400 MHz, DMSO-$d_6$) δ 13.1 (bs, 1H), 7.63-7.62 (m, 4H), 7.62-7.37 (m, 6H), 4.77 (q, J=7.6 Hz, 1H), 4.26 (q, J=8.0.0 Hz, 1H), 1.31 (d, J=6.8 Hz, 3H), 1.23 (d, J=7.2 Hz, 3H), 1.02 (s, 9H); MS m/z (M−H) 399.1.

Scheme 2: Synthesis of (S)-2-(tert-Butyl-diphenyl-silanyloxy)-propionic acid (S)-1-((S)-1-carboxy-ethoxycarbonyl)-ethyl ester (2-3):

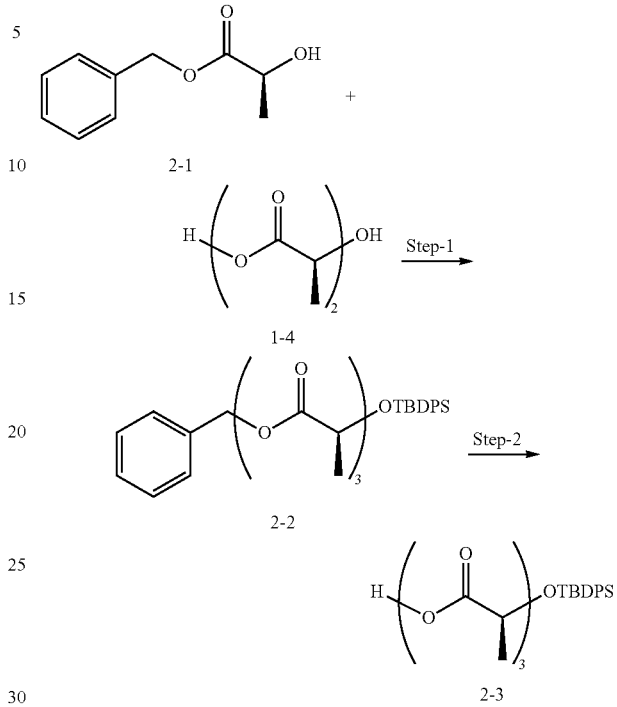

Step 1: (S)-2-(tert-Butyl-diphenyl-silanyloxy)-propionic acid (S)-1-((S)-1-benzyloxycarbonyl-ethoxycarbonyl)-ethyl ester (2-2)

To a solution of (S)-2-(tert-butyl-diphenyl-silanyloxy)-propionic acid (S)-1-carboxy-ethyl ester (1-4) (5.17 g, 7.22 mmol) in dichloromethane (10 mL) was added EDCI.HCl (2.12 g, 11.11 mmol), (S)-2-hydroxy-propionic acid benzyl ester (2-1) (1 g, 5.55 mmol), and 4-dimethylaminopyridine (670 mg, 0.55 mmol) at 0° C. The reaction mixture was allowed to stir at 25° C. for 1 hour, and the resulting reaction mixture was diluted with ethyl acetate (300 mL) and washed with water (2×50 mL). The crude product obtained upon evaporation of volatiles was purified by silica gel (230-400) column chromatography (3% ethyl acetate in hexane) to afford product 2-2 as a colorless liquid (4.3 g, 88%). $^1$H NMR (400 MHz, DMSO-$d_6$) δ 7.62-7.61 (m, 4H), 7.60-7.33 (m, 11H), 5.19-5.14 (m, 3H), 4.94 (q, J=6.8 Hz, 1H), 4.28 (q, J=6.8 Hz, 1H), 1.42 (d, J=7.2 Hz, 3H), 1.31 (d, J=6.4 Hz, 3H), 1.23 (d, J=7.2 Hz, 3H), 1.02 (s, 9H); MS m/z (M+NH$_4^+$) 580.3.

Step 2: (S)-2-(tert-Butyl-diphenyl-silanyloxy)-propionic acid (S)-1-((S)-1-carboxy-ethoxycarbonyl)-ethyl ester (2-3)

A solution of (S)-2-(tert-butyl-diphenyl-silanyloxy)-propionic acid (S)-1-((S)-1-benzyloxycarbonyl-ethoxycarbonyl)-ethyl ester (2-2) (7.0 g, 12.45) in methanol (40 mL) and 10% Pd/C (1.4 g, 50% wet) were added to a 100 mL autoclave vessel at 25-30° C. The reaction mixture was stirred at room temperature under hydrogen pressure (5 kg/cm$^2$) for 2 hours. After completion of the reaction, the reaction mixture was filtered through celite and concentrated under reduced pressure. The crude product obtained upon evaporation of volatiles was purified by silica gel (60-120) column chromatography (10% methanol in dichloromethane) to afford product 2-3 as a pale yellow liquid (5.8 g, 94%). $^1$H NMR (400 MHz, DMSO-$d_6$) δ 13.2 (bs, 1H), 7.61 (d, J=1.2 Hz, 4H), 7.60-7.40 (m, 6H), 4.99-4.91 (m, 2H), 1.39 (d, J=7.2 Hz, 3H), 1.32 (d, J=6.4 Hz, 3H), 1.29 (d, J=6.8 Hz, 3H), 1.02 (s, 9H); MS m/z (M−H) 471.3.

Scheme 3: Synthesis of (S)-2-(tert-Butyl-diphenyl-silanyloxy)-propionic acid (S)-1-[(S)-1-((S)-1-carboxy-ethoxycarbonyl)-ethoxycarbonyl]-ethyl ester (3-2):

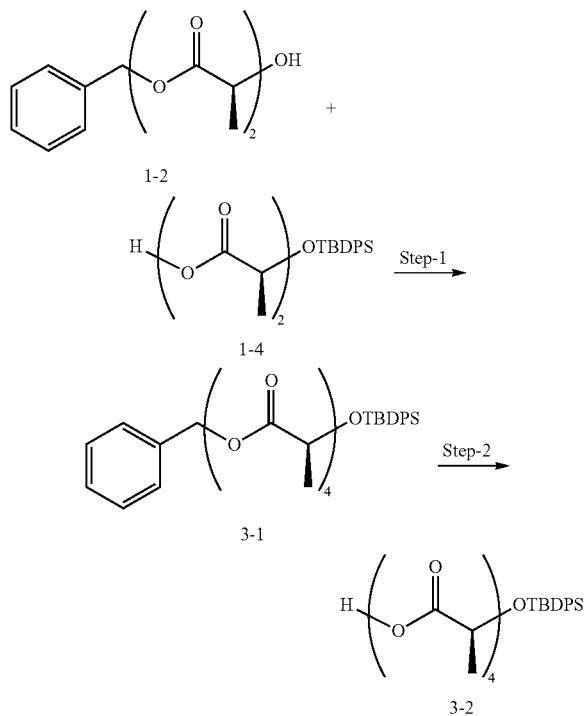

Step 1: (S)-2-(tert-Butyl-diphenyl-silanyloxy)-propionic acid (S)-1-[(S)-1-((S)-1-benzyloxycarbonyl-ethoxycarbonyl)-ethoxycarbonyl]-ethyl ester (3-1)

To a solution of (S)-2-hydroxy-propionic acid (S)-1-benzyloxycarbonyl-ethyl ester (1-2) (6.0 g, 33.2 mmol) and (S)-2-(tert-butyl-diphenyl-silanyloxy)-propionic acid (S)-1-carboxy-ethyl ester (1-4) (17.3 g, 7.77 mmol) in dichloromethane (60 mL) was added EDCI.HCl (8.2 g, 43.2 mmol, 1.5 eq) and 4-dimethylaminopyridine (405 mg, 3.3 mmol) at 0° C. The reaction mixture was allowed to stir at 25-30° C. for 1 hour, and the resulting reaction mixture was quenched with water (200 mL), extracted with dichloromethane (250×3 mL), dried over Na$_2$SO$_4$, and concentrated under reduced pressure. The crude product obtained upon evaporation of volatiles was purified by silica gel (60-120) column chromatography (10% methanol in dichloromethane) to afford product 3-1 as a pale yellow liquid (5.8 g, 94%). $^1$H NMR (400 MHz, DMSO-$d_6$) δ 7.60 (d, J=8 Hz, 4H), 7.49-7.33 (m, 11H), 5.20-5.15 (m, 4H), 4.95 (q, J=7.2 Hz, 1H), 4.29 (q, J=6.4 Hz, 1H), 1.43 (d, J=7.2 Hz, 3H), 1.39 (d, J=7.2 Hz, 3H), 1.31 (d, J=6.8 Hz, 3H), 1.28 (d, J=1.28 Hz, 3H), 1.02 (s, 9H); MS m/z (M+NH$_4^+$) 652.8.

Step 2: (S)-2-(tert-Butyl-diphenyl-silanyloxy)-propionic acid (S)-1-[(S)-1-((S)-1-carboxy-ethoxycarbonyl)-ethoxycarbonyl]-ethyl ester (3-2)

A solution of (S)-2-(tert-butyl-diphenyl-silanyloxy)-propionic acid (S)-1-[(S)-1-((S)-1-benzyloxycarbonyl-ethoxycarbonyl)-ethoxycarbonyl]-ethyl ester (3-1) (700 mg, 1.10 mmol) in methanol (10 mL) and 10% Pd/C (140 mg, 50% wet) were added to a 100 mL autoclave vessel at 25-30° C. The reaction mixture was stirred at room temperature under hydrogen pressure (5 kg/cm$^2$) for 2 hours. After completion of the reaction, the reaction mixture was filtered through celite and concentrated under reduced pressure. The crude product obtained upon evaporation of volatiles was purified by silica gel (60-120) column chromatography (10% methanol in dichloromethane) to afford product 3-2 as a pale yellow liquid (420 mg, 78%). $^1$H NMR (400 MHz, DMSO-$d_6$) δ 13.2 (bs, 1H), 7.61-7.60 (m, 4H), 7.59-7.40 (m, 6H), 5.16 (q, J=7.2 Hz 1H), 4.98-4.93 (m, 2H), 4.29 (q, J=6.8, 1H), 1.44 (d, J=7.2 Hz, 3H), 1.40 (d, J=7.2 Hz, 3H), 1.31-1.30 (m, 6H), 1.01 (s, 9H); MS m/z (M+NH$_4^+$) 562.3; MS m/z (M−H) 543.1.

Scheme 4: (S)-2-(tert-Butyl-diphenyl-silanyloxy)-propionic acid (S)-1-{(S)-1-[(S)-1-((S)-1-carboxy-ethoxycarbonyl)-ethoxycarbonyl]-ethoxycarbonyl}-ethyl ester (4-2):

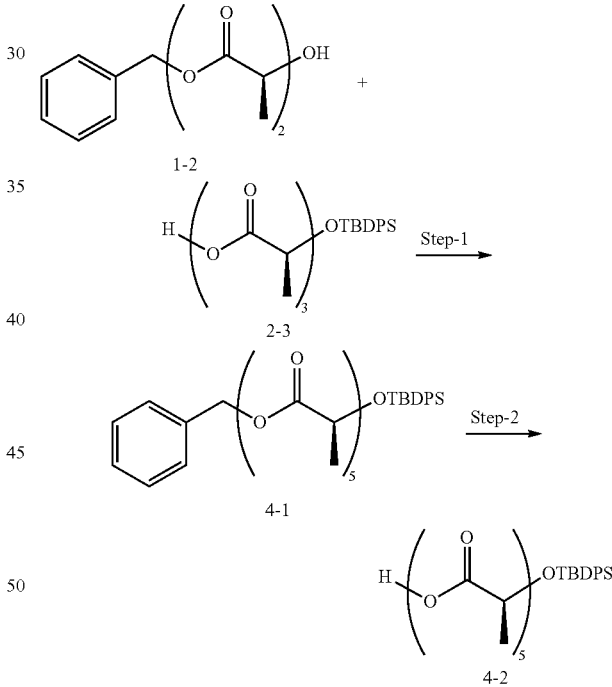

Step 1: (S)-2-(tert-Butyl-diphenyl-silanyloxy)-propionic acid (S)-1-{(S)-1-[(S)-1-((S)-1-benzyloxycarbonyl-ethoxycarbonyl)-ethoxycarbonyl]-ethoxycarbonyl}-ethyl ester (4-1)

EDCI.HCl (5.68 g, 29.76 mmol) and 4-dimethylaminopyridine (242 mg, 1.98 mmol) were added to a solution of (S)-2-hydroxy-propionic acid (S)-1-benzyloxycarbonyl-ethyl ester (1-2) (5.0 g, 19.84 mmol) and (S)-2-(tert-butyl-diphenyl-silanyloxy)-propionic acid (S)-1-((S)-1-carboxy-ethoxycarbonyl)-ethyl ester (2-3) (12.1 g, 25.79 mmol) in dichloromethane (50 mL) at 0° C. The reaction mixture was allowed to stir at 25-30° C. for 1 hour, and the resulting reaction mixture was quenched with water (200 mL), extracted with dichloromethane (250×3 mL), dried over sodium sulfate, and concentrated under reduced pressure. The crude product obtained upon evaporation of volatiles was purified by silica gel (230-400) column chromatography (6% ethyl acetate in hexane) to afford product 4-1 as a pale yellow liquid (9.1 g, 65%).

Step 2: (S)-2-(tert-Butyl-diphenyl-silanyloxy)-propionic acid (S)-1-{(S)-1-[(S)-1-((S)-1-carboxy-ethoxycarbonyl)-ethoxycarbonyl]-ethoxycarbonyl}-ethyl ester (4-2)

A solution of (S)-2-(tert-butyl-diphenyl-silanyloxy)-propionic acid (S)-1-{(S)-1-[(S)-1-((S)-1-benzyloxycarbonyl-ethoxycarbonyl)-ethoxycarbonyl]-ethoxycarbonyl}-ethyl ester (4-1) (9.1 g, 12.88 mmol) in methanol (50 mL) and 10% Pd/C (1.9 g, 50% wet) were added to a 100 mL autoclave vessel at 25-30° C. The reaction mixture was stirred at room temperature under hydrogen pressure (5 kg/cm$^2$) over a period of 2 hours. After completion of the reaction, the reaction mixture was filtered through celite and concentrated under reduced pressure. The crude product obtained upon evaporation of volatiles was purified by silica gel (60-120) column chromatography (10% methanol in dichloromethane) to afford product 4-2 as a pale yellow liquid (6.2 g, 78%). $^1$H NMR (400 MHz, DMSO-d$_6$) δ 13.1 (bs, 1H), 7.61-7.59 (m, 4H), 7.49-7.40 (m, 6H), 5.20-5.14 (m, 2H), 5.0-4.92 (m, 2H), 4.30-4.26 (m, 1H), 1.47-1.41 (m, 9H), 1.40-1.30 (m, 6H), 1.01 (s, 9H); MS m/z (M−H) 615.4.

Scheme 5: (S)-2-(tert-Butyl-diphenyl-silanyloxy)-propionic acid (S)-1-((S)-1-{(S)-1-[(S)-1-((S)-1-carboxy-ethoxycarbonyl)-ethoxycarbonyl]-ethoxycarbonyl}-ethoxycarbonyl)-ethyl ester (5-2):

Step 1: (S)-2-(tert-Butyl-diphenyl-silanyloxy)-propionic acid (S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethyl ester (5-1)

To a solution of (S)-2-hydroxy-propionic acid (S)-1-benzyloxycarbonyl-ethyl ester (1-2) (6.0 g, 23.8 mmol) and (S)-2-(tert-butyl-diphenyl-silanyloxy)-propionic acid (S)-1-[(S)-1-((S)-1-carboxy-ethoxycarbonyl)-ethoxycarbonyl]-ethyl ester (3-2) (16.8 g, 30.95 mmol) in dichloromethane (60 mL) was added EDCI.HCl (6.81 g, 35.7 mmol) and 4-dimethylaminopyridine (290 mg, 2.38 mmol) at 0° C. The reaction mixture was allowed to stir at 25-30° C. over a period of 1 hour, and the resulting reaction mixture was quenched with water (200 mL), extracted with dichloromethane (250×3 mL), dried over sodium sulfate, and concentrated under reduced pressure. The crude product obtained upon evaporation of volatiles was purified by silica gel (230-400) column chromatography (6% ethyl acetate in hexane) to afford product 5-1 as a pale yellow liquid (8.3 g, 46%). $^1$H NMR (400 MHz, DMSO-d$_6$) δ 7.64-7.56 (m, 4H), 7.53-7.29 (m, 11H), 5.24-5.08 (m, 6H), 4.95 (q, J=7.0 Hz, 1H), 4.29 (q, J=6.7 Hz, 1H), 1.50-1.20 (m, 12H), 1.02 (m, 6H), 1.01 (s, 9H); MS m/z (M+H) 796.7.

Step 2: (S)-2-(tert-Butyl-diphenyl-silanyloxy)-propionic acid (S)-1-((S)-1-{(S)-1-[(S)-1-((S)-1-carboxy-ethoxycarbonyl)-ethoxycarbonyl]-ethoxycarbonyl}-ethoxycarbonyl)-ethyl ester (5-2)

A solution of (S)-2-(tert-butyl-diphenyl-silanyloxy)-propionic acid (S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethyl ester (5-1) (8.3 g, 10.66 mmol) in methanol (40 mL) and 10% Pd/C (1.7 g, 50% wet) were added to a 250 mL autoclave vessel at 25-30° C. The reaction mixture was stirred at room temperature under hydrogen pressure (5 kg/cm$^2$) for 2 hours. After completion of the reaction, the reaction mixture was filtered through celite and concentrated under reduced pressure. The crude product obtained upon evaporation of volatiles was purified by silica gel (60-120) column chromatography (10% methanol in dichloromethane) to afford product 5-2 as a pale yellow liquid (5.9 g, 81%). $^1$H NMR (400 MHz, DMSO-d$_6$) δ 13.27 (bs, 1H), 7.64-7.57 (m, 4H), 7.54-7.37 (m, 6H), 5.15-5-21 (m, 3H), 5.01-4.92 (m, 2H), 4.29 (q, J=6.7 Hz, 1H), 1.47-1.44 (m, 12H), 1.23-1.28 (m, 6H), 1.04 (s, 9H); MS m/z (M−H) 687.6.

Scheme 6: (S)-2-(tert-Butyl-diphenyl-silanyloxy)-propionic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (6-2):

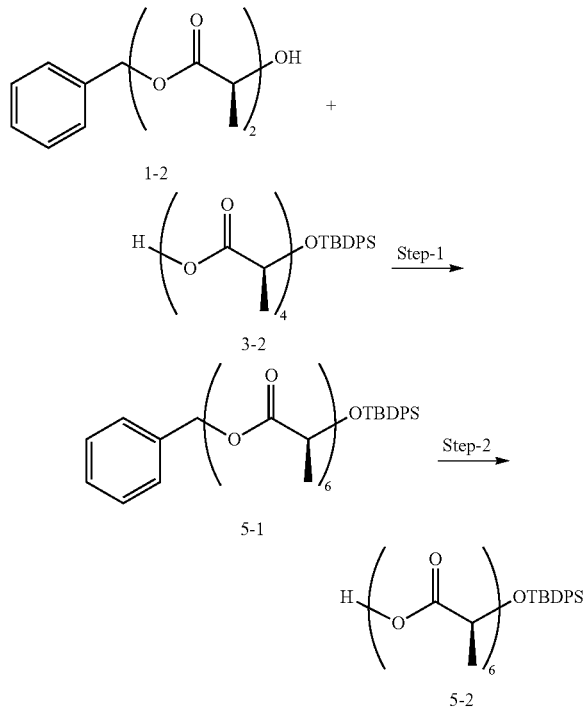

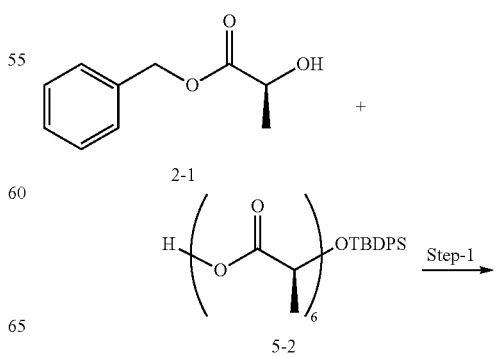

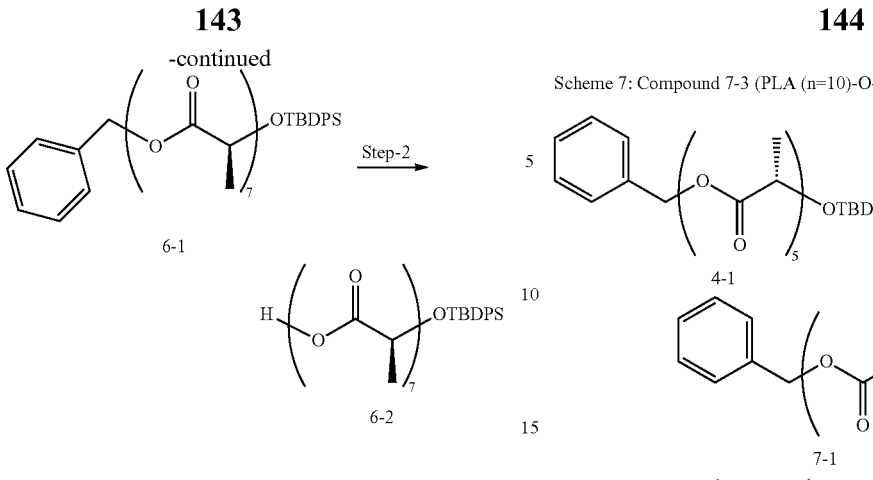

6-1

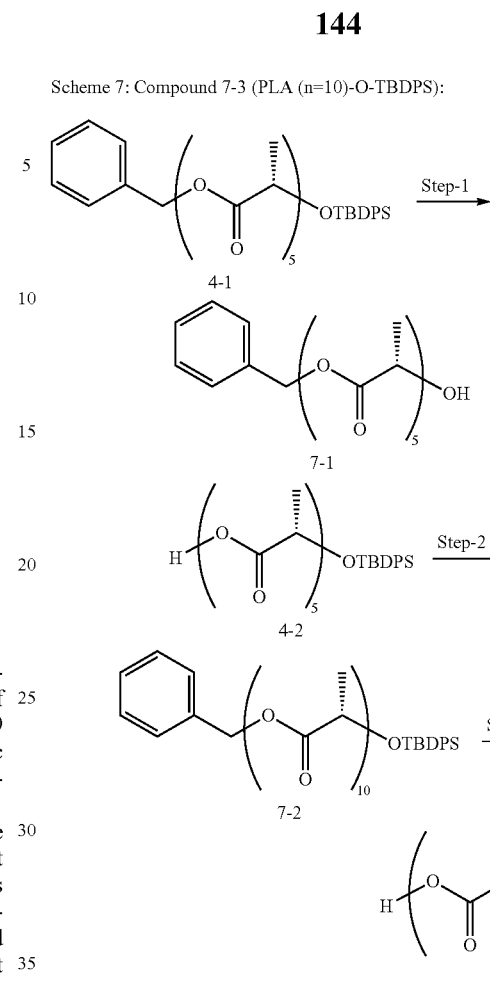

Scheme 7: Compound 7-3 (PLA (n=10)-O-TBDPS):

Step 1: (S)-2-(tert-Butyl-diphenyl-silanyloxy)-propionic acid (S)-1-[(S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethoxycarbonyl]-ethyl ester (6-1)

EDCI.HCl (3.17 g 0.16.64 mmol) and 4-dimethylaminopyridine (135 mg, 1.10 mmol) were added to a solution of (S)-2-hydroxy-propionic acid benzyl ester (2-1) (2 g, 11.09 mmol) and (S)-2-(tert-butyl-diphenyl-silanyloxy)-propionic acid (S)-1-((S)-1-{(S)-1-[(S)-1-((S)-1-carboxy-ethoxycarbonyl)-ethoxycarbonyl]-ethoxycarbonyl}-ethoxycarbonyl)-ethyl ester (5-2) (9.93 g, 14.42 mmol) in dichloromethane (20 mL) at 0° C. The reaction mixture was allowed to stir at 25-30° C. for 1 hour, and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (7% ethyl acetate in hexane) to afford product 6-1 as a pale yellow liquid (5.1 g, 53%). $^1$H NMR (400 MHz, DMSO-$d_6$) δ 7.64-7.56 (m, 4H), 7.53-7.30 (m, 11H), 5.24-5.15 (m, 7H), 4.95 (q, J=8 Hz, 1H), 4.29 (q, J=6.7 Hz, 1H), 1.48-1.41 (m, 15H), 1.35-1.21 (m, 6H), 1.02 (s, 9H); MS m/z (M+NH$_4^+$) 868.9.

Step 2: (S)-2-(tert-Butyl-diphenyl-silanyloxy)-propionic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (6-2)

(S)-2-(tert-butyl-diphenyl-silanyloxy)-propionic acid (S)-1-[(S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethoxycarbonyl]-ethyl ester (6-1) (5.1 g, 6.00 mmol) in methanol (30 mL) and 10% Pd/C (1.14 g, 50% wet) were added to a 250 mL autoclave vessel at 25-30° C. The reaction mixture was stirred at room temperature under hydrogen pressure (5 kg/cm$^2$) for 2 hours. After completion of the reaction, the reaction mixture was filtered through celite and concentrated under reduced pressure. The crude product obtained upon evaporation of volatiles was purified by silica gel (60-120) column chromatography (12% methanol in dichloromethane) to afford product 6-2 as a pale yellow liquid (3.66 g, 80%). $^1$H NMR (400 MHz, DMSO-$d_6$) δ 7.61 (bs, 1H), 7.62-7.60 (m, 4H), 7.41-7.51 (m, 6H), 5.1-5.3 (m, 4H), 4.90-4.89 (m, 2H), 4.3 (q, J=6.8 Hz, 1H), 1.50-1.37 (m, 15H), 1.35-1.18 (m, 6H), 1.02 (s, 9H); MS m/z (M+NH$_4^+$) 778.9.

Step 1: (S)-2-Hydroxy-propionic acid (S)-1-{(S)-1-[(S)-1-((S)-1-benzyloxycarbonyl-ethoxycarbonyl)-ethoxycarbonyl]-ethoxycarbonyl}-ethyl ester (7-1)

To a solution of (S)-2-(tert-butyl-diphenyl-silanyloxy)-propionic acid (S)-1-{(S)-1-[(S)-1-((S)-1-benzyloxycarbonyl-ethoxycarbonyl)-ethoxycarbonyl]-ethoxycarbonyl}-ethyl ester (4-1) (3.8 g, 5.38 mmol) in tetrahydrofuran (40 mL) were added tetra-n-butylammonium fluoride (8.09 mL, 1.0 M, 8.07 mmol) and acetic acid (0.48 g, 8.07 mmol) at 0° C. The reaction mixture was allowed to stir at room temperature over a period of 1 hour. The resulting reaction mixture was concentrated under reduced pressure and crude product obtained upon evaporation of the volatiles was purified by silica gel column chromatography (20% ethyl acetate in hexane) to afford product 7-1 as colorless liquid (1.3 g, 51%). $^1$H NMR (400 MHz, DMSO-$d_6$) δ 7.44-7.30 (m, 5H), 5.49 (d, J=5.9 Hz, 1H), 5.24-5.07 (m, 5H), 4.21 (m, 1H), 1.51-1.36 (m, 12H), 1.20 (d, J=6.8 Hz, 3H); MS m/z (M+NH$_4^+$) 486.3

Step 2: (S)-2-(tert-Butyl-diphenyl-silanyloxy)-propionic acid (S)-1-{(S)-1-[(S)-1-((S)-1-benzyloxycarbonyl-ethoxycarbonyl)-ethoxycarbonyl]-ethoxycarbonyl}-ethyl ester (7-2)

To a solution of (S)-2-hydroxy-propionic acid (S)-1-{(S)-1-[(S)-1-((S)-1-benzyloxycarbonyl-ethoxycarbonyl)-ethoxycarbonyl]-ethoxycarbonyl}-ethyl ester (7-1) (1.5 g, 3.20 mmol) and (S)-2-(tert-butyl-diphenyl-silanyloxy)-propionic acid (S)-1-{(S)-1-[(S)-1-((S)-1-carboxy-ethoxycarbonyl)-ethoxycarbonyl]-ethoxycarbonyl}-ethyl ester (4-2) (3.35 g, 5.44 mmol) in dichloromethane (50 mL) was added EDCI.HCl (1.22 g, 6.4 mmol), hydroxybenzotriazole (88 mg, 0.64 mmol), and 4-dimethylaminopyridine (39 mg, 0.32 mmol) at 0° C. The reaction mixture was allowed to stir at 25-30° C. over a period of 1 hour and the resulting reaction mixture was quenched with water (100 mL), extracted with dichloromethane (150×3 mL), dried over sodium sulfate, and concentrated under reduced pressure. The crude product obtained upon evaporation of volatiles was purified by silica gel (230-400) column chromatography (16% ethyl acetate in hexane) to afford product 7-2 as a pale yellow liquid (1.4 g, 41%). $^1$H NMR (400 MHz, DMSO-$d_6$) δ 7.60 (d, J=5.6 Hz, 4H), 7.53-7.30 (m, 11H), 5.25-5.11 (m, 9H), 4.95 (q, J=7.0 Hz, 1H), 4.29 (q, J=6.7 Hz, 1H), 1.50-1.37 (m, 24H), 1.35-1.21 (m, 6H), 1.02 (s, 9H); MS m/z (M+NH$_4^+$) 1084.6.

Step 3: Compound 7-3 (PLA (n=10)-O-TBDPS)

A solution of (S)-2-(tert-butyl-diphenyl-silanyloxy)-propionic acid (S)-1-{(S)-1-[(S)-1-((S)-1-benzyloxycarbonyl-ethoxycarbonyl)-ethoxycarbonyl]-ethoxycarbonyl}-ethyl ester (7-2) (1.4 g, 1.31 mmol) in methanol (15 mL) and 10% Pd/C (0.28 g, 50% wet) was added to a 100 mL autoclave vessel at 25-30° C. The reaction mixture was stirred at room temperature under hydrogen pressure (5 kg/cm$^2$) over a period of 2 hours. After completion of the reaction, the reaction mixture was filtered through celite and concentrated under reduced pressure. The crude product obtained upon evaporation of volatiles was purified by silica gel (60-120) column chromatography (10% methanol in dichloromethane) to afford product 7-3 as a pale yellow liquid (0.9 g, 70%). $^1$H NMR (400 MHz, DMSO-$d_6$) δ 7.64-7.57 (d, J=7.2 Hz, 4H), 7.53-7.37 (m, 6H), 5.20-5.19 (m, 7H), 4.99-4.92 (m, 2H), 4.26-4.31 (m, 1H), 1.50-1.37 (m, 24H), 1.28-1.30 (m, 6H), 1.02 (s, 9H); MS m/z (M+NH$_4^+$) 994.5

Scheme 8: Compound 8-3 (PLA (n = 12)-O—TBDPS):

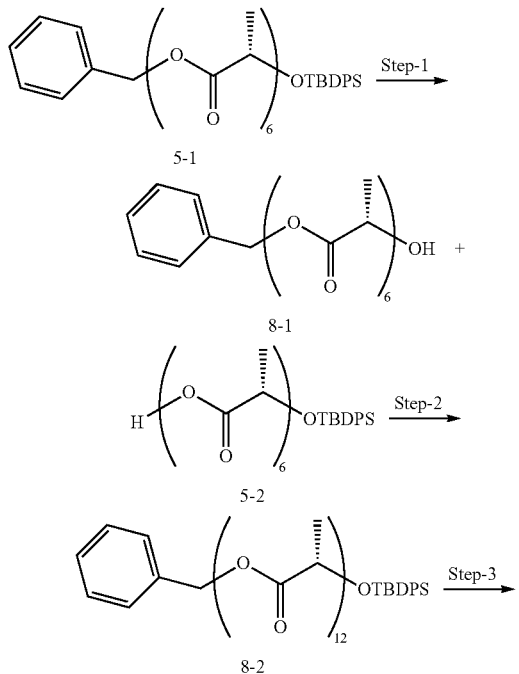

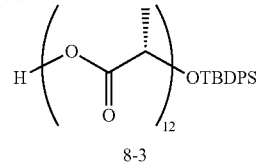

Step 1: (S)-2-Hydroxy-propionic acid (S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethyl ester (8-1)

To a solution of (S)-2-(tert-butyl-diphenyl-silanyloxy)-propionic acid (S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethyl ester 5-1 (6.0 g, 7.71 mmol) in tetrahydrofuran (60 mL) was added tetra-n-butyl ammonium fluoride (11.5 mL, 1.0 M, 11.56 mmol) and acetic acid (0.69 g, 11.56 mmol) at 0° C. The reaction mixture was allowed to stir at room temperature for 1 hour, and the resulting reaction mixture was concentrated under reduced pressure. The crude product obtained upon evaporation of the volatiles was purified by silica gel column chromatography (22% ethyl acetate in hexane) to afford product 8-1 as colorless liquid (1.7 g, 41%). $^1$H NMR (400 MHz, DMSO-$d_6$) δ 7.43-7.30 (m, 5H), 5.49 (d, J=5.9 Hz, 1H), 5.25-5.07 (m, 7H), 4.26-4.15 (m, 1H), 1.51-1.37 (m, 15H), 1.34-1.28 (m, 3H); MS m/z (M+NH$_4^+$) 558.1.

Step 2: (2S)-1-{[(2S)-1-{[(2S)-1-{[(2S)-1-{[(2S)-1-{[(2S)-1-{[(2S)-1-{[(2S)-1-{[(2S)-1-{[(2S)-1-(Benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-[(tert-butyldiphenylsilyl)oxy]propanoate (8-2)

To solution of (S)-2-(tert-butyl-diphenyl-silanyloxy)-propionic acid (S)-1-((S)-1-{(S)-1-[(S)-1-((S)-1-carboxy-ethoxycarbonyl)-ethoxycarbonyl]-ethoxycarbonyl}-ethoxycarbonyl)-ethyl ester 5.2 (2.81 g, 4.09 mmol) and (S)-2-hydroxy-propionic acid (S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethyl ester (8-1) (1.7 g, 3.14 mmol) in dichloromethane (20 mL) was added EDCI.HCl (1.2 g, 6.296 mmol), hydroxybenzotriazole (86 mg, 0.62 mmol), and 4-dimethylaminopyridine (38 mg, 0.314 mmol) at 0° C. The reaction mixture was allowed to stir at 25-30° C. over a period of 1 hour. The resulting reaction mixture was quenched with water (100 mL), extracted with dichloromethane (150×3 mL), dried over sodium sulfate, and concentrated under reduced pressure. The crude product obtained upon evaporation of volatiles was purified by silica gel (230-400) column chromatography (18% ethyl acetate in hexane) to afford product (8-2) as a pale yellow liquid 1.5 g (39%). $^1$H NMR (400 MHz, DMSO-$d_6$)$_6$ 7.60 (d, J=8.0 Hz, 4H), 7.59-7.32 (m, 11H), 5.25-5.13 (m, 12H), 4.95 (q, J=7.0 Hz, 1H), 4.28 (d, J=6.4 Hz, 1H), 1.35-1.50 (m, 30H), 1.26-0.98 (m, 6H), 0.90 (s, 9H); MS m/z (M+NH$_4^+$) 1228.6.

Step 3: Compound 8-3 (PLA (n=12)-O-TBDPS)

A solution of (2S)-1-{[(2S)-1-{[(2S)-1-{[(2S)-1-{[(2S)-1-{[(2S)-1-{[(2S)-1-{[(2S)-1-{[(2S)-1-{[(2S)-1-

(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-[(tert-butyldiphenylsilyl)oxy] propanoate (8-2) (1.5 g, 1.23 mmol) in methanol (15 mL) and 10% Pd/C (0.30 g, 50% wet) were added to a 100 mL autoclave vessel at 25-30° C. The reaction mixture was stirred at room temperature under hydrogen pressure (5 kg/cm$^2$) over a period of 2 hours. After completion of the reaction, the reaction mixture was filtered through celite and concentrated under reduced pressure. The crude product obtained upon evaporation of volatiles was purified by silica gel (60-120) column chromatography (10% methanol in dichloromethane) to afford product 8-3 as a pale yellow liquid 1.1 g (80%). $^1$H NMR (400 MHz, DMSO-d$_6$) δ 7.62 (d, J=7.2 Hz, 4H), 7.51-7.37 (m, 6H), 5.76 (s, 4H), 5.25-5.12 (m, 8H), 1.50-1.36 (m, 26H), 1.28-1.30 (m, 10H), 1.02 (s, 9H); MS m/z (M+NH$_4^+$) 1138.4.

Scheme 9: Compound 9-3 (PLA (n = 14)-O—TBDPS):

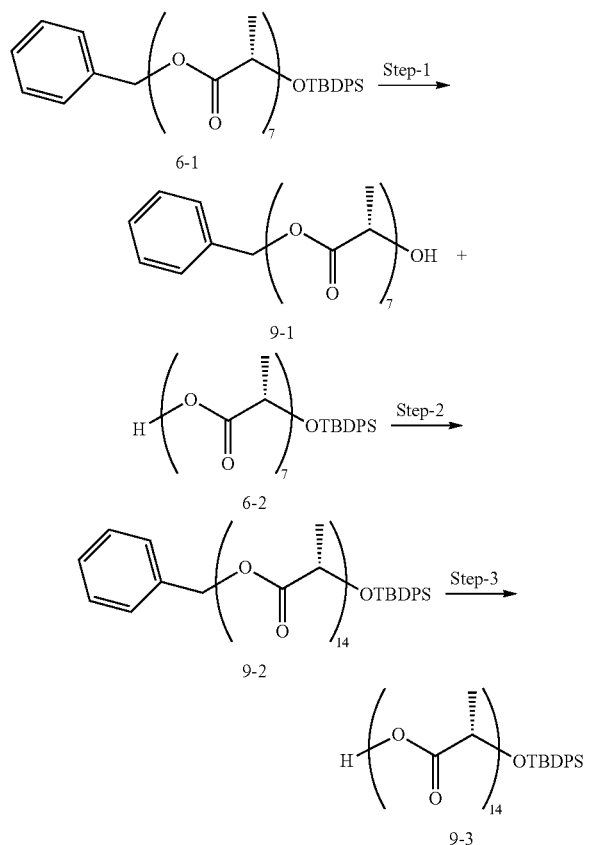

Step 1: (S)-2-Hydroxy-propionic acid (S)-1-[(S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethoxycarbonyl]-ethyl ester (9-1)

To a solution of (S)-2-(tert-butyl-diphenyl-silanyloxy)-propionic acid (S)-1-[(S)-1-((S)-1-{(S)-1-[(S)-1-((i)-1-benzyloxycarbonyl-ethoxycarbonyl)-ethoxycarbonyl]-ethoxycarbonyl}-ethoxycarbonyl)-ethoxycarbonyl]-ethyl ester (6-1) (6.0 g, 7.05 mmol) in tetrahydrofuran (60 mL) was added tetra-n-butyl ammonium fluoride (10.5 mL, 1.0 M, 10.57 mmol) and acetic acid (0.63 g, 10.57 mmol) at 0° C. The reaction mixture was allowed to stir at room temperature over a period of 1 hour, and the resulting reaction mixture was concentrated under reduced pressure. The crude product obtained upon evaporation of the volatiles was purified by silica gel column chromatography (22% ethyl acetate in hexane) to afford product 9-1 as colorless liquid 2.5 g (58%). $^1$H NMR (400 MHz, DMSO-d$_6$) δ 7.44-7.30 (m, 5H), 5.49 (d, J=5.9 Hz, 1H), 5.25-5.12 (m, 7H), 5.16-5.07 (m, 1H), 4.26-4.15 (m, 1H), 1.51-1.37 (m, 18H), 1.31-1.13 (m, 3H); MS m/z (M+NH$_4^+$) 630.7

Step 2: (2S)-1-{[(2S)-1-{[(2S)-1-{[(2S)-1-{[(2S)-1-{[(2S)-1-{[(2S)-1- {[(2S)-1-{[(2S)-1- {[(2S)-1-{[(2S)-1-{[(2S)-1-(Benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl] oxy}-1-oxopropan-2-yl]oxy}-1-oxopropan-2-yl] oxy}-1-oxopropan-2-yl]oxy}-1-oxopropan-2-yl] oxy}-1-oxopropan-2-yl]oxy}-1-oxopropan-2-yl (2S)-2-hydroxypropanoate (9-2)

To a solution of (S)-2-(tert-Butyl-diphenyl-silanyloxy)-propionic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (6-2) (4.65 g, 6.127 mmol) and (S)-2-hydroxy-propionic acid (S)-1-[(S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethoxycarbonyl]-ethyl ester (9-1) (2.5 g, 4.08 mmol) in dichloromethane (25 mL) was added EDCI.HCl (1.56 g, 8.168 mmol), hydroxybenzotriazole (112 mg, 0.816 mmol), and 4-dimethylaminopyridine (49 mg, 0.816 mmol) at 0° C. The reaction mixture was allowed to stir at 25-30° C. for 1 hour. The resulting reaction mixture was quenched with water (100 mL), extracted with dichloromethane (150×3 mL), dried over sodium sulfate, and concentrated under reduced pressure. The crude product obtained upon evaporation of volatiles was purified by silica gel (230-400) column chromatography (18% ethyl acetate in hexane) to afford product 9-2 as a pale yellow liquid 3.4 g (61%). $^1$H NMR (400 MHz, DMSO-d$_6$) δ 7.60 (dt, J=7.8, 1.4 Hz, 4H), 7.53-7.34 (m, 11H), 5.25-5.11 (m, 14H), 4.94 (q, J=7.6 Hz, 1H), 4.28 (q, J=7.1 Hz, 1H), 1.49-1.37 (m, 36H), 1.35-1.21 (m, 6H), 1.02 (s, 9H); MS m/z (M+NH$_4^+$) 1373.2

Step 3: Compound 9-3 (PLA (n=14)-O-TBDPS)

A solution of (2S)-1-{[(2S)-1-{[(2S)-1-{[(2S)-1-{[(2S)-1-{[(2S)-1-{[(2S)-1-{[(2S)-1-{[(2S)-1-{[(2S)-1-{[(2S)-1-{[(2S)-1-(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl] oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-hydroxypropanoate (9-2) (3.4 g, 2.50 mmol) in methanol (25 mL) and 10% Pd/C (0.70 g, 50% wet) were added to a 100 mL autoclave vessel were added at 25-30° C. The reaction mixture was stirred at room temperature under hydrogen pressure (5 kg/cm$^2$) over a period of 2 hours. After completion of the reaction, the reaction mixture was filtered through celite and concentrated under reduced pressure. The crude product obtained upon evaporation of volatiles was purified by silica gel (60-120) column chromatography (10% methanol in dichloromethane) to afford product 9-3 as a pale yellow liquid 2.5 g (83%). $^1$H NMR (400 MHz, DMSO-$d_6$) δ 7.64-7.57 (m, 4H), 7.51-7.37 (m, 6H), 5.25-5.09 (m, 11H), 4.93-4.95 (m, 2H), 4.28 (q, J=6.8, 1H), 1.50-1.42 (m, 34H), 1.46-1.35 (m, 3H), 1.32-1.30 (m, 6H), 1.02 (s, 9H); MS m/z (M+NH$_4^+$) 1282.9.

Scheme 10: (S)-2-[(S)-2-((S)-2-Acetoxy-propionyloxy)-propionyloxy]-propionic acid (10-4):

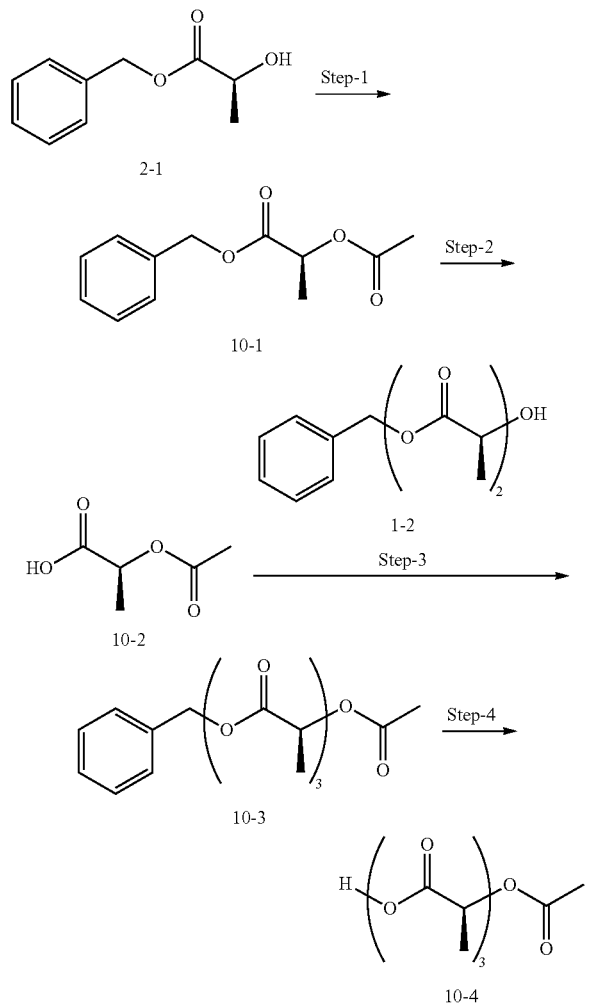

Step 1: (S)-2-Acetoxy-propionic acid benzyl ester (10-1)

To a solution of (S)-2-hydroxy-propionic acid benzyl ester (2-1) (10 g, 55.49 mmol) in dichloromethane (100 mL) was added 4-dimethylaminopyridine (0.676 g, 5.54 mmol) and acetic anhydride (7.8 mL, 83.24 mmol) at 0° C.

The reaction mixture stirred at 25-30° C. for 3 hours, and the resulting reaction mixture was quenched with water (200 mL), extracted with ethyl acetate (2×200 mL), and dried over sodium sulfate. Evaporation of volatiles under reduced pressure afforded product 10-1 as a pale yellow liquid (9.0 g, 97%).

Step 2: (S)-2-Acetoxy-propionic acid (10-2)

A solution of (S)-2-acetoxy-propionic acid benzyl ester (10-1) (9.0 g, 40.54 mmol) in methanol (50 mL) and 10% Pd/C (1.8 g, 50% wet) were added to a 250 mL autoclave vessel at 25-30° C. The reaction mixture was stirred at room temperature under hydrogen pressure (5 kg/cm$^2$) for 2 hours, and following consumption of starting materials, the reaction mixture was filtered through celite. Evaporation of the volatiles under reduced pressure afforded product (10-2) as a pale yellow liquid 4.35 g (81%).

Step 3: (S)-2-[(S)-2-((S)-2-Acetoxy-propionyloxy)-propionyloxy]-propionic acid (10-3)

To a solution of (S)-2-acetoxy-propionic acid (10-2) (4.35 g, 32.73 mmol) and (S)-2-hydroxy-propionic acid (S)-1-benzyloxycarbonyl-ethyl ester (1-2) (5.5 g, 21.82 mmol) in dichloromethane (50 mL) was added EDCI.HCl (8.33 g, 43.64 mmol) and 4-dimethylaminopyridine (266 mg, 2.182 mmol) at 0° C. The reaction mixture was allowed to stir at 25-30° C. for 1 hour. The resulting reaction mixture was quenched with water (100 mL), extracted with dichloromethane (150×3 mL), dried over sodium sulfate, and concentrated under reduced pressure. The crude product obtained upon evaporation of volatiles was purified by silica gel (230-400) column chromatography (8% ethyl acetate in hexane) to afford product 10-3 as a pale yellow liquid 4.6 g (58%). $^1$H NMR (400 MHz, DMSO-$d_6$) δ 7.39-7.36 (m, 5H), 5.20-5.16 (m, 4H), 5.15-5.20 (q, J=7.1 Hz, 1H), 2.07 (s, 3H), 1.50-1.38 (m, 9H); MS m/z (M+NH$_4^+$) 384.2.

Step 4: (S)-2-[(S)-2-((S)-2-Acetoxy-propionyloxy)-propionyloxy]-propionic acid (10-4)

A solution of (S)-2-[(S)-2-((S)-2-acetoxy-propionyloxy)-propionyloxy]-propionic acid (10-3) (4.6 g, 12.56 mmol) in methanol (30 mL) and 10% Pd/C (0.95 g, 50% wet) were added to a 100 mL autoclave vessel at 25-30° C. The reaction mixture was stirred at room temperature under hydrogen pressure (5 kg/cm$^2$) for 2 hours, and following consumption of starting materials, the reaction mixture was filtered through celite. Evaporation of volatiles under reduced pressure afforded product (10-4) as a pale yellow liquid (2.5 g, 71%). $^1$H NMR (400 MHz, DMSO-$d_6$) δ 13.19 (s, 1H), 5.17 (q, J=7.1 Hz, 1H), 5.02 (dq, J=24.5, 7.1 Hz, 2H), 2.07 (s, 3H), 1.50-1.38 (m, 9H); MS m/z (M–H) 275.1.

Scheme 11: (S)-2-{(S)-2-[(S)-2-((S)-2-Acetoxy-propionyloxy)-propionyloxy]-propionyloxy}-propionic acid (11-4):

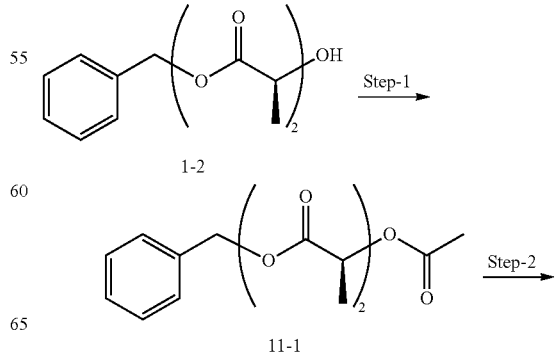

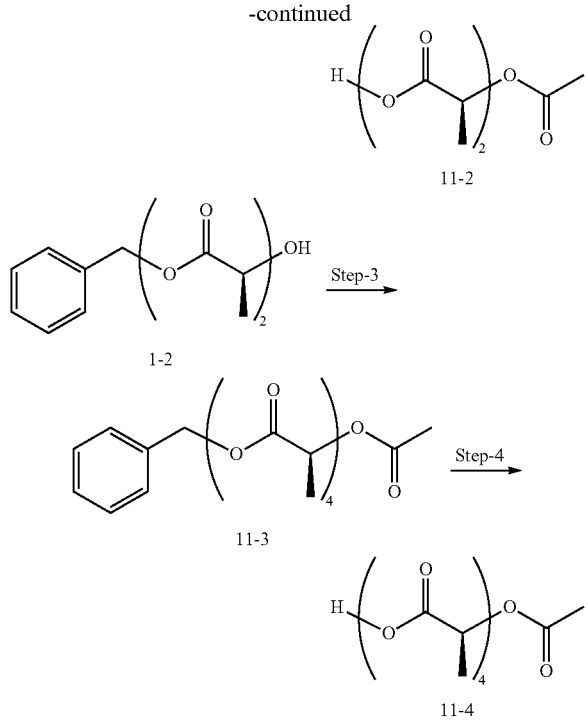

Step 1: (S)-2-((S)-2-Acetoxy-propionyloxy)-propionic acid benzyl ester (11-1)

To a solution of (S)-2-hydroxy-propionic acid (S)-1-benzyloxycarbonyl-ethyl ester (1-2) (5 g, 19.84 mmol) in dichloromethane (50 mL) was added 4-dimethylaminopyridine (0.24 g, 1.984 mmol) and acetic anhydride (2.8 mL, 29.76 mmol) at 0° C. The reaction mixture was stirred at 25-30° C. for 3 hours. And the resulting reaction mixture was quenched with water (200 mL), extracted with ethyl acetate (2×200 mL), and dried over sodium sulfate. Evaporation of volatiles under reduced pressure afforded product 11-1 as a pale yellow liquid (7.3 g, 73%).

Step 2: (S)-2-((S)-2-Acetoxy-propionyloxy)-propionic acid (11-2)

A solution of (S)-2-((S)-2-acetoxy-propionyloxy)-propionic acid benzyl ester (11-1) (7.3 g, 24.82) in methanol (40 mL) and 10% Pd/C (1.5 g, 50% wet) was added to a 250 mL autoclave vessel at 25-30° C. The reaction mixture was stirred at room temperature under hydrogen pressure (5 kg/cm$^2$) for 2 hours. After completion of the reaction, the reaction mixture was filtered through celite. Evaporation of volatiles under reduced pressure afforded product 11-2 as a pale yellow liquid (4.4 g, 81%). $^1$H NMR (400 MHz, DMSO-d$_6$) δ 13.13 (s, 1H), 5.00 (dq, J=20.0, 7.1 Hz, 2H), 2.07 (s, 3H), 1.42 (dd, J=7.1, 6.3 Hz, 6H); MS m/z (M−H) 203.1.

Step 3: (S)-2-{(S)-2-[(S)-2-((S)-2-Acetoxy-propionyloxy)-propionyloxy]-propionyloxy}-propionic acid benzyl ester (11-3)

To a solution of (S)-2-((S)-2-acetoxy-propionyloxy)-propionic acid (11-2) (4.3 g, 20.8 3 mmol) and (S)-2-hydroxy-propionic acid (S)-1-benzyloxycarbonyl-ethyl ester (1-2) (3.5 g, 13.88 mmol) in dichloromethane (50 mL) was added EDCI.HCl (5.3 g, 27.76 mmol) and 4-dimethylaminopyridine (169 mg, 1.38 mmol) at 0° C. The reaction mixture was allowed to stir at 25-30° C. for 1 hour. The resulting reaction mass was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (8% ethyl acetate in hexane) to afford product 11-3 as a pale yellow liquid (2.2 g, 36%). $^1$H NMR (400 MHz, DMSO-d$_6$) δ 7.43-7.30 (m, 5H), 5.24-5.08 (m, 5H), 5.03 (q, J=7.2 Hz, 1H), 2.07 (s, 3H), 1.44-1.40 (m, 12H); MS m/z (M+NH$_4^+$) 456.3.

Step 4: (S)-2-{(S)-2-[(S)-2-((3)-2-Acetoxy-propionyloxy)-propionyloxy]-propionyloxy}-propionic acid (11-4)

A solution of (S)-2-{(S)-2-[(S)-2-((S)-2-acetoxy-propionyloxy)-propionyloxy]-propionyloxy}-propionic acid benzyl ester (11-3) (2.2 g, 5.08 mmol) in methanol (15 mL) and 10% Pd/C (0.45 g, 50% wet) were added to a 100 mL autoclave vessel at 25-30° C. The reaction mixture was stirred at room temperature under hydrogen pressure (5 kg/cm$^2$) over a period of 2 hours. After completion of the reaction, the reaction mixture was filtered through celite. Evaporation of volatiles under reduced pressure afforded product 11-4 as a pale yellow liquid (1.1 g, 65%). $^1$H NMR (400 MHz, DMSO-d$_6$) δ 13.21 (s, 1H), 5.18 (qd, J=7.0, 3.1 Hz, 2H), 5.01 (dq, J=30.1, 7.1 Hz, 2H), 2.07 (s, 3H), 1.51-1.37 (m, 12H); MS m/z (M−H) 347.1.

Scheme 12: (S)-2-((S)-2-{(S)-2-[(S)-2-((S)-2-Acetoxy-propionyloxy)-propionyloxy]-propionyloxy}-propionyloxy)-propionic acid (12-2):

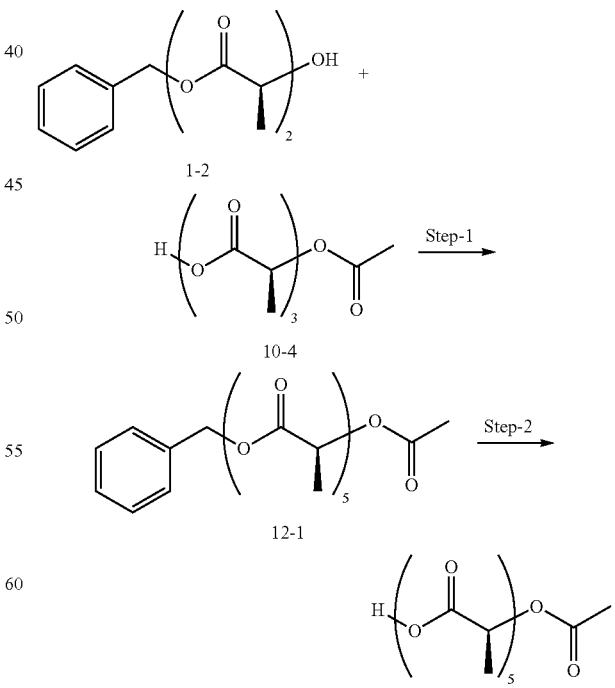

Step 1: (S)-2-((S)-2-{(S)-2-[(S)-2-((S)-2-Acetoxy-propionyloxy)-propionyloxy]-propionyloxy}-propionyloxy)-propionic acid benzyl ester (12-1)

To a solution of (S)-2-[(S)-2-((S)-2-acetoxy-propionyloxy)-propionyloxy]-propionic acid (10-4) (8.2 g, 29.76 mmol) and (S)-2-hydroxy-propionic acid (S)-1-benzyloxycarbonyl-ethyl ester (1-2) (5.0 g, 19.84 mmol) in dichloromethane (50 mL) was added EDCl.HCl (7.57 g, 39.68 mmol) and 4-dimethylaminopyridine (242 mg, 1.98 mmol) at 0° C. The reaction mixture was allowed to stir at 25-30° C. for 1 hour. The resulting reaction mass was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (6% ethyl acetate in hexane) to afford product 12-1 as a pale yellow liquid (6.2 g, 63%). $^1$H NMR (400 MHz, DMSO-$d_6$) δ 7.44-7.30 (m, 5H), 5.25-5.09 (m, 6H), 5.05 (q, J=7.0 Hz, 1H), 2.07 (s, 3H), 1.51-1.37 (m, 15H); MS m/z (M+NH$_4^+$) 528.3.

Step 2: (S)-2-((S)-2-{(S)-2-[(S)-2-((S)-2-Acetoxy-propionyloxy)-propionyloxy]-propionyloxy}-propionyloxy)-propionic acid (12-2)

A solution of (S)-2-((S)-2-{(S)-2-[(S)-2-((S)-2-Acetoxy-propionyloxy)-propionyloxy]-propionyloxy}-propionyloxy)-propionic acid benzyl ester (12-1) (6.2 g, 12.15 mmol) in methanol (30 mL) and 10% Pd/C (1.25 g, 50% wet) were added to a 100 mL autoclave vessel at 25-30° C. The reaction mixture was stirred at room temperature under hydrogen pressure (5 kg/cm$^2$) for 2 hours. After completion of the reaction, the reaction mixture was filtered through celite. Evaporation of volatiles under reduced pressure afforded product 12-2 as a pale yellow liquid (4.4 g, 86%). $^1$H NMR (400 MHz, DMSO-$d_6$) δ 13.17 (s, 1H), 5.25-5.14 (m, 3H), 5.02 (dq, J=25.2, 7.0 Hz, 2H), 2.07 (s, 3H), 1.50-1.38 (m, 15H); MS m/z (M+NH$_4^+$) 438.2.

Scheme 13: (S)-2-[(S)-2-((S)-2-{(S)-2-[(S)-2-((S)-2-Acetoxy-propionyloxy)-propionyloxy]-propionyloxy}-propionyloxy)-propionyloxy]-propionic acid (13-2):

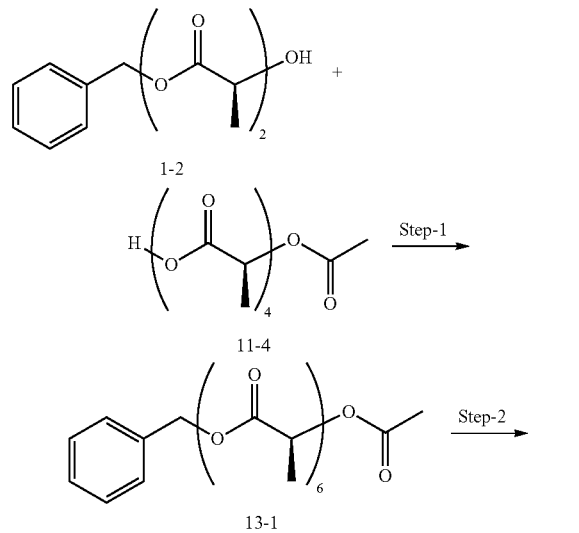

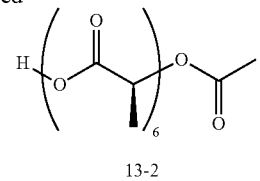

Step 1: (S)-2-[(S)-2-((S)-2-{(S)-2-[(S)-2-((S)-2-Acetoxy-propionyloxy)-propionyloxy]-propionyloxy}-propionyloxy)-propionyloxy]-propionic acid benzyl ester (13-1)

To a solution of (S)-2-{(S)-2-[(S)-2-((S)-2-acetoxy-propionyloxy)-propionyloxy]-propionyloxy}-propionic acid (11-4) (12.4 g, 35.71 mmol) and (S)-2-hydroxy-propionic acid (S)-1-benzyloxycarbonyl-ethyl ester (1-2) (6.0 g, 23.80 mmol) in dichloromethane (60 mL) was added EDCl.HCl (9.09 g, 47.60 mmol) and 4-dimethylaminopyridine (290 mg, 2.38 mmol) at 0° C. The reaction mixture was allowed to stir at 25-30° C. for 1 hour. The resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (6% ethyl acetate in hexane) to afford product 13-1 as a pale yellow liquid (8.3 g, 60%). $^1$H NMR (400 MHz, DMSO-$d_6$) δ 7.44-7.30 (m, 5H), 5.25-5.10 (m, 7H), 5.05 (q, J=7.0 Hz, 1H), 2.06 (s, 3H), 1.52-1.39 (m, 18H); MS m/z (M+NH$_4^+$) 600.2.

Step 2: (S)-2-[(S)-2-((S)-2-{(S)-2-[(S)-2-((S)-2-Acetoxy-propionyloxy)-propionyloxy]-propionyloxy}-propionyloxy)-propionyloxy]-propionic acid (13-2)

A solution of (S)-2-[(S)-2-((S)-2-{(S)-2-[(S)-2-((S)-2-acetoxy-propionyloxy)-propionyloxy]-propionyloxy}-propionyloxy)-propionyloxy]-propionic acid benzyl ester (13-1) (8.3 g, 14.26 mmol) in methanol (50 mL) and 10% Pd/C (1.65 g, 50% wet) were added to a 250 mL autoclave vessel at 25-30° C. The reaction mixture was stirred at room temperature under hydrogen pressure (5 kg/cm$^2$) for 2 hours. After completion of the reaction, the reaction mixture was filtered through celite. Evaporation of volatiles under reduced pressure afforded product 13-2 as a pale yellow liquid (5.7 g, 81%). $^1$H NMR (400 MHz, DMSO-$d_6$) δ 13.20 (s, 1H), 5.26-5.14 (m, 4H), 5.02 (dq, J=24.0, 7.1 Hz, 2H), 2.07 (s, 3H), 1.51-1.38 (m, 18H); MS m/z (M−H) 491.1.

Scheme 14: (S)-2-(tert-Butyl-diphenyl-silanyloxy)-propionic acid (14-2):

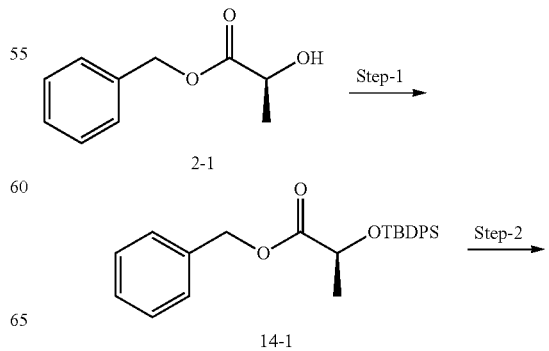

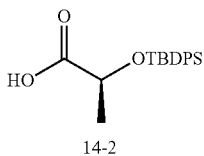

14-2

Step 1: (S)-2-(tert-Butyl-diphenyl-silanyloxy)-propionic acid benzyl ester (14-1)

To a solution of (S)-2-hydroxy-propionic acid benzyl ester 2-1 (5 g, 27.77 mmol) in dichloromethane (50 mL) was added triethylamine (7.8 mL, 55.55 mmol), TBDPS-C$_1$ (14.6 mL, 55.55 mmol), and a catalytic amount of 4-dimethylaminopyridine at 0° C. The reaction mixture was stirred at room temperature for 8 hours, and the resulting reaction mixture was quenched with water (200 mL) and extracted with ethyl acetate (2×150 mL). Evaporation of volatiles under reduced pressure afforded product 14-1 as pale yellow liquid (8.2 g, 70%).

Step 2: (S)-2-(tert-Butyl-diphenyl-silanyloxy)-propionic acid (14-2)

A solution of (S)-2-(tert-butyl-diphenyl-silanyloxy)-propionic acid benzyl ester 14-1 (8.2 g, 19.61 mmol) in methanol (50 mL) and 10% Pd/C (1.6 g, 50% wet) were added to a 250 mL autoclave vessel at 25-30° C. The reaction mixture was stirred at room temperature under hydrogen pressure (5 kg/cm$^2$) for 2 hours. After completion of the reaction, the reaction mixture was filtered through celite. Evaporation of volatiles under reduced pressure afforded product 14-2 as a pale yellow liquid (4.9 g, 76%). $^1$H NMR (400 MHz, DMSO-d$_6$) δ 12.49 (s, 1H), 7.62 (tt, J=6.8, 1.7 Hz, 4H), 7.55-7.33 (m, 6H), 4.16 (q, J=6.7 Hz, 1H), 1.31-1.13 (m, 3H), 1.02 (s, 9H); MS m/z (M−H) 327.1.

Scheme 15: (S)-2-tert-Butoxy-propionic acid (S)-1-((S)-1-carboxy-ethoxycarbonyl)-ethyl ester (15-3):

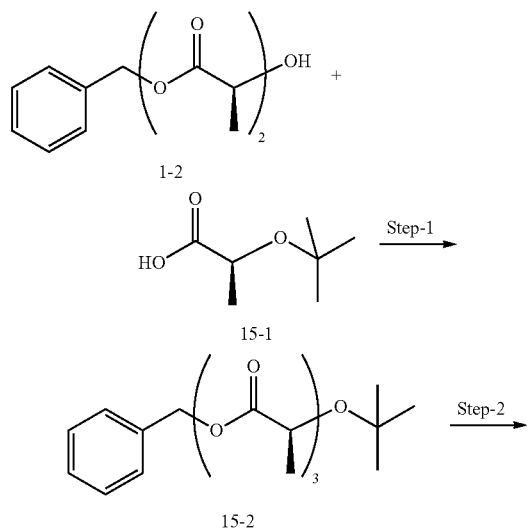

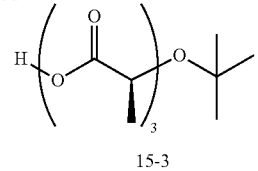

15-3

Step 1: (S)-2-tert-Butoxy-propionic acid (S)-1-((S)-1-benzyloxycarbonyl-ethoxy carbonyl)-ethyl ester (15-2)

To a solution of (S)-2-tert-butoxy-propionic acid (15-1) (0.38 g, 2.57 mmol) and (S)-2-hydroxy-propionic acid (S)-1-benzyloxycarbonyl-ethyl ester (1-2) (0.5 g, 1.98 mmol) in dichloromethane (10 mL) was added EDCI.HCl (0.57 g, 2.97 mmol) and 4-dimethylaminopyridine (24 mg, 0.19 mmol) at 0° C. The reaction mixture was allowed to stir at 25-30° C. for 1 hour. The resulting reaction mixture was quenched with water (50 mL), extracted with dichloromethane (50×3 mL), dried over sodium sulfate, and concentrated under reduced pressure. The crude product obtained upon evaporation of volatiles was purified by silica gel (230-400) column chromatography (6% ethyl acetate in hexane) to afford product 15-2 as a pale yellow liquid (450 mg, 60%). $^1$H NMR (400 MHz, Chloroform-d) δ 7.42-7.29 (m, 5H), 5.26-5.09 (m, 4H), 4.20 (q, J=6.9 Hz, 1H), 1.53 (d, J=7.1 Hz, 6H), 1.40 (d, J=6.8 Hz, 3H), 1.22 (s, 9H); MS m/z (M+NH$_4^+$) 398.2.

Step 2: (S)-2-tert-Butoxy-propionic acid (S)-1-((S)-1-carboxy-ethoxycarbonyl)-ethyl ester (15-3)

A solution of (S)-2-tert-butoxy-propionic acid (S)-1-((S)-1-benzyloxycarbonyl-ethoxycarbonyl)-ethyl ester (15-2) (450 mg, 1.18 mmol) in methanol (10 mL) and 10% Pd/C (50 mg, 50% wet) were added to a 100 mL autoclave vessel at 25-30° C. The reaction mixture was stirred at room temperature under hydrogen pressure (5 kg/cm$^2$) for 2 hours. After completion of the reaction, the reaction mixture was filtered through celite. Evaporation of volatiles under reduced pressure afforded product 15-3 as a pale yellow liquid (290 mg, 84%). $^1$H NMR (400 MHz, DMSO-d$_6$) δ 5.07 (q, J=7.0 Hz, 1H), 4.90 (q, J=7.0 Hz, 1H), 4.23 (q, J=6.8 Hz, 1H), 1.41 (dd, J=32.0, 7.1 Hz, 6H), 1.23 (d, J=6.8 Hz, 3H), 1.12 (s, 9H); MS m/z (M−H) 289.0.

Scheme 16: Octadecanoic acid (S)-1-{(S)-1-[(S)-1-((S)-1-carboxy-ethoxycarbonyl)-ethoxy carbonyl]-ethoxycarbonyl}-ethyl ester (16-5):

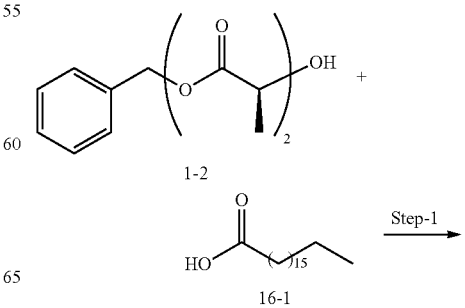

-continued

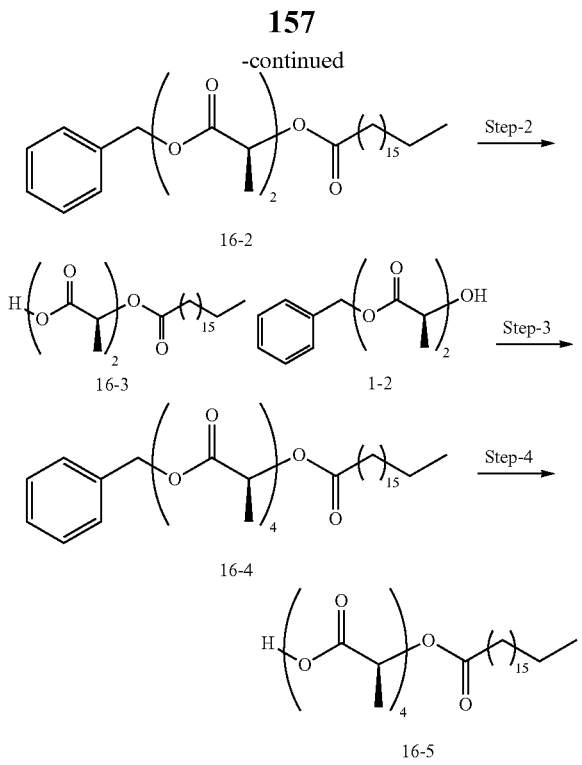

Step 1: Octadecanoic acid (S)-1-((S)-1-benzyloxy-carbonyl-ethoxycarbonyl)-ethyl ester (16-2)

To a solution of octadecanoic acid (16-1) (23.4 g, 82.53 mmol) and (S)-2-hydroxy-propionic acid (S)-1-benzyloxycarbonyl-ethyl ester (1-2) (16.0 g, 63.49 mmol) in dichloromethane (160 mL) was added EDCI.HCl (24.2 g, 126.9 mmol) and 4-dimethylaminopyridine (770 mg, 6.34 mmol) at 0° C. The reaction mixture was allowed to stir at 25-30° C. for 1 hour, and the resulting reaction mixture was quenched with water (500 mL), extracted with dichloromethane (500×3 mL), dried over sodium sulfate, and concentrated under reduced pressure. The crude product obtained upon evaporation of volatiles was purified by silica gel (230-400) column chromatography (2% ethyl acetate in hexane) to afford product 16-2 as a pale yellow liquid (18 g, 55%). $^1$H NMR (400 MHz, DMSO-$d_6$) δ 7.43-7.30 (m, 5H), 5.17-5.14 (m, 3H), 5.03 (q, J=7.2 Hz, 1H), 2.32 (t, J=7.3 Hz, 2H), 1.55-1.41 (m, 2H), 1.36 (d, J=7.1 Hz, 3H), 1.26 (d, J=6.1 Hz, 3H), 1.21-1.22 (m, 26H), 0.89 (t, J=6.4 Hz, 3H); MS m/z (M+NH$_4^+$) 536.7.

Step 2: Octadecanoic acid (S)-1-((S)-1-carboxy-ethoxycarbonyl)-ethyl ester (16-3)

A solution of octadecanoic acid (S)-1-((S)-1-benzyloxy-carbonyl-ethoxycarbonyl)-ethyl ester (16-2) (18 g, 34.74 mmol) in methanol (90 mL) and 10% Pd/C (3.6 g, 50% wet) were added to a 500 mL autoclave vessel at 25-30° C. The reaction mixture was stirred at room temperature under hydrogen pressure (5 kg/cm$^2$) over a period of 2 hours, and after completion of the reaction, the reaction mixture was filtered through celite. Evaporation of volatiles under reduced pressure afforded product 16-3 as a colorless low melting solid (12.5 g, 84%). $^1$H NMR (400 MHz, DMSO-$d_6$) δ 13.12 (s, 1H), 5.01 (dq, J=25.2, 7.0 Hz, 2H), 2.33 (t, J=7.3 Hz, 2H), 1.57-1.47 (m, 2H), 1.42 (t, J=6.7 Hz, 6H), 1.23-1.20 (m, 30H), 0.89-0.81 (m, 3H); MS m/z (M+NH$_4^+$) 446.7.

Step 3: Octadecanoic acid (S)-1-{(S)-1-[(S)-1-((S)-1-benzyloxycarbonyl-ethoxycarbonyl)-ethoxycarbonyl]-ethoxycarbonyl}-ethyl ester (16-4)

To a solution of octadecanoic acid (S)-1-((S)-1-carboxy-ethoxycarbonyl)-ethyl ester (16-3) (10.2 g, 23.80 mmol) and (S)-2-hydroxy-propionic acid (S)-1-benzyloxycarbonyl-ethyl ester (1-2) (4.0 g, 15.87 mmol) in dichloromethane (40 mL) was added EDCI.HCl (6.06 g, 31.74 mmol), hydroxybenzotriazole (428 mg, 3.174 mmol), and 4-dimethylaminopyridine (193 mg, 1.58 mmol) and at 0° C. The reaction mixture was allowed to stir at 25-30° C. for 1 hour. The resulting reaction mixture was quenched with water (500 mL), extracted with dichloromethane (500×3 mL), dried over sodium sulfate, and concentrated under reduced pressure. The crude product obtained upon evaporation of volatiles was purified by silica gel (230-400) column chromatography (3% ethyl acetate in hexane) to afford product 16-4 as a pale yellow liquid (6.1 g, 58%). $^1$H NMR (400 MHz, DMSO-$d_6$) δ 7.43-7.32 (m, 5H), 5.19-5.04 (m, 6H), 2.31-2.35 (m, 2H), 1.55-1.50 (m, 2H), 1.46-1.40 (m, 12H), 1.23-1.22 (m, 28H), 0.89-0.81 (m, 3H); MS m/z (M+NH$_4^+$) 680.4.

Step 4: Octadecanoic acid (S)-1-{(S)-1-[(S)-1-((S)-1-carboxy-ethoxycarbonyl)-ethoxycarbonyl]-ethoxycarbonyl}-ethyl ester (16-5)

A solution of octadecanoic acid (S)-1-{(S)-1-[(S)-1-((S)-1-benzyloxycarbonyl-ethoxycarbonyl)-ethoxycarbonyl]-ethoxycarbonyl}-ethyl ester (16-4) (6.1 g, 9.21 mmol) in methanol (40 mL) and 10% Pd/C (1.2 g, 50% wet) were added to a 250 mL autoclave vessel at 25-30° C. The reaction mixture was stirred at room temperature under hydrogen pressure (5 kg/cm$^2$) for 2 hours. After completion of the reaction, the reaction mixture was filtered through celite. Evaporation of volatiles under reduced pressure afforded product 16-5 as a colorless low melting solid (4.5 g, 85%). $^1$H NMR (400 MHz, DMSO-$d_6$) δ 13.2 (bs, 1H), 5.18 (qd, J=7.0, 2.4 Hz, 2H), 5.02 (dq, J=28.5, 7.0 Hz, 2H), 2.33 (t, J=7.3 Hz, 2H), 1.55-1.28 (m, 14H), 1.28 (m, 28H), 0.89-0.81 (m, 3H); MS m/z (M–H) 571.5.

Scheme 17: Octadecanoic acid (S)-1-[(S)-1-((S)-1-{(S)-1-[(S)-1-((S)1-carboxy-ethoxycarbonyl)-ethoxycarbonyl]-ethoxycarbonyl}-ethoxycarbonyl)-ethoxycarbonyl]-ethyl ester (17-2):

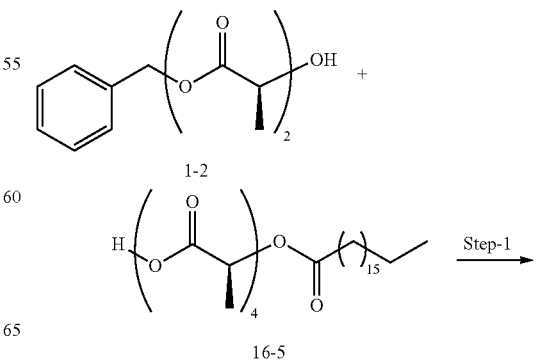

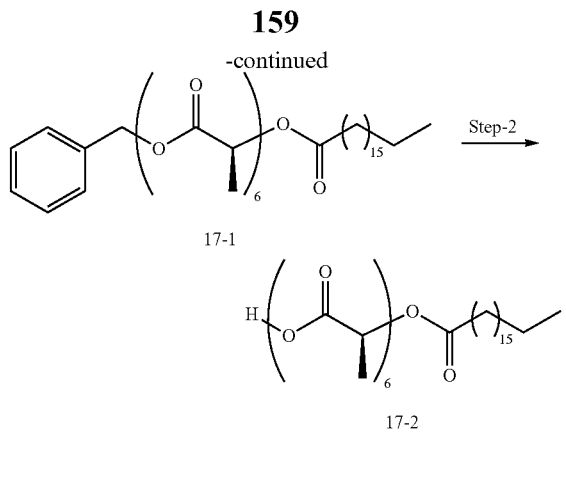

17-1

17-2

Step 1: Octadecanoic acid (S)-1-[(S)-1-((S)-1-{(S)-1-[(S)-1-((S)-1-benzyloxycarbonyl-ethoxycarbonyl)-ethoxycarbonyl]-ethoxycarbonyl)}-ethoxycarbonyl)-ethoxycarbonyl]-ethyl ester (17-1)

To a solution of octadecanoic acid (S)-1-{(S)-1-[(S)-1-((S)-1-carboxy-ethoxycarbonyl)-ethoxycarbonyl]-ethoxycarbonyl}-ethyl ester (16-5) (16.2 g, 28.37 mmol) and (S)-2-hydroxy-propionic acid (S)-1-benzyloxycarbonyl-ethyl ester (1-2) (5.5 g, 21.82 mmol) in dichloromethane (55 mL) was added EDCI.HCl (8.33 g, 43.64 mmol), hydroxybenzotriazole (602 mg, 4.36 mmol), and 4-dimethylaminopyridine (266 mg, 2.18 mmol) at 0° C. The reaction mixture was allowed to stir at 25-30° C. for 1 hour. The resulting reaction mixture was quenched with water (500 mL), extracted with dichloromethane (500×3 mL), dried over sodium sulfate, and concentrated under reduced pressure. The crude product obtained upon evaporation of volatiles was purified by silica gel (230-400) column chromatography (3% ethyl acetate in hexane) to afford product 17-1 as a pale yellow liquid (13.5 g, 76%). $^1$H NMR (400 MHz, DMSO-$d_6$) δ 7.43-7.32 (m, 5H), 5.25-5.13 (m, 7H), 5.01-5.00 (m, 1H), 2.31-2.35 (m, 2H), 1.53-1.37 (m, 20H), 1.25-1.23 (m, 28H), 0.89-0.81 (m, 3H); MS m/z (M+NH$_4^+$) 824.9.

Step 2: Octadecanoic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (17-2)

A solution of octadecanoic acid (S)-1-[(S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethoxycarbonyl]-ethyl ester (17-1) (13.5 g, 16.74 mmol) in methanol (80 mL) and 10% Pd/C (2.7 g, 50% wet) To a 250 mL autoclave vessel at 25-30° C. The reaction mixture was stirred at room temperature under hydrogen pressure (5 kg/cm$^2$) for 2 hours. After completion of the reaction, the reaction mixture was filtered through celite. Evaporation of volatiles under reduced pressure afforded product 17-2 as a colorless low melting solid (9.8 g, 81%). $^1$H NMR (400 MHz, DMSO-$d_6$) δ 5.25-5.13 (m, 4H), 5.06 (dq, J=27.5, 7.0 Hz, 1H), 5.02 (dq, J=27.5, 7.0 Hz, 1H), 2.33 (t, J=7.3 Hz, 2H), 1.55-1.36 (m, 18H), 1.26 (m, 30H), 0.89-0.81 (m, 3H); MS m/z (M−H) 715.7.

Scheme 18: Octadecanoic acid (S)-1-((S)-1-{(S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethoxycarbonyl}-ethoxycarbonyl)-ethyl ester (18-2):

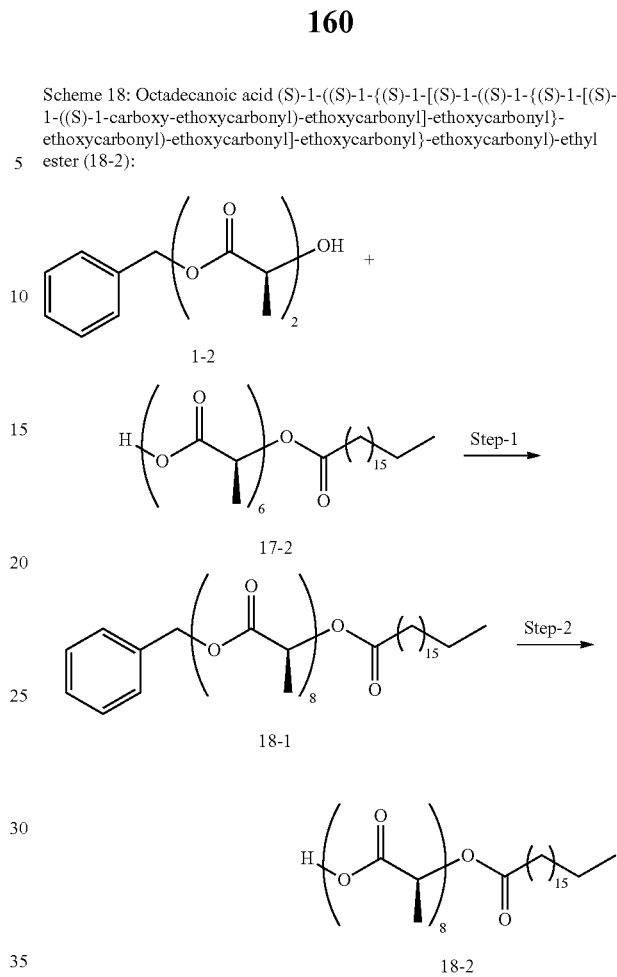

Step 1: (2S)-1-{[(2S)-1-{[(2S)-1-{[(2S)-1-{[(2S)-1-{[(2S)-1-{[(2S)-1-{[(2S)-1- (Benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy})-1-oxopropan-2-yl octadecanoate (18-1)

To a solution of octadecanoic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (17-2) (4.2 g, 6.19 mmol) and (S)-2-hydroxy-propionic acid (S)-1-benzyloxycarbonyl-ethyl ester (1-2) (1.2 g, 4.76 mmol) in dichloromethane (15 mL) was added EDCI.HCl (1.01 g, 9.52 mmol), hydroxybenzotriazole (131 mg, 0.95 mmol), and 4-dimethylaminopyridine (58 mg, 0.47 mmol) and at 0° C. The reaction mixture was allowed to stir at 25-30° C. for 1 hour. The resulting reaction mixture was quenched with water (100 mL), extracted with dichloromethane (150×3 mL), dried over sodium sulfate, and concentrated under reduced pressure. The crude product obtained upon evaporation of volatiles was purified by silica gel (230-400) column chromatography (12% ethyl acetate in hexane) to afford product 18-1 as a pale yellow liquid (3.5 g, 77%). 1H NMR (400 MHz, DMSO-$d_6$) δ 7.41-7.32 (m, 5H), 5.25-5.13 (m, 9H), 5.01-5.02 (m, 1H), 2.33 (t, J=7.3 Hz, 2H), 1.53-1.37 (m, 24H), 1.26-1.22 (m, 30H), 0.89-0.79 (m, 3H); MS m/z (M+NH$_4^+$) 969.0.

Step 2: Octadecanoic acid (S)-1-((S)-1-{(S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)---ethoxycarbonyl]-ethoxycarbonyl}-ethoxycarbonyl)-ethyl ester (18-2)

A solution of (2S)-1-{[(2S)-1-{[(2S)-1-{[(2S)-1-{[(2S)-1-{[(2S)-1-{[(2S)-1-(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl octadecanoate (18-1) (3.5 g, 3.68 mmol) in methanol (20 mL) and 10% Pd/C (0.7 g, 50% wet) were added to a 100 mL autoclave vessel at 25-30° C. The reaction mixture was stirred at room temperature under hydrogen pressure (5 kg/cm$^2$) over a period of 2 hours. After completion of the reaction, the reaction mixture was filtered through celite. Evaporation of volatiles under reduced pressure afforded product 18-2 as a colorless low melting solid (2.5 g, 79%). 1H NMR (400 MHz, DMSO-$d_6$) δ13.2 (bs, 1H), 5.26-5.13 (m, 6H), 5.08 (q, J=6.8 Hz, 1H), 5.01 (q, J=6.8 Hz, 1H), 2.33 (t, J=7.3 Hz, 2H), 1.55-1.36 (m, 26H), 1.32-1.23 (m, 30H), 0.89-0.81 (m, 3H); MS m/z (M+NH$_4$+) 879.0.

Example 2. Synthetic Examples of Dorzolmide Mono-Prodrugs

Scheme 19: (2S)-N-{[2S,4S)-4-(Ethylamino)-2-methyl-1,1-dioxo-2H,3H,4H-1λ$^6$-thieno[2,3-b]thiopyran-6-yl]sulfonyl}-2-hydroxypropanamide (19-3):

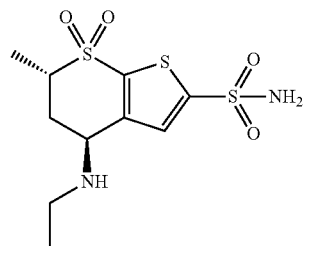

19-1

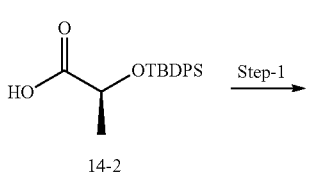

14-2

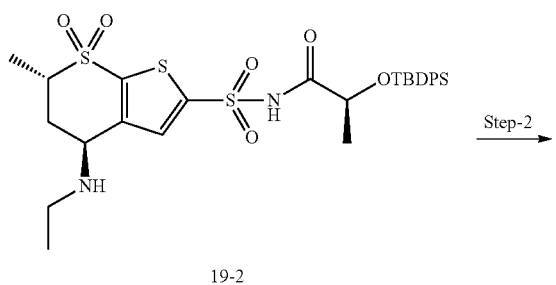

19-2

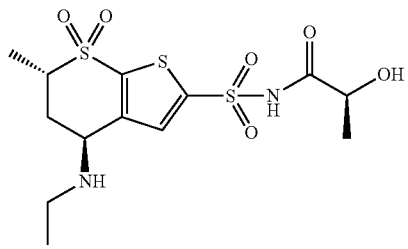

19-3

Step 1: (2S)-2-[(tert-Butyldiphenylsilyl)oxy]-N-{[(2S,4S)-4-(ethylamino)-2-methyl-1,1-dioxo-2H,3H,4H-1λ$^6$-thieno[2,3-b]thiopyran-6-yl]sulfonyl}propanamide (19-2)

To a solution of dorzolamide (19-1) (0.8 g, 2.22 mmol) in dichloromethane (10 mL) was added N,N-diisopropylethylamine (0.8 mL, 4.44 mmol) at 0° C. After 30 minutes, (S)-2-(tert-butyl-diphenyl-silanyloxy)-propionic acid (14-2) (1.01 g, 3.33 mmol), EDCI.HCl (0.763 g, 3.99 mmol), and 4-dimethylaminopyridine (0.027 g, 0.22 mmol) were added at 0° C. The reaction mixture was allowed to stir at 25-30° C. for 1 hour, and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (6% methanol in DCM) to afford product 19-2 as a pale yellow solid (1.3 g, 68%). $^1$H NMR (400 MHz, DMSO-$d_6$) δ 8.78 (bs, 2H), 7.71 (s, 1H), 7.65-7.61 (m, 4H), 7.45-7.31 (m, 6H), 4.64 (b s, 1H), 3.97 (q, J=6.8, 2H), 3.20 (bs, 1H), 3.01 (bs, 1H), 1.37 (d, J=6.8, 3H), 1.23-1.02 (m, 8H), 0.98 (s, 9H); MS m/z (M−H) 633.5; MS m/z (M+H) 635.3.

Step 2: (2S)—N-{[(2S,4S)-4-(Ethylamino)-2-methyl-1,1-dioxo-2H,3H,4H-1λ$^6$-thieno[2,3-b]thiopyran-6-yl]sulfonyl}-2-hydroxypropanamide (19-3)

To a solution of (2S)-2-[(tert-butyldiphenylsilyl)oxy]-N-{[(2S,4S)-4-(ethylamino)-2-methyl-1,1-dioxo-2H,3H,4H-1λ$^6$-thieno[2,3-b]thiopyran-6-yl]sulfonyl}propanamide (19-2) (1.3 g, 2.50 mmol) in tetrahydrofuran (15 mL) were added tetra-butyl ammonium fluoride (3.07 mL, 1.0M, 3.07 mmol) and acetic acid (0.18 g, 3.07 mmol) at 0° C. The reaction mixture was allowed to stir at room temperature for 12 hours, and the resulting reaction mixture was concentrated under reduced pressure. The crude product obtained upon evaporation of the volatiles was purified by silica gel column chromatography (5% methanol in ethyl acetate) to afford product 19-3 as an off-white solid (510 mg, 63%). $^1$H-NMR (400 MHz, DMSO-$d_6$) δ 7.39 (s, 1H), 4.00 (d, J=5 Hz 1H), 3.95-3.80 (m, 2H), 3.73 (quintet, 1H), 2.70-2.45 (m, 2H), 2.36-2.20 (m, 2H), 1.32 (d, 3H), 1.12 (d, 3H), 1.02 (t, 3H); MS m/z (M+H)$^+$ 397.1.

Scheme 20: (2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl (2S)-2-hydroxypropanoate (20-2):

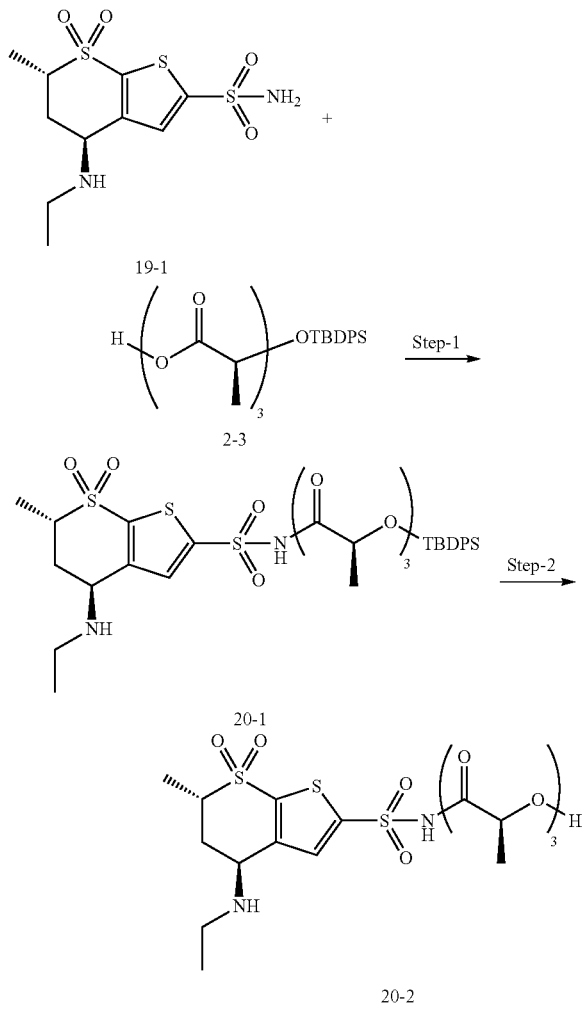

Step 1: (2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl (2S)-2-[(tert-butyldiphenylsilyl)oxy]propanoate (20-1)

To a solution of dorzolamide 19-1 (0.8 g, 2.22 mmol) in dichloromethane (10 mL) was added N,N-diisopropylethylamine (0.8 mL, 4.44 mmol) at 0° C. After 30 minutes, 2-(tert-butyl-diphenyl-silanyloxy)-propionic acid 1-(1-carboxy-ethoxycarbonyl)-ethyl ester (2-3) (1.01 g, 3.33 mmol), EDCI.HCl (0.763 g, 3.99 mmol) and 4-dimethylaminopyridine (0.027 g, 0.22 mmol) were added at 0° C. The reaction mixture was allowed to stir at 25-30° C. for 1 hour, and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (6% methanol in DCM) to afford product 20-1 as a pale yellow solid (1.3 g, 68%). ¹H NMR (400 MHz, DMSO-d₆) δ 7.6-7.40 (m, 11H), 4.9-4.7 (m, 2H), 4.3 (q, J=6.8 Hz, 1H), 4.0-3.8 (m, 2H), 3.6-3.5 (m, 1H), 3.3-3.1 (m, 1H), 2.8-2.6 (m, 2H), 2.4-2.2 (m, 2H), 1.4-1.2 (m, 16H), 1.02 (s, 9H); MS m/z (M+H) 779.4.

Step 2: (2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl (2S)-2-hydroxypropanoate (20-2)

To a solution of (2S)-1-[(1S)-1-({[(2S,4S)-4-(ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl (2S)-2-[(tert-butyldiphenylsilyl)oxy]propanoate (20-1) (1.0 g, 1.28 mmol) in tetrahydrofuran (15 mL) were added tetra-butyl ammonium fluoride (2.56 mL, 1.0 M, 2.56 mmol) and acetic acid (0.15 g, 2.56 mmol) at 0° C. The reaction mixture was allowed to stir at room temperature for 12 hours, and the resulting reaction mixture was concentrated under reduced pressure. The crude product obtained upon evaporation of the volatiles was purified by silica gel column chromatography (4% methanol in ethyl acetate) to afford product 20-2 as an off-white solid (400 mg, 57%). ¹H-NMR (400 MHz, DMSO-d₆) δ 7.36 (s, 1H), 5.41 (d, 1H), 5.02 (q, J=7.1 Hz, 1H), 4.79 (q, J=7.1 Hz, 1H), 4.18 (quintet, J=7.1 Hz, 1H), 3.95-3.75 (m, 2H), 2.70-2.45 (m, 2H), 2.35-2.20 (m, 2H), 1.48 (d, 2H), 1.36-1.24 (m, 9H), 1.02 (t, 3H); MS m/z (M+H)⁺ 540.6.

Scheme 21: (2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl (2S)-2-hydroxypropanoate (21-2):

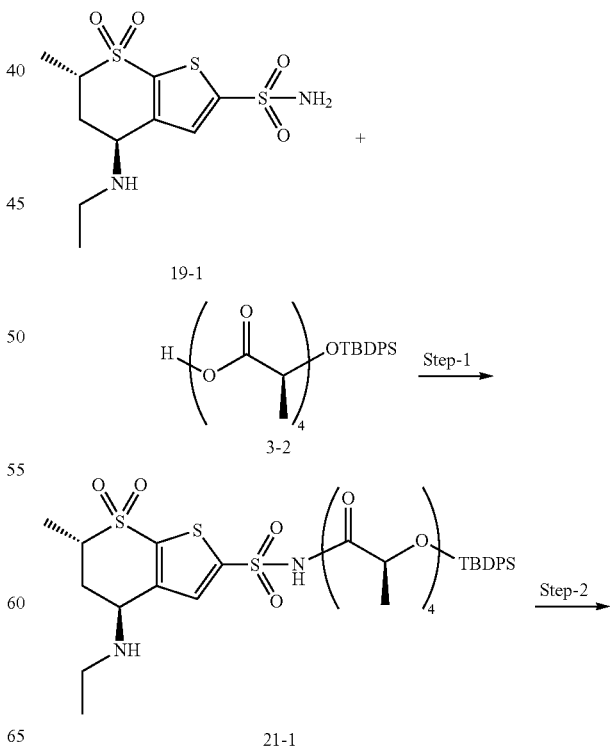

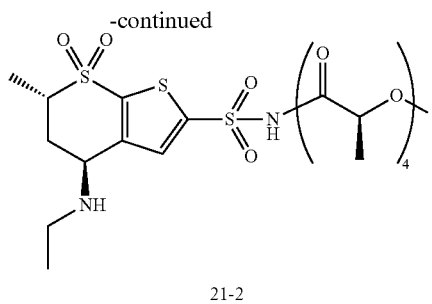

21-2

Step 1: (2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl (2S)-2-[(tert-butyldiphenylsilyl)oxy]propanoate (21-1)

To a solution of dorzolamide (19-1) (1.0 g, 2.7 mmol) in dichloromethane (10 mL) was added N,N-diisopropylethylamine (0.96 mL, 5.5 mmol) at 0° C. After 30 minutes, (S)-2-(tert-butyl-diphenyl-silanyloxy)-propionic acid (S)-1-[(S)-1-((S)-1-carboxy-ethoxycarbonyl)-ethoxycarbonyl]-ethyl ester (3-2) (2.27 g, 4.1 mmol), EDCI.HCl (0.79 g, 4.1 mmol) and 4-dimethylaminopyridine (33 g, 0.27 mmol) were added at 0° C. The reaction mixture was allowed to stir at 25-30° C. for 1 hour, and the resulting reaction mixture was quenched with water (150 mL), extracted with dichloromethane (200×3 mL), dried over sodium sulfate, and concentrated under reduced pressure. The crude product obtained upon evaporation of volatiles was purified by silica gel (230-400) column (6% methanol in DCM) to afford product 21-1 as an off-white solid (1.5 g, 65%). ¹H-NMR (400 MHz, DMSO-d₆) δ 7.60 (d, J=6.4, 4H), 7.59-7.39 (m, 7H), 5.06 (q, J=7.2 Hz, 1H), 4.92 (q, J=6.8 Hz, 1H), 4.28 (q, J=6.8 Hz, 1H), 3.8-4.0 (m, 2H), 3.6 (bs, 1H), 3.2 (bs, 1H), 1.46 (d, J=6.8, 3H), 1.36-1.24 (m, 12H), 1.02 (m, 12H); MS m/z (M+H) 851.4

Step 2: (2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl (2S)-2-hydroxypropanoate (21-2)

To a solution of (2S)-1-{[(2S)-1-[(1S)-1-({[(2S,4S)-4-(ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl (2S)-2-[(tert-butyldiphenylsilyl)oxy]propanoate (21-1) (1.8 g, 2.11 mmol) in tetrahydrofuran (20 mL) were added tetra-butyl ammonium fluoride (4.23 mL, 1.0M, 4.22 mmol) and acetic acid (0.25 g, 4.22 mmol) at 0° C. The reaction mixture was allowed to stir at room temperature for 12 hours, and the resulting reaction mixture was concentrated under reduced pressure. The crude product obtained upon evaporation of the volatiles was purified by silica gel column chromatography (4% methanol in ethyl acetate) to afford product 21-2 as an off-white solid (1.0 g, 77%). ¹H-NMR (400 MHz, DMSO-d₆) δ 7.37 (s, 1H), 5.48 (d, J=5.6 Hz, 1H), 5.0-5.15 (m, 2H), 4.79 (quintet, J=7.1 Hz, 1H), 4.25-4.15 (m, 1H), 3.95-3.80 (m, 2H), 2.70-2.45- (m, 2H), 2.40-2.20- (m, 2H), 1.52-1.43 (m, 6H), 1.36-1.24 (m, 9H), 1.02 (t, 3H); MS m/z (M+H)⁺ 613.2.

Scheme 22: (2S)-1-{[(2S)-1-{[(2S)-1-[(1S)-1-({[2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl (2S)-2-hydroxypropanoate (22-2):

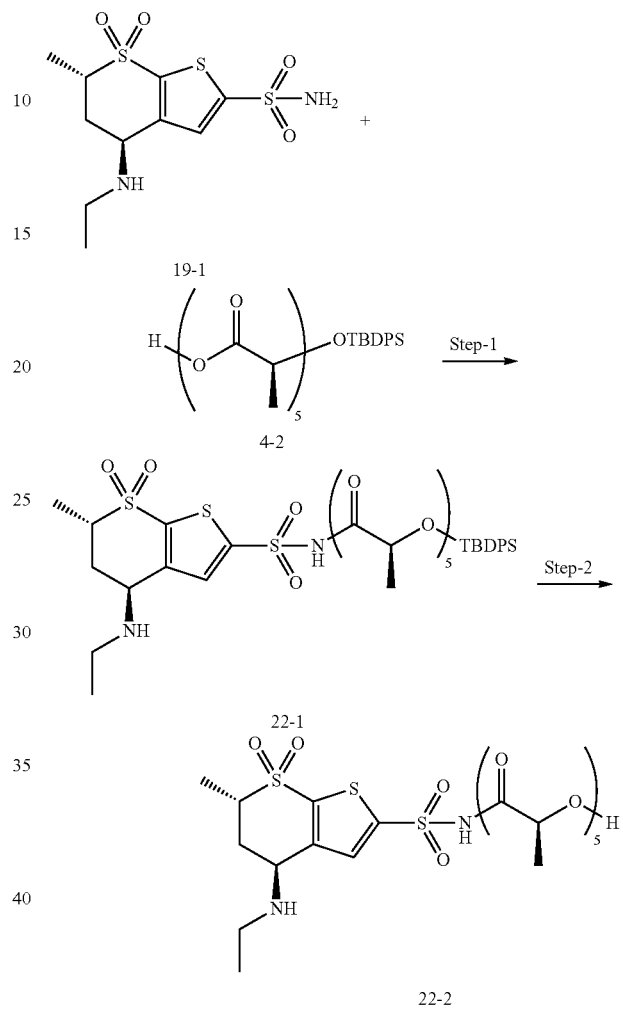

Step 1: (2S)-1-{[(2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl(2S)-2-[(tert-butyldiphenylsilyl)oxy]propanoate (22-1)

To a solution of dorzolamide (19-1) (1.0 g, 2.7 mmol) in dichloromethane (10 mL) was added N,N-diisopropylethylamine (0.96 mL, 5.5 mmol) at 0° C. After 30 minutes, (S)-2-(tert-butyl-diphenyl-silanyloxy)-propionic acid (S)-1-{(S)-1-[(S)-1-((S)-1-carboxy-ethoxycarbonyl)-ethoxycarbonyl]-ethoxycarbonyl}-ethyl ester (4-2) (3.78 g, 4.1 mmol), EDCI.HCl (0.79 g, 4.1 mmol), and 4-dimethylaminopyridine (33 g, 0.27 mmol) were added at 0° C. The reaction mixture was allowed to stir at 25-30° C. for 1 hour, and the resulting reaction mixture was quenched with water (150 mL), extracted with dichloromethane (200×3 mL), dried over sodium sulfate, and concentrated under reduced pressure. The crude product obtained upon evaporation of volatiles was purified by silica gel (230-400) column chromatography (6% methanol in DCM) to afford product as 22-1 an off-white solid (1.6 g, 63%). ¹H-NMR (400 MHz, DMSO-d$_6$) δ 7.60 (d, J=6.8, 4H), 7.51-7.40 (m, 7H), 5.17 (q, J=7.2 Hz, 2H), 5.07 (q, (q, J=6.8 Hz, 1H), 4.92 (q, J=7 Hz, 1H), 4.78 (q, J=6.8, 1H), 3.89 (m, 1H), 3.1-3.2 (m, 1H), 2.9-2.7 (m, 1H), 3.12-3.10 (m, 1H), 1.48-1.40 (m, 6H), 1.35-1.18 (m, 14H), 1.17-1.02 (m, 12H).

Step 2: (2S)-1-{[(2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl (2S)-2-hydroxypropanoate (22-2)

To a solution of (2S)-1-{[(2S)-1-{[(2S)-1-[(1S)-1-({[(2S, 4S)-4-(ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy})-1-oxopropan-2-yl]oxy}-1-oxopropan-2-yl(2S)-2-[(tert-butyldiphenylsilyl)oxy] propanoate (22-1) (1.0 g, 1.06 mmol) in tetrahydrofuran (10 mL) were added tetra-butyl ammonium fluoride (2.1 mL, 1.0M, 2.12 mmol) and acetic acid (0.12 g, 2.12 mmol) at 0° C. The reaction mixture was allowed to stir at room temperature for 12 hours, and the resulting reaction mixture was concentrated under reduced pressure. Crude product obtained upon evaporation of the volatiles was purified by silica gel column chromatography (4% methanol in ethyl acetate) to afford product 22-2 as an off-white solid (200 mg, 27%). ¹H-NMR (400 MHz, DMSO-d$_6$) δ 8.75 (bs, 2H), 7.71 (s, 1H), 5.47 (d, J=5.6 Hz, 1H), 5.20-5.07 (m, 3H), 4.81 (q, J=7 Hz, 1H), 4.61 (br, 1H), 4.21 (quintet, 1H), 4.15-4.25 (m, 1H), 4.00-3.90 (m, 1H), 3.3-2.9 (m, 2H), 2.6-2.5 (m, 2H), 1.52-1.40 (m, 9H), 1.36 (d, 3H), 1.35-1.22 (m, 6H), 1.17 (t, 3H). MS m/z (M+H)⁺ 685.2.

Scheme 23: (2S)-1-{[(2S)-1-{[(2S)-1-{[(2S)-1-{[(2S)-1-{[(2S)-1-{[(2S)-1-[(1S)-1-({[(2S,4S)-4-(Ethylamino)-2-methyl-1,1-dioxo-2H,3H, 4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-hydroxypropanoate (23-2):

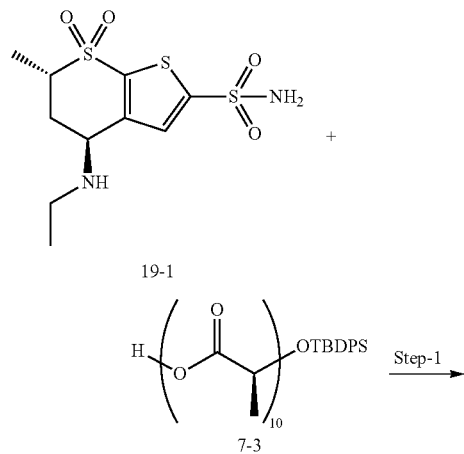

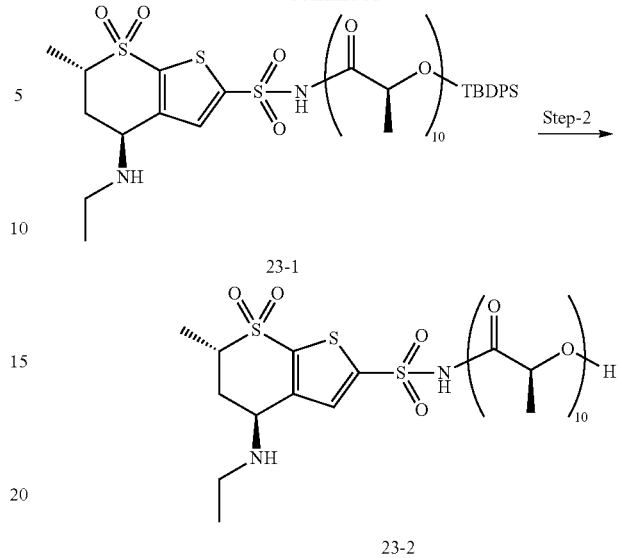

Step 1: (2S)-1-{[(2S)-1-{[(2S)-1-{[(2S)-1-{[(2S)-1-{[(2S)-1-{[(2S)-1-[(S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-[(tert-butyldiphenylsilyl)oxy]propanoate (23-1)

To a solution of dorzolamide (19-1) (0.35 g, 0.97 mmol) in dichloromethane (10 mL) was added N,N-diisopropylethylamine (0.25 mL, 1.94 mmol) at 0° C. After 30 minutes, (2S)-2-{[(2S)-2-{[(2S)-2-{[(2S)-2-{[(2S)-2-{[(2S)-2-{[(2S)-2-{[(2S)-2-{[(2S)-2-{[(2S)-2-[(tert butyldiphenylsilyl)oxy]propanoyl]oxy}propanoyl]oxy}propanoyl]oxy}propanoyl]oxy}propanoyl]oxy}propanoyl]oxy}propanoyl]oxy}propanoic acid (7-3) (1.42 g, 1.46 mmol), EDCI.HCl (0.37 g, 1.94 mmol), and 4-dimethylaminopyridine (12 mg, 0.097 mmol) were added at 0° C. The reaction mixture was allowed to stir at 25-30° C. for 1 hour, and the resulting reaction mixture was quenched with water (150 mL), extracted with dichloromethane (200×3 mL), dried over sodium sulfate, and concentrated under reduced pressure. The crude product obtained upon evaporation of volatiles was purified by silica gel (230-400) column chromatography (5% methanol in DCM) to afford product 23-1 as an off-white solid (0.9 g, 72%).

Step 2: (2S)-1-{[(2S)-1-{[(2S)-1-{[(2S)-1-{[(2S)-1-{[(2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-hydroxypropanoate (23-2)

To a solution of (2S)-1-{[(2S)-1-{[(2S)-1-{[(2S)-1-{[(2S)-1-{[(2S)-1-{[(2S)-1-{[(2S)-1-[(1S)-1-({[(2S,4S)-4-

(ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-[(tert-butyldiphenylsilyl)oxy]propanoate (23-1) (1.0 g, 1.06 mmol) in tetrahydrofuran (10 mL) was added tetra-butyl ammonium fluoride (1.17 mL, 1.0M, 1.17 mmol) and acetic acid (0.07 g, 1.17 mmol) at 0° C. The reaction mixture was allowed to stir at room temperature for 12 hours, and the resulting reaction mixture was concentrated under reduced pressure. The crude product obtained upon evaporation of the volatiles was purified by silica gel column chromatography (3% methanol in ethyl acetate) to afford product 23-2 as an off-white solid (350 mg, 42%). ¹H-NMR (400 MHz, DMSO-d₆) δ 8.75 (bs, 2H), 7.72 (s, 1H), 5.49 (d, J=6 Hz, 1H), 5.24-5.05 (m, 8H), 4.80 (q, 1H), 4.63 (brs, 1H), 4.21 (quintet, 1H), 4.0-3.9 (m, 1H), 3.3-3.12 (m, 1H), 3.08-2.91 (m, 1H), 2.5-2.6 (m, 2H), 1.53-1.42 (m, 27H), 1.36 (d, 3H), 1.33-1.26 (m, 6H), 1.21 (t, 3H); MS m/z (M+H)⁺ 1045.6.

Scheme 24: (2S)-1-{[(2S)-1-{[(2S)-1-{[(2S)-1-{[(2S)-1-{[(2S)-1-{[(2S)-1-{[(2S)-1-{[(2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-hydroxypropanoate (24-2):

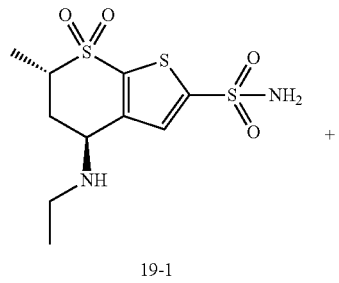

19-1

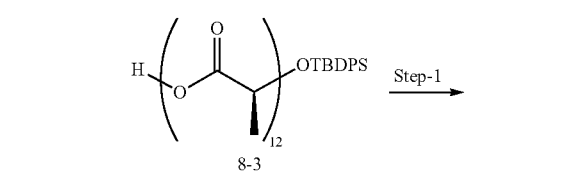

8-3

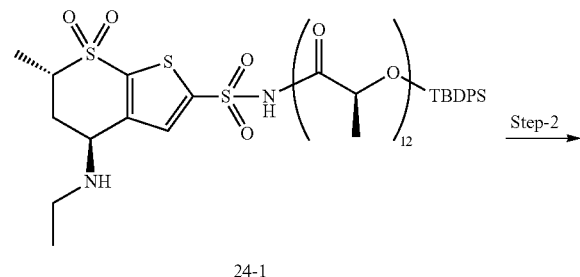

24-1

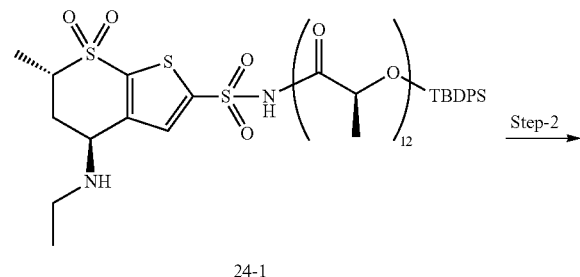

24-2

Step 1: (2S)-1-{[(2S)-1-{[(2S)-1-{[(2S)-1-{[(2S)-1-{[(2S)-1-{[(2S)-1- {[(2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy})-1-oxopropan-2-yl]oxy}-1-oxopropan-2-yl (2S)-2-[(tert-butyldiphenylsilyl)oxy]propanoate (24-1)

To a solution of dorzolamide (1.2 g, 3.32 mmol) in dichloromethane (20 mL) was added N,N-diisopropylethylamine (0.84 mL, 6.64 mmol) at 0° C. After 30 minutes, (2S)-2-{[(2S)-2-{[(2S)-2-{[(2S)-2-{[(2S)-2-{[(2S)-2-{[(2S)-2-{[(2S)-2-{[(2S)-2-{[(2S)-2-[(tert butyldiphenylsilyl)oxy]propanoyl]oxy}propanoyl]oxy}propanoyl]oxy}propanoyl]oxy}propanoyl]oxy}propanoyl]oxy}propanoyl]oxy}propanoyl]oxy}propanoyl]oxy}propanoic acid (8-3) (5.5 g, 4.96 mmol), EDCI.HCl (1.26 g, 6.64 mmol), and 4-dimethylaminopyridine (40 mg, 0.32 mmol) were added at 0° C. The reaction mixture was allowed to stir at 25-30° C. for 1 hour, and the resulting reaction mixture was quenched with water (400 mL), extracted with dichloromethane (300×3 mL), dried over sodium sulfate, and concentrated under reduced pressure. The crude product obtained upon evaporation of volatiles was purified by silica gel (230-400) column chromatography (4% methanol in DCM) to afford product as an off-white solid (4.0 g, 84%).

Step 2: (2S)-1-{[(2S)-1-{[(2S)-1-{[(2S)-1-{[(2S)-1-{[(2S)-1-{[(2S)-1- {[(2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-hydroxypropanoate (24-2)

To a solution of (2S)-1-{[(2S)-1-{[(2S)-1-{[(2S)-1-{[(2S)-1-{[(2S)-1-{[(2S)-1-{[(2S)-1-{[(2S)-1-[(1S)-1-({[(2S,4S)-4-(ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1- oxopropan-2-yl]oxy}-1-oxopropan-2-yl]oxy}-1-oxopropan-2-yl (2S)-2-[(tert-butyldiphenylsilyl)oxy]propanoate (24-1) (3.9 g, 2.73 mmol) in tetrahydrofuran (40 mL) were added tetra-butyl ammonium fluoride (4.09 mL, 1.0M, 4.09 mmol) and acetic acid (0.24 g, 4.09 mmol) at 0° C. The reaction mixture was allowed to stir at room temperature for 12 hours, and the resulting reaction mixture was concentrated under reduced pressure. Crude product obtained upon evaporation of the volatiles was purified by silica gel column chromatography (2% methanol in ethyl acetate) to afford product 24-2 as an off-white solid (2.3 g, 70%). $^1$H-NMR (400 MHz, DMSO-$d_6$) δ 8.75 (bs, 2H), 7.72 (s, 1H), 5.49 (d, J=6 Hz, 1H), 5.24-5.07 (m, 10H), 4.81 (q, 1H), 4.68-4.60 (m, 1H), 4.21 (quintet, 1H), 4.0-3.9 (m, 1H), 3.3-3.12 (m, 1H), 3.08-2.91 (m, 1H), 2.65-2.5 (m, 2H), 1.52-1.42 (m, 30H), 1.36 (d, 3H), 1.33-1.25 (m, 6H), 1.20 (t, 3H); MS m/z (M+H)$^+$1190.0.

Scheme 25: (2S)-1-{[2S)-1-{[2S)-1-{[2S)-1-{[2S)-1-{[2S)-1-{[2S)-1-{[2S)-1-{[2S)-1-{[2S)-1-{[2S)-1-[1S)-1-({[(2S,4S)-4-(Ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-hydroxypropanoate (25-2):

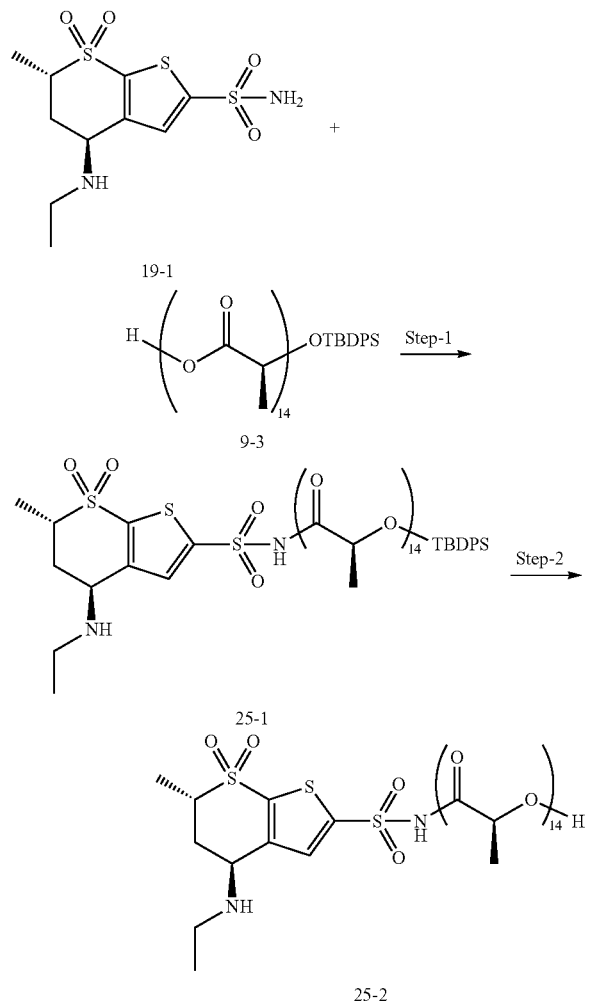

Step 1: (2S)-1-{[(2S)-1-{[(2S)-1-{[(2S)-1-{[(2S)-1-{[(2S)-1-{[(2S)-1- {[(2S)-1-{[(2S)-1-{[(2S)-1-{[(2S)-1-[(1S)-1-({[(2S,4S)-4-(Ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-[(tert-butyldiphenylsilyl)oxy]propanoate (25-1)

To a solution of dorzolamide (0.3 g, 0.83 mmol) in dichloromethane (10 mL) was added N,N-diisopropylethylamine (0.29 mL, 1.66 mmol) at 0° C. After 30 minutes, (2S)-2-{[(2S)-2-{[(2S)-2-{[(2S)-2-{[(2S)-2-{[(2S)-2-{[(2S)-2-{[(2S)-2-{[(2S)-2-{[(2S)-2-{[(2S)-2-{[(2S)-2-[(tert-butyldiphenylsilyl)oxy]propanoyl]oxy}propanoyl]oxy}propanoyl]oxy}propanoyl]oxy}propanoyl]oxy}propanoyl]oxy}propanoyl]oxy}propanoyl]oxy}propanoyl]oxy}propanoyl]oxy}propanoyl]oxy}propanoic acid (9-3) (1.58 g, 1.25 mmol), EDCI.HCl (0.31 g, 1.66 mmol), and 4-dimethylaminopyridine (10 mg, 0.08 mmol) were added at 0° C. The reaction mixture was allowed to stir at 25-30° C. for 1 hour, and the resulting reaction mixture was quenched with water (150 mL), extracted with dichloromethane (200×3 mL), dried over sodium sulfate, and concentrated under reduced pressure. The crude product obtained upon evaporation of volatiles was purified by silica gel (230-400) column chromatography (4% methanol in DCM) to afford product 25-1 as an off-white solid (1.1 g, 84%).

Step 2: (2S)-1-{[(2S)-1-{[(2S)-1-{[(2S)-1-{[(2S)-1-{[(2S)-1-{[(2S)-1- {[(2S)-1-{[(2S)-1-{[(2S)-1-{[(2S)-1-[(1S)-1-({[(2S,4S)-4-(Ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy})-1-oxopropan-2-yl]oxy}-1-oxopropan-2-yl]oxy}-1-oxopropan-2-yl]oxy})-1-oxopropan-2-yl]oxy})-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-hydroxypropanoate (25-2)

To a solution of (2S)-1-{[(2S)-1-{[(2S)-1-{[(2S)-1-{[(2S)-1-{[(2S)-1-{[(2S)-1-{[(2S)-1-{[(2S)-1-{[(2S)-1-{[(2S)-1-{[(2S)-1-[(2S)-1-({[(2S,4S)-4-(ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy})-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-[(tert-butyldiphenylsilyl)oxy]propanoate (25-1) (1.1 g, 0.69 mmol) in tetrahydrofuran (15 mL) were added tetra-butyl ammonium fluoride (1.04 mL, 1.0M, 1.04 mmol) and acetic acid (0.062 g, 1.04 mmol) at 0° C. The reaction mixture was allowed to stir at room temperature for 12 hours, and the resulting reaction mixture was concentrated under reduced pressure. Crude product obtained upon evaporation of the volatiles was purified by silica gel column chromatography (2% methanol in ethyl acetate) to afford product 25-2 as an off-white solid (0.5 g, 53%). $^1$H-NMR (400 MHz, DMSO-$d_6$) δ 8.75 (bs, 2H), 7.71 (s, 1H), 5.48 (d, J=6 Hz, 1H), 5.25-5.07 (m, 12H), 4.81 (q, 1H), 4.63 (bs, 1H), 4.20 (quintet, 1H), 4.0-3.9 (m, 1H), 3.30-3.12 (m, 1H), 3.08-2.90 (m, 1H), 1.50-1.40 (m, 36H), 1.36 (d, 3H), 1.34-1.24 (m, 6H), 1.20 (t, 3H); MS m/z (M+H)$^+$ 1333.8.

Scheme 26: (2S)-1-[(1S)-1-({[(2S,4S)-4-(Ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl (2S)-2-(acetyloxy)propanoate (26-1):

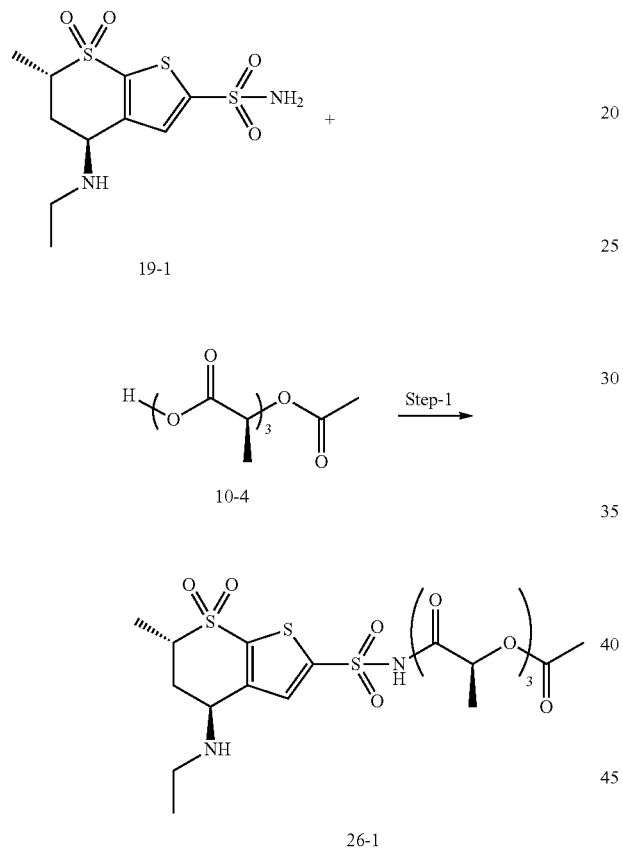

26-1

To a solution of dorzolamide (19-1) (0.2 g, 0.55 mmol) in dichloromethane (5 mL) was added N,N-diisopropylethylamine (0.2 mL, 1.11 mmol) at 0° C. After 30 minutes, (S)-2-[(S)-2-((S)-2-acetoxy-propionyloxy)-propionyloxy]-propionic acid (10-4) (0.23 g, 0.83 mmol), EDCI.HCl (159 mg, 0.83 mmol), and 4-dimethylaminopyridine (6 mg, 0.05 mmol) were added at 0° C. The reaction mixture was allowed to stir at 25-30° C. for 1 hour, and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (6% methanol in DCM) to afford product 26-1 as a pale yellow solid (100 mg, 31%). $^1$H-NMR (400 MHz, CDCl$_3$) δ 7.58 (s, 1H), 5.14 (q, J=7 Hz, 1H), 5.06 (q, J=7 Hz, 1H), 4.91 (q, J=7 Hz, 1H), 3.99 (br, 1H), 3.90-3.75 (m, 1H), 2.80-2.68 (m, 2H), 2.5-2.3 (m, 2H), 2.12 (s, 3H), 1.56-1.44 (m, 9H), 1.40 (d, 3H), 1.11 (t, 3H); MS m/z (M+H)$^+$ 583.2.

Scheme 27: (2S)-1-{[(2S)-1-[(1S)-1-({[(2S,4S)-4-(Ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl]oxy}-1-oxopropan-2-yl (2S)-2-(acetyloxy)propanoate (27-1):

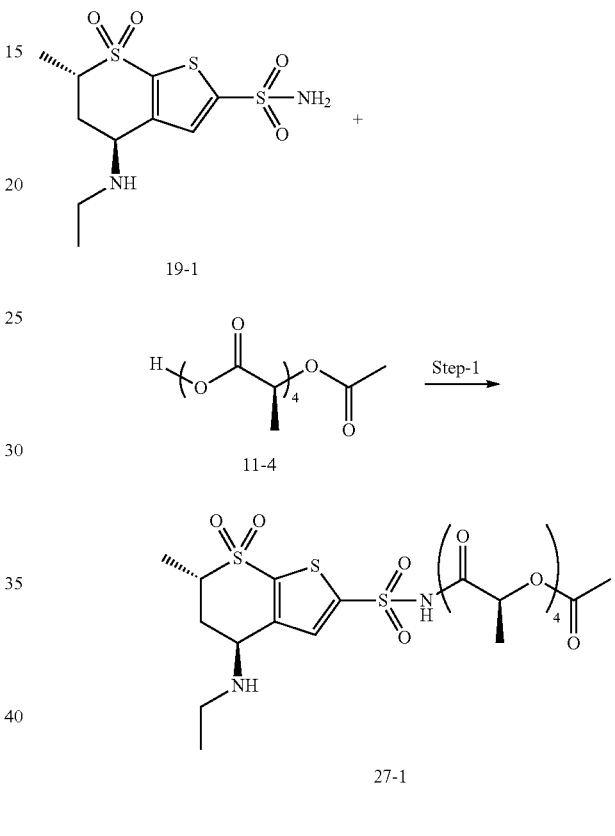

27-1

To a solution of dorzolamide (19-1) (0.5 g, 1.38 mmol) in dichloromethane (10 mL) was added N,N-diisopropylethylamine (0.5 mL, 2.77 mmol) at 0° C. After 30 minutes, (S)-2-{(S)-2-[(S)-2-((S)-2-acetoxy-propionyloxy)-propionyloxy]-propionyloxy}-propionic acid (11-4) (0.72 g, 2.08 mmol), EDCI.HCl (530 mg, 2.77 mmol), and 4-dimethylaminopyridine (16 mg, 0.13 mmol) were added at 0° C. The reaction mixture was allowed to stir at 25-30° C. for 1 hour, and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (6% methanol in DCM) to afford product 27-1 as a pale yellow solid (250 mg, 26%). $^1$H-NMR (400 MHz, MeOH-$d_4$) δ 7.70 (s, 1H), 5.21-5.10 (m, 2H), 5.06 (q, 1H), 4.65-4.55 (br, 1H), 3.86-3.74 (m. 1H), 3.20-3.05 (m, 2H), 2.74-2.54 (m, 2H), 2.08 (s, 3H), 1.58-1.45 (m, 12H), 1.42 (d, 3H), 1.32 (t, 3H); MS m/z (M+H)$^+$ 655.2.

Scheme 28: (2S)-1-{[(2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl (2S)-2-(acetyloxy)propanoate (28-1):

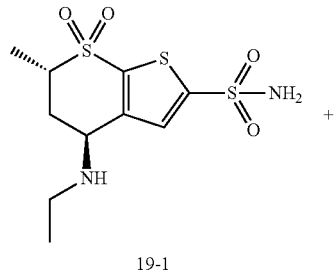

19-1

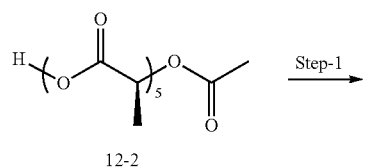

12-2

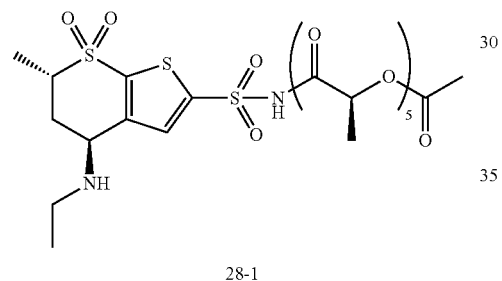

28-1

Scheme 29: (2S)-1-{[2S)-1-{[2S)-1-{[2S)-1-[1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl (2S)-2-(acetyloxy)propanoate (29-1):

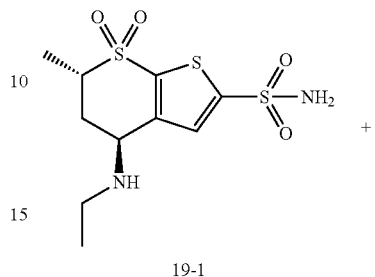

19-1

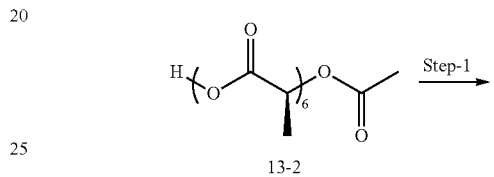

13-2

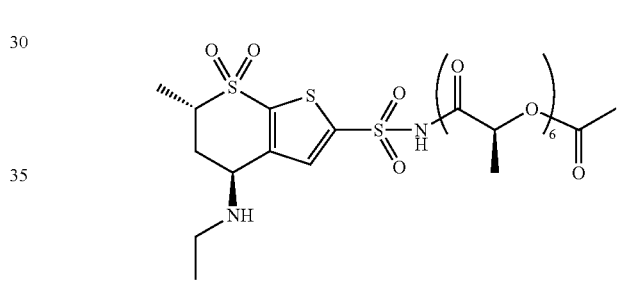

29-1

To a solution of dorzolamide (0.5 g, 1.38 mmol) in dichloromethane (10 mL) was added N,N-diisopropylethylamine (0.5 mL, 2.77 mmol) at 0° C. After 30 minutes, (S)-2-((S)-2-{(S)-2-[(S)-2-((S)-2-acetoxy-propionyloxy)-propionyloxy]-propionyloxy}-propionyloxy)-propionic acid (12-2) (0.87 g, 2.08 mmol), EDCI.HCl (530 mg, 2.77 mmol), and 4-dimethylaminopyridine (16 mg, 0.13 mmol) were added at 0° C. The reaction mixture was allowed to stir at 25-30° C. for 1 hour and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (6% methanol in dichloromethane) to afford product 28-1 as a pale yellow solid (390 mg, 38%). ¹H-NMR (400 MHz, DMSO-$d_6$) δ 8.75 (bs, 2H), 7.72 (s, 1H), 5.15-5.22 (m, 2H), 5.13-5.01 (m, 2H), 4.81 (q, J=7 Hz, 1H), 4.68-4.55 (m, 1H), 4.00-3.90 (m, 1H), 3.27-3.14 (m, 1H), 3.07-2.92 (m, 1H), 2.6-2.5 (m, 2H), 2.07 (s, 3H), 1.53-1.40 (m, 12H), 1.34 (d, 3H), 1.28 (d, 3H), 1.18 (t, 3H). MS m/z (M+H)⁺ 727.8.

To a solution of dorzolamide (19-1) (0.3 g, 0.833 mmol) in dichloromethane (5 mL) was added N,N-diisopropylethylamine (0.3 mL, 1.66 mmol) at 0° C. After 30 minutes, (S)-2-[(S)-2-((S)-2-{(S)-2-[(S)-2-((S)-2-acetoxy-propionyloxy)-propionyloxy]-propionyloxy}-propionyloxy]-propionic acid (13-2) (0.615 g, 1.25 mmol), EDCI.HCl (286 mg, 1.49 mmol), and 4-dimethylaminopyridine (10 mg, 0.083 mmol) were added at 0° C. The reaction mixture was allowed to stir at 25-30° C. for 1 hour and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (6% methanol in DCM) to afford product 29-1 as an off-white solid (130 mg, 20%). ¹H-NMR (400 MHz, MeOH-$d_4$) δ 7.73 (s, 1H), 5.21-5.12 (m, 4H), 5.06 (q, 1H), 4.88 (q, 1H), 4.60 (br, 1H), 3.75-3.86 (m. 1H), 3.10-3.23 (m, 2H), 2.76-2.56 (m, 2H), 2.09 (s, 3H), 1.58-1.45 (m, 18H), 1.41 (d, 3H), 1.32 (t, 3H); MS m/z (M+H)⁺ 799.4.

Scheme 30: (2S)-1-{[(2S)-1-{[(2S)-1-{[(2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl octadecanoate (30-1):

Scheme 31: (2S)-1-{[(2S)-1-{[(2S)-1-{[(2S)-1-{[(2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl octadecanoate (31-1):

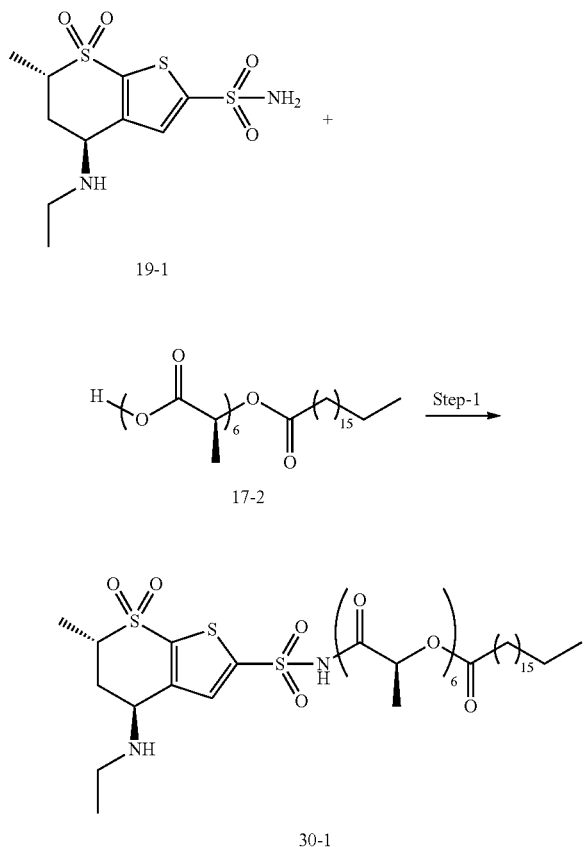

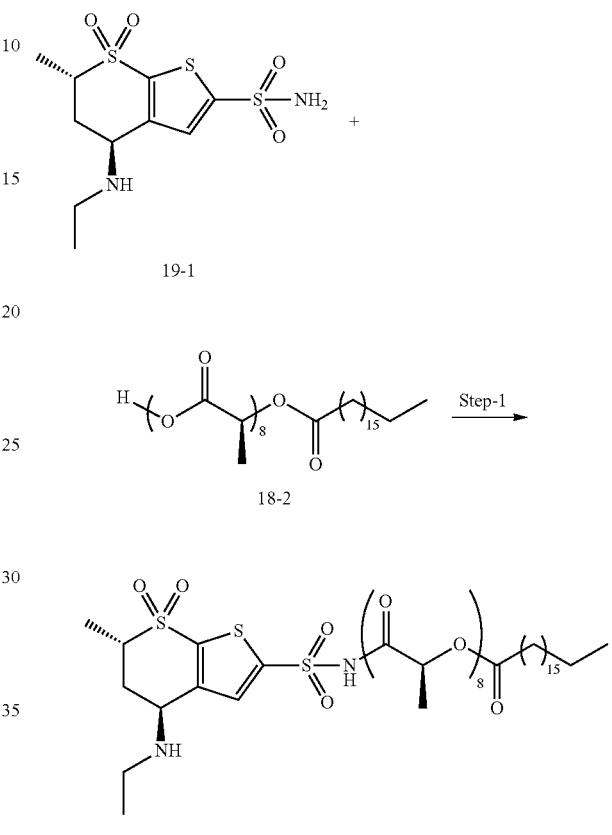

To a solution of dorzolamide (19-1) (0.3 g, 0.833 mmol) in dichloromethane (5 mL) was added N,N-diisopropylethylamine (0.3 mL, 1.66 mmol) at 0° C. After 30 minutes, octadecanoic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (17-2) (0.77 g, 1.08 mmol), EDCI.HCl (318 mg, 1.66 mmol), and 4-dimethylaminopyridine (10 mg, 0.083 mmol) were added at 0° C. The reaction mixture was allowed to stir at 25-30° C. for 1 hour and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (4% methanol in DCM) to afford product as an off-white solid (140 mg, 16%). ¹H-NMR (400 MHz, DMSO-$d_6$) δ 8.75 (bs, 2H), 7.72 (s, 1H), 5.23-5.15 (m, 3H), 5.14-5.00 (m, 2H), 4.81 (q, 1H), 4.66-4.57 (m, 1H), 4.00-3.93 (m, 1H), 3.30-2.94 (m, 2H), 2.7-2.4 (m, 2H), 2.32 (t, 2H), 1.55-1.15 (m, 54H), 0.83 (t, 3H); MS m/z (M+H)⁺ 1023.9.

To a solution of dorzolamide (19-1) (0.3 g, 0.833 mmol) in dichloromethane (5 mL) was added N,N-diisopropylethylamine (0.3 mL, 1.66 mmol) at 0° C. After 30 minutes, octadecanoic acid (S)-1-((S)-1-{(S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethoxycarbonyl}-ethoxycarbonyl)-ethyl ester (18-2) (1.07 g, 1.24 mmol), EDCI.HCl (318 mg, 1.66 mmol), and 4-dimethylaminopyridine (10 mg, 0.083 mmol) were added at 0° C. The reaction mixture was allowed to stir at 25-30° C. for 1 hour and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (4% methanol in dichloromethane) to afford product 31-1 as an off-white solid (350 mg, 36%). ¹H-NMR (400 MHz, DMSO-$d_6$) δ 8.75 (bs, 2H), 7.72 (s, 1H), 5.25-5.14 (m, 5H), 5.14-5.01 (m, 2H), 4.81 (q, 1H), 4.67-4.57 (m, 1H), 4.01-3.91 (m, 1H), 3.45-3.12 (m, 1H), 3.07-2.93 (m, 1H), 2.7-2.4 (m, 2H), 2.31 (t, 2H), 1.55-1.15 (m, 60H), 0.82 (t, 3H); MS m/z (M+H)⁺ 1168.4.

Example 3. Synthetic Examples of Brinzolmide Mono-Prodrugs

Scheme 32: (2S)-N-{[(4R)-4-(Ethylamino)-2-(3-methoxypropyl)-1,1-dioxo-2H,3H,4H-1λ⁶-thieno[3,2-e][1,2]thiazin-6-yl]sulfonyl}-2-hydroxypropanamide (32-3):

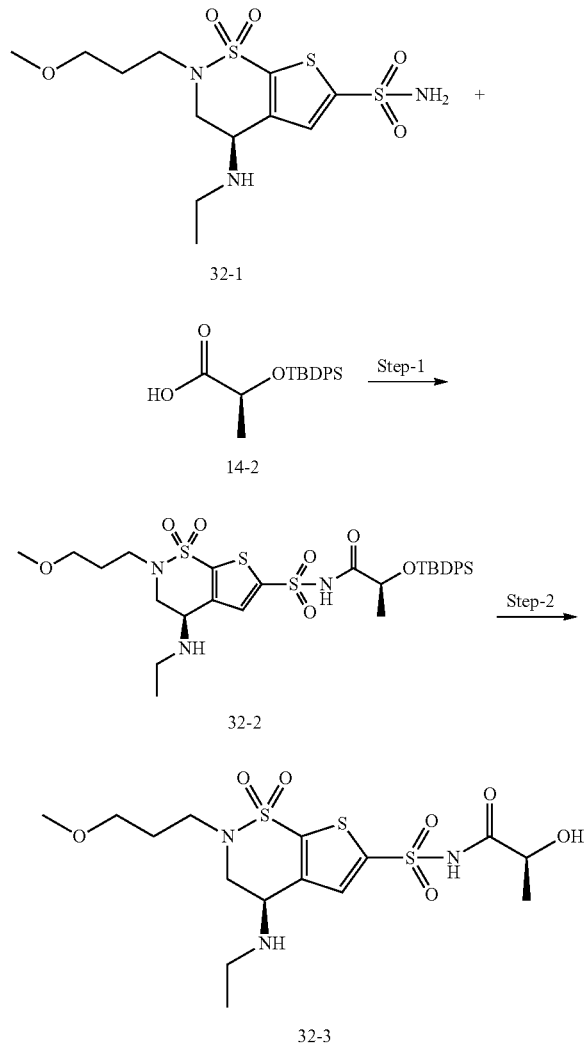

Step 1: (2S)-2-[(tert-Butyldiphenylsilyl)oxy]-N-{[(4R)-4-(ethylamino)-2-(3-methoxypropyl)-1,1-dioxo-2H,3H,4H-1λ⁶-thieno[3,2-e][1,2]thiazin-6-yl]sulfonyl}propanamide (32-2)

To a solution of brinzolamide (32-1) (1 g, 2.61 mmol) and (S)-2-(tert-butyl-diphenyl-silanyloxy)-propionic acid (14-2) (1.71 g, 5.22 mmol) in dichloromethane (10 mL) was added EDCI.HCl (0.99 g, 5.22 mmol) and 4-dimethylaminopyridine (310 mg, 0.26 mmol) at 0° C. The reaction mixture was allowed to stir at 25-30° C. for 1 hour and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel (230-400) column chromatography (6% methanol in DCM) to afford product as an off-white solid (1.1 g, 76%). ¹H NMR (400 MHz, DMSO-d₆) δ 9.14 (s, 1H), 9.01 (s, 1H), 7.83 (s, 1H), 7.70-7.50 (m, 4H), 7.4-7.2 (m, 6H), 4.9 (s, 1H), 4.15 (bs, 2H), 4.01 (q, J=7 Hz, 1H), 3.40 (s, 3H), 3.30 (s, 3H), 3.1 (s, 1H), 1.79 (quintet, 2H), 1.33-1.18 (m, 3H), 1.01 (s, 3H), 0.98 (s, 9H); MS m/z (M+H) 694.4.

Step 2: (2S)—N-{[(4R)-4-(Ethylamino)-2-(3-methoxypropyl)-1,1-dioxo-2H,3H,4H-1λ⁶-thieno[3,2-e][1,2]thiazin-6-yl]sulfonyl}-2-hydroxypropanamide (32-3)

To a solution of (2S)-2-[(tert-butyldiphenylsilyl)oxy]-N-{[(4R)-4-(ethylamino)-2-(3-methoxypropyl)-1,1-dioxo-2H,3H,4H-1λ⁶-thieno[3,2-e][1,2]thiazin-6-yl]sulfonyl}propanamide (32-2) (1.1 g, 1.19 mmol) in tetrahydrofuran (10 mL) were added tetra-butyl ammonium fluoride (1.43 mL, 1.14 mmol) and acetic acid (0.18 g, 3.01 mmol) at 0° C. The reaction mixture was allowed to stir at room temperature for 12 hours and the resulting reaction mixture was concentrated under reduced pressure. Crude product obtained upon evaporation of the volatiles was purified by silica gel column chromatography (5% methanol in ethyl acetate) to afford product 32-3 as an off-white solid (0.45 g, 62%). ¹H-NMR (400 MHz, DMSO-d₆) δ 9.3-8.8 (m, 2H), 7.83 (s, 1H), 4.90-4.75 (m, 1H), 4.12-3.96 (m, 3H), 3.77 (q, J=7 Hz, 1H), 3.41-3.34 (m, 3H), 3.23 (s, 3H), 3.22-3.12 (m, 1H), 3.11-2.97 (m, 2H), 1.83 (quintet, 2H), 1.21 (t, 3H), 1.13 (t, 3H); MS m/z (M+H)⁺

Scheme 33: (1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethyl (2S)-2-hydroxypropanoate (33-2):

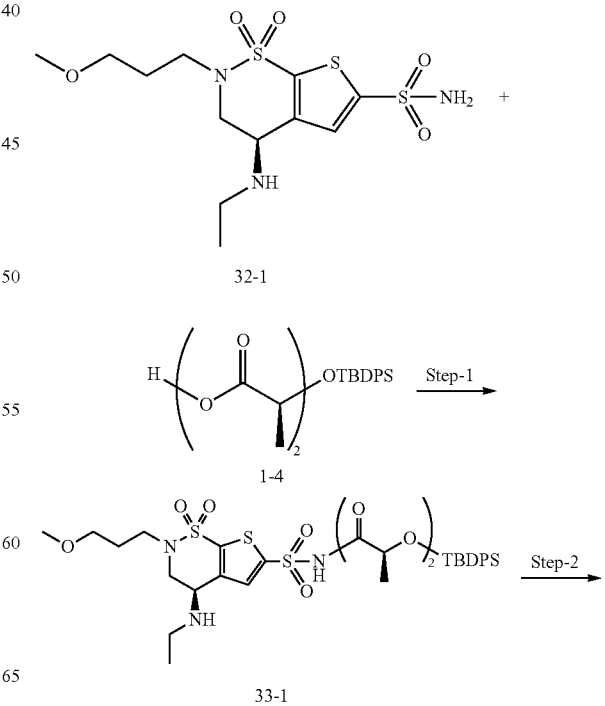

-continued

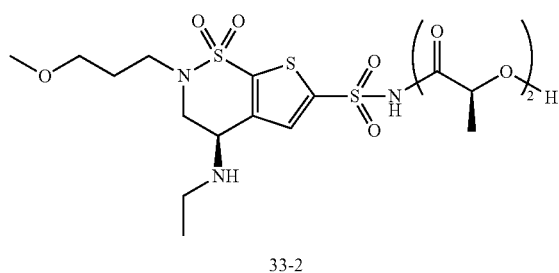

33-2

Step 1: (1S)-1-({[(4R)-4-(Ethylamino)-2-(3-methoxypropyl)-1,1-dioxo-2H,3H,4H-1)-1λ⁶-thieno[3,2-e][1,2]thiazin-6-yl]sulfonyl}carbamoyl)ethyl (2S)-2-[(tert-butyldiphenylsilyl)oxy]propanoate (33-1)

To a solution of brinzolamide (32-1) (0.1 g, 0.26 mmol) and (S)-2-(tert-butyl-diphenyl-silanyloxy)-propionic acid (S)-1-carboxy-ethyl ester (1-4) (0.17 g, 0.31 mmol) in dichloromethane (5 mL) was added EDCI.HCl (0.064 g, 0.33 mmol) and 4-dimethylaminopyridine (3 mg, 0.026 mmol) at 0° C. The reaction mixture was allowed to stir at 25-30° C. for 1 hour and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (6% methanol in DCM) to afford product 33-1 as an off-white solid (0.15 g, 65%).

Step 2: (1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethyl (2S)-2-hydroxypropanoate (33-2)

To a solution of (1S)-1-({[(4R)-4-(ethylamino)-2-(3-methoxypropyl)-1,1-dioxo-2H,3H,4H-1λ⁶-thieno[3,2-e][1,2]thiazin-6-yl]sulfonyl}carbamoyl)ethyl (2S)-2-[(tert-butyl-diphenylsilyl)oxy]propanoate (33-1) (1.0 g, 1.19 mmol) in tetrahydrofuran (10 mL) were added tetra-butyl ammonium fluoride (1.43 mL, 1.0M, 1.14 mmol) and acetic acid (0.18 g, 3.01 mmol) at 0° C. The reaction mixture was allowed to stir at room temperature for 12 hours and the resulting reaction mixture was concentrated under reduced pressure. Crude product obtained upon evaporation of the volatiles was purified by silica gel column chromatography (5% methanol in ethyl acetate) to afford product 33-2 as an off-white solid (450 mg, 62%). ¹H-NMR (400 MHz, DMSO-d₆) δ 7.46 (s, 1H), 5.26 (d, 1H), 4.78 (q, J=7 Hz, 1H), 4.08 (quintet, J=7 Hz, 1H), 4.05-3.96 (m, 1H), 3.78-3.65 (m, 2H), 3.43-3.30 (m, 3H), 3.22 (s, 3H), 3.17-3.10 (m, 1H), 2.6-2.5 (m, 2H), 1.79 (quintet, 2H), 1.30-1.21 (m, 6H), 1.01 (t, 3H); MS m/z (M+H)⁺ 582.2.

Scheme 34: (2S)-1-[1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl (2S)-2-hydroxypropanoate (34-2):

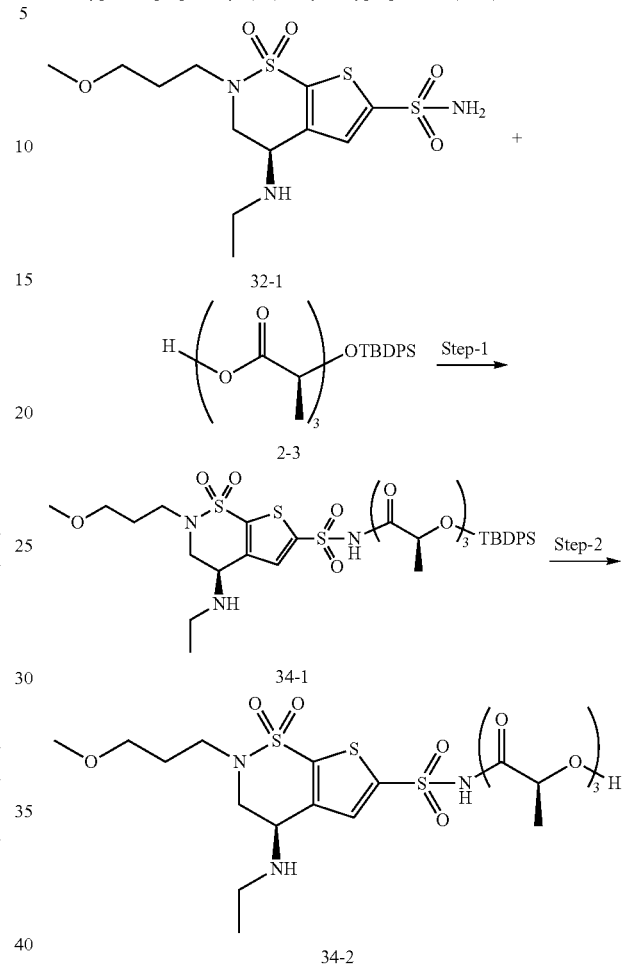

Step 1: (2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl (2S)-2-[(tert-butyldiphenylsilyl)oxy]propanoate (34-1)

To a solution of brinzolamide (32-1) (0.8 g, 2.00 mmol) and (S)-2-(tert-butyl-diphenyl-silanyloxy)-propionic acid (S)-1-((S)-1-carboxy-ethoxycarbonyl)-ethyl ester 2-3 (1.47 g, 3.10 mmol) in dichloromethane (10 mL) was added EDCI.HCl (0.59 g, 3.1 mmol) and 4-dimethylaminopyridine (25 mg, 0.20 mmol) at 0° C. The reaction mixture was allowed to stir at 25-30° C. for 1 hour and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (6% methanol in dichloromethane) to afford product 34-1 as an off-white solid (1.3 g, 76%). ¹H-NMR (400 MHz, DMSO-d₆) δ 7.60 (d, J=6.0, 4H), 7.59-7.40 (m, 7H), 4.81 (q, J=7 Hz, 1H), 4.79 (q, J=7 Hz, 1H), 4.27 (q, J=6.8, 1H), 3.76 (bs, 2H), 3.40-3.31 (m, 3H), 3.21 (s, 3H), 3.14-3.11 (m, 1H), 2.67-2.66 (m, 1H), 1.79 (quintet, J=7 Hz, 2H), 1.33-1.27-(m, 9H), 1.22 (s, 3H), 1.02 (s, 9H); MS m/z (M+H) 838.4

Step 2: (2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl (2S)-2-hydroxypropanoate (34-2)

To a solution of (2S)-1-[(1S)-1-({[(4R)-4-(ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl (2S)-2-[(tert-butyldiphenylsilyl)oxy]propanoate (34-1) (1.0 g, 1.19 mmol) in tetrahydrofuran (10 mL) were added tetra-butyl ammonium fluoride (1.43 mL, 1.0M, 1.14 mmol) and acetic acid (0.18 g, 3.01 mmol) at 0° C. The reaction mixture was allowed to stir at room temperature for 12 hours and the resulting reaction mixture was concentrated under reduced pressure. Crude product obtained upon evaporation of the volatiles was purified by silica gel column chromatography (5% methanol in ethyl acetate) to afford product 34-2 as off-white solid (450 mg, 62%). ¹H-NMR (400 MHz, DMSO-d₆) δ 7.47 (s, 1H), 5.44 (d, 1H), 5.01 (q, J=7 Hz, 1H), 4.79 (q, J=7 Hz, 1H), 4.18 (quintet, J=7 Hz, 1H), 4.05-3.96 (m, 1H), 3.81-3.66 (m, 2H), 3.42-3.30 (m, 3H), 3.22 (s, 3H), 3.16-3.07 (m, 1H), 2.6-2.5 (m, 2H), 1.78 (quintet, 2H), 1.47 (d, 3H), 1.33-1.21-\ (m, 6H), 0.99 (t, 3H); MS m/z (M+H)⁺ 600.3.

Scheme 35: (2S)-1-{[(2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl]oxy}-1-oxopropan-2-yl (2S)-2-hydroxypropanoate (35-2):

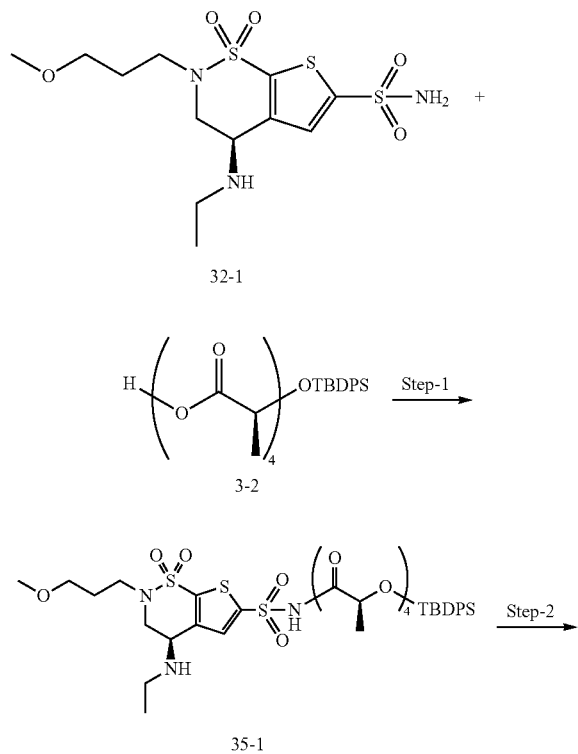

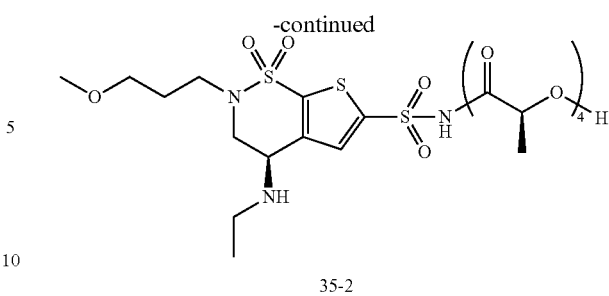

35-2

Step 1: (2S)-1-{[(2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl]oxy}-1-oxopropan-2-yl (2S)-2-[(tert-butyldiphenylsilyl)oxy]propanoate (35-1)

To a solution of brinzolamide (32-1) (0.1 g, 2.61 mmol) and (S)-2-(tert-butyl-diphenyl-silanyloxy)-propionic acid (S)-1-[(S)-1-((S)-1-carboxy-ethoxycarbonyl)-ethoxycarbonyl]-ethyl ester (3-2) (0.17 g, 3.12 mmol) in dichloromethane (5 mL) was added EDCI.HCl (64 mg, 0.33 mmol), 4-dimethylaminopyridine (3 mg, 0.026 mmol) at 0° C. The reaction mixture was allowed to stir at 25-30° C. for 1 hour and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (4% methanol in dichloromethane) to afford product 35-1 as an off-white solid (150 mg, 65%). ¹H-NMR (400 MHz, DMSO-d₆) δ 7.62 (d, J=6.4 Hz, 4H), 7.48-7.39 (m, 7H), 5.06 (q, J=7.2 Hz, 1H), 4.92 (q, J=7.2, 1H), 4.77 (q, J=6.4 Hz, 1H), 4.29-4.27 (m, 1H), 3.77-3.64 (m, 2H), 3.43-3.29 (m, 3H), 3.22 (s, 3H), 3.17-3.09 (m, 1H), 2.6-2.5 (m, 2H), 1.79 (quintet, 2H), 1.43-1.50 (m, 3H), 1.30-1.24 (m, 9H), 1.00 (s, 12H); MS m/z (M+H) 909.8

Step 2: (2S)-1-{[(2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl]oxy}-1-oxopropan-2-yl (2S)-2-hydroxypropanoate (35-2)

To a solution of (2S)-1-{[(2S)-1-[(1S)-1-({[(4R)-4-(ethylamino)-2-(3-methoxypropyl)-1,1-dioxo-2H, 3H,4H-1λ⁶-thieno[3,2-e][1,2]thiazin-6-yl]sulfonyl}carbamoyl)ethoxy]-1-oxopropan-2-yl]oxy}-1-oxopropan-2-yl (2S)-2-[(tert-butyldiphenylsilyl)oxy]propanoate (35-1) (250 mg, 0.27 mmol) in tetrahydrofuran (5 mL) was added tetra-butyl ammonium fluoride (0.27 mL, 1.0M, 0.27 mmol) and acetic acid (0.032 g, 0.54 mmol) at 0° C. The reaction mixture was allowed to stir at room temperature for 12 hours and the resulting reaction mixture was concentrated under reduced pressure. Crude product obtained upon evaporation of the volatiles was purified by silica gel column chromatography (5% methanol in ethyl acetate) to afford product 35-2 as off-white solid (130 mg, 72%). ¹H-NMR (400 MHz, DMSO-d₆) δ 7.47 (s, 1H), 5.47 (d, 1H), 5.13-5.04 (m, 2H), 4.79 (q, 1H), 4.20 (quintet, 1H), 4.05-3.97 (m, 1H), 3.77-3.64 (m, 2H), 3.43-3.29 (m, 3H), 3.22 (s, 3H), 3.17-3.09 (m, 1H), 2.6-2.5 (m, 2H), 1.79 (quintet, 2H), 1.43-1.50 (m, 6H), 1.30-1.24 (m, 6H), 1.00 (t, 3H); MS m/z (M+H)+ 671.8.

Scheme 36: (2S)-1-[(1S)-1-({[(4R)-4-(Ethylamino)-2-(3-methoxypropyl)-1,1-dioxo-2H,3H,4H-1λ6-thieno[3,2-e][1,2]thiazin-6-yl]sulfonyl}carbamoyl)ethoxy]-1-oxopropan-2-yl(2S)-2-(acetyloxy) propanoate (36-1):

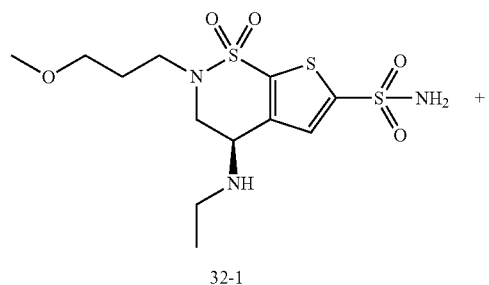

2H), 2.06 (s, 3H), 1.80 (quintet, 2H), 1.48 (d, 3H), 1.42 (d, 3H), 1.29 (d, 3H), 1.03 (t, 3H). MS m/z (M+H)+ 642.3.

Scheme 37: (2S)-1-{[(2S)-1-[(1S)-1-({[(4R)-4-(Ethylamino)-2-(3-methoxypropyl)-1,1-dioxo-2H,3H,4H-1λ6-thieno[3,2-e][1,2]thiazin-6-yl]sulfonyl}carbamoyl)ethoxy]-1-oxopropan-2-yl]oxy}-1-oxopropan-2-yl (2S)-2-(acetyloxy)propanoate (37-1):

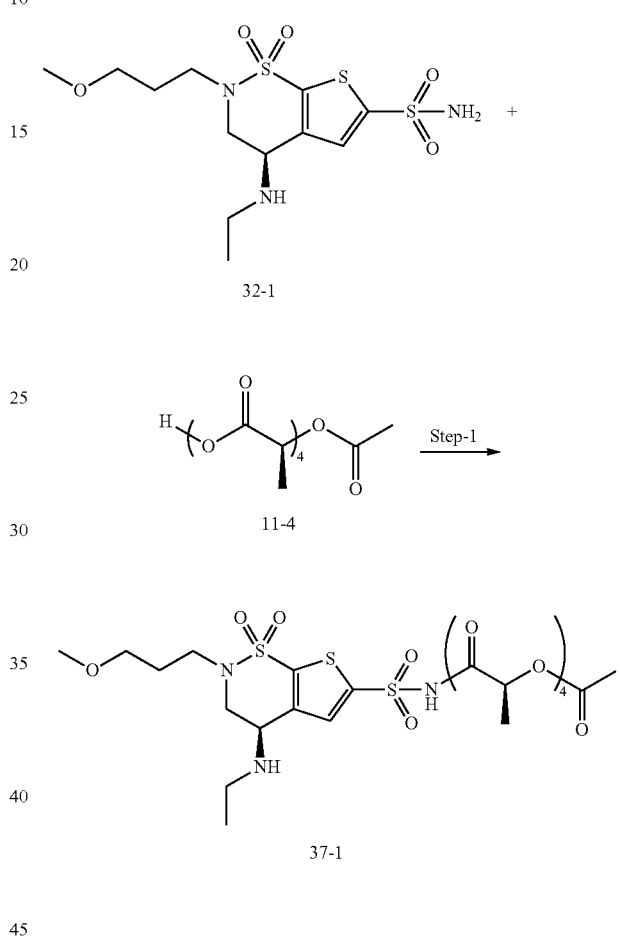

To a solution of brinzolamide (32-1) (0.2 g, 0.52 mmol) and (S)-2-[(S)-2-((S)-2-acetoxy-propionyloxy)-propionyloxy]-propionic acid (10-4) (0.21 g, 0.78 mmol) in dichloromethane (5 mL) was added EDCI.HCl (150 mg, 0.78 mmol) and 4-dimethylaminopyridine (6 mg, 0.05 mmol) at 0° C. The reaction mixture was allowed to stir at 25-30° C. for 1 hour and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel (230-400) column chromatography (6% methanol in DCM) to afford product 36-1 as an off-white solid (250 mg, 75%). 1H-NMR (400 MHz, DMSO-d6) δ 7.49 (s, 1H), 5.11-4.99 (m, 2H), 4.79 (q, 1H), 4.11-3.95 (m, 1H), 3.80-3.64 (m, 2H), 3.40-3.31 (m, 3H), 3.22 (s, 3H), 3.18-3.08 (m, 1H), 2.6-2.5 (m, To a solution of brinzolamide (32-1) (0.3 g, 0.78 mmol) and (S)-2-{(S)-2-[(S)-2-((S)-2-acetoxy-propionyloxy)-propionyloxy]-propionyloxy}-propionic acid (11-4) (0.35 g, 1.01 mmol) in dichloromethane (10 mL) was added EDCI-.HCl (224 mg, 1.17 mmol) and 4-dimethylaminopyridine (9 mg, 0.07 mmol) at 0° C. The reaction mixture was allowed to stir at 25-30° C. for 1 hour and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel (230-400) column chromatography (8% methanol in dichloromethane) to afford product 37-1 as an off-white solid (150 mg, 27%). 1H-NMR (400 MHz, DMSO-d6) δ 9.11 (bs, 1H), 8.99 (bs, 1H), 7.81 (s, 1H), 5.02-5.20 (m, 3H), 4.90-4.78 (m, 2H), 4.13-3.96 (m, 2H), 3.43-3.01 (m, 9H), 2.07 (s, 3H), 1.82 (quintet, 2H), 1.51-1.40 (m, 9H), 1.30 (d, 3H), 1.21 (t, 3H). MS m/z (M+H)+ 714.3.

Scheme 38: (2S)-1-{[(2S)-1-{[(2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl]oxy}-1-oxopropan-2-yl]oxy}-1-oxopropan-2-yl(acetyloxy)propanoate (38-1):

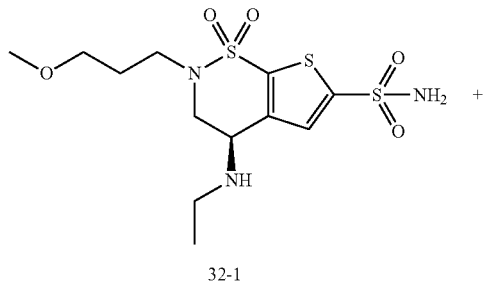

32-1

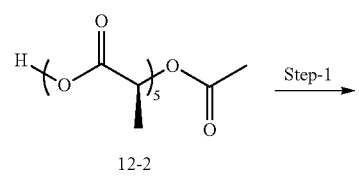

12-2

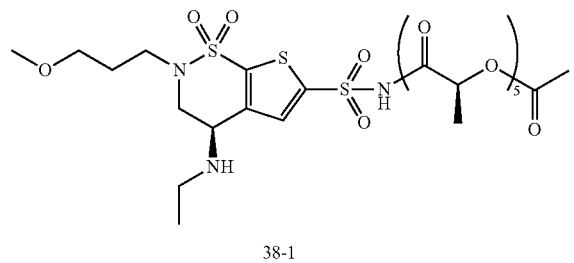

38-1

Scheme 39: (2S)-1-{[(2S)-1-{[(2S)-1-{[(2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl (2S)-2-(acetyloxy)propanoate (39-1):

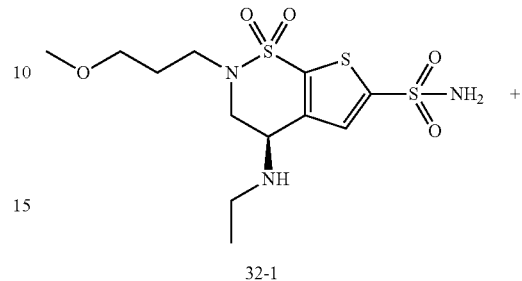

32-1

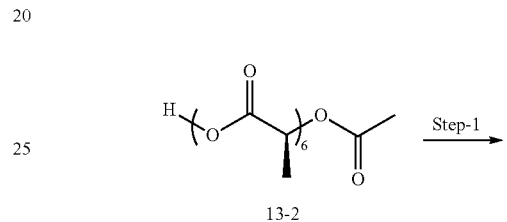

13-2

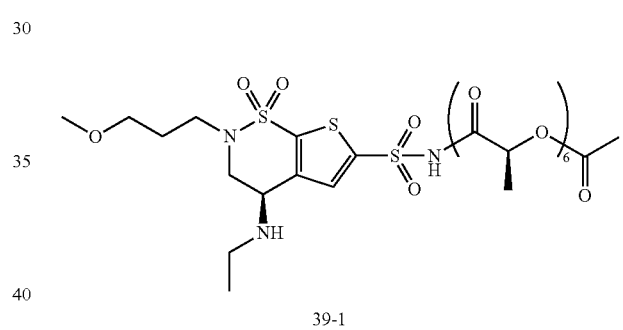

39-1

To a solution of brinzolamide (32-1) (0.5 g, 1.30 mmol) and (S)-2-((S)-2-{(S)-2-[(S)-2-((S)-2-acetoxy-propionyloxy)-propionyloxy]-propionyloxy}-propionyloxy)-propionic acid (12-2) (0.87 g, 2.08 mmol) in dichloromethane (5 mL) was added EDCI.HCl (500 mg, 2.61 mmol), 4-dimethylaminopyridine (15 mg, 0.13 mmol) at 0° C. The reaction mixture was allowed to stir at 25-30° C. for 1 hour and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel (230-400) column chromatography (8% methanol in DCM) to afford product 38-1 as an off-white solid (260 mg, 26%). $^1$H-NMR (400 MHz, DMSO-d$_6$) δ 9.12 (bs, 1H), 8.98 (bs, 1H), 7.81 (s, 1H), 5.22-5.15 (m, 2H), 5.13-5.01 (m, 2H), 4.90-4.77 (m, 2H), 4.12-3.92 (m, 2H), 3.41-3.34 (m, 3H), 3.22-2.96 (m, 6H), 2.07 (s, 3H), 1.83 (quintet, 2H), 1.51-1.39 (m, 12H), 1.30 (d, 3H), 1.21 (t, 3H); MS m/z (M+H)$^+$ 786.6.

To a solution of brinzolamide (32-1) (0.3 g, 0.78 mmol) and (S)-2-[(S)-2-((S)-2-{(S)-2-[(S)-2-((S)-2-acetoxy-propionyloxy)-propionyloxy]-propionyloxy}-propionyloxy)-propionyloxy]-propionic acid 13-2 (0.57 g, 1.17 mmol) in dichloromethane (10 mL) was added EDCI.HCl (268 mg, 1.40 mmol) and 4-dimethylaminopyridine (9 mg, 0.07 mmol) at 0° C. The reaction mixture was allowed to stir at 25-30° C. for 1 hour and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel (230-400) column chromatography (6% methanol in dichloromethane) to afford product 39-1 as an off-white solid (220 mg, 32%). $^1$H-NMR (400 MHz, DMSO-d$_6$) δ 9.12 (bs, 1H), 8.99 (bs, 1H), 7.81 (s, 1H), 5.24-5.16 (m, 3H), 5.13-5.01 (m, 2H), 4.90-4.77 (m, 2H), 4.15-3.92 (m, 2H), 3.41-3.31 (m, 3H), 3.22-2.97 (m, 6H), 2.07 (s, 3H), 1.83 (quintet, 2H), 1.52-1.40 (m, 15H), 1.30 (d, 3H), 1.21 (t, 3H); MS m/z (M+H)$^+$ 858.4.

Scheme 40: (2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl (2S)-2-(tert-butoxy)propanoate (40-1):

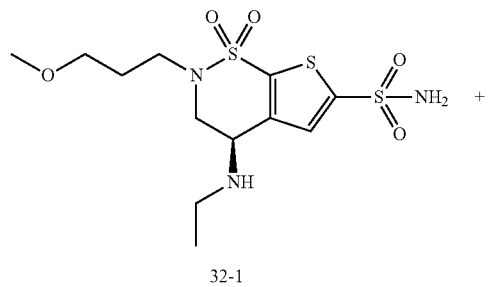

32-1

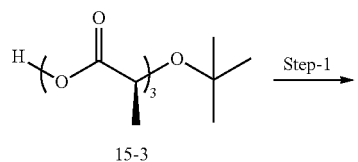

15-3

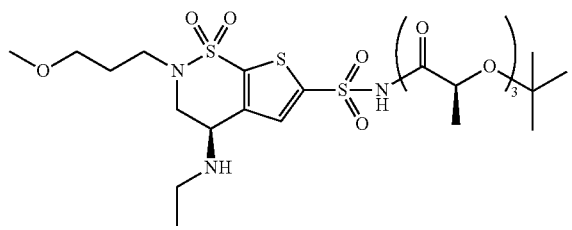

40-1

Scheme 41: (2S)-1-{[(2S)-1-{[(2S)-1-{[(2S)-1-{[(2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl octadecanoate (41-1):

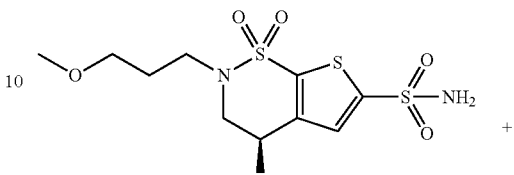

32-1

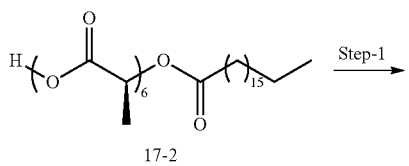

17-2

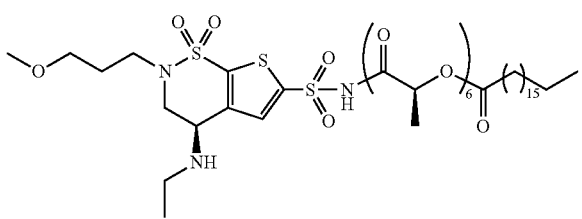

41-1

To a solution of brinzolamide (0.3 g, 0.78 mmol) and (S)-2-tert-butoxy-propionic acid (S)-1-((S)-1-carboxy-ethoxycarbonyl)-ethyl ester (15-3) (0.29 g, 1.01 mmol) in dichloromethane (10 mL) was added EDCI.HCl (224 mg, 1.17 mmol) and 4-dimethylaminopyridine (9 mg, 0.07 mmol) at 0° C. The reaction mixture was allowed to stir at 25-30° C. for 1 hour and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel (230-400) column chromatography (6% methanol in ethyl acetate) to afford product as 40-1 an off-white solid (125 mg, 24%). $^1$H-NMR (400 MHz, DMSO-d$_6$) δ 7.49 (s, 1H), 5.01 (q, J=7 Hz, 1H), 4.79 (q, J=7 Hz, 1H), 4.22 (q, J=7 Hz, 1H), 4.05-3.95 (m, 1H), 3.82-3.65 (m, 2H), 3.43-3.33 (m, 3H), 3.22 (s, 3H), 3.18-3.08 (m, 1H), 2.6-2.5 (m, 2H), 1.80 (quintet, 2H), 1.45 (d, 3H), 1.29 (d, 3H), 1.22 (d, 3H), 1.11 (s, 9H), 1.02 (t, 3H); MS m/z (M+H)$^+$ 656.3.

To a solution of brinzolamide (32-1) (0.35 g, 0.91 mmol) and octadecanoic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (17-2) (0.98 g, 1.37 mmol) in dichloromethane (5 mL) were added EDCI.HCl (349 mg, 1.82 mmol) and 4-dimethylaminopyridine (11 mg, 0.09 mmol) at 0° C. The reaction mixture was allowed to stir at 25-30° C. for 1 hour and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (8% methanol in DCM) to afford product 41-1 as an off-white solid (350 mg, 35%). $^1$H-NMR (400 MHz, DMSO-d$_6$) δ 9.12 (bs, 1H), 9.01 (bs, 1H), 7.84 (bs, 1H), 5.24-5.01 (m, 5H), 4.90-4.75 (m, 2H), 4.15-3.90 (m, 2H), 3.41-3.30 (m, 3H), 3.24-2.90 (m, 6H), 2.33 (t, 2H), 1.84 (quintet, 2H), 1.52-1.35 (m, 15H), 1.35-0.98 (m, 36H), 0.81 (t, 3H); MS m/z (M+H)$^+$ 1083.3.

Scheme 42: (2S)-1-{[(2S)-1-{[(2S)-1-{[(2S)-1{[(2S)-1-{[(2S)-1{[(2S)-1-{[(2S)-1-[(1S)-1-({[(4R)-4-(Ethylamino)-2-(3-methoxypropyl)-1,1-dioxo-2H,3H,4H-1λ⁶-thieno[3,2-e][1,2]thiazin-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl octadecanoate (42-1):

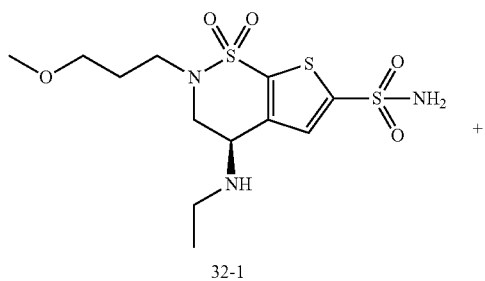

32-1

+

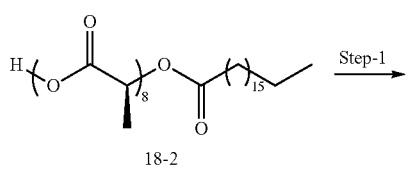

18-2

Step-1 →

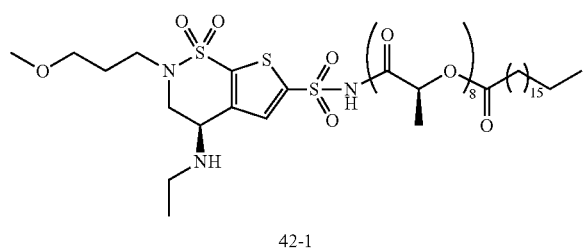

42-1

To a solution of brinzolamide (32-1) (0.3 g, 0.78 mmol) and octadecanoic acid (S)-1-((S)-1-{(S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethoxycarbonyl}-ethoxycarbonyl)-ethyl ester (18-2) (1.01 g, 1.17 mmol) in dichloromethane (5 mL) was added EDCI·HCl (300 mg, 1.56 mmol) and 4-dimethylaminopyridine (9 mg, 0.07 mmol) at 0° C. The reaction mixture was allowed to stir at 25-30° C. for 1 hour and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (8% methanol in DCM) to afford product 42-1 as an off-white solid (245 mg, 25%). ¹H-NMR (400 MHz, DMSO-d₆) δ 9.1 (bs, 2H), 7.82 (bs, 1H), 5.24-5.15 (m, 5H), 5.14-5.01 (m, 2H), 4.83-4.73 (m, 2H), 4.15-3.90 (m, 2H), 3.41-3.30 (m, 3H), 3.24-2.85 (m, 6H), 2.33 (t, 2H), 1.82 (quintet, 2H), 1.54-1.35 (m, 21H), 1.34-0.95 (m, 36H), 0.82 (t, 3H). MS m/z (M+H)⁺ 1227.4.

Example 4. Synthetic Examples of Latanoprost Mono-Prodrugs

Scheme 43: Propan-2-yl (5Z)-7-[3,5-bis({[(2S)-2-{[(2S)-2-{[(2S)-2-(acetyloxy)propanoyl]oxy}propanoyl]oxy}propanoyl]oxy})-2-(3-{[(2S-2-{[(2S)-2-{[(2S)-2-(acetyloxy)propanoyl]oxy}propanoyl]oxy}propanoyl]oxy}-5-phenylpentyl)cyclopentyl]hept-5-enoate (43-2):

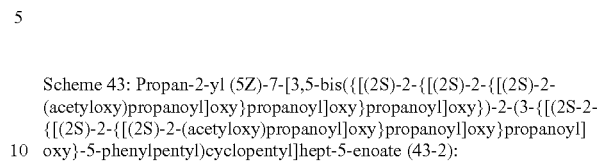

43-1

+

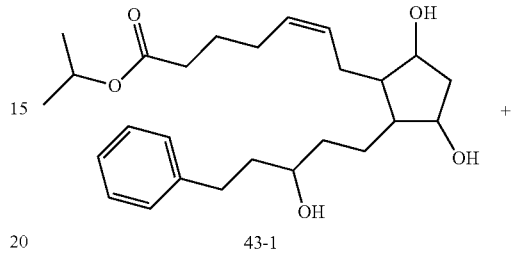

10-4

Step-1 →

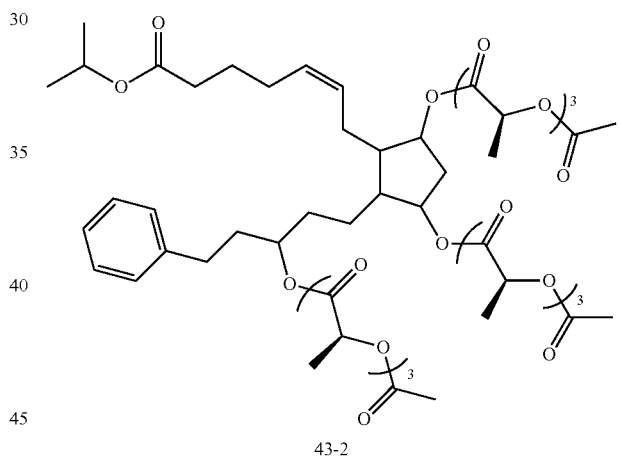

43-2

To a solution of lantanoprost (43-1) (0.1 g, 0.23 mmol) and (S)-2-[(S)-2-((S)-2-acetoxy-propionyloxy)-propionyloxy]-propionic acid (10-4) (0.22 g, 0.80 mmol) in dichloromethane (5 mL) was added EDCI.HCl (0.15 g, 0.00083 mol) and 4-dimethylaminopyridine (8 mg, 0.06 mmol) at 0° C. The reaction mixture was allowed to stir at 25-30° C. for 48 hours and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (30% ethyl acetate in hexane) to afford product 43-2 as a colorless wax (100 mg, 37%). ¹H-NMR (400 MHz, DMSO-d₆) δ 7.29-7.22 (m, 2H), 7.21-7.12 (m, 3H), 5.40-5.25 (m, 2H), 5.25-4.98 (m, 9H), 4.97-4.79 (m, 4H), 2.21 (t, J=7 Hz, 2H), 2.19-2.07 (m, 2H), 2.06 (s, 9H), 2.04-1.72 (m, 8H), 1.72-1.32 (m, 35H), 1.15 (d, 6H); MS m/z (M+H)⁺ 1207.8, (M+NH₄)⁺ 1224.8.

Scheme 44: Propan-2-yl (5Z)-7-{3,5-bis](2S)-2-{[(2S)-2-{[(2S)-2-{[(2S)-2-(acetyloxy)propanoyl]oxy}propanoyl]oxy}propanoyl]oxy}propanamido]-2-{3-[(2S-2-[(2S)-2-{[(2S)-2-{[(2S)-2-(acetyloxy)propanoyl]oxy}propanoyl]oxy}propanoyl]oxy}propanamido]-5-phenylpentyl}cyclopentyl}hept-5-enoate (44-1):

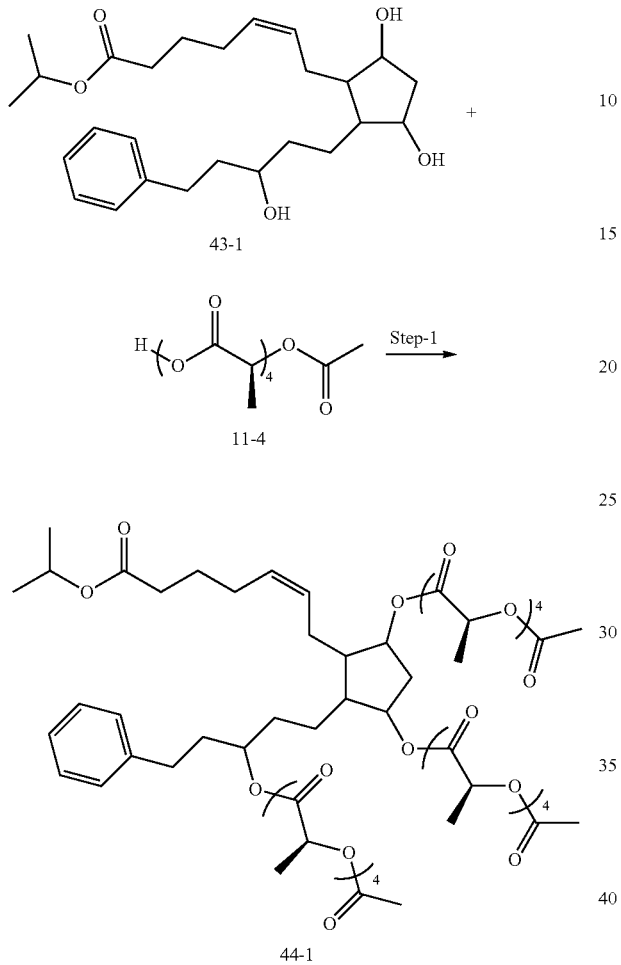

Scheme 45: Propan-2-yl (5Z)-7-[3,5-bis({[(2S)-2-{[(2S)-2-{[(2S)-2-{[(2S)-2-(acetyloxy)propanoyl]oxy}propanoyl]oxy}propanoyl]oxy}propanoyl]oxy})-2-(3-{[(2S)-2-{[(2S)-2-{[(2S)-2-{[(2S)-2-(acetyloxy)propanoyl]oxy}propanoyl]oxy}propanoyl]oxy}propanol]oxy}propanol]oxy}-5-phenylpentyl)cylopentyl]hept-5-enoate (45-1):

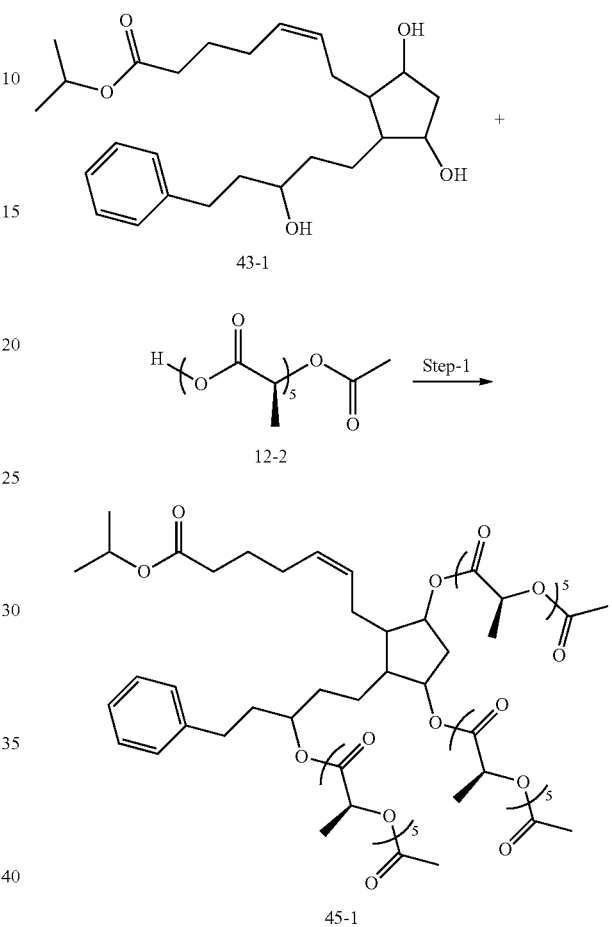

To a solution of lantanoprost (43-1) (0.1 g, 0.23 mmol) and (S)-2-{(S)-2-[(S)-2-((S)-2-acetoxy-propionyloxy)-propionyloxy]-propionyloxy}-propionic acid (11-4) (0.35 g, 0.92 mmol) in dichloromethane (5 mL) was added EDCI·HCl (0.176 g, 0.92 mmol) and 4-dimethylaminopyridine (14 mg, 0.11 mmol) at 0° C. The reaction mixture was allowed to stir at 25-30° C. for 28 hours and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (30% ethyl acetate in hexane) to afford product 44-1 as a colorless wax (200 mg, 60%). $^1$H-NMR (400 MHz, DMSO-$d_6$) δ 7.29-7.22 (m, 2H), 7.19-7.12 (m, 3H), 5.39-5.25 (m, 2H), 5.25-4.98 (m, 12H), 4.96-4.79 (m, 4H), 2.21 (t, J=7 Hz, 2H), 2.19-2.07 (m, 2H), 2.06 (s, 9H), 2.05-1.72 (m, 8H), 1.72-1.33 (m, 44H), 1.15 (d, 6H); MS m/z (M+H)$^+$ 1423.7, (M+NH$_4$)$^+$ 1440.8.

To a solution of lantanoprost (43-1) (0.1 g, 0.23 mmol) and (S)-2-((S)-2-{(S)-2-[(S)-2-((S)-2-acetoxy-propionyloxy)-propionyloxy]-propionyloxy}-propionyloxy)-propionic acid (12-2) (0.48 g, 0.11 mmol) in dichloromethane (5 mL) was added EDCI.HCl (0.22 g, 1.15 mmol) and 4-dimethylaminopyridine (14 mg, 0.11 mmol) at 0° C. The reaction mixture was allowed to stir at 25-30° C. for 48 hours and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (30% ethyl acetate in hexane) to afford product 45-1 as a colorless wax (200 mg, 54%). $^1$H-NMR (400 MHz, DMSO-$d_6$) δ 7.29-7.22 (m, 2H), 7.20-7.13 (m, 3H), 5.37-5.25 (m, 2H), 5.25-5.00 (m, 15H), 4.94-4.77 (m, 4H), 2.21 (t, J=7 Hz, 2H), 2.19-2.07 (m, 2H), 2.06 (s, 9H), 2.04-1.72 (m, 8H), 1.72-1.33 (m, 53H), 1.15 (d, 6H); MS m/z (M+NH$_4$)$^+$ 1657.5.

Scheme 46: Propan-2-yl (5Z)-7-[3,5-bis({[(2S)-2-{[(2S)-2-{[(2S)-2-{[(2S)-2-{[(2S)-2-(acetyloxy)propanoyl]oxy}propanoyl]oxy}propanoyl]oxy}propanoyl]oxy}propanoyl]oxy})propanol]oxy})-2-(3-{[(2S)-2-{[(2S)-2-{[(2S)-2-{[(2S)-2-{[(2S)-{[(2S)-2-(acetyloxy)propanoyl]oxy}propanoyl]oxy}propanoyl]oxy}propanoyl]oxy}propanoyl]oxy}propanoyl]oxy}-5-phenylpentyl)cylopentyl]hept-5-enoate (46-1):

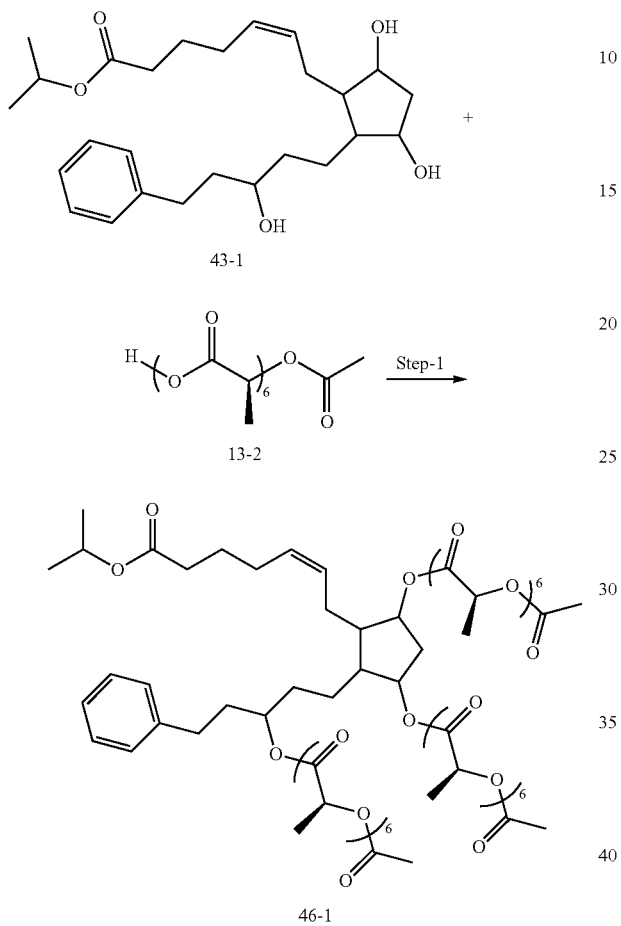

To a solution of lantanoprost (43-1) (0.1 g, 0.23 mmol) and (S)-2-[(S)-2-((S)-2-{(S)-2-[(S)-2-((S)-2-acetoxy-propionyloxy)-propionyloxy]-propionyloxy}-propionyloxy)-propionyloxy]-propionic acid (13-2) (0.68 g, 0.13 mmol) in dichloromethane (5 mL) was added EDCI.HCl (0.26 g, 1.13 mmol) and 4-dimethylaminopyridine (16 mg, 0.13 mmol) at 0° C. The reaction mixture was allowed to stir at 25-30° C. for 48 hours and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (30% ethyl acetate in hexane) to afford product 46-1 as a colorless wax (150 mg, 35%). $^1$H-NMR (400 MHz, DMSO-$d_6$) δ 7.28-7.22 (m, 2H), 7.19-7.12 (m, 3H), 5.37-5.25 (m, 2H), 5.25-5.01 (m, 18H), 4.94-4.78 (m, 4H), 2.21 (t, J=7 Hz, 2H), 2.19-2.07 (m, 2H), 2.06 (s, 9H), 2.04-1.72 (m, 8H), 1.72-1.34 (m, 62H), 1.15 (d, 6H). MS m/z (M+NH$_4$)$^+$ 1873.5.

Example 5. Synthetic Examples of Sunitinib Mono-Prodrugs

Scheme 47: 3-{[(3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl]carbamoyl}propanoic acid (47-3):

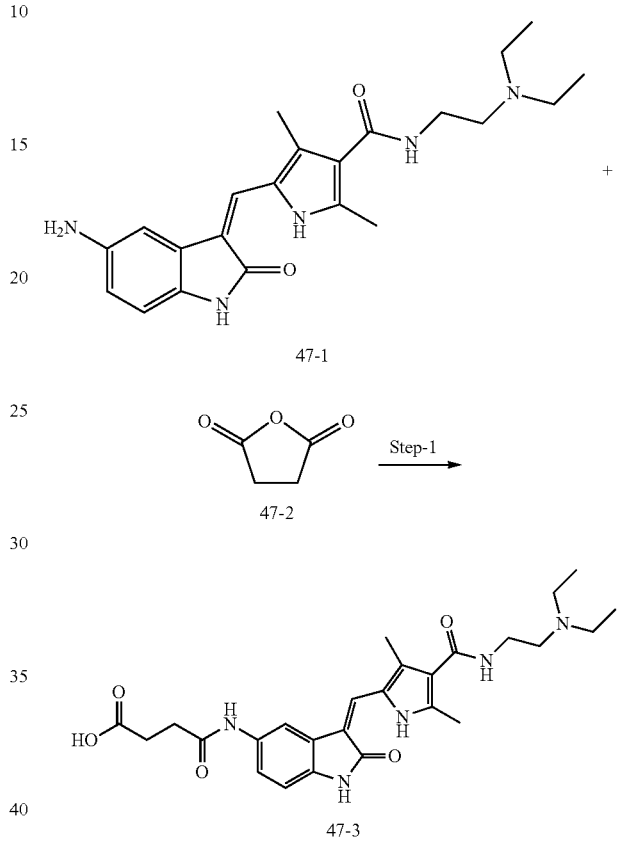

To a solution of 5-[5-amino-2-oxo-1,2-dihydro-indol-(3Z)-ylidenemethyl]-2,4-dimethyl-1H-pyrrole-3-carboxylic acid (2-diethylamino-ethyl)-amide (0.6 g, 0.51 mmol) and dihydro-furan-2,5-dione (0.166 g, 1.66 mmol) in dichloromethane (12 mL) was added 4-dimethylaminopyridine (37 mg, 0.15 mmol) at 0° C. After stirring at room temperature for 6 hours, the resulting reaction mixture was filtered to afford product 47-3 as a yellow solid (500 mg, 66%). $^1$H-NMR (400 MHz, DMSO-$d_6$) δ 13.64 (s, 1H), 10.83 (s, 1H), 10.09 (s, 1H), 7.89 (s, 1H), 7.47-7.42 (m, 2H), 7.27-7.19 (dd, J=2 & 8 Hz, 1H), 6.80 (d, J=8 Hz, 1H), 3.27 (q, J=6 Hz, 2H), 2.65-2.45 (m, 10H), 2.43, (s, 3H), 2.39 (s, 3H), 0.97 (t, 6H). MS m/z (M+H)$^+$ 496.4.

Scheme 48: 5-Hydroxy Sunitinib (48-3):

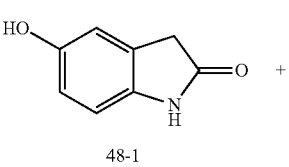

197

-continued

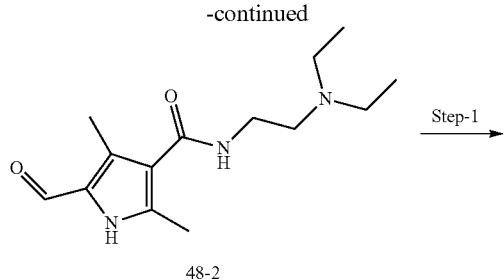

48-2

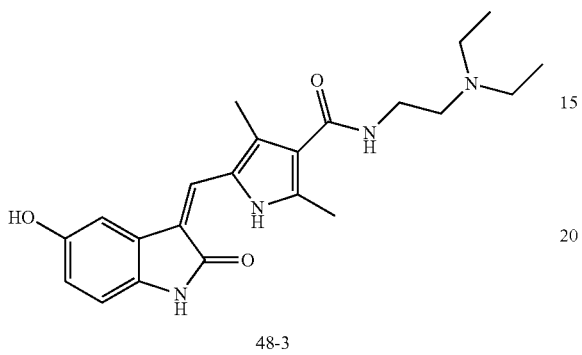

48-3

To a solution of 5-hydroxy-1,3-dihydro-indol-2-one (48-1) (3.37 g, 22.61 mmol) and 5-formyl-2,4-dimethyl-1H-pyrrole-3-carboxylic acid (2-diethylamino-ethyl)-amide (48-2) (6.0 g, 22.61 mol) in ethanol (120 mL) was added piperidine (0.2 mL, 2.26 mmol) and the reaction mixture was refluxed at 90° C. for 4 hours. The reaction mixture was then concentrated and washed with diethyl ether (25 mL) and ethyl acetate (25 mL) to afford product 48-3 as an orange color solid (5.5 g, 61%). ¹H-NMR (400 MHz, DMSO-d₆) δ 13.71 (s, 1H), 10.59 (s, 1H), 8.91 (s, 1H), 7.49 (s, 1H), 7.39 (t, 1H), 7.16 (d, J=2 Hz, 1H), 6.66 (d, J=8 Hz, 1H), 6.56 (dd, J=2 & 8 Hz, 1H), 3.29 (q, 2H), 2.6-2.5 (m, 6H), 2.45, (s, 3H), 2.43 (s, 3H), 0.99 (t, 6H); MS m/z (M+H)⁺ 397.3.

Scheme 49: (3Z)-3-[(4-{[2-(Diethylamino)ethyl]carbamoyl}-3,5-dimetyl-1H-pyrrol-2-yl)methylidene]-2-oxo-2,3-dihydro-1H-indol-5-yl (2S)-2-{[(2S)-2-(acetyloxy) propanoyl]oxy}propanoate (49-1):

198

-continued

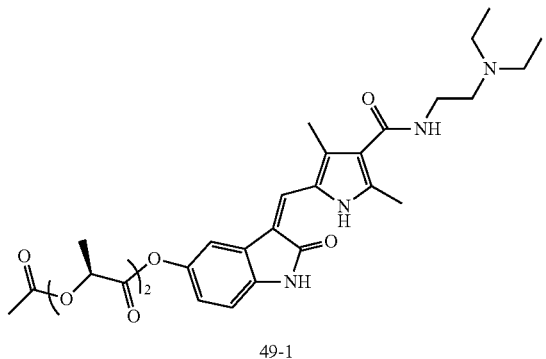

49-1

To a solution of (S)-2-((S)-2-acetoxy-propionyloxy)-propionic acid (11-2) (0.388 g, 1.9 mmol) in dichloromethane (5 mL) was added N,N-diisopropylethylamine (0.36 ml, 1.96 mmol), EDCI.HCl (0.363 g, 1.9 mmol), 5-hydroxy Sunitinib (48-1) (0.3 g, 0.76 mmol), and 4-dimethylaminopyridine (9 mg, 0.076 mmol) at 0° C. After stirring at 25-30° C. for 3 hours, the reaction mixture was filtered and concentrated under reduced pressure. The crude product obtained upon concentration of volatiles was purified by preparative HPLC to afford product 49-1 as an orange color solid (0.13 g, 29%). ¹H-NMR (400 MHz, DMSO-d₆) δ 13.68 (s, 1H), 10.98 (s, 1H), 7.71 (s, 1H), 7.65 (d, J=2 Hz, 1H), 7.49 (t, 1H), 6.89 (d, J=8 Hz, 1H), 6.83 (dd, J=2 & 8 Hz, 1H), 5.38 (q, J=7 Hz, 1H), 5.10 (q, J=7 Hz, 1H), 2.7-2.5 (m, 6H), 2.44, (s, 3H), 2.42 (s, 3H), 2.09 (s, 3H), 1.64 (d, J=7 Hz, 3H), 1.46 (d, J=7 Hz, 3H), 0.99 (t, 6H); MS m/z (M+H)⁺ 583.4.

Scheme 50: (3Z)-3-[(4-{[2-(Diethylamino)ethyl]carbamoyl}-3,5-dimetyl-1H-pyrrol-2-yl)methylidene]-2-oxo-2,3-dihydro-1H-indol-5-yl (2S)-2-{[(2S)-2-(acetyloxy)propanoyl]oxy}propanoyl]oxy} propanoate (50-1):

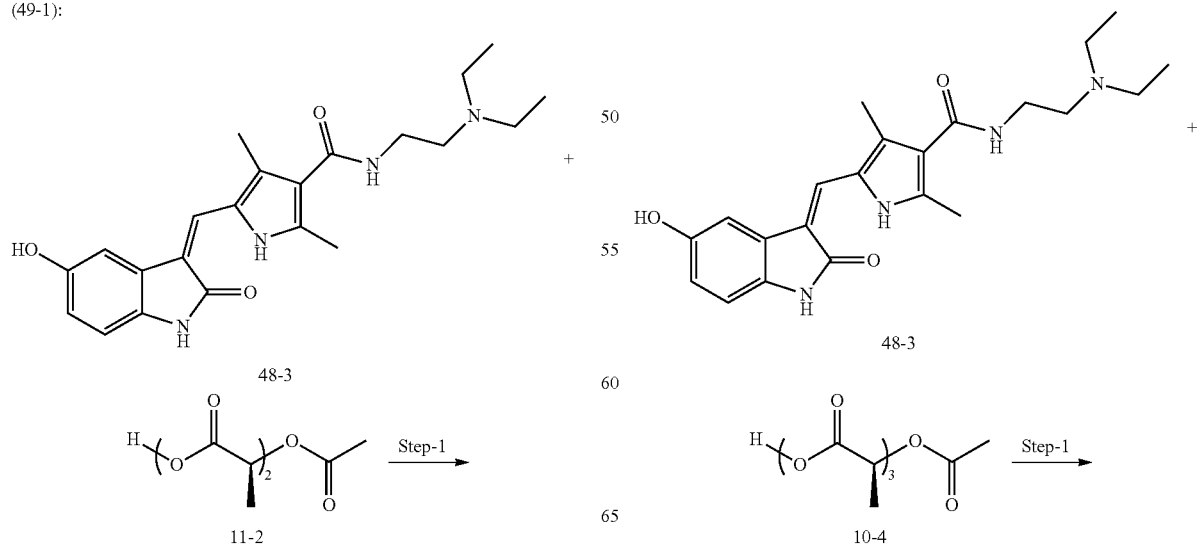

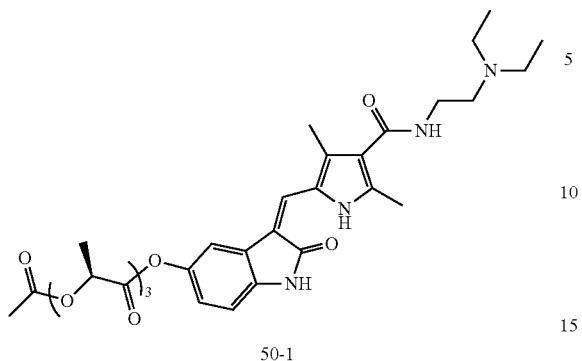

50-1

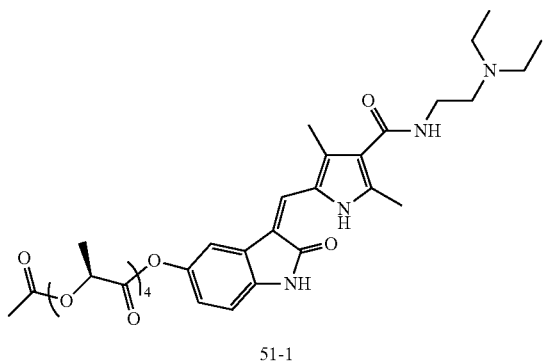

51-1

To a solution of (S)-2-[(S)-2-((S)-2-acetoxy-propionyloxy)-propionyloxy]-propionic acid (10-4) (0.52 g, 1.9 mmol) in dichloromethane (5 mL) was added N,N-diisopropylethylamine (0.36 ml, 1.96 mmol), EDCI.HCl (0.363 g, 1.9 mmol), 5-hydroxy Sunitinib (48-3) (0.3 g, 0.76 mmol) and 4-dimethylaminopyridine (9 mg, 0.076 mmol) at 0° C. After stirring at 25-30° C. for 3 hours, the reaction mixture was filtered and concentrated under reduced pressure. The crude product obtained upon concentration of volatiles was purified by preparative HPLC to afford product 50-1 as an orange color solid (0.15 g, 30%). $^1$H-NMR (400 MHz, DMSO-d$_6$) δ 13.68 (s, 1H), 10.98 (s, 1H), 7.71 (s, 1H), 7.65 (d, J=2 Hz, 1H), 7.49 (t, J=6 Hz, 1H), 6.89 (d, J=8 Hz, 1H), 6.84 (dd, J=2 & 8 Hz, 1H), 5.40 (q, J=7 Hz, 1H), 5.25 (q, J=7 Hz, 1H), 5.07 (q, J=7 Hz, 1H), 3.31 (q, J=6 Hz, 2H), 2.69-2.50 (m, 6H), 2.45, (s, 3H), 2.42 (s, 3H), 2.07 (s, 3H), 1.64 (d, J=7 Hz, 3H), 1.50 (d, J=7 Hz, 3H), 1.46 (d, J=7 Hz, 3H), 0.99 (t, 6H); MS m/z (M+H)$^+$ 655.4.

To a solution of (S)-2-{(S)-2-[(S)-2-((S)-2-acetoxy-propionyloxy)-propionyloxy]-propionyloxy}-propionic acid (11-4) (0.65 g, 1.89 mmol) in dichloromethane (5 mL) was added N,N-diisopropylethylamine (0.36 ml, 1.96 mmol), EDCI.HCl (0.363 g, 1.9 mmol), 5-hydroxy Sunitinib (48-3) (0.3 g, 0.76 mmol), and 4-dimethylaminopyridine (9 mg, 0.076 mmol) at 0° C. After stirring at 25-30° C. for 3 hours, the reaction mixture was filtered and concentrated under reduced pressure. The crude product obtained upon concentration of volatiles was purified by preparative HPLC to afford product 51-1 as an orange color solid (0.13 g, 23%). $^1$H-NMR (400 MHz, DMSO-d$_6$) δ 13.68 (s, 1H), 10.98 (s, 1H), 7.70 (s, 1H), 7.65 (d, J=2 Hz, 1H), 7.46 (t, 1H), 6.89 (d, J=8 Hz, 1H), 6.83 (dd, J=2 & 8 Hz, 1H), 5.41 (q, J=7 Hz, 1H), 5.26 (q, J=7 Hz, 1H), 5.22 (q, J=7 Hz, 1H), 5.05 (q, J=7 Hz, 1H), 2.69-2.5 (m, 6H), 2.44, (s, 3H), 2.42 (s, 3H), 2.07 (s, 3H), 1.64 (d, J=7 Hz, 3H), 1.51-41 (m, 9H), 0.98 (t, 6H); MS m/z (M+H)$^+$ 727.5.

Scheme 51: (3Z)-3-[(4-{[2-(Diethylamino)ethyl]carbamoyl}-3,5-dimetyl-1H-pyrrol-2-yl)methylidene]-2-oxo-2,3-dihydro-1H-indol-5-yl (2S)-2-{[(2S)-2-{[(2S)-2-{[(2S)-2-(acetyloxy) propanoyl]oxy}propanol]oxy}propanoyl]oxy}propanoate (51-1):

Scheme 52: (3Z)-3-[(4-{[2-(Diethylamino)ethyl]carbamoyl}3,5-dimethyl-1H-pyrrol-2-yl)methylidene]-2-oxo-2,3-dihydro-1H-indol-5-yl (2S)-2-{[(2S)-2-{[(2S)-2-{[(2S)-2-(acetyloxy)propanoyl]oxy}propanoyl]oxy}propanoyl]oxy}propanoate (52-1):

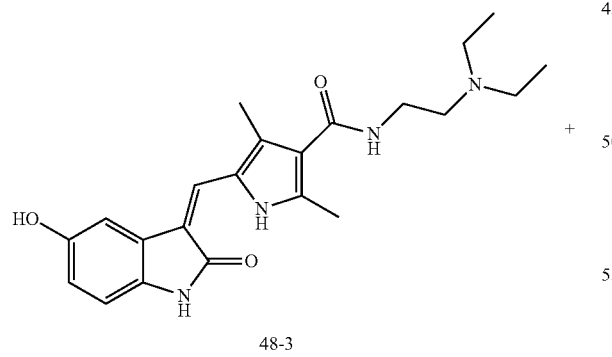

48-3

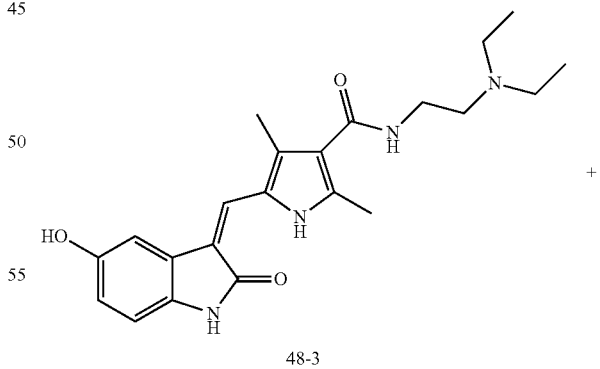

48-3

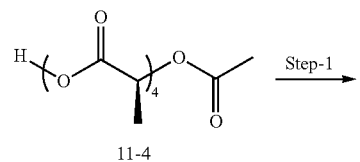

11-4

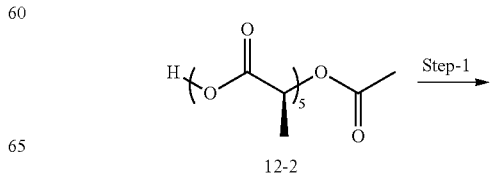

12-2

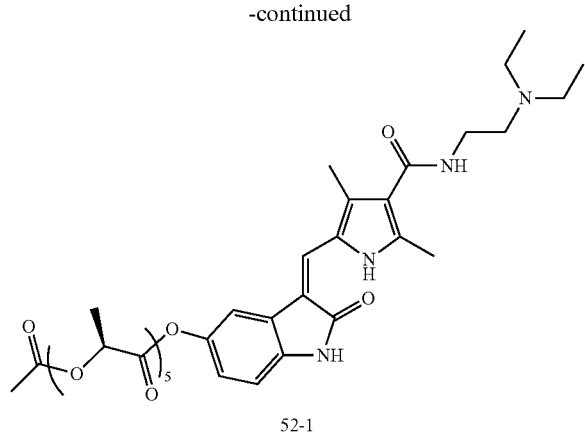

52-1

To a solution of (S)-2-((S)-2-{(S)-2-[(S)-2-((S)-2-acetoxy-propionyloxy)-propionyloxy]-propionyloxy}-propionyloxy)-propionic acid (12-2) (0.79 g, 1.89 mmol) in dichloromethane (5 mL) was added N,N-diisopropylethylamine (0.36 ml, 1.96 mmol), EDCI.HCl (0.363 g, 1.9 mmol), 5-hydroxy Sunitinib (48-3) (0.3 g, 0.76 mmol), and 4-dimethylaminopyridine (9 mg, 0.076 mmol) at 0° C. After stirring at 25-30° C. for 3 hours, the reaction mixture was filtered and concentrated under reduced pressure. The crude product obtained upon concentration of volatiles was purified by preparative HPLC to afford product 52-1 as an orange color solid (0.24 g, 40%). $^1$H-NMR (400 MHz, DMSO-$d_6$) δ 13.68 (s, 1H), 10.98 (s, 1H), 7.70 (s, 1H), 7.65 (d, J=2 Hz, 1H), 7.45 (t, 1H), 6.89 (d, J=8 Hz, 1H), 6.83 (dd, J=2 & 8 Hz, 1H), 5.41 (q, J=7 Hz, 1H), 5.30-5.17 (m, 3H), 5.05 (q, J=7 Hz, 1H), 3.35-3.2 (m, 2H), 2.6-2.5 (m, 6H), 2.44, (s, 3H), 2.42 (s, 3H), 2.06 (s, 3H), 1.64 (d, J=7 Hz, 3H), 1.52-40 (m, 12H), 0.98 (t, 6H). MS m/z (M+H)$^+$ 799.6.

(2S)-1-{[(2S)-1-{[(3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl]oxy}-1-oxopropan-2-yl]oxy}-1-oxopropan-2-yl (2S)-2-hydroxypropanoate (53-2)

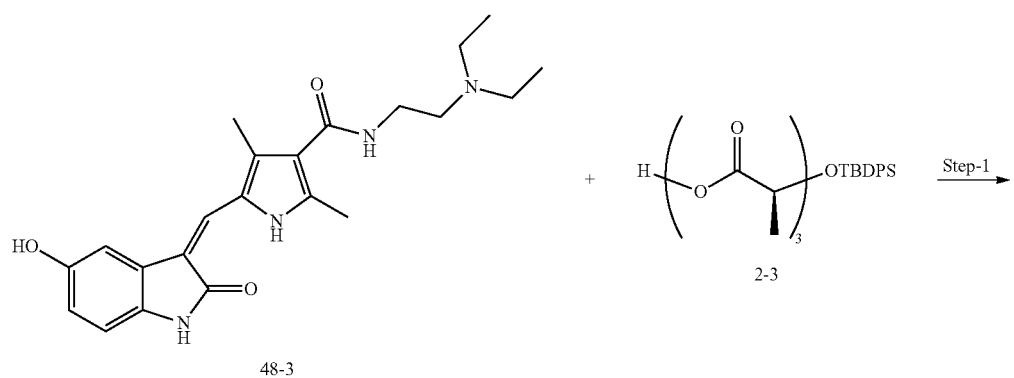

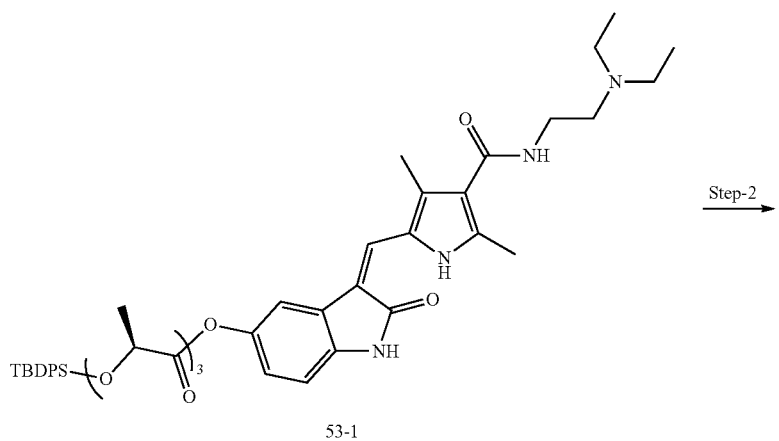

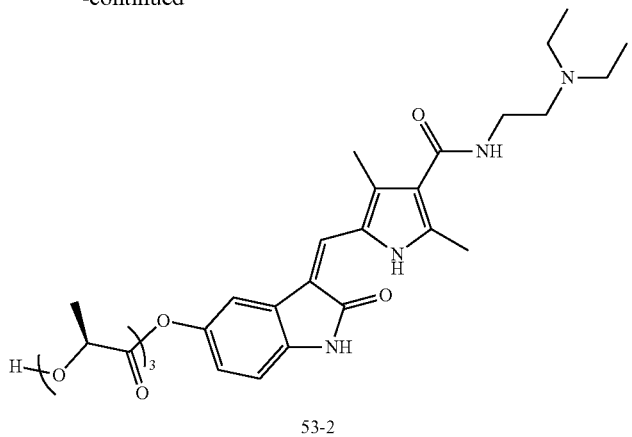

53-2

Step 1: (S)-2-(tert-Butyl-diphenyl-silanyloxy)-propionic acid (S)-1-((S)-1-{3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yloxycarbonyl}-ethoxycarbonyl)-ethyl ester (53-1)

To a solution of 5-hydroxy Sunitinib (48-3) (0.2 g, 0.50 mmol) and (S)-2-(tert-butyl-diphenyl-silanyloxy)-propionic acid (S)-1-((S)-1-carboxy-ethoxycarbonyl)-ethyl ester (2-3) (0.35 g, 0.75 mmol) in dichloromethane (10 mL) was added N,N-diisopropylethylamine (0.2 mL, 1.109 mmol) HATU (0.310 g, 0.80 mmol), and 4-dimethylaminopyridine (3 mg, 0.026 mmol) at 0° C. The reaction mixture was allowed to stir at 25-30° C. for 2 hours and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (4% methanol in DCM) to afford product 53-1 as a orange solid (190 mg, 44%).

Step 2: (2S)-1-{[(2S)-1-{[(3Z)-3-[(4-{[2-(Diethyl-amino)ethyl]carbamoyl}-3,5-dimethyl-1H-pyrrol-2-yl)methylidene]-2-oxo-2,3-dihydro-1H-indol-5-yl]oxy}-1-oxopropan-2-yl]oxy}-1-oxopropan-2-yl (2S)-2-hydroxypropanoate (53-2)

To a solution of (S)-2-(tert-butyl-diphenyl-silanyloxy)-propionic acid (S)-1-((S)-1-{3-[1-[4-(2-diethylamino-ethyl-carbamoyl)-3,5-dimethyl-1H-pyrrol-2-yl]-meth-(Z)-ylidene]-2-oxo-2,3-dihydro-1H-indol-5-yloxycarbonyl}-ethoxycarbonyl)-ethyl ester (53-1) (3.0 g, 3.52 mmol) in dichloromethane (30 mL) was added trifluoroacetic acid (15 ml, 5V) at 0° C. After stirring at room temperature for 48 hours, the resulting reaction mixture was submerged in an ice bath and neutralized with trimethylamine. Excess solvents were removed in vacuo, the residue was diluted with dichloromethane and washed with water. The crude product obtained upon evaporation of volatiles was purified by column chromatography to afford product 53-2 as a reddish brown solid (0.7 g, 33%). $^1$H-NMR (400 MHz, DMSO-d$_6$) δ 11.02 (s, 1H), 7.78-7.69 (m, 2H), 7.66 (d, J=2 Hz, 1H), 6.90 (d, J=8 Hz, 1H), 6.84 (dd, J=2 & 8 Hz, 1H), 5.52 (d, J=6 Hz, 1H), 5.40 (q, J=7 Hz, 1H), 5.17 (q, J=7 Hz, 1H), 4.23 (quintet, 1H), 3.60-3.44 (m, 2H), 3.24-2.90 (m, 6H), 2.47, (s, 3H), 2.44 (s, 3H), 1.64 (d, J=7 Hz, 3H), 1.48 (d, J=7 Hz, 3H), 1.32 (d, J=7 Hz, 3H), 1.16 (t, 6H); MS m/z (M+H)$^+$ 613.4.

Scheme 54: (2S)-1-{[(2S)-1-{[(3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl]oxy}-1-oxopropan-2-yl]oxy}-1-oxopropan-2-yl (2S)-2-hydroxypropanoate (54-2):

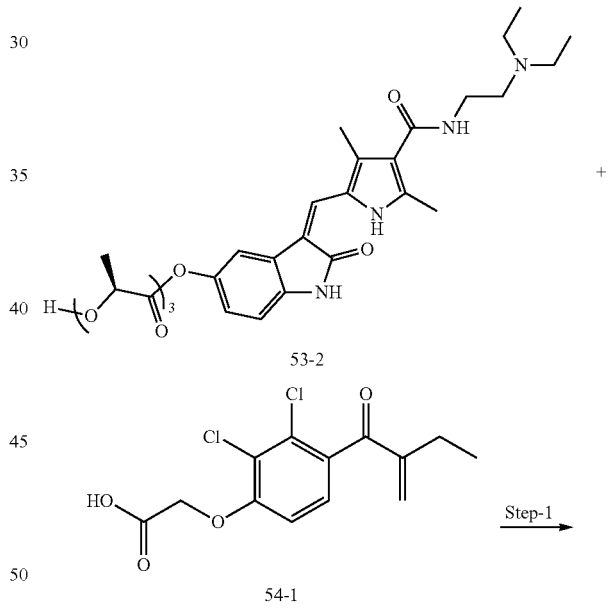

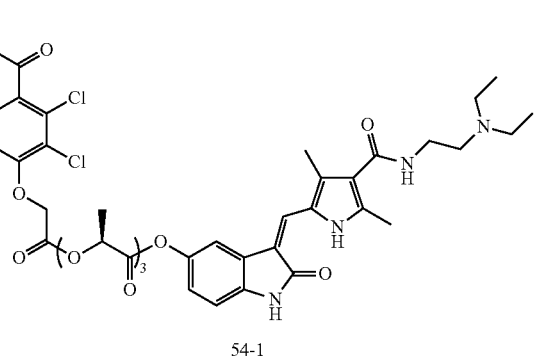

54-1

To a solution of ethacrynic acid (54-1) (0.098 g, 0.32 mmol) in dichloromethane (5 ml) was added N,N-diisopropylethylamine (0.1 ml, 0.65 mmol), HATU (0.186 g, 0.48 mmol), (S)-2-hydroxy-propionic acid (S)-1-((S)-1-{3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yloxycarbonyl}-ethoxycarbonyl)-ethyl ester (53-2) (0.2 g, 0.32 mmol) and 4-dimethylaminopyridine (0.0039 g, 0.032 mmol) at 0° C. After stirring for 12 hours at room temperature, the reaction mixture was quenched with water and extracted with ethyl acetate. The organic layer were dried over sodium sulfate and concentrated under reduced pressure. The residue was then purified by preparative HPLC to afford product 54-2 as an orange solid (60 mg, 44%). $^1$H-NMR (400 MHz, DMSO-d$_6$) δ 13.69 (s, 1H), 10.99 (s, 1H), 7.71 (s, 1H), 7.65 (d, J=2 Hz, 1H), 7.52 (t, 1H), 7.31 (d, J=9 Hz, 1H), 7.16 (d, J=9 Hz, 1H), 6.89 (d, J=8 Hz, 1H), 6.83 (dd, J=2 & 8 Hz, 1H), 6.06 (s, 1H), 5.55 (s, 1H), 5.40 (q, J=7 Hz, 1H), 5.32-5.10 (m, 4H), 3.36-3.30 (m, 2H), 2.73-2.61 (m, 6H), 2.45 (s, 3H), 2.42 (s, 3H), 2.42-2.29 (m, 2H), 1.63 (d, J=7 Hz, 3H), 1.52-1.46 (m, 6H), 1.09-0.097 (m, 9H); MS m/z (M+H)$^+$ 897.7 and 899.7.

Example 6. Synthetic Examples of Dorzolmide-Sunitinib Bis-Prodrugs

Scheme 55: (3Z)-3-[(4-{[2-(Diethylamino)ethyl] carbamoyal}-3,5-dimethyl-1H-pyrrol-2-yl) methylidene]-2-oxo-2,3-dihydro-1H-indol-5yl 1-(2S)-1-[(1S)-1-({[(2S,4S)-4-(ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl butanedioate (55-4):

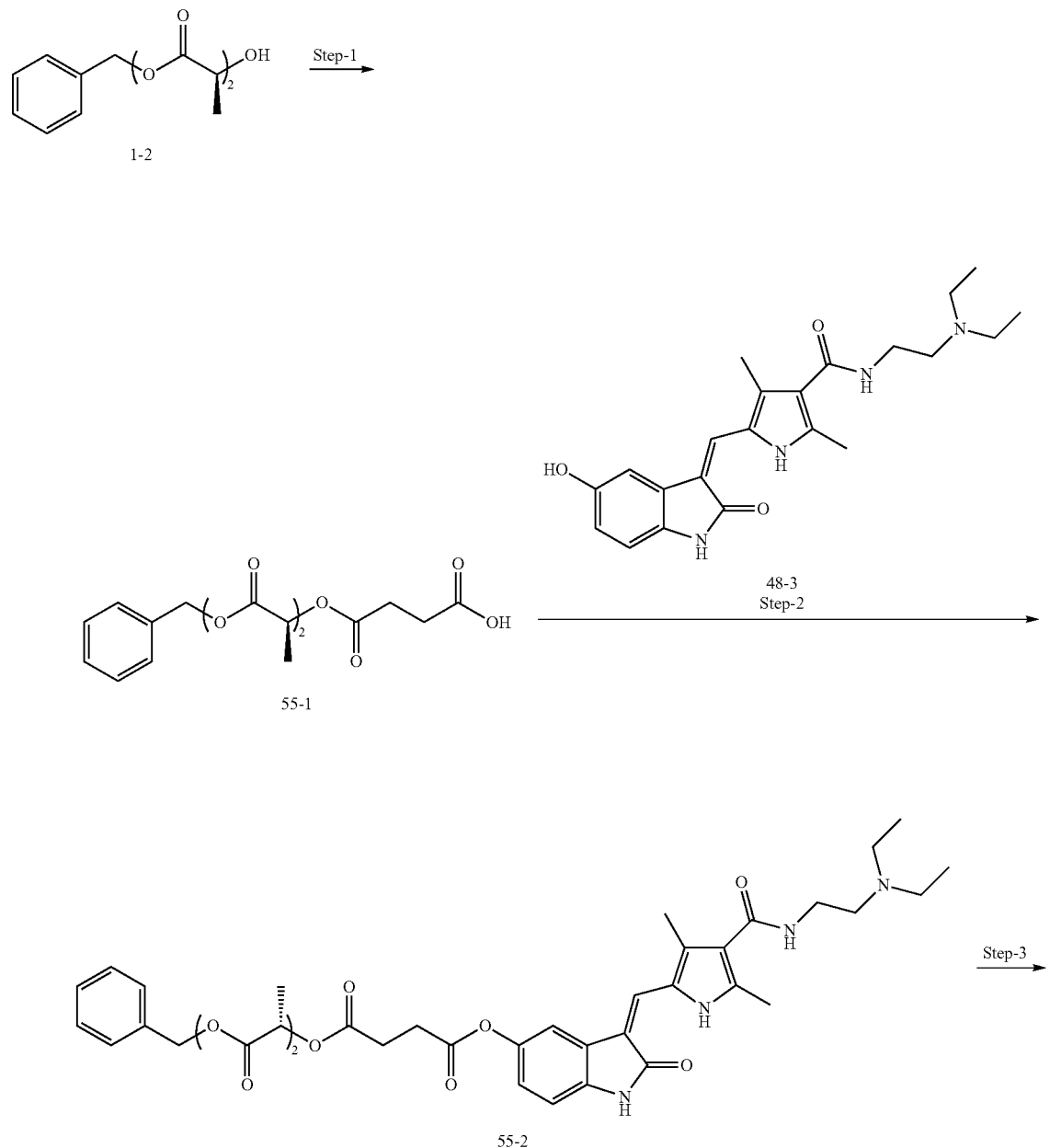

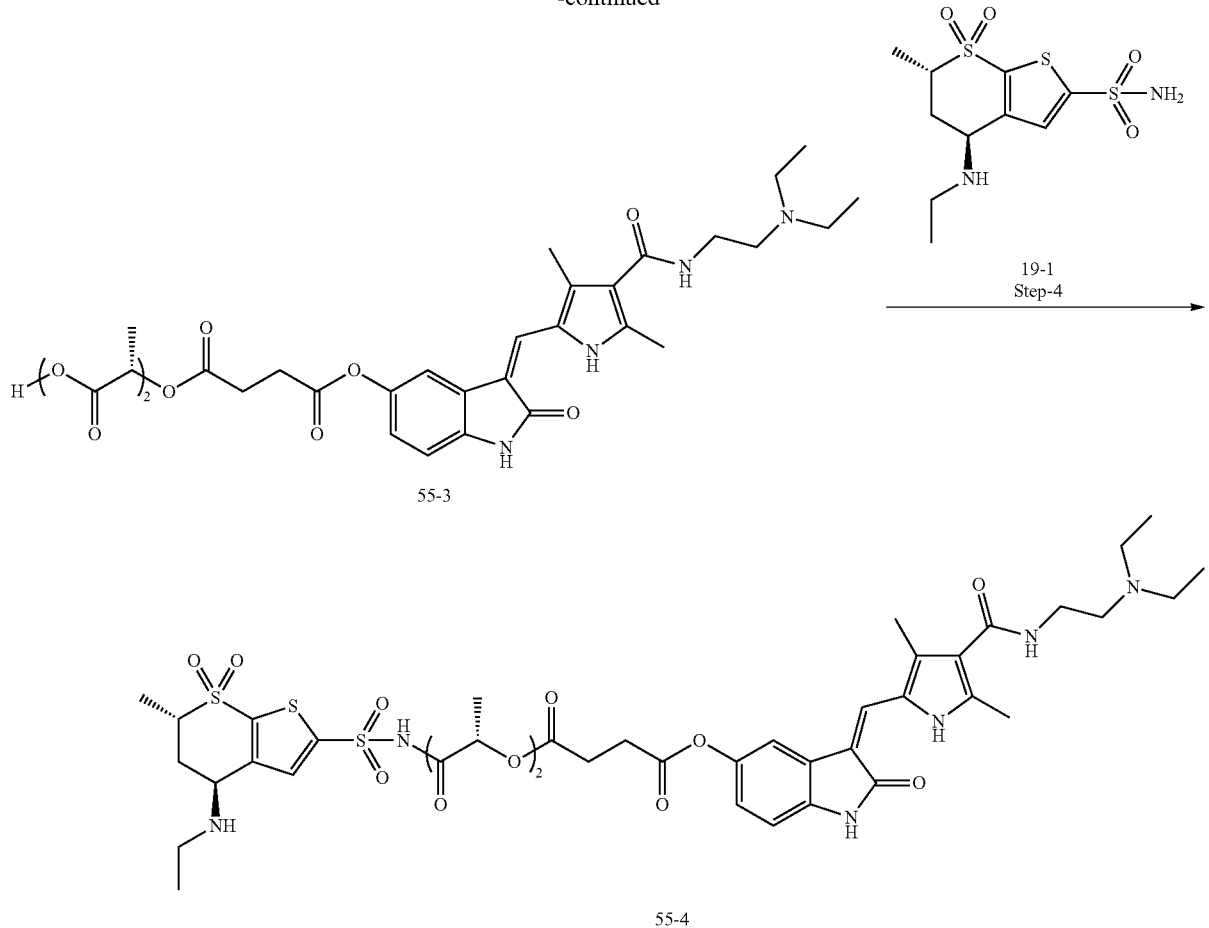

Step 1: 4-{[(2S)-1-{[(2S)-1-(Benzyloxy)-1-oxopropan-2-yl]oxy}-1-oxopropan-2-yl]oxy}-4-oxobutanoic acid (55-1)

To a solution of succinic acid (0.93 g, 3.96 mmol) in dichloromethane (10 mL) was added EDCI.HCl (2.27 g, 11.9 mmol), hydroxybenzotriazole (0.109 g, 0.79 mmol), (S)-2-hydroxy-propionic acid (S)-1-benzyloxycarbonyl-ethyl ester (1-2) (1.0 g, 3.96 mmol) and 4-dimethylaminopyridine (48 mg, 0.39 mmol) at 0° C. The reaction mixture was allowed to stir at 25-30° C. for 1 hour, and the resulting reaction mixture was quenched with water (100 mL), extracted with dichloromethane (150×3 mL), dried over sodium sulfate, and concentrated under reduced pressure. The crude product obtained upon evaporation of volatiles was purified by silica gel (230-400) column chromatography (3% methanol in dichloromethane) to afford a pale yellow liquid (1.0 g, 71%). $^1$H NMR (400 MHz, DMSO-$d_6$) δ 12.25 (s, 1H), 7.44-7.30 (m, 5H), 5.19 (m, 3H), 5.05 (q, J=7.2 Hz, 1H), 2.62-2.48 (m, 4H), 1.5 (d, J=6.8 Hz, 3H), 1.4 (d, J=6.8 Hz, 3H); MS m/z (M−H) 251.0.

Step 2: Succinic acid (S)-1-((S)-1-benzyloxycarbonyl-ethoxycarbonyl)-ethyl ester 3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yl ester (55-2)

To a solution of 4-{[(2S)-1-{[(2S)-1-(benzyloxy)-1-oxopropan-2-yl]oxy}-1-oxopropan-2-yl]oxy}-4-oxobutanoic acid (55-1) (0.26 g, 0.756 mmol) in dimethylformamide (2 mL) was added N,N-diisopropylethylamine (0.19 mL, 1.05 mmol), HATU (0.306 g, 0.807 mmol), and hydroxy sunitinb (48-3) (0.2 g, 0.504 mmol) at 0° C. The reaction mixture was allowed to stir at 25-30° C. for 2 hours and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel column chromatography (5% methanol in DCM) to afford an orange solid (200 mg, 55%). $^1$H NMR (400 MHz, DMSO-$d_6$) δ 13.73 (s, 1H), 10.98 (s, 1H), 9.12 (s, 1H), 7.77 (s, 1H), 7.63 (s, 1H), 7.61 (s, 1H), 7.43-7.29 (m, 6H), 6.91-6.80 (m, 2H), 5.23-5.06 (m, 4H), 3.70-3.56 (m, 3H), 3.22-3.30 (m, 6H), 2.85 (dd, J=15.5, 8.9 Hz, 2H), 2.45 (d, J=14.7 Hz, 2H), 2.4-2.61 (m, 6H), 1.46 (d, J=6.8 Hz, 3H), 1.39 (d, J=7.2 Hz, 3H), 1.15 (m, 6H); MS m/z (M+H) 731.7.

Step 3: (2S)-2-{[(2S)-2-[(4-{[(3Z)-3-[(4-{2-(Diethylamino)ethylcarbamoyl}-3,5-dimethyl-1H-pyrrol-2-yl)methylidene]-2-oxo-2,3-dihydro-1H-indol-5-yl]oxy}-4-oxobutanoyl)oxy]propanoyl]oxy}propanoic acid (55-3)

To a 100 mL autoclave vessel was added a solution of succinic acid (S)-1-((S)-1-benzyloxycarbonyl-ethoxycarbonyl)-ethyl ester 3-[1-[4-(2-diethylamino-ethylcarbamoyl)-3, 5-dimethyl-1H-pyrrol-2-yl]-meth-(Z)-ylidene]-2-oxo-2,3-dihydro-1H-indol-5-yl ester (55-2) (0.2 g, 0.27 mmol) in methanol (10 mL) and 10% Pd/C (40 mg, 50% wet) at 25-30° C. The reaction mixture was stirred at room temperature under hydrogen pressure (1 kg/cm$^2$) for 30 minutes. After completion of the reaction, the reaction mixture was filtered through celite. Then volatiles were evaporated under reduced pressure to afford a reddish orange solid (160 mg, 91%). $^1$H NMR (400 MHz, DMSO-d$_6$) δ 13.72 (s, 1H), 10.98 (s, 1H), 7.76 (s, 1H), 7.68 (s, 1H), 7.61 (d, J=2.1 Hz, 1H), 6.91-6.80 (m, 2H), 5.11 (q, J=7.0 Hz, 1H), 4.99 (q, J=7.0 Hz, 1H), 3.54-3.65 (m, 3H), 3.1-3.32 (m, 6H), 2.91-2.74 (m, 2H), 2.45 (d, J=14.7 Hz, 2H), 2.5-2.7 (m, 6H), 1.50-1.38 (m, 6H), 1.36-1.15 (m, 6H); MS m/z (M+H) 641.6.

Step 4: (3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl 1-(2S)-1-[(1S)-1-({[(2S,4S)-4-(ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl butanedioate (55-4)

To a solution of dorzolamide (19-1) (0.8 g, 2.22 mmol) in dichloromethane (10 mL) was added N,N-diisopropylethyl-amine (0.05 mL, 0.311 mmol) at 0° C. After 30 minutes, succinic acid (S)-1-((S)-1-carboxy-ethoxycarbonyl)-ethyl ester 3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yl ester (55-3) (0.18 g, 0.25 mmol), EDCI.HCl (59 mg, 0.311 mmol), hydroxybenzotriazole (5 mg, 0.038 mmol), and 4-dimethylaminopyridine (0.1 mg, 0.138 mmol) were added at 0° C. The reaction mixture was allowed to stir at 25-30° C. for 2 hours and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel column chromatography (5% methanol in DCM) to afford an orange solid (50 mg, 38%). $^1$H-NMR (400 MHz, DMSO-d$_6$) δ 13.71 (s, 1H), 10.96 (s, 1H), 7.70-7.65 (m, 2H), 7.61 (s, Hz, 1H), 7.5-7.3 (m, 1H), 6.90-6.81 (m, 2H), 5.03 (q, 1H), 4.79 (q, 1H), 3.93-3.82 (m, 2H), 3.6-3.5 (m, 2H), 2.9-3.3 (m, 6H), 2.87-2.81 (m, 2H), 2.79-2.72 (m, 2H), 2.46 (s, 3H), 2.43 (s, 3H), 1.48 (d, 3H), 1.36-1.00 (m, 12H), 0.88-0.86 (m, 3H). MS m/z (M+H)$^+$ 947.7.

Scheme 56: (3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl 1-(2S)-1-{[(2S)-1-[(1S)-1-({[(2S,4S)-4-(ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl]oxy}-1-oxopropan-2-yl butanedioate (56-5):

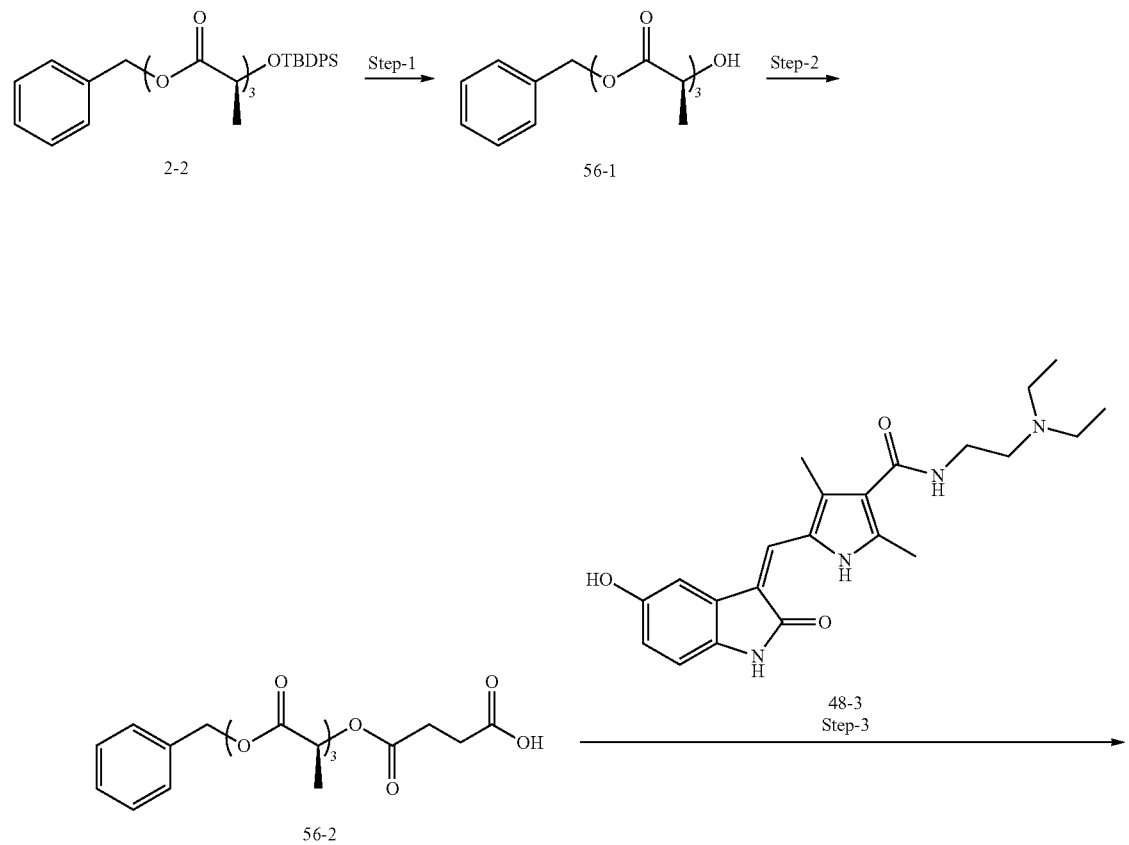

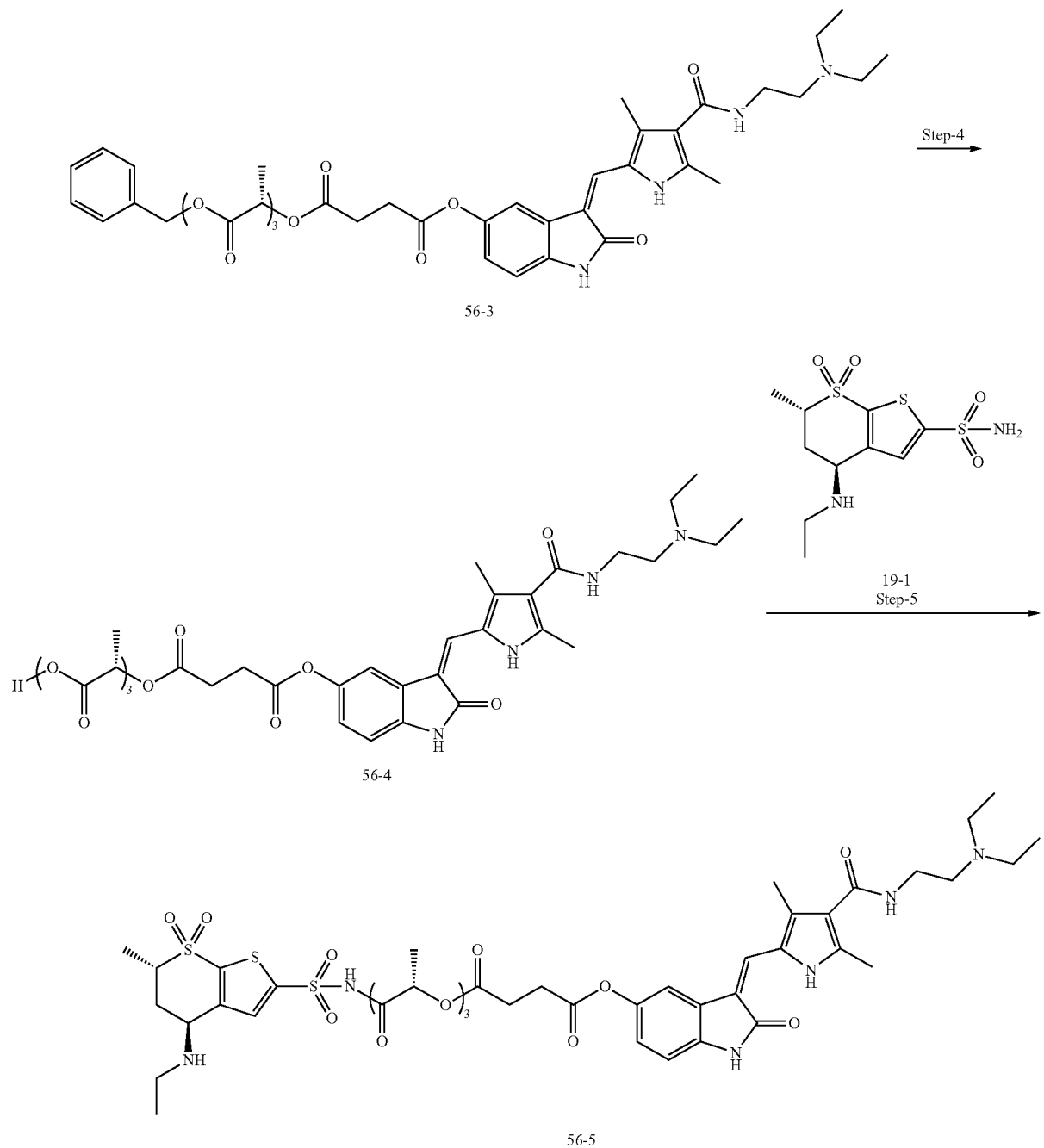

Step 1: (2S)-1-{[(2S)-1-(Benzyloxy)-1-oxopropan-2-yl]oxy}-1-oxopropan-2-yl (2S)-2-hydroxypropanoate (56-1)

To a solution of (S)-2-(tert-butyl-diphenyl-silanyloxy)-propionic acid (S)-1-((S)-1-benzyloxycarbonyl-ethoxycarbonyl)-ethyl ester (2-2) (6.5 g, 11.55 mmol) in tetrahydrofuran (65 mL) was added tetra-n-butylammonium fluoride (17.32 mL, 17.32 mmol) and acetic acid (1.03 mL, 17.32 mmol) at 0° C. The reaction mixture was allowed to stir at room temperature for 1 hour and the resulting reaction mixture was concentrated under reduced pressure. Crude product obtained upon evaporation of the volatiles was purified through silica gel column chromatography (20% ethyl acetate in hexane) to afford a colorless liquid (2.5 g, 67%).

Step 2: 4-{[(2S)-1-{[(2S)-1-{[(2S)-1-(Benzyloxy)-1-oxopropan-2-yl]oxy}-1-oxopropan-2-yl]oxy}-1-oxopropan-2-yl]oxy}-4-oxobutanoic acid (56-2)

To a solution of succinic acid (1.8 g, 15.4 mmol) in dichloromethane (20 mL) was added N,N-diisopropylethylamine (4.2 mL, 23.14 mmol), EDCI.HCl (4.4 g, 23.14 mmol), hydroxybenzotriazole (212 mg, 1.54 mmol), (2S)-1-{[(2S)-1-(benzyloxy)-1-oxopropan-2-yl]oxy}-1-oxopropan-2-yl (2S)-2-hydroxypropanoate (56-1) (2.5 g, 7.7 mmol), and 4-dimethylaminopyridine (93 mg, 0.77 mmol) at 0° C. The reaction mixture was allowed to stir at 25-30° C. for 1 hour and the resulting reaction mixture was quenched with water (100 mL), extracted with dichloromethane (150×3 mL), dried over sodium sulfate, and concentrated under reduced pressure. The crude product obtained upon evaporation of volatiles was purified by silica gel (230-400) column chromatography (2% methanol in DCM) to afford a colorless liquid (2.1 g, 65%).

Step 3: 1-(2S)-1-{[(2S)-1-{[(2S)-1-(Benzyloxy)-1-oxopropan-2-yl]oxy}-1-oxopropan-2-yl]oxy}-1-oxopropan-2-yl (3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl butanedioate (56-3)

To a solution of 4-{[(2S)-1-{[(2S)-1-{[(2S)-1-(benzyloxy)-1-oxopropan-2-yl]oxy}-1-oxopropan-2-yl]oxy}-1-oxopropan-2-yl]oxy}-4-oxobutanoic acid (56-2) (2.0 g, 4.53 mmol) in dimethylformamide (5 mL) were added N,N-diisopropylethylamine (1.1 mL, 6.05 mmol), HATU (1.8 g, 4.83 mmol) and 5-hydroxyl Sunitinib (48-3) (1.2 g, 3.02 mmol) at 0° C. The reaction mixture was allowed to stir at 25-30° C. for 5 hours and the resulting reaction mixture was quenched with water (30 mL), extracted with dichloromethane (50×3 mL), dried over sodium sulfate, and concentrated under reduced pressure. The crude product obtained upon evaporation of volatiles was purified by silica gel (230-400) column chromatography (4% methanol in DCM) to afford a reddish brown solid (1.6 g, 66%).

Step 4: (2S)-2-{[(2S)-2-{[(2S)-2-[(4-{[(3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl]oxy}-4-oxobutanoyl)oxy]propanoyl]oxy}propanoyl]oxy}propanoic acid (56-4)

To a 100 mL autoclave vessel was added a solution of 1-(2S)-1-{[(2S)-1-{[(2S)-1-(benzyloxy)-1-oxopropan-2-yl]oxy}-1-oxopropan-2-yl]oxy}-1-oxopropan-2-yl (3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl butanedioate (56-3) (1.5 g, 1.87 mmol) in methanol (30 mL) and 10% Pd/C (220 mg, 50% wet) at 25-30° C. The reaction mixture was stirred at room temperature under hydrogen pressure (1 kg/cm²) for 30 minutes. After completion of the reaction, the reaction mixture was filtered through celite. Then volatiles were evaporated under reduced pressure to afford a reddish orange solid 1.0 g (76%).

Step 5: (3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl 1-(2S)-1-{[(2S)-1-[(1S)-1-({[(2S,4S)-4-(ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl butanedioate (56-5)

To a solution of dorzolamide (0.2 g, 0.555 mmol) in dichloromethane (5 mL) was added N,N-diisopropylethylamine (0.16 mL, 0.889 mmol) at 0° C. After 30 minutes, succinic acid (S)-1-[(S)-1-((S)-1-carboxy-ethoxycarbonyl)-ethoxycarbonyl]-ethyl ester 3-[1-[4-(2-diethylamino-ethyl carbamoyl)-3,5-dimethyl-1H-pyrrol-2-yl]-meth-(Z)-ylidene]-2-oxo-2,3-dihydro-1H-indol-5-yl ester (0.514 g, 0.722 mmol), EDCI.HCl (0.169 g, 0.889 mmol), hydroxybenzotriazole (15 mg, 0.111 mmol), and 4-dimethylaminopyridine (7 mg, 0.055 mmol) were added at 0° C. The reaction mixture was allowed to stir at 25-30° C. for 2 hours and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel column chromatography (5% methanol in DCM) to afford an orange solid (80 mg, 31%). ¹H-NMR (400 MHz, DMSO-d₆) δ 13.72 (s, 1H), 10.96 (s, 1H), 7.72-7.66 (m, 2H), 7.60 (d, J=2 Hz, 1H), 7.43 (s, 1H), 6.91-6.82 (m, 2H), 5.16-5.07 (m, 2H), 4.79 (q, J=7 Hz, 1H), 4.05-3.84 (m, 2H), 3.55-3.45 (m, 2H), 3.05-2.94 (m, 6H), 2.88-2.82 (m, 2H), 2.80-2.72 (m, 2H), 2.70-2.55 (m, 2H), 2.46, (s, 3H), 2.43 (s, 3H), 2.42-2.25 (m, 2H), 1.50-1.42 (m, 6H), 1.34-1.23 (m, 6H), 1.15 (t, 6H), 1.04 (t, 3H). MS(+) m/z (M+H)⁺ 1019.5. MS(−) m/z (M−H)⁺ 1017.8.

Scheme 57: (2S)-1-{[(2S)-1-[(1S)-1-({[(2S,4S)-4-(Ethylamino)-2-methyl-1,1-dioxo-2H,3H,4H-1λ⁶-thieno[2,3-b]thiopyran-6-yl]sulfonyl}carbamoyl)ethoxy]-1-oxopropan-2-yl]oxy}-1-oxopropan-2-yl 3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyal}propanoate (57-3):

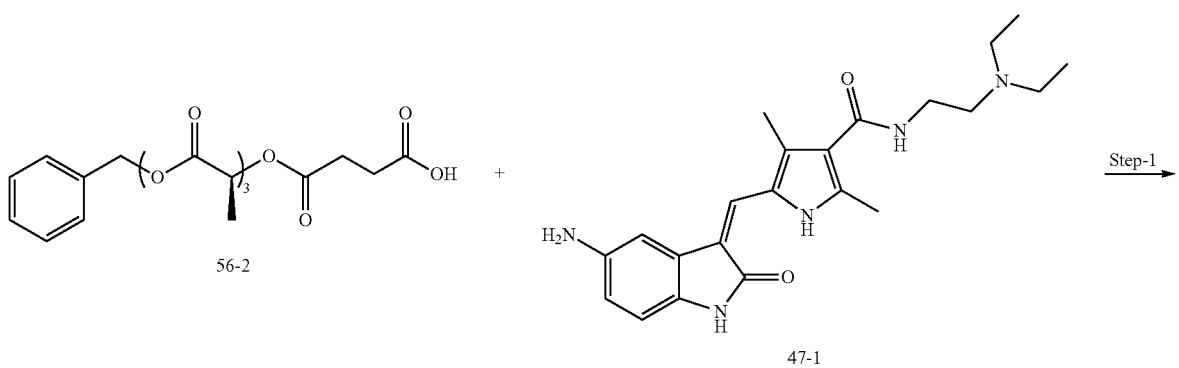

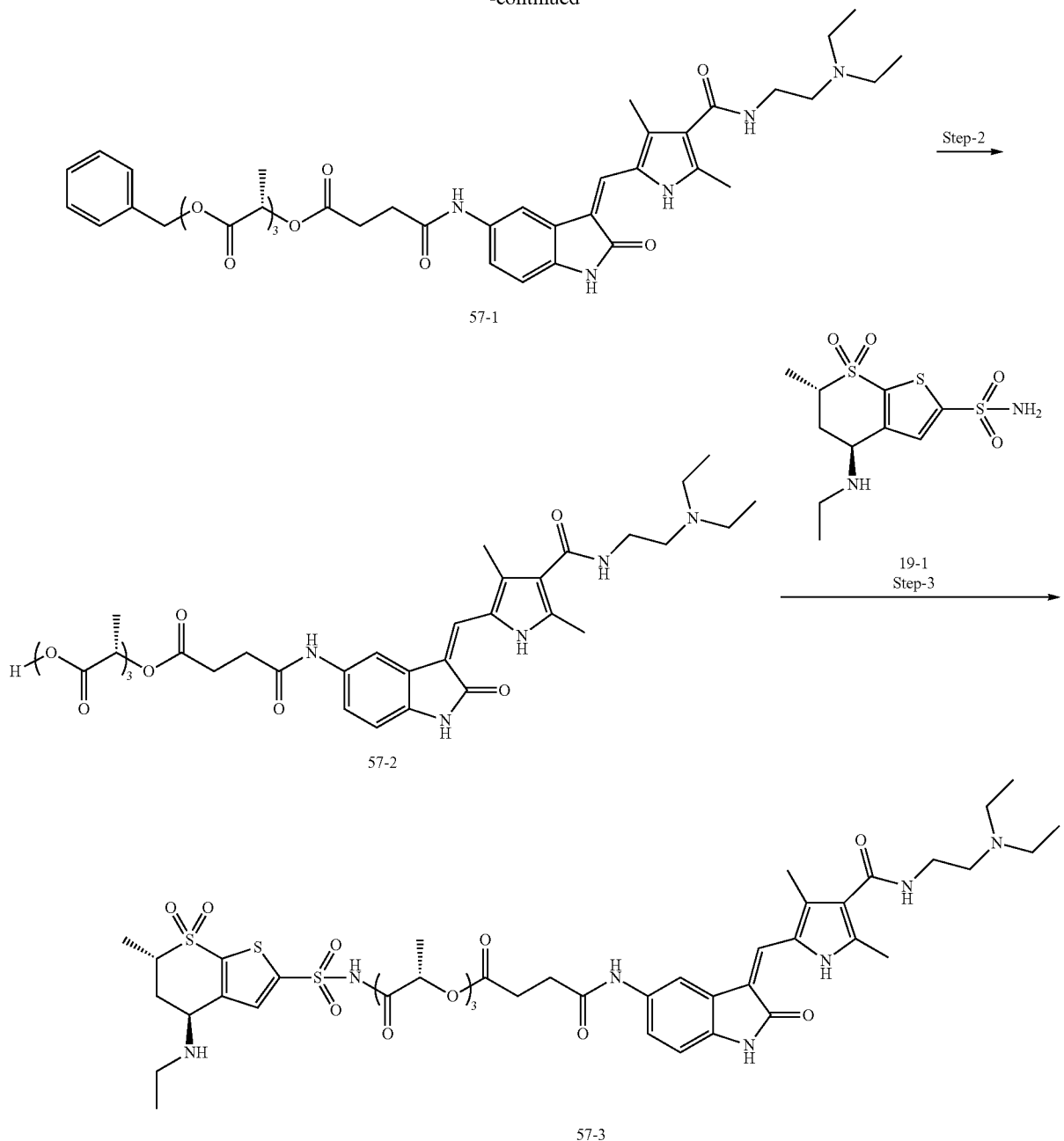

Step 1: N-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indol-5-yl}-succinamic acid (S)-1-[1(S)-1-((S)-1-benzyloxycarbonyl-ethoxycarbonyl)-ethoxycarbonyl]-ethyl ester (57-1)

To a solution of succinic acid mono-{(S)-1-[(S)-1-((S)-1-benzyloxycarbonyl-ethoxycarbonyl)-ethoxycarbonyl]-ethyl} ester (56-2) (2.4 g, 5.68 mmol) in dimethylformamide (5 mL) was added N,N-diisopropylethylamine (1.3 mL, 7.58 mmol), HATU (2.3 g, 6.06 mmol), and 5-amino Sunitinib (47-1) (1.5 g, 3.79 mmol) at 0° C. The reaction mixture was allowed to stir at 25-30° C. for 30 minutes and the resulting reaction mixture was quenched with water (30 mL), extracted with dichloromethane (50×3 mL), dried over sodium sulfate, and concentrated under reduced pressure. The crude product obtained upon evaporation of volatiles was purified through silica gel (230-400) column chromatography (2% methanol in DCM) to afford a reddish brown solid (2.1 g, 69%).

Step 2: N-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indol-5-yl}-succinamic acid (S)-1[(S)-1-((S)-1-carboxy-ethoxycarbonyl)-ethoxycarbonyl]-ethyl ester (57-2)

To a 100 mL autoclave vessel was added a solution of N-{3-[1-[4-(2-diethylamino-ethylcarbamoyl)-3,5-dimethyl-1H-pyrrol-2-yl]-meth-(Z)-ylidene]-2-oxo-2,3-dihydro-1H- indol-5-yl}-succinamic acid (S)-1-[(S)-1-((S)-1-benzyloxy-carbonyl-ethoxycarbonyl)-ethoxycarbonyl]-ethyl ester (57-1) (1.5 g, 1.87 mmol) in methanol (30 mL) and 10% Pd/C (220 mg, 50% wet) at 25-30° C. The reaction mixture was stirred at room temperature under hydrogen pressure (1 kg/cm$^2$) for 30 minutes. After completion of the reaction, the reaction mixture was filtered through celite. Then volatiles were evaporated under reduced pressure to afford a reddish orange solid (0.9 g, 69%).

Step 3: (2S)-{[(2S)-1-[(1S)-1-({[(2S,4S)-4-(Ethyl-amino)-2-methyl-1,1-dioxo-2H,3H,4H-1λ$^6$-thieno[2,3-b]thiopyran-6-yl]sulfonyl}carbamoyl)ethoxy]-1-oxopropan-2-yl]oxy}-1-oxopropan-2-yl 3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoate (57-3)

To a solution of dorzolamide (19-1) (0.15 g, 0.416 mmol) in dichloromethane (5 mL) was added N,N-diisopropylethylamine (0.12 mL, 0.666 mmol) at 0° C. After 30 minutes, N-{3-[1-[4-(2-diethyl amino-ethyl carbamoyl)-3,5-dimethyl-1H-pyrrol-2-yl]-meth-(Z)-ylidene]-2-oxo-2,3-dihydro-1H-indol-5-yl}-succinamic acid (S)-1 [(S)-1-((S)-1-carboxy-ethoxycarbonyl)-ethoxycarbonyl]-ethyl ester (57-2) (0.385 g, 0.541 mmol), EDCI.HCl (0.127 g, 0.666 mmol), hydroxybenzotriazole (11 mg, 0.0833 mmol), and 4-dimethylaminopyridine (5 mg, 0.0416 mmol) were added at 0° C. The reaction mixture was allowed to stir at 25-30° C. for 2 hours and the resulting reaction mixture was quenched with water (50 mL), extracted with dichloromethane (50×3 mL), dried over sodium sulfate, and concentrated under reduced pressure. The crude product obtained upon evaporation of volatiles was purified through silica gel column chromatography (5% methanol in DCM) to afford an orange solid (110 mg, 25%). $^1$H-NMR (400 MHz, DMSO-d$_6$) δ 13.70 (s, 1H), 10.85 (s, 1H), 9.87 (s, 1H), 7.93 (bs, 1H), 7.65 (t, 1H), 7.46 (s, 1H), 7.41 (bs, 1H), 7.21-7.15 (m, 1H), 6.81 (d, 1H), 5.13-5.04 (m, 2H), 4.79 (q, J=7 Hz, 1H), 3.98-3.82 (m, 2H), 3.5-3.4 (m, 2H), 3.05-2.85 (m, 6H), 2.75-2.55 (m, 6H), 2.45, (s, 3H), 2.41 (s, 3H), 2.40-2.23 (m, 2H), 1.50-1.40 (m, 6H), 1.35-1.24 (m, 6H), 1.13 (t, 6H), 1.04 (t, 3H). MS(+) m/z (M+H)$^+$ 1018.7 and (M+2H)$^{++}$ 510.0.

Scheme 58: (3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl 1-(2S)-1-{[(2S)-1-{[(2S)-1-[(1S)-1-({[(2S,4S)-4-(ethylamino)-2-methyl-1,1-dioxo-2H,3H,4H-1λ$^6$–thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl butanedioate (58-5):

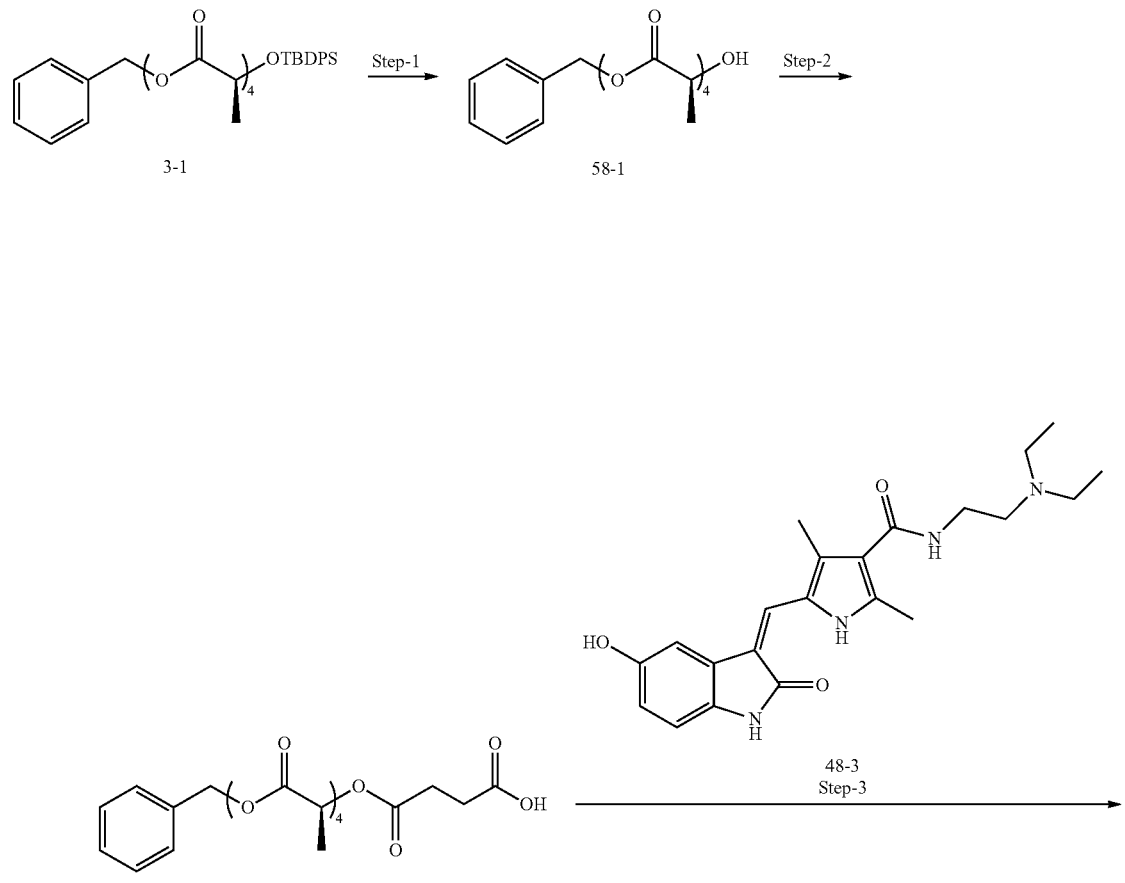

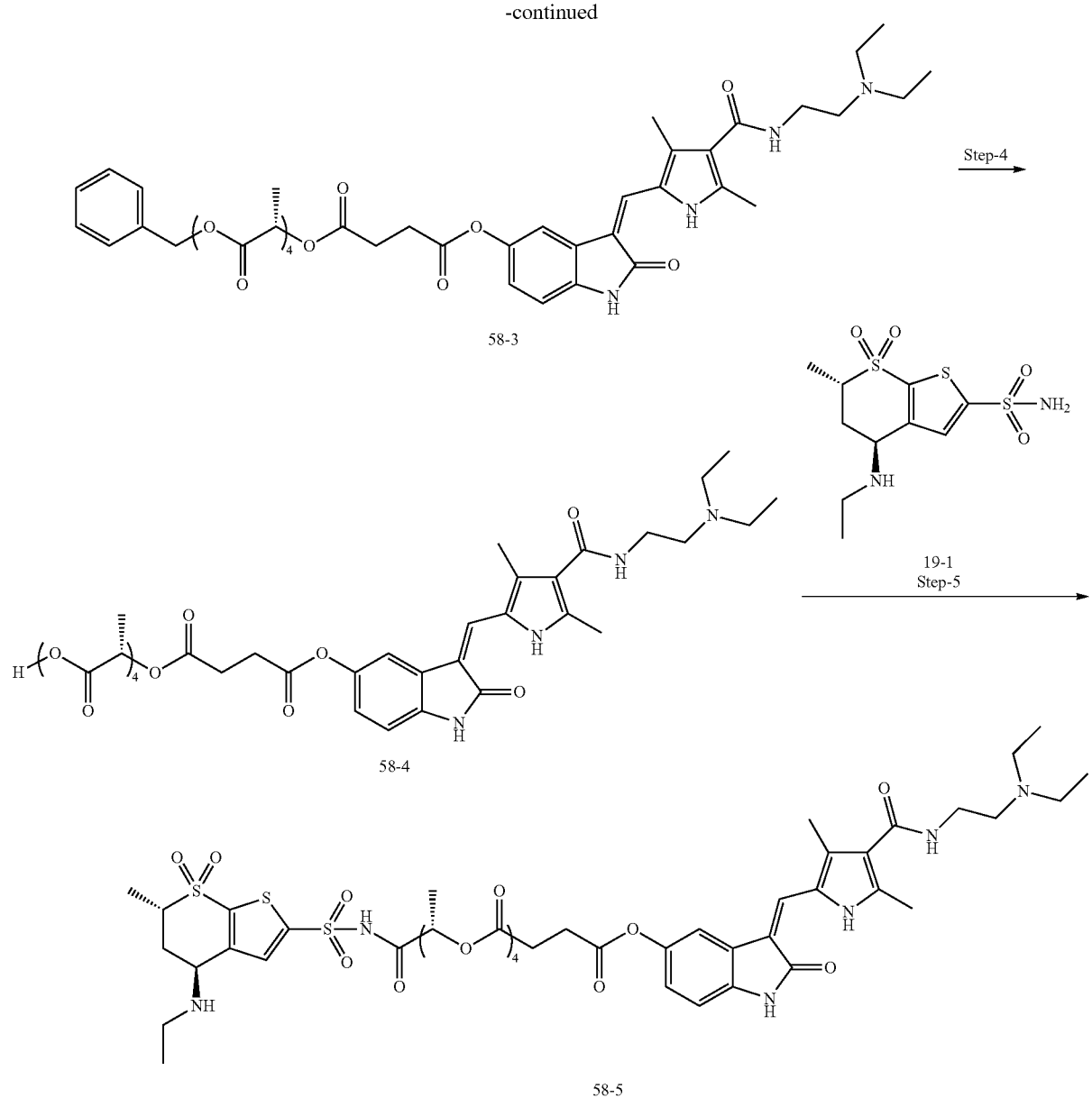

Step 1: (S)-2-Hydroxy-propionic acid (S)-1-[(S)-1-((S)-1-benzyloxycarbonyl-ethoxycarbonyl)-ethoxy-carbonyl]-ethyl ester (58-1)

To a solution of (S)-2-(tert-butyl-diphenyl-silanyloxy)-propionic acid (S)-1-[(S)-1-((S)-1-benzyloxycarbonyl-ethoxycarbonyl)-ethoxycarbonyl]-ethyl ester (3-1) (11.0 g, 0.0173 mol) in tetrahydrofuran (110 mL) was added tetra-n-butylammonium fluoride (25.6 mL, 1.0 M, 0.0259 mol) and acetic acid (1.5 mL, 0.0259 mol) at 0° C. The reaction mixture was allowed to stir at room temperature for 1 hour and the resulting reaction mixture was concentrated under reduced pressure. Crude product obtained upon evaporation of the volatiles was purified by silica gel column chromatography (20% Ethyl acetate in hexane) to give product as colorless liquid (5.5 g, 80%). 1H NMR (400 MHz, DMSO-$d_6$) δ 7.44-7.30 (m, 5H), 5.49 (d, J=5.9 Hz, 1H), 5.23-5.07 (m, 5H), 4.26-4.15 (m, 1H), 1.43 (dd, J=13.1, 7.0 Hz, 9H), 1.28 (d, J=6.8 Hz, 3H); MS m/z (M+NH$_4^+$) 414.0

Step 2: Succinic acid mono-((S)-1-{(S)-1-[(S)-1-((S)-1-benzyloxycarbonyl-ethoxycarbonyl)-ethoxy-carbonyl]-ethoxycarbonyl}-ethyl) ester (58-2)

To a solution of succinic acid (1.7 g, 15.1 mmol) in dichloromethane (10 mL) was added N,N-diisopropylethyl-amine (4 mL, 22.7 mmol), EDCI.HCl (4.33 g, 22.7 mmol), hydroxybenzotriazole (208 mg, 1.51 mmol), (S)-2-hydroxy-propionic acid (S)-1-[(S)-1-((S)-1-benzyloxycarbonyl-ethoxycarbonyl)-ethoxycarbonyl]-ethyl ester (58-1) (3 g, 7.5 mmol), and 4-dimethylaminopyridine (92 mg, 0.75 mmol) at 0° C. The reaction mixture was allowed to stir at 25-30° C. for 1 hour and the resulting reaction mixture was quenched with water (100 mL), extracted with dichloromethane (150×3 mL), dried over sodium sulfate, and concentrated under reduced pressure. The crude product obtained upon evaporation of volatiles was purified by silica gel (230-400) column chromatography (2% methanol in DCM) to afford a colorless liquid (2.5 g, 66%). 1H NMR (400 MHz, DMSO- $d_6$) δ 12.25 (s, 1H), 7.43-7.30 (m, 5H), 5.24-5.16 (m, 5H), 5.17 (q, J=7.2, 1H), 2.67-2.47 (m, 4H), 1.50-1.33 (m, 12H); MS m/z (M+NH$_4^+$) 514.6

Step 3: Succinic acid (S)-1-{(S)-1-[(S)-1-((S)-1-benzyloxycarbonyl-ethoxycarbonyl)-ethoxycarbonyl]-ethoxycarbonyl}-ethyl ester 3-[1-[4-(2-diethyl-amino-ethylcarbamoyl)-3,5-dimethyl-1H-pyrrol-2-yl]-meth-(Z)-ylidene]-2-oxo-2,3-dihydro-1H-indol-5-yl ester (58-3)

To a solution of succinic acid mono-((S)-1-{(S)-1-[(S)-1-((S)-1-benzyloxycarbonyl-ethoxycarbonyl)-ethoxycarbonyl]-ethoxycarbonyl}-ethyl) ester (1.8 g, 3.7 mmol) in dimethylformamide (5 mL) was added N,N-diisopropylethylamine (0.19 mL, 1.05 mmol), HATU (1.5 g, 4.0 mmol), and 5-hydroxyl Sunitinib (1.0 g, 2.5 mmol) at 0° C. The reaction mixture was allowed to stir at 25-30° C. for 2 hours and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel column chromatography (5% methanol in DCM) to afford a reddish brown solid (1.5 g, 68%). 1H NMR (400 MHz, DMSO-d$_6$) δ 9.08 (s, 1H), 7.76-7.73 (m, 1H), 7.69 (s, 1H), 7.61 (d, J=2.1 Hz, 1H), 7.43-7.29 (m, 6H), 6.92-6.80 (m, 2H), 5.25-5.08 (m, 6H), 3.56 (m, 3H), 3.23 (m, 6H), 2.91-2.82 (m, 2H), 2.81-2.70 (m, 2H), 2.45 (d, J=14.4 Hz, 6H), 1.50-1.37 (m, 12H), 1.26-1.21 (m, 6H); MS m/z (M+H) 875.7.

Step 4: Succinic acid (S)-1-{(S)-1-[(S)-1-((S)-1-carboxy-ethoxycarbonyl)-ethoxycarbonyl]-ethoxycarbonyl}-ethyl ester 3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yl ester (58-4)

To a 100 mL autoclave vessel was added a solution of succinic acid (S)-1-{(S)-1-[(S)-1-((S)-1-benzyloxycarbonyl-ethoxycarbonyl)-ethoxycarbonyl]-ethoxycarbonyl}-ethyl ester 3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yl ester (58-3) (1 g, 1.14 mmol) in methanol (20 mL) and 10% Pd/C (150 mg, 50% wet) at 25-30° C. The reaction mixture was stirred at room temperature under hydrogen pressure (1 kg/cm$^2$) for 30 minutes. After completion of the reaction, the reaction mixture was filtered through celite. Then volatiles were evaporated under reduced pressure to afford a reddish orange solid (0.8 g, 89%). 1H NMR (400 MHz, DMSO-d$_6$) δ 13.8 (s, 1H), 10.97 (s, 1H), 7.8 (m, 1H), 7.70 (s, 1H), 7.60 (s, 1H), 6.80-6.90 (m, 2H), 5.25-5.09 (m, 4H), 4.92 (q, J=6.8 Hz, 1H), 3.54 (d, J=6.3 Hz, 2H), 3.1-3.3 (m, 6H), 2.98-2.6 4H), 2.3-2.5 (m, 6H), 1.48-1.30 (m, 12H), 1.25-1.19 (6H); MS m/z (M+H) 785.9.

Step 5: (3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl 1-(2S)-1-{[(2)-1-{[(2S)-1-[(1S)-1-({[(2S,4S)-4-(ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl butanedioate (58-5)

To a solution of dorzolamide (19-1) (0.3 g, 0.83 mmol) in dichloromethane (5 mL) was added N,N-diisopropylethylamine (0.25 mL, 1.33 mmol) at 0° C. After 30 minutes, succinic acid (S)-1-{(S)-1-[(S)-1-((S)-1-carboxy-ethoxycarbonyl)-ethoxycarbonyl]-ethoxycarbonyl}-ethyl ester 3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yl ester (58-4) (0.85 g, 1.08 mmol), EDCI.HCl (0.25 g, 1.33 mmol), hydroxybenzotriazole (23 mg, 0.166 mmol), and 4-dimethylaminopyridine (10 mg, 0.08 mmol) were added at 0° C. The reaction mixture was allowed to stir at 25-30° C. for 2 hours and the resulting reaction mixture was quenched with water (100 mL), extracted with dichloromethane (200×3 mL), dried over sodium sulfate, and concentrated under reduced pressure. The crude product obtained upon evaporation of volatiles was purified by silica gel column chromatography (5% methanol in DCM) to afford an orange solid (350 mg, 38%). $^1$H-NMR (400 MHz, DMSO-d$_6$) δ 13.72 (s, 1H), 10.96 (s, 1H), 7.74-7.67 (m, 2H), 7.60 (d, J=2 Hz, 1H), 7.52-7.41 (m, 1H), 6.90-6.82 (m, 2H), 5.21-5.04 (m, 3H), 4.79 (q, J=7 Hz, 1H), 4.2-3.8 (m, 2H), 3.57-3.44 (m, 2H), 3.25-2.95 (m, 6H), 2.87-2.81 (m, 2H), 2.80-2.72 (m, 2H), 2.70-2.55 (m, 2H), 2.46, (s, 3H), 2.43 (s, 3H), 2.42-2.24 (m, 2H), 1.50-1.42 (m, 9H), 1.34 (d, 3H), 1.29 (d, 3H), 1.18 (t, 6H), 1.06 (t, 3H). MS(+) m/z (M+H)$^+$ 1091.6.

Example 7. Synthetic Examples of Brinzolmide-Sunitinib Bis-Prodrugs

Scheme 59: (3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl 1-(2S)-1-{[(2S)-1-[(1S)-1-({[(4R)-4-(ethylamino)-2-(3-methoxypropyl)-1,1-dioxo-2H,3H,4H-1λ$^6$-thieno[3,2-e][1,2]thiazin-6-yl]sulfonyl}carbamoyl)ethoxy]-1-oxopropan-2-yl]oxy}-1-oxopropan-2-yl butanedioate (59-1):

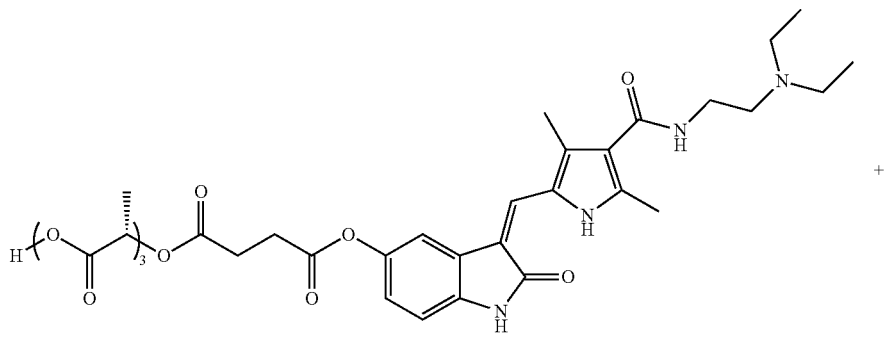

56-4

-continued

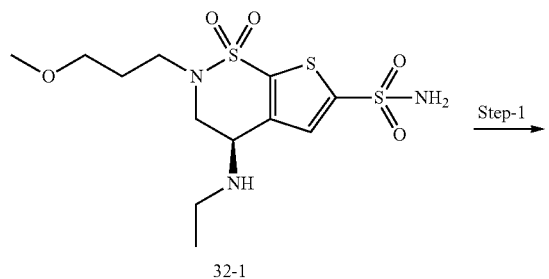

32-1

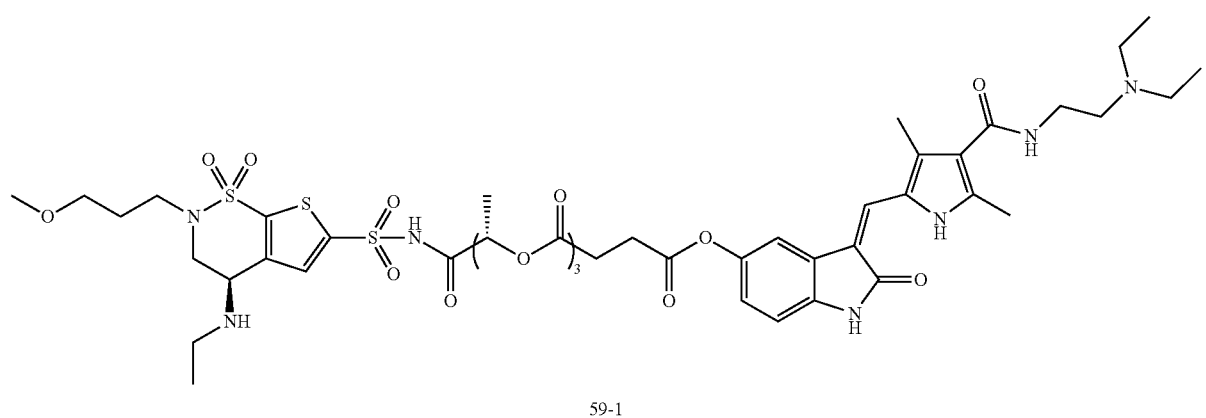

59-1

To a solution of brinzolamide (32-1) (0.2 g, 0.52 mmol) and succinic acid (S)-1-[(S)-1-((S)-1-carboxy-ethoxycarbonyl)-ethoxycarbonyl]-ethyl ester 3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yl ester (56-4) (0.48 g, 0.677 mmol) in dichloromethane (10 mL) was added EDCI.HCl (0.149 g, 0.783 mmol), hydroxybenzotriazole (14 mg, 0.104 mmol), and 4-dimethylaminopyridine (6 mg, 0.052 mmol) at 0° C. The reaction mixture was allowed to stir at 25-30° C. for 2 hours and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel column chromatography (6% methanol in DCM) to afford an orange solid (150 mg, 26%). $^1$H-NMR (400 MHz, DMSO-$d_6$) δ 13.72 (s, 1H), 10.96 (s, 1H), 7.71 (bs, 1H), 7.68 (s, 1H), 7.60 (d, J=2 Hz, 1H), 7.51 (t, 1H), 6.90-6.82 (m, 2H), 5.15-5.04 (m, 2H), 4.79 (q, J=7 Hz, 1H), 4.15-4.00 (m, 1H), 3.85-3.70 (m, 2H), 3.60-3.45 (m, 2H), 3.45-3.35 (m, 2H), 3.22 (s, 3H), 3.22-3.05 (m, 6H), 2.86-2.80 (m, 2H), 2.80-2.73 (m, 2H), 2.70-2.55 (m, 2H), 2.47 (s, 3H), 2.44 (s, 3H), 1.77 (quintet, 2H), 1.50-1.42 (m, 6H), 1.28 (d, 3H), 1.20 (t, 6H), 1.03 (t, 3H). MS(+) m/z (M+H)$^+$ 1078.6 and (M+2H)$^{++}$539.9.

Scheme 60: (3Z)-3-[(4-{[2-(Diethylamino)ethyl]carbamoyl}-3,5-dimethyl-1H-pyrrol-2-yl)methylidene]-2-oxo-2,3-dihydro-1H-indol-5-yl 1-(2S)-1-{[(2S)-1-{[(2S)-1-[(1S)-1-({[(4R)-4-(ethylamino)-2-(3-methoxypropyl)-1,1-dioxo-2H,3H,4H-1λ$^6$-thieno[3,2-e][1,2]thiazin-6-yl]sulfonyl}carbamoyl)ethoxy]-1-oxopropan-2-yl]oxy}-1-oxopropan-2-yl]oxy}-1-oxopropan-2-yl butanedioate (60-1):

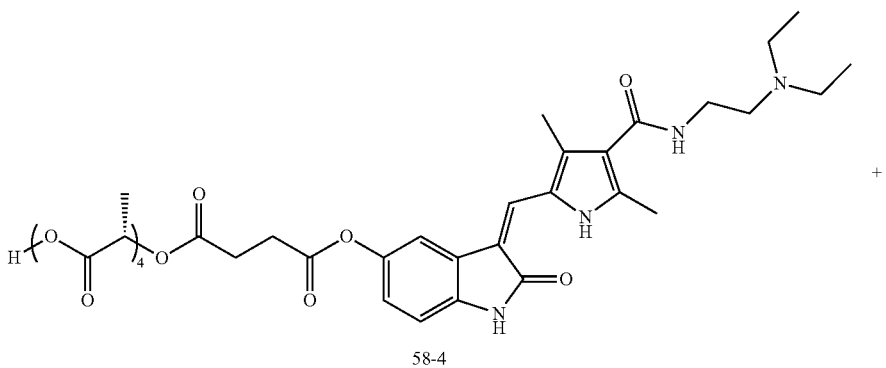

58-4

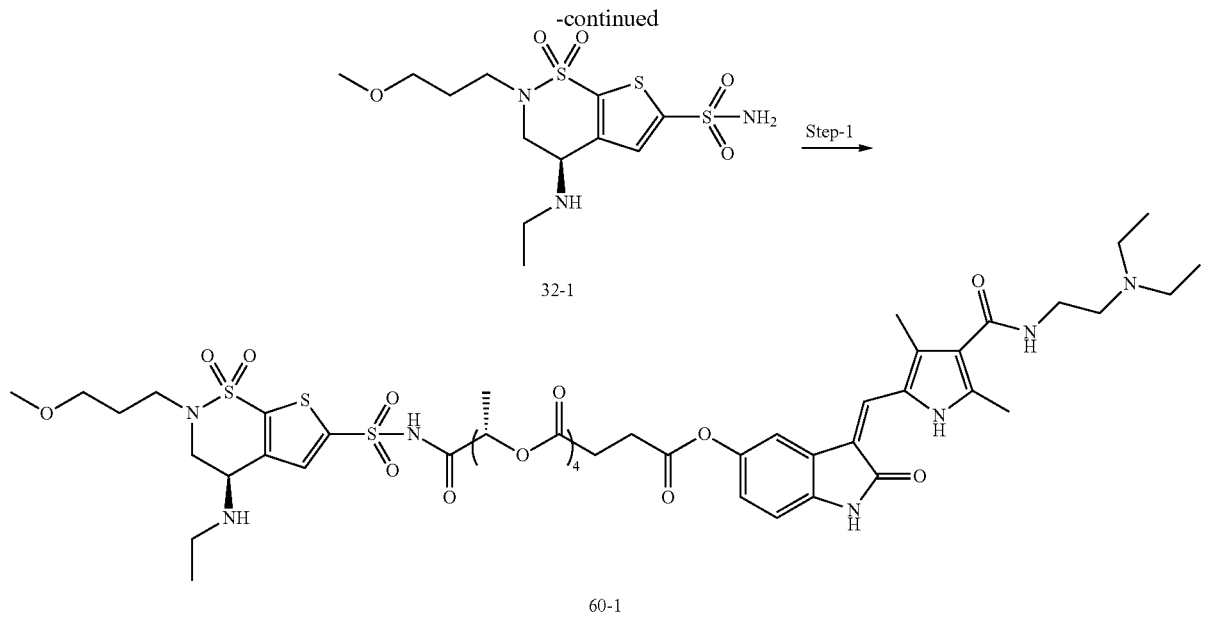

To a solution of brinzolamide (32-1) (0.2 g, 0.52 mmol) and succinic acid (S)-1-{(S)-1-[(S)-1-((S)-1-carboxy-ethoxycarbonyl)-ethoxycarbonyl]-ethoxycarbonyl}-ethyl ester 3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yl ester (58-4) (0.56 g, 0.71 mmol) in dichloromethane (10 mL) was added EDCI.HCl (0.149 g, 0.78 mmol), hydroxybenzotriazole (14 mg, 0.10 mmol), and 4-dimethylaminopyridine (6 mg, 0.052 mmol) at 0° C. The reaction mixture was allowed to stir at 25-30° C. for 2 hours and the resulting reaction mixture was quenched with water (50 mL), extracted with dichloromethane (50×3 mL), dried over sodium sulfate, and concentrated under reduced pressure. The crude product obtained upon evaporation of volatiles was purified by silica gel (230-400) column chromotography (6% methanol in DCM) to afford an orange solid (280 mg, 46%). $^1$H-NMR (400 MHz, DMSO-$d_6$) δ 13.73 (s, 1H), 10.97 (s, 1H), 7.72 (bs, 1H), 7.68 (s, 1H), 7.60 (d, J=2 Hz, 1H), 7.50 (bs, 1H), 6.89-6.81 (m, 2H), 5.19-5.03 (m, 3H), 4.79 (q, J=7 Hz, 1H), 4.15-4.00 (m, 1H), 3.8-3.7 (m, 2H), 3.56-3.45 (m, 2H), 3.45-3.35 (m, 2H), 3.22 (s, 3H), 3.22-3.06 (m, 6H), 2.86-2.80 (m, 2H), 2.80-2.72 (m, 2H), 2.70-2.55 (m, 2H), 2.47 (s, 3H), 2.43 (s, 3H), 1.79 (quintet, 2H), 1.50-1.43 (m, 9H), 1.28 (d, 3H), 1.19 (t, 6H), 1.02 (t, 3H). MS(+) m/z (M+H)$^+$ 1151.2.

Scheme 61: (3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl 5-{ethyl[(4R)-6-{[(2S)-2-{[(2S)-2-{[(2S)-2-hydroxypropanoyl]oxy}propanoyl]oxy}propanamido]sulfonyl}-2-(3-methoxypropyl)-1,1-dioxo-2H,3H,4H-1λ$^6$-thieno[3,2-e][1,2]thiazin-4-yl]carbamoyl}pentanoate (61-2) and (3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl 1-(2S)-1-{[(2S)-1-[(1S)-1-({[(4R)-4-(ethylamino)-2-(3-methoxypropyl)-1,1-dioxo-2H,3H,4H,-1λ$^6$-thieno[3,2-e][1,2]thiazin-6-yl]sulfonyl}carbamoyl)ethoxy]-1-oxopropan-2-yl]oxy}-1-oxopropan-2-yl hexanedioate (61-3):

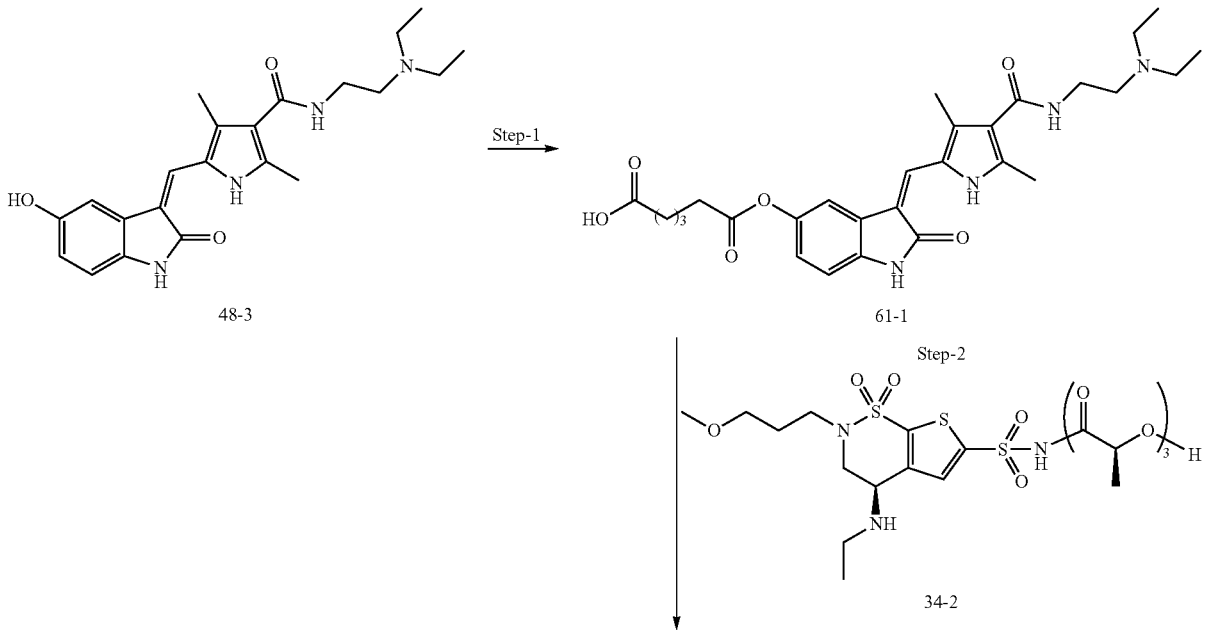

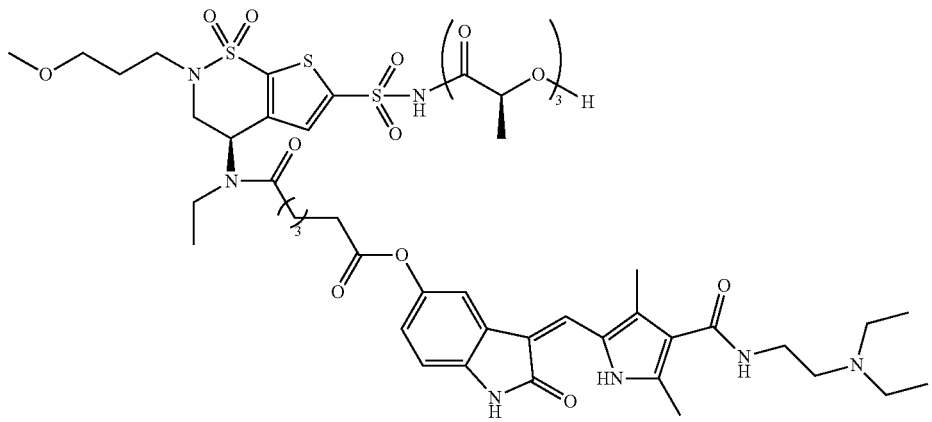

61-2

+

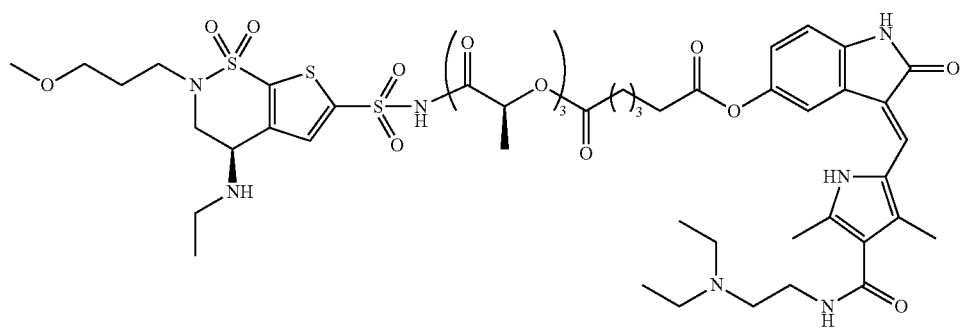

61-3

Step 1: Hexanedioic acid mono-{3-[1-[4-(2-diethyl-amino-ethylcarbamoyl)-3,5-dimethyl-1H-pyrrol-2-yl]-meth-(Z)-ylidene]-2-oxo-2,3-dihydro-1H-indol-5-yl} ester (61-1)

To a solution of hexanedioic acid (0.368 g, 2.52 mmol) in dichloromethane (20 mL) was added N,N-diisopropylethylamine (0.69 mL, 3.78 mmol), HATU (1.15 g, 3.02 mmol), 5-hydroxy Sunitinib (48-3) (0.1 g, 2.52 mol), and 4-dimethylaminopyridine (30 mg, 0.25 mmol) at 0° C. The reaction mixture was allowed to stir at 25-30° C. for 1 hour and the resulting reaction mixture was quenched with water (100 mL), extracted with dichloromethane (150×3 mL), dried over sodium sulfate, and concentrated under reduced pressure. The crude product obtained upon evaporation of volatiles was purified by silica gel (230-400) column chromatography (8% methanol in dichloromethane) to afford an orange solid (500 mg, 37%). $^1$H NMR (400 MHz, DMSO-$d_6$) δ 13.67 (s, 1H), 12.03 (s, 1H), 10.93 (s, 1H), 7.68 (s, 1H), 7.63 (s, 1H), 7.49 (t, J=5.6 Hz, 1H), 6.90-6.82 (m, 2H), 2.67-2.53 (m, 4H), 2.43 (m, 6H), 1.63 (m, 4H), 1.02 (t, J=7.1 Hz, 6H); MS m/z (M+H) 525.3.

Step 2: (3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl 5-{ethyl[(4R)-6-{[(2S)-2-{[(2S)-2-{[(2S)-2-hydroxypropanoyl]oxy}propanoyl]oxy}propanamido]sulfonyl}-2-(3-methoxypropyl)-1,1-dioxo-2H,3H,4H-1$\lambda^6$-thieno[3,2-e][1,2]thiazin-4-yl]carbamoyl}pentanoate (61-2) and (3Z)-3-[(4-{2-(diethylamino)ethyl]carbamoyl}-3,5-dimethyl-1H-pyrrol-2-yl)methylidene]-2-oxo-2,3-dihydro-1H-indol-5-yl 1-(2S)-1-{[(2S)-1-[(1S)-1-({[(4R)-4-(ethylamino)-2-(3-methoxypropyl)-1,1-dioxo-2H,3H,4H-1$\lambda^6$-thieno[3,2-e][1,2]thiazin-6-yl]sulfonyl}carbamoyl)ethoxy]-1-oxopropan-2-yl]oxy}-1-oxopropan-2-yl hexanedioate (61-3)

To a solution of hexanedioic acid mono-{3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yl} ester (61-1) (0.272 g, 0.52 mmol) in dimethylformamide (5 mL) was added N,N-diisopropylethylamine (0.15 mL, 0.80 mmol), HATU (0.228 g, 0.60 mmol), (2S)-1-[(1S)-1-({[(4R)-4-(ethylamino)-2-(3-methoxypropyl)-1,1-dioxo-2H,3H,4H-1$\lambda^6$-thieno[3,2-e][1,2]thiazin-6-yl]sulfonyl}carbamoyl)ethoxy]-1-oxopropan-2-yl (2S)-2-hydroxypropanoate (34-2) (0.24 g, 0.40 mmol) and 4-dimethylaminopyridine (30 mg, 0.25 mmol) at 0° C. The reaction mixture was allowed to stir at 25-30° C. for 1 hour and the resulting reaction mixture was quenched with water (100 mL), extracted with dichloromethane (150×3 mL), dried over sodium sulfate, and concentrated under reduced pressure. The crude mixture obtained upon evaporation of volatiles was purified by silica gel column chromatography (10% methanol in dichloromethane) to afford compounds 61-2 (35 mg) and 61-3 (35 mg) (18%).

61-2: $^1$H-NMR (400 MHz, DMSO-$d_6$) δ 13.67 (s, 1H), 10.9 (bs, 1H), 7.68 (s, 2H), 7.64 (bs, 1H), 7.42 (t, 1H), 7.06 (s, 1H), 6.9-6.8 (m, 2H), 5.4 (bs, 1H), 5.01 (q, 1H), 4.77 (q, 1H), 4.19 (quintet, 1H), 3.84-3.65 (m, 2H), 3.5-3.25 (m, nH), 2.6-2.4 (m, 12H), 1.82 (quintet, 2H), 1.75-1.60 (m, 4H), 1.46 (d, 3H), 1.27 (d, 3H), 1.20-1.05 (m, 2H), 1.00-0.92 (m, 9H). MS(+) m/z (M+H)$^+$ 1106.8.

61-3: $^1$H-NMR (400 MHz, DMSO-$d_6$) δ 13.73 (s, 1H), 10.95 (s, 1H), 9.3-8.9 (bs, 1H), 7.80-7.68 (m, 2H), 7.63 (d, J=2 Hz, 1H), 7.50 (bs, 1H), 6.89-6.82 (m, 2H), 5.11-5.02 (m, 2H), 4.79 (q, J=7 Hz, 1H), 4.15-3.95 (m, 1H), 3.84-3.65 (m, 2H), 3.64-3.55 (m, 2H), 3.4-3.1 (m, 12H), 2.7-2.5 (m, 4H), 2.47 (s, 3H), 2.41 (s, 3H), 1.81 (quintet, 2H), 1.75-1.60 (m, 4H), 1.48 (d, 3H), 1.44 (d, 3H), 1.29 (d, 3H), 1.21 (t, 6H), 1.00 (t, 3H). MS(+) m/z (M+H)$^+$ 1106.7.

Example 8. General Routes of Synthesis to Compounds of Formula I and Formula II Scheme 62:

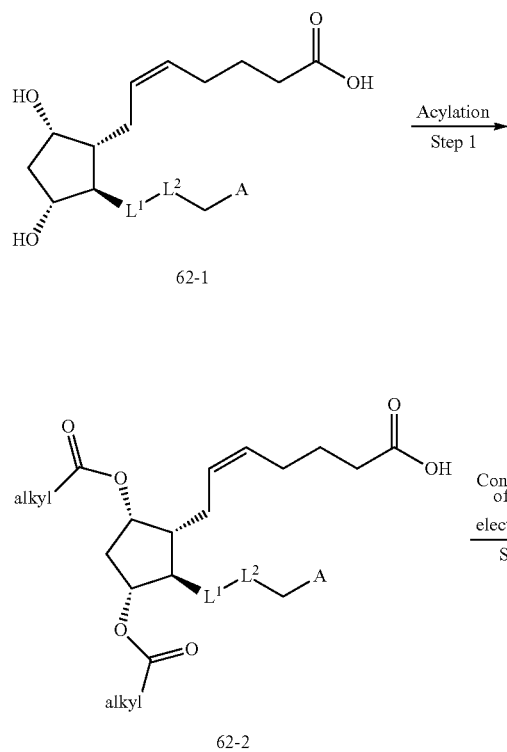

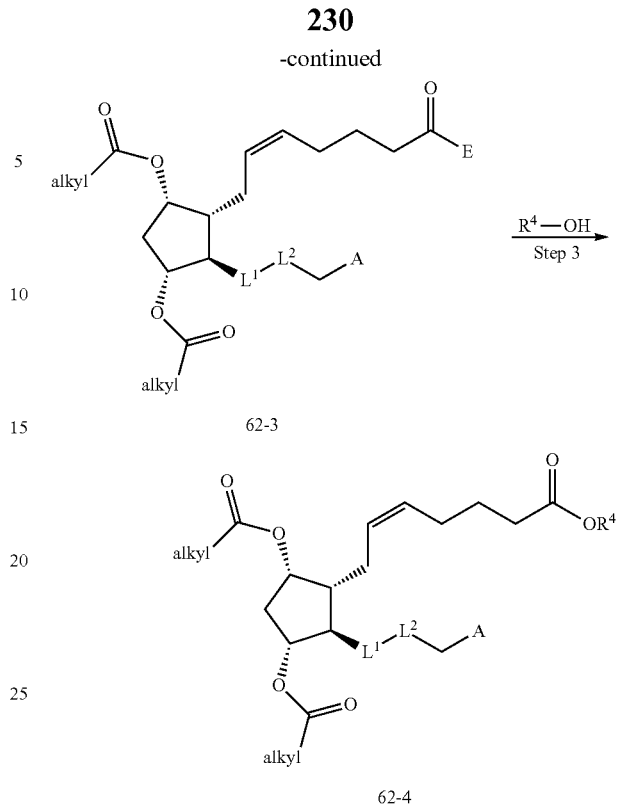

Scheme 62: A compound of the present invention can be prepared, for example, from a prostaglandin. In Step 1 the prostaglandin's (62-1) hydroxyl groups are acylated as known in the art to afford a protected species (62-2). In Step 2 the protected species (62-2) is converted to an activated electrophile (62-3) as known in the art to subsequently be reacted with an appropriately substituted alcohol in Step 3 to afford an ester (62-4) which in a typical embodiment is hydrophobic to afford a compound of Formula I. In Step 1, if a hydroxyl group is present on $L^2$ it is acylated.

Scheme 63:

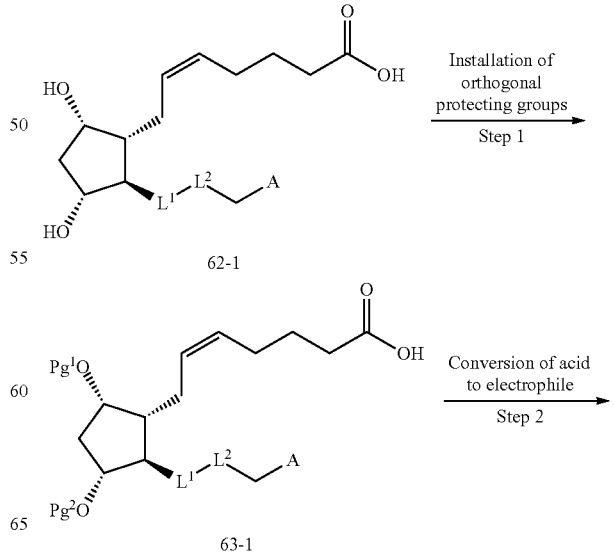

Scheme 63, continued:
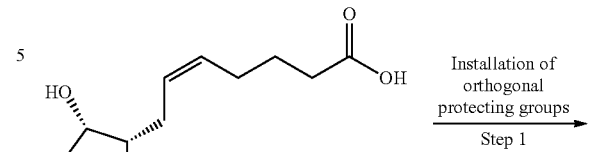
62-1
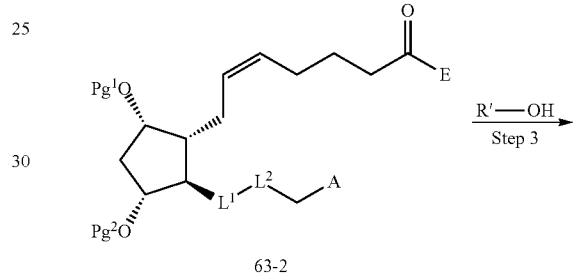
63-1
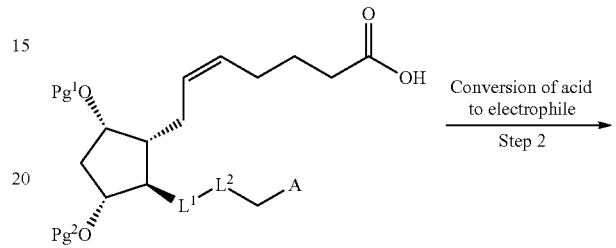
63-2
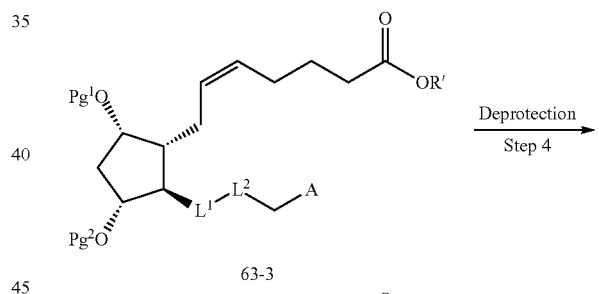
63-3
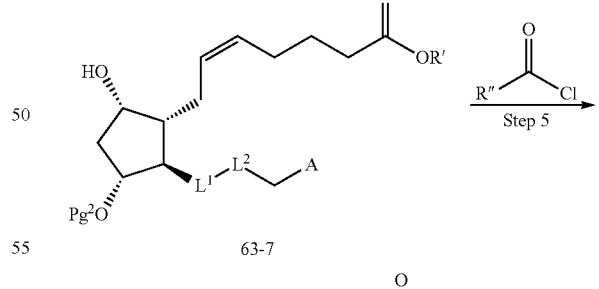
63-7
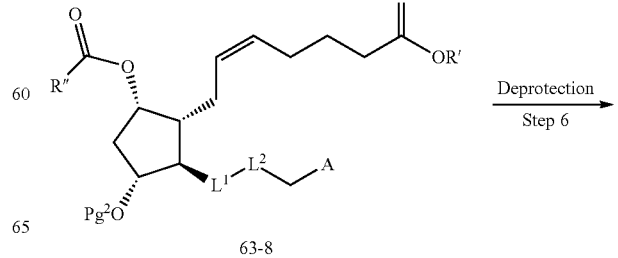
63-8
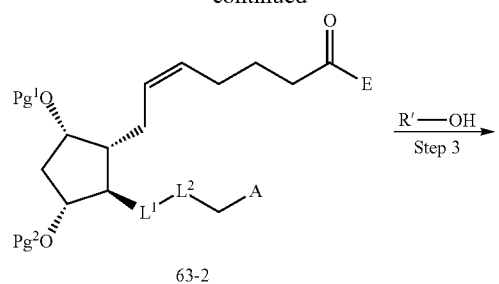
63-2
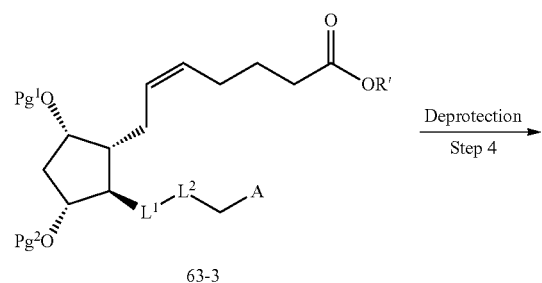
63-3
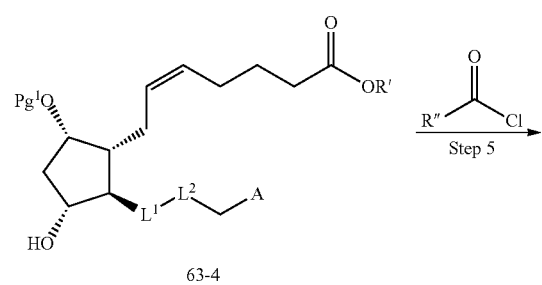
63-4
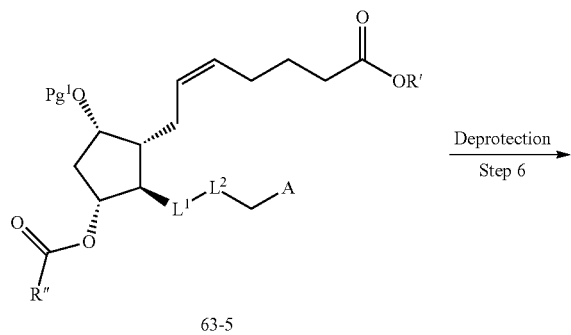
63-5
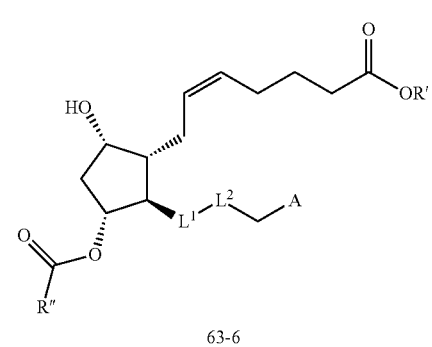
63-6
R' = R⁴ or R⁶
R" = R⁴ or R⁶

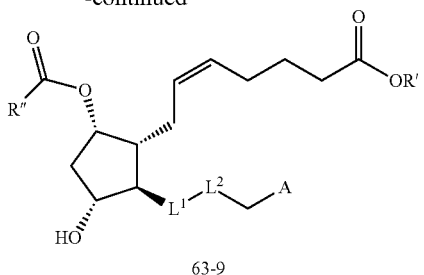

R' = R⁴ or R⁶
R" = R⁴ or R⁶

Scheme 63: A compound of the present invention can be prepared with various different substituents, for example, from a prostaglandin. In Step 1 the prostaglandin's (62-1) hydroxyl groups are orthogonally protected as known in the art to afford a protected species (63-1). In Step 2 the protected species (63-1) is converted to an activated electrophile (63-2) as known in the art to subsequently be reacted with an appropriately substituted alcohol in Step 3 to afford an ester (63-3). In Step 4 the prostaglandin is selectively deprotected to afford a selectively protected species (63-4 or 63-7). In Step 5 the prostaglandin (63-4 or 63-7) is subjected to an appropriately substituted acyl chloride to afford an ester (63-5 or 63-8). In Step 6 the prostaglandin (63-5 or 63-8) is further deprotected to afford a compound of either Formula I (63-6) or Formula II (63-7) depending on the choice of acyl chloride and alcohol functionality.

Example 9. Representative Routes of Synthesis to Compounds of Formula I and Formula II Scheme 64:

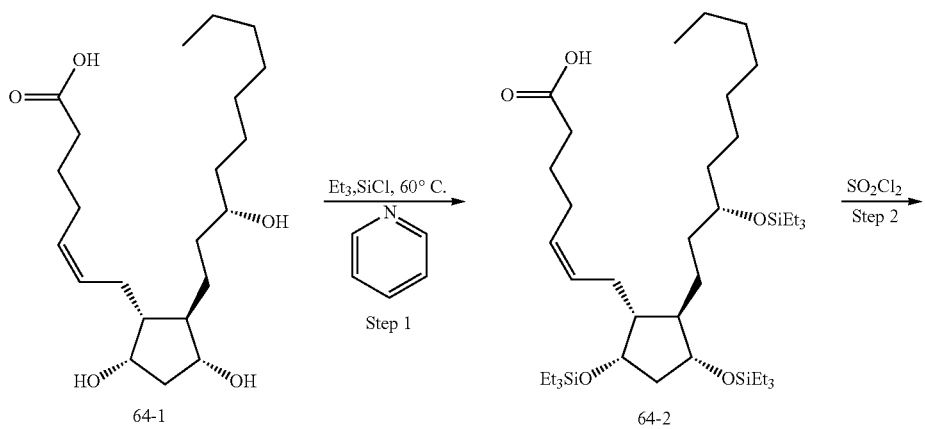

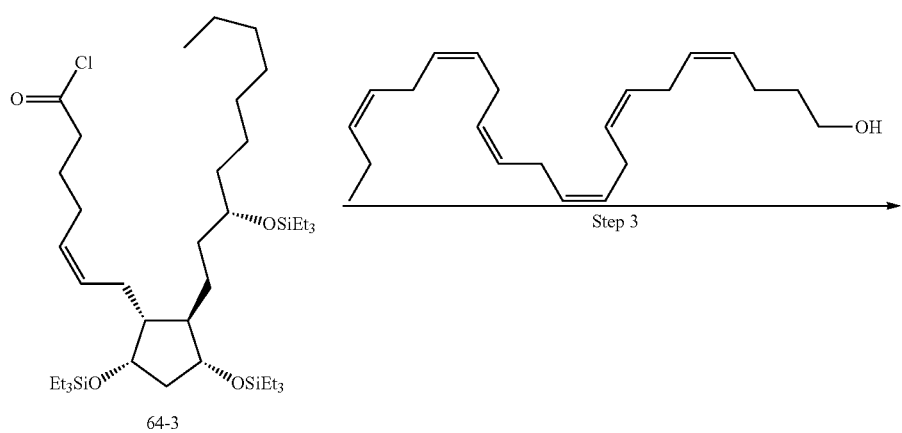

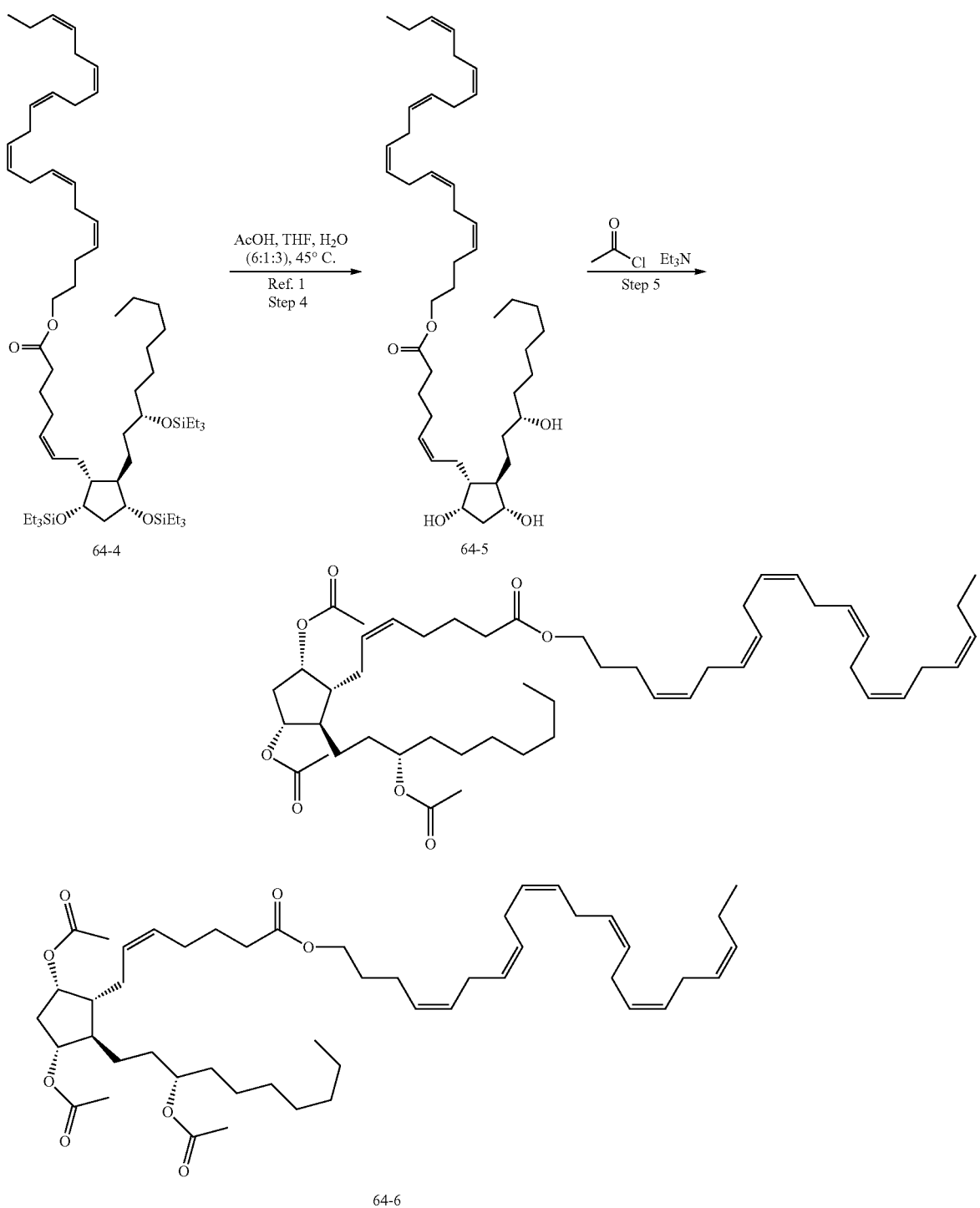

1. W. R. Roush and S. Russo-Rodriguez, *J. Org. Chem.*, 52, 598 (1987)

Scheme 64: A compound of the present invention can be prepared, for example, from a prostaglandin. In Step 1 the prostaglandin's (64-1) hydroxyl groups are protected as known in the art with a silyl chloride to afford a protected species (64-2). In Step 2 the appropriately substituted carboxylic acid (64-2) is subjected to thionyl chloride as known in the art to afford an acyl chloride (64-3). In Step 3 the appropriately substituted acyl chloride (64-3) is subjected to an alcohol to afford an ester (64-4) which in a typical embodiment is hydrophobic. In Step 4 the appropriately substituted silyl ethers (64-5) are deprotected to afford a hydroxyl species (64-5). In Step 5 the appropriately substituted alcohol (65-5) is acylated as known in the art to afford a compound (64-6) of Formula I.

Scheme 65:
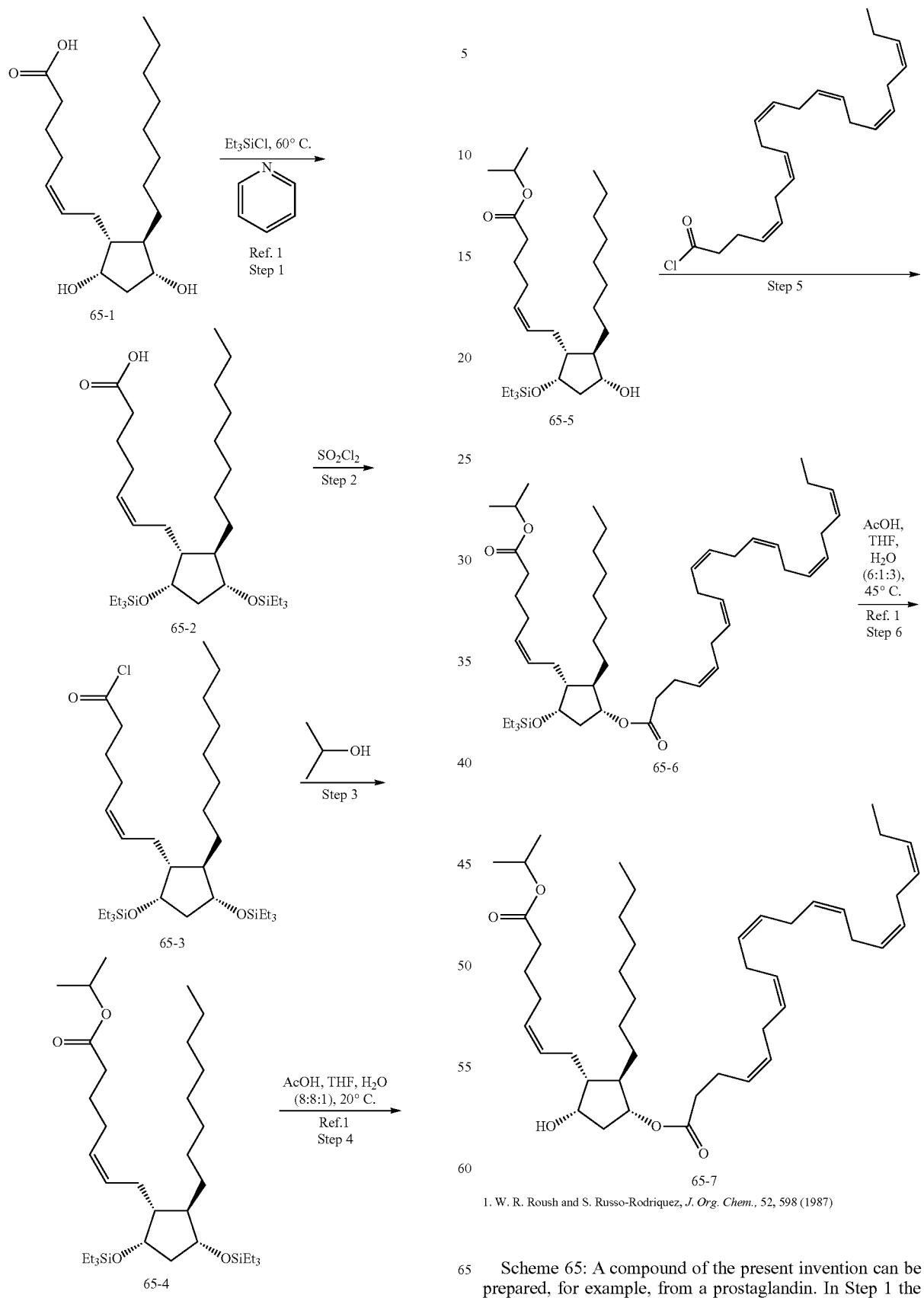
1. W. R. Roush and S. Russo-Rodriquez, *J. Org. Chem.*, 52, 598 (1987)
Scheme 65: A compound of the present invention can be prepared, for example, from a prostaglandin. In Step 1 the prostaglandin's (65-1) hydroxyl groups are protected as known in the art with a silyl chloride to afford a protected species (65-2). In Step 2 the appropriately substituted carboxylic acid (65-2) is subjected to thionyl chloride as known in the art to afford an acyl chloride (65-3). In Step 3 the appropriately substituted acyl chloride (65-3) is subjected to an alcohol to afford an ester (65-4). In Step 4 the less hindered silyl ether (65-4) is deprotected as disclosed by Roush to afford a partially protected prostaglandin (65-5). In Step 5 the appropriately substituted alcohol (65-5) is subjected to an acyl chloride to afford an ester (65-6), which in a typical embodiment is hydrophobic. In Step 6 the remaining silyl ether(s) (65-6) are deprotected as known in the art to afford a compound (65-7) of Formula 1.

Scheme 66:

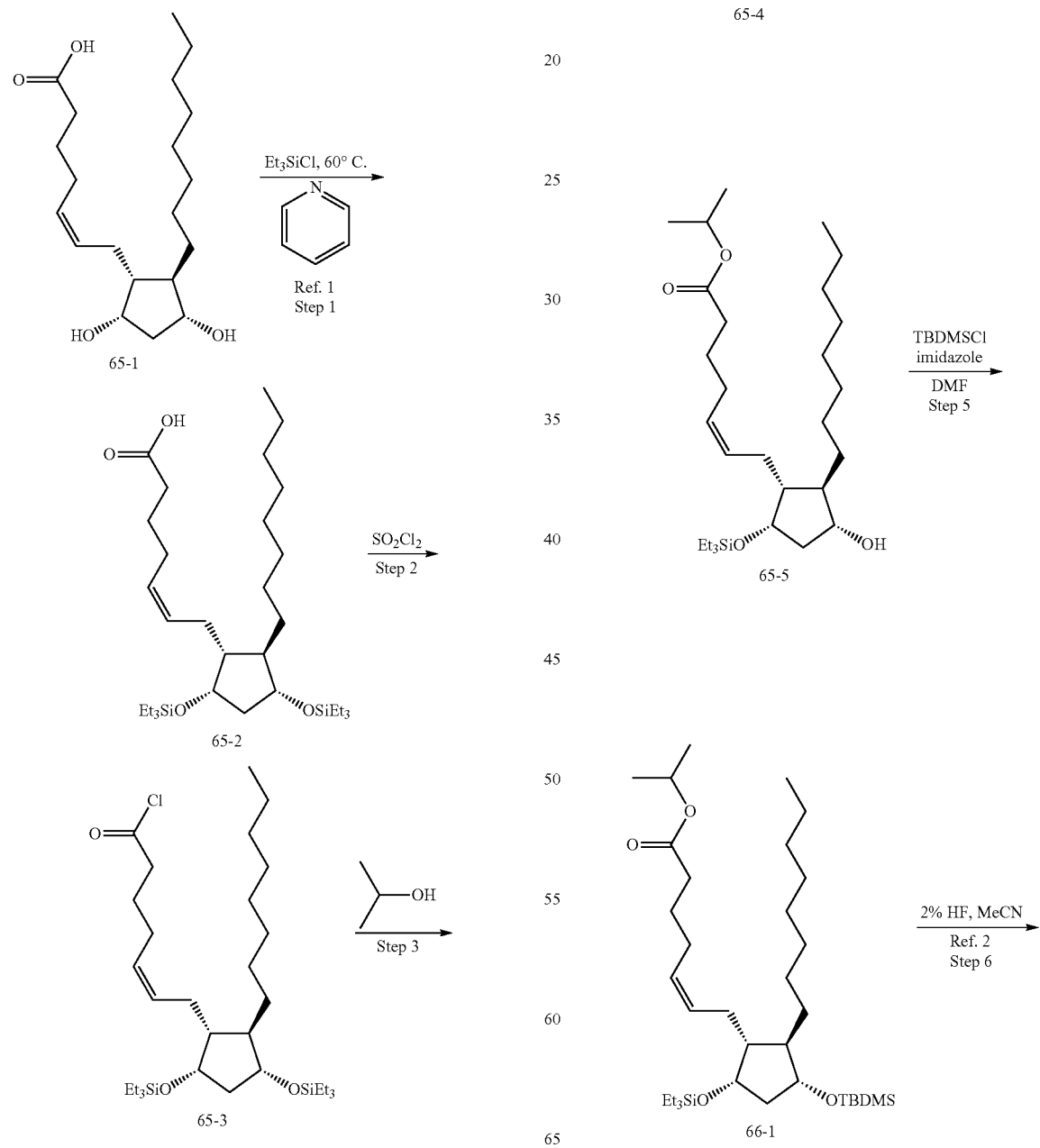

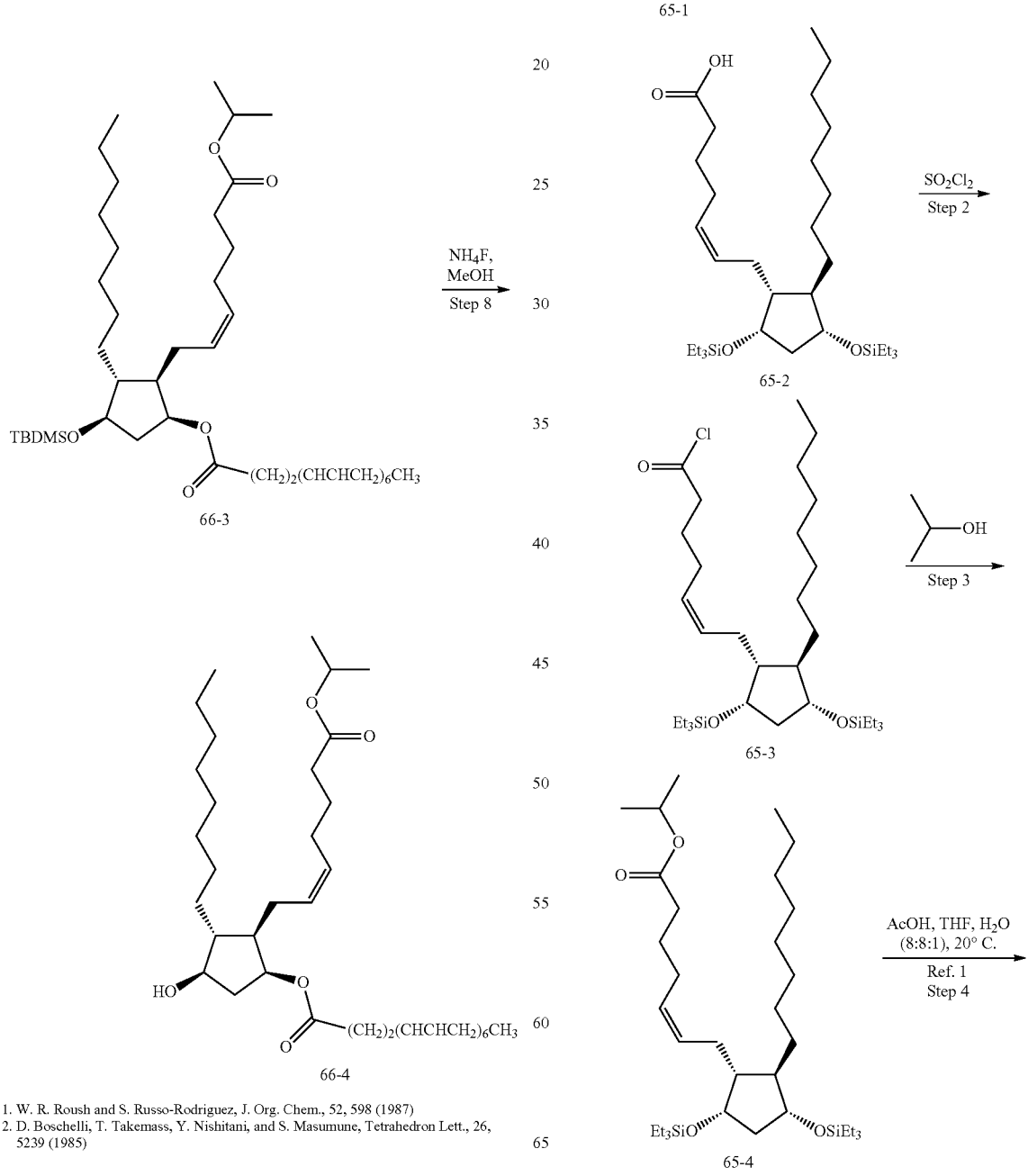
1. W. R. Roush and S. Russo-Rodriguez, J. Org. Chem., 52, 598 (1987)
2. D. Boschelli, T. Takemass, Y. Nishitani, and S. Masumune, Tetrahedron Lett., 26, 5239 (1985)

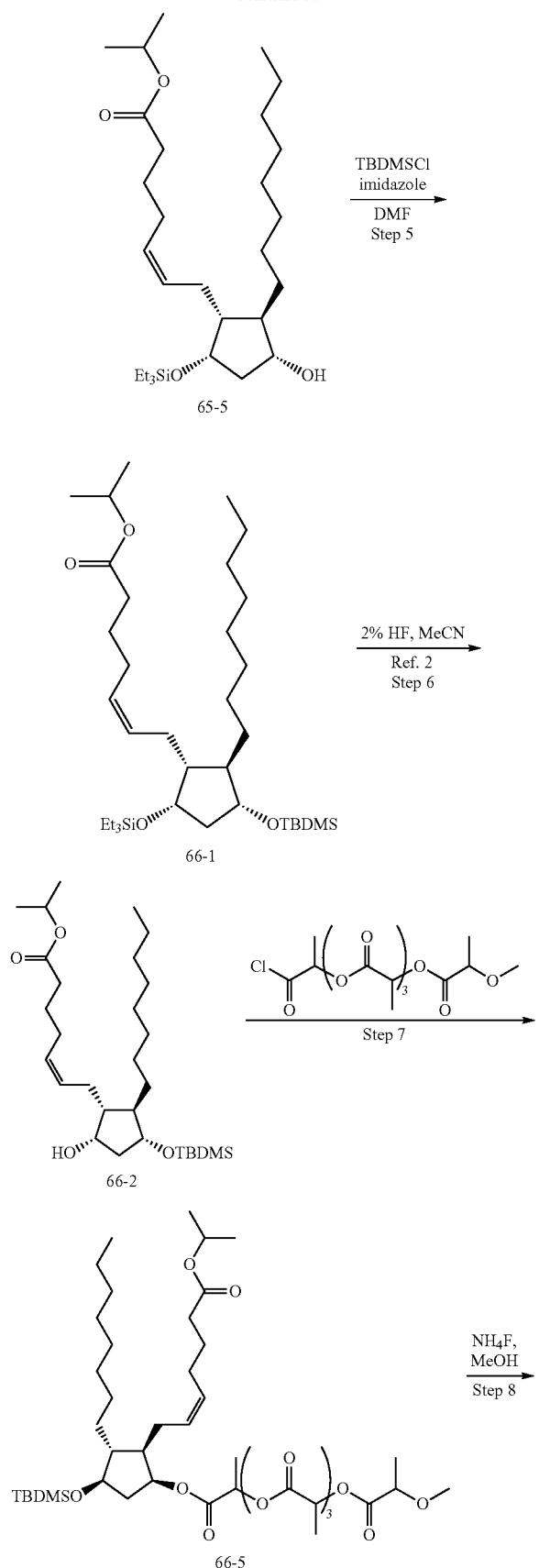

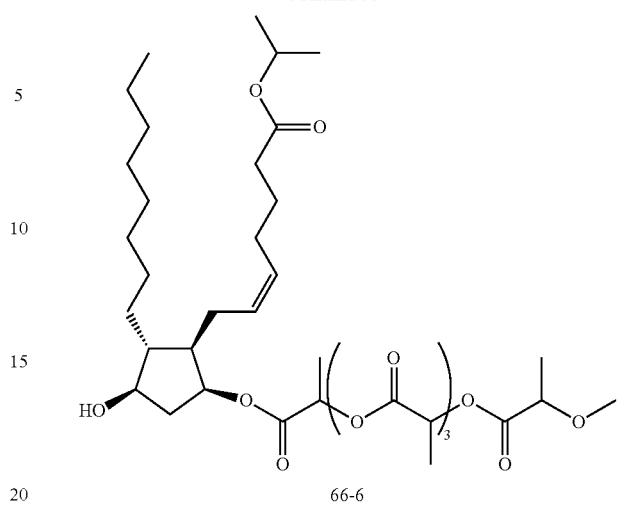

66-6

1. W. R. Roush and S. Russo-Rodriguez, J. Org. Chem., 52, 598 (1987)
2. D. Boschelli, T. Takemass, Y. Nishitani, and S. Masumune, Tetrahedron Lett., 26, 5239 (1985)

Scheme 66: A compound of the present invention can be prepared, for example, from a prostaglandin. In Step 1 the prostaglandin's (65-1) hydroxyl groups are protected as known in the art with a silyl chloride to afford a protected species (65-2). In Step 2 the appropriately substituted carboxylic acid (65-2) is subjected to thionyl chloride as known in the art to afford an acyl chloride (65-3). In Step 3 the appropriately substituted acyl chloride (65-3) is subjected to an alcohol to afford an ester (65-4). In Step 4 the less hindered silyl ether is deprotected as disclosed by Roush to afford a partially protected prostaglandin (65-5). In Step 5 the appropriately substituted alcohol is subjected to a bulky silyl chloride to afford an orthogonally protected species (66-1). In Step 6 the least bulky silyl ether is deprotected as disclosed by Boschelli to afford a partially protected prostaglandin (66-2). In Step 7 the appropriately substituted alcohol is subjected to an acyl chloride to afford an ester (66-3 or 66-5), which in a typical embodiment is hydrophobic. In Step 8 the remaining silyl ether(s) are deprotected as known in the art to afford a compound of Formula I (66-4) or Formula II (66-6).

Example 10. General Routes of Synthesis to Compounds of Formula III, Formula IV, Formula V, and Formula VI Scheme 67:

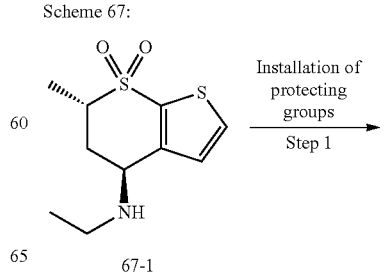

67-1

245
-continued

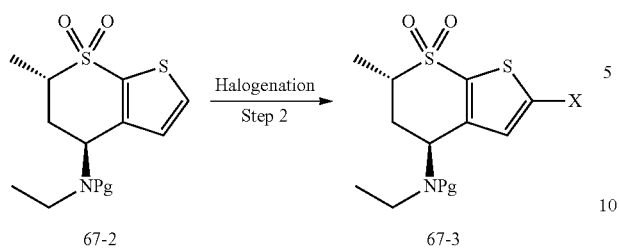

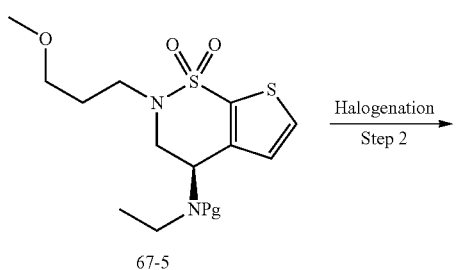

246
-continued

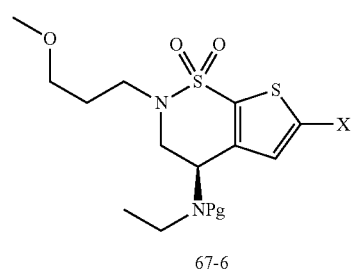

Scheme 67: A compound of the present invention can be prepared, for example, from precursors to various carbonic anhydrase inhibitors (CAIs). In Step 1 the CAI precursor (67-1, 67-4, 67-7) is protected as known in the art to afford a protected species (67-2, 67-5, 67-8). In Step 2 the protected species is halogenated as known the art to allow further functionalization en route to compounds of Formula III (67-6), Formula IV (67-3), Formula V (67-8), and Formula VI (67-8).

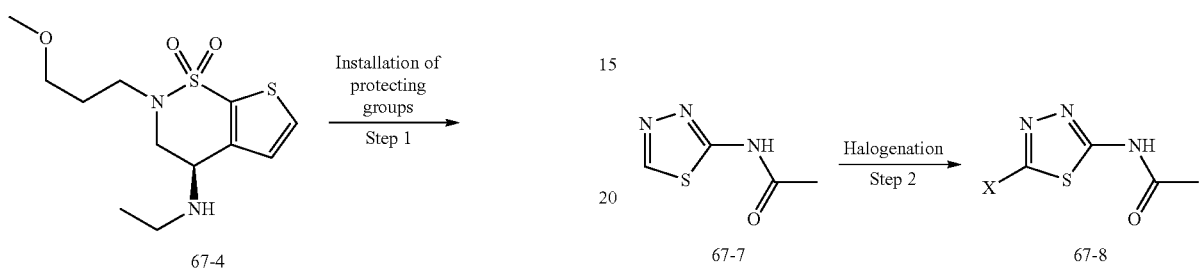

Scheme 68:

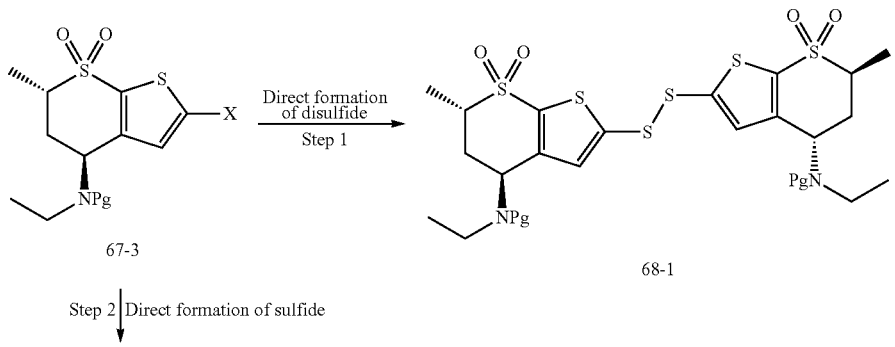

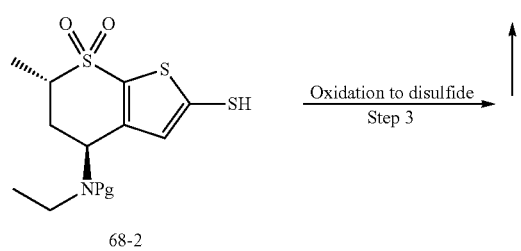

Scheme 68: A compound of the present invention can be prepared, for example, from precursors to various carbonic anhydrase inhibitors (CAIs). In Step 1 the CAI precursor (67-3) is directly converted to a disulfide species (68-1). Alternatively, in Step 2 the protected species is first converted to a sulfide (68-2) and then in Step 3 oxidized to a disulfide species (68-1) to allow further functionalization en route to compounds of Formula III, Formula IV, Formula V, or Formula VI.

anhydrase inhibitors (CAIs). In Step 1 the CAI precursor (68-1) is directly converted to a sulfinyl species (69-1). In Step 2 the sulfinyl species is converted to either an aldimine or a ketamine (69-2) which in a typical embodiment is hydrophobic. In Step 3 the sulfinyl aldimine or ketimine is converted to a sulfonyl aldimine or ketamine (69-3). In Step 4 the sulfonyl aldimine or ketimine is deprotected to afford a compound (69-4) of Formula III, Formula IV, Formula V, or Formula VI.

Scheme 69:

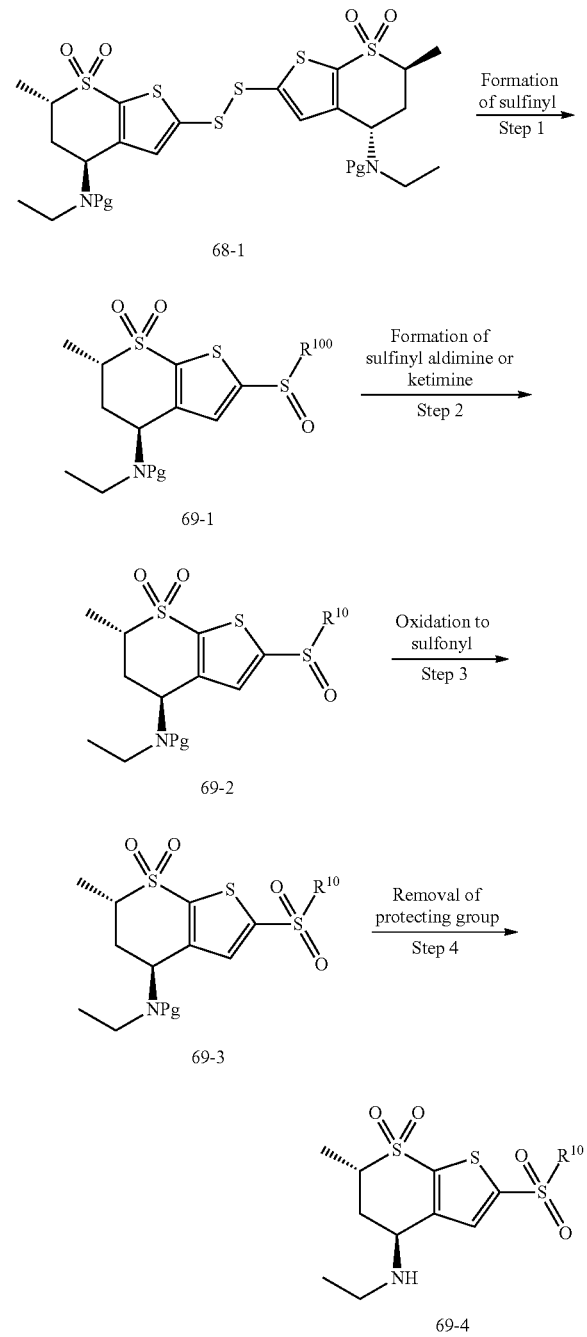

Scheme 70:

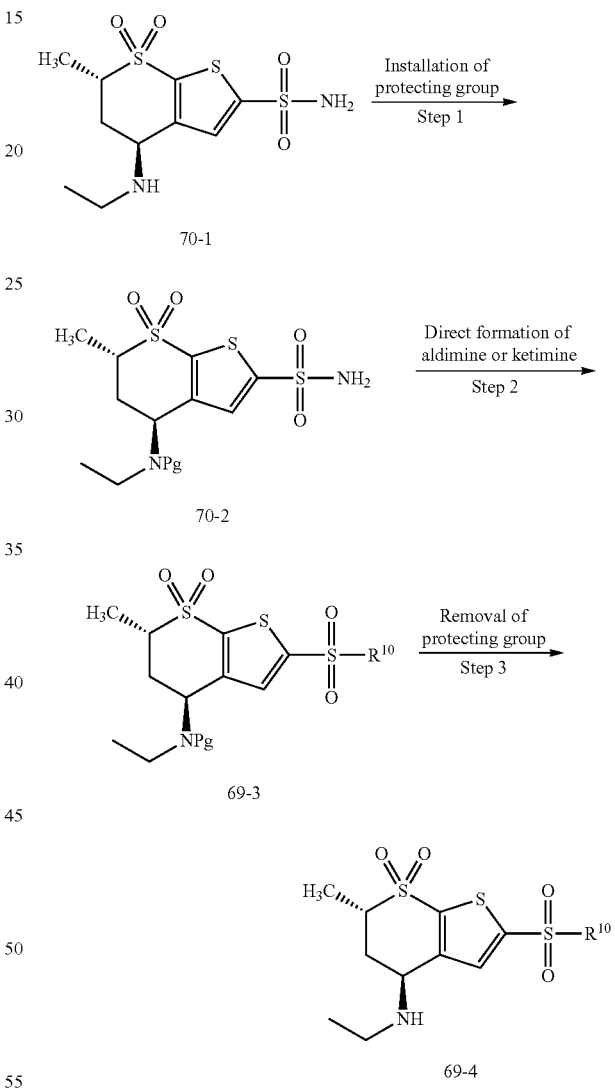

Scheme 69: A compound of the present invention can be prepared, for example, from precursors to various carbonic Scheme 70: A compound of the present invention can be prepared, for example, from various carbonic anhydrase inhibitors (CAIs). In Step 1 the CAI precursor (70-1) is protected as known in the art to afford a protected species (70-2). In Step 2 the sulfonyl species is converted to either an aldimine or a ketimine (69-3) which in a typical embodiment is hydrophobic. In Step 3 the sulfonyl aldimine or ketimine is deprotected as known in the art to afford a compound (69-4) of Formula III, Formula IV, Formula V, or Formula VI.

Example 11. Representative Routes of Synthesis to Compounds of Formula III, Formula IV, Formula V, and Formula VI Scheme 71:

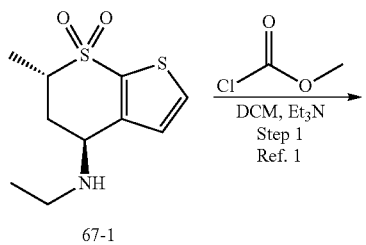

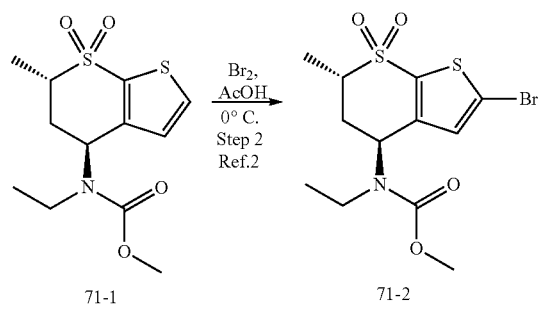

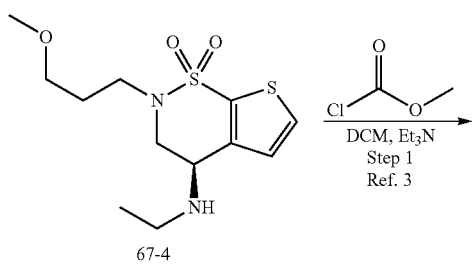

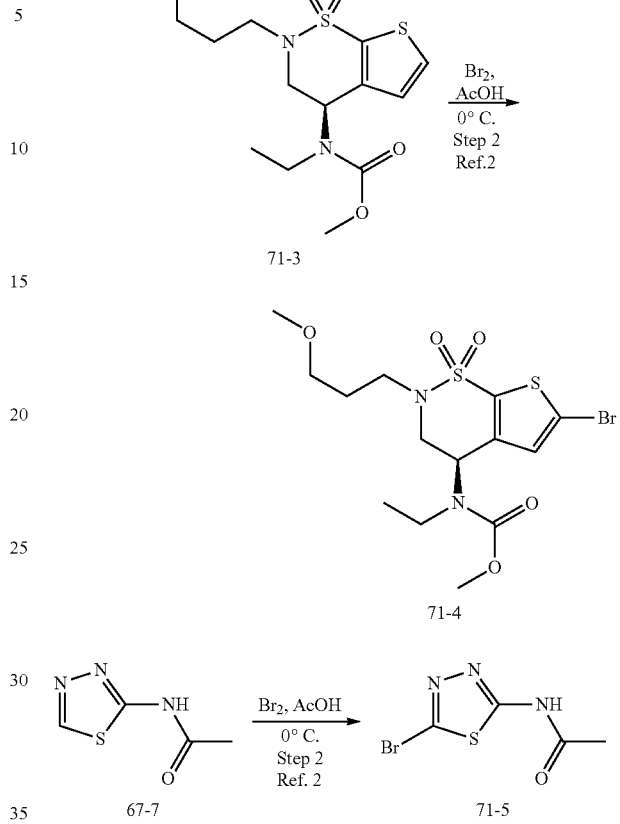

1. Rajendiran, C., et al. (2015). Pharma Chem. 7(1): 68-76, 69 pp.
2. Hu, J., et al. (2014). Chem. Biol. Drug Des. 84(6): 642-647.
3. Bao, J., et al. (2014). CN 103755727

Scheme 71: A compound of the present invention can be prepared, for example, from precursors to various carbonic anhydrase inhibitors (CAIs). In Step 1 the appropriately substituted CAI precursor (67-1, 67-4, 67-7) is protected as known in the art to afford a carbamate protected species (71-1, 71-3). In Step 2 the appropriately substituted CAI precursor is subjected to bromine as known in the art to afford an aryl bromide (71-2, 71-4, 71-5).

Scheme 72:

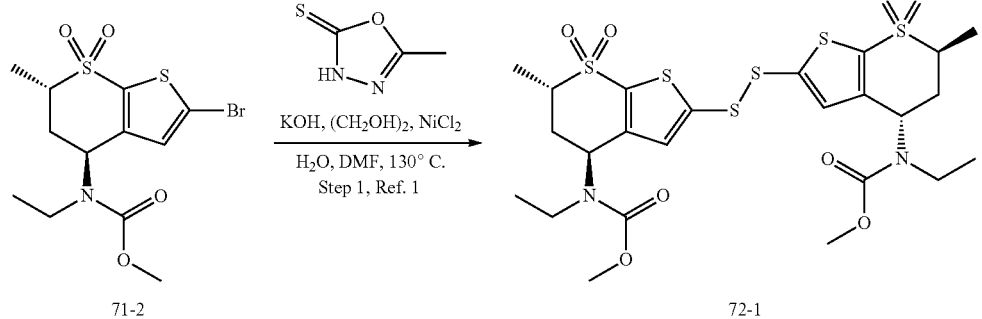

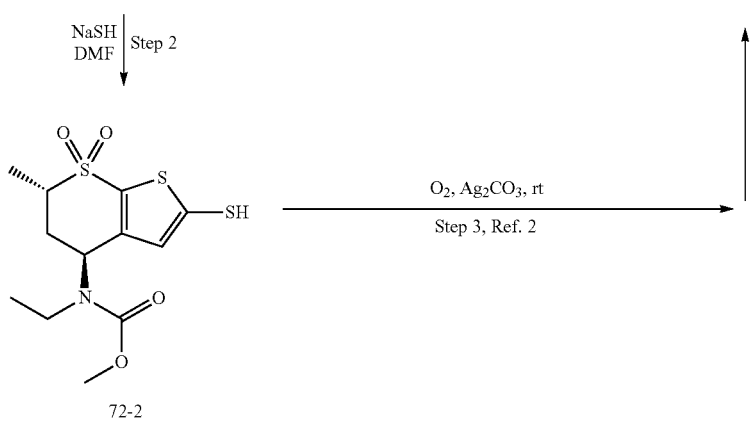

1. Soleiman-Beigi, M. and F. Mohammadi (2015). Synlett 26(7): 911-914.
2. Gholami, A. and H. Bahramipur (2015). J. Indian Chem. Soc. 92(3): 379-381.

Scheme 72: A compound of the present invention can be prepared, for example, from precursors to various carbonic anhydrase inhibitors (CAIs). In Step 1 the appropriately substituted CAI precursor (71-2) is directly converted to a disulfide species (72-1) using a method disclosed by Soleiman and coworkers. Alternatively, in Step 2 the protected species (71-2) is first converted to a sulfide (72-2) and then in Step 3 oxidized to a disulfide species (72-1) using a method disclosed by Gholami to allow further functionalization en route to compounds of Formula III, Formula IV, Formula V, and Formula VI.

Scheme 73:

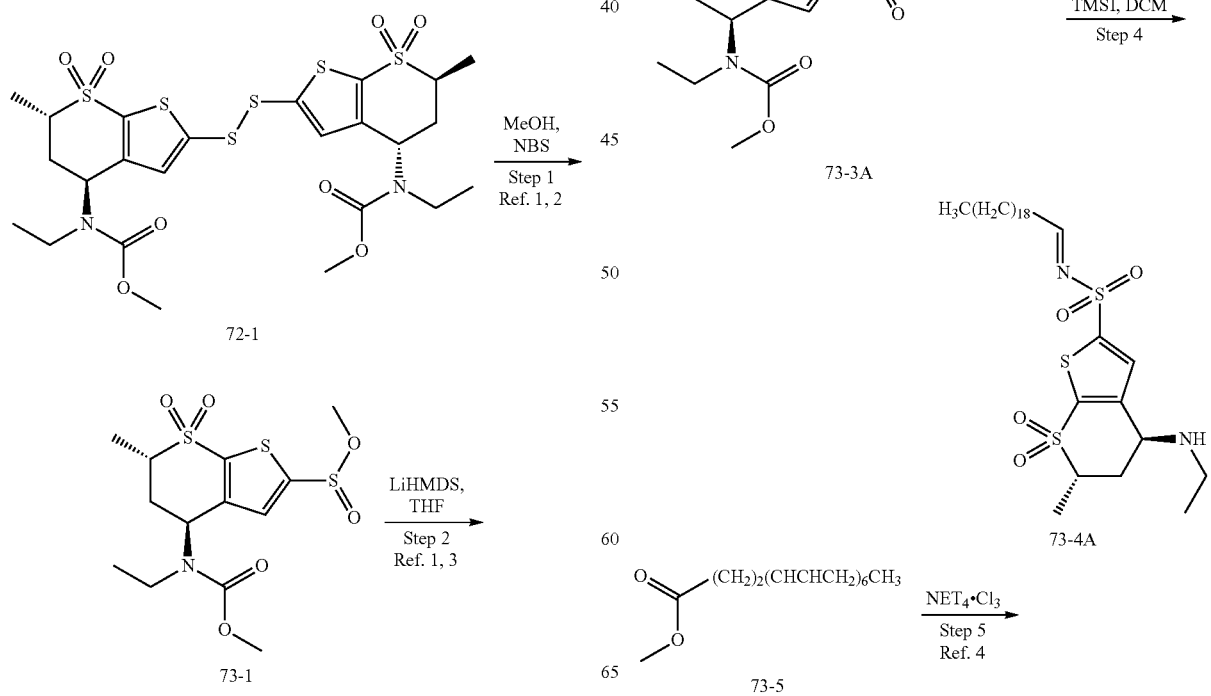

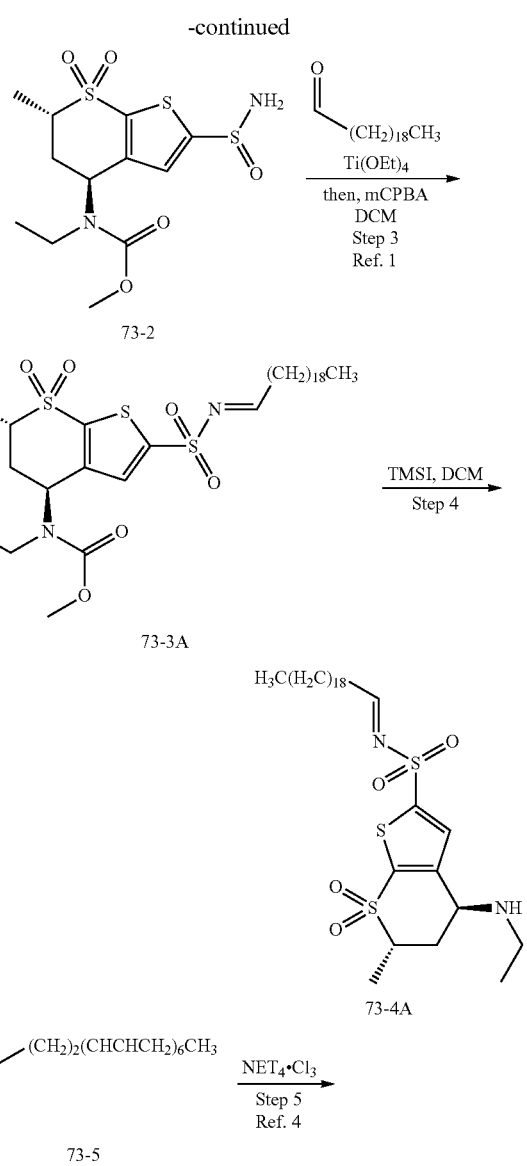

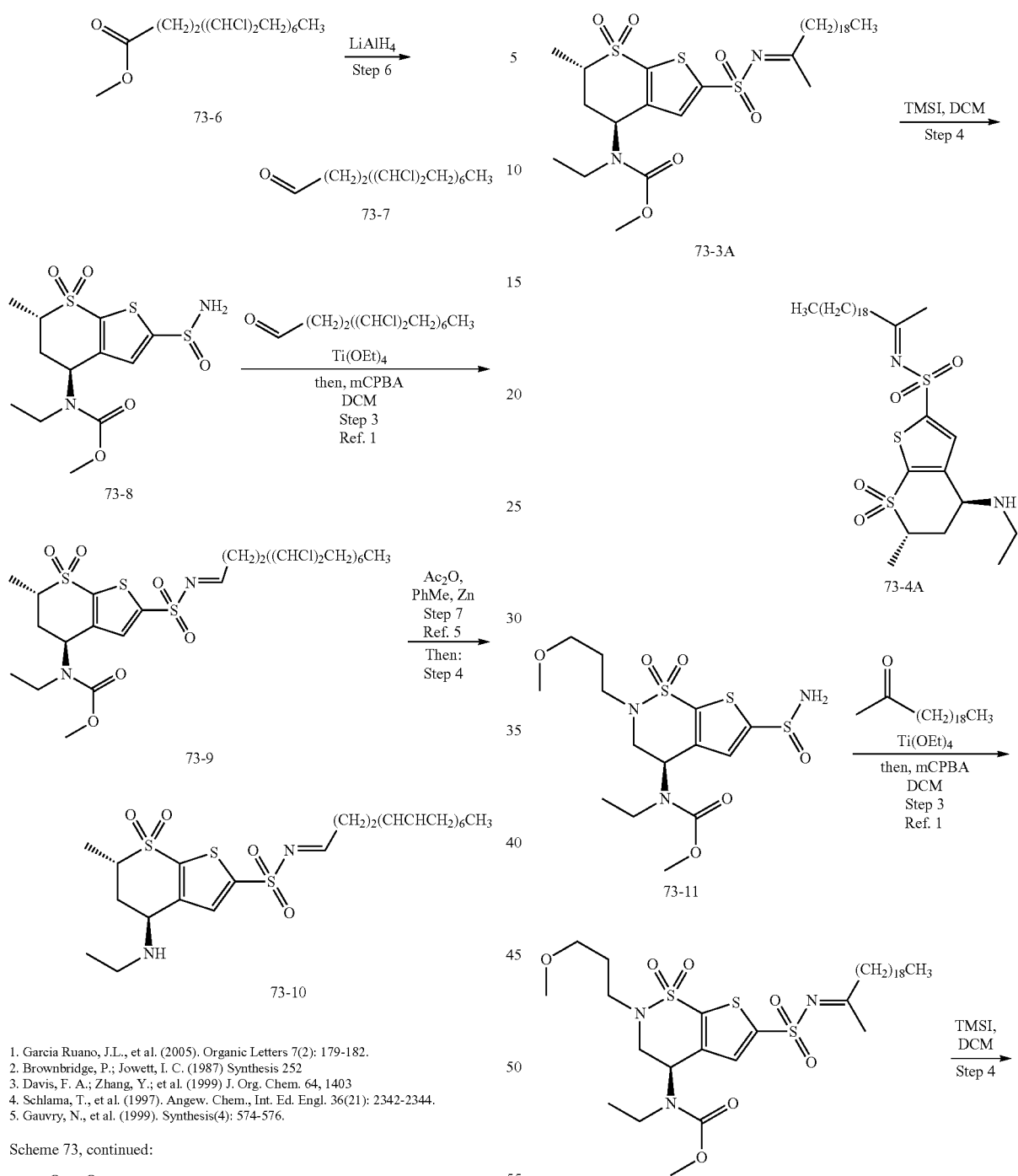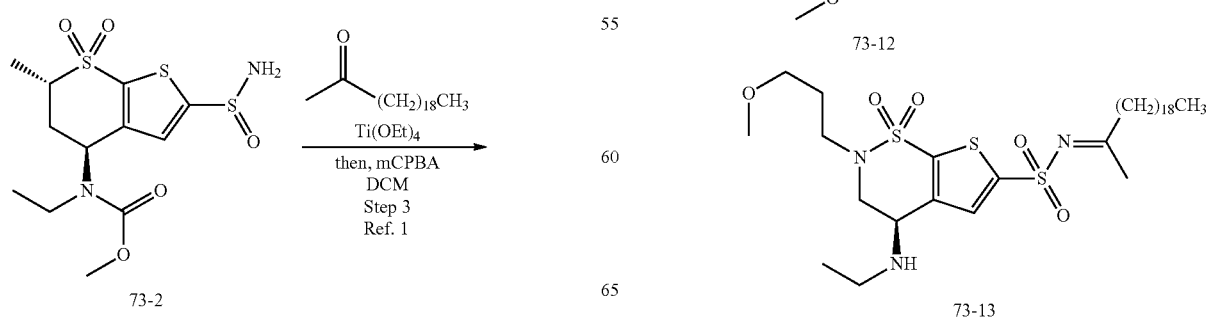

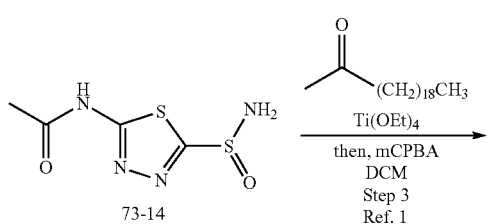

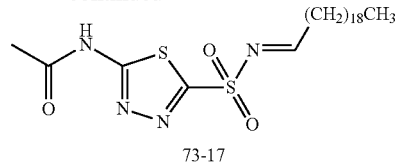

1. Garcia Ruano, J.L., et al. (2005). Organic Letters 7(2): 179-182.
2. Brownbridge, P.; Jowett, I. C. (1987) Synthesis 252
3. Davis, F. A.; Zhang, Y.; et al. (1999) J. Org. Chem. 64, 1403
4. Schlama, T., et al. (1997). Angew. Chem., Int. Ed. Engl. 36(21): 2342-2344.
5. Gauvry, N., et al. (1999). Synthesis(4): 574-576.

Scheme 73: A compound of the present invention can be prepared, for example, from precursors to various carbonic anhydrase inhibitors (CAIs). In Step 1 the appropriately substituted CAI precursor (72-1) is subjected to an alcohol and N-bromosuccinimide to afford a sulfinyl species (73-1). In Step 2 the appropriately substituted sulfinyl species is converted to a sulfonamide (73-2) as known in the art. In Step 3 the appropriately substituted sulfonamide (73-2, 73-8, 73-11, 73-14) is subjected to an aldehyde or ketone to afford an aldimine (73-3A, 73-3B, 73-9) or ketamine (73-12, 73-15, 73-17) respectively, which in a typical embodiment is hydrophobic. In Step 4 the sulfonyl aldimine or ketimine is deprotected as known in the art to afford a compound of Formula III (73-13), Formula IV (73-4A and 73-4B), Formula V, or Formula VI. In Step 5 an appropriately substituted unsaturated fatty ester (73-5) is protected as known in the art to afford a poly-chloro ester (73-6). In Step 6 the appropriately substituted ester is reduced with LAH as known in the art to afford an aldehyde (67-7). In Step 7 an appropriately substituted sulfonyl aldimine (73-9) can be deprotected as known in the art to afford an unsaturated sulfonyl aldimine (73-10) of Formula III, Formula IV, Formula V, or Formula VI.

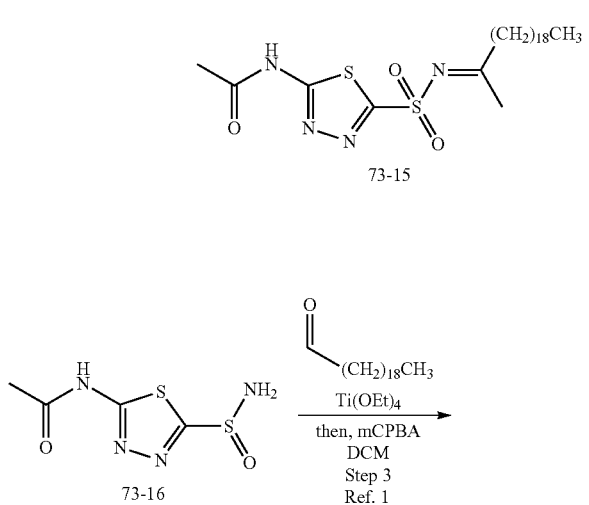

Schemw 74:

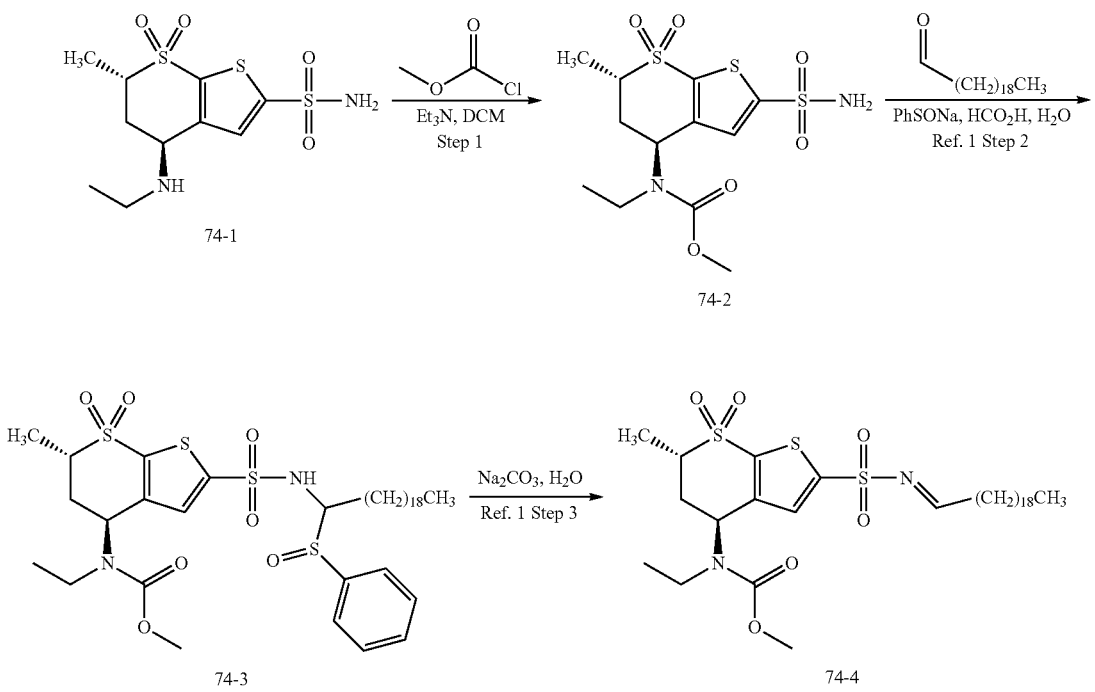

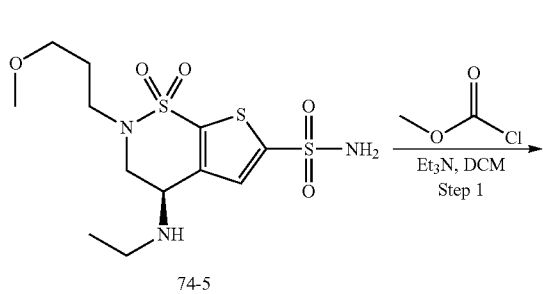
74-5
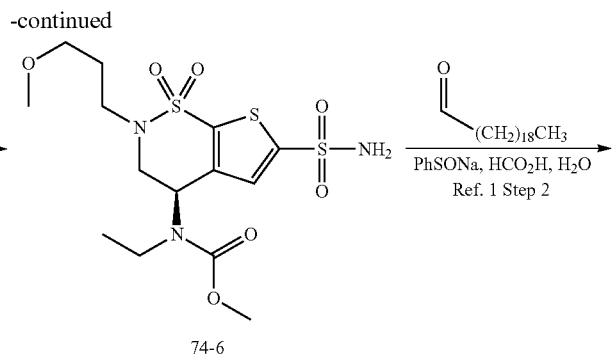
74-6
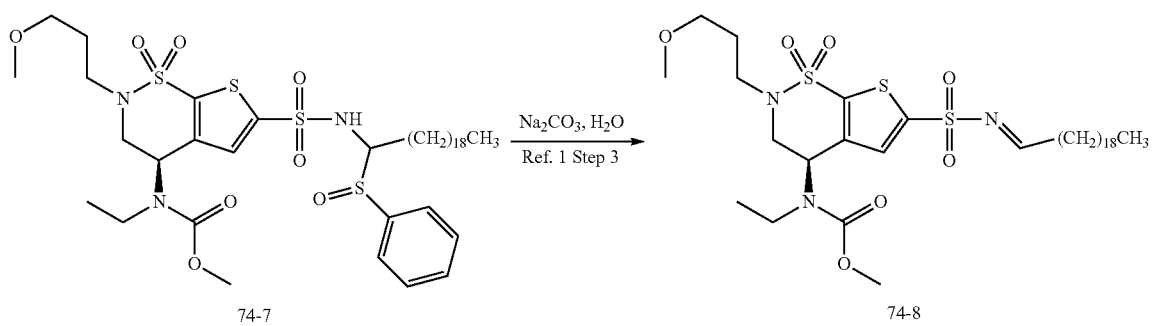
74-7 → 74-8
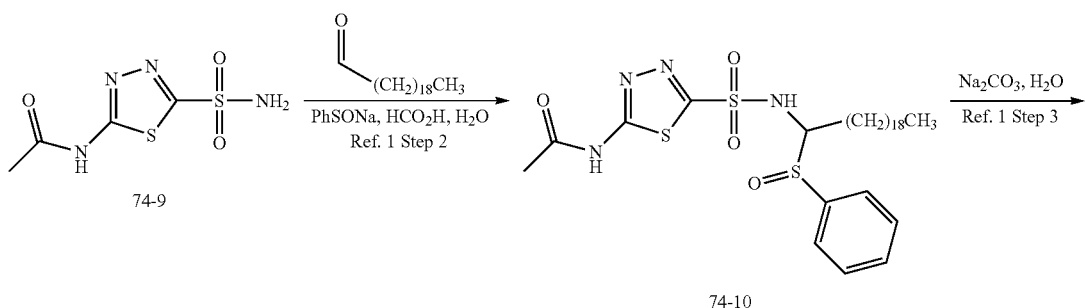
74-9 → 74-10
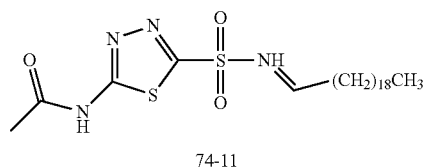
74-11
Scheme 74, continued:
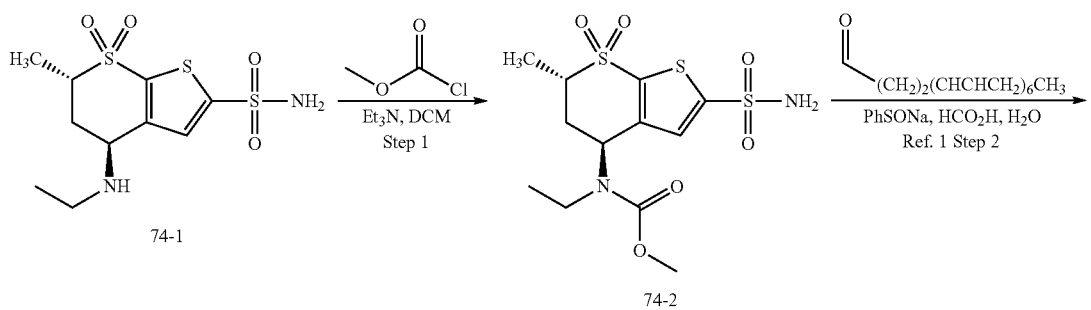
74-1 → 74-2

-continued
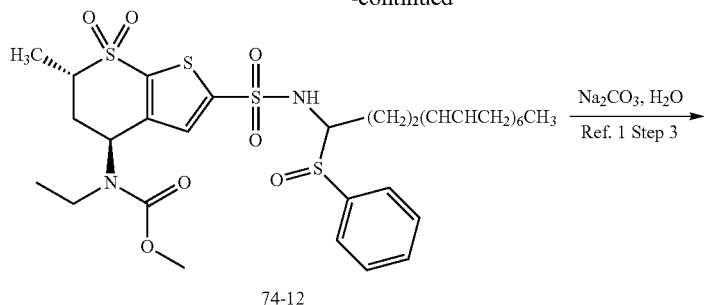
74-12
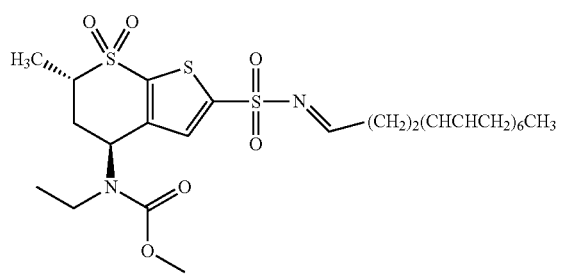
74-13
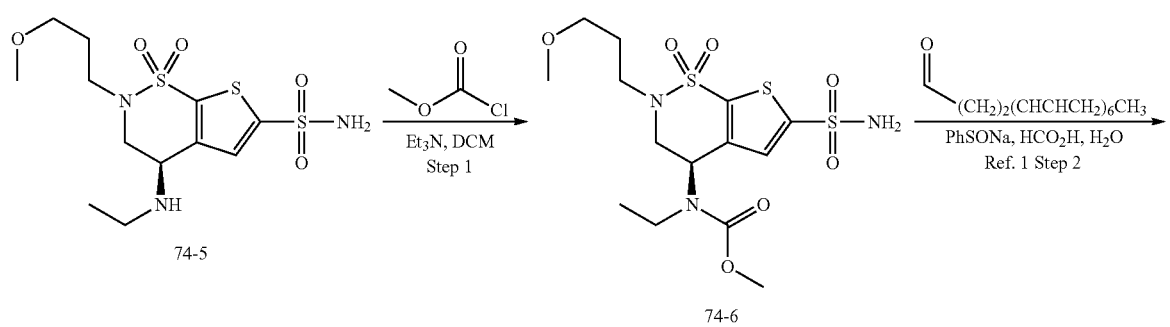
74-5    74-6
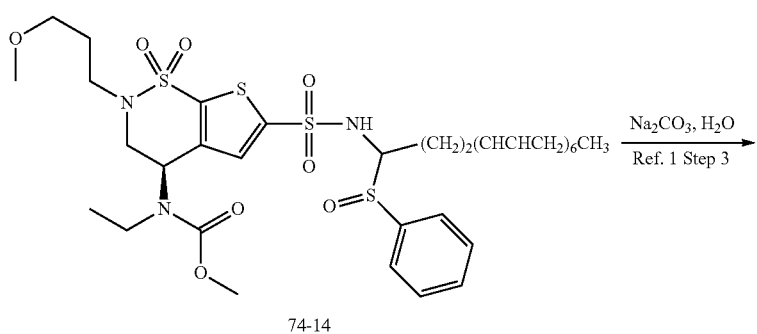
74-14
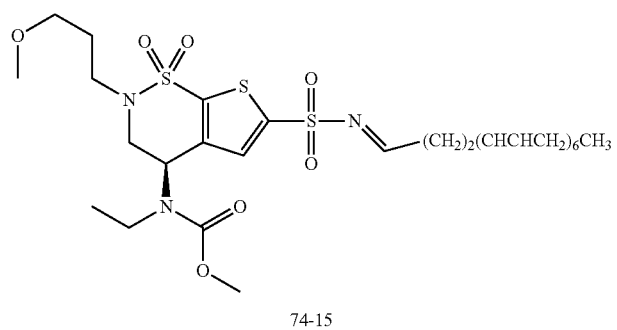
74-15

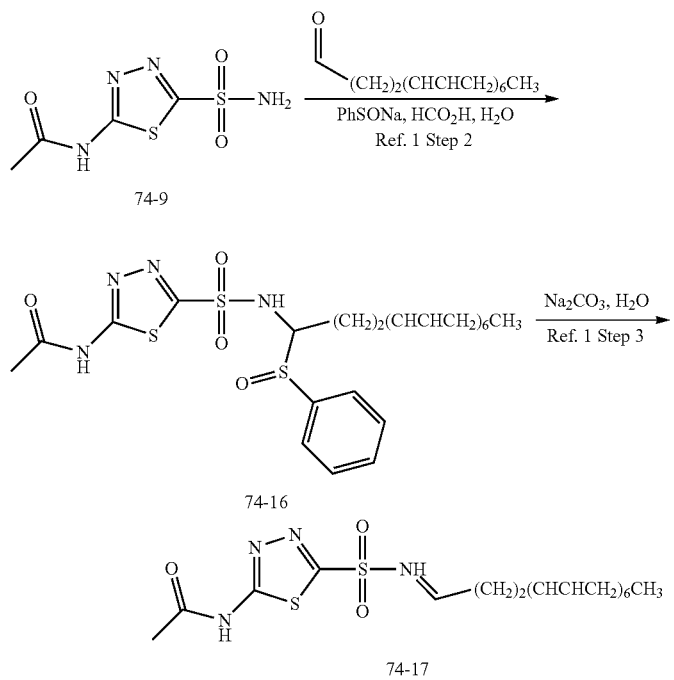

1. Org. Lett., 2006, 8, 2977-2980

Scheme 74: A compound of the present invention can be prepared, for example, from various carbonic anhydrase inhibitors (CAIs). In Step 1 the appropriately substituted CAI precursor (74-1, 74-5) is protected as known in the art to afford a carbamate species (74-2, 74-6, 74-16). In Step 2 the sulfonyl species is subjected to an aldehyde as known in the art to afford an aldimine precursor (74-3, 74-7, 74-10, 74-12, 74-14, 74-16), which in a typical embodiment is hydrophobic. In Step 3 the de-sulfination affords an aldimine that is a protected compound (74-4, 74-8, 74-11, 74-13, 74-15, 74-17) of Formula III, Formula IV, Formula V, or Formula VI.

Example 12. General Routes of Synthesis to Compounds of Formula VII

Scheme 75:

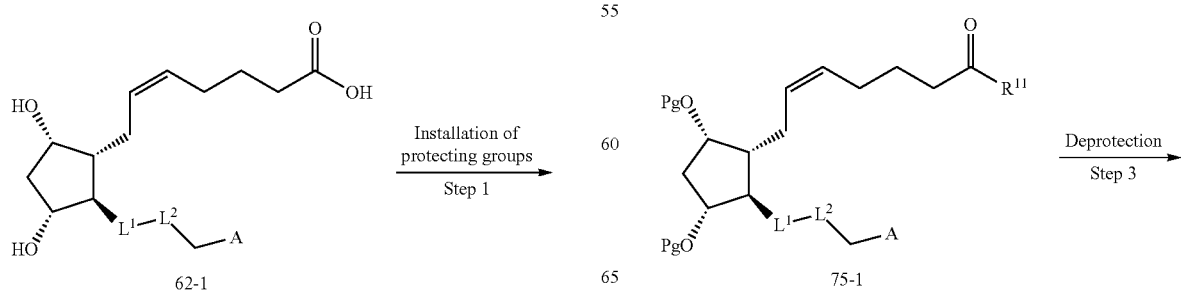

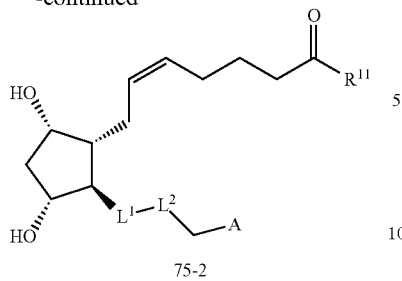

75-2

Scheme 75: A compound of the present invention can be prepared, for example, from a prostaglandin and a carbonic anhydrase inhibitor. In Step 1 the prostaglandin's (62-1) hydroxyl groups are protected as known in the art to afford a protected species (63-1). In Step 2 the protected species (63-1) is converted to an activated electrophile (63-2) as known in the art to subsequently be reacted with an appropriately substituted nucleophile in Step 3 to afford an ester or amide with attachment either directly or indirectly through a linker to a carbonic anhydrase inhibitor (75-1). In Step 4 the prostaglandin covalently bound to a carbonic anhydrase inhibitor is deprotected to afford a compound of Formula VII (75-2).

Example 13. Representative Routes of Synthesis to Compounds of Formula VII

Scheme 76:

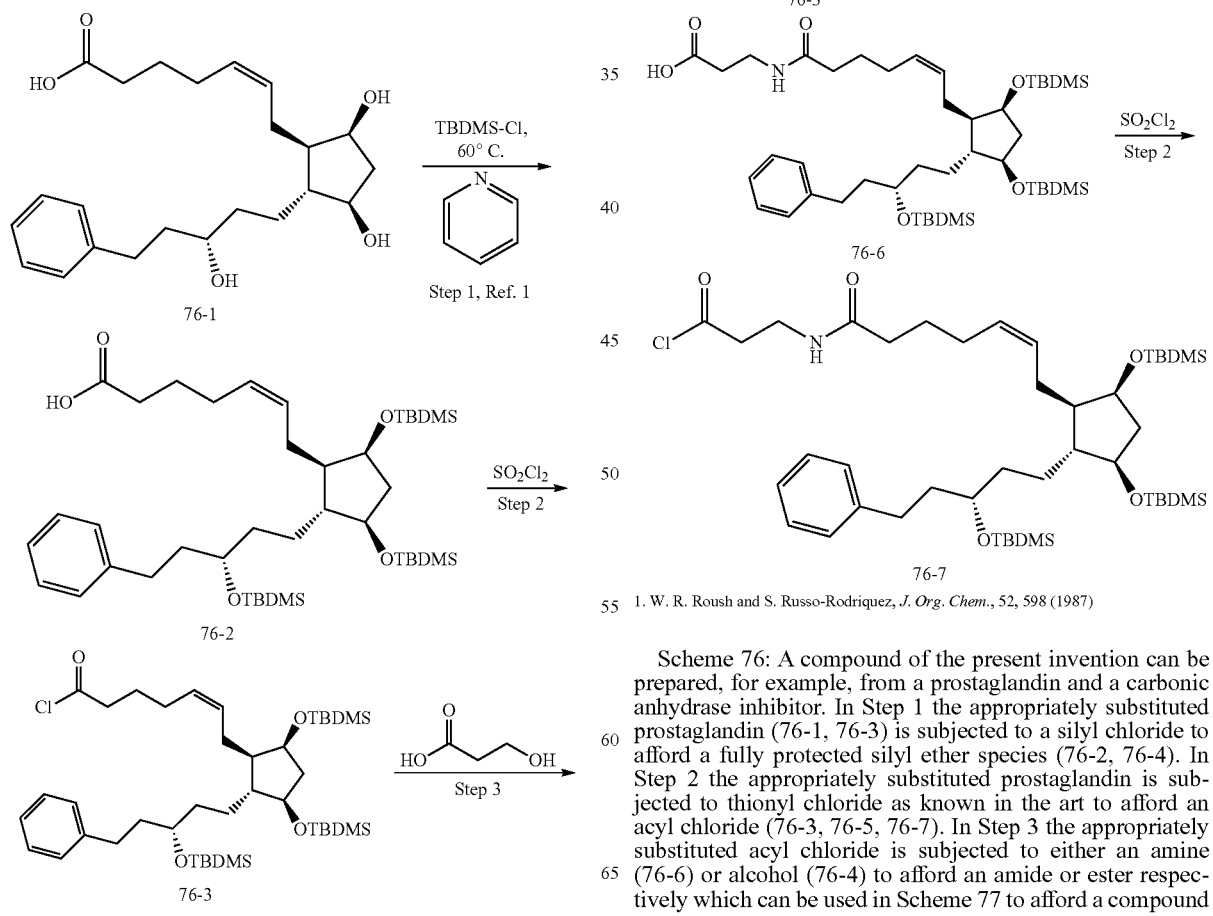

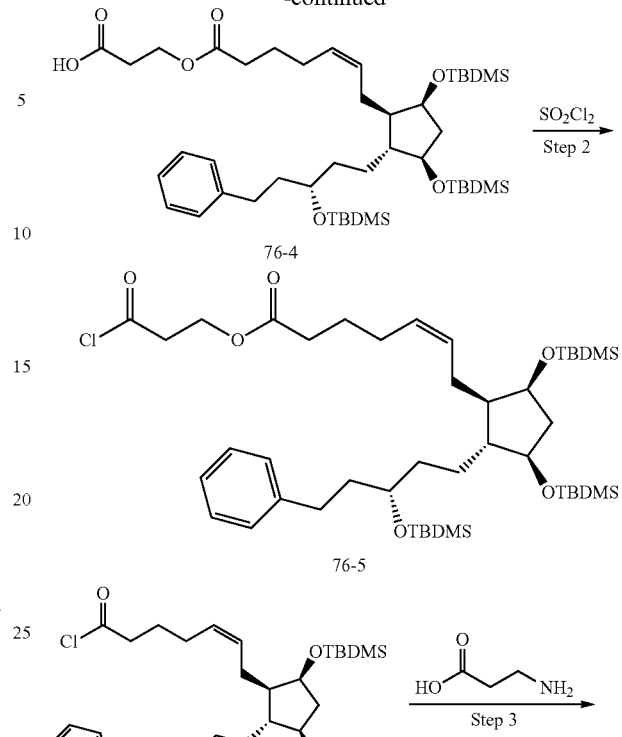

1. W. R. Roush and S. Russo-Rodriquez, *J. Org. Chem.*, 52, 598 (1987)

Scheme 76: A compound of the present invention can be prepared, for example, from a prostaglandin and a carbonic anhydrase inhibitor. In Step 1 the appropriately substituted prostaglandin (76-1, 76-3) is subjected to a silyl chloride to afford a fully protected silyl ether species (76-2, 76-4). In Step 2 the appropriately substituted prostaglandin is subjected to thionyl chloride as known in the art to afford an acyl chloride (76-3, 76-5, 76-7). In Step 3 the appropriately substituted acyl chloride is subjected to either an amine (76-6) or alcohol (76-4) to afford an amide or ester respectively which can be used in Scheme 77 to afford a compound of Formula VII.

Scheme 77
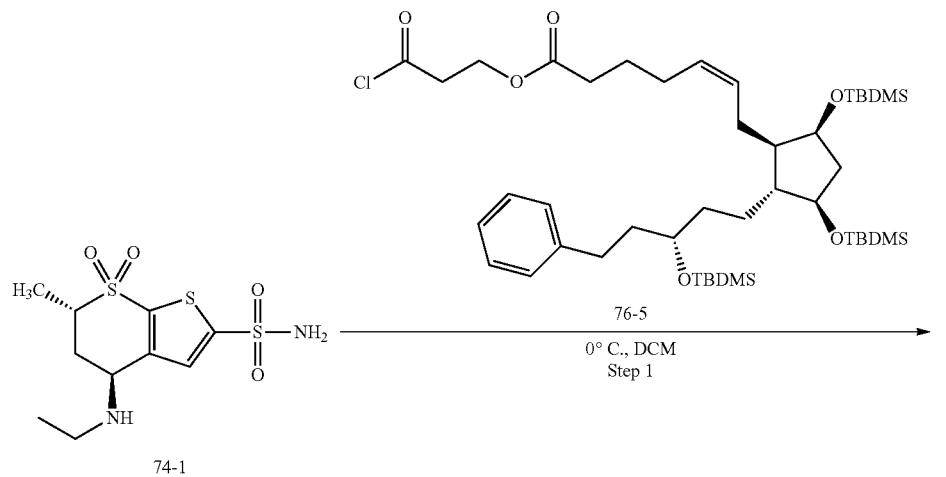
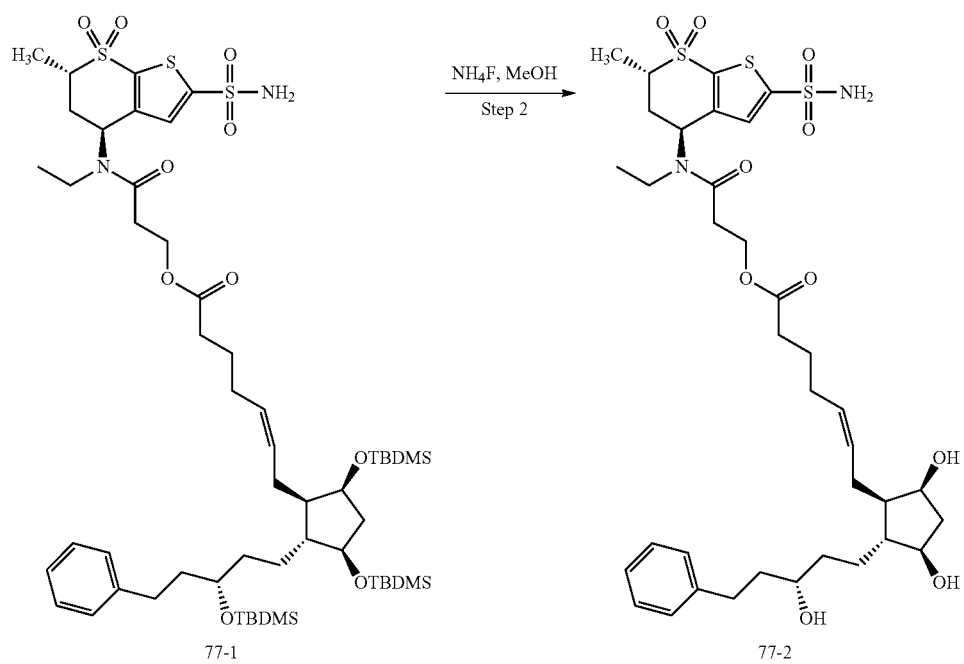
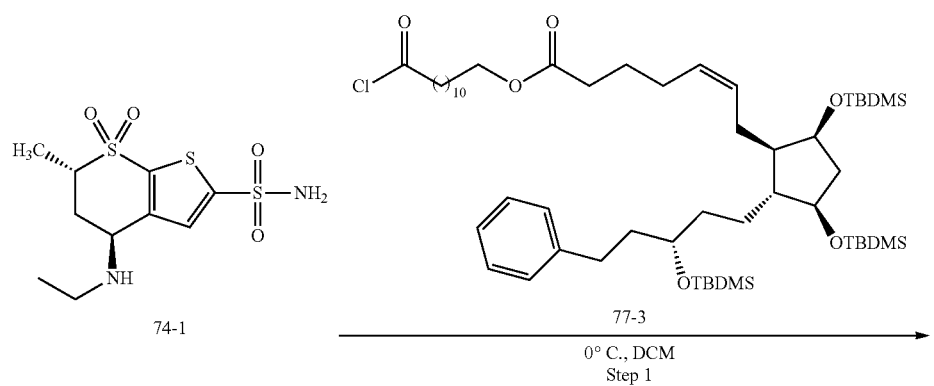

-continued
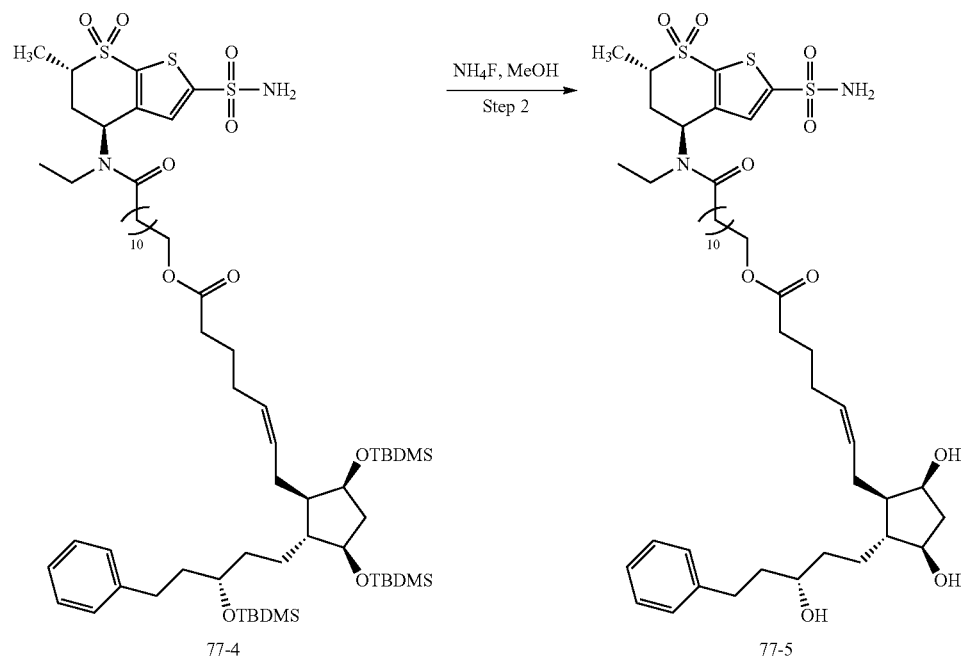
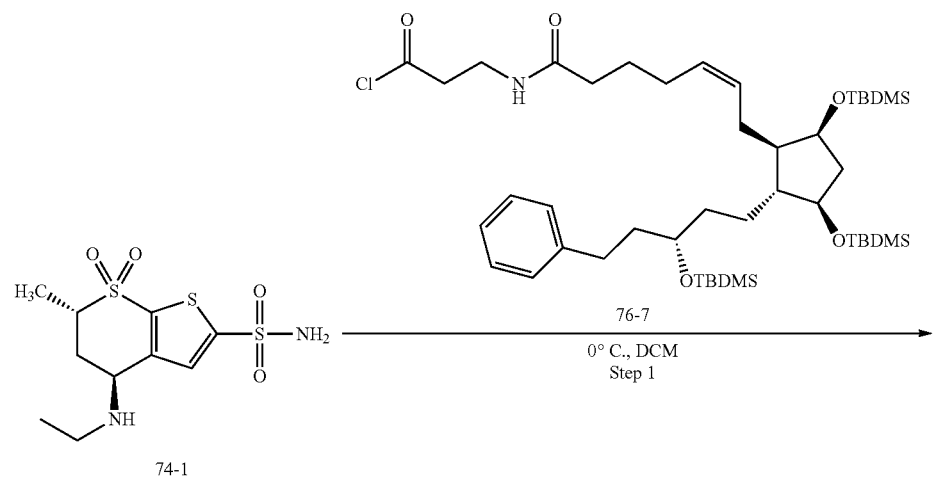

-continued
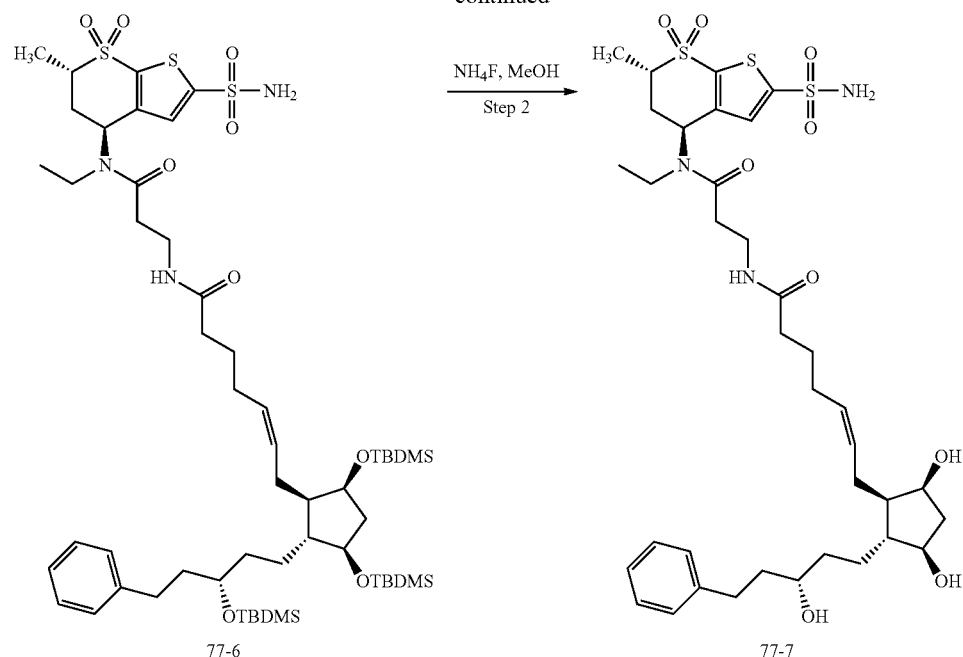
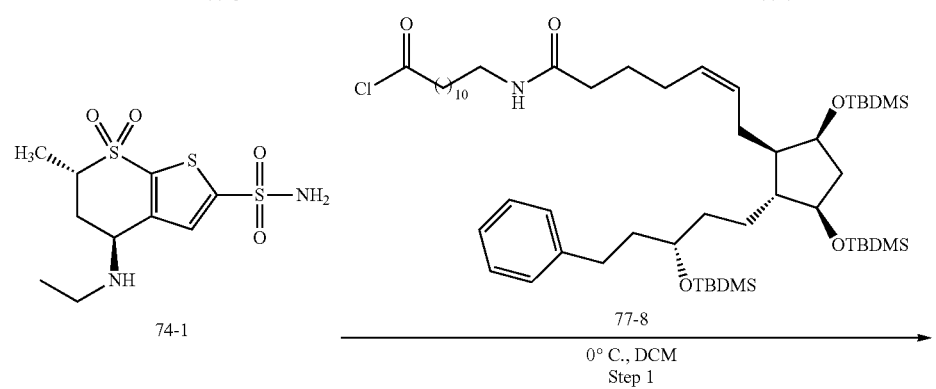
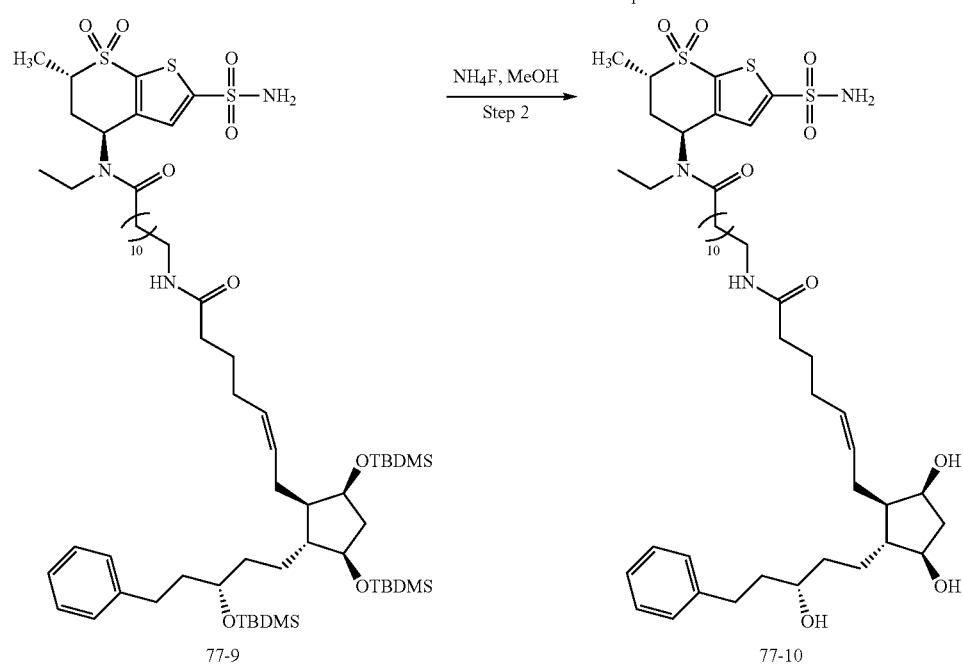

Scheme 77: A compound of the present invention can be prepared, for example, from a prostaglandin and a carbonic anhydrase inhibitor. In Step 1 the previously prepared acyl chloride (76-5, 77-3, 76-7, 77-8) is subjected to a carbonic anhydrase inhibitor (CAI) (74-1) to afford a prostaglandin coupled to a CAI species (77-1, 77-4, 77-6, 77-9). In Step 2 the appropriately substituted coupled species is deprotected as known in the art to afford a compound (77-2, 77-5, 77-7, 77-10) of Formula VII.

Scheme 78:

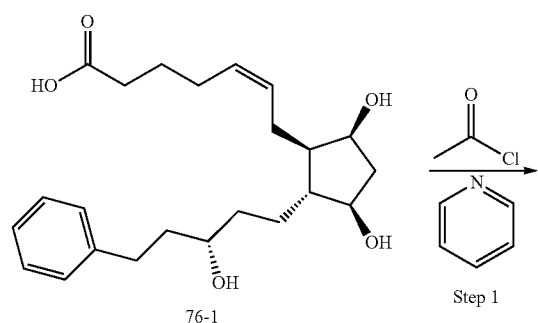

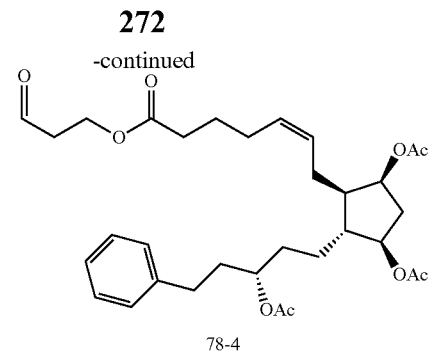

78-4

Scheme 78: A compound of the present invention can be prepared, for example, from a prostaglandin and a carbonic anhydrase inhibitor. In Step 1 the appropriately substituted prostaglandin (76-1) is subjected to an acyl chloride to afford a fully protected ester species (78-1). In Step 2 the appropriately substituted prostaglandin is subjected to thionyl chloride as known in the art to afford an acyl chloride (78-2). In Step 3 the appropriately substituted acyl chloride is subjected to either an amine or alcohol to afford an amide or ester (78-3) respectively with a protected aldehyde attached. In Step 4 the appropriately substituted acetal is subjected to acid as known in the art to afford an aldehyde (78-4) which can be used in Scheme 79 to afford a compound of Formula VII.

Scheme 79:

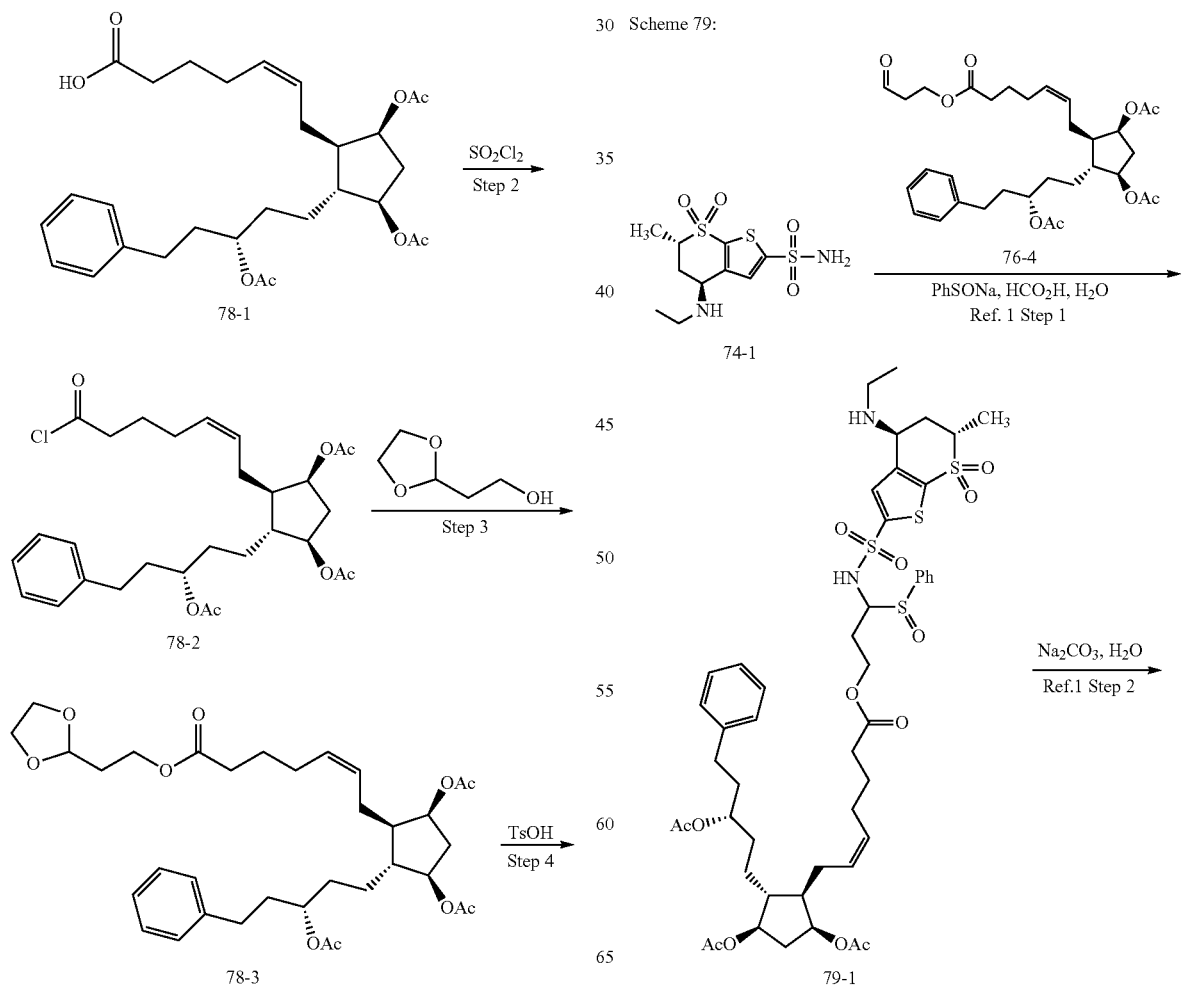

273

-continued

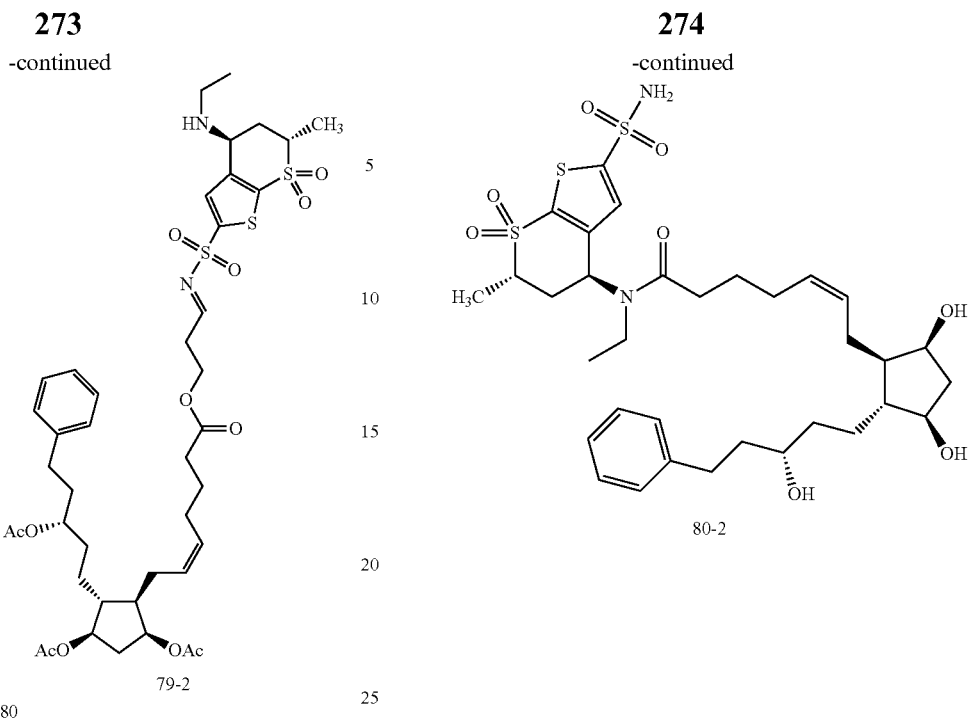

79-2

1. Org. Lett., 2006, 8, 2977-2980

Scheme 79: A compound of the present invention can be prepared, for example, from a prostaglandin and a carbonic anhydrase inhibitor. In Step 1 the previously prepared aldehyde (76-4) is subjected to a carbonic anhydrase inhibitor (CAI) (74-1) to afford a prostaglandin coupled to a CAI species (79-1). In Step 2 the appropriately substituted coupled species is desulfinated as known in the art to afford a compound (79-2) of Formula VII.

Scheme 80:

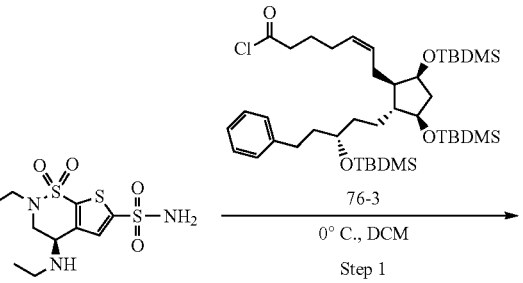

274

-continued 80-2

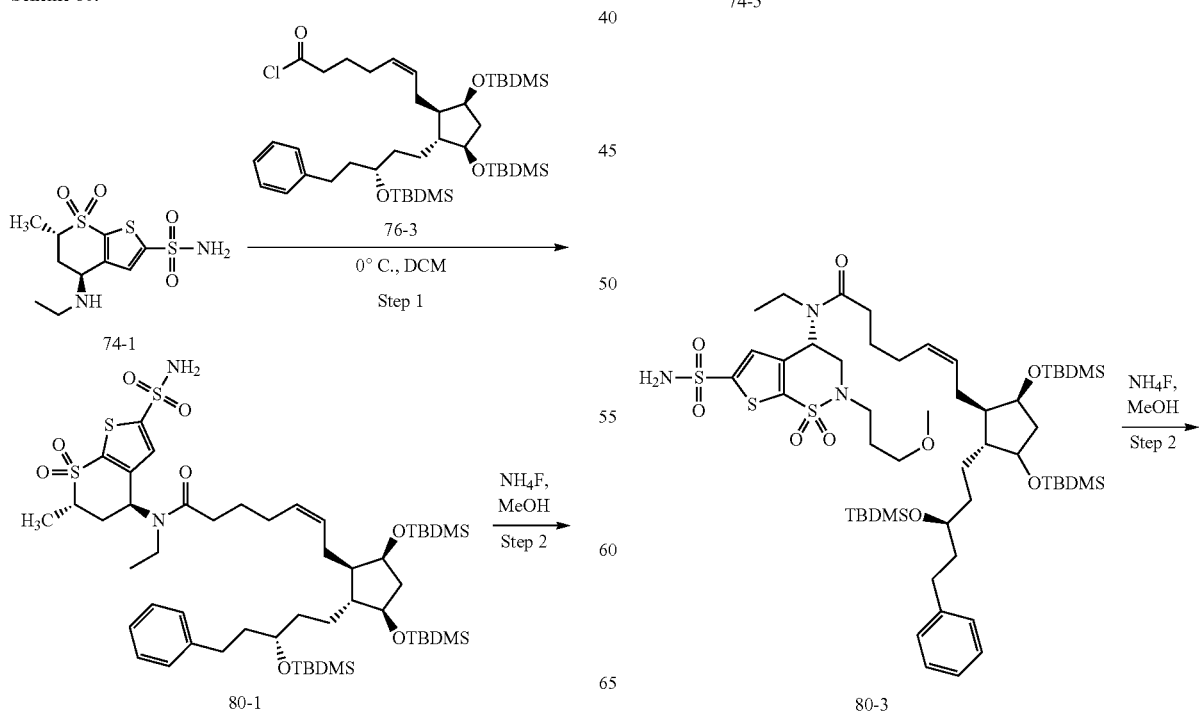

275

-continued

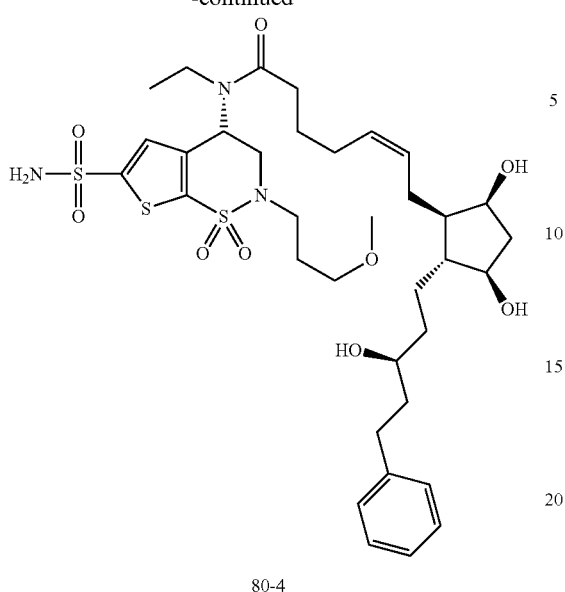

80-4

Scheme 80: A compound of the present invention can be prepared, for example, from a prostaglandin and a carbonic anhydrase inhibitor (CAI). In Step 1 the appropriately substituted CAI (74-1, 74-5) is subjected to an acyl chloride of a prostaglandin (76-3) to afford an amide (80-1, 80-3). In Step 2 the appropriately substituted amide is deprotected to afford a compound (80-2, 80-4) of Formula VII.

Example 14. General Routes of Synthesis to Compounds of Formula VIII

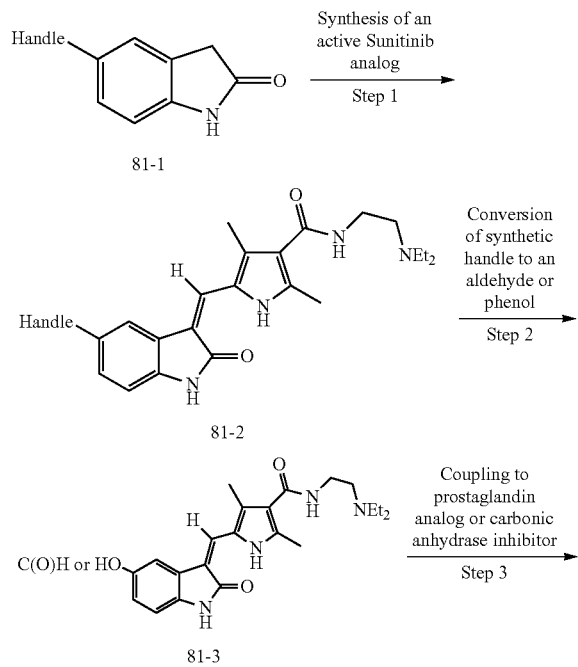

276

-continued

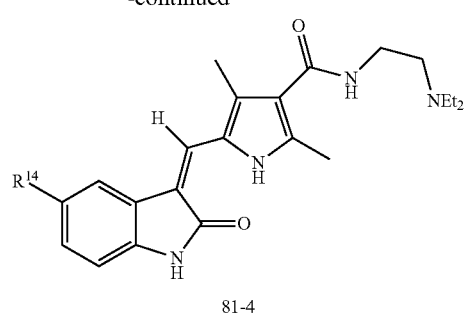

81-4

Scheme 81: A compound of the present invention can be prepared, for example, from a Sunitinib derivative and either a prostaglandin or a carbonic anhydrase inhibitor (CAI). In Step 1 a commercially available Sunitinib precursor (81-1) is converted to a Sunitinib derivative (81-2) as known in the art. In Step 2 the synthetic handle (81-2) is converted to either an aldehyde (to couple with a CAI) or a phenol (to couple with a prostaglandin) (81-3). In Step 3 the two compounds are covalently bound as known in the art to afford a compound (81-4) of Formula VIII.

Example 15. Representative Routes of Synthesis to Compounds of Formula VIII

Scheme 82:

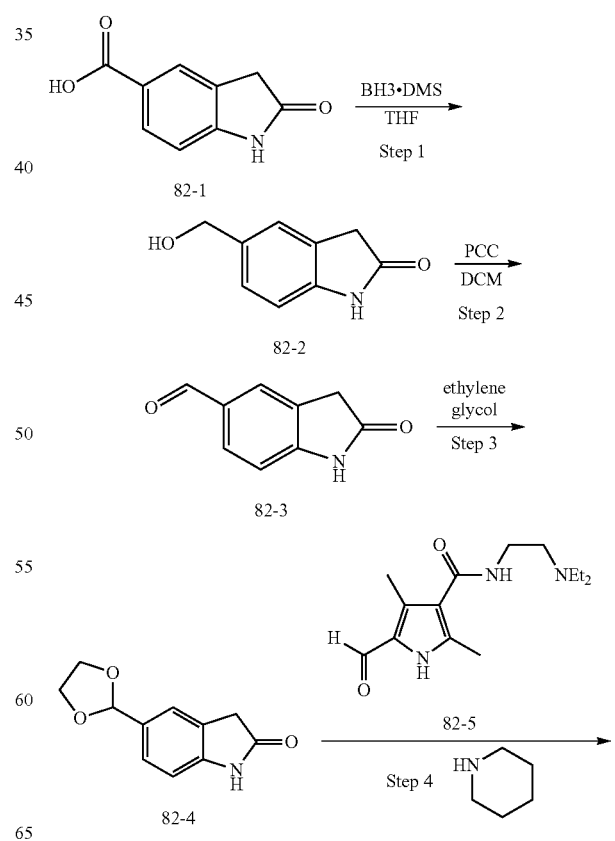

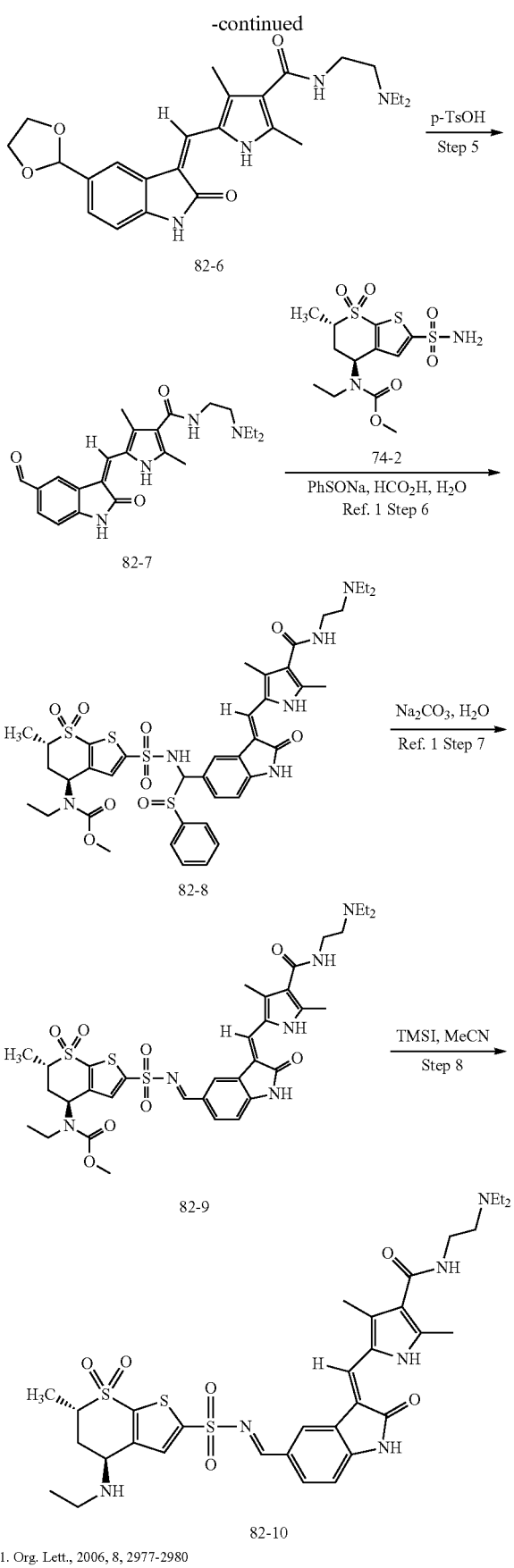

Scheme 82: A compound of the present invention can be prepared, for example, from a carbonic anhydrase inhibitor (CAI) and a Sunitinib derivative. In Step 1 the appropriately substituted carboxylic acid (82-1) is subjected to borane complexed with DMS to afford an alcohol (82-2). In Step 2 the appropriately substituted alcohol (82-2) is oxidized as known in the art to afford an aldehyde (82-3). In Step 3 the appropriately substituted aldehyde (82-3) is subjected to ethylene glycol to afford a cyclic acetal (82-4). In Step 4 the appropriately substituted heterocycle (82-4) is subjected to an aldehyde (82-5) as known in the art to afford a conjugated alkene (82-6). In Step 5 the appropriately substituted acetal (82-6) is deprotected with acid as known in the art to afford an aldehyde (82-7). In Step 6 the appropriately substituted Sunitinib derivative (82-7) is subjected to a CAI (74-2) to afford a coupled species (82-8). In Step 7 the appropriately substituted species is desulfinated as known in the art to afford an aldimine (82-9). In Step 8 the appropriately substituted carbamate (82-9) is deprotected as known in the art to afford a compound (82-10) of Formula VIII.

Scheme 83:

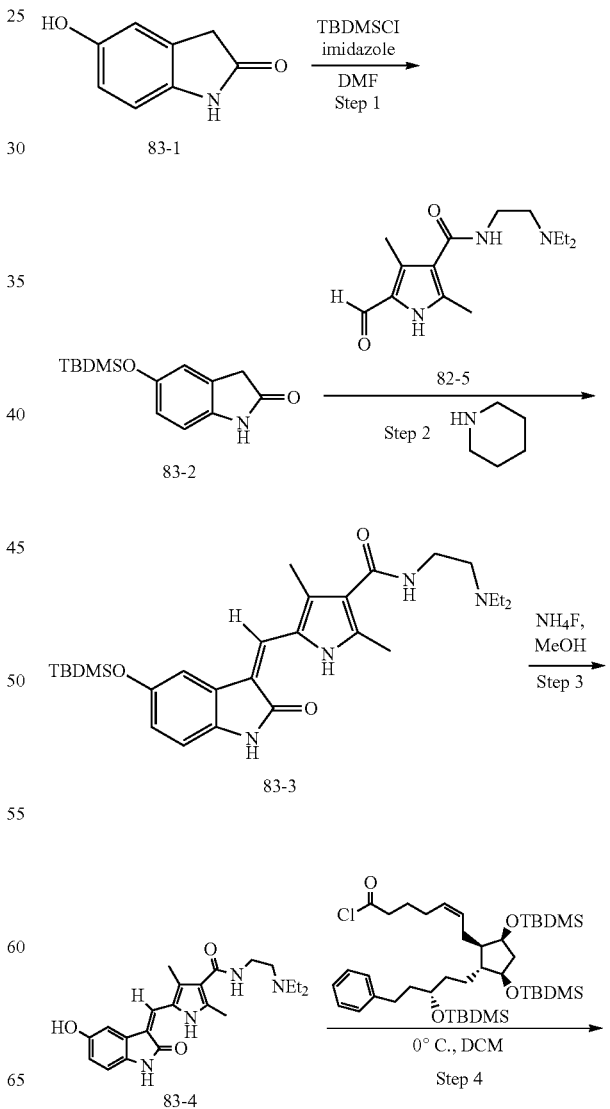

1. Org. Lett., 2006, 8, 2977-2980

279
-continued

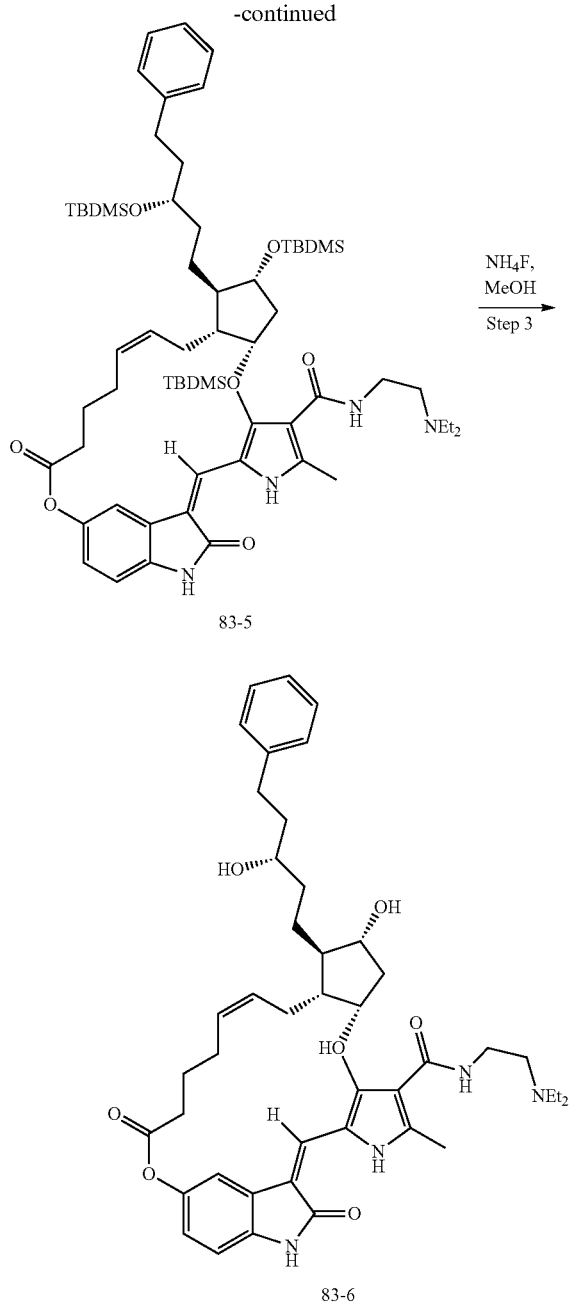

280
Example 16. Representative Routes of Synthesis to Compounds of Formula IX Scheme 84:

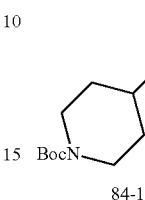

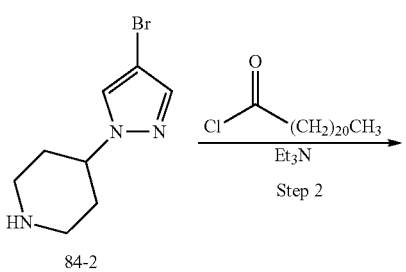

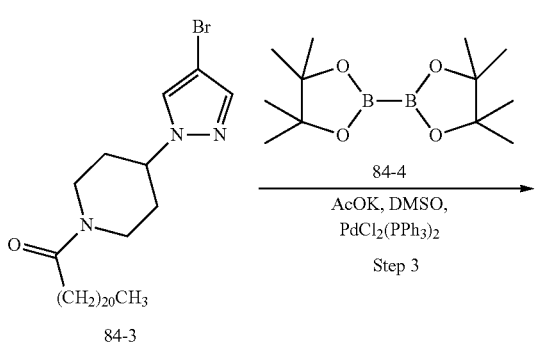

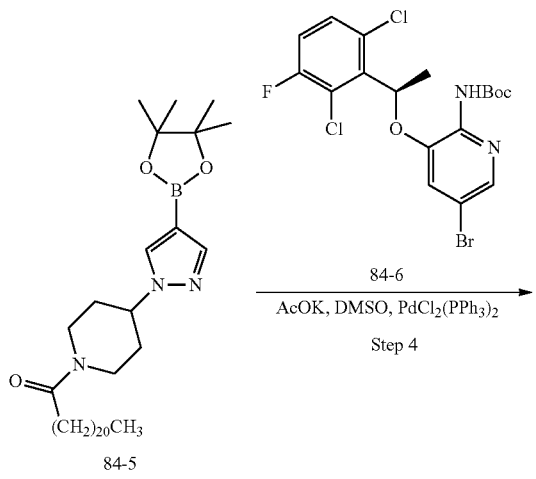

Scheme 83: A compound of the present invention can be prepared, for example, from a prostaglandin and a Sunitinib derivative. In Step 1 the appropriately substituted phenol (83-1) is subjected to a silyl chloride as known in the art to afford a silyl ether (83-2). In Step 2 the appropriately substituted heterocycle (82-2) is subjected to an aldehyde (82-5) as known in the art to afford a conjugated alkene (83-3). In Step 3 the appropriately substituted silyl ether (83-3) is deprotected as known in the art to afford a phenol (83-4). In Step 4 the appropriately substituted Sunitinib derivative (83-4) is subjected to an acyl chloride of a prostaglandin (76-3) to afford a coupled species (83-5) which upon deprotection is a compound (83-6) of Formula VIII.

281

-continued

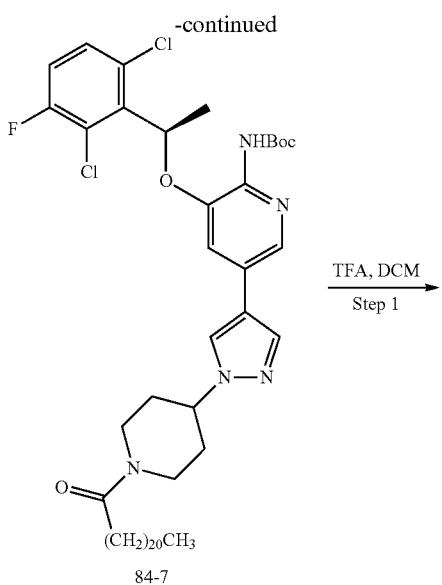

84-7

84-8

Scheme 84: A compound of the present invention can be prepared, for example, from a derivative of Crizotonib. In Step 1 the appropriately protected piperidine (84-1) is subjected to acidic conditions to remove the Boc group and afford an amine (84-2). In Step 2 the appropriately substituted piperidine (84-2) is acylated as known in the art to afford an amide (84-3). In Step 3 the appropriately substituted halo-pyrazole (84-3) is subjected to a bis-boronic ester (84-4) as known in the art to afford a boronic ester (84-5). In Step 4 the appropriately substituted boronic ester (84-5) is coupled with an aryl bromide (84-6) with catalytic palladium to afford a protected derivative of Crizotinib (84-7) which is Boc-deprotected (84-8) to afford a compound of Formula IX.

282

Example 17. Representative Routes of Synthesis to Compounds of Formula X

Scheme 85:

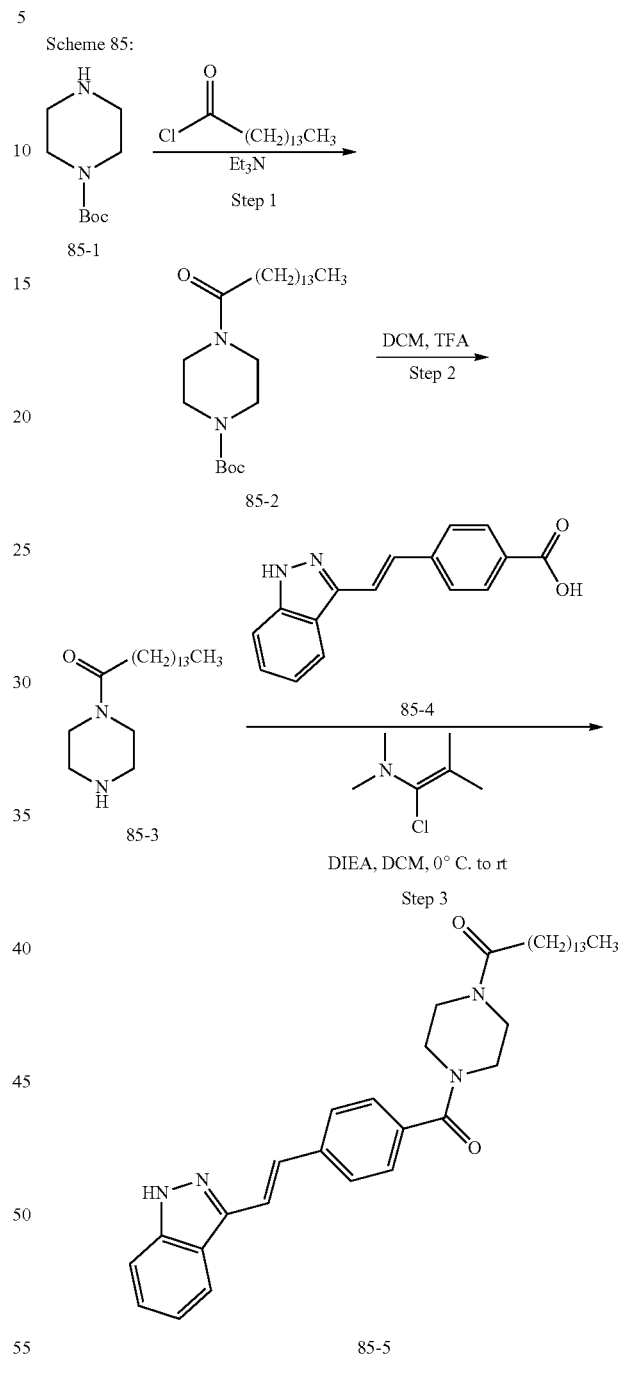

Scheme 85: A compound of the present invention can be prepared, for example, from a derivative of KW-2449. In Step 1 the appropriately mono-protected piperazine (85-1) is acylated as known in the art to afford an amide (85-2). In Step 2 the appropriately substituted piperazine (85-2) is subjected to acidic conditions to remove the Boc group and afford an amine (85-3). In Step 3 the appropriately substituted amine (85-3) is coupled to an aryl carboxylic acid (85-4) as known in the art to afford a compound (85-5) of Formula X.

Example 18. Representative Routes of Synthesis to Compounds of Formula XI

Scheme 86:

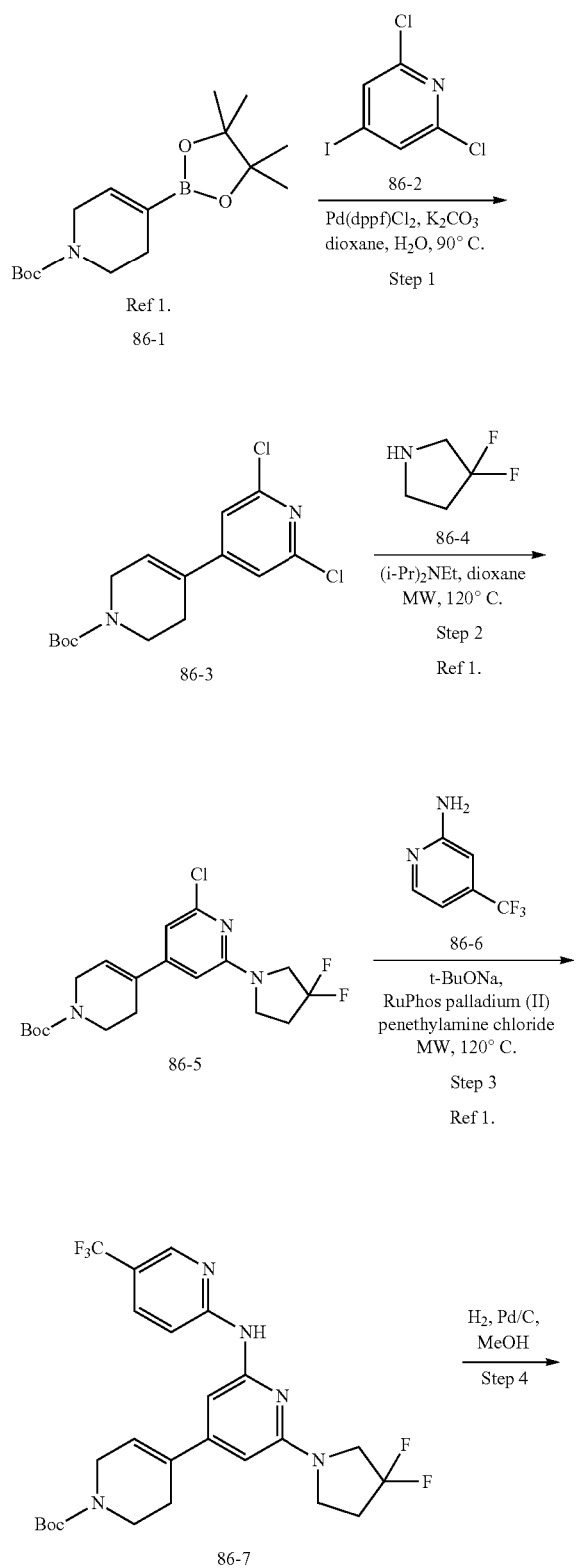

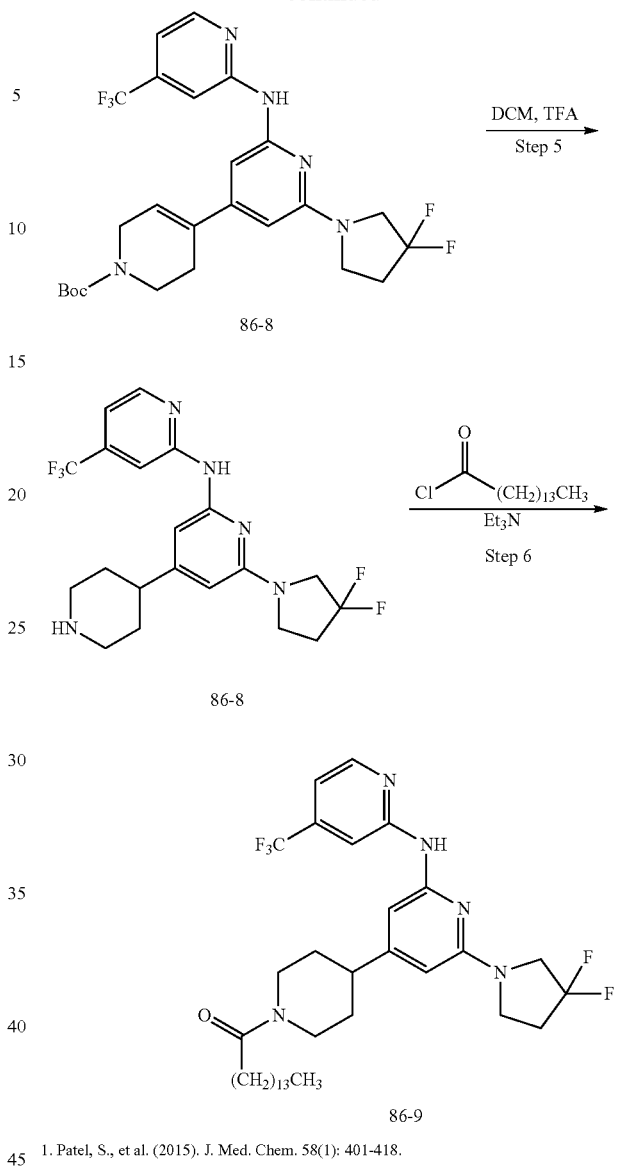

1. Patel, S., et al. (2015). J. Med. Chem. 58(1): 401-418.

Scheme 86: A compound of the present invention can be prepared, for example, from various piperidino based DLK inhibitors. In Step 1 the boronic ester (86-1) as described in the literature is coupled to an aryl iodide (86-2) in the presence of catalytic palladium to afford a heterocycle (86-3). In Step 2 the appropriately substituted aryl chloride (86-3) is subjected to nucleophilic conditions as known in the art to afford a functionalized aryl chloride (86-5). In Step 3 the appropriately substituted aryl chloride (86-5) is subjected to nucleophilic conditions again as known in the art to afford a complex species (86-7). In Step 4 the appropriately substituted piperidino double bond is reduced with palladium catalyst to afford a protected piperidine species (86-8). In Step 5 the appropriately substituted piperdine species (86-8) is subjected to acidic conditions to remove the Boc group and afford an amine (86-9). In Step 6 the appropriately substituted amine (86-9) is acylated as known in the art with a variety of acyl chlorides to afford a compound (86-10) of Formula XI.

Example 19. Representative Routes of Synthesis to Compounds of Formula XII Scheme 87

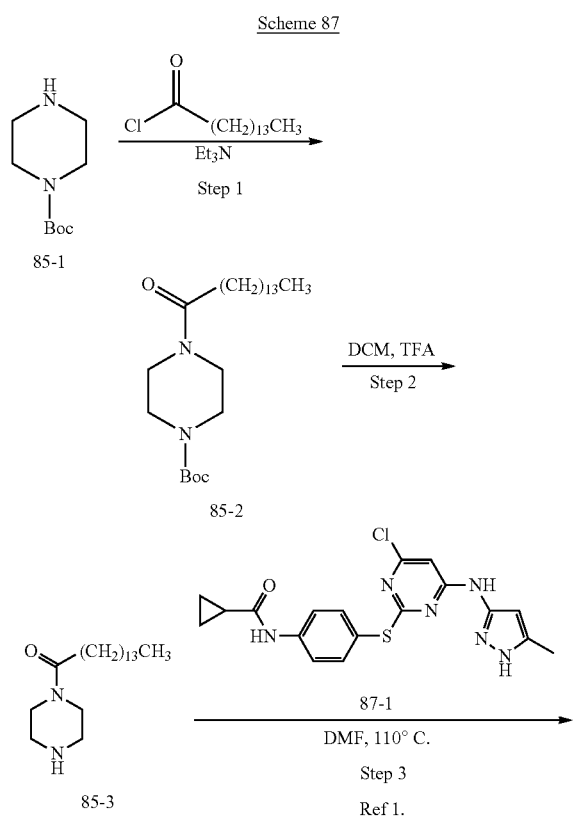

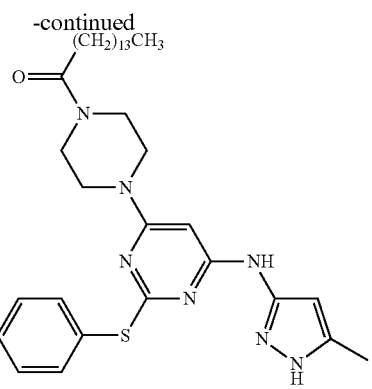

1. Bebbington, D., et al. (2009). Bioorg. Med. Chem. Lett. 19(13): 3586-3592.

1. Bebbington, D., et al. (2009). Bioorg. Med. Chem. Lett. 19(13): 3586-3592.

Scheme 87: A compound of the present invention can be prepared, for example, from a derivative of Tozasertib. In Step 1 the appropriately mono-protected piperazine (85-1) is acylated as known in the art to afford an amide (85-2). In Step 2 the appropriately substituted piperazine (85-2) is subjected to acidic conditions to remove the Boc group and afford an amine (85-3). In Step 3 the appropriately substituted amine (85-3) is subjected to an aryl chloride (87-1) as known in the art to afford a compound (87-2) of Formula XII.

Example 20. Non-Limiting Examples of Compounds of Formula I

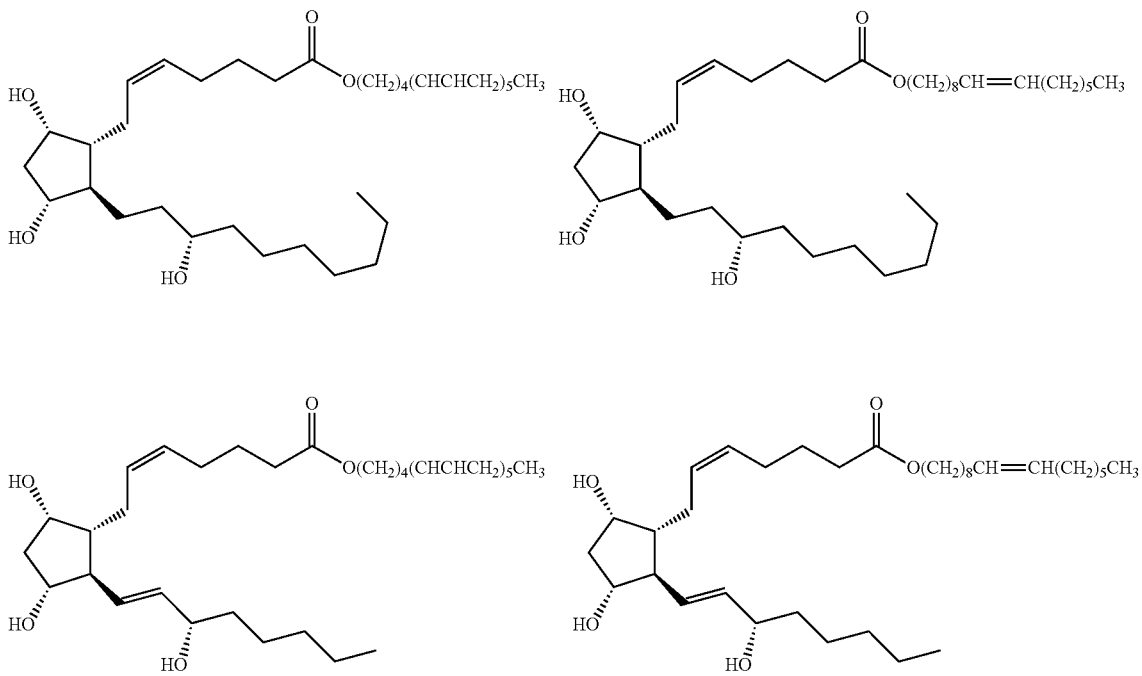

287
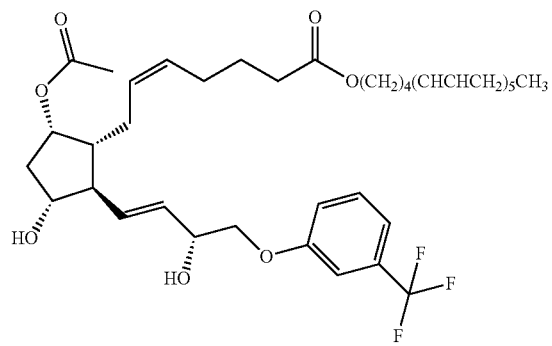
288
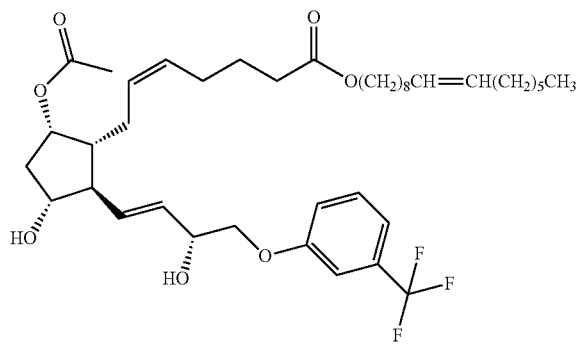
-continued
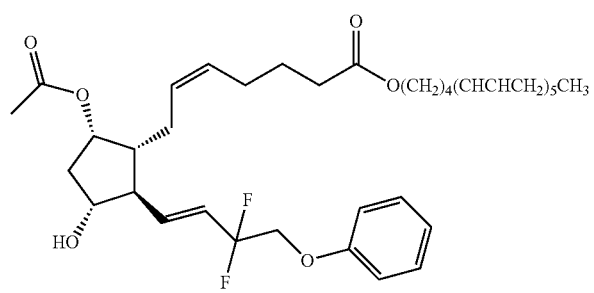
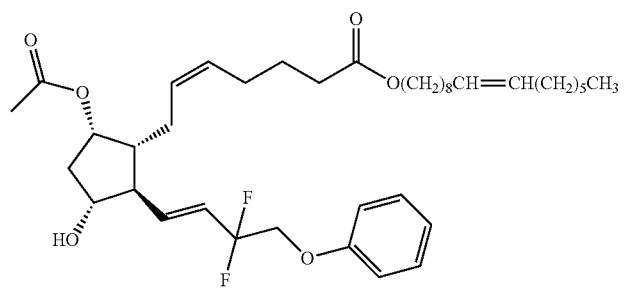
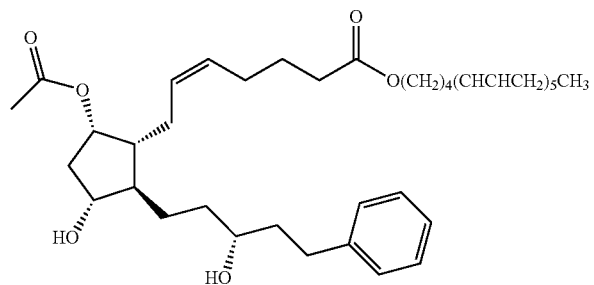
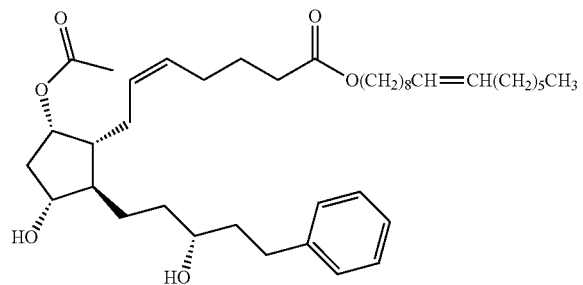

-continued
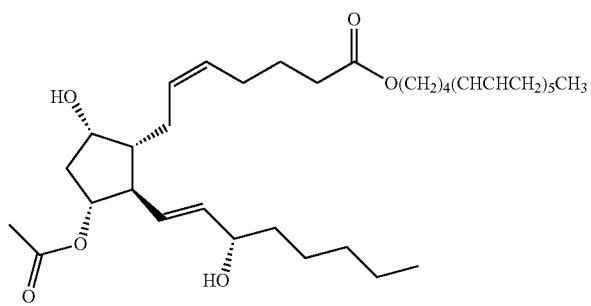
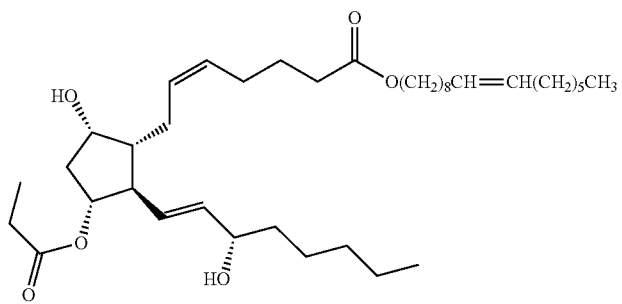
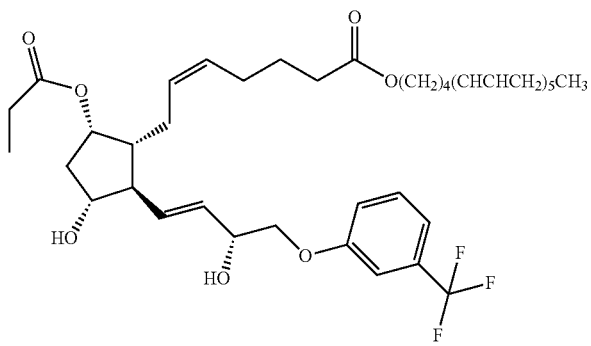
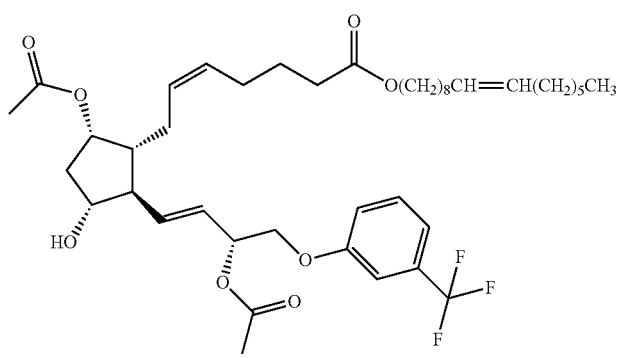
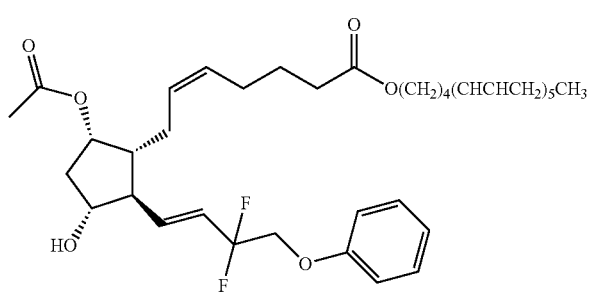

-continued
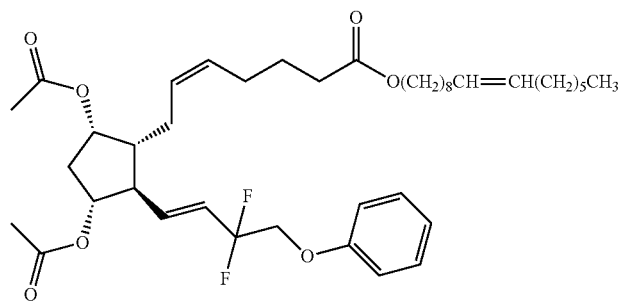
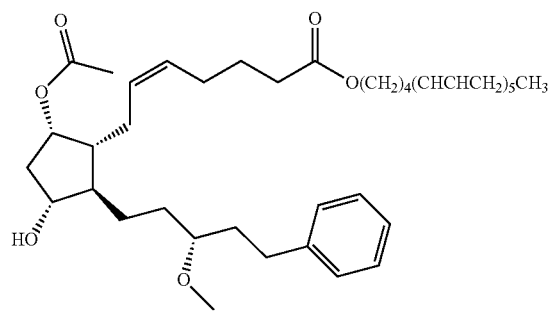
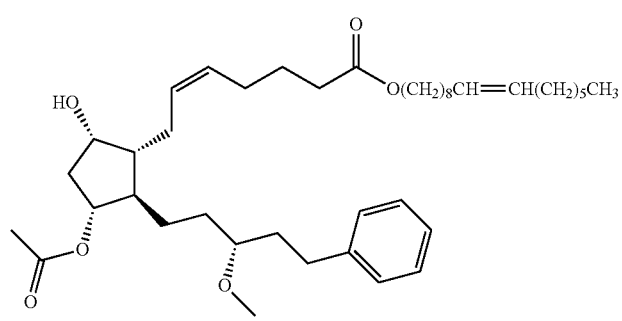
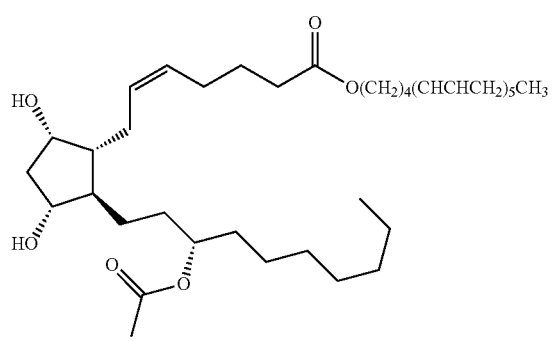
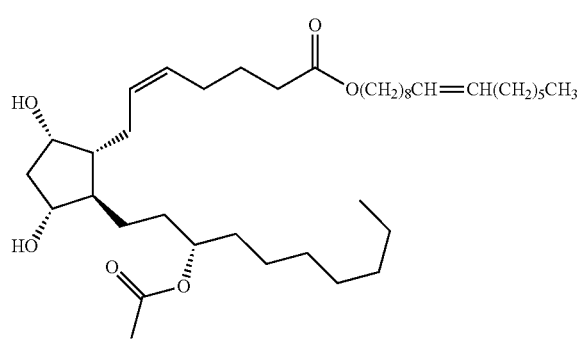

-continued
293
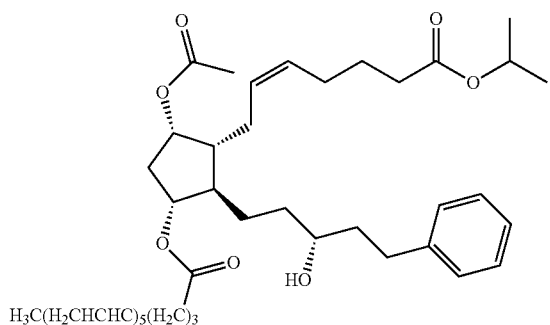
294
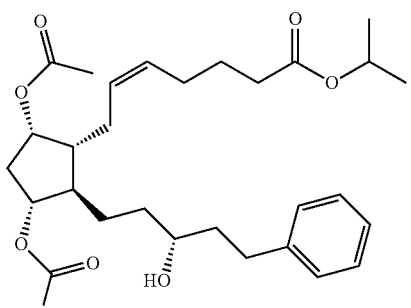
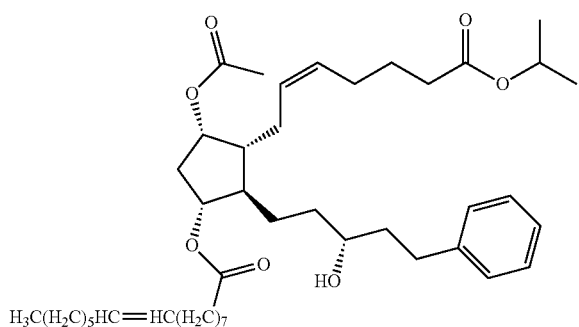
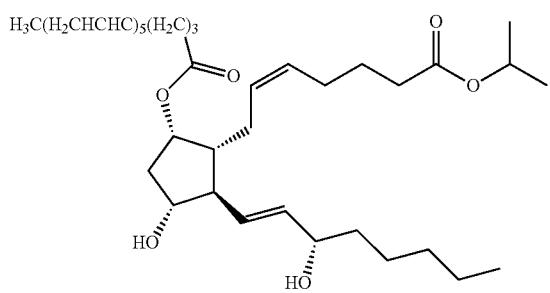
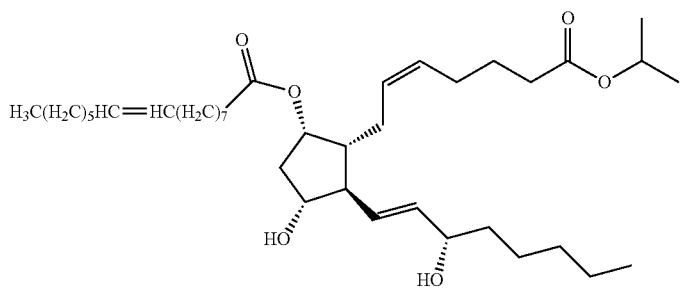
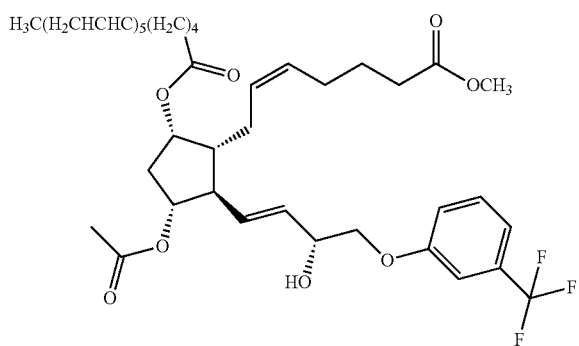

-continued
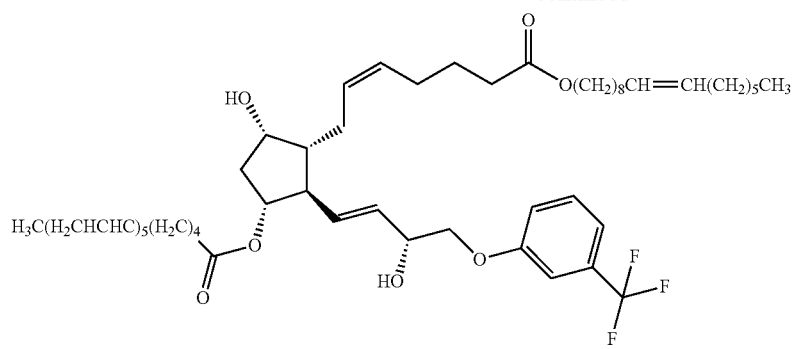
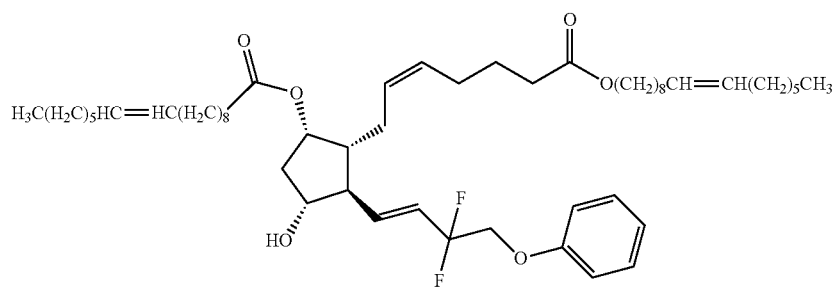
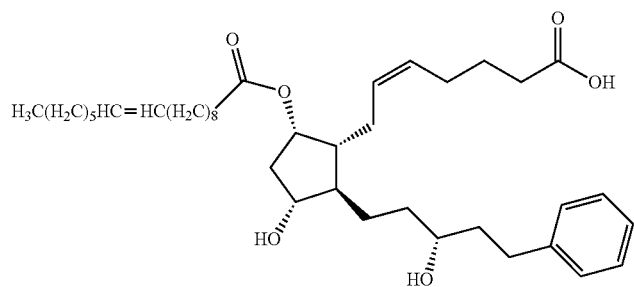
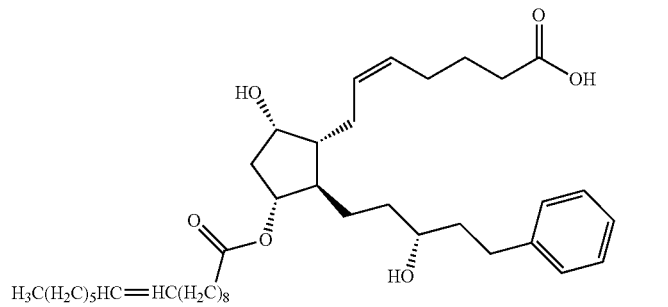
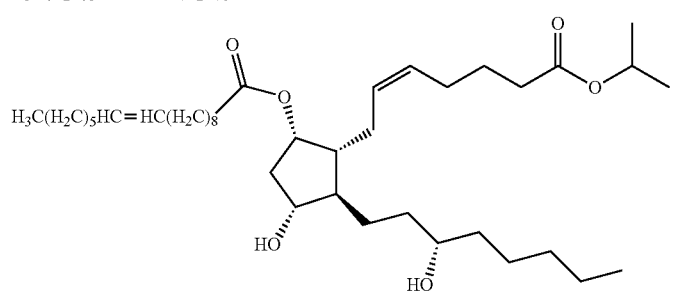

-continued
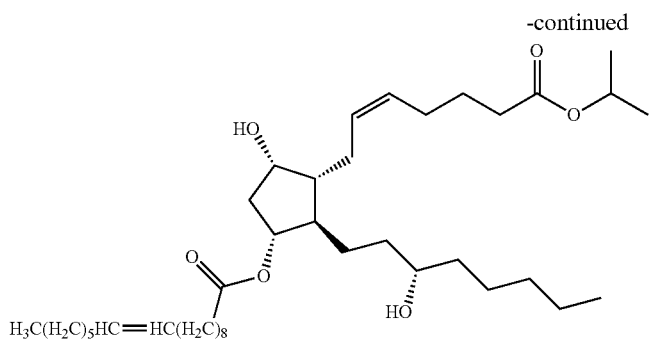
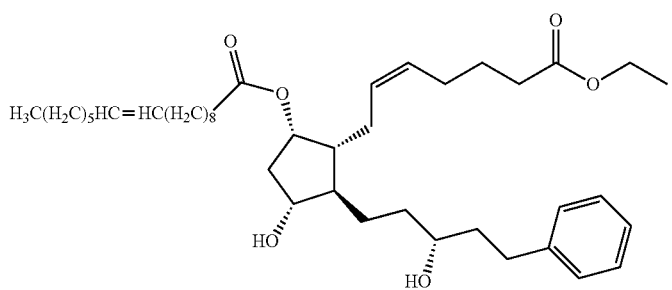
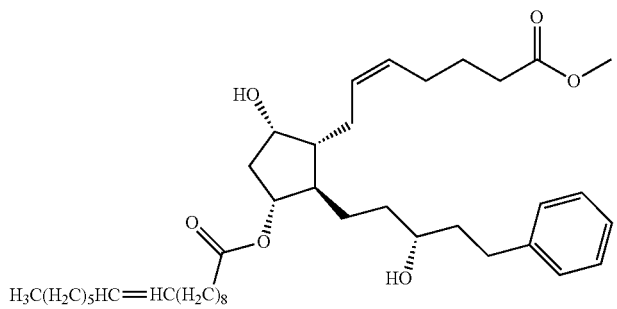
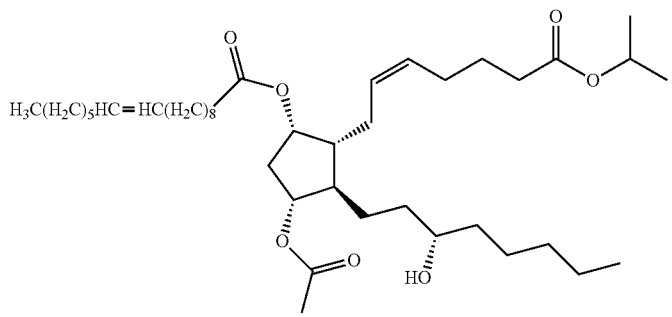
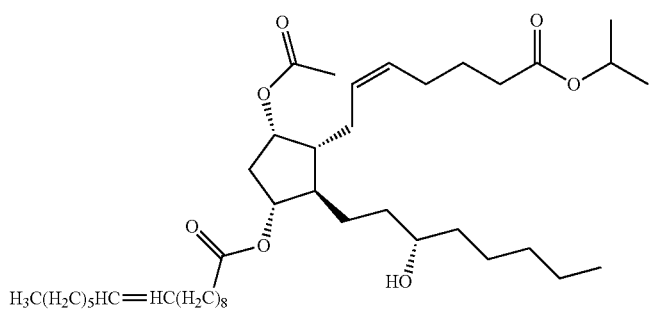

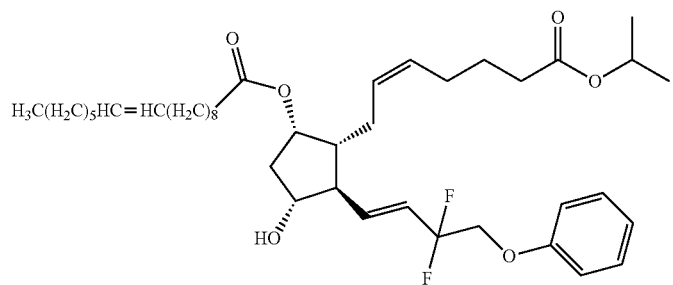
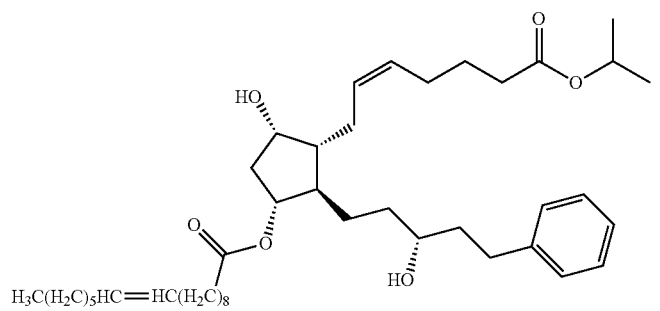
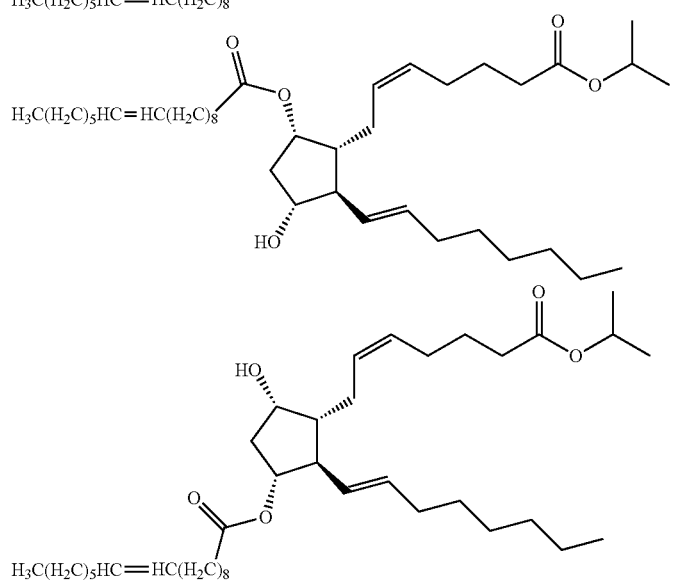
Example 21. Non-Limiting Examples of Compounds of Formula II
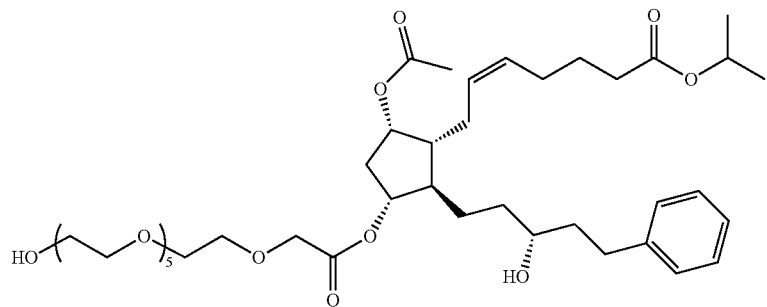

-continued
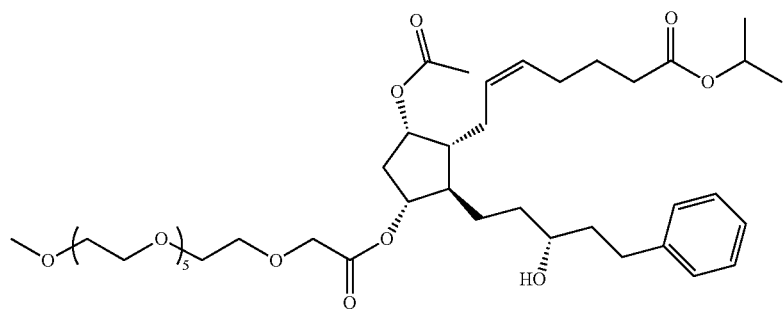
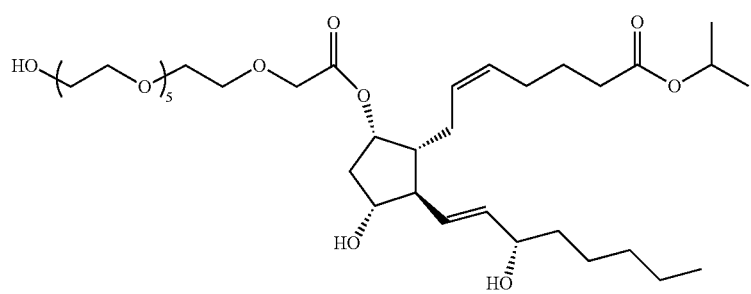
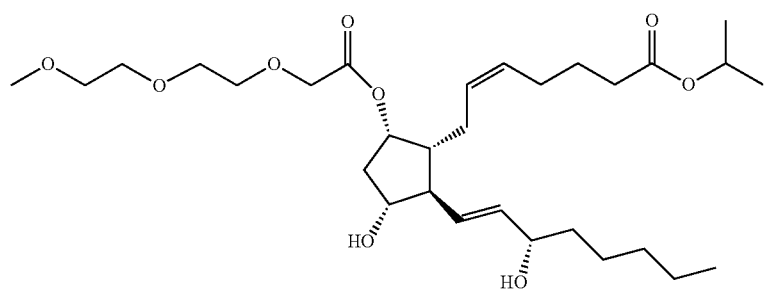
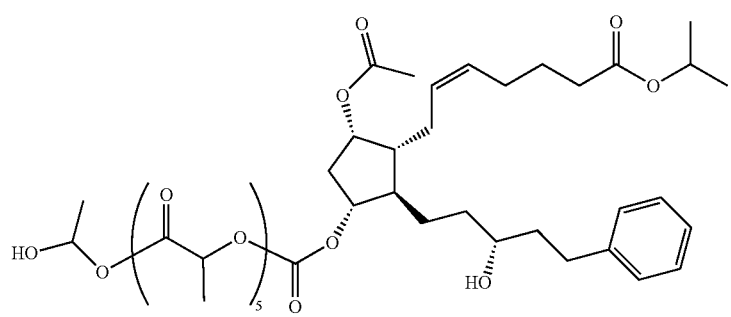
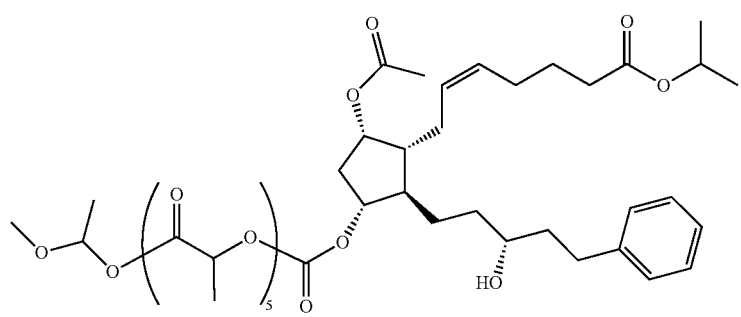

-continued
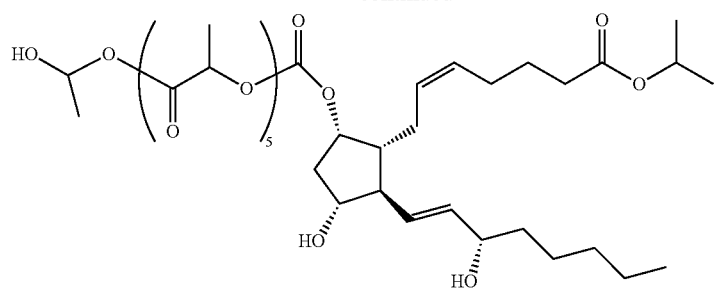
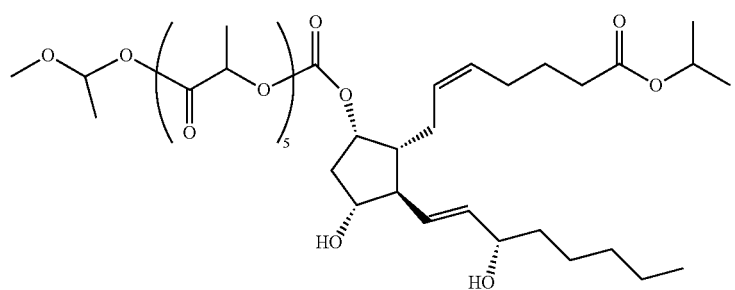
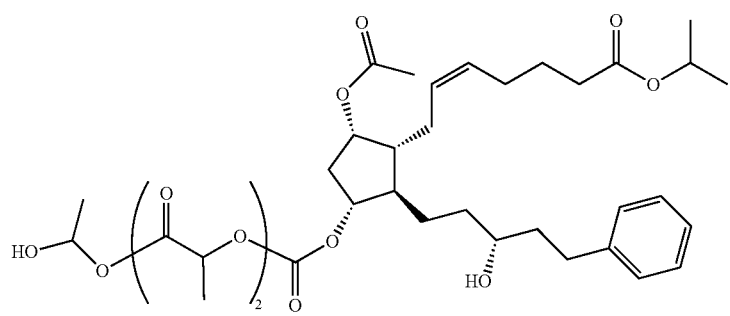
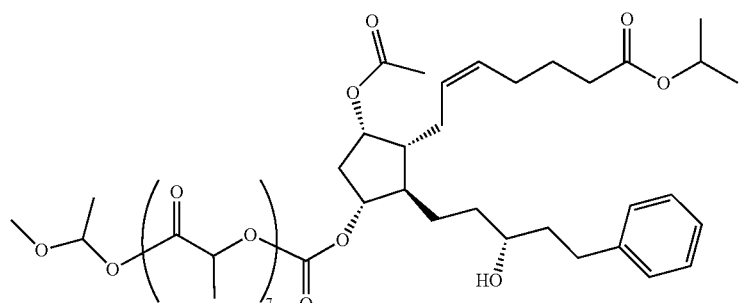
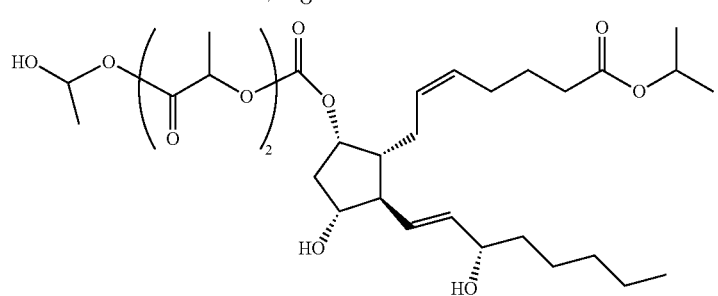

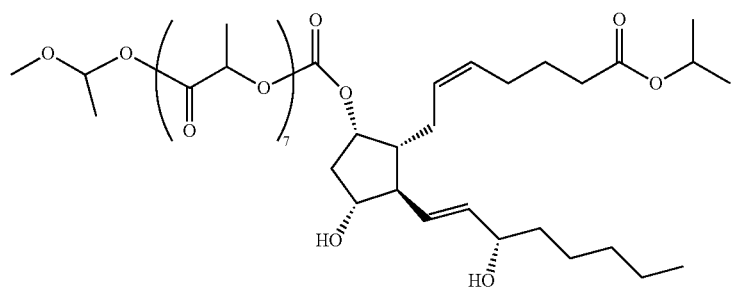
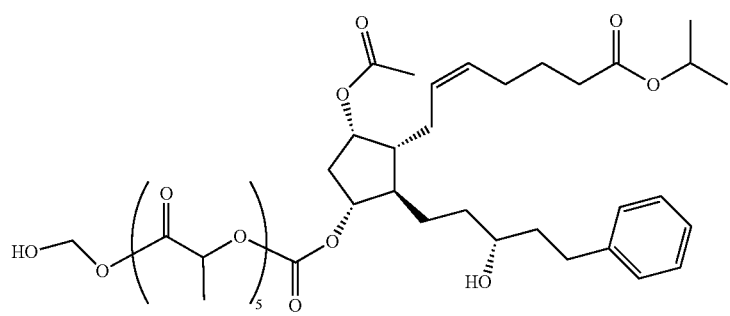
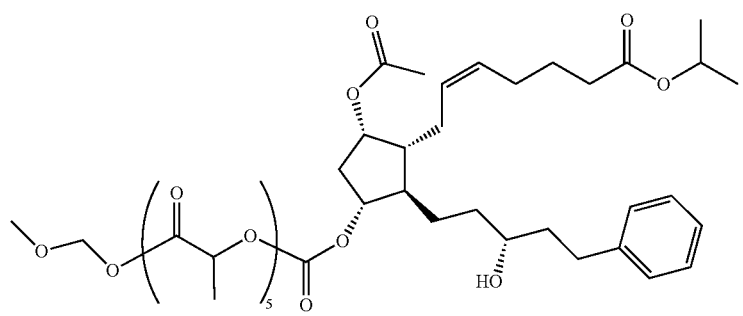
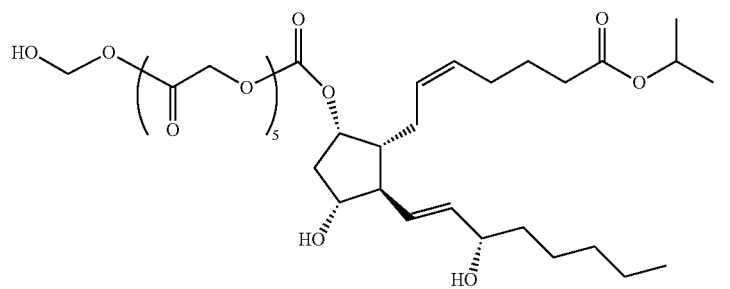
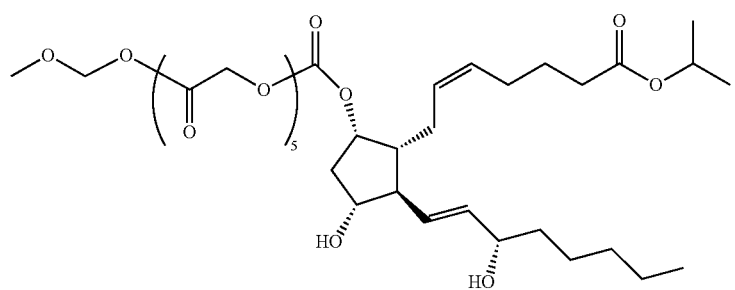

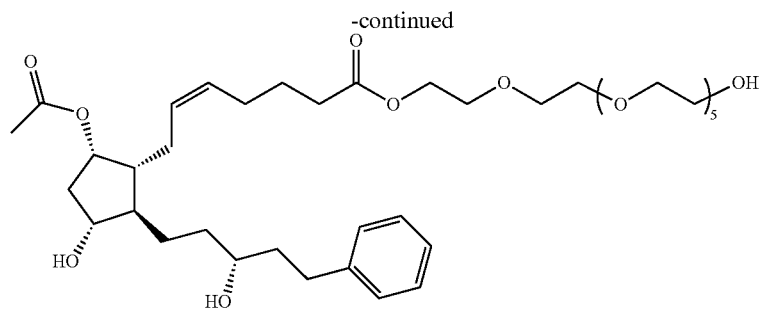
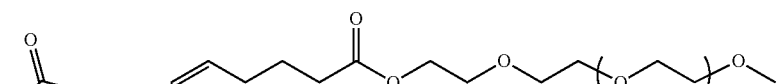
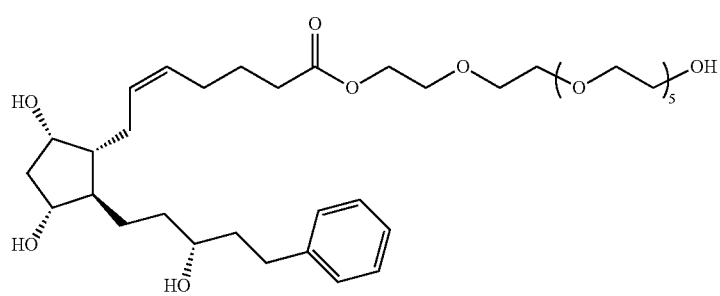
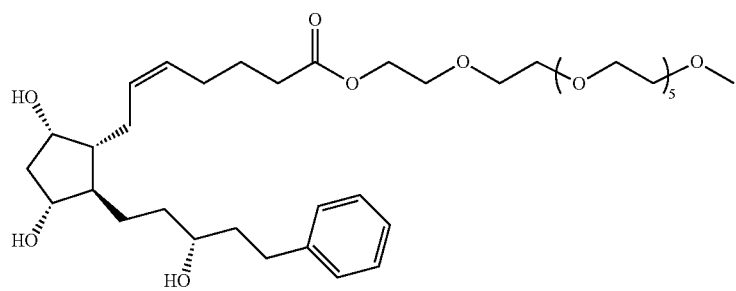
Example 22. Non-Limiting Examples of Compounds of Formula III, Formula IV, Formula V, and Formula VI
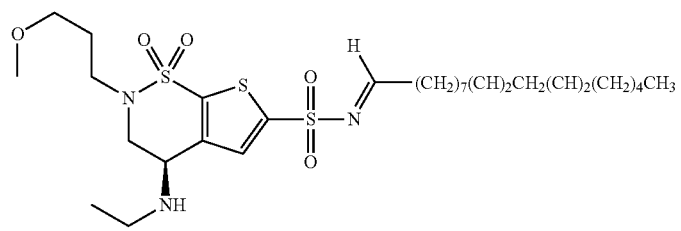

-continued
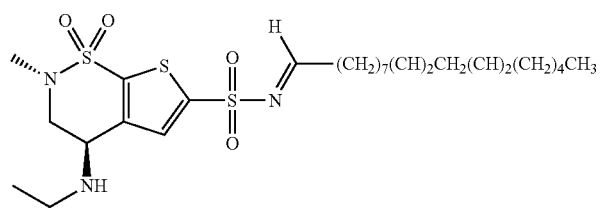
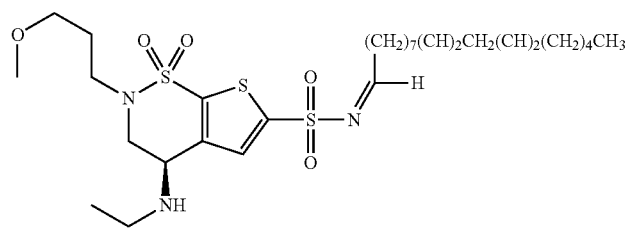
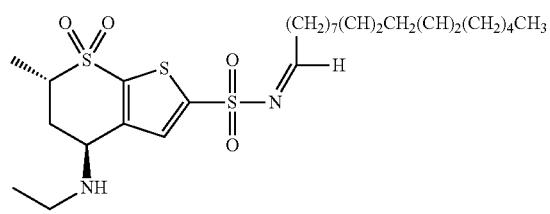
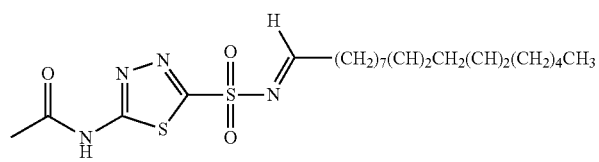
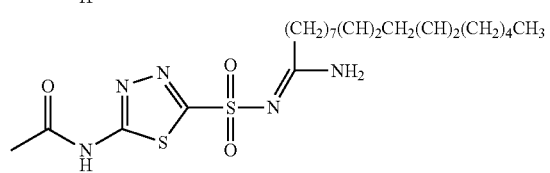
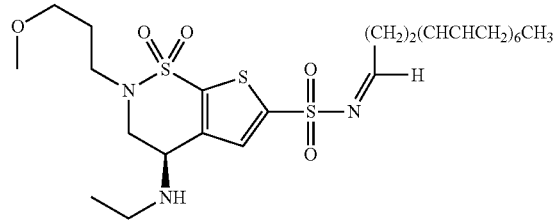
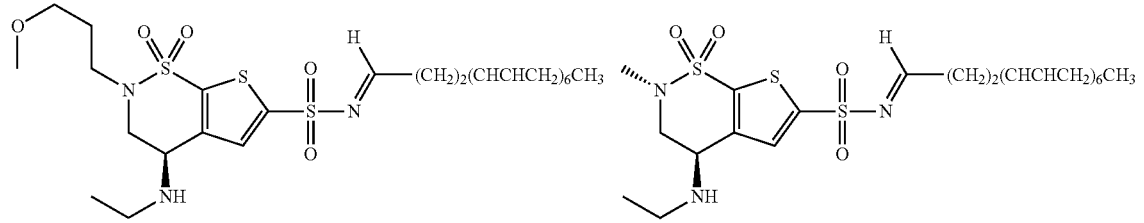
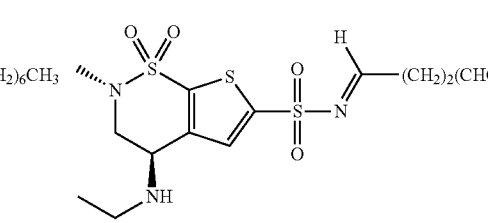
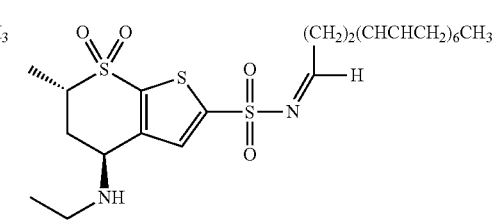
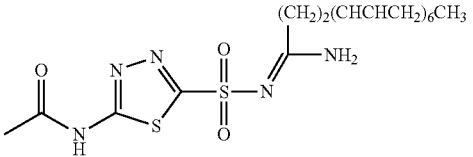

311 312
-continued
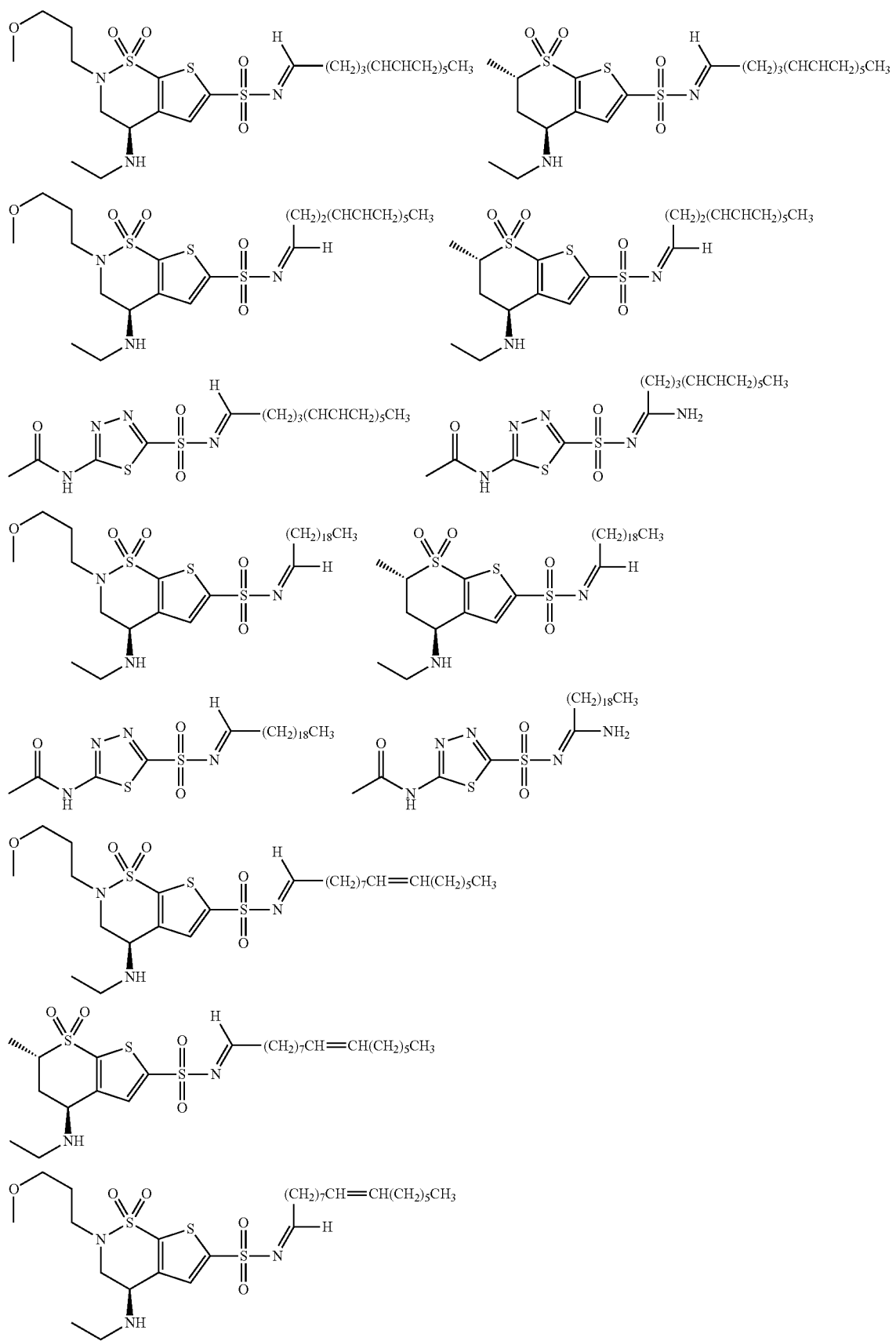

-continued
| 313 | 314 |
|---|---|
| 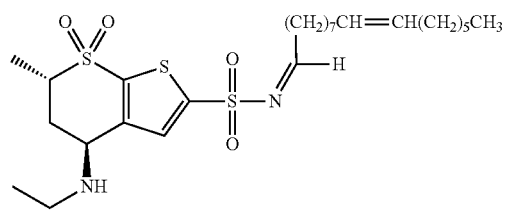 | |
| 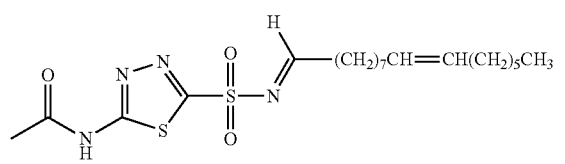 | 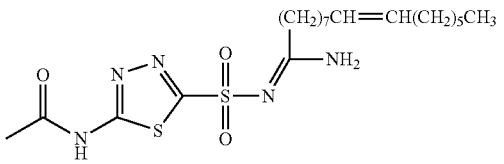 |
| 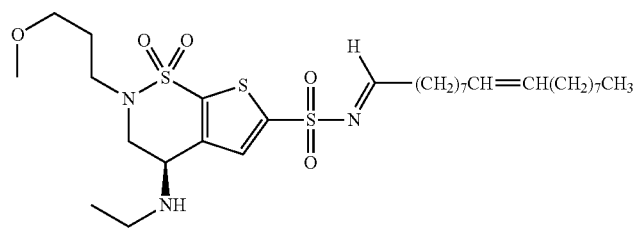 | |
| 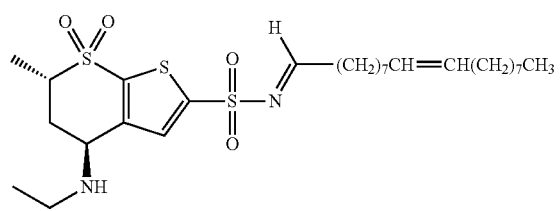 | |
| 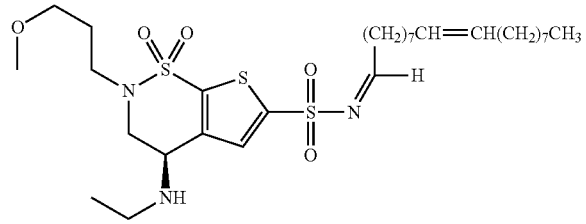 | |
| 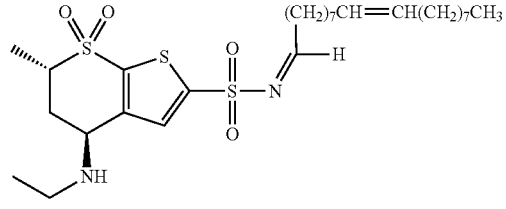 | |
| 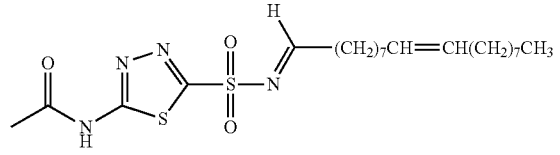 | 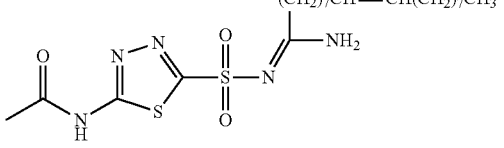 |
| 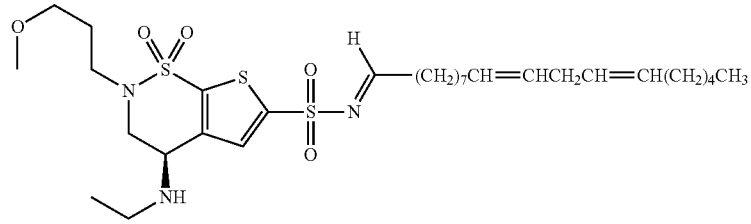 | |

-continued
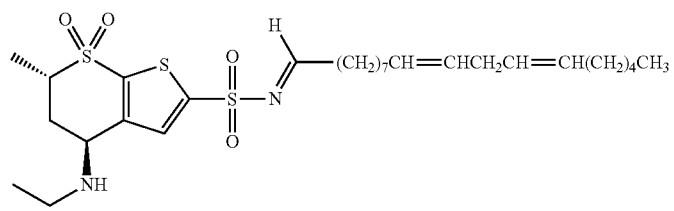
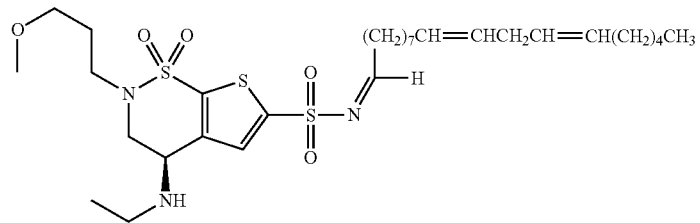
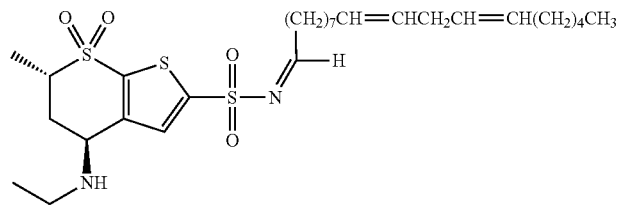
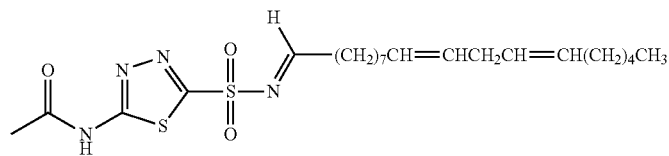
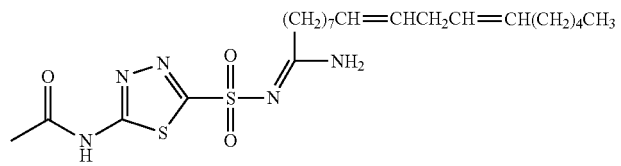
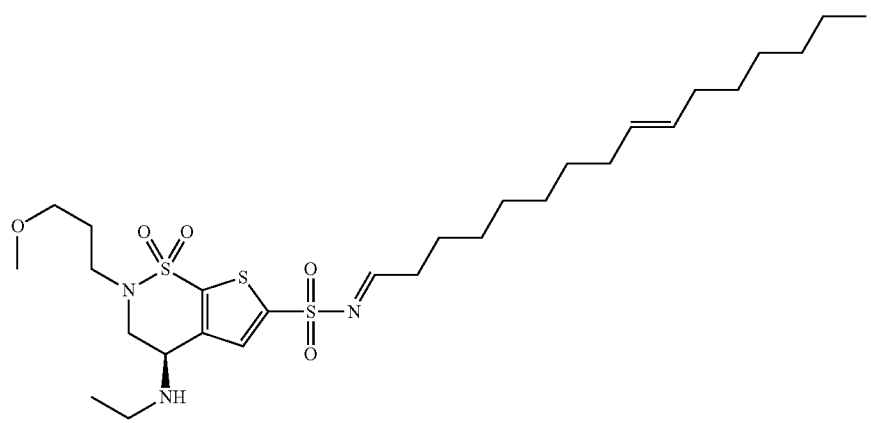

-continued
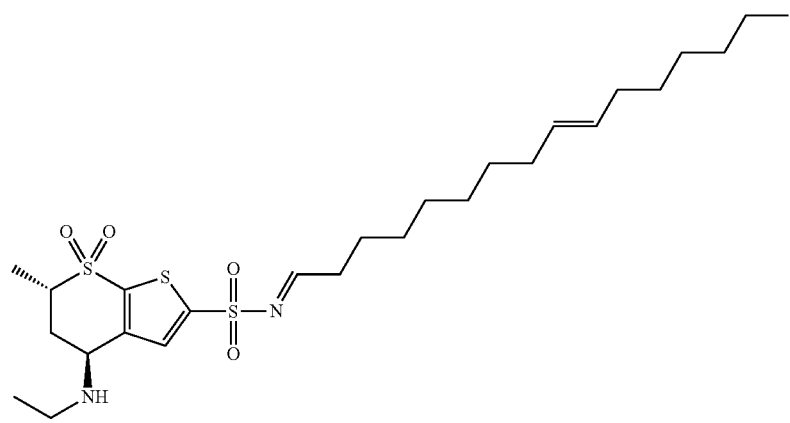
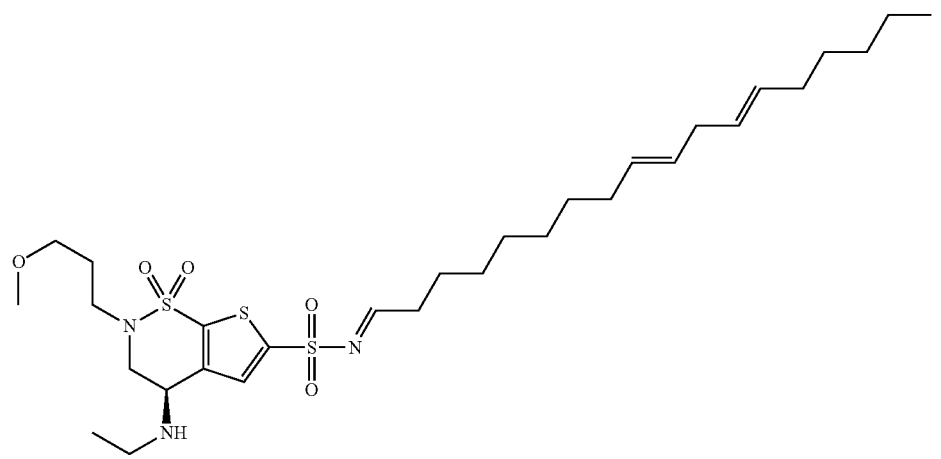
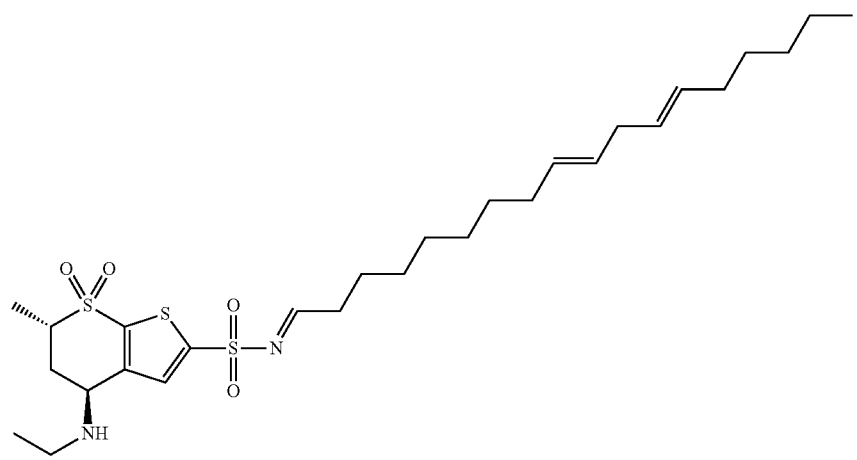

-continued
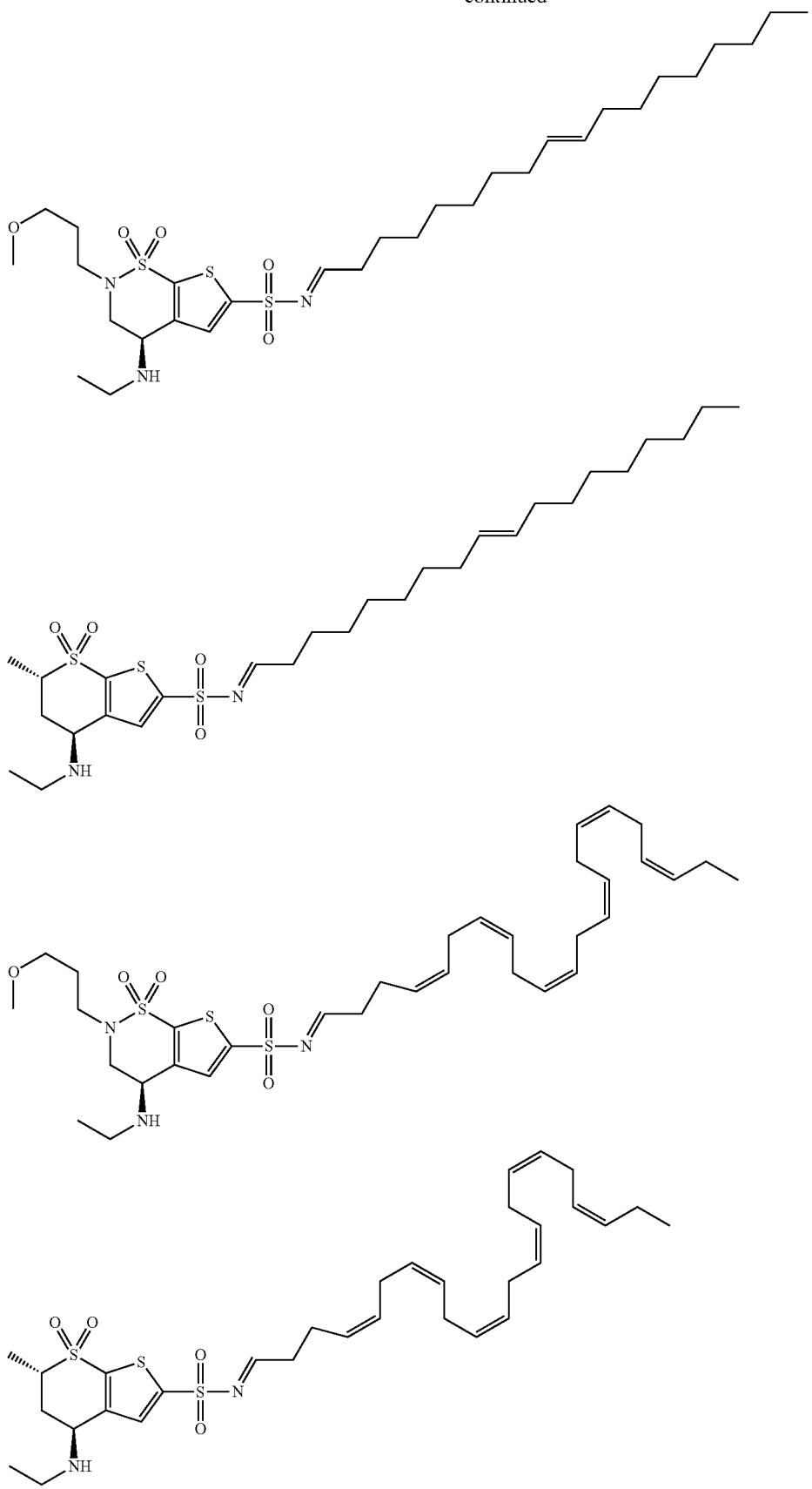

Example 23. Non-Limiting Examples of Compounds of Formula VII
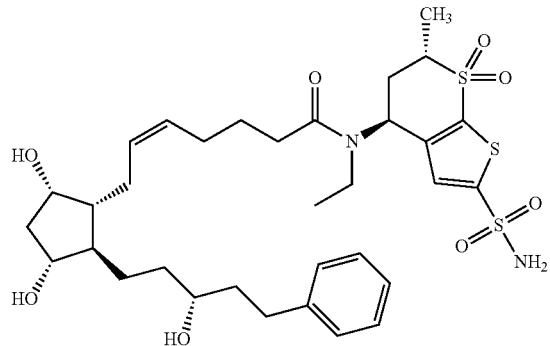
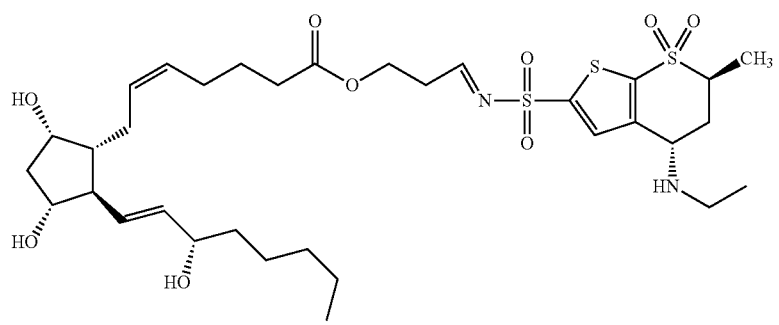
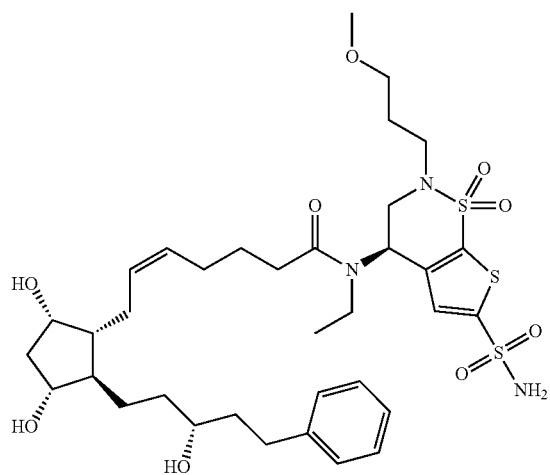
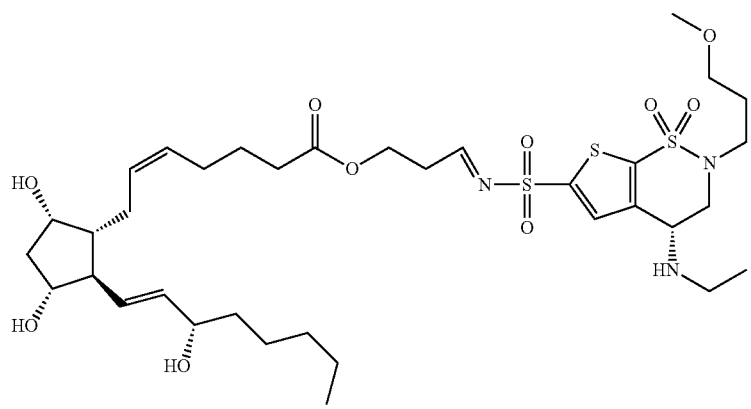

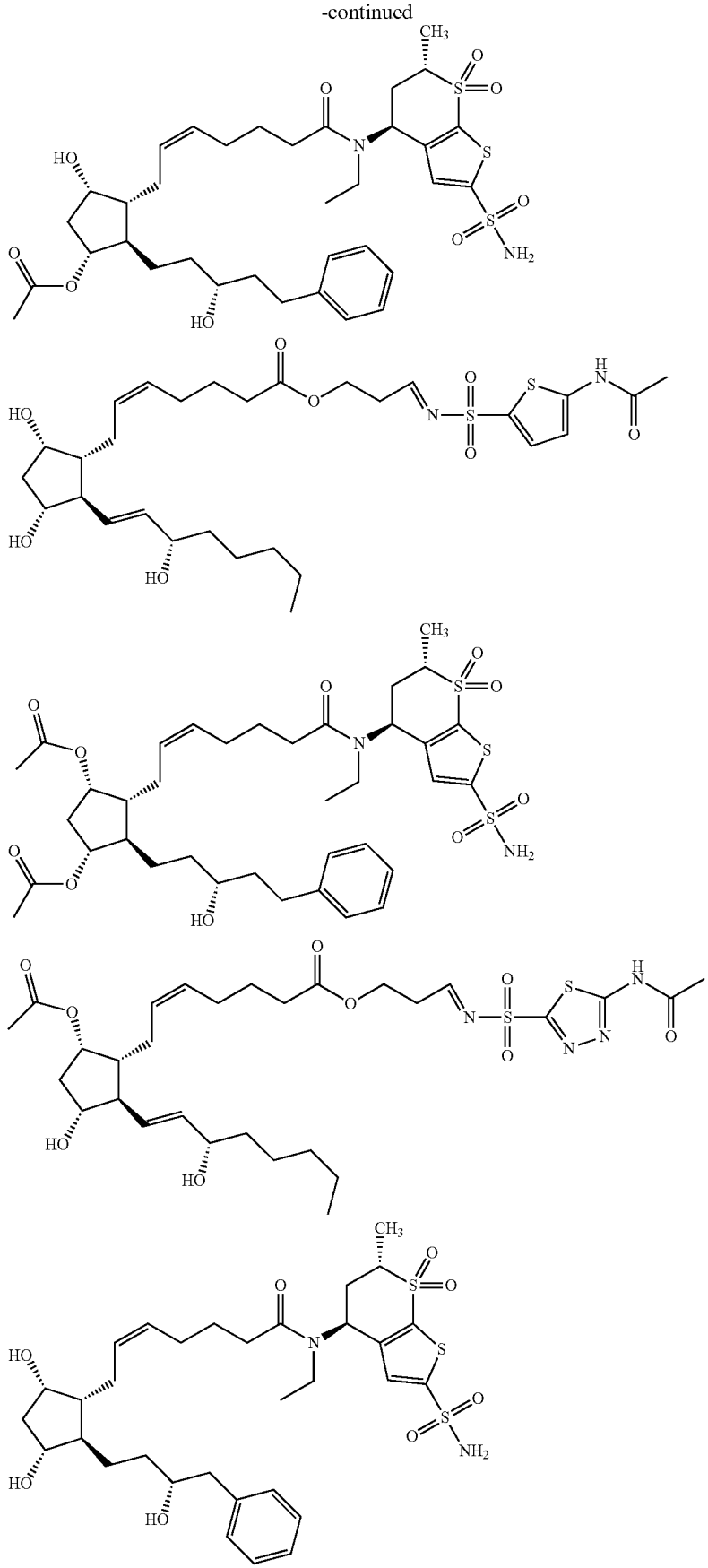

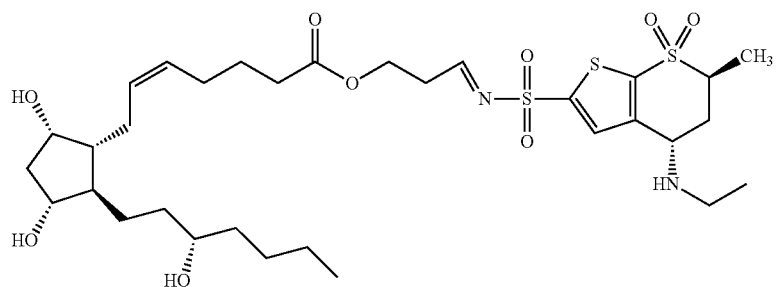
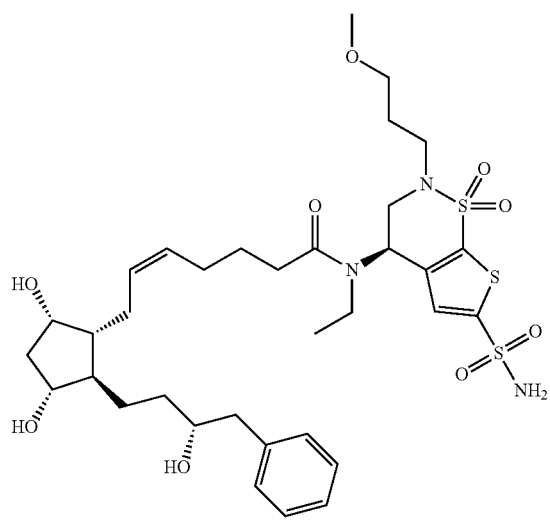
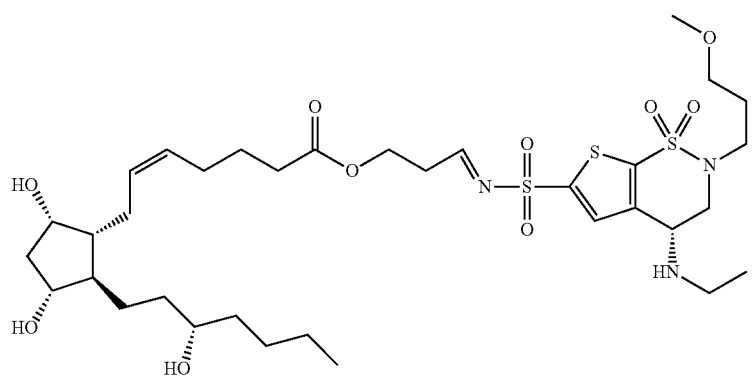
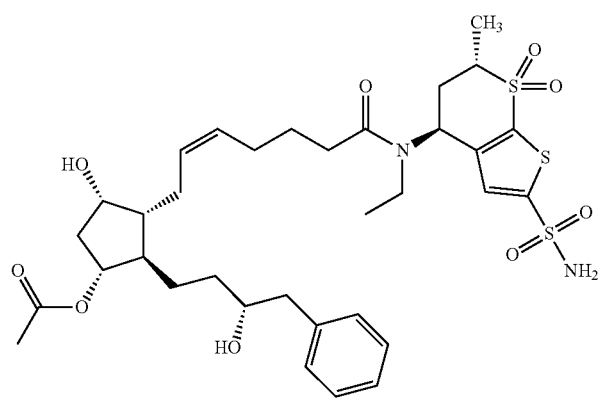

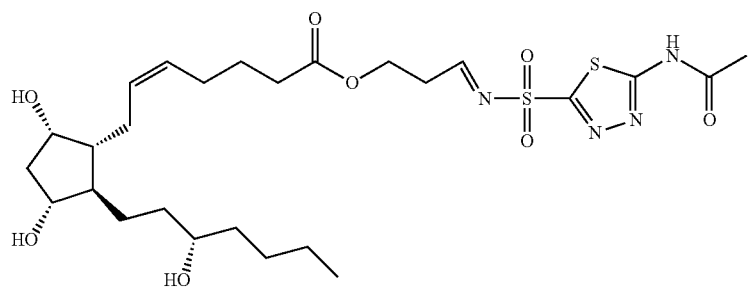
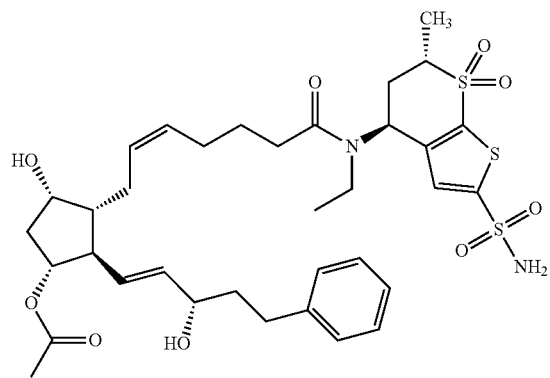
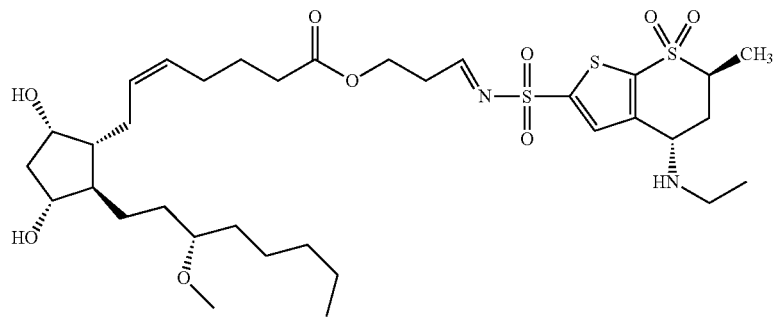
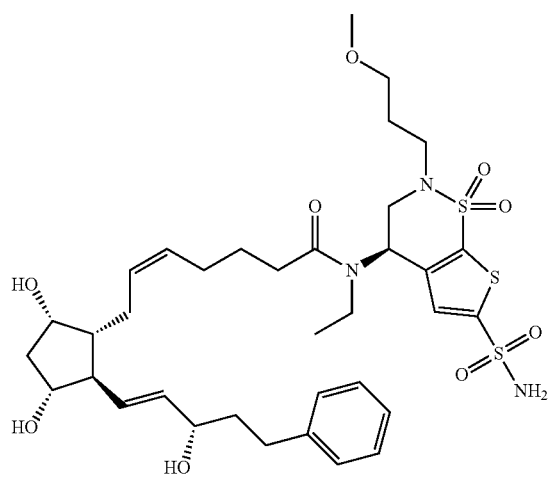

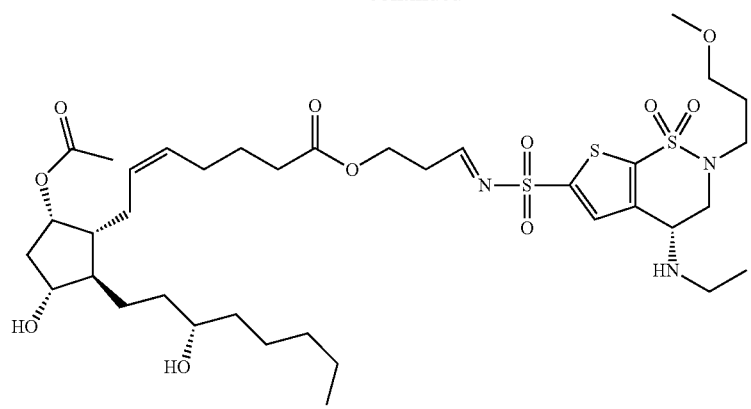
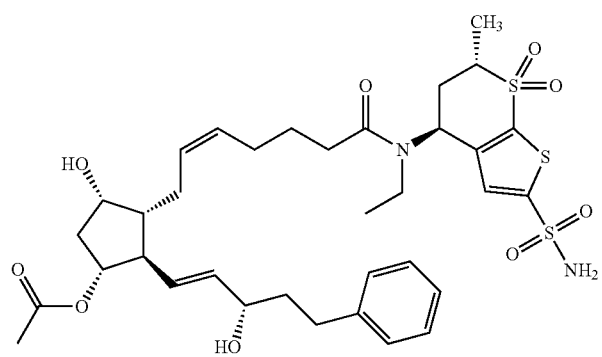
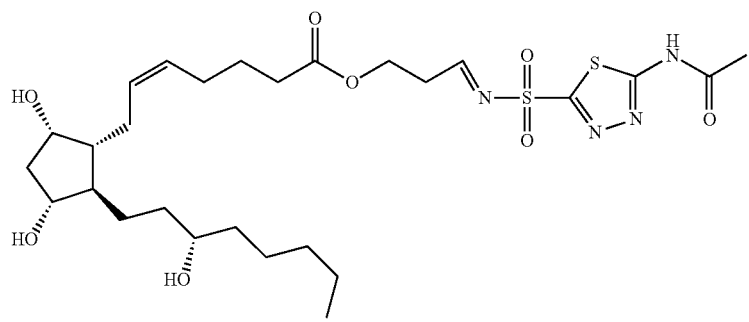
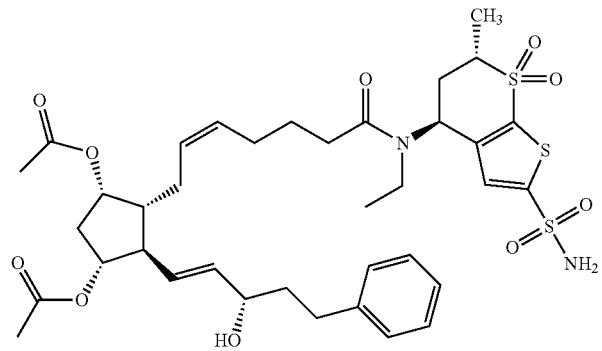

-continued
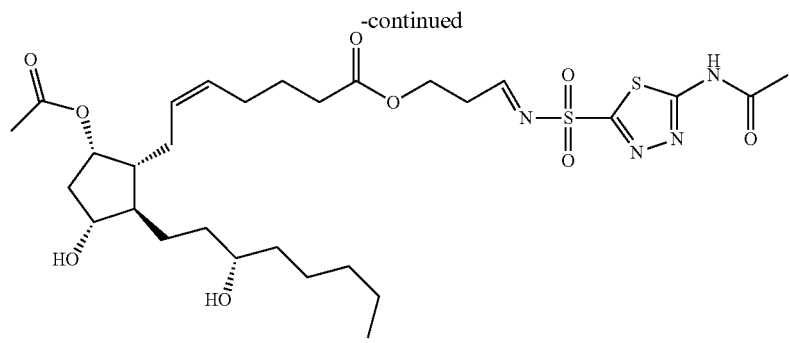
Example 24. Non-Limiting Examples of Compounds of Formula VII'
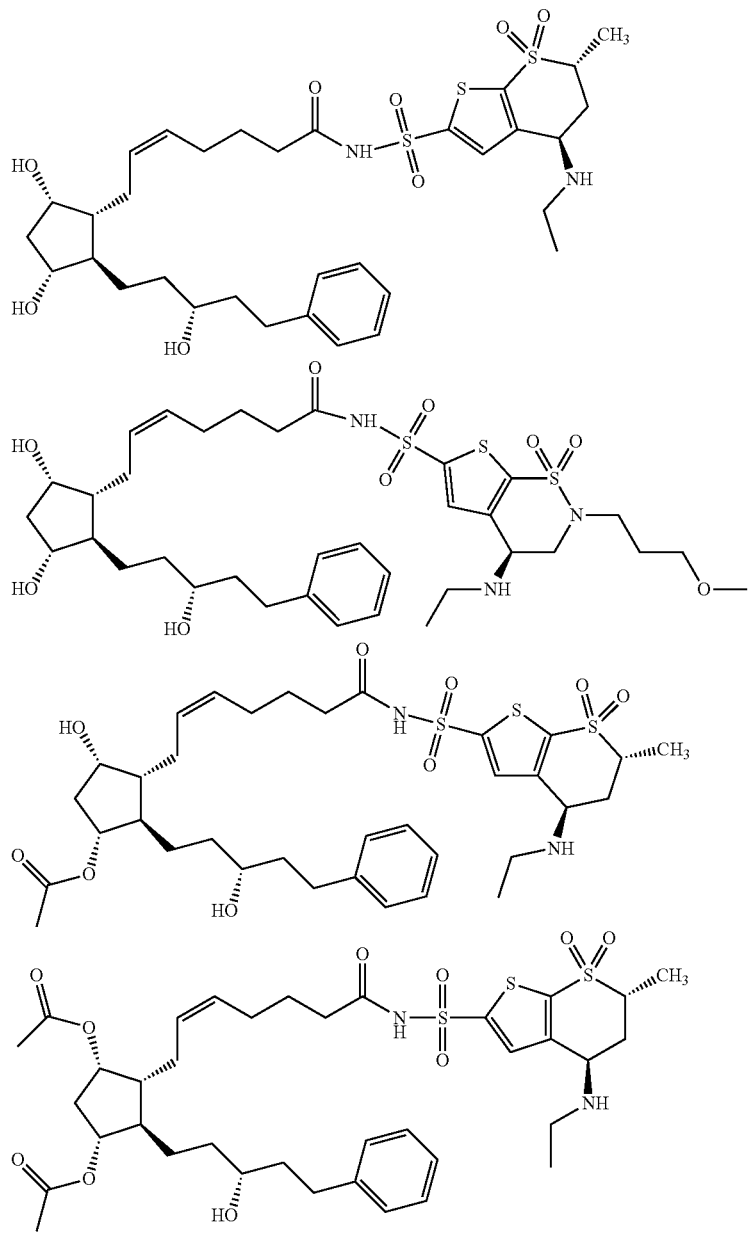

-continued
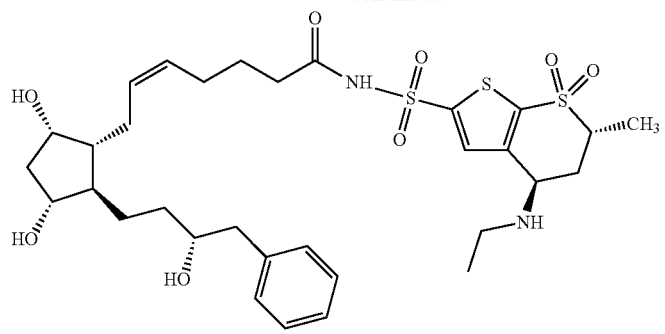
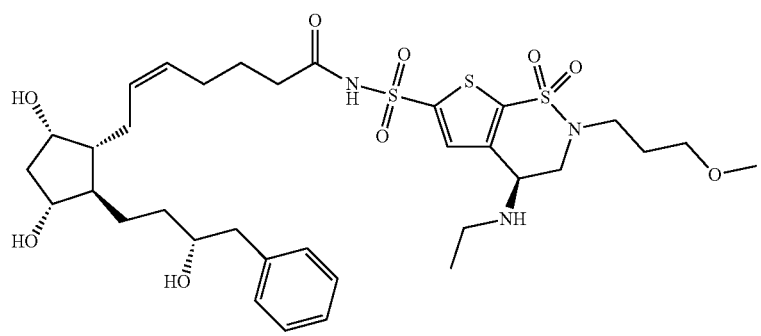
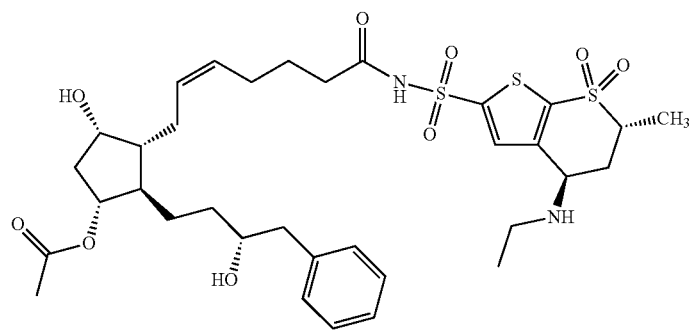
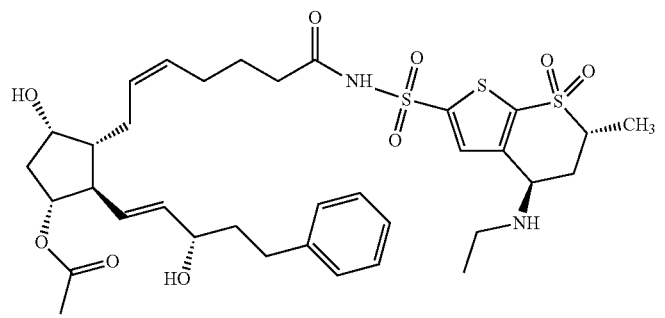
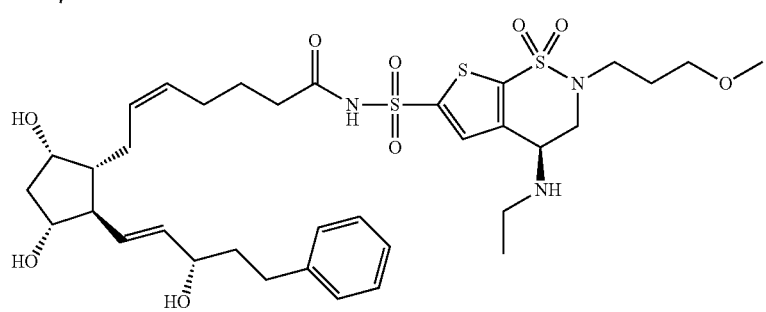

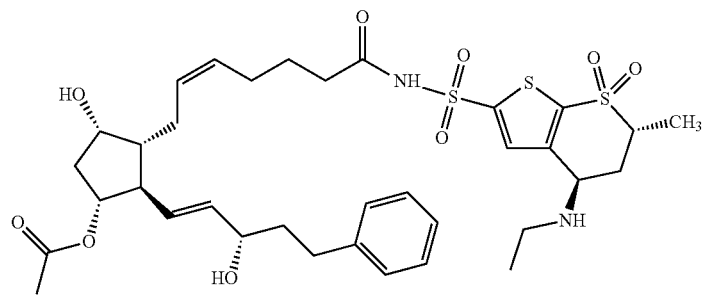
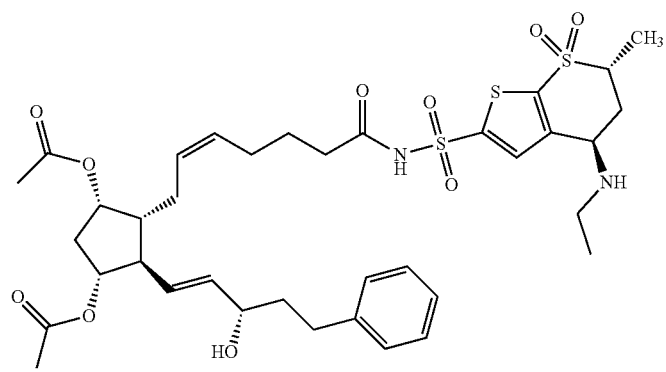 [SMILES: CCN[C@@H]1C[C@@H](C)S(=O)(=O)c2sc(S(=O)(=O)NC(=O)CCC/C=C\C[C@@H]3[C@@H](/C=C/[C@@H](O)CCc4ccccc4)[C@H](OC(C)=O)C[C@@H]3OC(C)=O)cc21]
Example 25. Non-Limiting Examples of Compounds of Formula VIII
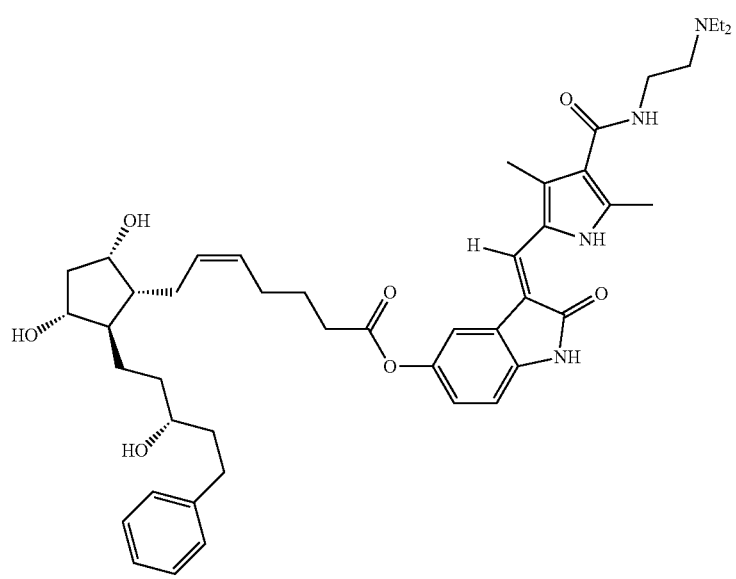

-continued
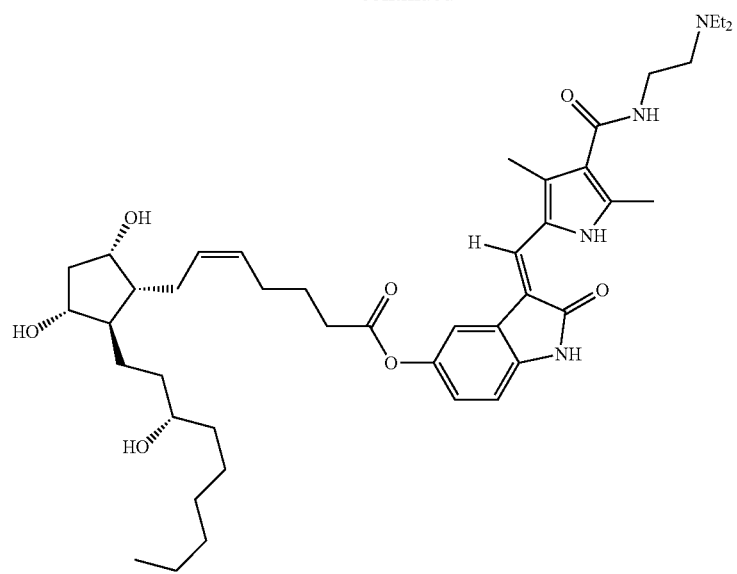
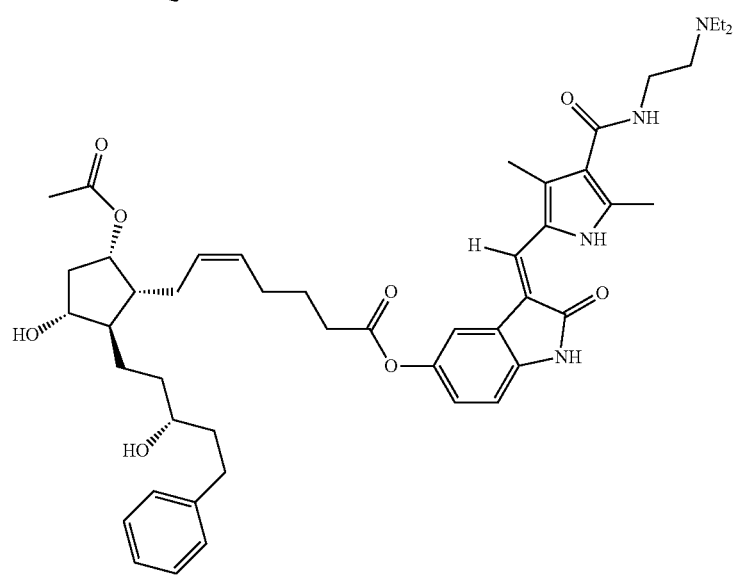
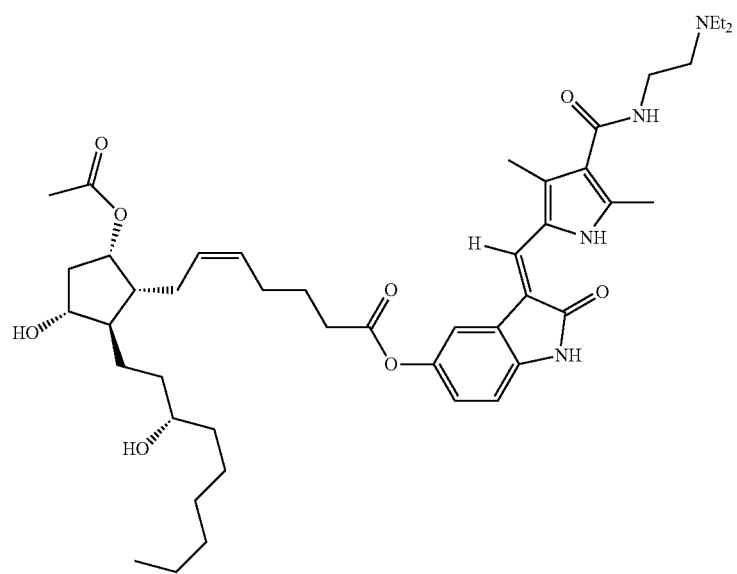

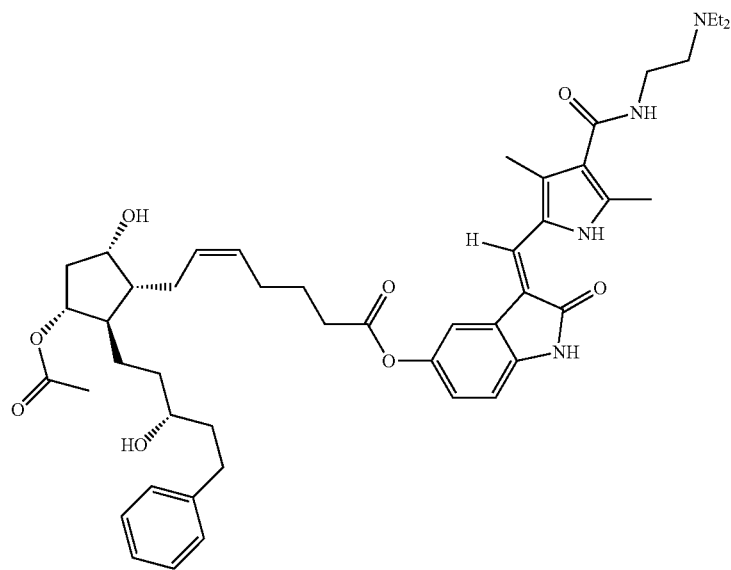
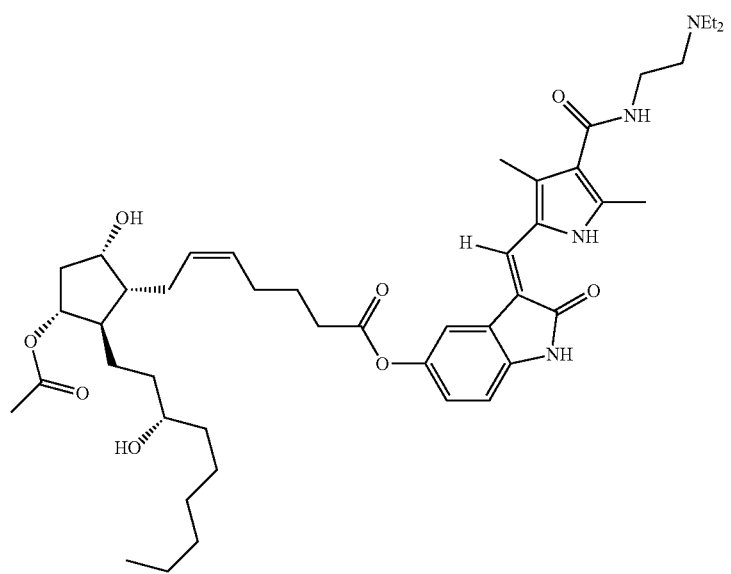
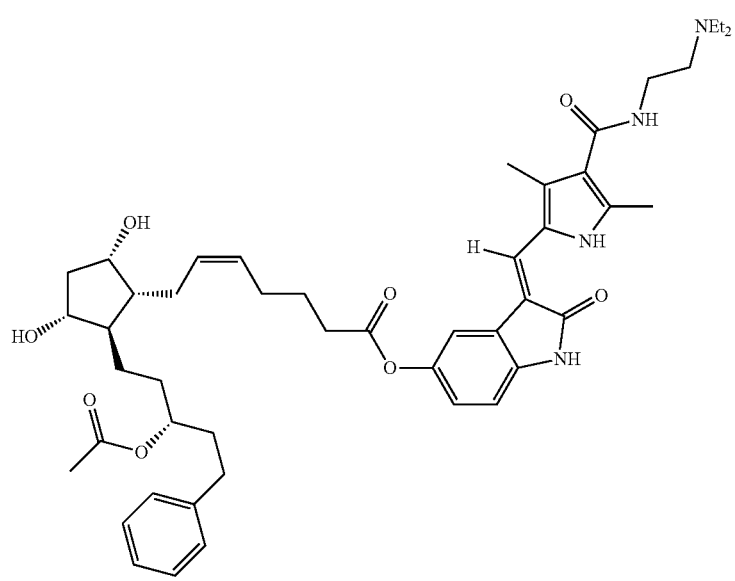

-continued
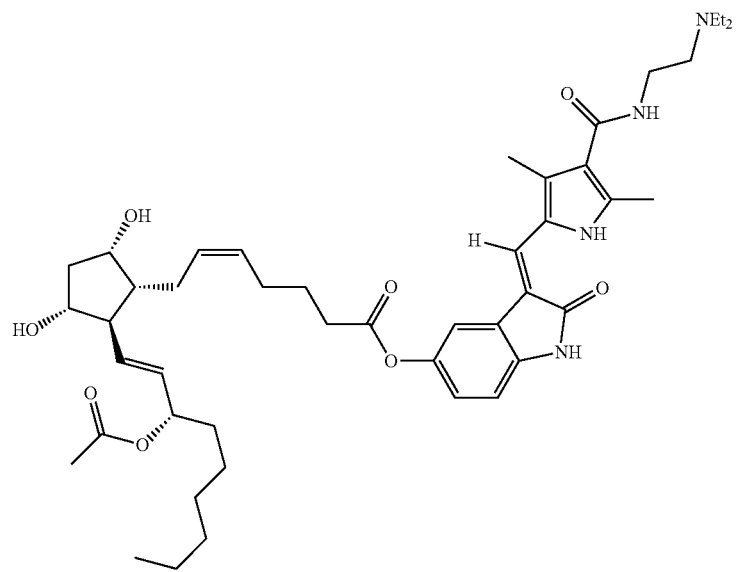
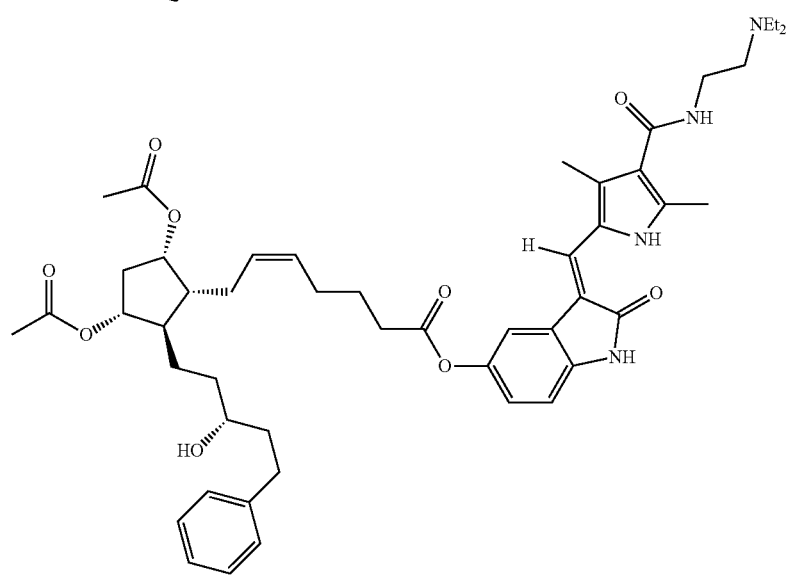
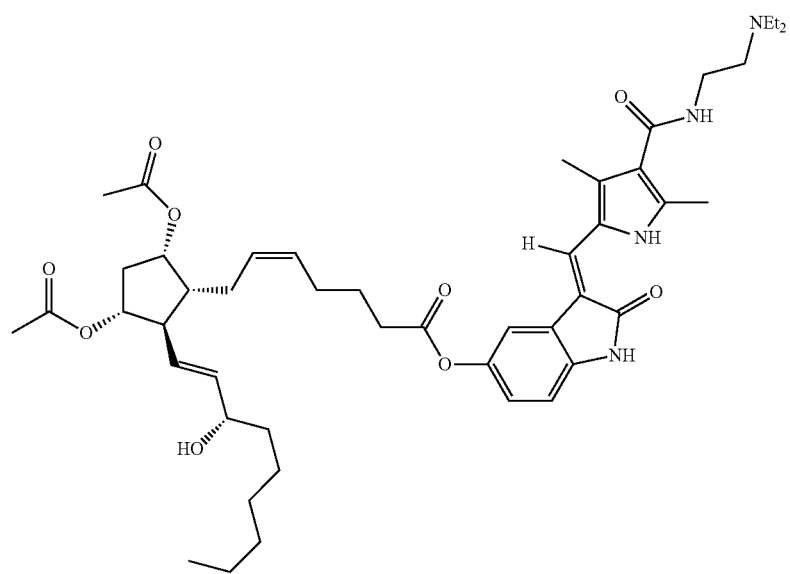

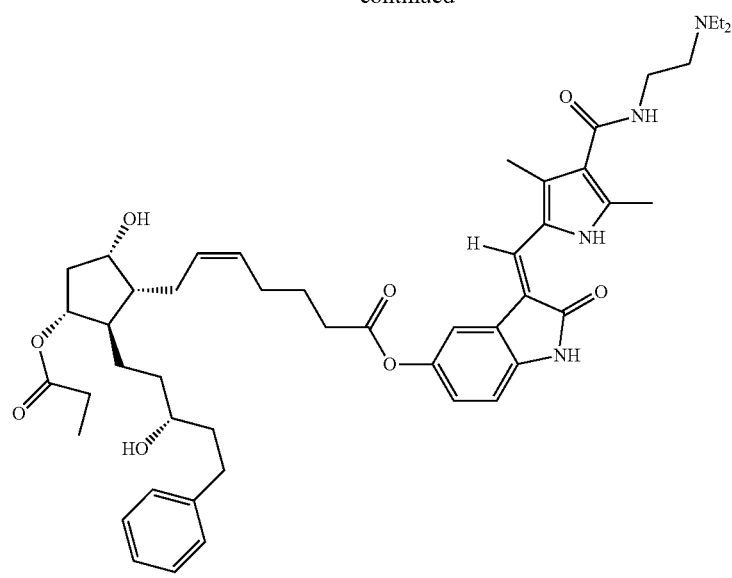
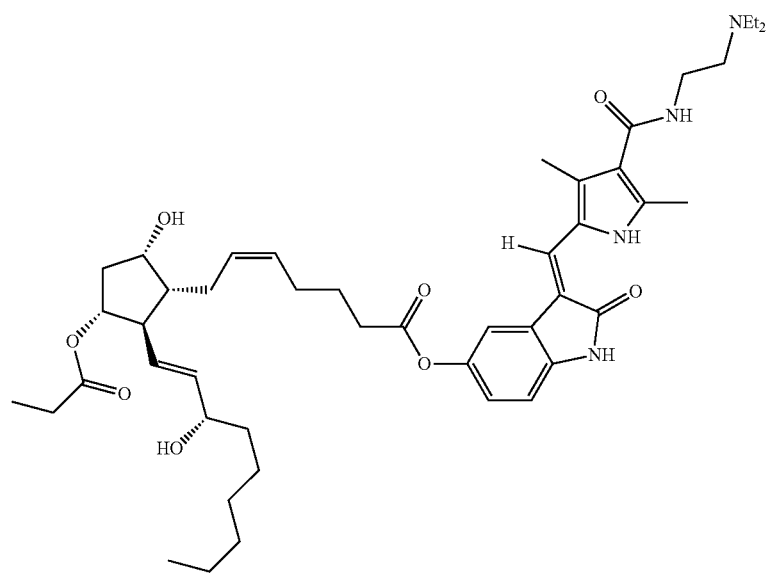
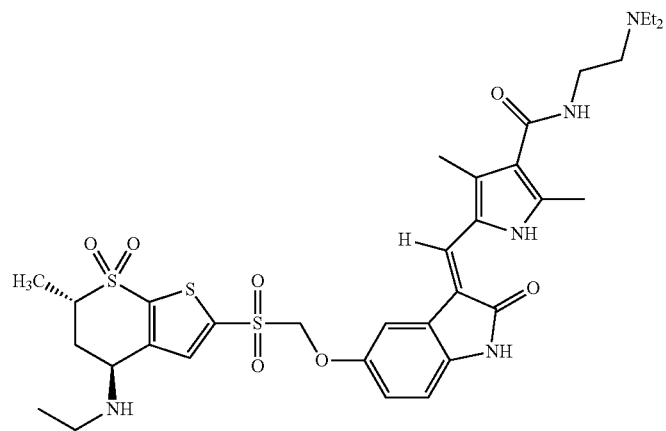

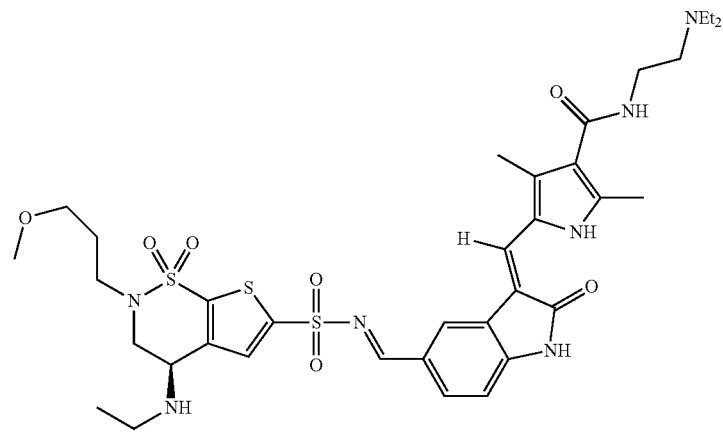
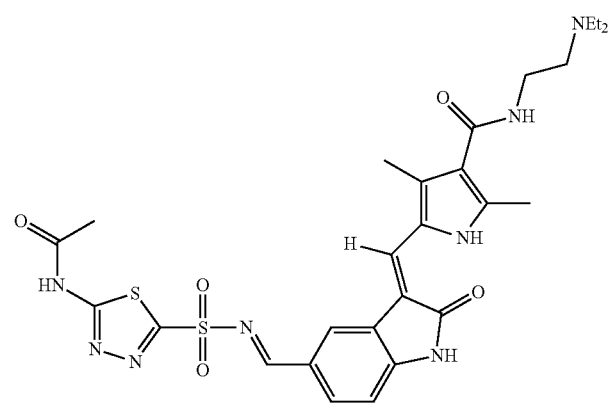
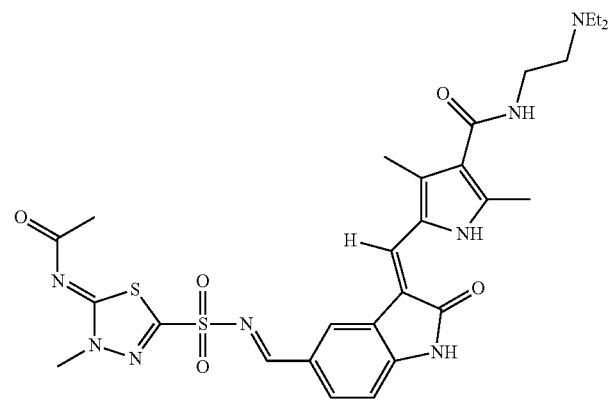

Example 26. Non-Limiting Examples of Compounds of Formula IX
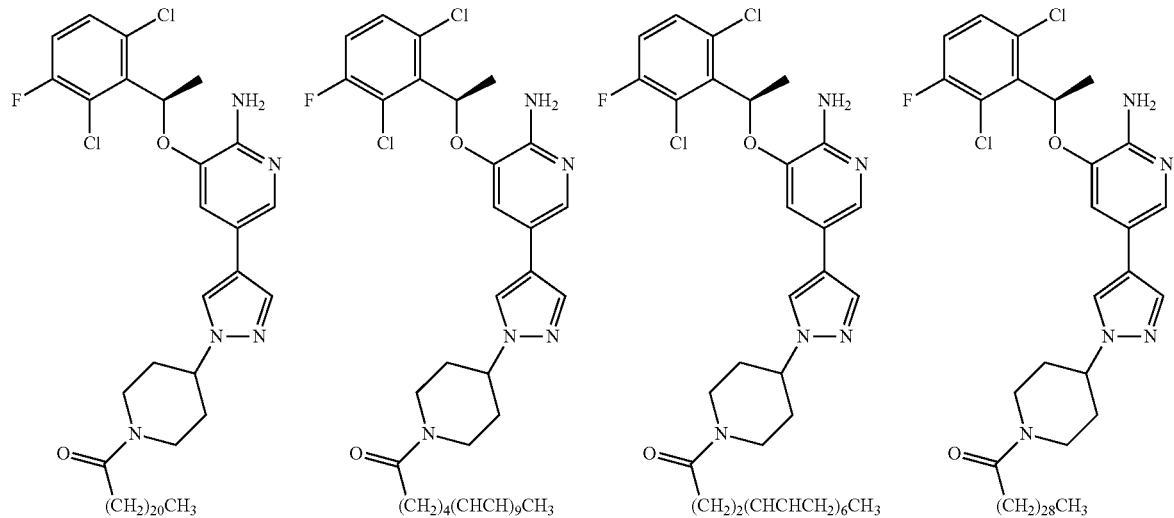
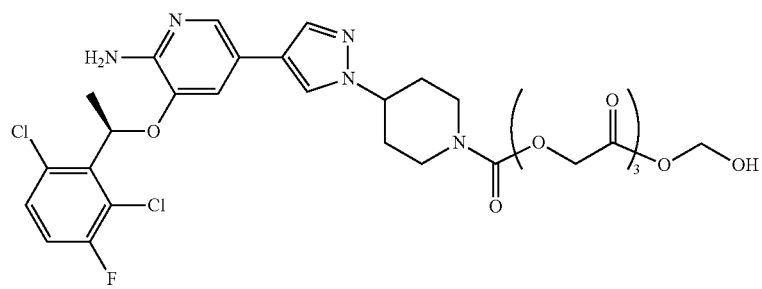
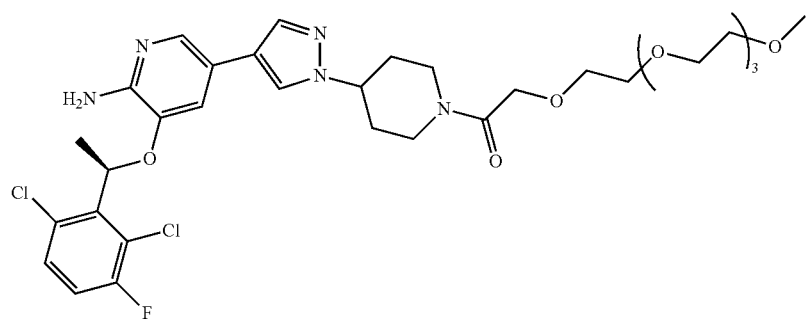
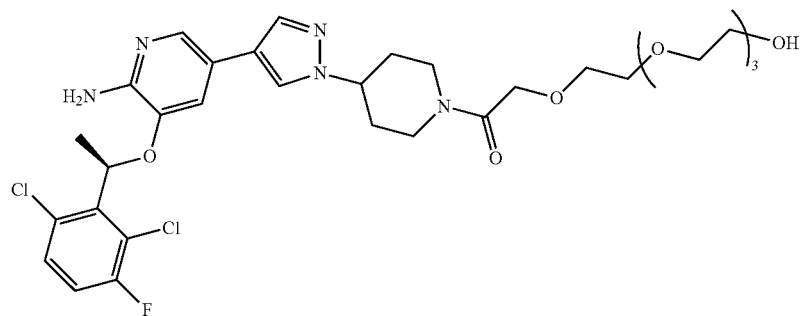

-continued
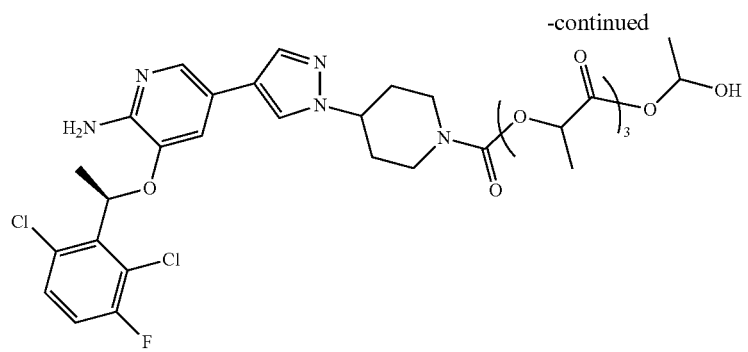
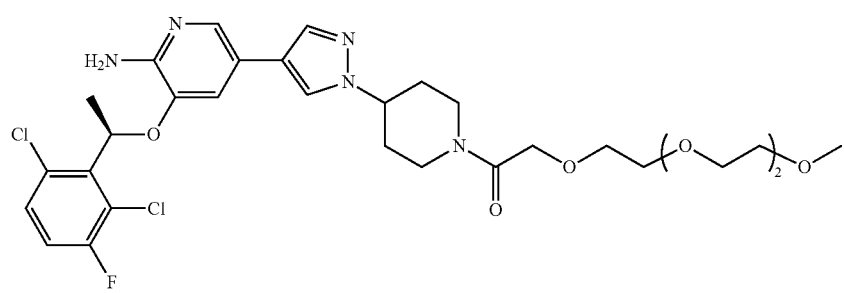
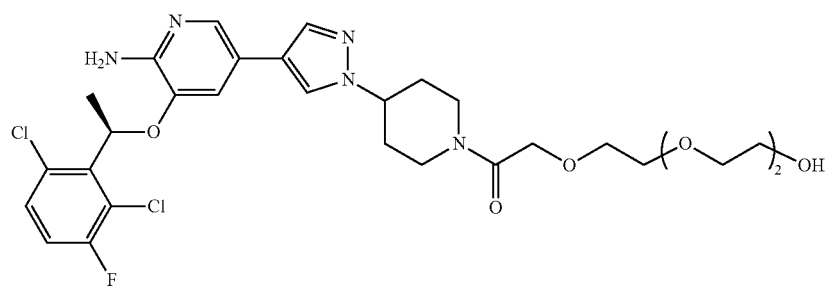
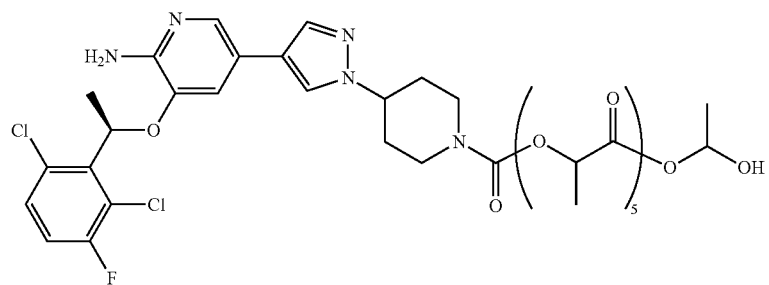
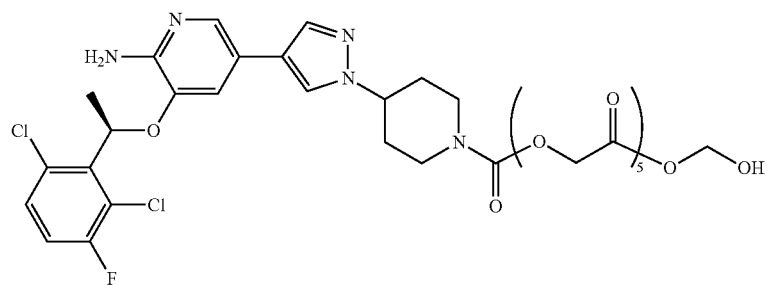

Example 27. Non-Limiting Examples of Compounds of Formula X
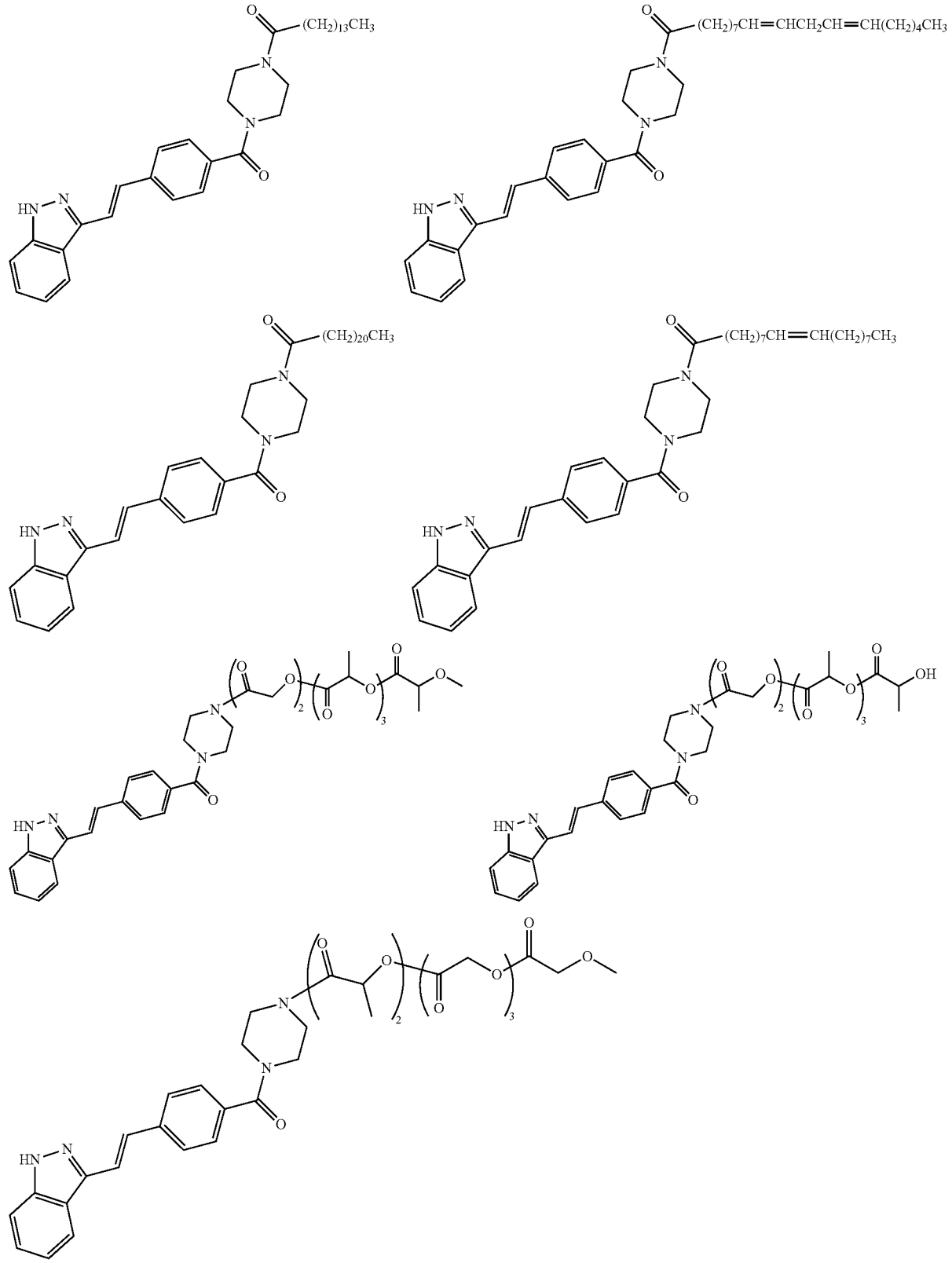

-continued
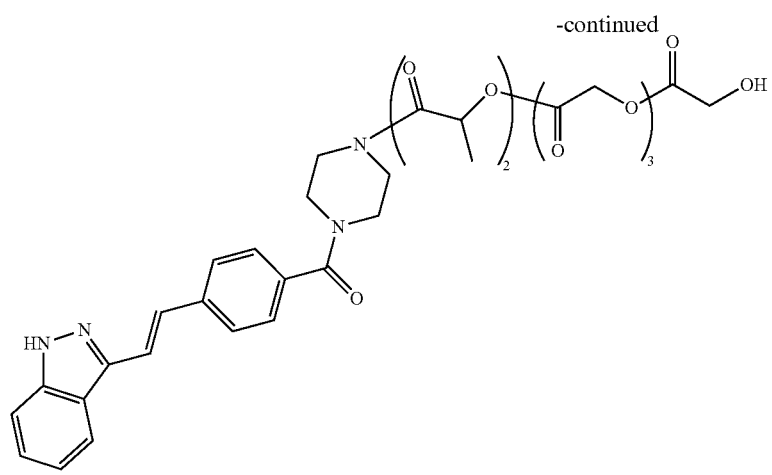
Example 28. Non-Limiting Examples of Compounds of Formula XI
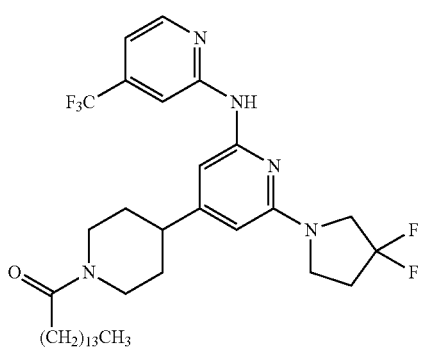
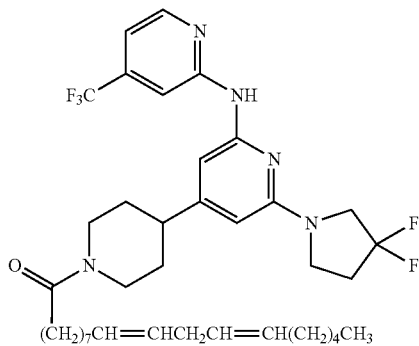
-continued
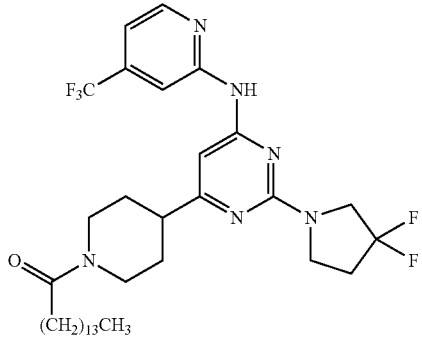
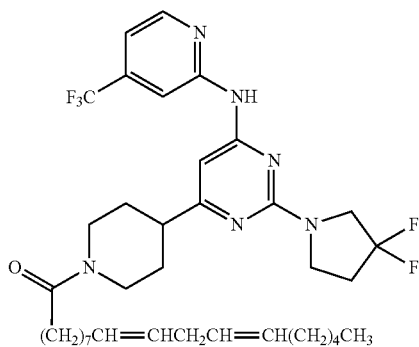
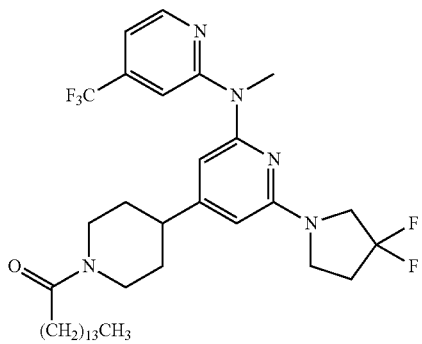
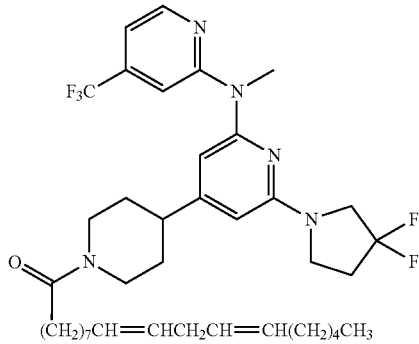

355
-continued
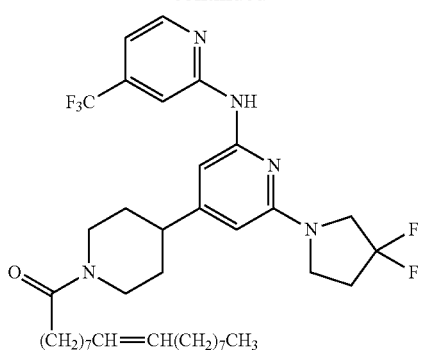
356
-continued
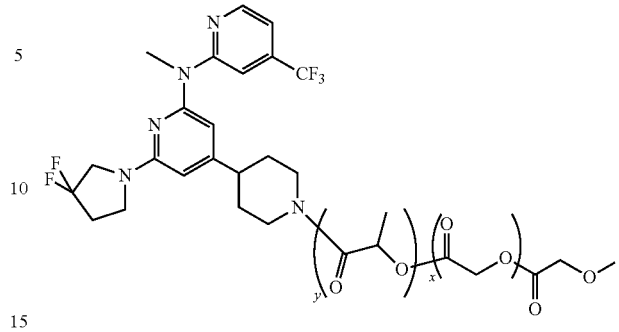
Example 29. Non-Limiting Examples of Compounds of Formula XII
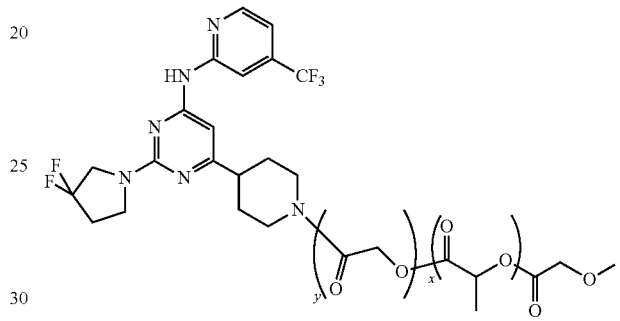

357
-continued
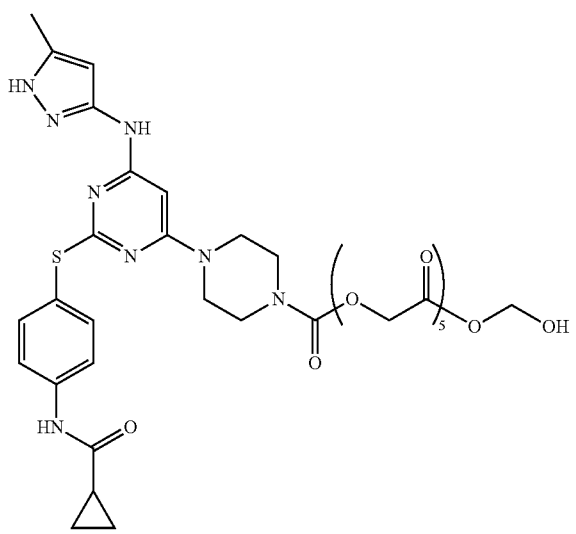
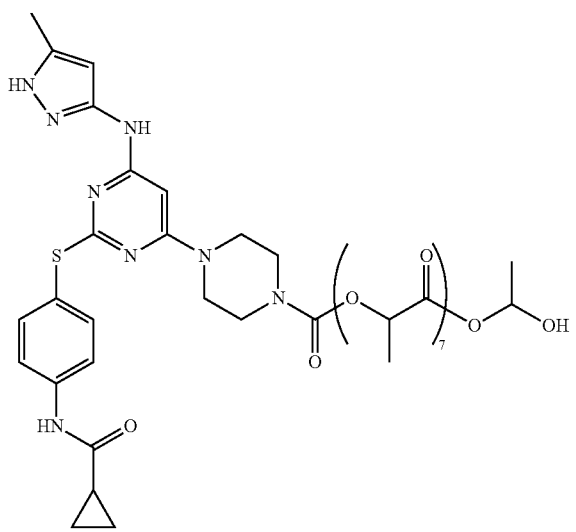
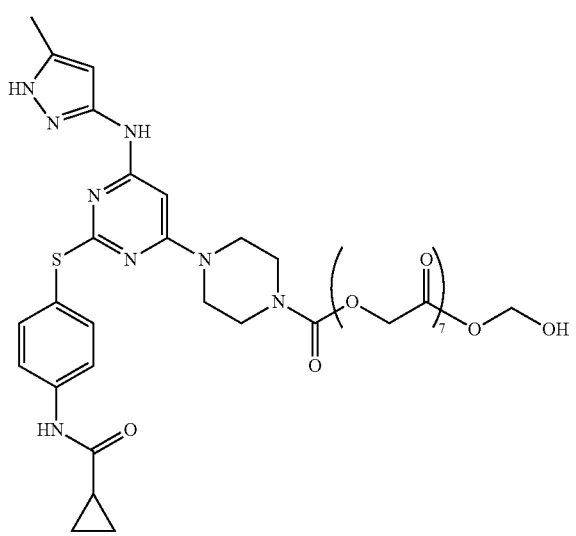
358
-continued
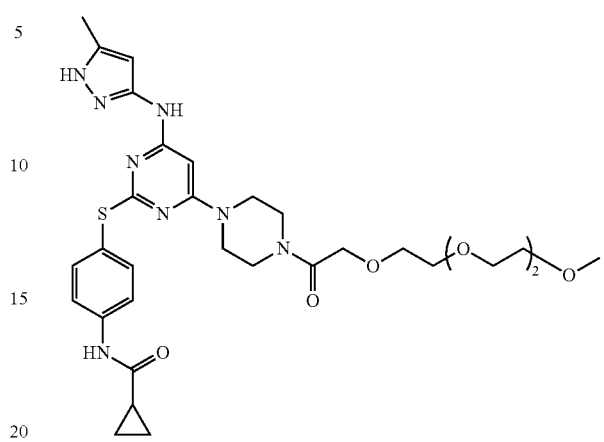
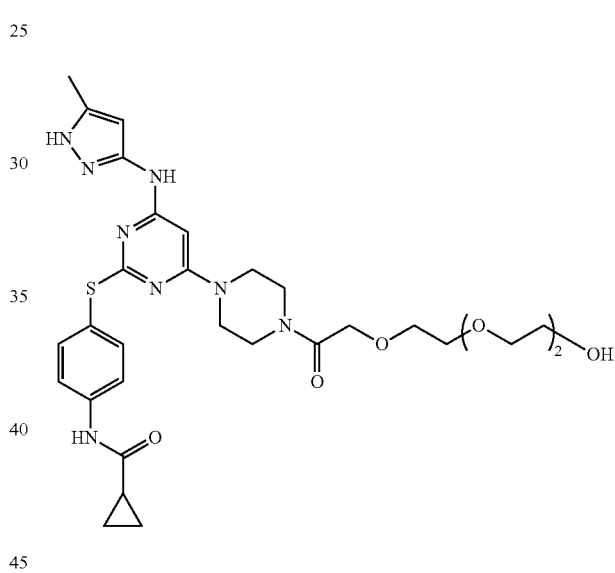
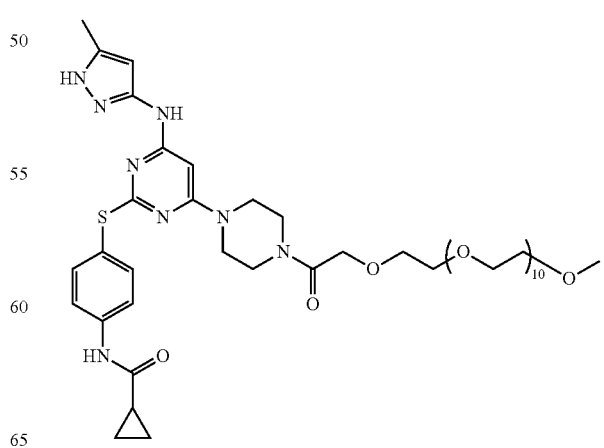

Example 30. Non-Limiting Examples of Compounds of Formula XIV
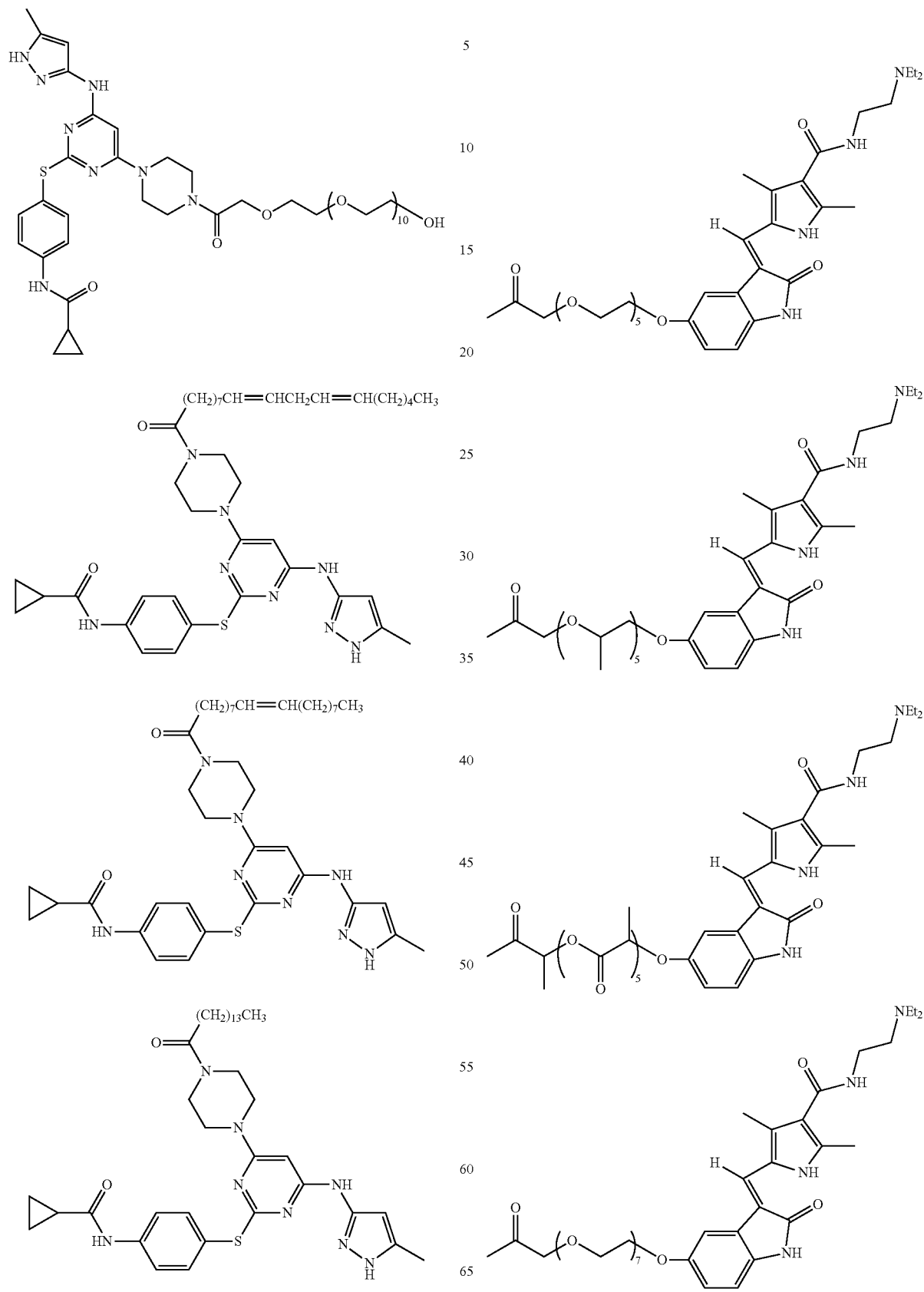

361
-continued
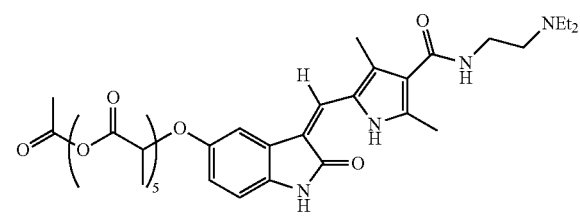
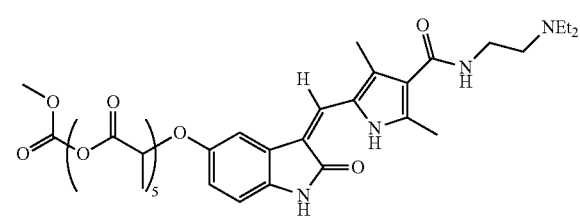
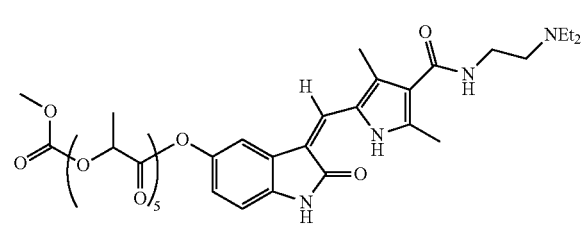
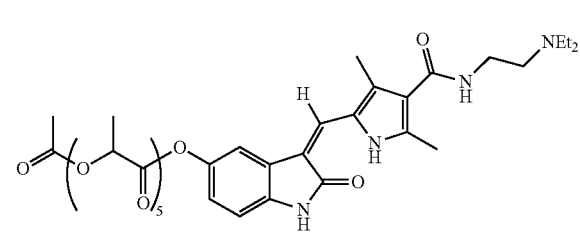
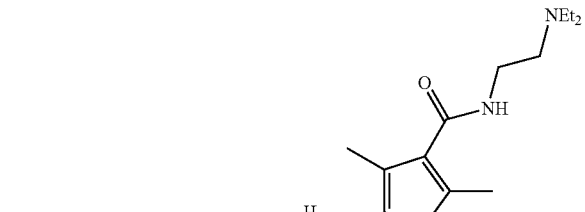
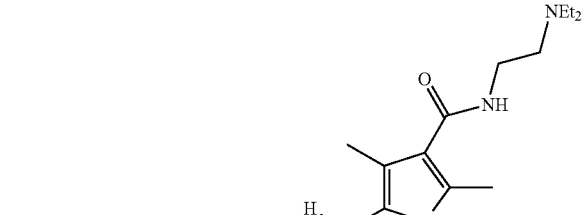
362
-continued
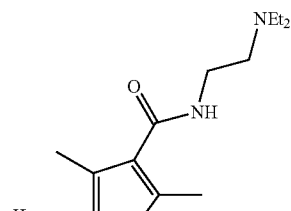
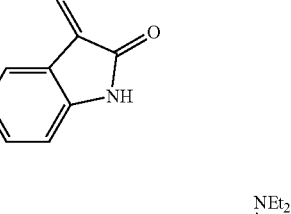
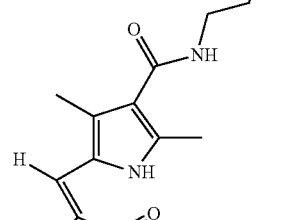
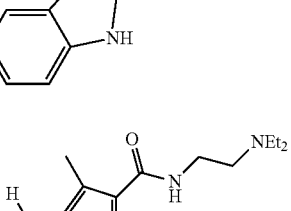
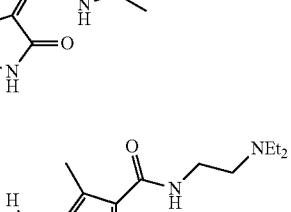
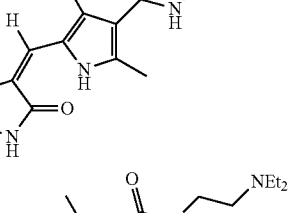

363
-continued
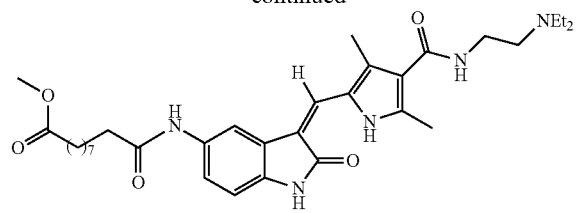
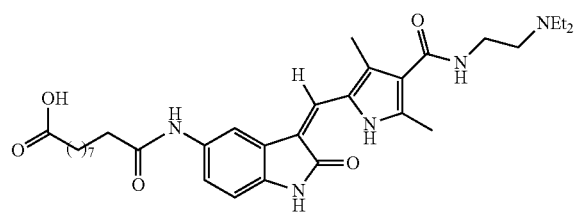
364
-continued
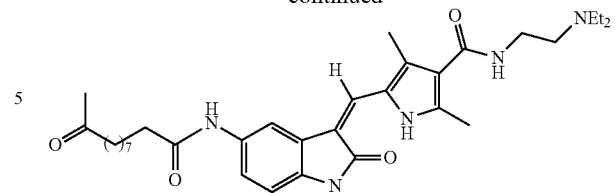
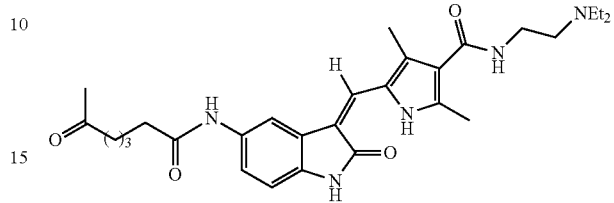
Example 31. Non-Limiting Examples of Compounds of Formula XV
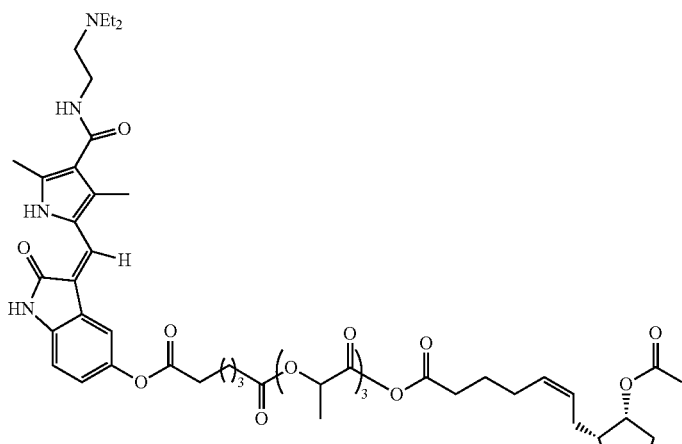
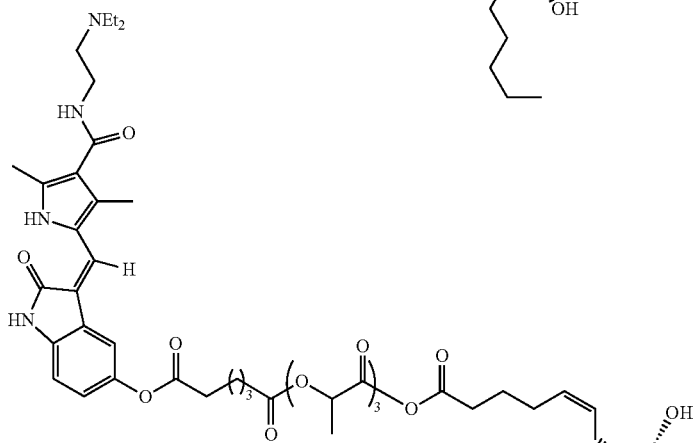

-continued
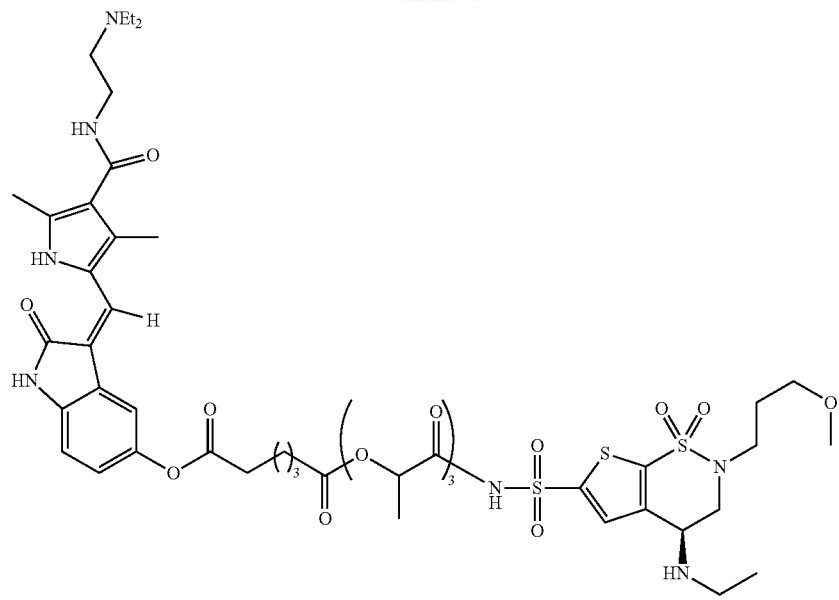
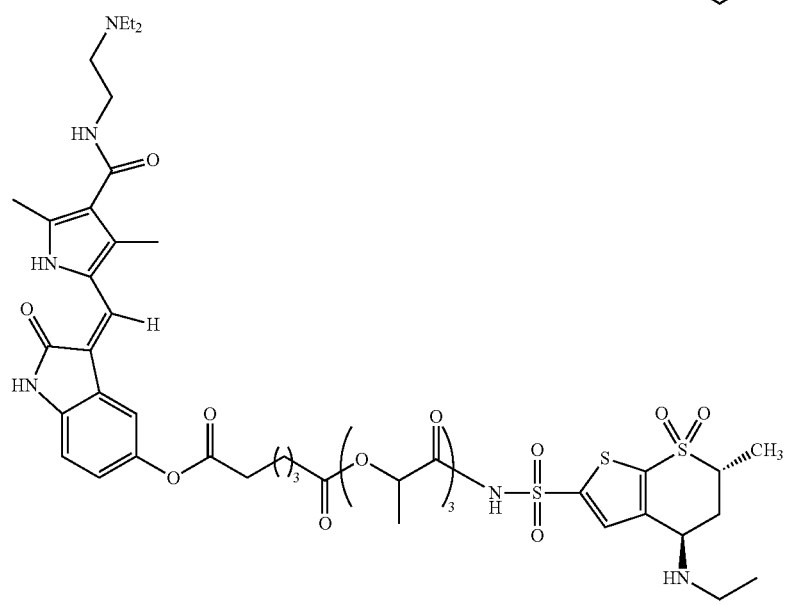
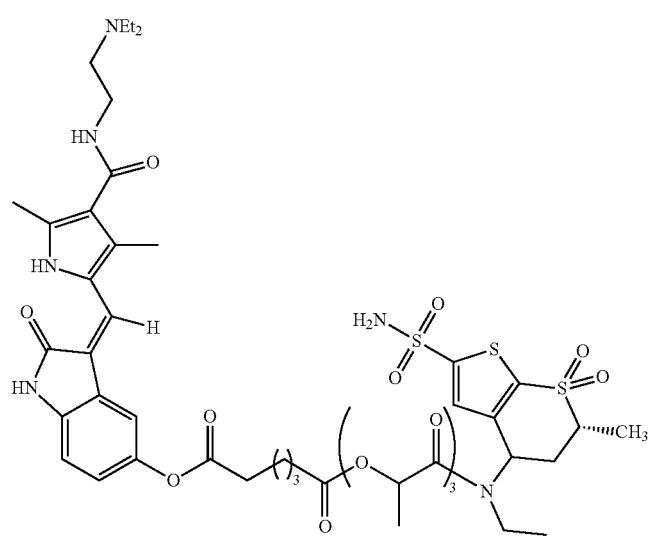

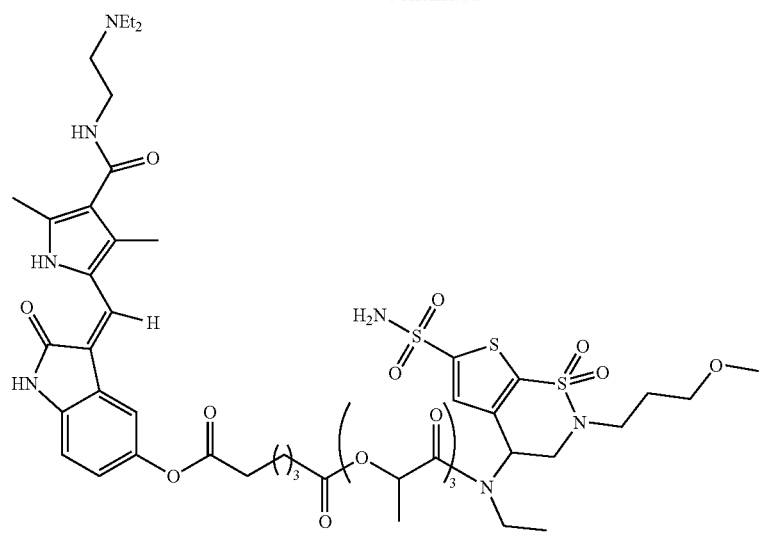
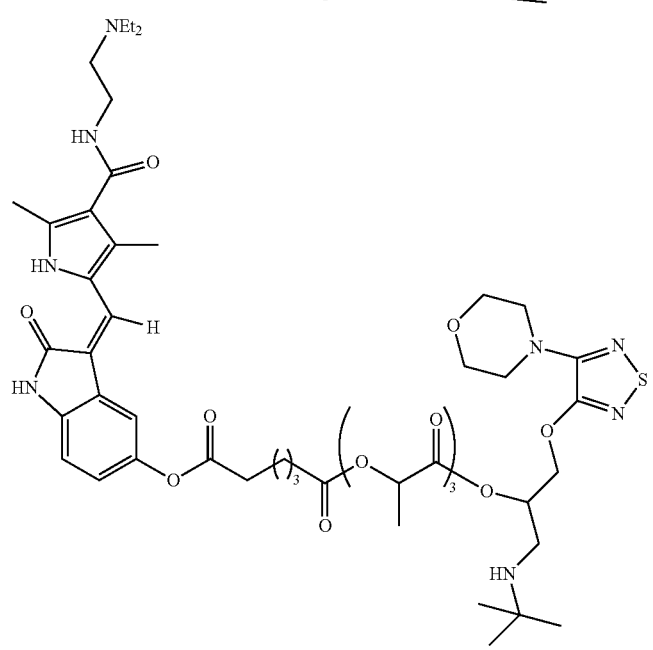
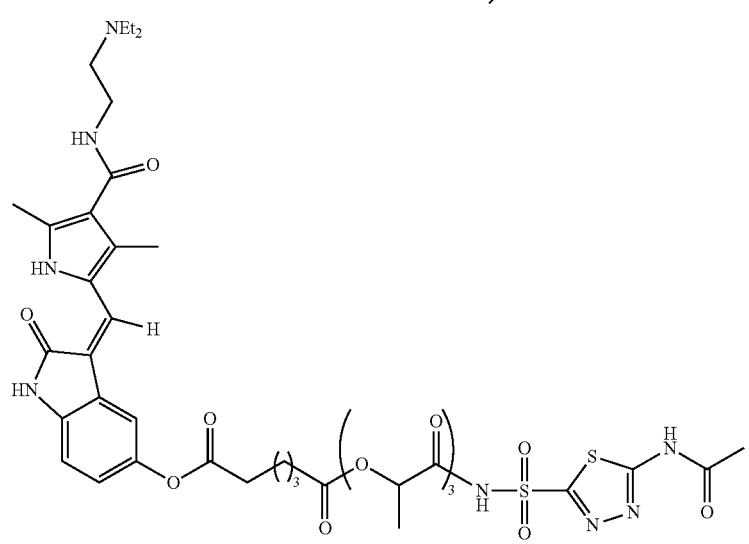

-continued
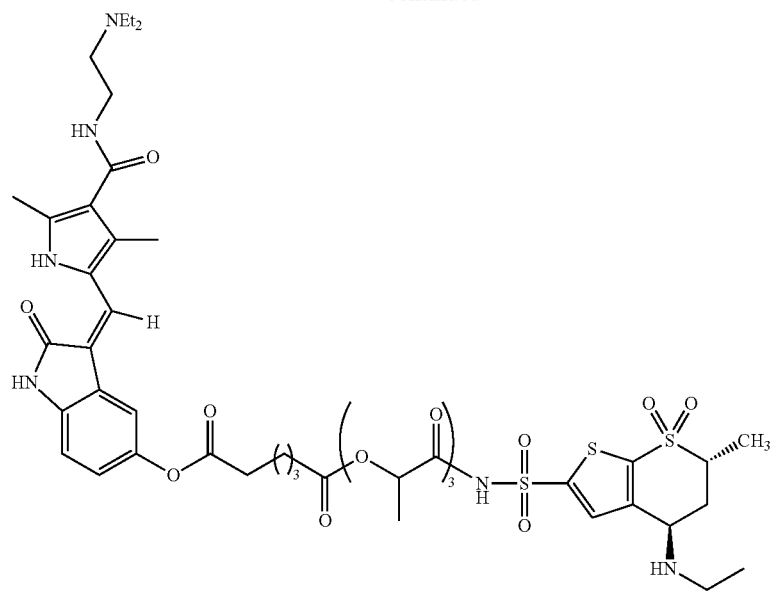
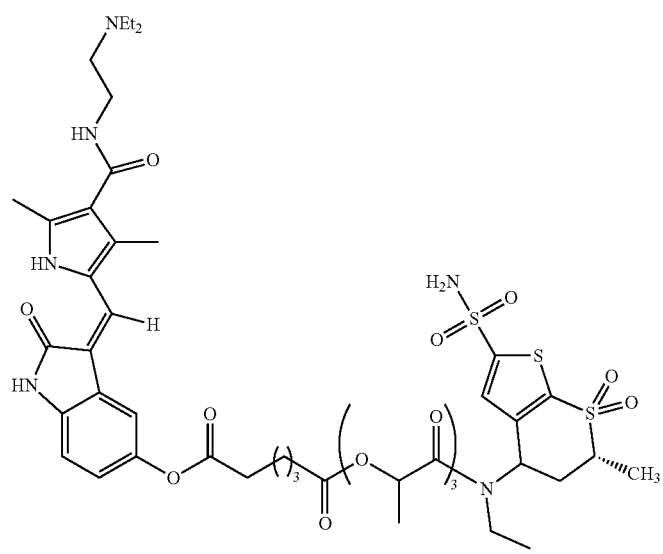
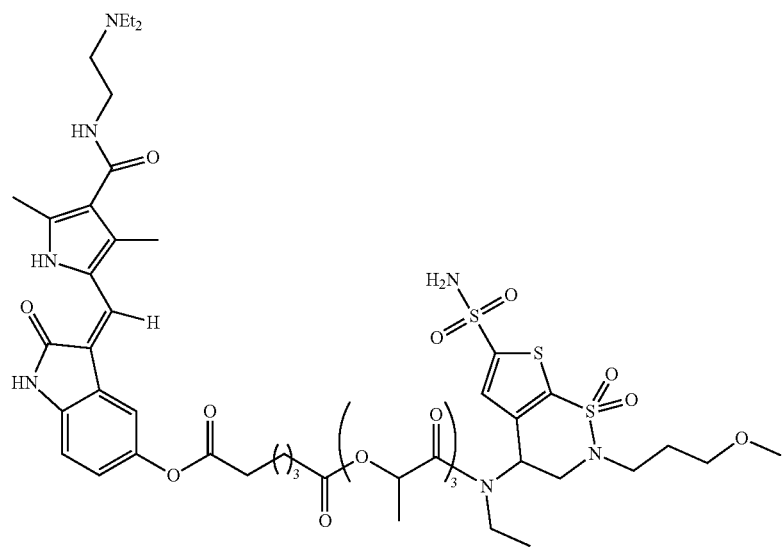

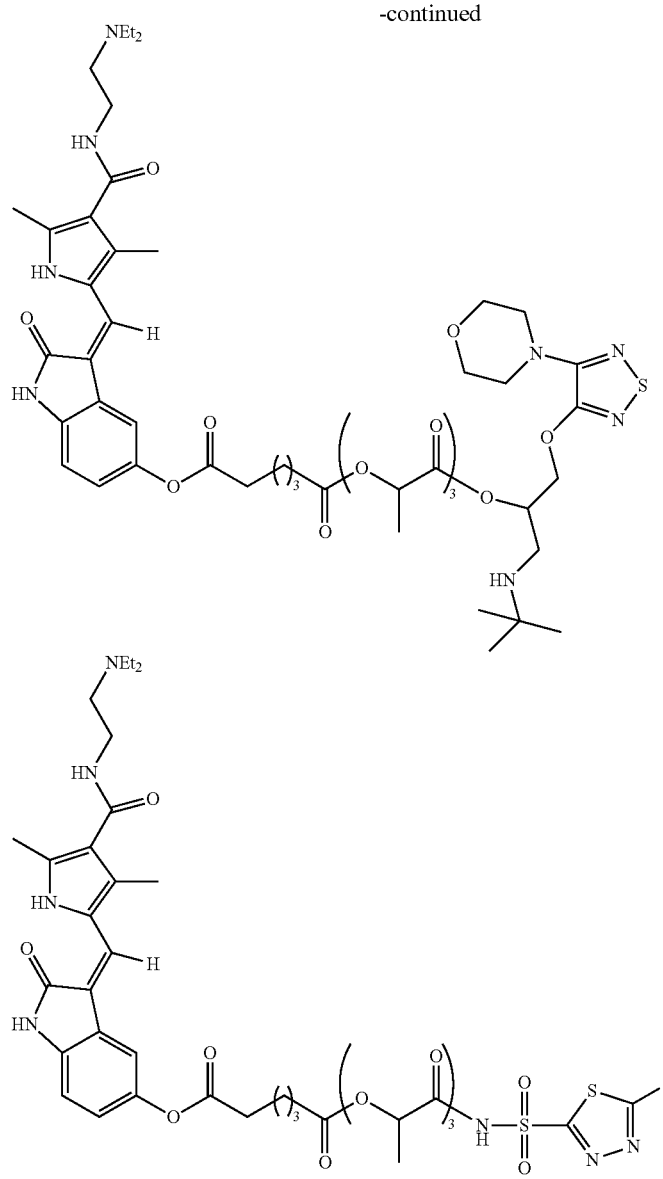
Example 32. Non-Limiting Examples of Compounds of Formula XVI
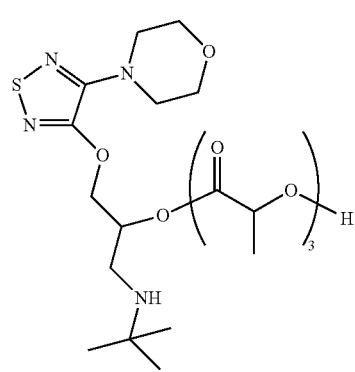
-continued
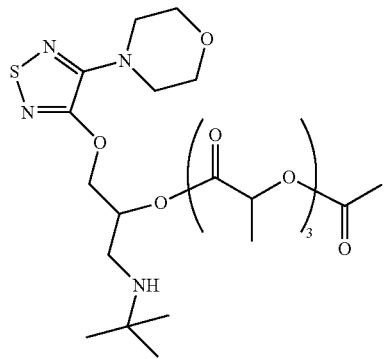

373
-continued
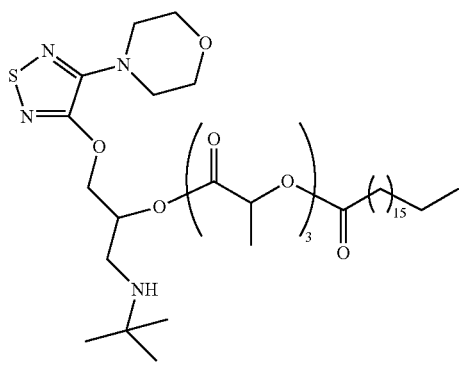
374
-continued
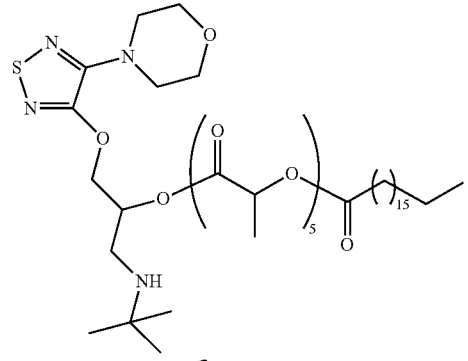
Example 33. Non-Limiting Examples of Compounds of Formula XVII
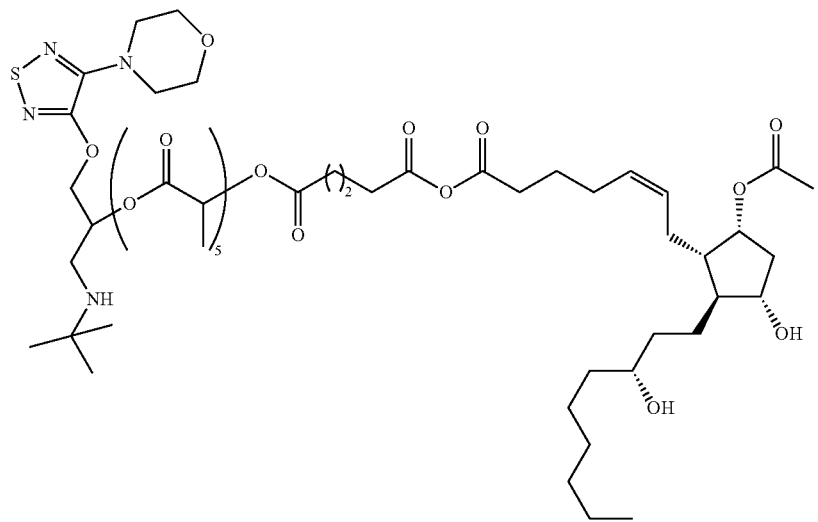

-continued
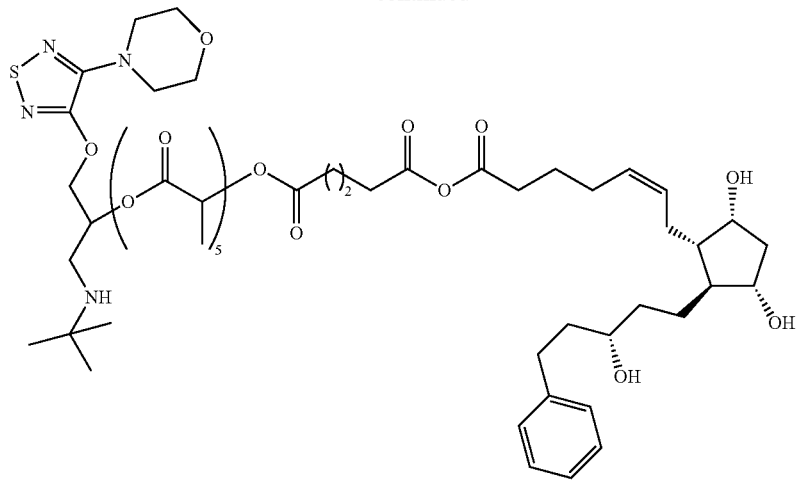
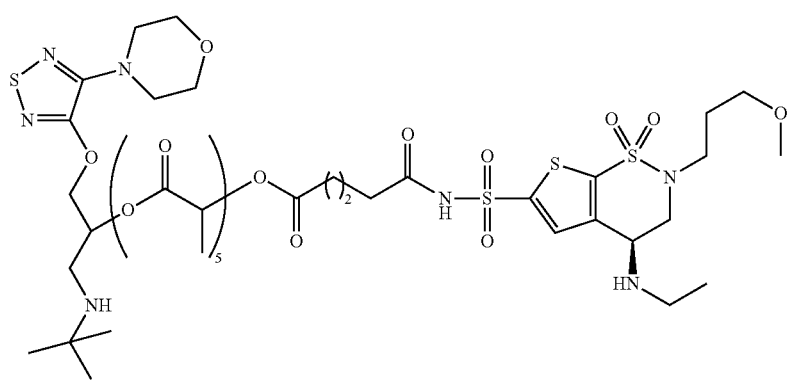
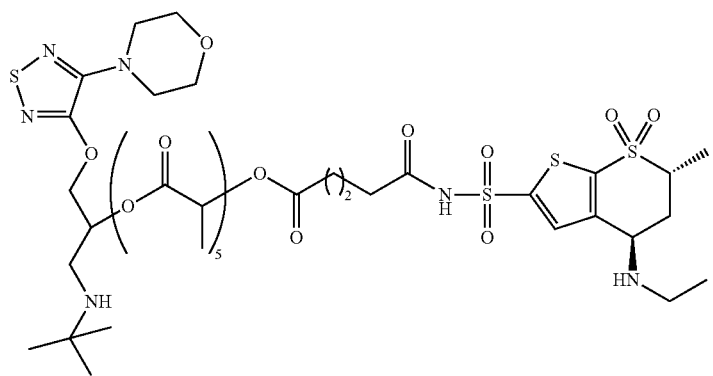
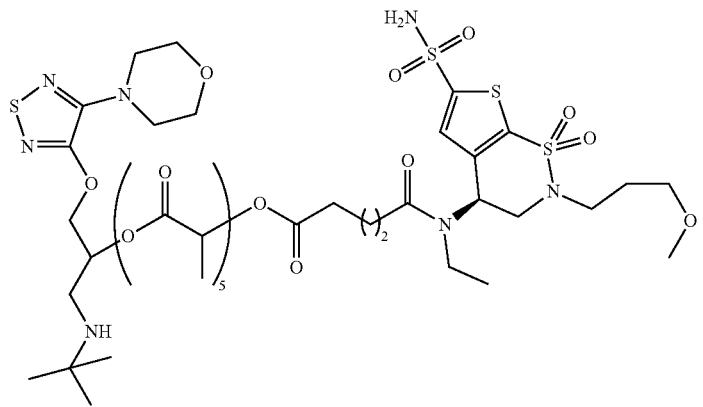

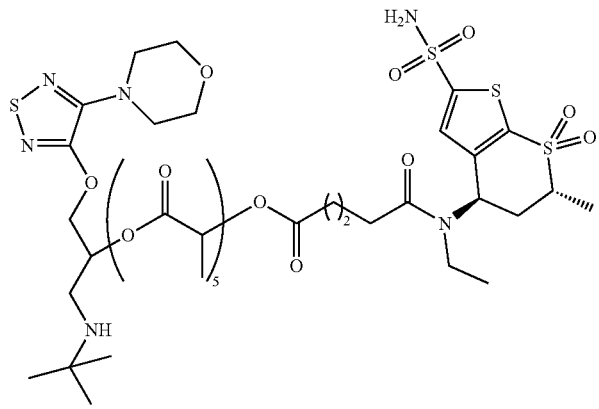
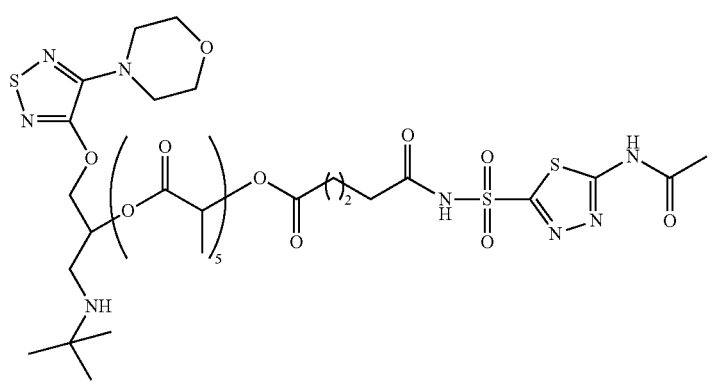
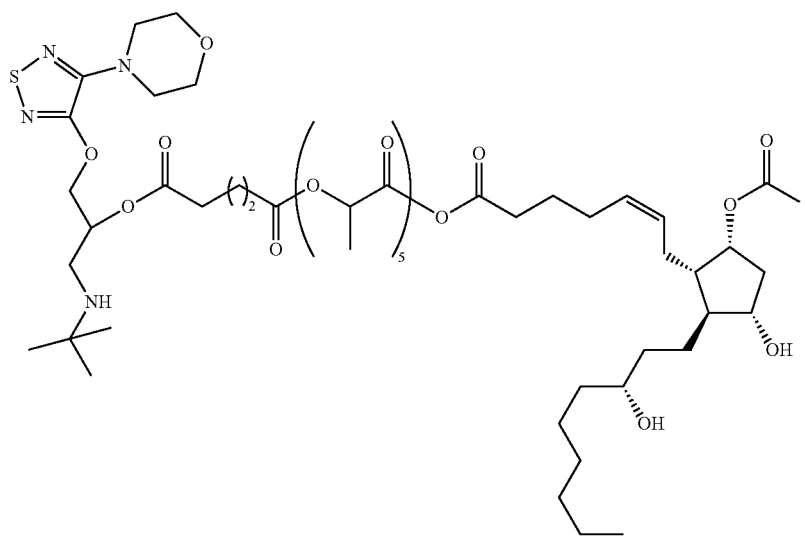

-continued
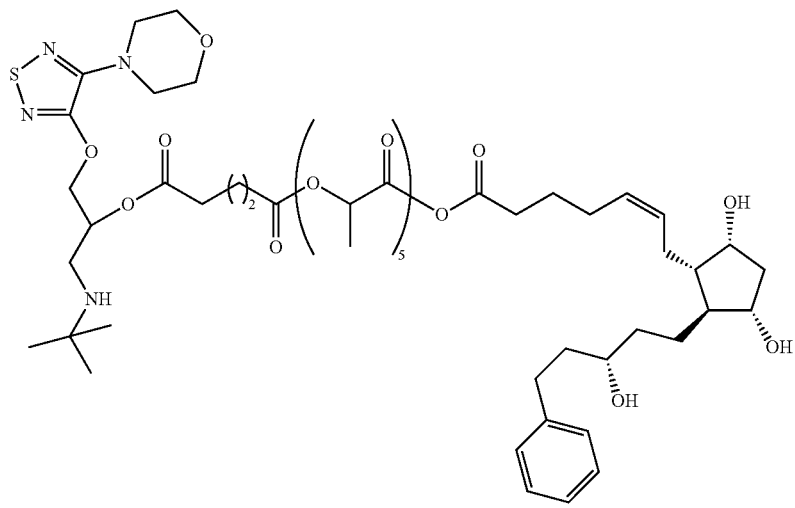
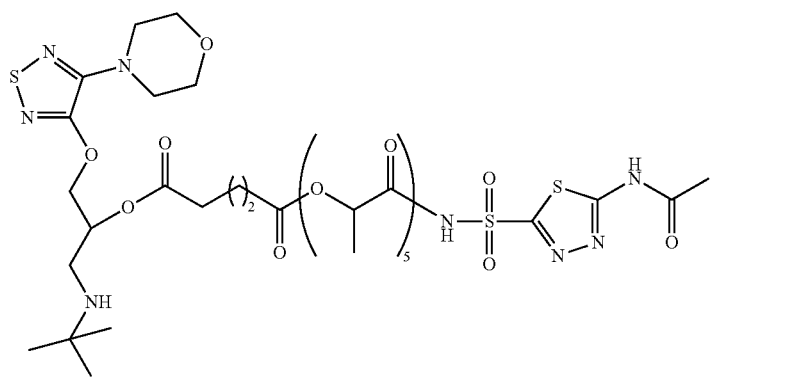
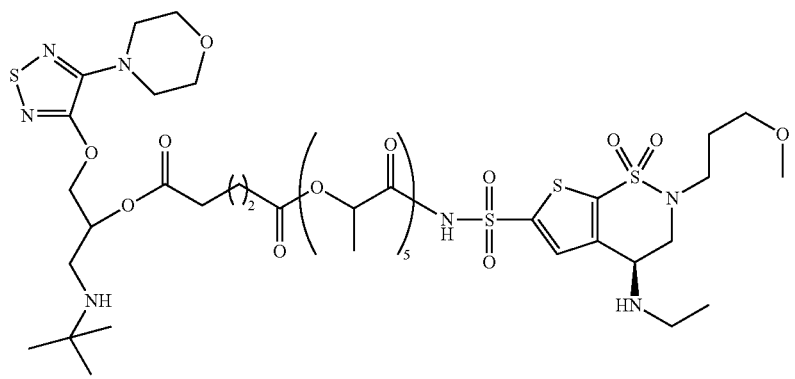
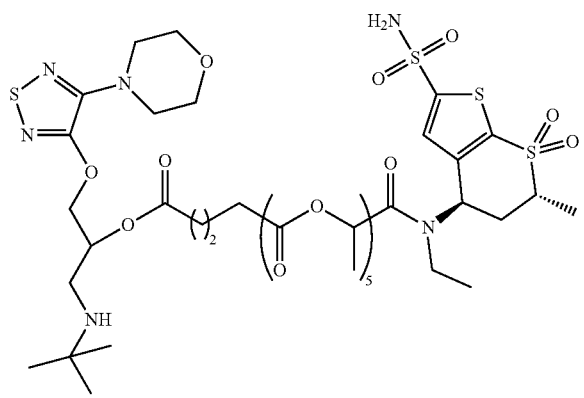

-continued

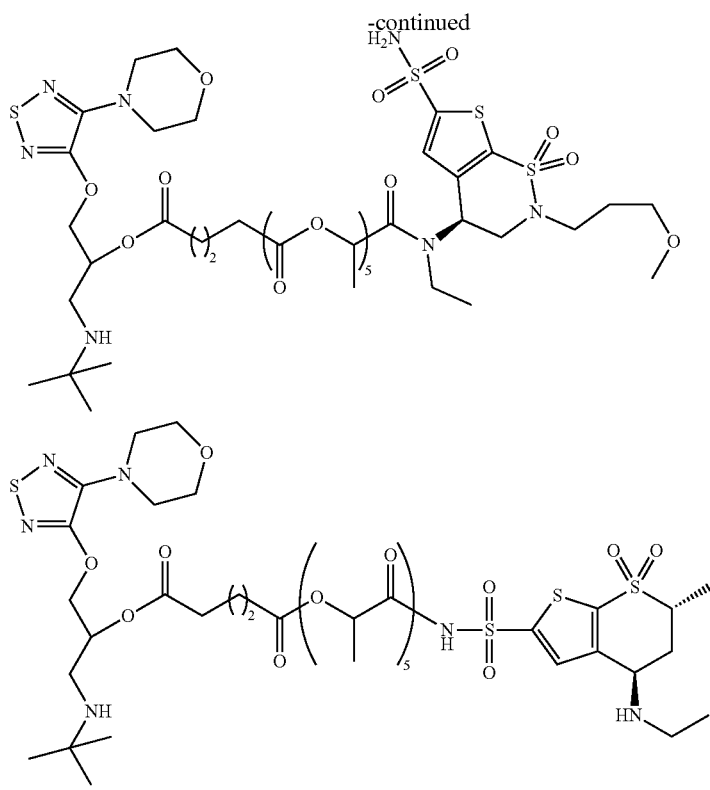

Example 34. Analytical Method Development for Compounds Containing Carbonic Anhydrase Inhibitors (CAIs)

Determination of Maximal Absorptive Wavelength

Solutions of brinzolamide and dorzolamide and their covalent conjugates of polylactic acid (PLA) were individually prepared in methanol at a concentration of 100 μg/mL. The samples were scanned at a wavelength range of 200-800 nm using a Genesys 105 UV-VIS spectrophotometer (Thermo Scientific). From the respective absorption spectra, 254 nm was selected as the detection wavelength for brinzolamide, dorzolamide and their PLA conjugates.

HPLC Method for Brinzolamide, Dorzolamide and their PLA Conjugates

A reversed phase performance liquid chromatographic method was developed for the simultaneous determination of brinzolamide or dorzolamide and their conjugates with varying PLA. Successful chromatographic separation was achieved using an Agilent 1260 Infinity HPLC equipped with a diode array and a multiple wavelength detector with an XTERRA C8 column (5 m, 4.6 mm×150 mm) as the stationary phase. The mobile phase consisted of a 5-95% acetonitrile (MeCN) gradient over 4 minutes followed by a second rapid gradient change of MeCN concentration from 95% to 5% between 5 and 5.5 min (Table 1). The flow rate was 1.0 mL/min and the detection wavelength was 254 nm. The injection volume was 10 μL. The analysis was performed at 25° C. Both water and MeCN contained 0.1% (v/v) formic acid (FA). Retention times are illustrated in Table 2. From the overlay of the individual chromatograms, the method provides adequate resolution for chromagraphic separation of parent and PLA conjugated compounds with different numbers of lactic acid (LA) units and functional end-groups.

TABLE 1

HPLC gradient for separation of brinzolamide, dorzolamide and their PLA-conjugates

| Time (min) | A (water + 0.1% FA) | B (MeCN + 0.1% FA) |
|---|---|---|
| 0 | 95 | 5 |
| 4 | 5 | 95 |
| 5 | 5 | 95 |
| 5.5 | 95 | 5 |
| 7 | 95 | 5 |

TABLE 2

Relative retention times (RRT) of brinzolamide, dorzolamide and their PLA-conjugates

| PLA Repeat Units | Brinzolamide RRT (min) | Dorzolamide RRT (min) |
|---|---|---|
| Parent | 3.64 | 2.95 |
| n = 1 | 3.91 | 3.65 |
| n = 2 | 4.07 | — |
| n = 3 | 4.18 | 4.00 |
| n = 4 | 4.35 | 4.20 |
| Acetyl, n = 3 | 4.53 | 4.45 |
| Acetyl, n = 4 | 4.72 | 4.60 |
| Acetyl, n = 5 | 4.90 | 4.78 |
| Acetyl, n = 6 | 5.05 | 4.98 | n is the number of LA repeat units conjugated to the parent compound

Example 35. Analytical Method Development for Compounds Containing Latanoprost Determination of Maximal Absorptive Wavelength Latanoprost and latanoprost-Acetyl PLA conjugates were dissolved in DMSO at a concentration of 100 μg/mL. The samples were scanned at a wavelength range of 200-800 nm using a Genesys 105 UV-VIS spectrophotometer (Thermo Scientific). From the respective absorption spectra, 210 nm was selected as the detection wavelength.

HPLC Method for Latanoprost and PLA-Conjugated Latanoprost

Chromatographic separation of latanoprost parent compound and its PLA conjugated derivatives was achieved using an Agilent 1260 Infinity HPLC equipped with a diode array and a multiple wavelength detector with an XTERRA C8 column (5 μm, 4.6 mm×150 mm) as the stationary phase. The gradient separation method is outlined in Table 3. The analysis was performed at an injection volume of 50 μL, a flow rate of 1.2 mL/min and a detection wavelength of 210 nm at 25° C. Retention times for latanoprost and PLA-conjugated compounds are illustrated in Table 4.

TABLE 3

HPLC gradient method for separation of latanoprost derivatives

| Time (min | A (water + 0.1% FA) | B (MeCN + 0.1% FA) |
| --- | --- | --- |
| 0 | 95 | 5 |
| 6 | 40 | 60 |
| 7 | 5 | 95 |
| 8 | 5 | 95 |
| 9 | 95 | 5 |
| 15 | 95 | 5 |

TABLE 4

Relative retention times of latanoprost and its derivatives

| PLA Repeat Units | RRT (min) |
| --- | --- |
| Parent | 9.66 |
| Acetyl, n = 3 | 10.15 |
| Acetyl, n = 4 | 10.48 |
| Acetyl, n = 5 | 10.71 | n is the number of LA repeat units conjugated to the parent compound.

Example 36. Determination of Drug Solubility

For each test, approximately 5-10 mg was transferred to a 10 mL glass vial. Aqueous or organic solvent was added to each vial to achieve an overall concentration of 50 mg/mL. After vortexing aggressively for 2-3 minutes and sonicating in a bath sonicator for 5 minutes, undissolved drug was spun down at 1200 rpm for 5 minutes to generate a pellet. The supernatant was collected and filtered through a 0.2 m nylon syringe filter into HPLC vials for drug content analysis. Drug concentration was determined by comparing against a standard calibration curve.

Solubility of Compounds Containing Brinzolamide, Dorzolamide or Latanoprost

Drug solubility in aqueous and organic solvent can inform on the potential for said drug to be encapsulated within microparticles and its release kinetics once it has been encapsulated. Herein, drug solubility was evaluated to better predict and select compounds that may be amenable to particle encapsulation. As demonstrated in Table 5, brinzolamide exhibits low aqueous solubility (<1 mg/mL), but high solubility in DMSO (>50 mg/mL), whereas dorzolamide is characterized by high aqueous solubility and low organic solubility. Interestingly, chemical modification by the addition of a short PLA (n=2-4) via an amide linkage to the sulfonamide nitrogen significantly increased the aqueous solubility of brinzolamide from <1 mg/mL to >50 mg/mL, respectively. However, when the terminal lactate is acetylated and the number of LA repeat units is greater than 3, the aqueous solubility of brinzolamide conjugates remains low (<1 mg/mL). Chemical modification of dorzolamide significantly enhanced the organic solubility of dorzolamide only when the number of LA units exceeded 3 or when the terminal unit was acetylated. Aqueous solubility of dorzolamide was significantly decreased from >50 mg/mL to <1 mg/mL when conjugated to PLA (n>3) and capped with an acetyl group.

Similar to brinzolamide, latanoprost exhibited very low aqueous solubility and high organic solubility. Conjugation of PLA and acetylation of the terminal lactate unit did not significantly alter its aqueous solubility, but did decrease its organic solubility from greater than 50 mg/mL to less than 25 mg/mL.

All bifunctional conjugates with sunitinib exhibited low aqueous solubility and high organic solubility (less than 1 mg/mL in aqueous solution and greater than 50 mg/mL in DMSO), respectively.

TABLE 5

Solubility of brinzolamide, dorzolamide, latanoprost and their PLA conjugates

| | | Solubility | | |
| --- | --- | --- | --- | --- |
| Compound | Compound number | Water (mg/mL) | DMSO (mg/mL) | DCM (mg/mL) |
| Brinzolamide | Brinzolamide | <1.0 | >50 | <7.5 |
| Brinzolamide-PLA (n = 2) | 33-2 | >50 | >50 | >50 |
| Brinzolamide-PLA (n = 3) | 34-2 | >50 | >50 | >50 |
| Brinzolamide-PLA (n = 4) | 35-2 | >50 | >50 | >50 |
| Brinzolamide-Acetyl PLA (n = 3) | 36-1 | >50 | >50 | >50 |
| Brinzolamide-Acetyl PLA (n = 4) | 37-1 | <1.0 | >50 | >50 |
| Brinzolamide-Acetyl PLA (n = 5) | 38-1 | <1.0 | >50 | >50 |
| Brinzolamide-Acetyl PLA (n = 6) | 39-1 | <1.0 | >50 | >50 |
| Dorzolamide | Dorzolamide | >50 | <1.0 | <1.0 |
| Dorzolamide-PLA (n = 3) | 20-2 | >50 | <2.0 | <5.0 |
| Dorzolamide-PLA (n = 4) | 21-2 | >50 | >50 | >50 |
| Dorzolamide-Acetyl PLA (n = 3) | 26-1 | >50 | >50 | >50 |
| Dorzolamide-Acetyl PLA (n = 4) | 27-1 | <1.0 | >50 | >50 |
| Dorzolamide-Acetyl PLA (n = 5) | 28-1 | <1.0 | >50 | >50 |
| Dorzolamide-Acetyl PLA (n = 6) | 29-1 | <1.0 | >50 | >50 |
| Latanoprost | Latanoprost | <1.0 | >50 | >50 |
| Latanoprost-Acetyl PLA (n = 3) | 43-2 | <1.0 | <25 | — |
| Latanoprost-Acetyl PLA (n = 4) | 44-1 | <1.0 | <25 | — |
| Latanoprost-Acetyl PLA (n = 5) | 45-1 | <1.0 | <50 | — |
| 5-Amino sunitinib | 47-1 | <1.0 | >50 | — |
| Dorzolamide-PLA (n = 3)-succinate-5-amino sunitinib | 57-3 | <1.0 | >50 | — |
| Dorzolamide-PLA (n = 3)-succinate-5-hydroxy sunitinib | 56-5 | <1.0 | >50 | — |
| Dorzolamide-PLA (n = 4)-succinate-5-hydroxyl sunitinib | 58-5 | <1.0 | >50 | — |

TABLE 5-continued

Solubility of brinzolamide, dorzolamide, latanoprost and their PLA conjugates

| Compound | Compound number | Solubility Water (mg/mL) | Solubility DMSO (mg/mL) | Solubility DCM (mg/mL) |
|---|---|---|---|---|
| Brinzolamide-PLA (n = 4)-succinate-5-hydroxy sunitinib | 60-1 | <1.0 | >50 | — |
| 5-hydroxyl sunitinib-PLA (n = 3)-Etacrynic acid | 54-1 | <1.0 | >50 | — |
| Brinzolamide-PLA (n = 3)-adipate-5-hydroxyl sunitinib (isomer-1) | 61-3 | <1.0 | >50 | — |
| Brinzolamide-PLA (n = 3)-adipate-5-hydroxyl sunitinib (isomer-2) | 61-2 | <1.0 | >50 | — |

Example 37. In Vitro Stability

In Vitro Stability of Brinzolamide NCEs

Brinzolamide and brinzolamide-PLA NCEs were first dissolved in PBS (pH 7) containing 10% DMSO (v/v) at a concentration of 1 mg/mL. The samples were incubated at 37° C. or 50° C. to simulate physiological and accelerated degradation conditions, respectively. At various time points, 100 µL of the solution was collected, diluted 10-fold with MeCN+0.1% formic acid, filtered through a 0.2 m nylon syringe filter and analyzed by RP-HPLC.

Figure 2:
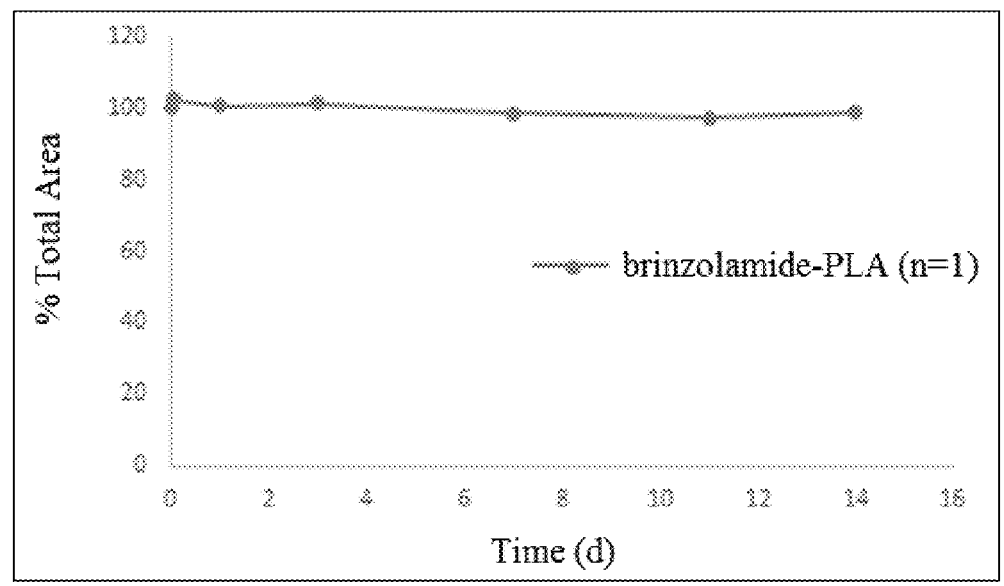
FIG. 2 illustrates the stability of brinzolamide-PLA (n=1) (32-3) at physiological conditions (37° C.) over 14 days. The x-axis represents time (days) and the y-axis represents the amount of undegraded brinzolamide-PLA (n=1) (32-3) as a percentage of the total brinzolamide amount as analyzed by RP-HPLC.
Figure 3:
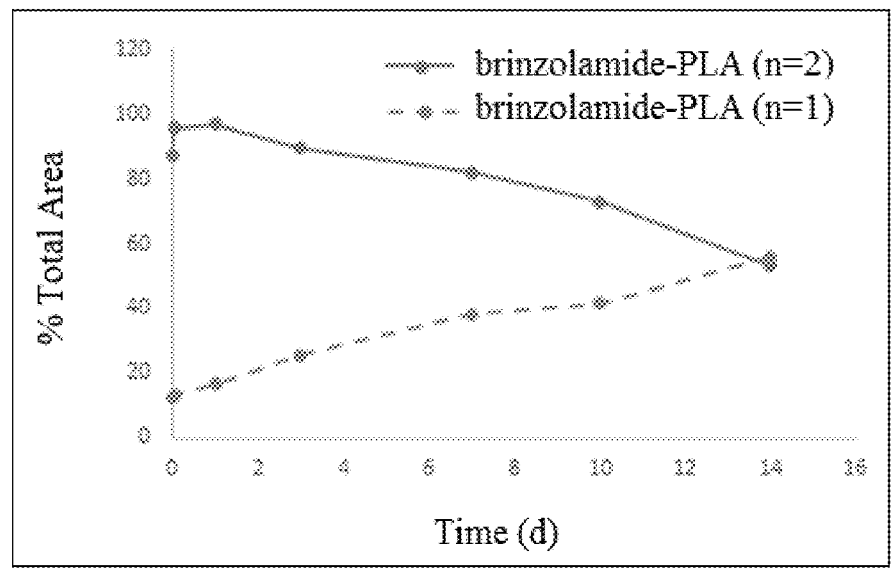
FIG. 3 illustrates the percentage of brinzolamide-PLA (n=2) (33-2) that is degraded to brinzolamide-PLA (n=1) (32-3) at physiological conditions (37° C.) over 14 days. The x-axis represents time (days) and the y-axis represents the amount of each undegraded brinzolamide-PLA analog as a percentage of the total brinzolamide amount as analyzed by RP-HPLC.
Figure 4:
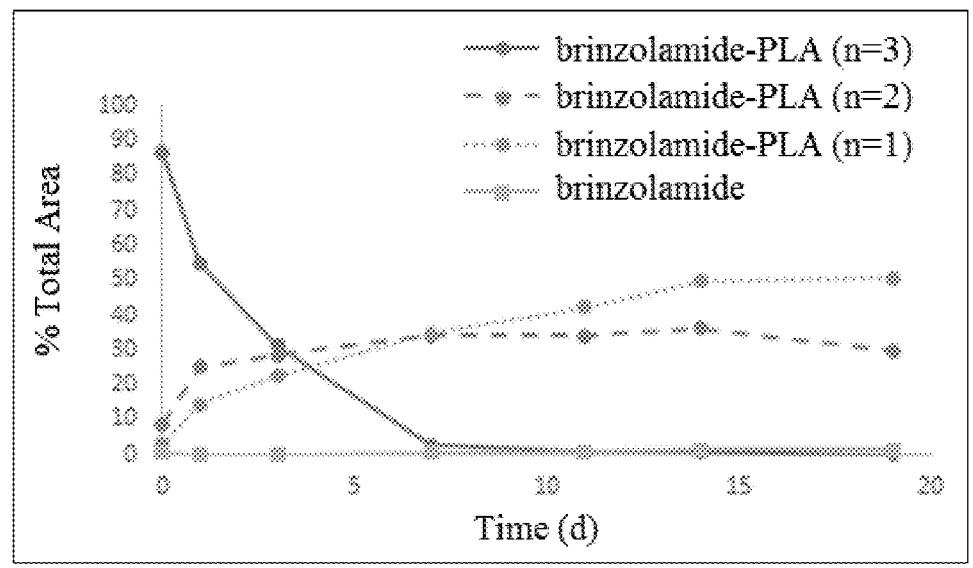
FIG. 4 illustrates the percentage of brinzolamide-PLA (n=3) (34-2) that is degraded to brinzolamide-PLA (n=2) (33-2), brinzolamide-PLA (n=1) (32-3), and parent brinzolamide at physiological conditions (37° C.) over 19 days. The x-axis represents time (days) and the y-axis represents the amount of each undegraded brinzolamide-PLA analog as a percentage of the total brinzolamide amount as analyzed by RP-HPLC.
Figure 5:
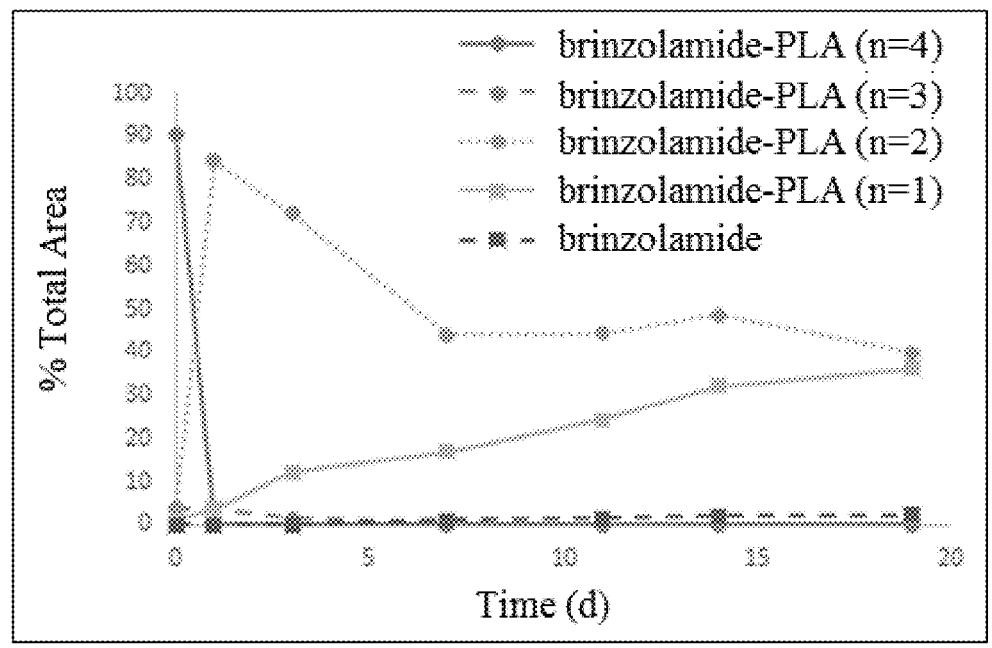
FIG. 5 illustrates the percentage of brinzolamide-PLA (n=4) (35-2) that is degraded to brinzolamide-PLA (n=3) (34-2), brinzolamide-PLA (n=2) (33-2), brinzolamide-PLA (n=1) (32-3), and parent brinzolamide at physiological conditions (37° C.) over 19 days. The x-axis represents time (days) and the y-axis represents the amount of each undegraded brinzolamide-PLA analog as a percentage of the total brinzolamide amount as analyzed by RP-HPLC.

As shown in FIG. 1, brinzolamide remained relatively stable across the 14 day incubation period at physiological and accelerated conditions. Similarly, the prodrug brinzolamide-PLA (n=1) (32-3) demonstrated high stability in vitro at 37° C. with >98% of the primary compound remaining at 14 days (FIG. 2). Increase in the length of PLA chain resulted in an increase in the degradation rate of the primary compound with loss of PLA monomers. As shown in FIG. 3, the linkage between LA 1 and 2 in brinzolamide-PLA (n=2) (33-2) is relatively stable, but it breaks down over time, and approximately 53% of the primary compound remained after the 14 day incubation period. FIG. 4 shows the degradation profile of brinzolamide-PLA (n=3) (34-2). As the n=1 amide bond is highly stable, minimal degradation to the parent compound was detected at the end of the 19 day incubation. Interestingly, as the number of LA repeat units increased to 4, the propensity of the LA units to hydrolyze in pairs was clearly evident. As shown in FIG. 5, the primary compound rapidly loses lactate units in pairs to generate brinzolamide-PLA (n=2) (33-2). After only one day of incubation at 37° C., approximately 93% of the primary compound (brinzolamide-PLA (n=4) (35-2)) had degraded to brinzolamide-PLA (n=2) (33-2).

Figure 6:
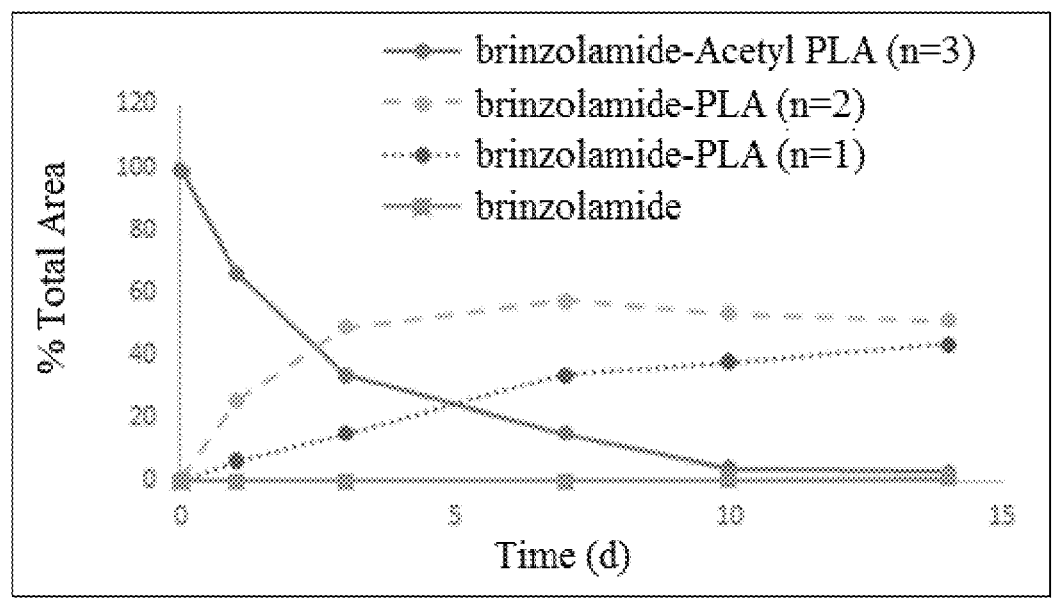
FIG. 6 illustrates the percentage of brinzolamide-acetyl PLA (n=3) (36-1) that is degraded to brinzolamide-PLA (n=2) (33-2), brinzolamide-PLA (n=1) (32-3), and parent brinzolamide at physiological conditions (37° C.) over 19 days. The x-axis represents time (days) and the y-axis represents the amount of each undegraded brinzolamide-PLA analog as a percentage of the total brinzolamide amount as analyzed by RP-HPLC.
Figure 7:
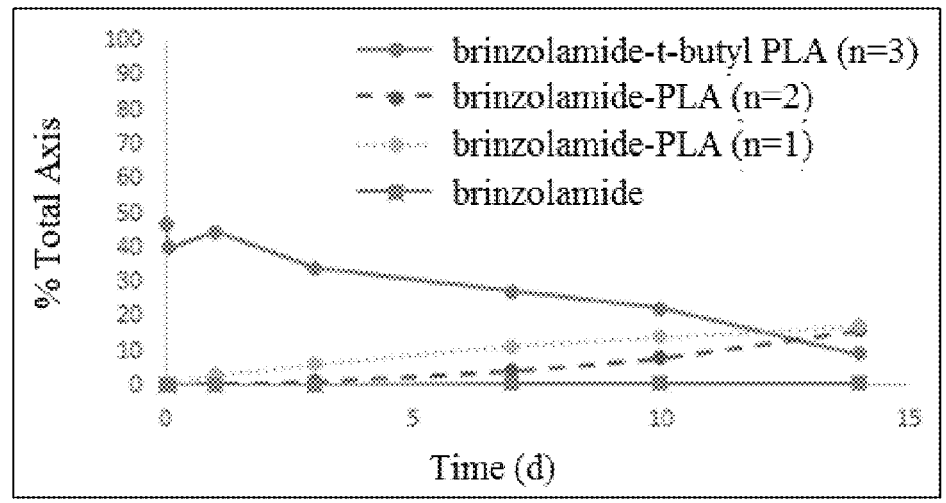
FIG. 7 illustrates the percentage of brinzolamide-t-butyl PLA (n=3) (40-1) that is degraded to brinzolamide-PLA (n=2) (33-2), brinzolamide-PLA (n=1) (32-3), and parent brinzolamide at physiological conditions (37° C.) over 19 days. The x-axis represents time (days) and the y-axis represents the amount of each undegraded brinzolamide-PLA analog as a percentage of the total brinzolamide amount as analyzed by RP-HPLC.
Figure 8:
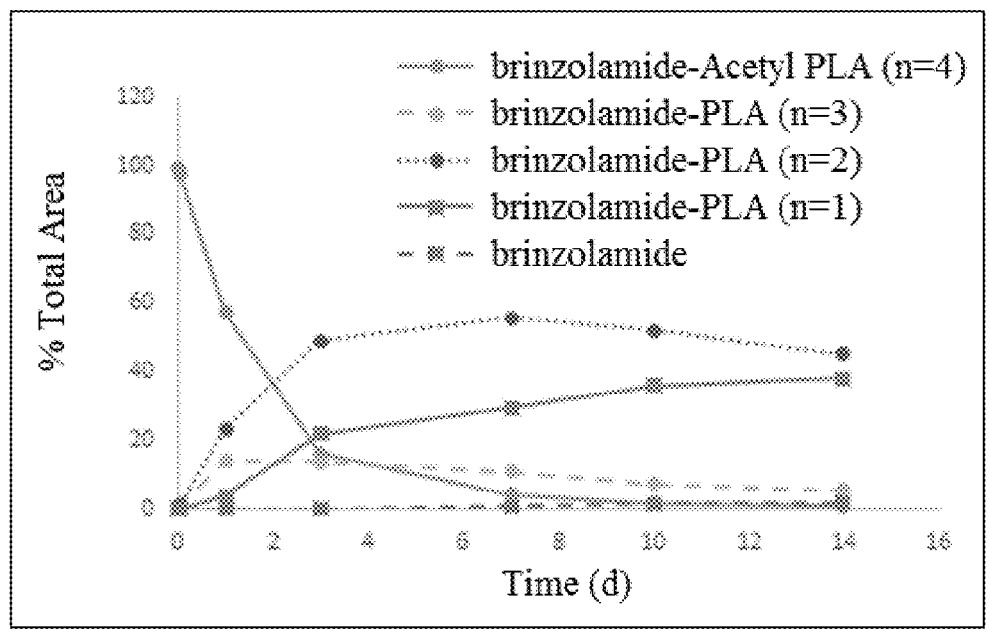
FIG. 8 illustrates the percentage of brinzolamide-acetyl PLA (n=4) (37-1) that is degraded to brinzolamide-PLA (n=3) (34-2), brinzolamide-PLA (n=2) (33-2), brinzolamide-PLA (n=1) (32-3), and parent brinzolamide at physiological conditions (37° C.) over 19 days. The x-axis represents time (days) and the y-axis represents the amount of each undegraded brinzolamide-PLA analog as a percentage of the total brinzolamide amount as analyzed by RP-HPLC.
Figure 9:
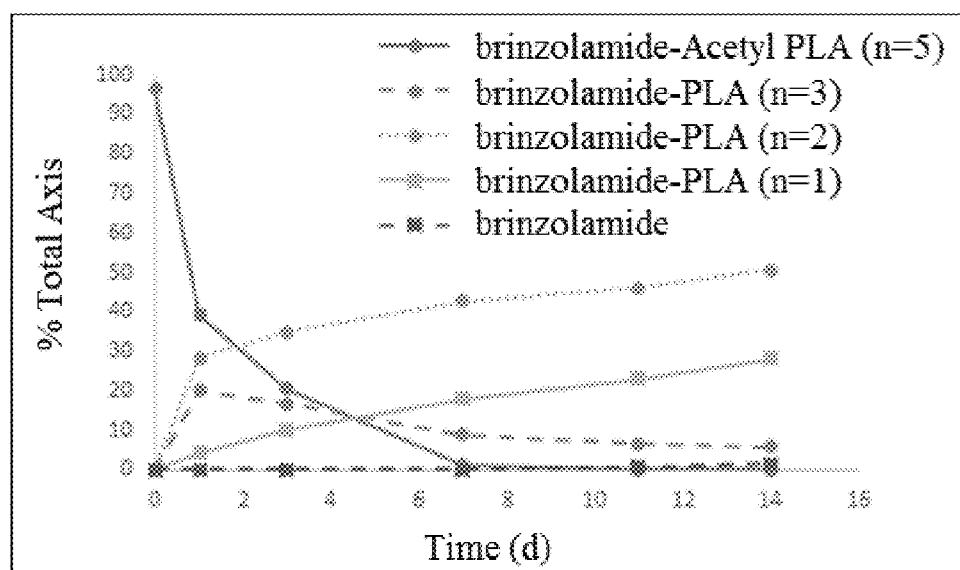
FIG. 9 illustrates the percentage of brinzolamide-acetyl PLA (n=5) (38-1) that is degraded to brinzolamide-PLA (n=3) (34-2), brinzolamide-PLA (n=2) (33-2), brinzolamide-PLA (n=1) (32-3), and parent brinzolamide at physiological conditions (37° C.) over 19 days. The x-axis represents time (days) and the y-axis represents the amount of each undegraded brinzolamide-PLA analog as a percentage of the total brinzolamide amount as analyzed by RP-HPLC.
Figure 10:
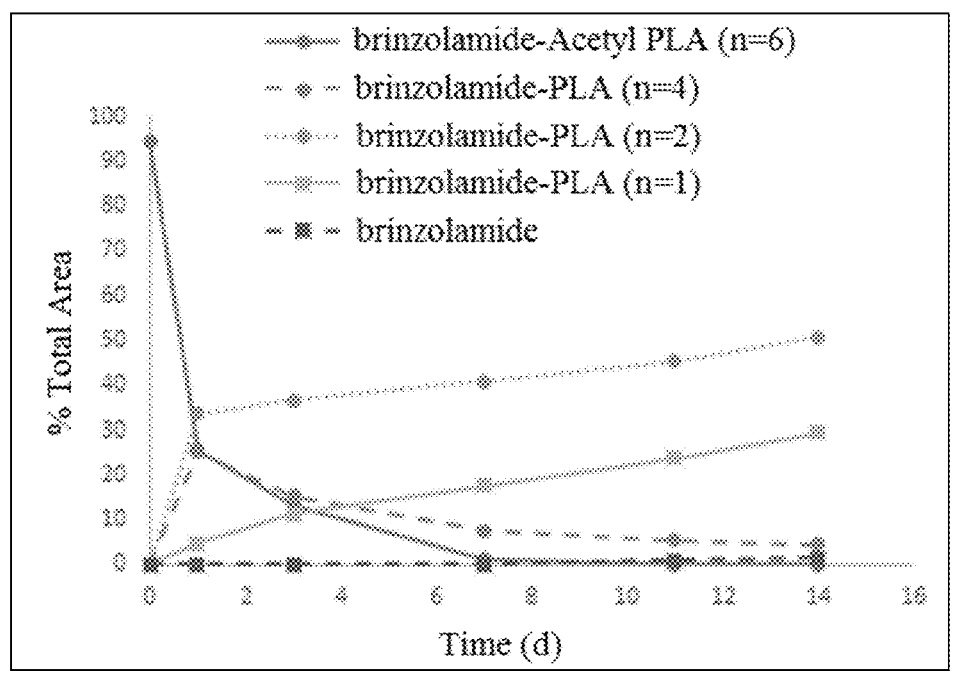
FIG. 10 illustrates the percentage of brinzolamide-acetyl PLA (n=6) (39-1) that is degraded to brinzolamide-PLA (n=4) (35-2), brinzolamide-PLA (n=2) (33-2), brinzolamide-PLA (n=1) (32-3), and parent brinzolamide at physiological conditions (37° C.) over 19 days. The x-axis represents time (days) and the y-axis represents the amount of each undegraded brinzolamide-PLA analog as a percentage of the total brinzolamide amount as analyzed by RP-HPLC.

As illustrated in FIG. 6, capping the terminal hydroxyl with an acetyl group enhances the stability of the primary compound in vitro over the uncapped derivative. At day 7, approximately 2.7% of the primary brinzolamide-PLA (n=3) (34-2) remained, whereas in comparison, approximately 15.4% of brinzolamide-acetyl PLA (n=3) (36-1) remained at day 7. Additionally, substitution of the acetyl end group with a butyl group resulted in a significant increase in the stability of the compound. As shown in FIG. 7, the degradation kinetics of the primary brinzolamide-t-butyl PLA (n=3) (40-1) was significantly slower than its acetylated (36-1) or uncapped counterpart (34-2). FIG. 8, FIG. 9, and FIG. 10 reinforce the idea that lactate units are cleaved in pairs.

In summary, the kinetics of hydrolysis is slowest for brinzolamide-PLA (n=1) (32-3), followed by the t-butyl and O-acetyl terminated derivatives, with the —OH terminated derivatives exhibiting the fastest rate of degradation. Under 50-60° C. incubation, the rate of degradation increased rapidly, yet similar trends in the kinetic of degradation were observed. For example, the tendency for hydrolysis to occur in pairs of lactate and the enhanced stability afforded by t-butyl and O-acetyl capped compounds over uncapped compounds was still prominent under accelerated conditions (data not shown).

In Vitro Stability of Dorzolamide NCEs

Figure 11:
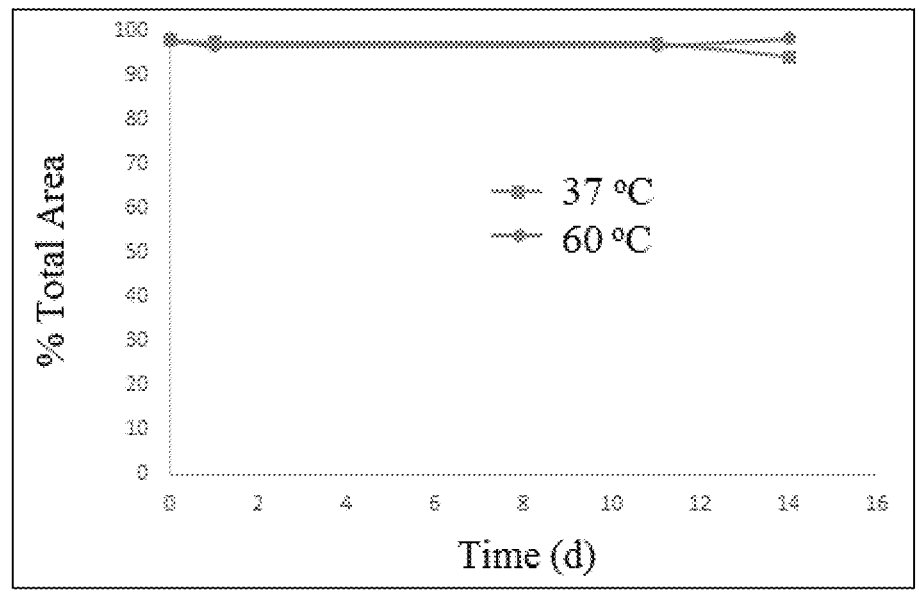
FIG. 11 illustrates the stability of dorzolamide at physiological conditions (37° C.) and at accelerated degradation conditions (60° C.) over 14 days. The x-axis represents time (days) and the y-axis represents the amount of undegraded dorzolamide as a percentage of the total dorzolamide amount as analyzed by RP-HPLC.
Figure 12:
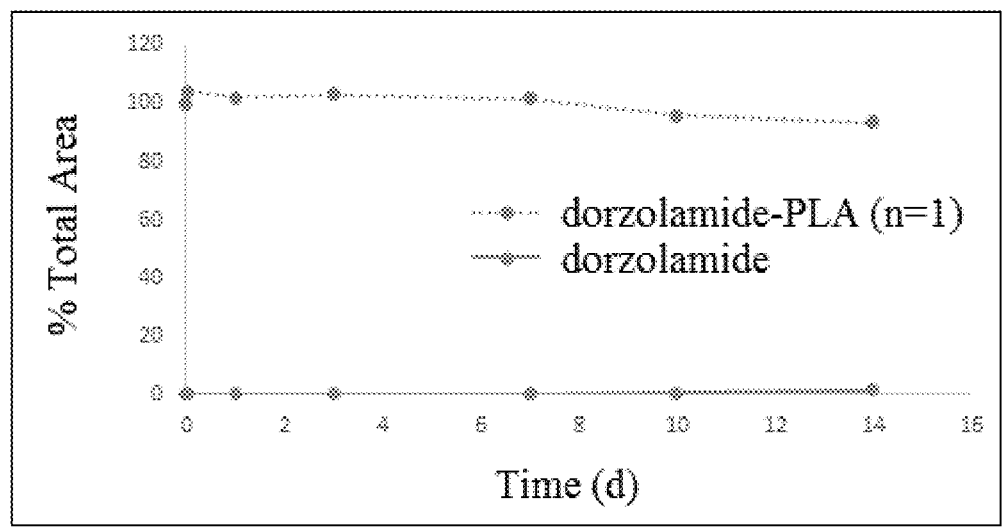
FIG. 12 illustrates the percentage of dorzolamide-PLA (n=1) (19-3) that is degraded to dorzolamide at physiological conditions (37° C.) over 14 days. The x-axis represents time (days) and the y-axis represents the amount of each undegraded dorzolamide-PLA analog as a percentage of the total dorzolamide amount as analyzed by RP-HPLC.
Figure 13:
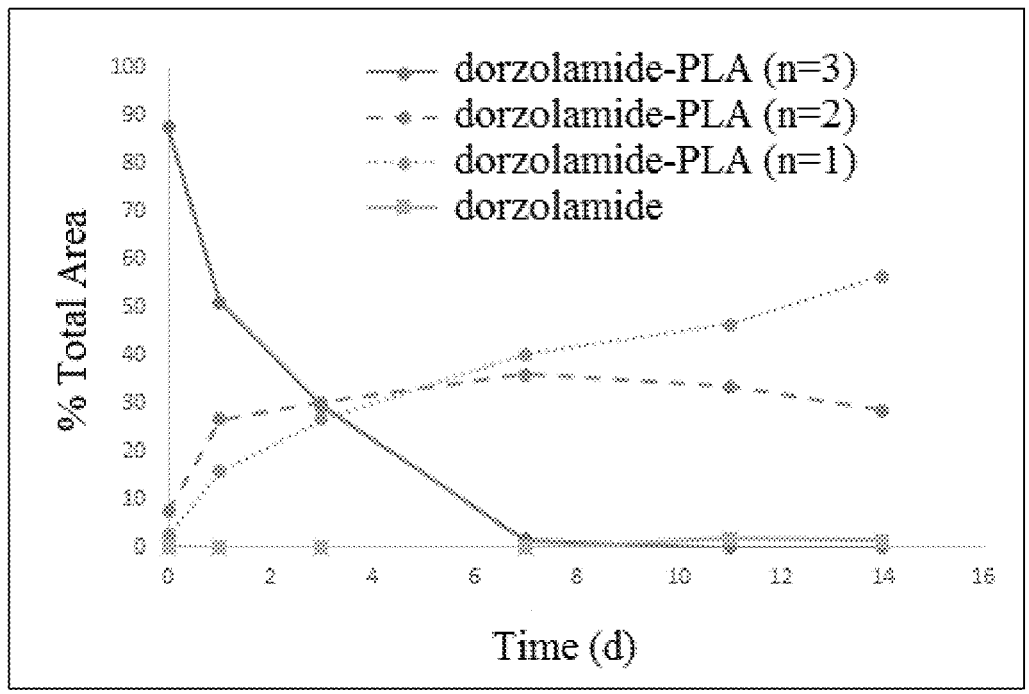
FIG. 13 illustrates the percentage of dorzolamide-PLA (n=3) (20-2) that is degraded to dorzolamide-PLA (n=2), dorzolamide-PLA (n=1) (19-3), and parent dorzolamide at physiological conditions (37° C.) over 14 days. The x-axis represents time (days) and the y-axis represents the amount of each undegraded dorzolamide-PLA analog as a percentage of the total dorzolamide amount as analyzed by RP-HPLC.
Figure 14:
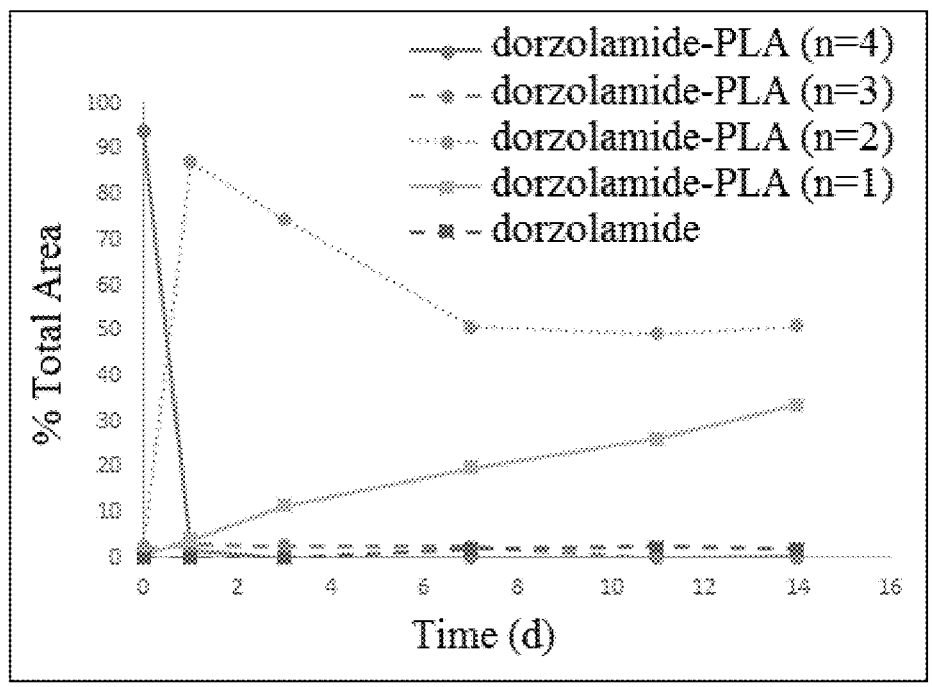
FIG. 14 illustrates the percentage of dorzolamide-PLA (n=4) (21-2) that is degraded to dorzolamide-PLA (n=3) (20-2), dorzolamide-PLA (n=2), dorzolamide-PLA (n=1) (19-3), and parent dorzolamide at physiological conditions (37° C.) over 14 days. The x-axis represents time (days) and the y-axis represents the amount of each undegraded dorzolamide-PLA analog as a percentage of the total dorzolamide amount as analyzed by RP-HPLC.
Figure 15:
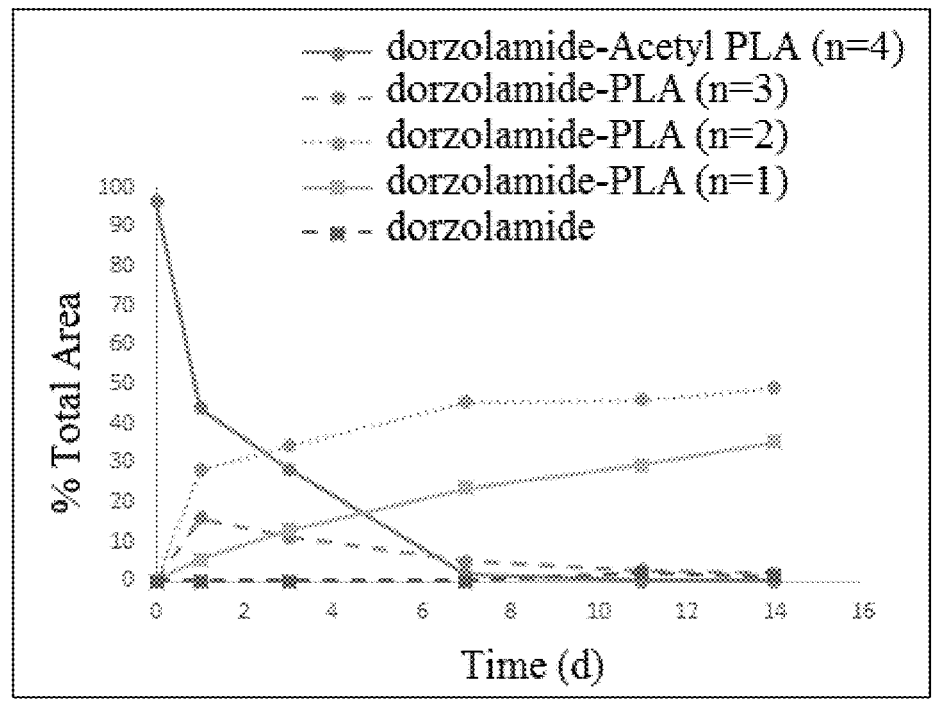
FIG. 15 illustrates the percentage of dorzolamide-acetyl PLA (n=3) (27-1) that is degraded to dorzolamide-PLA (n=3) (20-2), dorzolamide-PLA (n=2), dorzolamide-PLA (n=1) (19-3), and parent dorzolamide at physiological conditions (37° C.) over 14 days. The x-axis represents time (days) and the y-axis represents the amount of each undegraded dorzolamide-PLA analog as a percentage of the total dorzolamide amount as analyzed by RP-HPLC.
Figure 16:
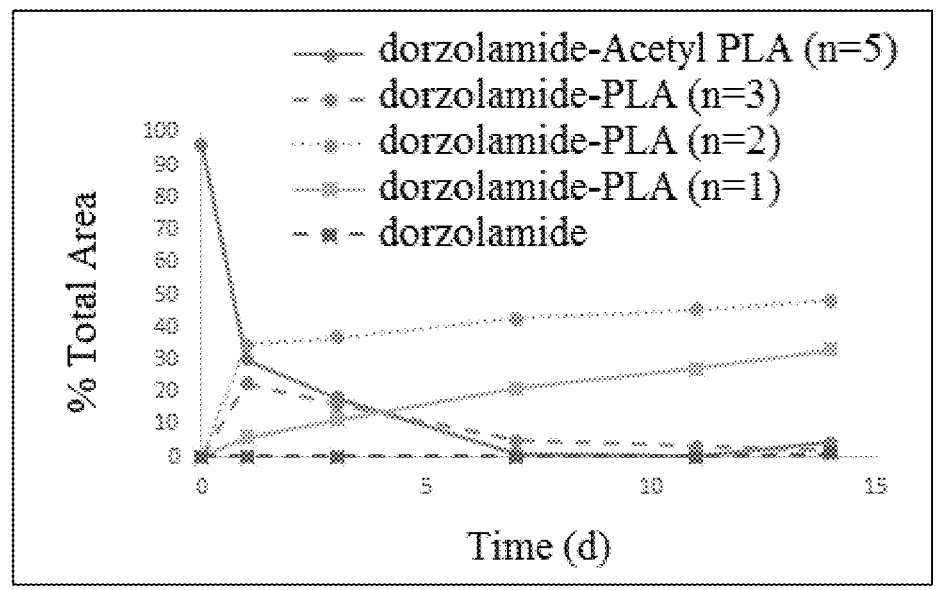
FIG. 16 illustrates the percentage of dorzolamide-acetyl PLA (n=5) (28-1) that is degraded to dorzolamide-PLA (n=3) (20-2), dorzolamide-PLA (n=2), dorzolamide-PLA (n=1) (19-3), and parent dorzolamide at physiological conditions (37° C.) over 14 days. The x-axis represents time (days) and the y-axis represents the amount of each undegraded dorzolamide-PLA analog as a percentage of the total dorzolamide amount as analyzed by RP-HPLC.
Figure 17:
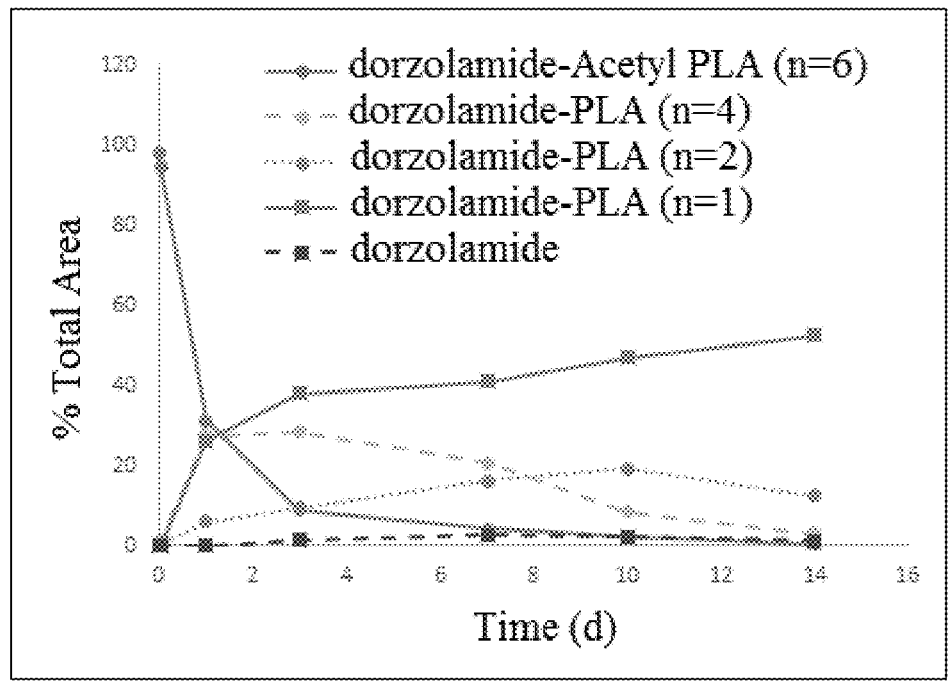
FIG. 17 illustrates the percentage of dorzolamide-acetyl PLA (n=6) (29-1) that is degraded to dorzolamide-PLA (n=4) (21-2), dorzolamide-PLA (n=2), dorzolamide-PLA (n=1) (19-3), and parent dorzolamide at physiological conditions (37° C.) over 14 days. The x-axis represents time (days) and the y-axis represents the amount of each undegraded dorzolamide-PLA analog as a percentage of the total dorzolamide amount as analyzed by RP-HPLC.
Figure 18:
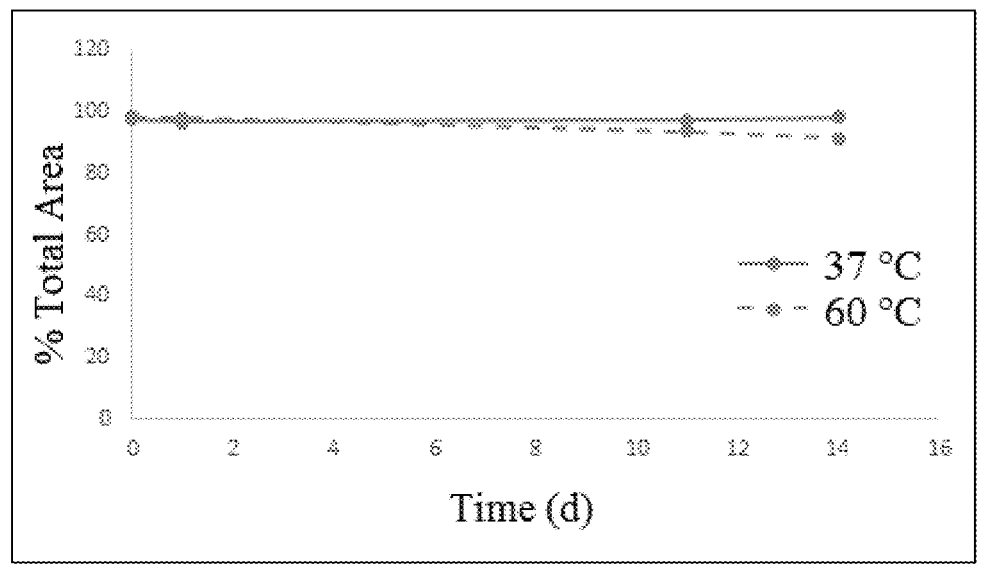
FIG. 18 illustrates the stability of latanoprost at physiological conditions (37° C.) and at accelerated degradation conditions (60° C.) over 14 days. The x-axis represents time (days) and the y-axis represents the amount of undegraded latanoprost as a percentage of the total latanoprost amount as analyzed by RP-HPLC.
Figure 19:
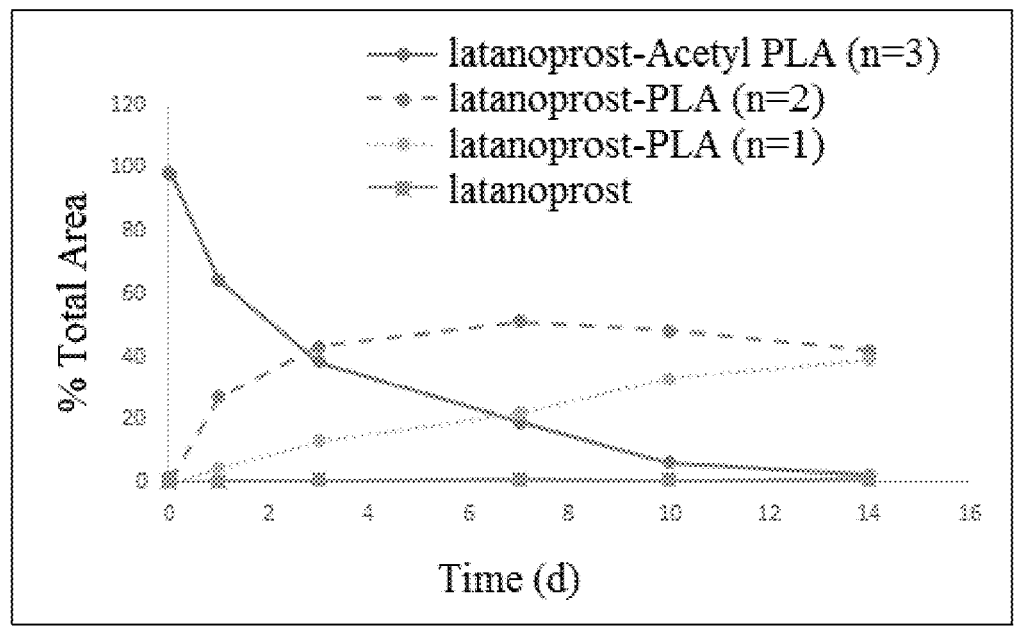
FIG. 19 illustrates the percentage of latanoprost-PLA (n=3) (43-2) that is degraded to latanoprost-PLA (n=2), latanoprost-PLA (n=1), and parent latanoprost at physiological conditions (37° C.) over 14 days. The x-axis represents time (days) and the y-axis represents the amount of each undegraded latanoprost-PLA analog as a percentage of the total latanoprost amount as analyzed by RP-HPLC.
Figure 20:
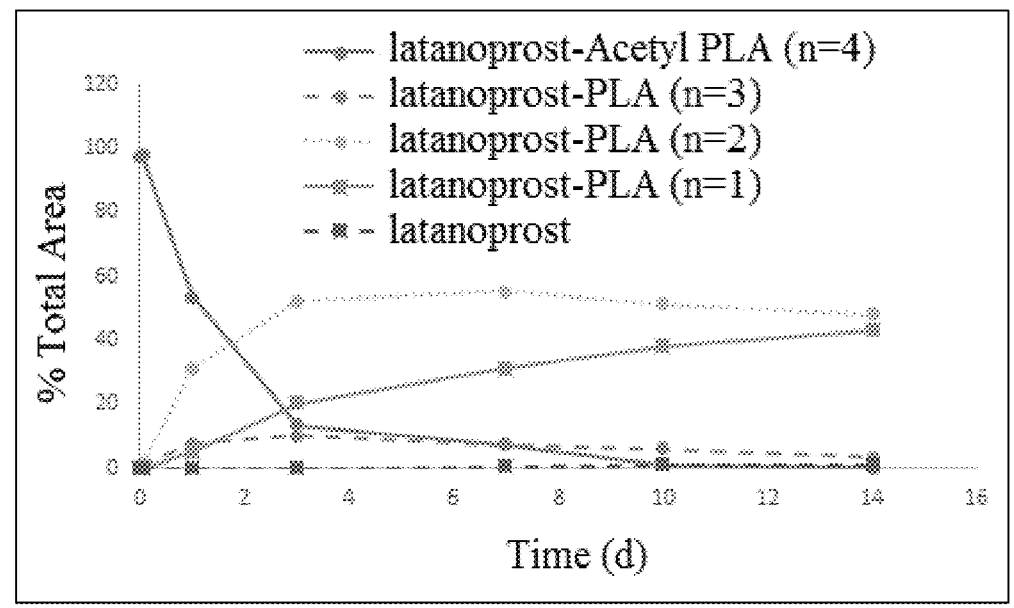
FIG. 20 illustrates the percentage of latanoprost-acetyl PLA (n=4) (44-1) that is degraded to latanoprost-PLA (n=3), latanoprost-PLA (n=2), latanoprost-PLA (n=1), and parent latanoprost at physiological conditions (37° C.) over 14 days. The x-axis represents time (days) and the y-axis represents the amount of each undegraded latanoprost-PLA analog as a percentage of the total latanoprost amount as analyzed by RP-HPLC.
Figure 21:
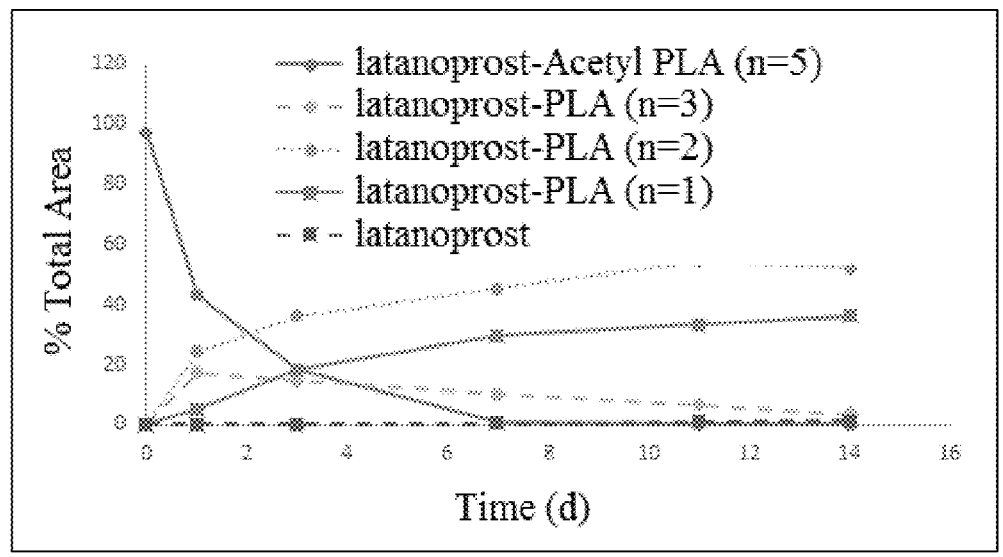
FIG. 21 illustrates the percentage of latanoprost-acetyl PLA (n=5) (45-1) that is degraded to latanoprost-PLA (n=3), latanoprost-PLA (n=2), latanoprost-PLA (n=1), and parent latanoprost at physiological conditions (37° C.) over 14 days. The x-axis represents time (days) and the y-axis represents the amount of each undegraded latanoprost-PLA analog as a percentage of the total latanoprost amount as analyzed by RP-HPLC.
Figure 22:
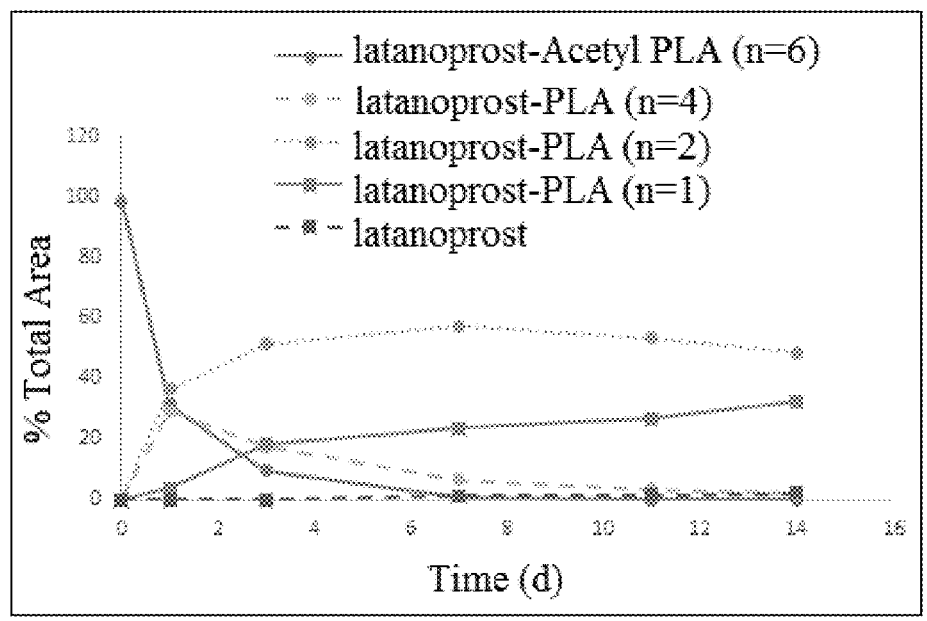
FIG. 22 illustrates the percentage of latanoprost-acetyl PLA (n=6) (46-1) that is degraded to latanoprost-PLA (n=4), latanoprost-PLA (n=2), latanoprost-PLA (n=1), and parent latanoprost at physiological conditions (37° C.) over 14 days. The x-axis represents time (days) and the y-axis represents the amount of each undegraded latanoprost-PLA analog as a percentage of the total latanoprost amount as analyzed by RP-HPLC.

The in vitro stability of dorzolamide and PLA conjugated NCEs were evaluated using the same method as that described above for brinzolamide and its derivatives. Similar to brinzolamide, dorzolamide was found to be highly stable with minimal degradation at 37° C. and 60° C. for up to 14 days (FIG. 11). The kinetics of degradation of dorzolamide NCEs were comparable to those observed with the brinzolamide NCEs; dorzolamide-PLA (n=1) (19-3) was the most stable, followed by O-acetyl derivatives, and uncapped derivatives with —OH were the least stable. Similarly, it was clear that the LA units were hydrolyzed in pairs (FIG. 12, FIG. 13, FIG. 14, FIG. 15, and FIG. 16). Under accelerated conditions (50° C.), the rate of degradation rapidly increased, yet the trends in degradation kinetics remained the same as the degradation kinetics at 37° C. (data not shown).

In Vitro Stability of Latanoprost NCEs

Latanoprost and latanoprost-PLA conjugates were solubilized with the addition of 20% (v/v) DMSO and subsequently suspended to a concentration of 1 mg/mL in PBS (pH 7.0). The samples were incubated at 37° C. and at various time points, aliquots were collected, diluted 10-fold with MeCN:water (1:1), filtered through a 0.2 m nylon syringe filter, and analyzed by RP-HPLC.

Similar to brinzolamide and dorzolamide, the prostaglandin agonist exhibited good stability throughout the 14 day incubation period. The prodrugs of latanoprost exhibited the same preferential tendency to lose lactate units in pairs.

In Vitro Stability of Bifunctional Conjugates

The in vitro stability of the bifunctional conjugates of brinzolamide or dorzolamide with sunitinib was evaluated through analysis of the presence or absence of the signal corresponding to the carbonic anhydrase inhibitor at 254 nm. Briefly, brinzolamide-PLA (n=4)-succinate-5-hydroxy-sunitinib (60-1) or dorzolamide-PLA (n=4)-succinate-5-hydroxy-sunitinib (58-5) was first dissolved in a solution of PBS (pH 7.0) with 20% DMSO (v/v) and incubated at 37° C. or 60 OC for 14 days. At various time points, 100 uL of the solution was collected, diluted 10-fold with MeCN:water (1:1), filtered through a 0.2 µm syringe filter, and analyzed on an HPLC at a detection wavelength of 254 nm.

Figure 23A:
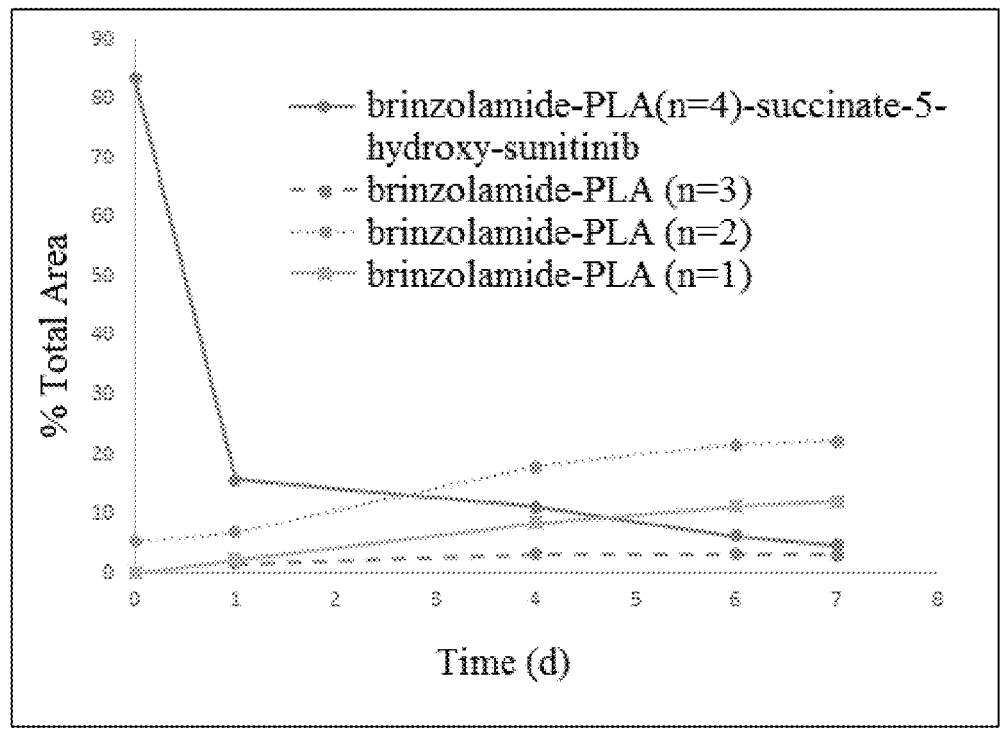
FIG. 23A illustrates the percentage of brinzolamide-PLA (n=4)-succinate-5-hydroxy-Sunitinib (60-1) that is degraded to brinzolamide-PLA (n=3) (34-2), brinzolamide-PLA (n=2) (33-2), brinzolamide-PLA (n=1) (32-3), and parent brinzolamide at physiological conditions (37° C.) over 7 days. The x-axis represents time (days) and the y-axis represents the amount of each undegraded brinzolamide-PLA analog as a percentage of the total brinzolamide amount as analyzed by RP-HPLC.
Figure 23B:
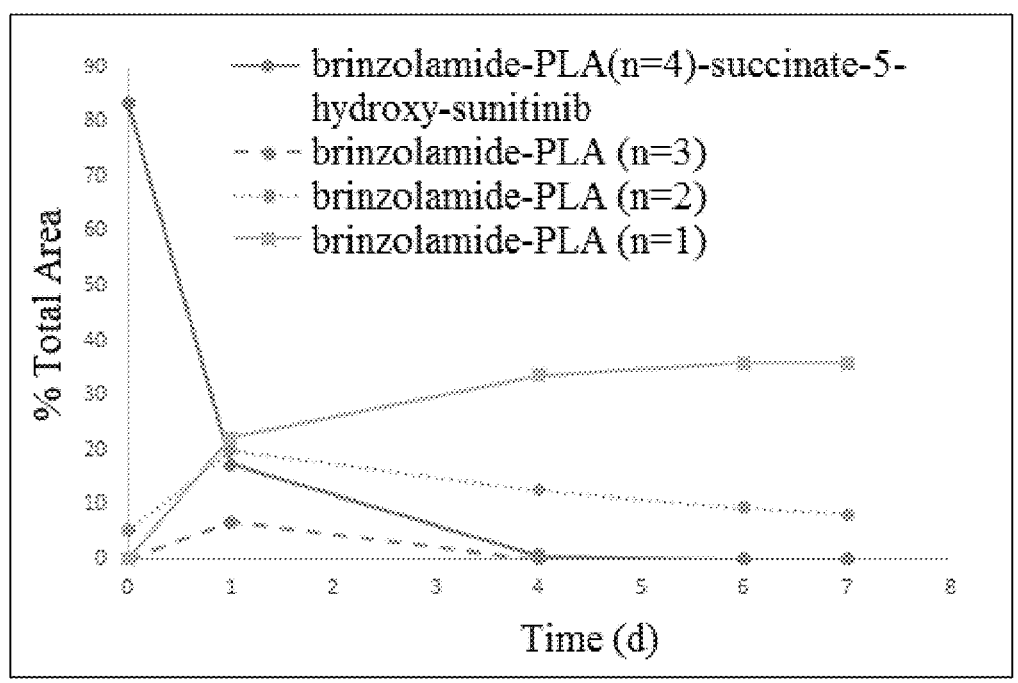
FIG. 23B illustrate the percentage of brinzolamide-PLA (n=4)-succinate-5-hydroxy-Sunitinib (60-1) that is degraded to brinzolamide-PLA (n=3) (34-2), brinzolamide-PLA (n=2) (33-2), brinzolamide-PLA (n=1) (32-3), and parent brinzolamide at accelerated degradation conditions (50° C.) over 7 days. The x-axis represents time (days) and the y-axis represents the amount of each undegraded brinzolamide-PLA analog as a percentage of the total brinzolamide amount as analyzed by RP-HPLC.
Figure 24A:
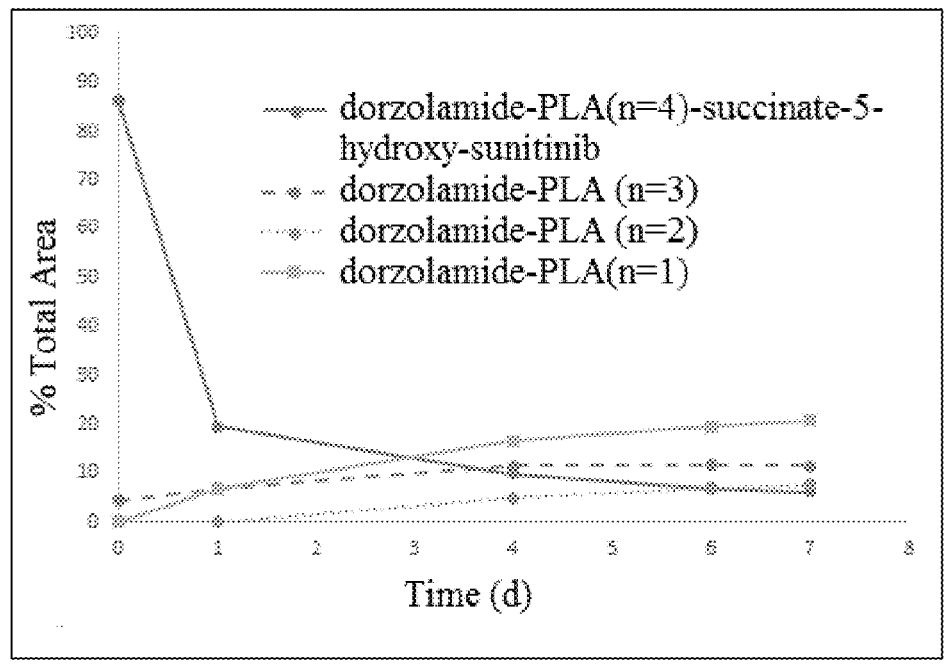
FIG. 24A illustrates the percentage of dorzolamide-PLA (n=4)-succinate-5-hydroxy-Sunitinib (58-5) that is degraded to dorzolamide-PLA (n=3) (20-2), dorzolamide-PLA (n=2), dorzolamide-PLA (n=1) (19-3), and parent dorzolamide at physiological conditions (37° C.) over 14 days. The x-axis represents time (days) and the y-axis represents the amount of each undegraded dorzolamide-PLA analog as a percentage of the total dorzolamide amount as analyzed by RP-HPLC.
Figure 24B:
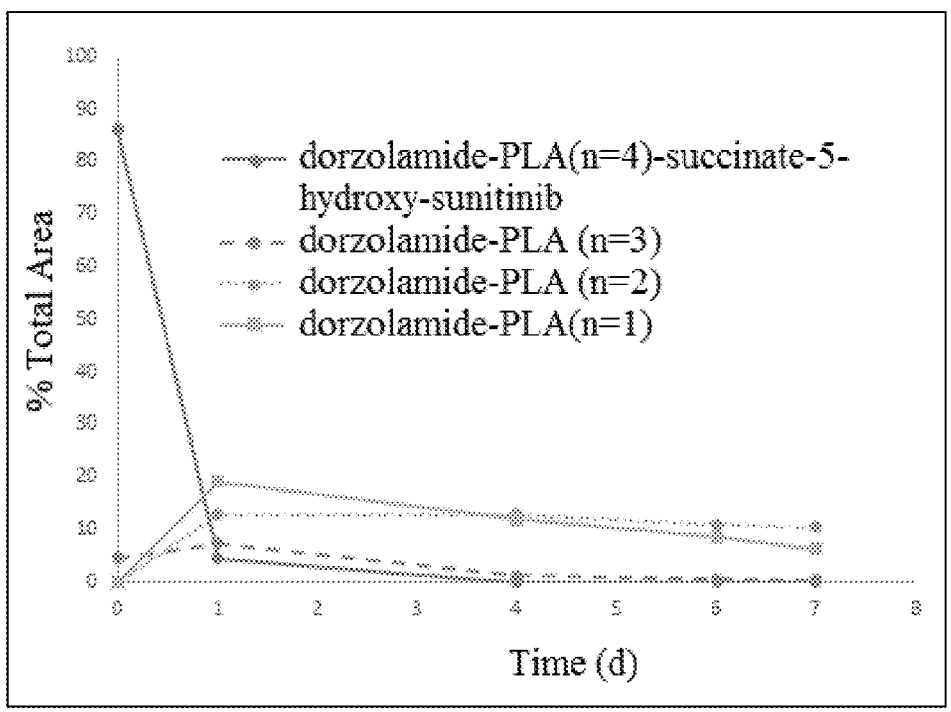
FIG. 24B illustrates the percentage of dorzolamide-PLA (n=4)-succinate-5-hydroxy-Sunitinib (58-5) that is degraded to dorzolamide-PLA (n=3) (20-2), dorzolamide-PLA (n=2), dorzolamide-PLA (n=1) (19-3), and parent dorzolamide at accelerated degradation conditions (50° C.) over 14 days. The x-axis represents time (days) and the y-axis represents the amount of each undegraded dorzolamide-PLA analog as a percentage of the total dorzolamide amount as analyzed by RP-HPLC.
Figure 25A:
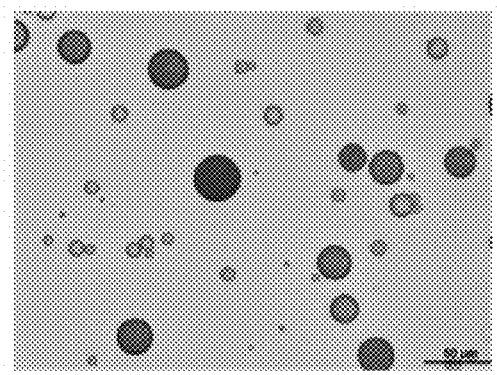
FIG. 25A is a light microscopy image at 40× magnification of particles encapsulating brinzolamide-acetyl PLA (n=5) (38-1)
Figure 25B:
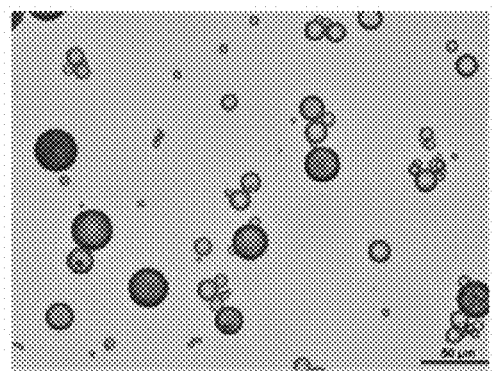
FIG. 25B is a light microscopy image at 40× magnification of particles prepared with high polymer concentration (200 mg/mL) encapsulating brinzolamide-acetyl PLA (n=5) (38-1)
Figure 25C:
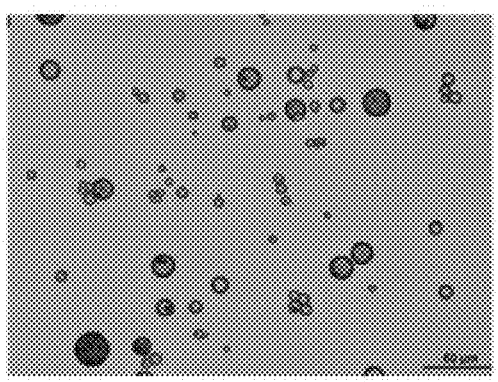
FIG. 25C is a light microscopy image at 40× magnification of particles encapsulating dorzolamide-acetyl PLA (n=5) (28-1)
Figure 25D:
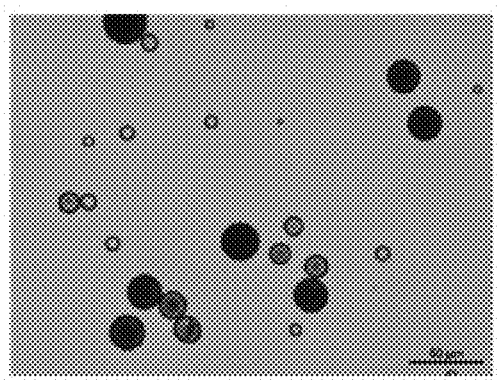
FIG. 25D is a light microscopy image at 40× magnification of particles encapsulating latanoprost-acetyl PLA (n=5) (45-1)

The degradation kinetic of brinzolamide-PLA (n=4)-succinate-5-hydroxy-sunitinib (60-1) at 37° C. and 60° C. is presented in FIG. 23 A and FIG. 23B, respectively. At 1 day, the primary biconjugate was rapidly hydrolyzed, resulting in the generation of brinzolamide-PLA with 1-3 lactate units. The PLA (n=4) signal decreased from 83% to 15.7% after one day of incubation. At 37° C., the generation and degradation of brinzolamide-PLA (n=3) remained relatively static over the time course of the experiment, whereas the amount of brinzolamide-PLA (n=2) and brinzolamide-PLA (n=1) increased over time. In contrast, under elevated temperature, the rate of degradation to brinzolamide-PLA (n=1)

was significantly faster than that at physiological temperature. Similar degradation kinetics can be observed for dorzolamide-PLA(n=4)-succinate-5-hydroxy-sunitinib (58-5) with degradation of the primary dorzolamide-PLA (n=4) signal rapidly decreasing after one day. However, in contrast to the brinzolamide-PLA(n=4)-succinate-5-hydroxy-sunitinib (60-1) biconjugate, the primary site of hydrolysis for dorzolamide-PLA(n=4)-succinate-5-hydroxy-sunitinib (58-5) was between the first and second lactate units, which resulted in the rapid generation of dorzolamide-PLA (n=1).

Example 38. Bioactivity of Conjugates of Carbonic Anhydrase Inhibitors (CAIs)

The generation of aqueous humor is dependent on the production of bicarbonate from carbonic anhydrase isoenzyme II, which is abundantly found in non-pigmented ciliary body epithelium. Carbonic anhydrase (CA) catalyzes the reversible hydration of carbon dioxide to carbonic acid, which subsequently dissociates to form protons and bicarbonate anions. Increase in bicarbonate affects fluid transport dynamics indirectly through $Na^+$ regulation. Carbonic anhydrase inhibitors actively block carbonic anhydrase activity, which results in reduced production of bicarbonate ions and thus decreases fluid transport resulting in decreased intraocular pressure.

The brinzolamide- and dorzolamide-PLA monofunctional conjugates and bifunctional conjugates were screened for their carbonic anhydrase inhibitory potential. The catalytic activity of carbonic anhydrase II was assessed by a colorimetric method, in which 4-nitrophenyl acetate is hydrolyzed to acetate and nitrophenolate. The nitrophenolate ionizes to generate a bright yellow anion that is readily detected by measuring its absorbance at 350-400 nm. Briefly, 140 μL of assay solution (HEPES and Tris buffer solution (20 mM, pH 7)) was dispensed into Eppendorf tubes and purified bovine erythrocyte carbonic anhydrase II (20 μL, 0.1 mg/mL in purified water) was added to the vial. Subsequently, 20 μL of the test compound (0.01-1000 nM) dissolved in DMSO was added to the reaction vial and allowed to equilibrate for 15 minutes with the enzyme. Acetazolamide was added as a positive control and 100% DMSO was added as a negative control. The reaction was initiated with the addition of 20 μL of 4-nitrophenyl acetate (0.7 mM in ethanol). The absorbance was measured at 400 nm for 15 minutes using a Genesys 105 UV-VIS spectrophotometer (Thermo Scientific). (DMSO did not interfere with the level of CA activity or specificity in this assay.) The assay was conducted in triplicate and the normalized data was analyzed using GraphPad Prism version 4.0 and fit to a 4-parameter non-linear sigmoidal dose-response model to generate $IC_{50}$ values.

The parent compounds demonstrated the highest inhibition of carbonic anhydrase activity.

Increasing the length of the LA units resulted in a reduction of bioactivity (Table 6). In addition, capping the terminal group of PLA with an acetyl group did not significantly alter the bioactivitity of the compound. The $IC_{50}$ for brinzolamide-PLA (n=3) (34-2) vs brinzolamide-acetyl PLA (n=3) (36-1) was 21.5±11.2 vs. 20.7±9.54, respectively. However, all tested compounds maintained relatively high bioactivity within the nanomolar range. Bioconjugates of brinzolamide- or dorzolamide-PLA with sunitinib (60-1, 58-5, 57-3 & 56-5) exhibited the lowest inhibitory activity, possibly owing to steric hindrance of sunitinib and PLA conjugated to the CAIs.

Table 6. Bioactivity of Conjugates Containing CAIs

TABLE 6

| Bioactivity of conjugates containing CAIs | | |
|---|---|---|
| Compound | Compound number | $IC_{50}$ (nM, n = 2) |
| Brinzolamide | Brinzolamide | 5.21 ± 4.14 |
| Brinzolamide-PLA (n = 1) | 32-3 | 5.78 ± 3.78 |
| Brinzolamide-PLA (n = 2) | 33-2 | 10.7 ± 7.27 |
| Brinzolamide-PLA (n = 3) | 34-2 | 21.5 ± 11.2 |
| Brinzolamide-Acetyl PLA (n = 3) | 36-1 | 20.7 ± 9.54 |
| Brinzolamide-Acetyl PLA (n = 4) | 37-1 | 41.5 ± 11.2 |
| Brinzolamide-Acetyl PLA (n = 5) | 38-1 | 102.1 ± 31.4 |
| Brinzolamide-Acetyl PLA (n = 6) | 39-1 | 171.6 ± 35.6 |
| Dorzolamide | Dorzolamide | 1.35 ± 0.64 |
| Dorzolamide-PLA (n = 1) | 19-3 | 3.32 ± 2.71 |
| Dorzolamide-PLA (n = 3) | 20-2 | 14.1 ± 5.07 |
| Dorzolamide-PLA (n = 4) | 21-2 | 48.5 ± 10.5 |
| Dorzolamide-Acetyl PLA (n = 3) | 26-1 | 16.4 ± 7.25 |
| Dorzolamide-Acetyl PLA (n = 4) | 27-1 | 44.1 ± 14.8 |
| Dorzolamide-Acetyl PLA (n = 5) | 28-1 | 89.2 ± 18.1 |
| Dorzolamide-PLA (n = 3)-succinate-5-hydroxy sunitinib | 57-3 | 195.1 ± 45.3 |
| Dorzolamide-PLA (n = 3)-succinate-5-amino sunitinib | 56-5 | 184.5 ± 44.8 |
| Dorzolamide-PLA (n = 4)-succinate-5-hydroxy sunitinib | 58-5 | 221.6 ± 36.3 |
| Brinzolamide-PLA (n = 4)-succinate-5-hydroxy sunitinib | 60-1 | 247.4 ± 49.12 |

$IC_{50}$—half-maximal inhibitory concentration

Example 39. Encapsulation of Conjugates in Polymer Microparticles

Materials
poly(D,L-lactic-co-glycolic acid (PLGA, 75:25 lactic acid to glycolic acid ratio, 4A, Evonik)
poly(D,L-lactic-co-glycolic acid (PLGA, 50:50 lactic acid to glycolic acid ratio)-poly(ethylene glycol)5000
poly vinyl alcohol (Mr ~25K, 88% hydrolyzed, Polysciences)
D-α-tocopherol poly(ethylene glycol)1000 succinate (Sigma Aldrich)
Phosphate-buffered saline (pH 7.4)
Ultrapure cell culture grade water
All other chemicals were A.C.S. reagent grade (VWR)
Microparticle Preparation Microparticles containing prodrugs of brinzolamide or dorzolamide-PLA were formulated using an oil-in-water solvent evaporation microencapsulation method. The polymer was initially dissolved in a water immiscible organic solvent to which dissolved drug was added. Briefly, 280 mg of PLGA (LA:GA=75:25, 4A) and 2.8 mg of $PLGA_{50/50}$-$PEG_{5k}$ was dissolved in 2 mL of methylene chloride. The CAI (45 mg) was dissolved in 1 mL of DMSO after vigorous vortexing and ultrasonication in a bath sonicator and added to the polymer solution. The aqueous phase consisted of 200 mL of PBS with 1% PVA or D-α-tocopherol poly(ethylene glycol)$_{1000}$ succinate as a surfactant to stabilize the emulsification. The aqueous phase was mixed at 5000 rpms using a Silverson L5A-M benchtop mixer. The dispersed phase was rapidly added to the aqueous phase and allowed to mix at 5000 rpms for 1 minute to generate an oil-in-water emulsion and disperse the materials as droplets. The organic solution was allowed to evaporate under constant stirring at 500 rpms for 2 hours at 25° C. or at 4° C. in an ice bath. The particle suspension was allowed to settle for 30 min, after which the solution was decanted and remaining particles were collected, suspended in distilled deionized water, and washed 3 times using water via centrifugation at 1000 rpms for 5 minutes to remove any residual solvent. The pellet was collected and lyophilized overnight.

Particle Size Analysis

Particle size and size distribution was determined using a Beckman Coulter Multsizer IV with a 100 μm diameter aperture based on a sample size of at least 50,000 counts. Particle size is expressed as volume-weighted mean diameters. Briefly, 2-5 mg of particles were suspended in 1 mL of double distilled water and added to a beaker containing 100 mL of ISOTON II solution. Measurements were obtained once the coincidence of particles reached 6-10%. Table 7 outlines the size and size distribution of the microparticles generated for each test compound. Particle size can vary depending upon a number of variables including polymer concentration, mixing-speed, mixing-time, dispersed/aqueous phase ratio, etc. Particles were formulated with volume-weighted mean diameters ranging from approximately 18 m to 28 m depending on the formulation parameters.

TABLE 7

Particle size of microparticles encapsulating drug conjugates
*Particles were generated at room temperature with 1% PVA as a surfactant in the aqueous phase

| Compound | Compd # | Mean (μm) | SD | d10 | d50 | d90 |
|---|---|---|---|---|---|---|
| brinzolamide-PLA (n = 4) | 35-2 | 23.0 | 7.48 | 11.9 | 20.8 | 38.4 |
| dorzolamide-PLA(n = 4) | 21-2 | 23.0 | 8.53 | 13.3 | 21.8 | 21.8 |
| brinzolamide-Acetyl PLA(n = 4) | 37-1 | 24.9 | 8.27 | 17.2 | 25.0 | 32.6 |
| dorzolamide-Acetyl PLA(n = 4) | 27-1 | 26.4 | 8.94 | 18.3 | 26.3 | 34.1 |
| brinzolamide-Acetyl PLA(n = 5) | 38-1 | 23.0 | 7.73 | 11.9 | 20.8 | 38.4 |
| dorzolamide-Acetyl PLA(n = 5) | 28-1 | 23.0 | 8.06 | 13.3 | 21.8 | 34.8 |
| dorzolamide-Acetyl PLA(n = 5, no DMSO) | 28-1 | 17.9 | 6.49 | 9.69 | 16.3 | 34.8 |
| latanoprost-Acetyl PLA(n = 4) | 44-1 | 28.1 | 8.58 | 16.6 | 26.5 | 41.6 |
| [1]brinzolamide-Acetyl PLA(n = 5) | 38-1 | 26.5 | 7.98 | 18.4 | 25.9 | 36.6 |
| [2]brinzolamide-Acetyl PLA(n = 5) | 38-1 | 27.4 | 7.86 | 17.2 | 27.4 | 37.9 |
| [1]dorzolamide-Acetyl PLA(n = 5) | 28-1 | 19.7 | 9.45 | 8.88 | 18.3 | 31.1 |
| [1]latanoprost-Acetyl PLA(n = 5) | 45-1 | 26.44 | 9.18 | 12.2 | 27.5 | 38.2 |

[1]Particles generated at 4° C. with D-α-tocopherol poly(ethylene glycol)$_{1000}$ succinate as the surfactant.
[2]Particles generated at 4° C. with D-α-tocopherol poly(ethylene glycol)$_{1000}$ succinate as the surfactant with increased polymer concentration (200 mg/mL).

Drug Loading

To determine the % drug loading (DL), 10 mg of particles was weighed into a glass scintillation vial and dissolved with 10 mL of MeCN:water (1:1, v/v). The solution was filtered through a 0.2 m nylon syringe filter and the drug content was determined by RP-HPLC referenced against a standard calibration curve. The drug loading results are presented in Table 8. Interestingly, all particles generated at 25° C. with 1% PVA in the aqueous phase exhibited low drug loading regardless of the encapsulated drug (<1.0% DL), but results in Table 8 suggest that loading is influenced by the presence of the functional group on the terminal lactate. Loading of acetylated test compounds was approximately 5-fold higher than those with uncapped hydroxyl on the terminal lactate units (0.14 vs. 1.00 and 0.22 vs. 0.98%, respectively for brinzolamide and dorzolamide).

Loading was also dependent on the rate of solidification of the particles and the surfactant used in the emulsification process. Preparing particles at 4° C. and with D-α-tocopherol poly(ethylene glycol)$_{1000}$ succinate to stabilize the emulsification resulted in significant enhancement in drug loading. For example, % DL of brinzolamide-acetyl PLA (n=5) (38-1) was 0.73% when particles were formulated at room temperature using 1% PVA as the surfactant compared to 7.39% when particles were formulated at 4° C. using D-α-tocopherol poly(ethylene glycol)$_{1000}$ succinate as the surfactant. In addition, increasing polymer concentration also resulted in a nominal increase in % DL. Brinzolamide-acetyl PLA (n=5) (38-1) content increased from 7.39% to 8.89% when the polymer concentration increased from 140 mg/mL to 200 mg/mL, respectively.

TABLE 8

Drug loading of microparticles encapsulating the drug conjugates

| Compound | Compound number | % DL |
|---|---|---|
| brinzolamide-PLA (n = 4) | 35-2 | 0.14 |
| dorzolamide-PLA(n = 4) | 21-2 | 0.22 |
| brinzolamide-Acetyl PLA(n = 4) | 36-1 | 1.00 |
| dorzolamide-Acetyl PLA(n = 4) | 27-1 | 0.98 |
| brinzolamide-Acetyl PLA(n = 5) | 38-1 | 0.73 |
| dorzolamide-Acetyl PLA(n = 5) | 28-1 | 0.92 |
| dorzolamide-Acetyl PLA(n = 5, no DMSO) | 28-1 | 0.82 |
| latanoprost-Acetyl PLA(n = 4) | 44-1 | 0.53 |
| [1]brinzolamide-Acetyl PLA(n = 5) | 38-1 | 7.39 |
| [2]brinzolamide-Acetyl PLA(n = 5) | 38-1 | 8.89 |
| [1]dorzolamide-Acetyl PLA(n = 5) | 28-1 | 8.71 |
| [1]latanoprost-Acetyl PLA(n = 5) | 45-1 | 3.57 |

[1]Particles generated at 4° C. with D-α-tocopherol poly(ethylene glycol)$_{1000}$ succinate as the surfactant.
[2]Particles generated at 4° C. with D-α-tocopherol poly(ethylene glycol)$_{1000}$ succinate as the surfactant with increased polymer concentration (200 mg/mL).

Particle Morphology

Particle morphology was assessed using a Nikon Eclipse TS-100 light microscope. Briefly, 3-5 mg of particles were suspended in 1 mL of water. A volume of 10 uL of the particle suspension was transferred onto a glass slide and imaged directly. In general, particles were found to be spherical in morphology (FIG. 25A, FIG. 25B, FIG. 25C, and FIG. 25D).

Drug Release

In vitro drug release kinetics was evaluated in a release medium of PBS and 1% Tween 20 (pH 7.4). Briefly, 10 mg of particles were transferred to glass scintillation vials and 4 mL of the release medium was added to suspend the particles. Samples were prepared in duplicate. The particles were mixed by gentle vortexing and incubated on an orbital shaker at 150 rpm at 37° C. At various time points, 3 mL of release media was collected and analyzed for drug content and 3 mL of fresh media was added to replace the sample that was collected. Collected release samples were frozen and stored at −80° C. until analysis for drug content. The collected samples were filtered through a 0.2 m syringe filter and analyzed by RP-HPLC.

Figure 26:
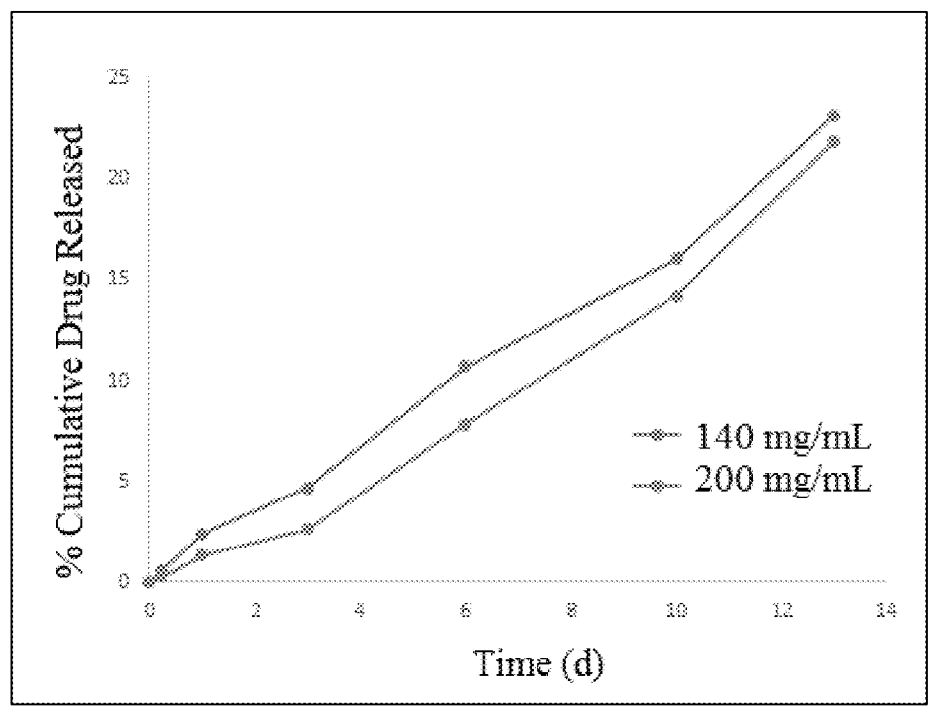
FIG. 26 illustrates the drug release kinetics of brinzolamide-acetyl PLA (n=5) (38-1) from particles prepared with polymer concentration of 140 mg/mL and 200 mg/mL over 14 days. The x-axis represents time (days) and the y-axis represents the percent of cumulative drug released as analyzed by RP-HPLC.

FIG. 26 illustrates the cumulative release profile for particles encapsulating brinzolamide-acetyl PLA (n=5) (38-1). The cumulative release profiles of both formulations exhibited relatively low burst release (0.62% and 0.20% released at 3 hours, respectively). At 13 days, the release profile with particles formulated with a polymer concentration of 140 mg/mL (% DL=7.39) was relatively linear, although the overall release rate was slightly higher than for particles prepared at a higher polymer concentration (200 mg/mL, % DL=8.89). At 13 days, approximately 21-23% of the drug had been released from the particles. The rate of release of brinzolamide-acetyl PLA (n=5) (38-1) may be attributed to its high hydrophobicity and hydrophobic interactions between the drug and the polymer matrix. Increasing the hydrophobicity of the polymer by selecting a higher LA:GA ratio polymer or PLA may further decrease the rate of release.

Figure 27:
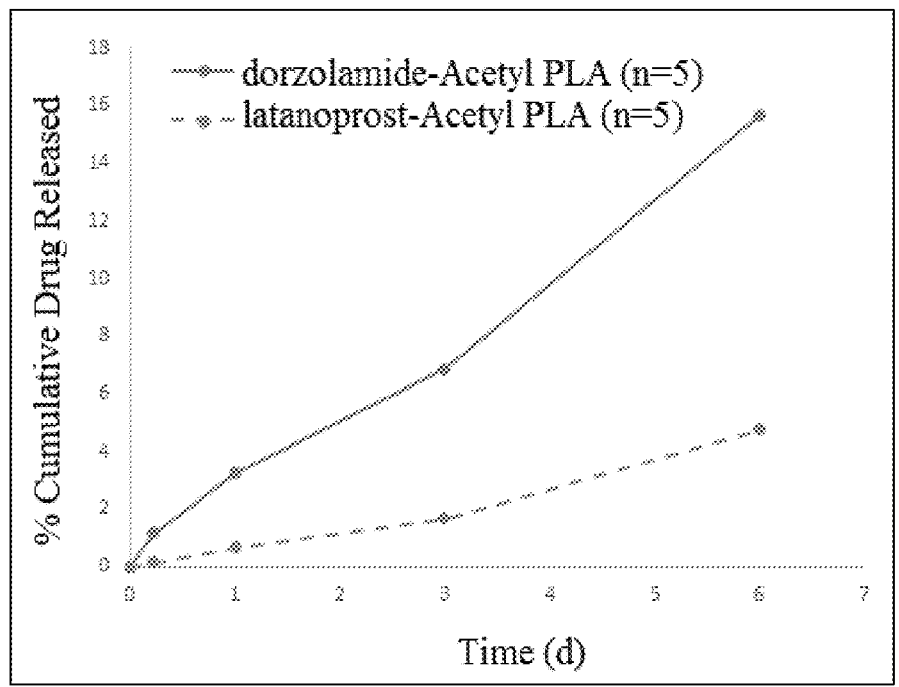
FIG. 27 illustrates the drug release kinetics of dorzolamide-acetyl PLA (n=5) (28-1) and latanoprost-Acetyl PLA (n=5) (45-1) from particles prepared with PLGA microparticles over 6 days. The x-axis represents time (days) and the y-axis represents the percent of cumulative drug released as analyzed by RP-HPLC.

In vitro release profiles of dorzolamide-acetyl PLA (n=5) (28-1) and latanoprost-acetyl PLA (n=5) (45-1) are shown in FIG. 27. The release kinetics for dorzolamide-acetyl PLA (n=5) (28-1) is significantly faster than latanoprost-acetyl PLA (n=5) (45-1); approximately 6.86% of dorzolamide-acetyl PLA (n=5) (28-1) released after 6 days compared to 1.67% for latanoprost-acetyl PLA (n=5) (45-1). This may be attributed to the differences in hydrophobicity between the CAIs and latanoprost. Burst release was also significantly higher for dorzolamide-acetyl PLA (n=5) (28-1) than latanoprost-acetyl PLA (n=5) (45-1). At 3 hours, approximately 1.17% of dorzolamide-acetyl PLA (n=5) (28-1) had been released compared to 0.15% for latanoprost-acetyl PLA (n=5) (45-1). The microparticle compositions described herein have demonstrated the potential to load and release one or more prodrugs for the management of elevated intraocular pressure for a prolonged period.

Example 40. Non-Limiting Examples of Compounds of Formula I, II, III, IV, XIV, XV, XVI, and XVII Table 9 shows illustrative compounds of Formula I, II, III, IV, XIV, XV, XVI, and XVII with characterizing data.

TABLE 9

Non-limiting Examples of Synthesized Compounds

| Comp. # | Structure |
|---|---|
| 19-3 | 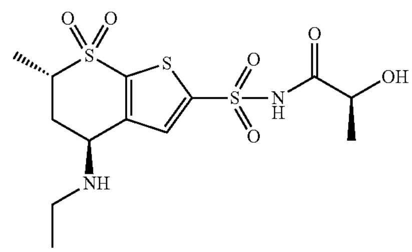 [SMILES: CCN[C@H]1C[C@H](C)S(=O)(=O)c2sc(S(=O)(=O)NC(=O)[C@H](C)O)cc21] |
| 20-2 | 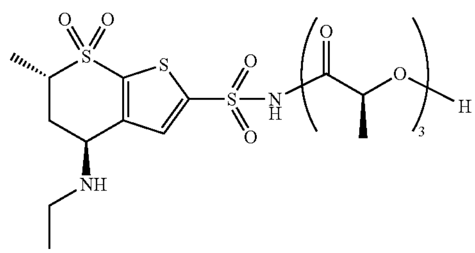 |
| 21-2 | 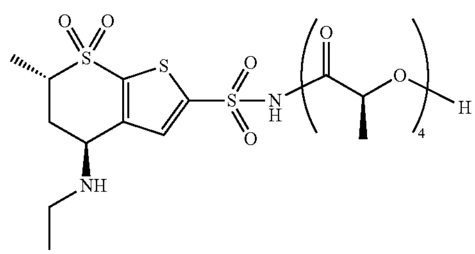 |
| 22-2 | 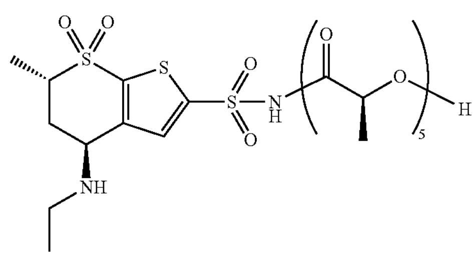 |

TABLE 9-continued

Non-limiting Examples of Synthesized Compounds

| Comp. # | Structure |
|---|---|
| 23-2 | (structure with n=10) |
| 24-2 | (structure with n=12) |
| 25-2 | (structure with n=14) |
| 26-1 | (structure with n=3) |
| 27-1 | (structure with n=4) |
| 28-1 | (structure with n=5) |

TABLE 9-continued

Non-limiting Examples of Synthesized Compounds

| Comp. # | Structure |
|---|---|
| 29-1 | 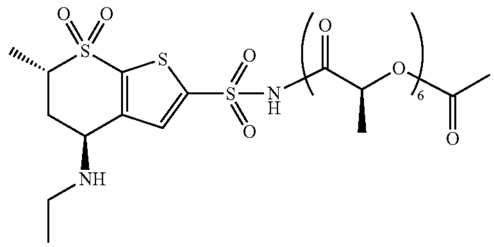 |
| 30-1 | 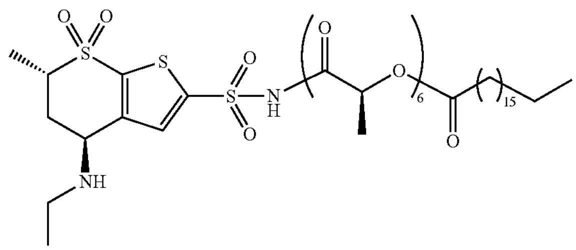 |
| 31-1 | 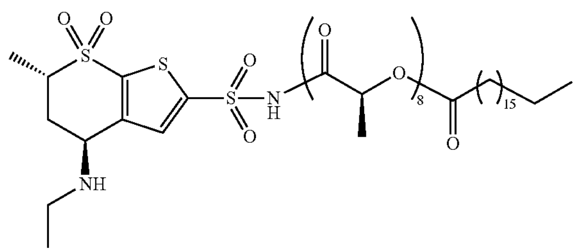 |
| 32-3 | 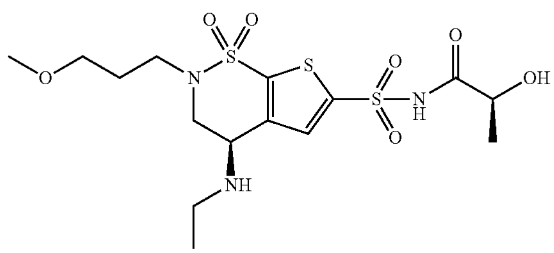 [SMILES: CCN[C@H]1CN(CCCOC)S(=O)(=O)c2sc(S(=O)(=O)NC(=O)[C@H](C)O)cc21] |
| 33-2 | 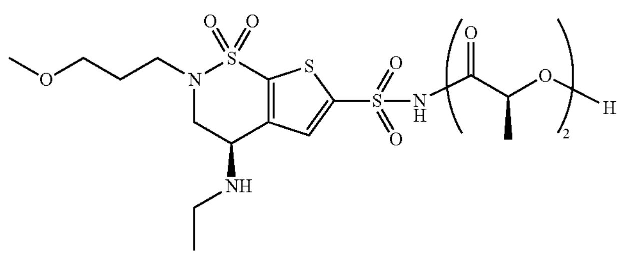 |
| 34-2 | 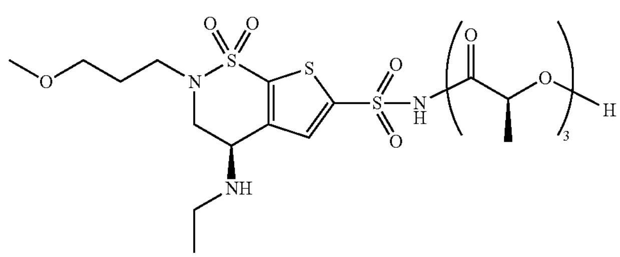 |

TABLE 9-continued
Non-limiting Examples of Synthesized Compounds
| Comp. # | Structure |
|---|---|
| 35-2 | 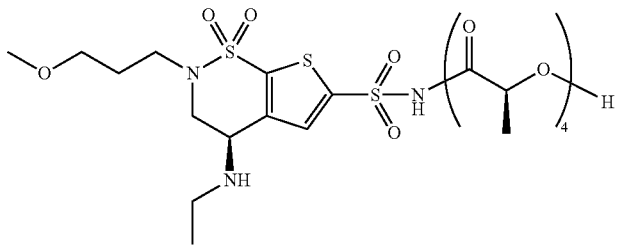 |
| 36-1 | 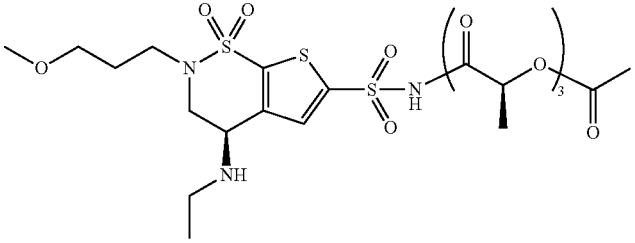 |
| 37-1 | 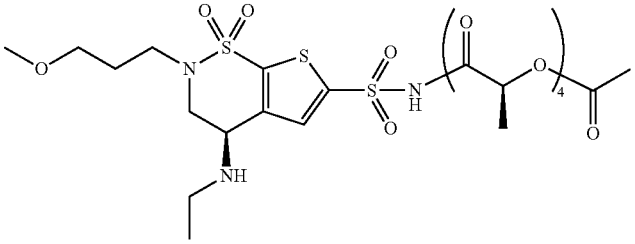 |
| 38-1 | 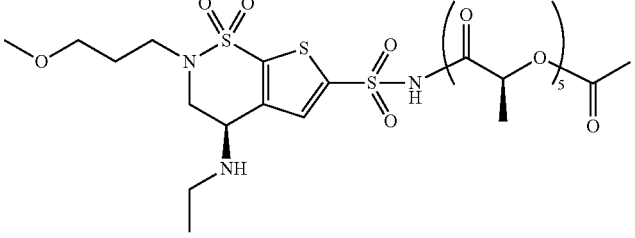 |
| 39-1 | 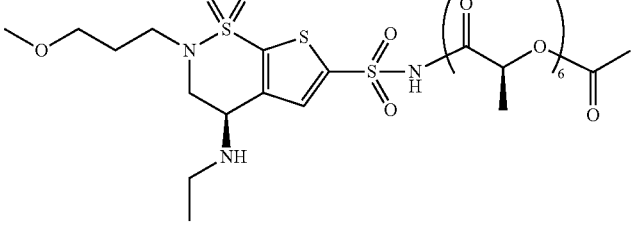 |
| 40-1 | 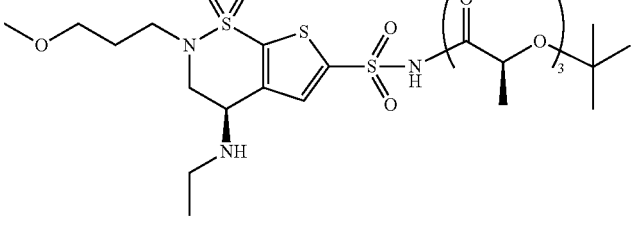 |

TABLE 9-continued
Non-limiting Examples of Synthesized Compounds
| Comp. # | Structure |
|---|---|
| 41-1 | 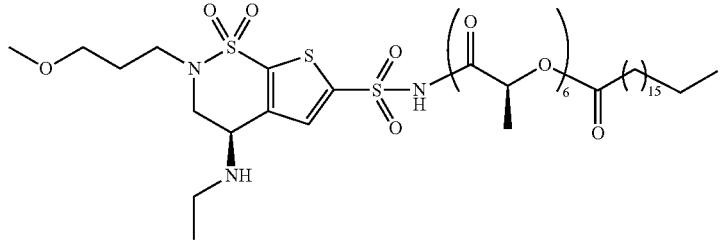 |
| 42-1 | 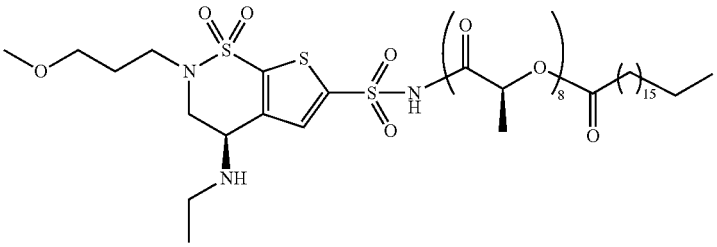 |
| 43-2 | 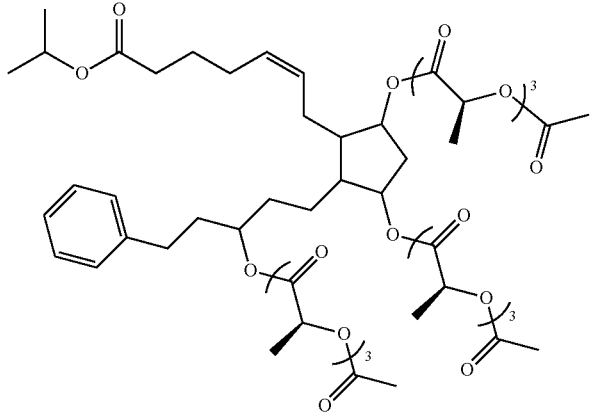 |
| 44-1 | 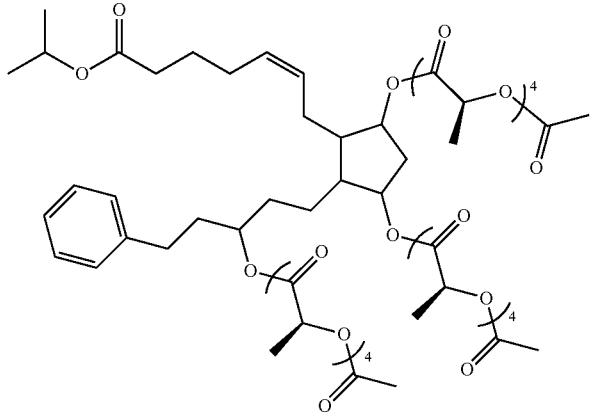 |

TABLE 9-continued

Non-limiting Examples of Synthesized Compounds

| Comp. # | Structure |
|---|---|
| 45-1 | 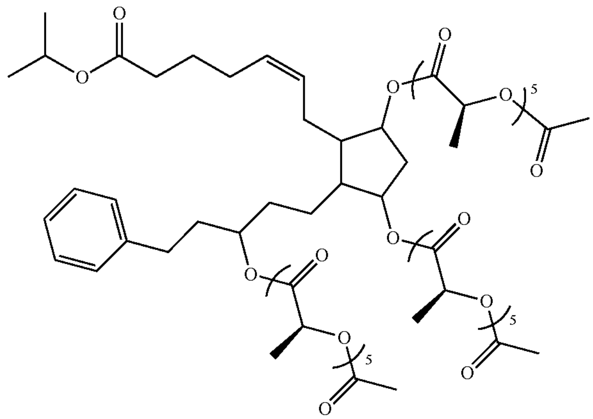 |
| 46-1 | 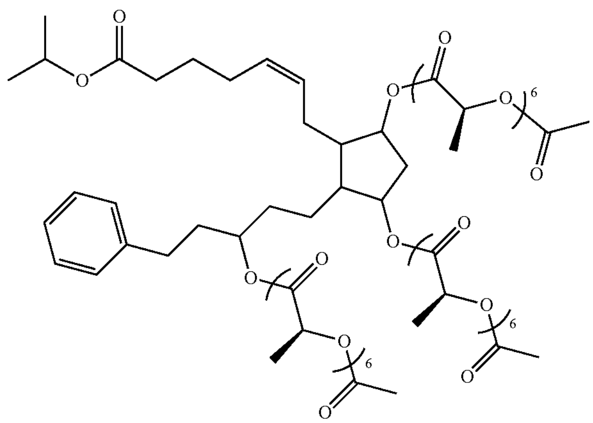 |
| 47-3 | 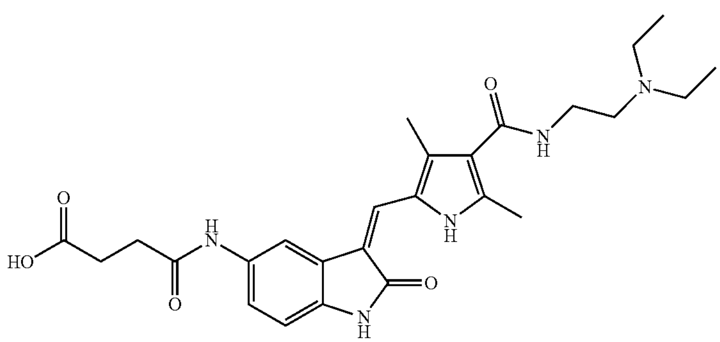 [SMILES: CCN(CC)CCNC(=O)c1c(C)[nH]c(/C=C2\C(=O)Nc3ccc(NC(=O)CCC(=O)O)cc32)c1C] |
| 48-3 | 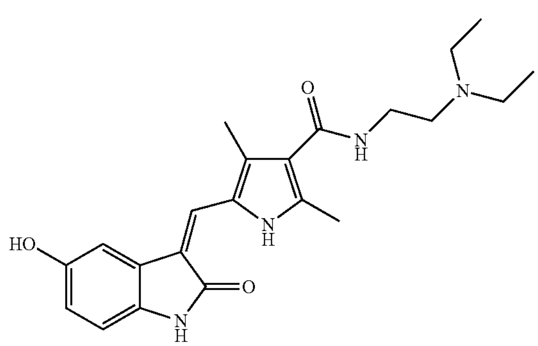 [SMILES: CCN(CC)CCNC(=O)c1c(C)[nH]c(/C=C2\C(=O)Nc3ccc(O)cc32)c1C] |

TABLE 9-continued

Non-limiting Examples of Synthesized Compounds

| Comp. # | Structure |
|---|---|
| 49-1 | 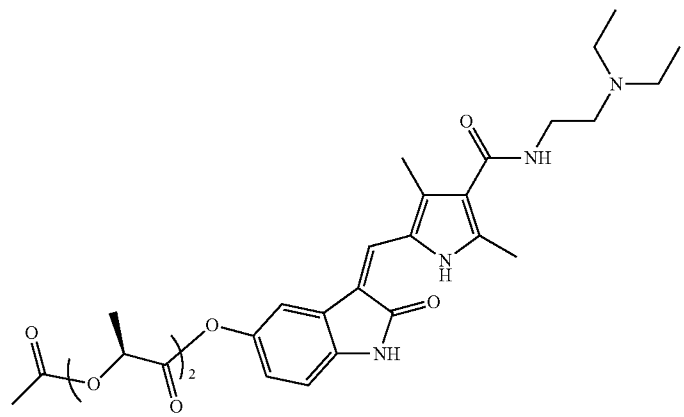 |
| 50-1 | 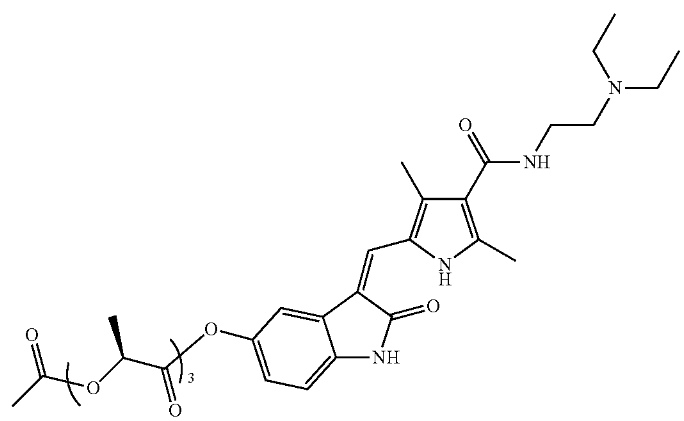 |
| 51-1 | 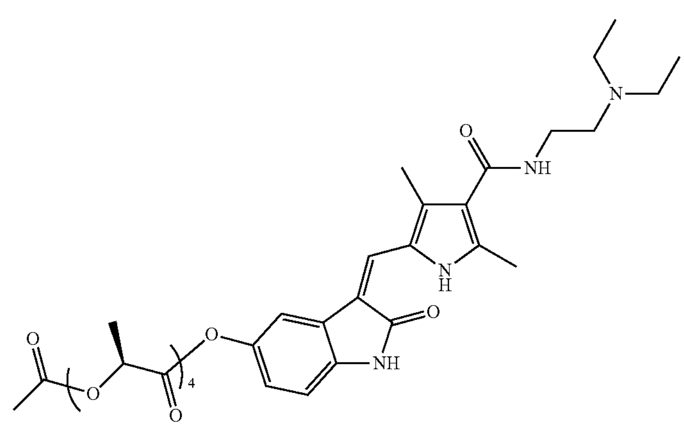 |

TABLE 9-continued

Non-limiting Examples of Synthesized Compounds

| Comp. # | Structure |
|---|---|
| 52-1 | 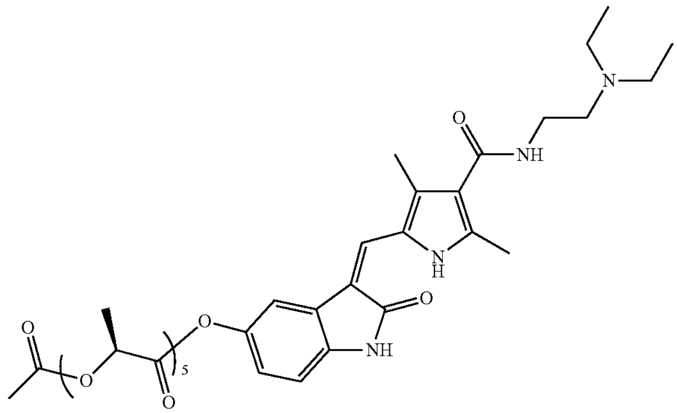 |
| 53-2 | 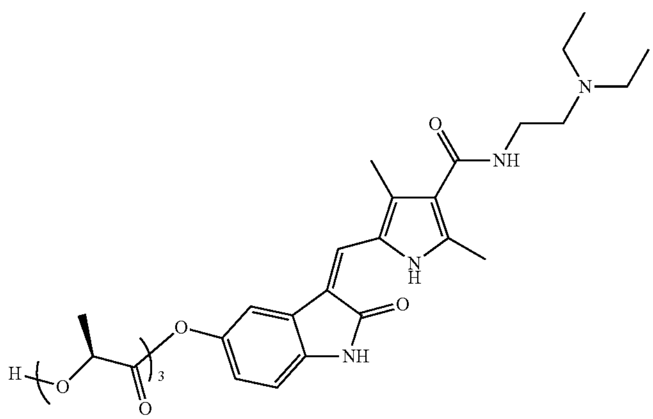 |
| 54-1 | 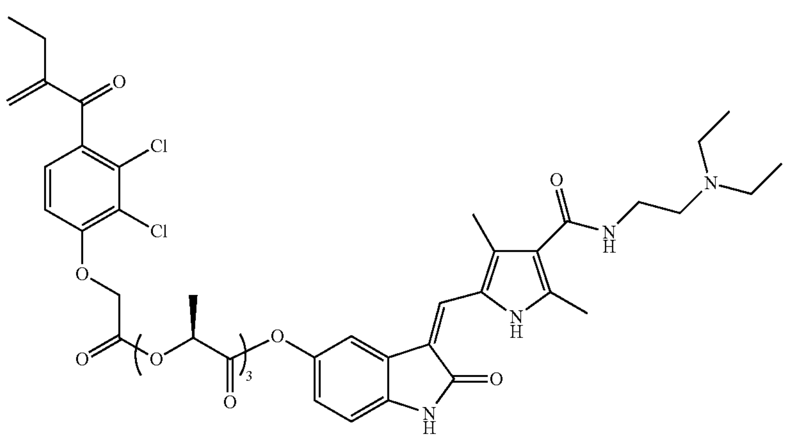 |

TABLE 9-continued

Non-limiting Examples of Synthesized Compounds

| Comp. # | Structure |
|---|---|
| 55-4 | 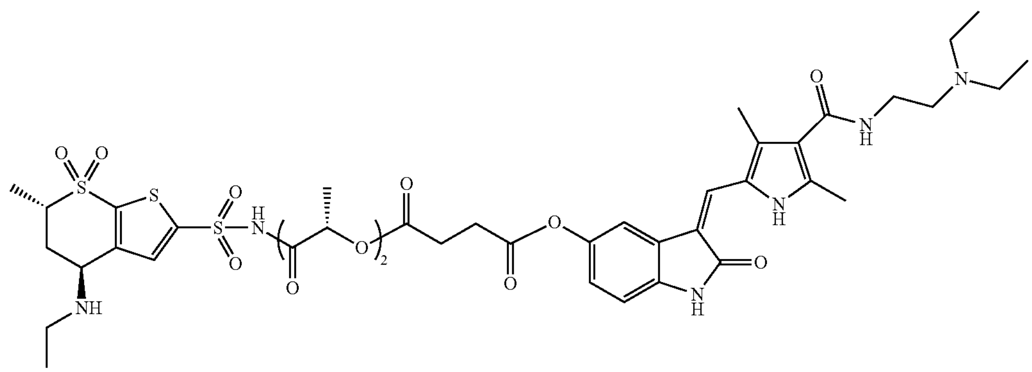 |
| 56-5 | 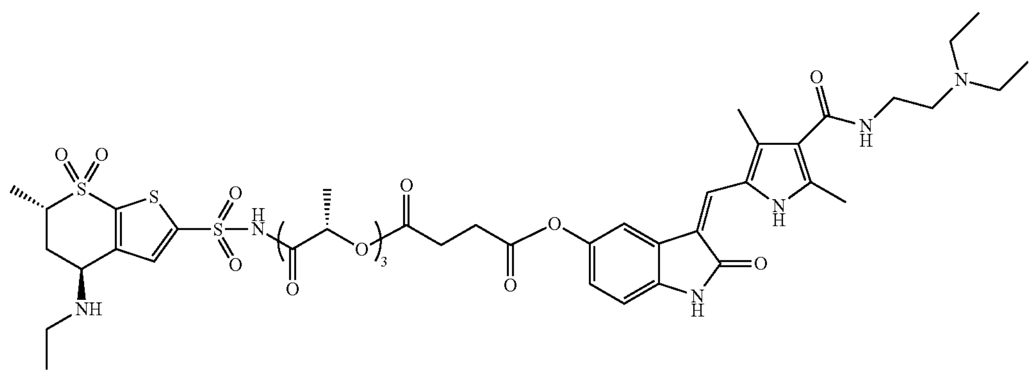 |
| 57-3 | 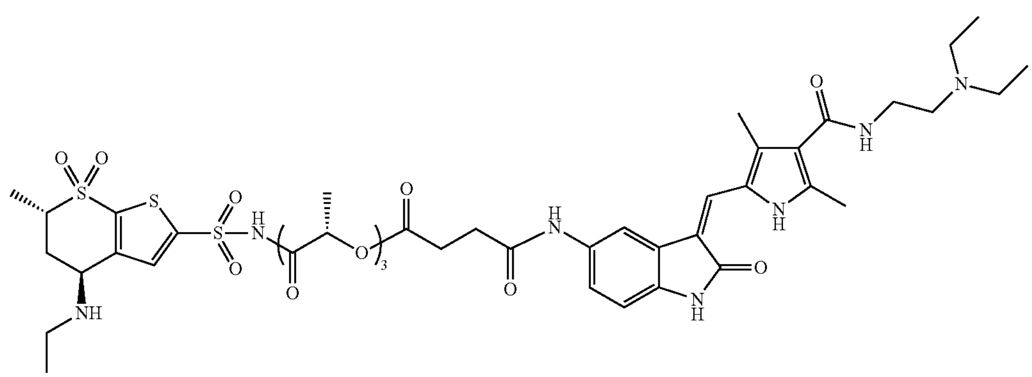 |
| 58-5 | 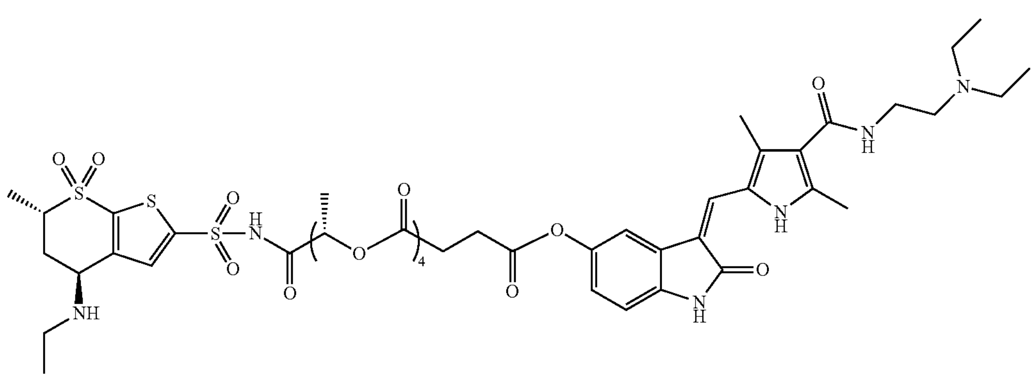 |

TABLE 9-continued

Non-limiting Examples of Synthesized Compounds

| Comp. # | Structure |
|---|---|
| 59-1 | 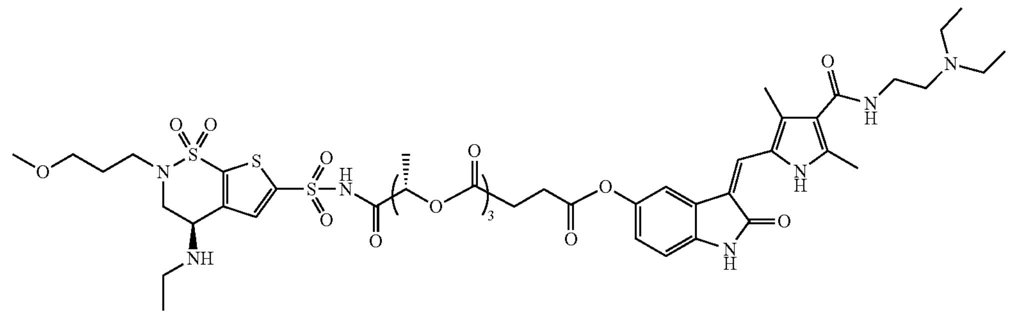 |
| 60-1 | 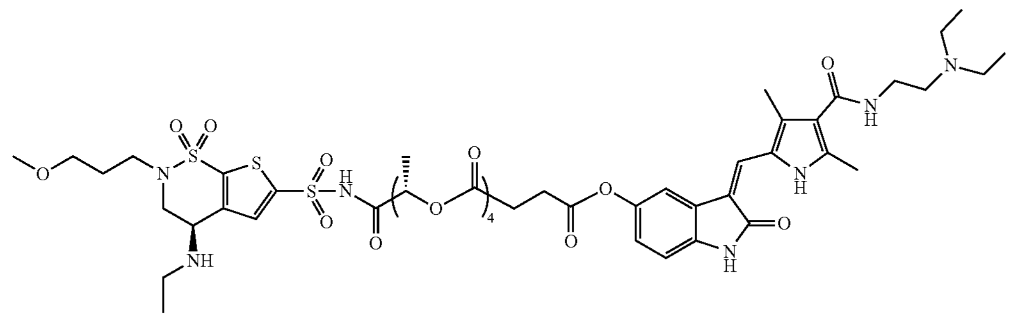 |
| 61-2 | 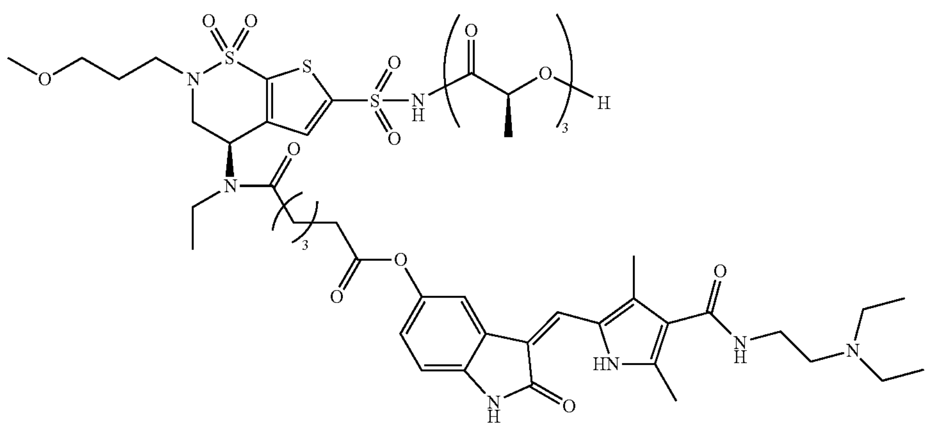 |
| 61-3 | 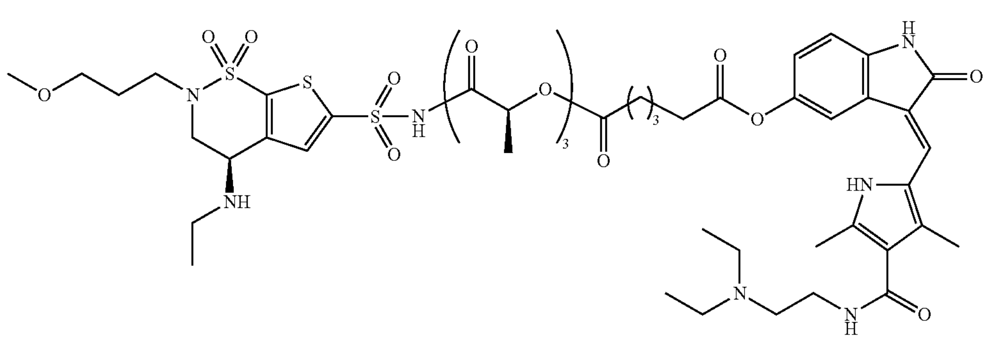 |

This specification has been described with reference to embodiments of the invention. However, one of ordinary skill in the art appreciates that various modifications and changes can be made without departing from the scope of the invention as set forth herein. Accordingly, the specification is to be regarded in an illustrative rather than a restrictive sense, and all such modifications are intended to be included within the scope of invention.

What is claimed is:
1. A compound of Formula:

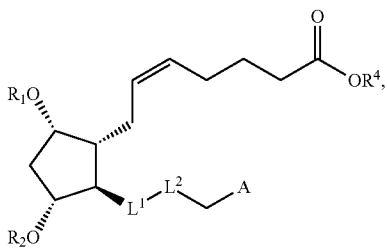

or a pharmaceutically acceptable salt thereof;
wherein:
$L^1$ is selected from:

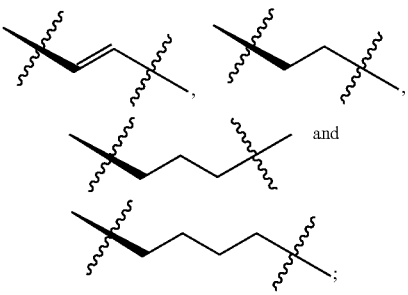

$L^2$ is selected from:

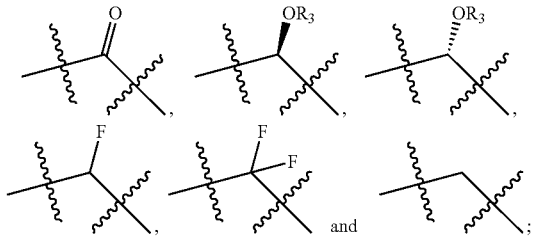

A is selected from: H, alkyl, cycloalkyl, cycloalkylalkyl, heterocycle, heterocycloalkyl, aryl, arylalkyl, heteroaryl, heteroarylalkyl, aryloxy, and alkyloxy;
$R^1$, $R^2$, and $R^3$ are selected from: —C(O)$R^4$, C(O)A, and hydrogen wherein either $R^1$ or $R^2$ cannot be hydrogen and wherein $R^1$, $R^2$, and $R^3$ can be further optionally substituted with $R^5$;
$R^4$ is selected from:
(i) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, and —$C_{10}$-$C_{30}$alkenylalkynyl; or
(ii) an unsaturated fatty acid residue selected from linoleic acid, docosahexaenoic acid, eicosapentaenoic acid, alpha-linolenic acid, stearidonic acid, γ-linolenic acid, arachidonic acid, docosatetraenoic acid, palmitoleic acid, vaccenic acid, paullinic acid, oleic acid, elaidic acid, gondoic acid, nervonic acid and mead acid; and
$R^5$ is selected from: halogen, hydroxyl, cyano, mercapto, amino, aryl, alkyl, alkoxy, alkenyl, alkynyl, cycloalkyl, cycloalkylalkyl, heterocyclyl, heterocycloalkyl, aryl, arylalkyl, heteroaryl, heteroarylalkyl, aryloxy, —S(O)$_2$alkyl, —S(O)alkyl, —P(O)(Oalkyl)$_2$, B(OH)$_2$, —Si(CH$_3$)$_3$, —COOH, —COOalkyl, —CONH$_2$.

2. A pharmaceutical composition comprising a compound of claim 1 in a pharmaceutically acceptable carrier.

3. The compound of claim 1, wherein $L^1$ is selected from and

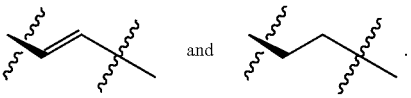

4. The compound of claim 1, wherein $L^2$ is

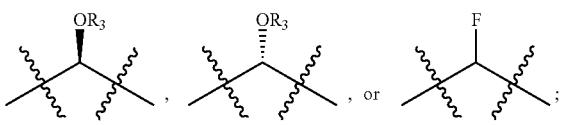

wherein
$R^3$ is hydrogen or C(O)A; and
A is alkyl.

5. The compound of claim 1, wherein A is selected from H, alkyl, aryloxy, aryl, and heteroaryl.

6. The compound of claim 5, wherein A is selected from alkyl or aryloxy.

7. The compound of claim 1, wherein $R^1$ and $R^2$ are selected from —C(O)$R^4$, C(O)A, and hydrogen, wherein
either $R^1$ or $R^2$ cannot be hydrogen; and
$R^4$ is defined as in claim 1.

8. The compound of claim 7, wherein $R^4$ is selected from —$C_{10}$-$C_{30}$alkyl, —$C_{10}$-$C_{30}$alkenyl, —$C_{10}$-$C_{30}$alkynyl, and $C_{10}$-$C_{30}$alkenylalkynyl.

9. The compound of claim 8, wherein $R^4$ is selected from (CH$_2$)$_4$(CHCHCH$_2$)$_5$CH$_3$ and (CH$_2$)$_8$CH=CH(CH$_2$)$_5$CH$_3$.

10. The compound of claim 1, wherein $R^4$ is selected from —$C_{10}$-$C_{30}$alkyl, —$C_{10}$-$C_{30}$alkenyl, —$C_{10}$-$C_{30}$alkynyl, and $C_{10}$-$C_{30}$alkenylalkynyl.

11. The compound of claim 10, wherein $R^4$ is selected from (CH$_2$)$_4$(CHCHCH$_2$)$_5$CH$_3$ and (CH$_2$)$_8$CH=CH(CH$_2$)$_5$CH$_3$.

12. The compound of claim 3, wherein $L^2$ is

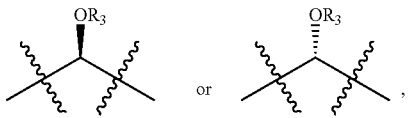

wherein $R^3$ is hydrogen.

13. The compound of claim 12, wherein A is alkyl, aryloxy, or aryl.

14. The compound of claim 13, wherein A is alkyl or aryloxy.

15. The compound of claim 13, wherein $R^4$ is selected from (CH$_2$)$_4$(CHCHCH$_2$)$_5$CH$_3$ and (CH$_2$)$_8$CH=CH(CH$_2$)$_5$CH$_3$.

16. The compound of claim 15, wherein $R^1$ is hydrogen and $R^2$ is C(O)A wherein A is defined as in claim 1.

17. The compound of claim 16, wherein A is alkyl or aryloxy.
18. The compound of claim 15, wherein $R^1$ is C(O)A and $R^2$ is hydrogen wherein A is defined as in claim 1.
19. The compound of claim 18, wherein A is alkyl or aryloxy.
20. A compound of formula
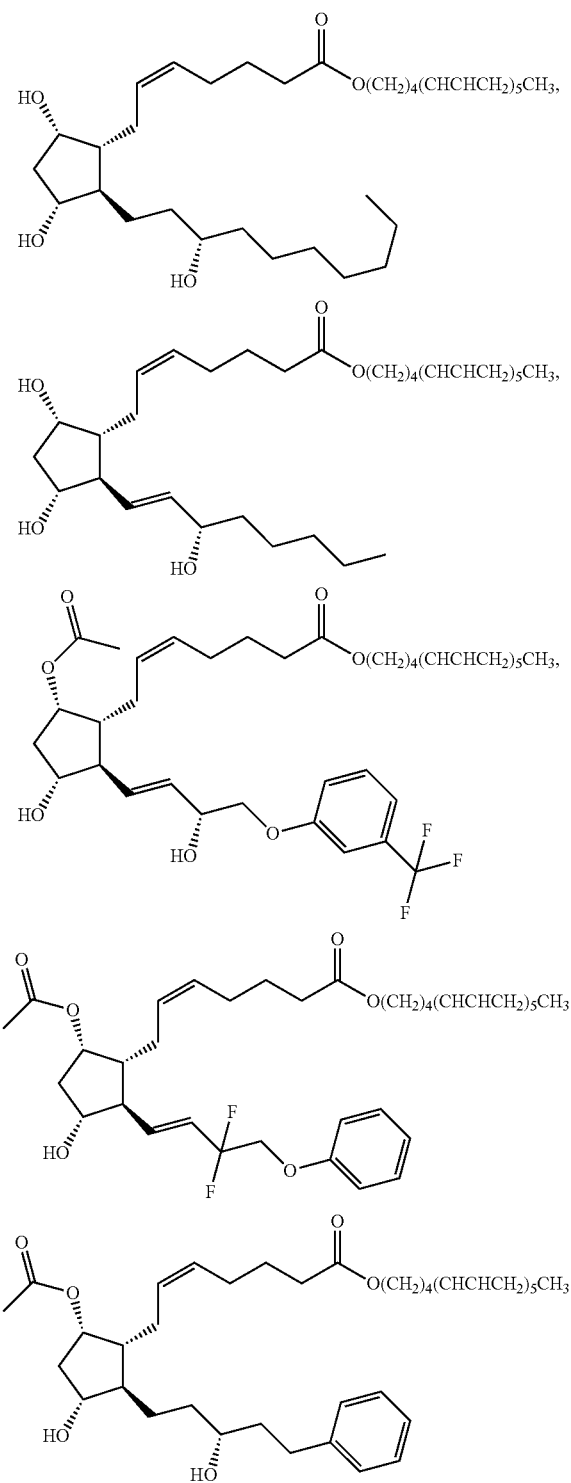
-continued
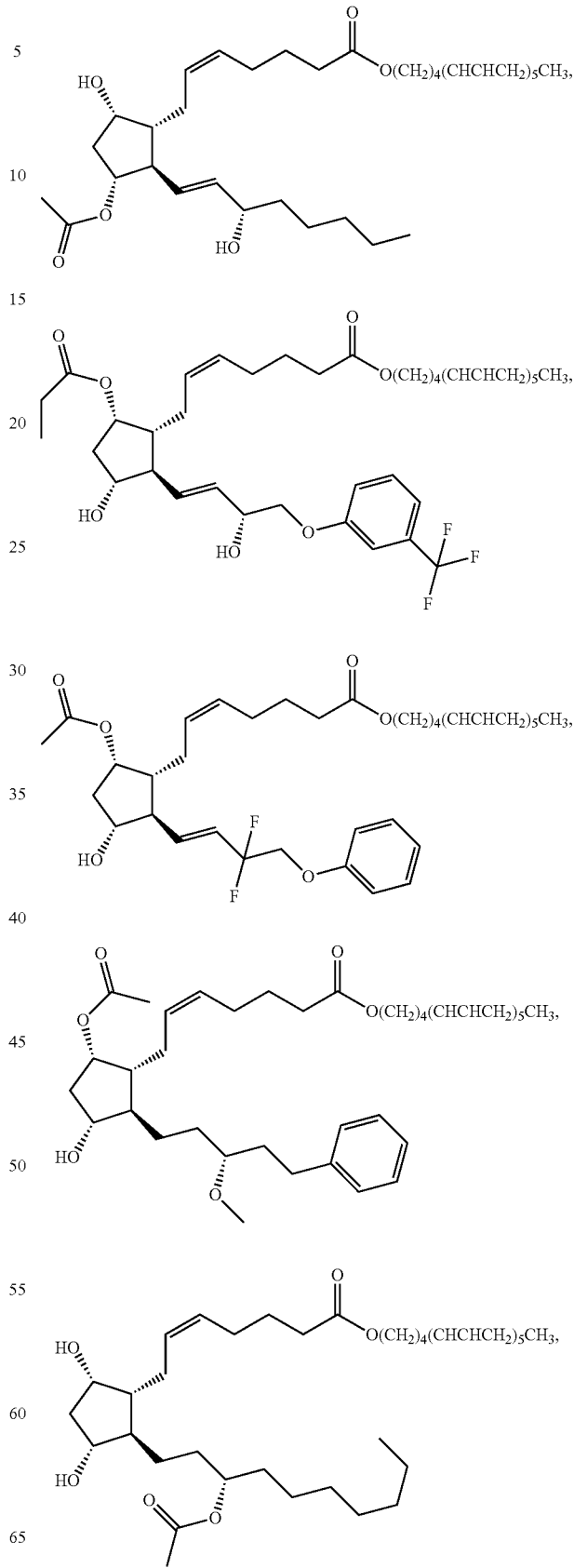

415
-continued
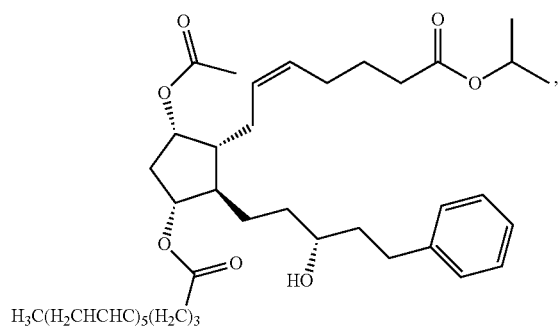
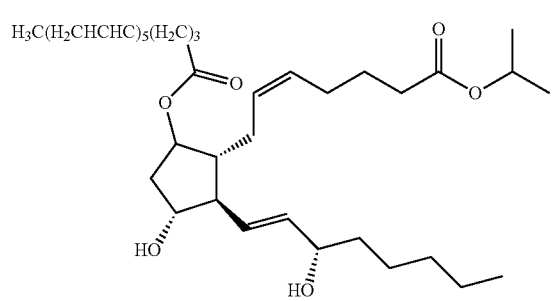
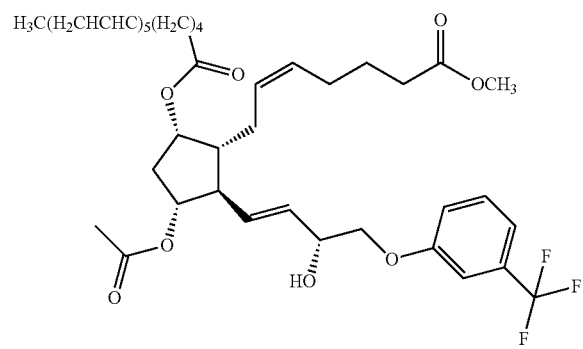
or a pharmaceutically acceptable salt thereof.
21. The compound of claim 20 of the formula
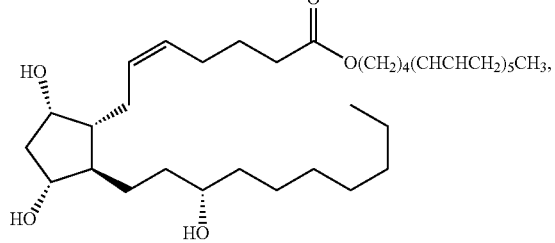
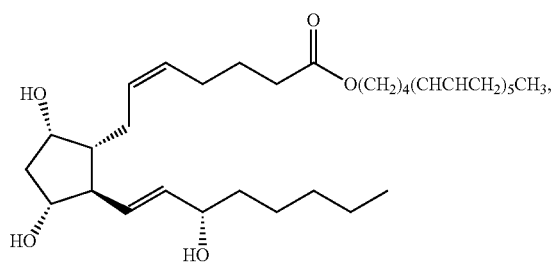
416
-continued
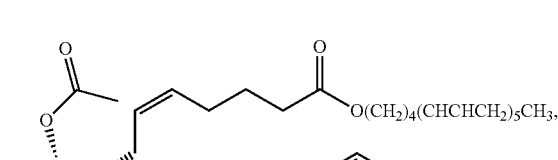
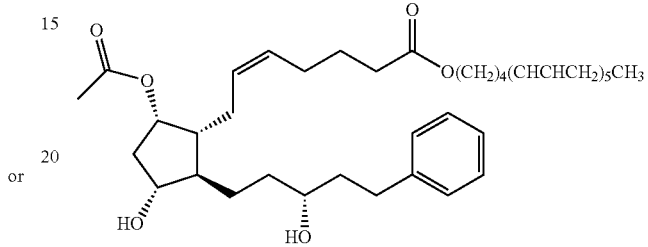
or
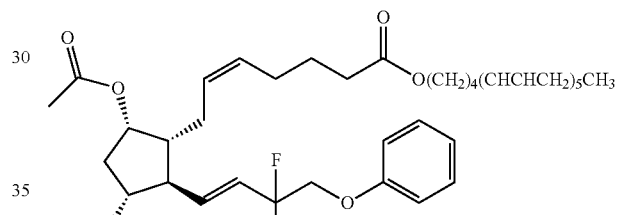
or a pharmaceutically acceptable salt thereof.
22. The compound of claim 20 of the formula
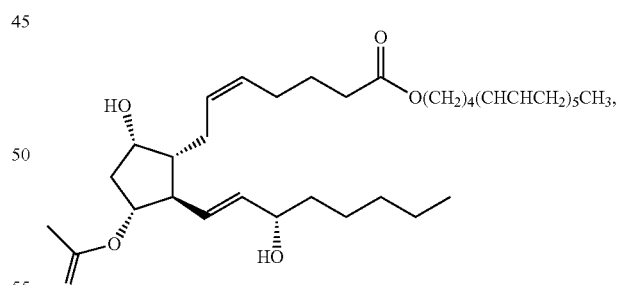
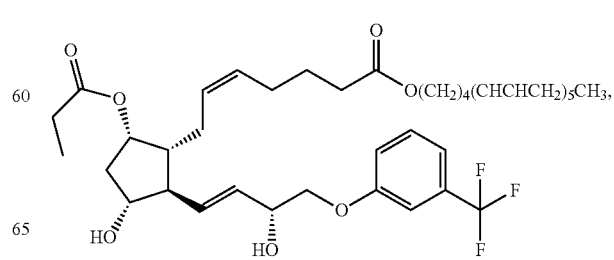

-continued
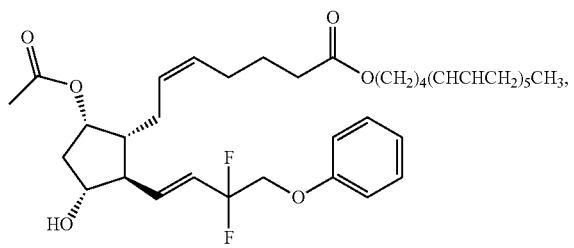
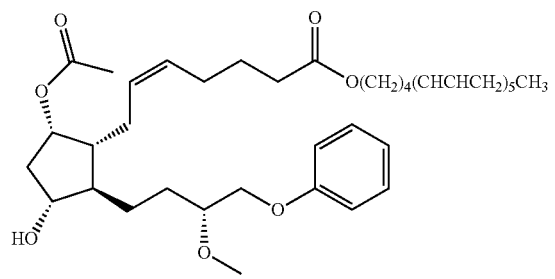
or
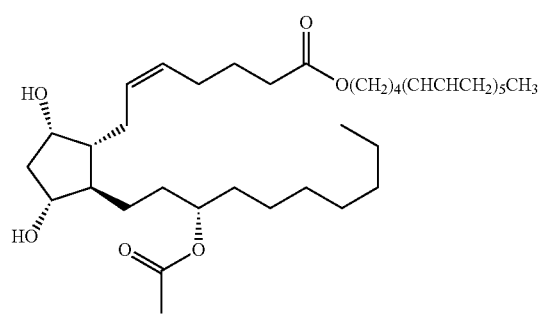
or a pharmaceutically acceptable salt thereof.
23. The compound of claim 20 of the formula
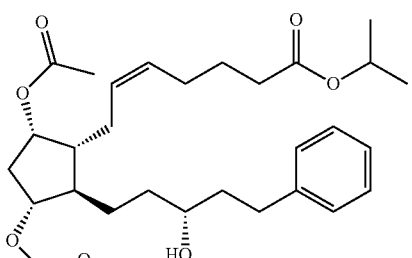
$H_3C(H_2CHCHC)_5(H_2C)_3$
$H_3C(H_2CHCHC)_5(H_2C)_3$
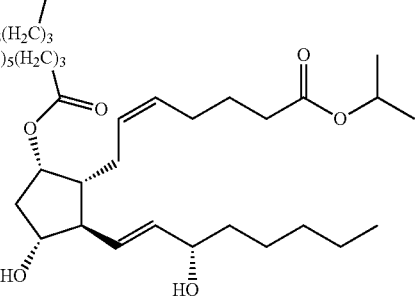
or
$H_3C(H_2CHCHC)_5(H_2C)_4$
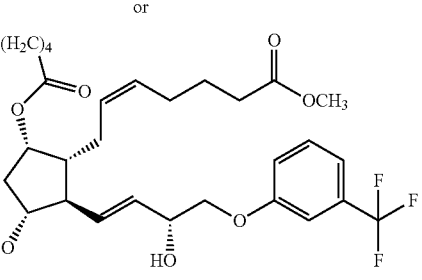
or a pharmaceutically acceptable salt thereof.
24. A compound of formula
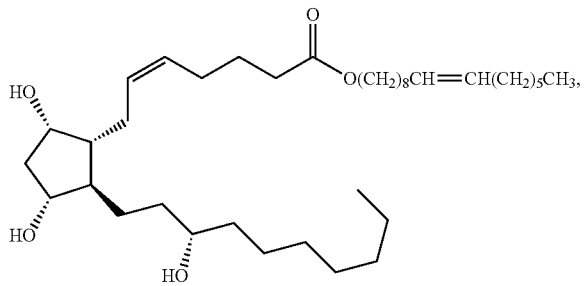
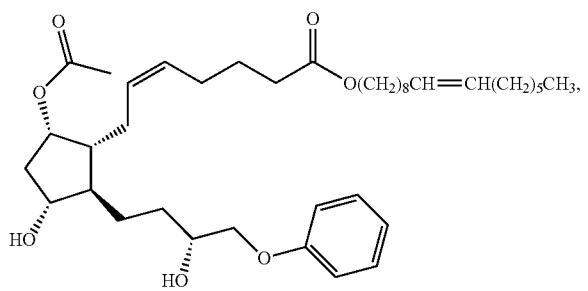

-continued
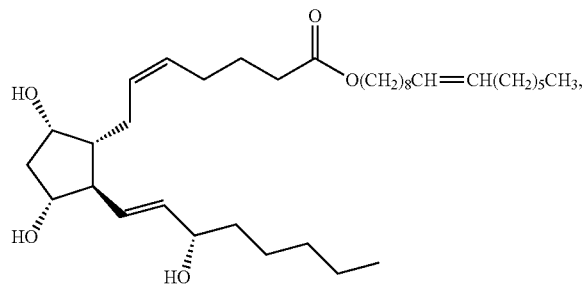
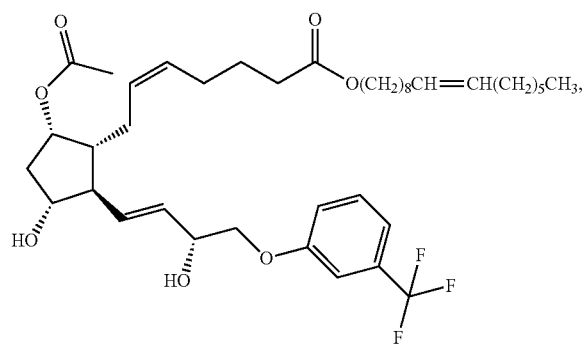
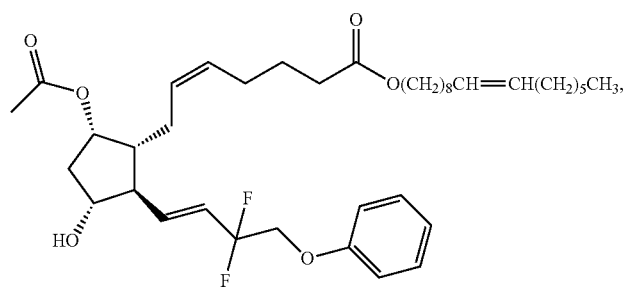
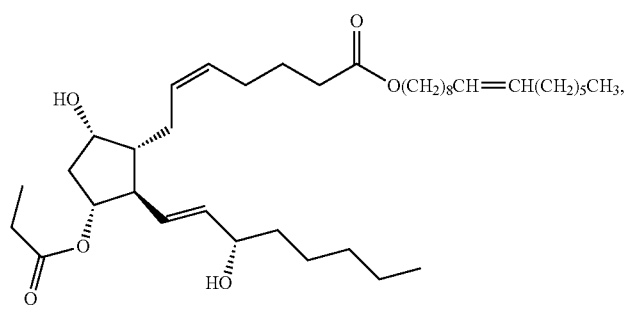
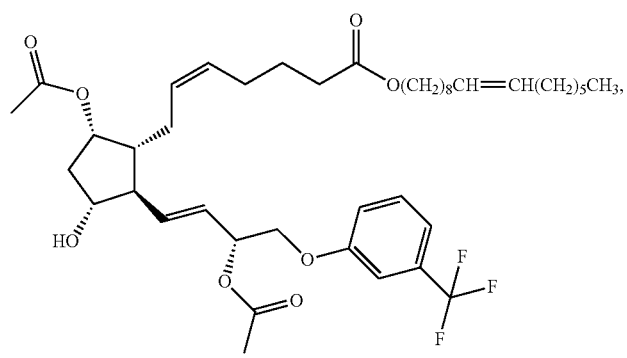

-continued
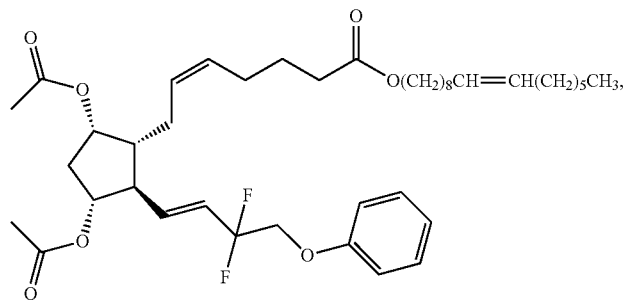
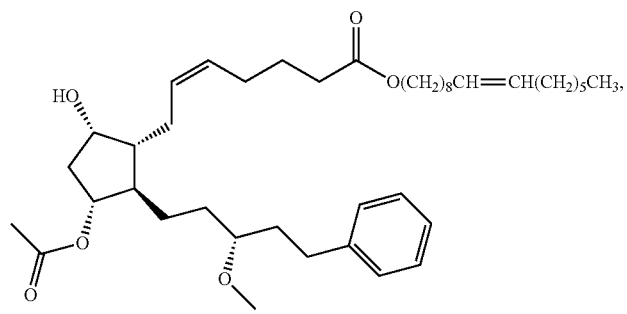
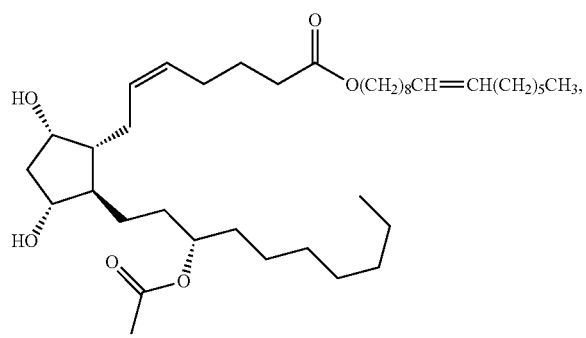
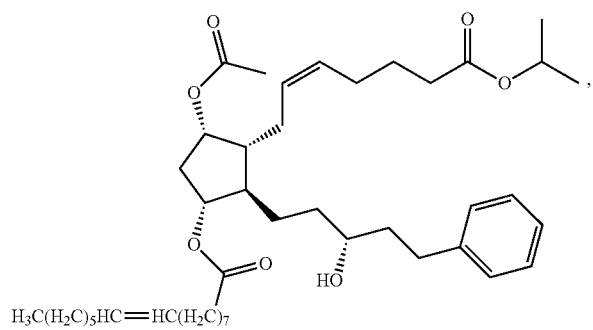
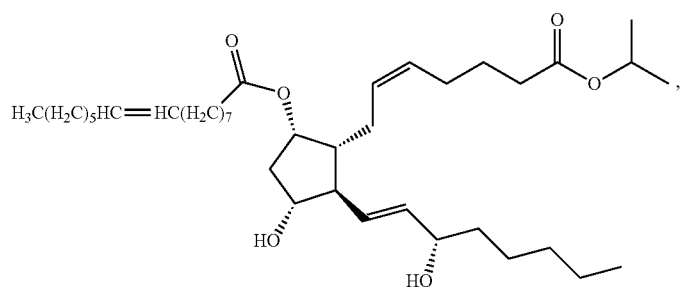

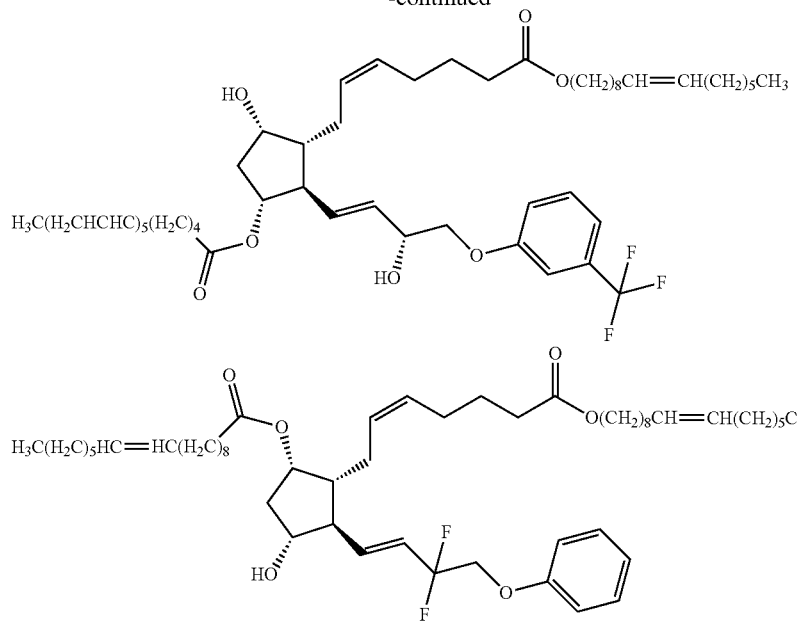
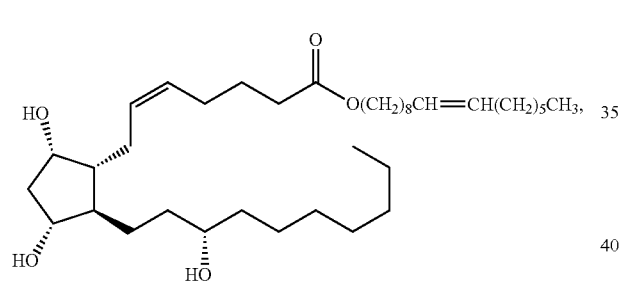
or a pharmaceutically acceptable salt thereof.
25. The compound of claim 24 of the formula
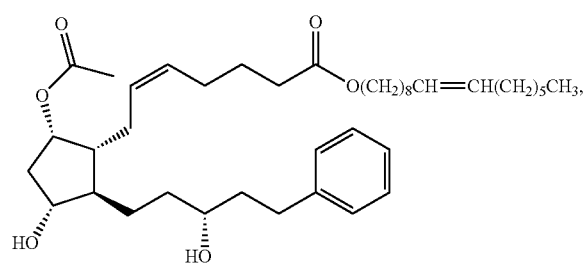
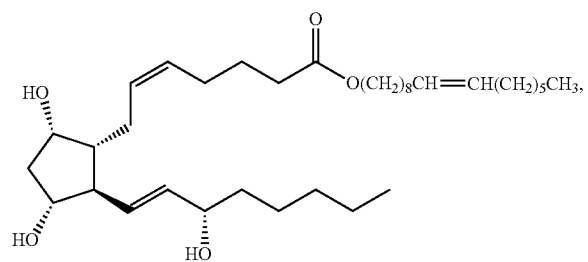
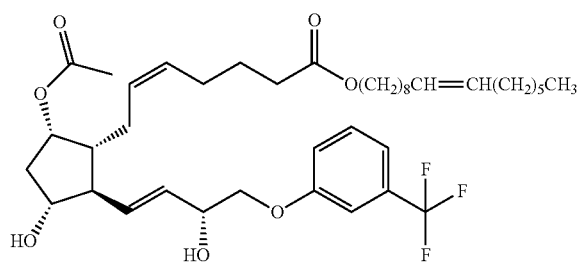
or
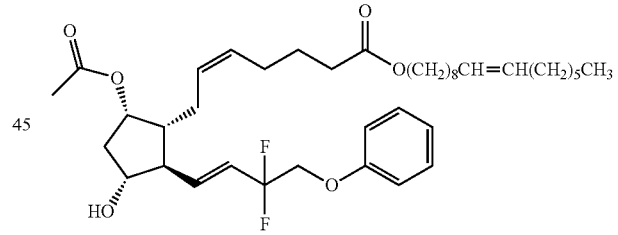
or a pharmaceutically acceptable salt thereof.
26. The compound of claim 24 of the formula
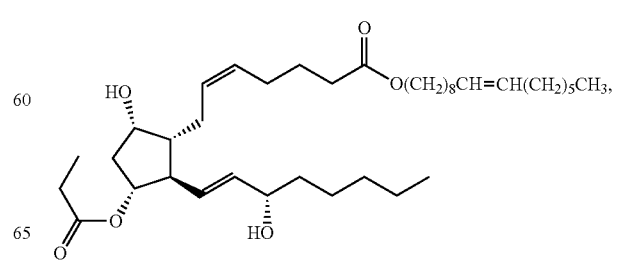

425
-continued
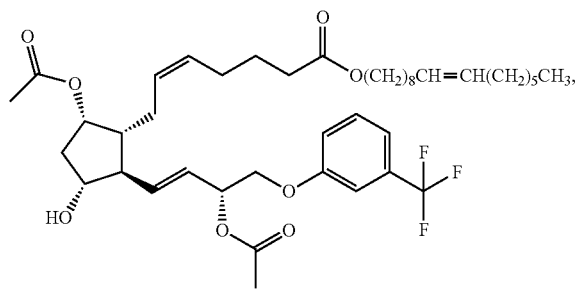
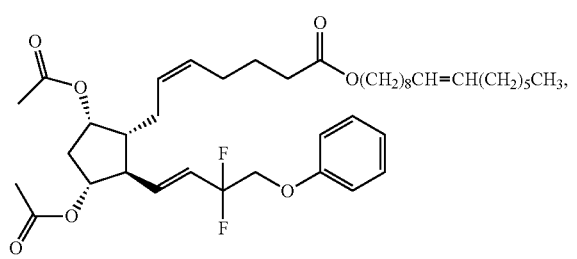
426
-continued
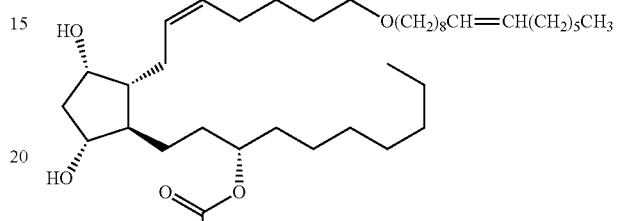
or
or a pharmaceutically acceptable salt thereof.
27. The compound of claim 24 of the formula
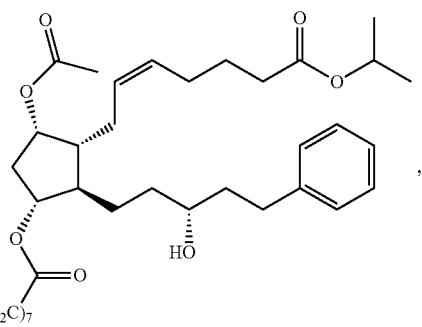
,
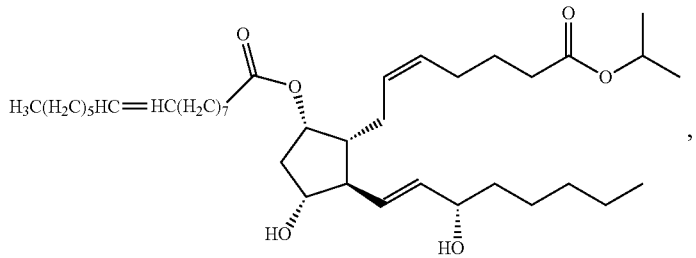
,
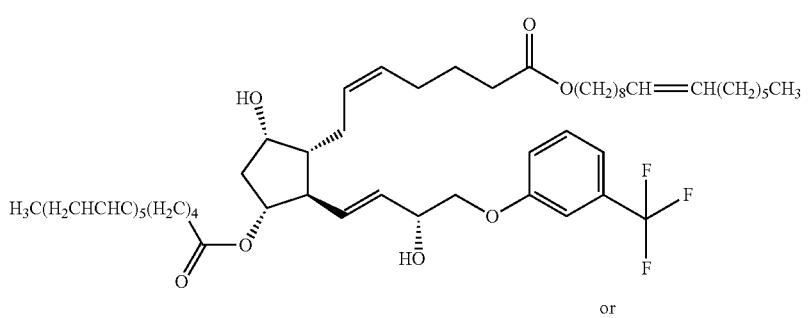
or -continued
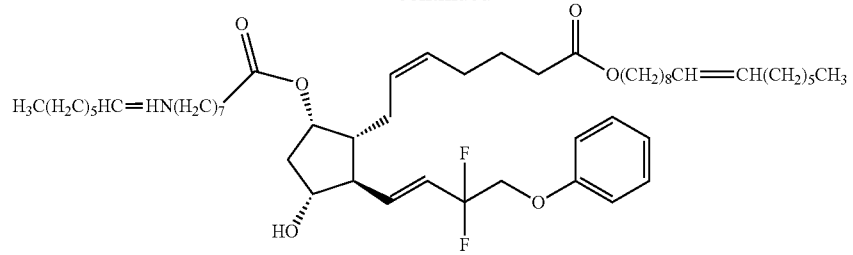
or a pharmaceutically acceptable salt thereof.
* * * * *

UNITED STATES PATENT AND TRADEMARK OFFICE
CERTIFICATE OF CORRECTION

PATENT NO. : 9,808,531 B2
APPLICATION NO. : 15/273686
DATED : November 7, 2017
INVENTOR(S) : Cleland et al.

Page 1 of 3

It is certified that error appears in the above-identified patent and that said Letters Patent is hereby corrected as shown below:

Column 56, Lines 45-55 approx. 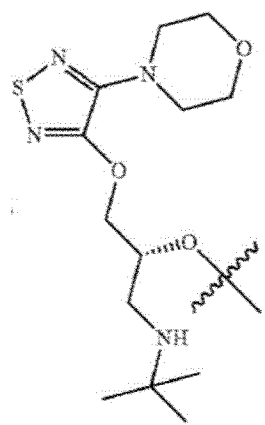 should read 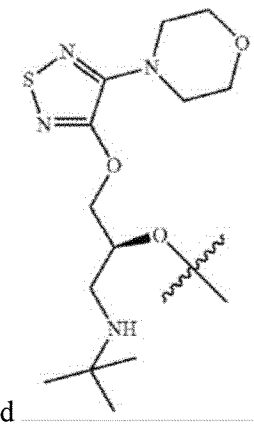 ;

Column 59, Lines 40-50 approx. 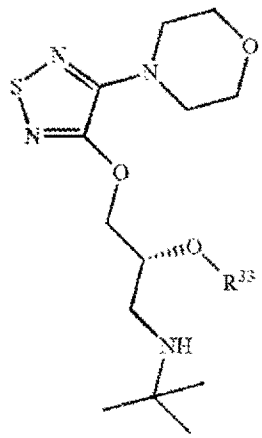 should read 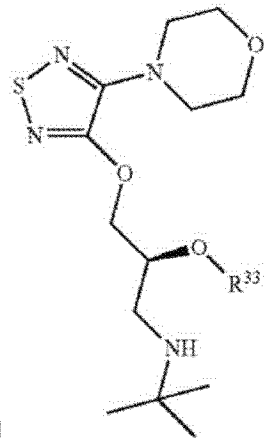 ;

Signed and Sealed this
Fourteenth Day of August, 2018

Andrei Iancu
*Director of the United States Patent and Trademark Office*

CERTIFICATE OF CORRECTION (continued)
U.S. Pat. No. 9,808,531 B2

Column 60, Lines 50-60 approx. 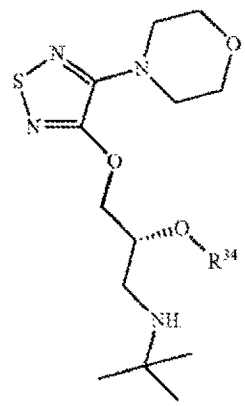 should read 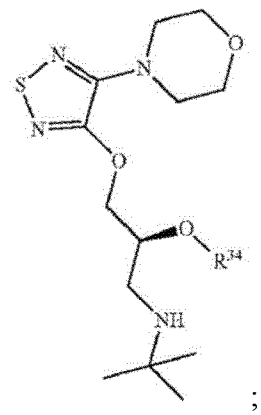 ;

Column 64, Lines 55-65 approx. 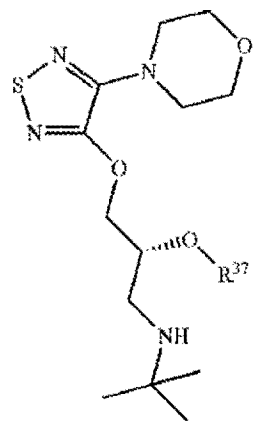 should read 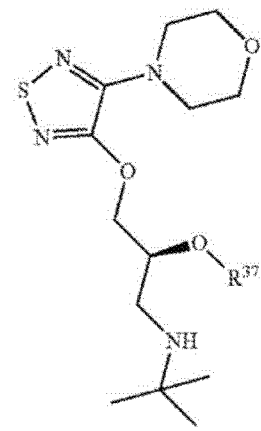 ;

Column 91, Lines 5-15 approx. 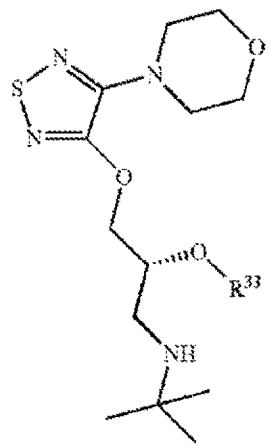 should read 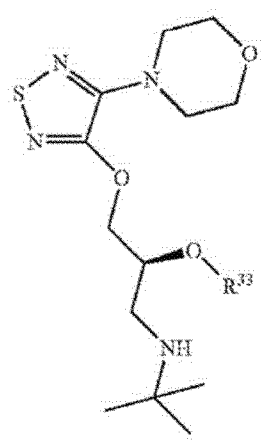 ;

CERTIFICATE OF CORRECTION (continued)
U.S. Pat. No. 9,808,531 B2

Column 91, Lines 20-30 approx. 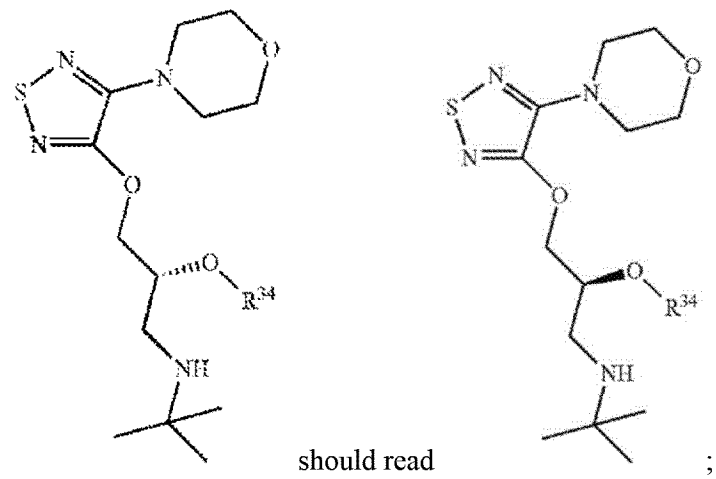 should read

Column 91, Lines 35-45 approx. 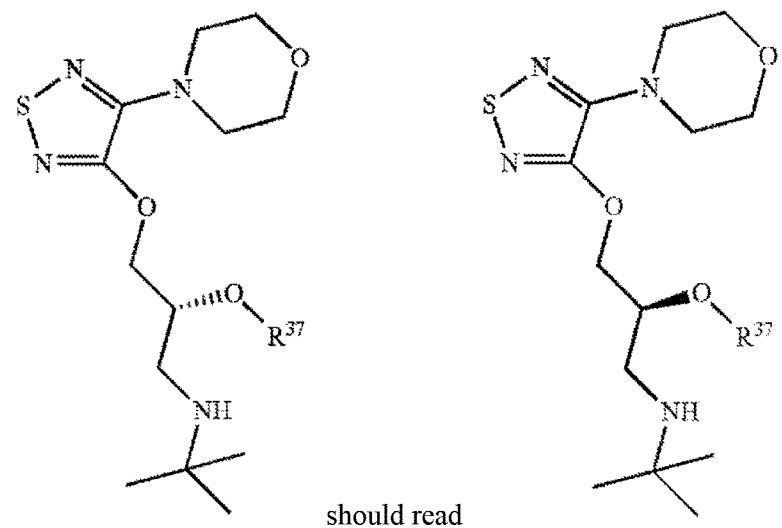 should read